(12) United States Patent
Murakata et al.

(10) Patent No.: US 7,745,641 B2
(45) Date of Patent: Jun. 29, 2010

(54) NITROGEN-CONTAINING HETEROCYCLIC COMPOUND

(75) Inventors: Chikara Murakata, Sunto-gun (JP); Nobuyoshi Amishiro, Sunto-gun (JP); Toshiyuki Atsumi, Sunto-gun (JP); Yoshinori Yamashita, Tokyo (JP); Takeshi Takahashi, Numazu (JP); Ryuichiro Nakai, San Diego, CA (US); Hisashi Tagaya, Sunto-gun (JP); Hiroko Takahashi, Sunto-gun (JP); Jun Funahashi, Sunto-gun (JP); Junichiro Yamamoto, Sunto-gun (JP); Yuichi Fukuda, Sunto-gun (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 292 days.

(21) Appl. No.: 11/918,778

(22) PCT Filed: Apr. 19, 2006

(86) PCT No.: PCT/JP2006/308224
§ 371 (c)(1),
(2), (4) Date: Oct. 18, 2007

(87) PCT Pub. No.: WO2006/112479
PCT Pub. Date: Oct. 26, 2006

(65) Prior Publication Data
US 2009/0054407 A1    Feb. 26, 2009

(30) Foreign Application Priority Data
Apr. 19, 2005    (JP)    ............... 2005-120953

(51) Int. Cl.
C07D 207/00    (2006.01)
A61K 31/40    (2006.01)
(52) U.S. Cl. ............ 548/519; 514/414
(58) Field of Classification Search ........... 548/519; 514/414
See application file for complete search history.

(56) References Cited

U.S. PATENT DOCUMENTS

| | | |
|---|---|---|
| 5,491,144 A | 2/1996 | Trinks et al. |
| 5,663,336 A | 9/1997 | Trinks et al. |
| 2005/0026976 A1 | 2/2005 | Curtin et al. |
| 2005/0054670 A1 | 3/2005 | Tegley et al. |
| 2005/0101518 A1 | 5/2005 | Solow-Cordero et al. |
| 2005/0130943 A1 | 6/2005 | Wallace et al. |
| 2005/0182061 A1 | 8/2005 | Green et al. |
| 2005/0261298 A1 | 11/2005 | Solow-Cordero et al. |
| 2005/0267108 A1 | 12/2005 | Hsieh et al. |
| 2007/0032459 A1 | 2/2007 | Solow-Cordero et al. |

FOREIGN PATENT DOCUMENTS

| | | |
|---|---|---|
| CA | 2 069 857 | 12/1992 |
| JP | 05-163240 | 6/1993 |
| JP | 5-163240 | 6/1993 |
| JP | 10-231285 | 9/1998 |
| WO | 2004/108672 | 12/2004 |
| WO | 2005/095341 | 10/2005 |
| WO | 2007/047646 | 4/2007 |

OTHER PUBLICATIONS

Kubinyi (3D QSAR in Drug Design: Ligand-Protein Interactions and Molecular Similarity, vol. 2-3, Springer, 1998, 800 pages), TOC and pp. 243-244 provided.*
Curtin, et al., "Isoindolinone ureas: a novel class of KDR kinase inhibitors", Bioorganic & Medicinal Chemistry Letters, vol. 14, No. 17 (2004) 4505-09.
Takami, et al., "Design and synthesis of Rho kinase inhibitors (I)", Bioorganic & Medicinal Chemistry Letters, vol. 12, No. 9 (2004) 2115-37.

* cited by examiner

Primary Examiner—Rebecca L Anderson
Assistant Examiner—Robert Havlin
(74) Attorney, Agent, or Firm—Fitzpatrick, Cella, Harper & Scinto

(57) ABSTRACT

The present invention provides a nitrogen-containing heterocyclic compound represented by formula (I):

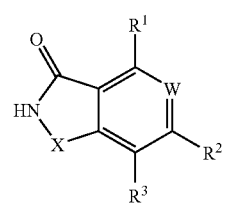

(I)

{wherein W represents a nitrogen atom or —CH—;
X represents —C(=O)— or —CHR$^4$— (wherein R$^4$ represents a hydrogen atom, or the like};
R$^1$ represents a group represented by the following formula:

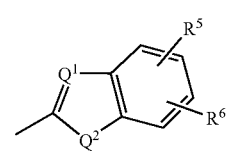

[wherein Q$^1$ represents a nitrogen atom or —CR$^8$— (wherein R$^8$ represents a hydrogen atom, substituted or unsubstituted lower alkyl, or the like). Q$^2$ represents —NR$^{15}$— (wherein R$^{15}$ represents a hydrogen atom, or the like) and R$^5$ and R$^6$ may be the same or different and each represents a hydrogen atom, substituted or unsubstituted lower alkyl, or the like]; and
R$^2$ and R$^3$ may be the same or different and each represents a hydrogen atom, halogen, substituted or unsubstituted lower alkyl, or the like} or a pharmaceutically acceptable salt thereof, and the like.

21 Claims, No Drawings

NITROGEN-CONTAINING HETEROCYCLIC COMPOUND

TECHNICAL FIELD

The present invention relates to a nitrogen-containing heterocyclic compound or a pharmaceutically acceptable salt thereof having an antitumor activity or the like.

BACKGROUND ART

Fibroblast growth factor receptors (FGFRs) are receptor-type protein tyrosine kinases (PTK). FGFRs are enzymes that are activated by dimerization caused by the binding of a fibroblast growth factor (FGF), which is a ligand of the kinases, and that phosphorylate various proteins, which are intracellular substrates, and thus relate to proliferation and differentiation of cells. It is known that FGFRs include four subtypes, namely, FGFR1 to FGFR4 [Expert Opinion on Therapeutic Targets, Vol. 6, p. 469 (2002)]. Recently, according to results of the examination of patient specimens, the FGFR3 gene is overexpressed by a chromosome translocation in about 25% of patients having multiple myeloma [Blood, Vol. 92, p. 3025 (1998)]. In addition, the FGF is highly expressed in the bone marrow of patients having multiple myeloma, and thus it is believed that activation of FGFR3 signals occurs in multiple myeloma cells that express, FGFR3 [Blood, Vol. 101, p. 2775 (2003)]. Furthermore, an active mutation of FGFR3 in cell strain and patient specimens of multiple myeloma is known, and it is believed that, by transmitting cell proliferation signals, such a constant-activation causes infinite proliferation of cells, and this is an important cause of multiple myeloma [Blood, Vol. 97 p. 729 (2001)]. Furthermore, overexpression and active mutation of FGF or FGFR have been reported in various types of cancers other than multiple myeloma (for example, pituitary tumor, myeloproliferative disease, renal cancer, urinary bladder cancer, colon cancer, head and neck cancer, skin cancer, stomach cancer, non-Hodgkin's lymphoma, brain tumor, breast cancer, and ovarian cancer) [Expert Opinion on Therapeutic Targets, Vol. 6, p. 469 (2002) and Nature, Vol. 411, p. 355 (2001)]. Accordingly, it is believed that an FGFR inhibitor is useful as a therapeutic agent for various cancers such as multiple myeloma.

Aurora kinases are serine/threonine kinases that are activated during the cell division phase (G2/M phase) and it has been reported that Aurora kinases are involved in centrosome duplication, chromosome separation, cytokinesis and the like. It is known that Aurora kinases include three subtypes, namely, Aurora A, Aurora B, and Aurora C. Among these, Aurora A is present on chromosome 20q13 whose amplification has been reported in various types of cancers. Overexpression of Aurora A has been frequently observed in breast cancer, colon cancer, urinary bladder cancer, pancreatic cancer, stomach cancer, ovarian cancer, esophageal cancer, liver cancer and the like, and the correlation between Aurora A and the degree of malignancy or the prognosis of the diseases has also been reported [Trends in Cell Biology, Vol. 9, p. 454 (1999); British Journal of Cancer, Vol. 84, p. 824 (2001); Journal of National Cancer Institute, Vol. 94, p. 1320 (2002); Clinical Cancer Research, Vol. 9, p. 1420 (2003); Clinical Cancer Research, Vol. 11, p. 1827 (2005); and Clinical Cancer Research, Vol. 10, p. 2065 (2004)]. It has been reported that Aurora B is also overexpressed together with Aurora A in clinical specimens of breast cancer and colon cancer [Oncogene, Vol. 14, p. 2195 (1997); and EMBO Journal, Vol. 17, p. 3052 (1998)]. It is believed that such an abnormal activity of mitotic kinase is one of the causes of chromosome instability, which is a characteristic of many cancer cells. Accordingly, it is believed that an Aurora inhibitor is useful as a therapeutic agent for various cancers such as colon cancer.

Fms-like tyrosine kinase 3 (hereinafter referred to as Flt-3) is a receptor-type protein tyrosine kinase (PTK) belonging to a platelet-derived growth factor receptor (PDGFR) family. Flt-3 is an enzyme that is activated by dimerization caused by the binding of an Flt-3 ligand, which is a ligand of the kinase, and that phosphorylates various proteins, which are intracellular substrates, and thus relates to proliferation and differentiation of cells. It is known that, Flt-3 is particularly expressed in hematopoietic stem cells, and Flt-3 or Flk-2 (Fetai liver kinase-2) plays an important role in proliferation thereof [Cell, Vol. 65, p. 1143 (1991)]. Recently, results of examination of specimens from leukemia patients showed that activation of Flt-3 occurs without ligand binding to Flt-3 by a mutation caused by inserting a repetitive sequence of tyrosine residue in the juxtamembrane domain of Flt-3 (internal tandem duplication (ITD)) [Leukemia, Vol. 11, p. 1447 (1997)]. It has also been reported that a similar activation of Flt-3 is caused by a mutations including elongation or shortening of the amino-acid sequence in the juxtamembrane domain of Flt-3 [Blood, Vol. 96, p. 3907 (2000)]. In addition, it has been reported that Flt-3 is activated by a point mutation of an amino acid in the kinase domain of Flt-3 [Blood, Vol. 97, p. 2434 (2001)]. It is believed that such a constitutive activation based on these Flt-3 mutations causes infinite proliferation of cells by transmitting cell proliferation signals and therefore is an important cause of leukemia. Accordingly, it is believed that an Flt-3 inhibitor is useful as a therapeutic agent for various cancers such as leukemia. Drugs such as SU11248, CHIR-258, CT53518, CEP-701, and PKC412 have been reported as drugs that act on Flt-3. It is known that these drugs exhibit an antitumor activity in leukemia-transplant mice [Blood, Vol. 101, p. 3597 (2003); Clinical Cancer Research, Vol. 11, p. 5281 (2005); Cancer Cell, Vol. 1, p. 421 (2002); Blood, Vol. 99, p. 3885 (2002); and Cancer Cell, Vol. 1, p. 433 (2002)].

As described above, inhibitors against a kinase relating to proliferation, differentiation or malignant alteration of cancer cells have attracted attention as novel antitumor agents. For example, Imatinib that selectively inhibits Abl kinase is clinically used as a drug that has low toxicity and a high clinical effect to chronic leukemia patients [New England Journal of Medicine], Vol. 345, p. 645 (2002)]. Drugs such as PD173074, PKC412, BIBF1000, CHIR-258, and SU5402 have been reported to act on FGFR. It is known that these drugs exhibit an antitumor activity in several evaluation models [Blood, Vol. 103, p. 3521 (2004); Leukemia, Vol. 18, p. 962 (2004); Oncogene, Vol. 24, p. 8259 (2005); Blood, Vol. 107, p. 2079 (2006); Blood, Vol. 105, p. 2941 (2005); and Clinical cancer research, Vol. 11, p. 2702 (2005)]. Examples of known drugs that inhibit Aurora kinases include Hesperadin [The Journal of Cell Biology, Vol. 161, p. 281 (2003); US2003/0069299], ZM447439 [The Journal of Cell Biology, Vol. 161, p. 267 (2003); WO01/21596], PHA-680632 [Journal of Medicinal Chemistry, Vol. 48, p. 3080 (2005); WO02/12242], AZD1152 [Journal of Medicinal Chemistry, Vol. 49, p. 955 (2006), Bioorganic & Medicinal Chemistry Letters, Vol. 16, p. 1320 (2006); WO04/058781], JNJ-7706621 [Journal of Medicinal Chemistry, Vol. 48, p. 4208 (2005)], VX-680 [Current Topics in Medicinal Chemistry, Vol. 5, p. 199 (2005); and Expert Opinion on Therapeutic Patents, Vol. 15, p. 1169 (2005)], or the like. It has been reported that VX-680 exhibits an antitumor activity in human-tumor-transplant mouse and rat models [Nature Review. Cancer, Vol. 4, p. 927 (2004); and Nature Medicine, Vol. 3, p. 262 (2004)]. It has been reported that JNJ-7706621 exhibits an antitumor activity in human-tumor-transplant mouse models [Cancer Research, Vol. 65, p. 9038 (2005)]. However, drugs that simultaneously inhibit several kinases having an important role in cancers and exhibit an antitumor activity by mechanisms based on the inhibition of the function of the kinases have not been reported. Accordingly, drugs that not only inhibit a respective kinase but also target several kinases simultaneously are expected to be useful as novel antitumor agents.

Isoindolinone derivatives having an inhibitory activity against vascular endothelial growth factor receptor (VEGFR2)/kinase insert domain receptor (KDR) are known (Patent Documents 1 to 3 and Non-Patent Document 1).

Phthalimide derivatives having an inhibitory activity against AKT, 3-phosphoinositide-dependent protein kinase-1 (PDK-1), p70 ribosomal S6 kinase (p70S6K), and p160-Rho-associated coiled-coil-containing protein kinase (ROCK) are known (Patent Document 4).

Isoindolinone derivatives having an inhibitory activity against mitogen-activated protein kinase kinase (MEK) are known (Patent Document 5).

Patent Document 1: WO 04/108672

Patent Document 2: U.S. Patent Application Publication 2005/0026976

Patent Document 3: WO 04/021532

Patent Document 4: WO 05/039564

Patent Document 5: WO 05/051300

Non-Patent Document 1: "Bioorganic & Medicinal Chemistry Letters", Vol. 14, p. 4505, 2004

DISCLOSURE OF INVENTION

Problems to be Solved by the Invention

An object of the present invention is to provide a nitrogen-containing heterocyclic compound or a pharmaceutically acceptable salt thereof having an antitumor activity or the like.

Means for Solving the Problems

The present invention relates to the following items (1) to (20).

(1) A Nitrogen-Containing Heterocyclic Compound Represented by Formula (I):

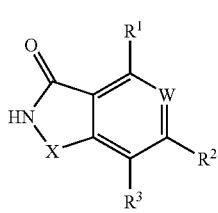

(I)

<wherein W represents a nitrogen atom or —CH—;

X represents —C(=O)— or —CHR$^4$— (wherein R$^4$ represents a hydrogen atom, hydroxy, substituted or unsubstituted lower alkyl, substituted or unsubstituted cycloalkyl, or substituted or unsubstituted lower alkoxy);

R$^1$ represents a group represented by the following formula:

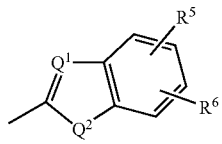

[wherein Q$^1$ represents a nitrogen atom or —CR$^8$— (wherein R$^8$ represents a hydrogen atom, halogen, nitro, hydroxy, cyano, carboxy, substituted or unsubstituted lower alkyl, substituted or unsubstituted cycloalkyl, substituted or unsubstituted aralkyl, substituted or unsubstituted lower alkenyl, substituted or unsubstituted lower alkynyl, substituted or unsubstituted aryl, a substituted or unsubstituted heterocyclic group, substituted or unsubstituted lower alkanoyl, substituted or unsubstituted aroyl, substituted or unsubstituted heteroaroyl, substituted or unsubstituted lower alkoxy, substituted or unsubstituted lower alkoxycarbonyl, —CONR$^9$R$^{10}$ (wherein R$^9$ and R$^{10}$ may be the same or different and each represents a hydrogen atom, substituted or unsubstituted lower alkyl, substituted or unsubstituted cycloalkyl, substituted or unsubstituted aryl, substituted or unsubstituted aralkyl, a substituted or unsubstituted heterocyclic group, substituted or unsubstituted lower alkanoyl, substituted or unsubstituted aroyl, or substituted or unsubstituted heteroaroyl, or R$^9$ and R$^{10}$ are combined together with the adjacent nitrogen atom thereto to form a substituted or unsubstituted heterocyclic group) or —NR$^{11}$R$^{12}$ [wherein R$^{11}$ and R$^{12}$ may be the same or different and each represents a hydrogen atom, substituted or unsubstituted lower alkyl, substituted or unsubstituted cycloalkyl, substituted or unsubstituted aryl, substituted or unsubstituted aralkyl, a substituted or unsubstituted heterocyclic group, substituted or unsubstituted lower alkanoyl, substituted or unsubstituted aroyl, substituted or unsubstituted heteroaroyl, substituted or unsubstituted lower alkylsulfonyl, substituted or unsubstituted arylsulfonyl, or —CONR$^{13}$R$^{14}$ (wherein R$^{13}$ and R$^{14}$ are the same as R$^9$ and R$^{10}$ defined above, respectively)]};

Q$^2$ represents an oxygen atom, a sulfur atom, or —NR$^{15}$— [wherein R$^{15}$ represents a hydrogen atom, substituted or unsubstituted lower alkyl, substituted or unsubstituted cycloalkyl, substituted or unsubstituted aralkyl, substituted or unsubstituted lower alkenyl, substituted or unsubstituted aryl, a substituted or unsubstituted heterocyclic group, substituted or unsubstituted lower alkanoyl, substituted or unsubstituted aroyl, substituted or unsubstituted heteroaroyl, substituted or unsubstituted lower alkoxycarbonyl, substituted or unsubstituted lower alkylsulfonyl, or substituted or unsubstituted arylsulfonyl, or —CONR$^{16}$R$^{17}$ (wherein R$^{16}$ and R$^{17}$ are the same as R$^9$ and R$^{10}$ defined above, respectively)]; and R$^5$ and R$^6$ may be the same or different and each represents a hydrogen atom, halogen, nitro, hydroxy, cyano, carboxy, substituted or unsubstituted lower alkyl, substituted or unsubstituted cycloalkyl, substituted or unsubstituted aralkyl, substituted or unsubstituted lower alkenyl, substituted or unsubstituted lower alkynyl, substituted or unsubstituted aryl, a substituted or unsubstituted heterocyclic group, substituted or unsubstituted lower alkanoyl, substituted or unsubstituted lower alkoxycarbonyl, substituted or unsubstituted aroyl, substituted or unsubstituted heteroaroyl, —S(O)m$^1$R$^{18}$ (wherein m$^1$ represents an integer of 0 to 2, R$^{18}$ represents a hydrogen atom, hydroxy, substituted or unsubstituted lower alkoxy, substituted or unsubstituted lower alkyl, substituted or unsubstituted cycloalkyl, substituted or unsubstituted aralkyl, substituted or unsubstituted lower alkenyl, substituted or unsubstituted aryl, a substituted or unsubstituted heterocyclic group, or —NR$^{19}$R$^{20}$ (wherein R$^{19}$ and R$^{20}$ are the same as R$^9$ and R$^{10}$ defined above, respectively)], —OR$^{21}$ [wherein R$^{21}$ represents substituted or unsubstituted lower alkyl, substituted or unsubstituted cycloalkyl, substituted or unsubstituted aralkyl, substituted or unsubstituted lower alkenyl, substituted or unsubstituted aryl, a substituted or unsubstituted heterocyclic group, substituted or unsubstituted lower alkanoyl, substituted or unsubstituted aroyl, substituted or unsubstituted heteroaroyl, —CONR$^{22}$R$^{23}$ (wherein R$^{22}$ and R$^{23}$ are the same as R$^9$ and R$^{10}$ defined above, respectively), or —S(O)m$^2$R$^{24}$ (wherein m$^2$ is the same as m$^1$ defined above, and R$^{24}$ is the same as R$^{18}$ defined above)], —CONR$^{25}$R$^{26}$ (wherein R$^{25}$ and R$^{26}$ are the same as R$^9$ and R$^{10}$ defined above, respectively), or —NR$^{27}$R$^{28}$ (wherein R$^{27}$ and R$^{28}$ are the same as R$^{11}$ and R$^{12}$ defined above, respectively)]; and R$^2$ and R$^3$ may be the same or different and each represents a hydrogen atom, halogen, nitro, hydroxy, cyano, carboxy, substituted or unsubstituted lower alkyl, substituted or unsubstituted cycloalkyl, substituted or unsubstituted aralkyl, substituted or unsubstituted lower alkenyl, substituted or unsubstituted lower alkynyl, substituted or unsubstituted aryl, a substituted or unsubstituted heterocyclic group, substituted or unsubstituted lower alkanoyl, substituted or unsubstituted lower alkoxycarbonyl, substituted or unsubstituted aroyl, substituted or unsubstituted heteroaroyl, —S(O)m$^3$R$^{29}$ (wherein m$^3$ is the same as m$^1$ defined above, and R$^{29}$ is the same as R$^{18}$ defined above), —OR$^{30}$ (wherein R$^{30}$ is the same as R$^{21}$ defined above), —CONR$^{31}$R$^{32}$ (wherein R$^{31}$ and R$^{32}$ are the same as R$^9$ and R$^{10}$ defined above, respectively), or —NR$^{33}$R$^{34}$ (wherein R$^{33}$ and R$^{34}$ are the same as R$^{11}$ and R$^{12}$ defined above, respectively)> or a pharmaceutically acceptable salt thereof.

(2) The nitrogen-containing heterocyclic compound or the pharmaceutically acceptable salt thereof according to above (1), wherein Q$^1$ is —CH—.

(3) The nitrogen-containing heterocyclic compound or the pharmaceutically acceptable salt thereof according to above (1) or (2), wherein Q$^2$ is —NR$^{15}$— (wherein R$^5$ is the same as that defined above).

(4) The nitrogen-containing heterocyclic compound or the pharmaceutically acceptable salt thereof according to above (1) or (2), wherein Q$^2$ is —NH—.

(5) The nitrogen-containing heterocyclic compound or the pharmaceutically acceptable salt thereof according to any one of above (1) to (4), wherein R$^6$ is a hydrogen atom, and R$^5$ is substituted or unsubstituted lower alkyl or —CONR$^{25}$R$^{26}$ (wherein R$^{25}$ and R$^{26}$ are the same as those defined above, respectively).

(6) The nitrogen-containing heterocyclic compound or the pharmaceutically acceptable salt thereof according to any one of above (1) to (4), wherein R$^6$ is a hydrogen atom, and R$^5$ is —S(O)m$^1$R$^{18}$ (wherein m$^1$ and R$^{18}$ are the same as those defined above, respectively), —OR$^{21}$ (wherein R$^{21}$ is the same as that defined above), or —NR$^{27}$R$^{28}$ (wherein R$^{27}$ and R$^{28}$ are the same as those defined above, respectively).

(7) The nitrogen-containing heterocyclic compound or the pharmaceutically acceptable salt thereof according to any one of above (1) to (6), wherein R$^2$ is a hydrogen atom, and R$^3$ is halogen, hydroxy, substituted or unsubstituted aryl, a substituted or unsubstituted heterocyclic group, or —OR$^{30}$ (wherein R$^{30}$ is the same as that defined above).

(8) The nitrogen-containing heterocyclic compound or the pharmaceutically acceptable salt thereof according to any one of above (1) to (6), wherein R$^2$ is halogen, hydroxy, unsubstituted lower alkyl, unsubstituted lower alkenyl, unsubstituted lower alkynyl, substituted or unsubstituted aryl, a substituted or unsubstituted aromatic heterocyclic group, or —OR$^{30}$ (wherein R$^{30}$ is the same as that defined above), and R$^3$ is halogen, hydroxy, substituted or unsubstituted aryl, a substituted or unsubstituted heterocyclic group, or —OR$^{30}$ (wherein R$^{30}$ is the same as that defined above).

(9) The nitrogen-containing heterocyclic compound or the pharmaceutically acceptable salt thereof according to any one of above (1) to (8), wherein X is —(C=O)—.

(10) The nitrogen-containing heterocyclic compound or the pharmaceutically acceptable salt thereof according to any one of above (1) to (8), wherein X is —CHR$^4$— (wherein R$^4$ is the same as that defined above).

(11) The nitrogen-containing heterocyclic compound or the pharmaceutically acceptable salt thereof according to any one of above (1) to (10), wherein W is a nitrogen atom.

(12) The nitrogen-containing heterocyclic compound or the pharmaceutically acceptable salt thereof according to any one of above (1) to (10), wherein W is —CH—.

(13) A pharmaceutical composition comprising, as an active ingredient, the nitrogen-containing heterocyclic compound or the pharmaceutically acceptable salt thereof described in any one of above (1) to (12).

(14) A protein kinase inhibitor comprising, as an active ingredient, the nitrogen-containing heterocyclic compound or the pharmaceutically acceptable salt thereof described in any one of above (1) to (12).

(15) A fibroblast growth factor receptor (FGFR) inhibitor comprising, as an active ingredient, the nitrogen-containing heterocyclic compound or the pharmaceutically acceptable salt thereof described in any one of above (1) to (12).

(16) An Aurora inhibitor comprising, as an active ingredient, the nitrogen-containing heterocyclic compound or the pharmaceutically acceptable salt thereof described in any one of above (1) to (12).

(17) A Fms-like tyrosine kinase 3 (Flt-3) inhibitor comprising, as an active ingredient, the nitrogen-containing heterocyclic compound or the pharmaceutically acceptable salt thereof described in any one of above (1) to (12).

(18) An antitumor agent comprising, as an active ingredient, the nitrogen-containing heterocyclic compound or the pharmaceutically acceptable salt thereof described in any one of above (1) to (12).

(19) A therapeutic agent for hematopoietic tumor comprising, as an active ingredient, the nitrogen-containing heterocyclic compound or the pharmaceutically acceptable salt thereof described in any one of above (1) to (12).

(20) A therapeutic agent for treating leukemia, myeloma, or lymphoma comprising, as an active ingredient, the nitrogen-containing heterocyclic compound or the pharmaceutically acceptable salt thereof described in any one of above (1) to (12).

EFFECT OF THE INVENTION

The present invention provides a nitrogen-containing heterocyclic compound or a pharmaceutically acceptable salt thereof having an antitumor activity or the like.

BEST MODE FOR CARRYING OUT THE INVENTION

Hereinafter, compounds represented by general formula (I) are referred to as Compound (I). The same shall apply to the compounds of the other formula numbers.

Each of the groups of formula (I) are defined as follows.

(i) The halogen includes each atoms of fluorine, chlorine, bromine, and iodine.

(ii) Examples of the lower alkyl, and the lower alkyl moieties of the lower alkoxy, the lower alkoxycarbonyl, and the lower alkylsulfonyl include linear or branched alkyl having 1 to 10 carbons. More specific examples thereof include methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl or the like.

(iii) Examples of the cycloalkyl include cycloalkyl having 1 to 10 carbons. More specific examples thereof include cyclopropyl, cyclobutyl, cyclopentyl, cyclohexyl, cycloheptyl, cyclooctyl, cyclodecyl, noradamantyl, adamantyl, bicyclo[2.2.1]heptyl, bicyclo[2.2.2]octyl, bicyclo[3.3.0]octyl, bicyclo[3.3.1]nonyl or the like.

(iv) Examples of the lower alkenyl include linear or branched alkenyl having 2 to 10 carbons. More specific examples thereof include vinyl, allyl, 1-propenyl, 1-butenyl, 3-butenyl, 2-pentenyl, 4-pentenyl, 2-hexenyl, 5-hexenyl, 2-decenyl, 9-decenyl or the like.

(v) Examples of the lower alkynyl include linear or branched alkynyl having 2 to 10 carbons. More specific examples thereof include ethynyl, 2-propynyl, 3-butynyl, 4-pentynyl, 5-hexynyl, 9-decynyl or the like.

(vi) The alkylene moieties of the aralkyl are the same as moieties produced by removing one hydrogen atom from the lower alkyl (ii) defined above.

(vii) Examples of the aryl, and the aryl moieties of the aroyl, the arylsulfonyl, and the aralkyl include monocyclic aryl and fused aryl in which two or more rings are fused. More specific examples thereof include aryl having 6 to 14 carbon atoms that constitute the ring, such as phenyl, naphthyl, indenyl and anthranyl.

(viii) Examples of the lower alkanoyl include linear or branched lower alkanoyl having 1 to 8 carbons. More specific examples thereof include formyl, acetyl, propionyl, butyryl, isobutyryl, valeryl, isovaleryl, pivaloyl, hexanoyl, heptanoyl, octanoyl or the like.

(ix) Examples of the heterocyclic group include a aromatic heterocyclic group, a heteroalicyclic group and the like.

Examples of the aromatic heterocyclic group include monocyclic aromatic heterocyclic groups and fused aromatic heterocyclic groups in which two or more rings are fused. The type and number of heteroatoms contained in the aromatic heterocyclic group are not particularly limited. For example, the aromatic heterocyclic group may contain at least one heteroatom selected from the group consisting of a nitrogen atom, a sulfur atom, and an oxygen atom. More specific examples thereof include aromatic heterocyclic groups having 5 to 14 annular atoms such as furyl, thienyl, pyrrolyl, imidazolyl, pyrazolyl, triazolyl, tetrazolyl, oxazolyl, oxadiazolyl, thiazolyl, pyridyl, pyrazinyl, pyrimidinyl, pyridazinyl, triazinyl, indolyl, indazolyl, benzimidazolyl, benzofuryl, benzothienyl, benzoxazolyl, benzothiazolyl, quinolyl, isoquinolyl, phthalazinyl, naphthyridinyl, quinoxalinyl, quinazolinyl, cinnolinyl, purinyl, coumarinyl and the like.

Examples of the heteroalicyclic group include monocyclic heteroalicyclic groups and fused heteroalicyclic groups in which two or more rings are fused. The type and number of heteroatoms contained in the heteroalicyclic group are not particularly limited. For example, the heteroalicyclic group may contain at least one heteroatom selected from the group consisting of a nitrogen atom, a sulfur atom, and an oxygen atom. More specific examples thereof include heteroalicyclic groups having 3 to 14 annular atoms such as pyrrolidinyl, thiazolidinyl, oxazolidinyl, piperidyl, azepanyl, 1,2-dihydropyridyl, piperazinyl, homopiperazinyl, morpholinyl, thiomorpholinyl, pyrazolinyl, oxazolinyl, dioxolanyl, tetrahydropyranyl, tetrahydrothiopyranyl, tetrahydrofuryl, tetrahydroquinolyl, tetrahydroisoquinolyl, tetrahydroquinoxalinyl, octahydroquinolyl, dihydroindolyl, soisoindolinyl and the like.

(x) Examples of the heterocyclic group formed together with the adjacent nitrogen atom thereto include five- or six-membered monocyclic heteroalicyclic groups containing at least one nitrogen atom (wherein the monocyclic heteroalicyclic group may further contain another nitrogen atom, an oxygen atom, or a sulfur atom), bicyclic or tricyclic fused heteroalicyclic group containing at least one nitrogen atom in which three- to eight-membered rings are fused (wherein the fused heteroalicyclic group may further contain another nitrogen atom, an oxygen atom, or a sulfur atom). More specific examples thereof include monocyclic heteroalicyclic groups and fused heteroalicyclic groups having 3 to 14 annular atoms such as pyrrolidinyl, piperidino, piperazinyl, morpholino, thiomorpholino, homopiperidino, homopiperazinyl, tetrahydropyridyl, tetrahydroquinolyl, tetrahydroisoquinolyl and the like.

(xi) Examples of the hetetoaryl moiety in the heteroaroyl include furyl, thienyl, pyrrolyl, imidazolyl, pyrazolyl, triazolyl, tetrazolyl, oxazolyl, oxadiazolyl, thiazolyl, pyridyl, pyrazinyl, pyrimidinyl, pyridazinyl, triazinyl, indolyl, indazolyl, benzimidazolyl, benzoxazolyl, benzothiazolyl, quinolyl, isoquinolyl, phthalazinyl, naphthyridinyl, quinoxalinyl, quinazolinyl, cinnolinyl, purinyl, coumarinyl and the like.

(xii) Examples of the substituents in the substituted lower alkyl, the substituted lower alkoxy, the substituted lower alkylsulfonyl, the substituted cycloalkyl, the substituted lower alkenyl, the substituted lower alkynyl, the substituted lower alkoxycarbonyl, and the substituted lower alkanoyl which may be the same or different and which are 1 to 3 in number, include (xii-a) halogen;

(xii-b) hydroxy;

(xii-c) oxo;

(xii-d) cyano;

(xii-e) carboxy;

(xii-f) lower alkoxycarbonyl;

(xii-g) arylsulfonyl;

(xii-h) heteroaroyl;

(xii-i) substituted or unsubstituted cycloalkyl [examples of the substituent in the substituted cycloalkyl, which is 1 to 3 in number, include halogen, hydroxy, lower alkoxy, substituted or unsubstituted lower alkyl (examples of the substituent in the substituted lower alkyl, which is 1 to 3 in number, include halogen, hydroxy, cyano, lower alkoxy and the like), and the like];

(xii-j) substituted or unsubstituted lower alkoxy (examples of the substituent in the substituted lower alkoxy, which is 1 to 3 in number, include halogen, hydroxy, lower alkoxy and the like);

(xii-k) substituted or unsubstituted aryl (examples of the substituent in the substituted aryl, which is 1 to 3 in number, include carboxy, lower alkoxycarbonyl and the like);

(xii-l) substituted or unsubstituted heterocyclic groups {examples of the substituent in the substituted heterocyclic groups, which is 1 to 3 in number, include halogen, hydroxy, oxo, lower alkoxy, lower alkoxycarbonyl, lower alkylsulfonyl, lower alkanoyl, substituted or unsubstituted lower alkyl [examples of the substituent in the substituted lower alkyl, which is 1 to 3 in number, include halogen, hydroxy, cyano, substituted or unsubstituted lower alkoxy (examples of the substituent in the substituted lower alkoxy, which is 1 to 3 in number, include halogen, hydroxy and the like)], substituted or unsubstituted aryl (examples of the substituent in the substituted aryl, which is 1 to 3 in number, include halogen, hydroxy, cyano, lower alkyl, lower alkoxy and the like), and a substituted or unsubstituted heterocyclic group (examples of the substituent in the substituted heterocyclic group, which is 1 to 3 in number, include halogen, hydroxy, cyano, lower alkyl, lower alkoxy and the like)};

(xii-m) $NR^{35}R^{36}$ (wherein $R^{35}$ and $R^{36}$ may be the same or different and each represents a hydrogen atom, lower alkoxycarbonyl, lower alkenyl, lower alkynyl, lower alkanoyl, substituted or unsubstituted lower alkyl [examples of the substituent in the substituted lower alkyl, which is 1 to 3 in number, include halogen, amino, hydroxy, carboxy, carbamoyl, lower alkanoyl, substituted or unsubstituted lower alkoxy (examples of the substituent in the substituted lower alkoxy, which is 1 to 3 in number, include halogen, hydroxy and the like), lower alkoxycarbonyl, substituted or unsubstituted cycloalkyl (examples of the substituent in the substituted cycloalkyl, which is 1 to 3 in number, include halogen, hydroxy, substituted or unsubstituted lower alkyl (examples of the substituent in the substituted lower alkyl, which is 1 to 3 in number, include halogen, hydroxy and the like) and the like], mono- or di-lower alkylamino, a heterocyclic group and the like], substituted or unsubstituted cycloalkyl (examples of the substituent in the substituted cycloalkyl, which is 1 to 3 in number, include halogen, amino, hydroxy and the like), substituted or unsubstituted aralkyl (examples of the substituent in the substituted aralkyl, which is 1 to 3 in number, include halogen, hydroxy, cyano, lower alkoxy and the like), substituted or unsubstituted aryl [examples of the substituent in the substituted aryl, which is 1 to 3 in number, include halogen, amino, hydroxy, substituted or unsubstituted lower alkyl (examples of the substituent in the substituted lower alkyl, which is 1 to 3 in number, include halogen, hydroxy and the like), a substituted or unsubstituted heterocyclic group (examples of the substituent in the substituted heterocyclic group, which is 1 to 3 in number, include halogen, hydroxy, lower alkyl, lower alkoxy and the like) and the like], a substituted or unsubstituted heterocyclic group [examples of the substituent in the substituted heterocyclic group, which is 1 to 3 in number, include halogen, amino, hydroxy, substituted or unsubstituted lower alkyl (examples of the substituent in the substituted lower alkyl, which is 1 to 3 in number, include halogen, hydroxy and the like), or a substituted or unsubstituted heterocyclic group (examples of the substituent in the substituted heterocyclic group, which is 1 to 3 in number, include halogen, hydroxy, lower alkyl, lower alkoxy and the like) and the like]; and (xii-n) $CONR^{37}R^{38}$ (wherein $R^{37}$ and $R^{38}$ may be the same or different and each represents a hydrogen atom, substituted or unsubstituted lower alkyl [examples of the substituent in the substituted lower alkyl, which is 1 to 3 in number, include halogen, amino, hydroxy, carboxy, carbamoyl, substituted or unsubstituted lower alkoxy (examples of the substituent in the substituted lower alkoxy, which is 1 to 3 in number, include halogen, hydroxy and the like), lower alkoxycarbonyl, substituted or unsubstituted cycloalkyl (examples of the substituent in the substituted cycloalkyl, which is 1 to 3 in number, include halogen, hydroxy and the like), mono- or di-(lower alkyl)amino, a heterocyclic group and the like], substituted or unsubstituted cycloalkyl (examples of the substituent in the substituted cycloalkyl, which is 1 to 3 in number, include halogen, amino, hydroxy and the like), or lower alkanoyl, or $R^{37}$ and $R^{38}$ are combined together with the adjacent nitrogen atom thereto to form a heterocyclic group).

In the definition of the substituents (xii) in the substituted lower alkyl, substituted lower alkoxy, substituted lower alkylsulfonyl, substituted cycloalkyl, substituted lower alkenyl, substituted lower alkynyl, substituted lower alkoxycarbonyl, and substituted lower alkanoyl, the halogen is the same as those defined (i) above; the lower alkyl, and the lower alkyl moieties of the lower alkoxy, the lower alkoxycarbonyl, and the lower alkylsulfonyl are the same as those defined in (ii) above; the cycloalkyl is the same as those defined (iii) above; the lower alkenyl is the same as those defined (iv) above; the lower alkynyl is the same as those defined (v) above; the alkylene moieties of the aralkyl are the same as those defined in (vi) above; the aryl, and the aryl moieties of the arylsulfonyl, and the aralkyl are the same as those defined (vii) above; the lower alkanoyl is the same as those defined in (viii) above; the heterocyclic groups are the same as those defined (ix) above; the heterocyclic groups formed together with the adjacent nitrogen atom thereto are the same as those defined in (x) above; and the heteroaryl moiety in the heteroaroyl is the same as those defined in (xi) above. The lower alkyl moieties of the mono- or di-(lower alkyl)amino are the same as those defined in (i) above, and the two lower alkyl moieties of the di-(lower alkyl)amino may be the same or different.

(xiii) Examples of the substituents in the substituted aryl, the substituted aroyl, the substituted aralkyl, the substituted arylsulfonyl, the substituted-heteroaroyl, the substituted heterocyclic group, and the substituted heterocyclic group formed together with the adjacent nitrogen atom thereto which may be the same or different and which are 1 to 3 in number, include (xiii-a) halogen;

(xiii-b) hydroxy;

(xiii-c) nitro;

(xiii-d) cyano;

(xiii-e) formyl;

(xiii-f) carboxy;

(xiii-g) lower alkoxycarbonyl;

(xiii-h) aralkyloxy;

(xiii-i) substituted or unsubstituted lower alkyl [the substituents in the substituted lower alkyl are the same as those defined (xii) above];

(xiii-j) substituted or unsubstituted lower alkoxy [the substituents in the substituted lower alkoxy are the same as those defined in (xii) above];

(xiii-k) substituted or unsubstituted lower alkanoyl [the substituents in the substituted lower alkanoyl are the same as those defined in (xii) above];

(xiii-l) substituted or unsubstituted lower alkylsulfonyl [the substituents in the substituted lower alkylsulfonyl are the same as those defined in (xii) above];

(xiii-m) substituted or unsubstituted aroyl [examples of the substituent in the substituted aroyl, which is 1 to 3 in number, include halogen, nitro, hydroxy, cyano, carboxy, lower alkanoyl, lower alkoxycarbonyl, aralkyl, aroyl, substituted or unsubstituted lower alkyl (examples of the substituent in the substituted lower alkyl, which is 1 to 3 in number, include hydroxy and the like), and substituted or unsubstituted lower alkoxy (examples of the substituent in the substituted lower alkoxy, which is 1 to 3 in number, include hydroxy and the like) and the like];

(xiii-n) substituted or unsubstituted heteroaroyl [the substituents in the substituted heteroaroyl are the same as the substituents defined in the substituted aroyl (xiii-m) above];

(xiii-o) substituted or unsubstituted heterocyclic groups [the substituents in the substituted heterocyclic groups are the same as the substituents defined in the substituted aroyl (xiii-m) above];

(xiii-p) $NR^{39}R^{40}$ (wherein $R^{39}$ and $R^{40}$ may be the same or different and each represents a hydrogen atom, substituted or unsubstituted lower alkyl [the substituents in the substituted lower alkyl are the same as those defined (xii) above], substituted or unsubstituted lower alkanoyl [the substituents in the substituted lower alkanoyl are the same as those defined (xii) above], substituted or unsubstituted aryl [the substituents in the substituted aryl are the same as the substituents defined in the substituted aroyl (xiii-m) above], or substituted or unsubstituted aroyl [the substituents in the substituted aroyl are the same as the substituents defined in the substituted aroyl (xiii-m) above]}; and (xiii-q) $CONR^{41}R^{42}$ {wherein $R^{41}$ and $R^{42}$ may be the same or different and each represents a hydrogen atom, substituted or unsubstituted lower alkyl [the substituents in the substituted lower alkyl are the same as those defined (xii) above], substituted or unsubstituted aryl [the substituents in the substituted aryl are the same as the substituents defined in the substituted aroyl (xiii-m) above], or substituted or unsubstituted aroyl [the substituents in the substituted aroyl are the same as the substituents defined in the substituted aroyl (xiii-m) above], or $R^{41}$ and $R^{42}$ are combined together with the adjacent nitrogen atom thereto to form a substituted or unsubstituted heterocyclic group [the substituents in the substituted heterocyclic group formed together with the adjacent nitrogen atom thereto are the same as the substituents defined in the substituted aroyl (xiii-m) above]} and the like.

Examples of the substituents in the substituted heterocyclic group and the substituted heterocyclic group formed together with the adjacent nitrogen atom thereto may include substituents defined in (xiii-r) and (xiii-s) below in addition to the substituents defined in (xiii-a) to (xiii-q) above:

(xiii-r) oxo; and (xiii-s) —$O(CR^{43}R^{44})_n O$— (wherein $R^{43}$ and $R^{44}$ may be the same or different and each represents a hydrogen atom, lower alkyl, or the like; n represents 2 or 3; and the two terminal oxygen atoms bond to a same carbon atom of a substituted heterocyclic group or a substituted heterocyclic group formed together with the adjacent nitrogen atom).

In the definition of the substituents (xiii) in the substituted aryl, the substituted aroyl, the substituted aralkyl, the substituted arylsulfonyl, the substituted heteroaroyl, the substituted heterocyclic group, and the substituted heterocyclic group formed together with the adjacent nitrogen atom, the halogen is the same as those defined in (i) above; the lower alkyl, and the lower alkyl moieties of the lower alkoxy, the lower alkoxycarbonyl, and the lower alkylsulfonyl are the same as those defined in (ii) above; the alkylene moieties of the aralkyl and the aralkyloxy are the same as those defined in (vi) above; the aryl, and the aryl moieties of the aralkyl, the aralkyloxy, and the aroyl are the same as those defined (vii) above; the lower alkanoyl is the same as those defined in (viii) above; the heterocyclic groups are the same as those defined (ix) above; the heterocyclic groups formed together with the adjacent nitrogen atom thereto are the same as those defined in (x) above; and the heteroaryl moiety in the heteroaroyl is the same as those defined in (xi) above.

Examples of pharmaceutically acceptable salts of Compound (I) include pharmaceutically acceptable acid addition salts, metal salts, ammonium salts, organic amine addition salts, and amino acid addition salts and the like. Examples of the acid addition salts include inorganic acid salts such as hydrochlorides, sulfates, and phosphates; and organic acid salts such as acetates, trifluoroacetates, maleates, fumarates, tartrates, citrates, lactates, aspartates, and glutamates. Examples of the metal salts include alkali metal salts such as sodium salts and potassium salts; alkaline earth metal salts such as magnesium salts and calcium salts; aluminum salts; zinc salts; and the like. Examples of the ammonium salts includes salts of ammonium, tetramethylammonium, or the like. Examples of the organic amine addition salts include addition salts of morpholine, piperidine, or the like. Examples of the amino acid addition salts include addition salts of lysine, glycine, phenylalanine, or the like.

Examples of cancers that can be treated with an antitumor agent containing, as an active ingredient, the nitrogen-containing heterocyclic compound of the present invention or the pharmaceutically acceptable salt thereof include cancer derived from hematopoietic tumor, breast cancer, uterine body cancer, uterine cervix cancer, prostatic cancer, urinary bladder cancer, renal cancer, stomach cancer, esophageal cancer, liver cancer, biliary tract cancer, colon cancer, rectal cancer, pancreatic cancer, lung cancer, oral cavity and pharynx cancer, osteosarcoma, melanoma, and cancer derived from brain tumor.

The hematopoietic tumor is a tumor of, for example, blood cells or the like. Specific examples of clinical conditions based on such a tumor include leukemia such as chronic myelocytic leukemia or acute myelocytic leukemia; myeloma such as multiple myeloma; lymphoma and the like.

Examples of protein kinases that are targeted by a protein kinase inhibitor comprising, as an active ingredient, the nitrogen-containing heterocyclic compound of the present invention or a pharmaceutically acceptable salt thereof include fibroblast growth factor receptors (FGFRs), Aurora kinases, Fms-like tyrosine kinase 3 (Flt-3), vascular endothelial growth factor receptor (VEGFR) c-Kit, platelet-derived growth factor (PDGFR), tropomyosin receptor kinase (Trk), Abl, lymphocyte-specific kinase (Lck) and the like.

Examples of diseases related to the above protein kinases include cell proliferative diseases. Cell proliferative diseases include, for example, diseases related to cell proliferation. Specific examples thereof include psoriasis, restenosis (for example, stent-induced restenosis or the like), endometriosis, regional ileitis, Hodgkin' disease, arthritis (for example, chronic arthritis and the like), eye diseases (for example, diabetic retinopathy, neovascular glaucoma and the like), renal diseases (for example, glomerulonephritis, diabetic nephropathy, malignant nephrosclerosis and the like), thrombotic microangiopathy syndrome, transplant rejection, glomerulopathy, fibrous diseases (for example, hepatocirrhosis, mesangial cell proliferative disease, arteriosclerosis and the like), vascular reocclusion after therapy with a balloon catheter, senile spots, contact dermatitis and the like.

The production methods of Compound (I) will now be described.

In the production methods described below, when a defined group is changed under the condition of the method to be employed or is not suitable for employing the method, a target compound can be obtained by employing methods of introducing and eliminating a protective group that are normally used in synthetic organic chemistry [for example, Protective Groups in Organic Synthesis third edition, written by T. W. Greene, John Wiley & Sons Inc. (1999)] and the like. In addition, the order of reaction steps, such as the introduction of a substituent, can be changed, if necessary.

Compound (I) can be produced by, for example, reaction steps descried below.

Production Method 1

Compound (IA) can be produced from Compound (AA-1) obtained by a method similar to a known method [Journal of the American Chemical Society, Vol. 78, p. 1631 (1956), or HETEROCYCLES, Vol. 45, p. 2217 (1997)] by a step described below.

Step 1

Compound (IA) can be synthesized by reacting Compound (AA-1) with 1 to 30 equivalents of Compound (AB) in the presence of 0.001 to 1 equivalent of a transition metal catalyst, in a solvent at a temperature in the range of −50° C. to 200° C. for 5 minutes to 100 hours. In this step, 0.01 to 30 equivalents of an appropriate additive may be added so as to accelerate the reaction.

Examples of the solvent include methanol, ethanol, dichloromethane, acetonitrile, toluene, ethyl acetate, tetrahydrofuran (THF), 1,4-dioxane, N,N-dimethylformamide (DMF), N-methylpyrrolidone (NMP), water and the like. These may be used alone or in combinations.

Examples of the transition metal catalyst include palladium catalysts such as palladium acetate, tetrakis(triphenylphosphine)palladium, palladium chloride, palladium bromide, bis(triphenylphosphine)palladium chloride, and dichlorobis(acetonitrile)palladium; nickel catalysts such as nickel chloride, nickel acetylacetonate, bis(1,5-cyclooctadiene)nickel and nickel bromide; and the like.

Examples of the additive include triphenylphosphine, tri (o-tolyl)phosphine, 1,1'-bis(diphenylphosphino)ferrocene, 1,2-bis(diphenylphosphino)propane, 2,2'-bis(diphenylphosphino)-1,1'-binaphthyl, 1,2-bis(diphenylphosphino)ethane, silver oxide, copper iodide, lithium chloride, cesium fluoride, triethylamine, diethylamine, sodium hydroxide, potassium hydroxide, sodium carbonate and the like. These may be used alone or in combinations.

Production Method 2

Compound (IAa) can be produced by reacting Compound (AA-2) with Compound (AC). When $T^1$ in Compound (AA-2) is a protective group such as a 1-methyl-1-phenylethyl, Compound (IAa) can be produced by reacting Compound (AA-2) with Compound (AC) and then conducting deprotection.

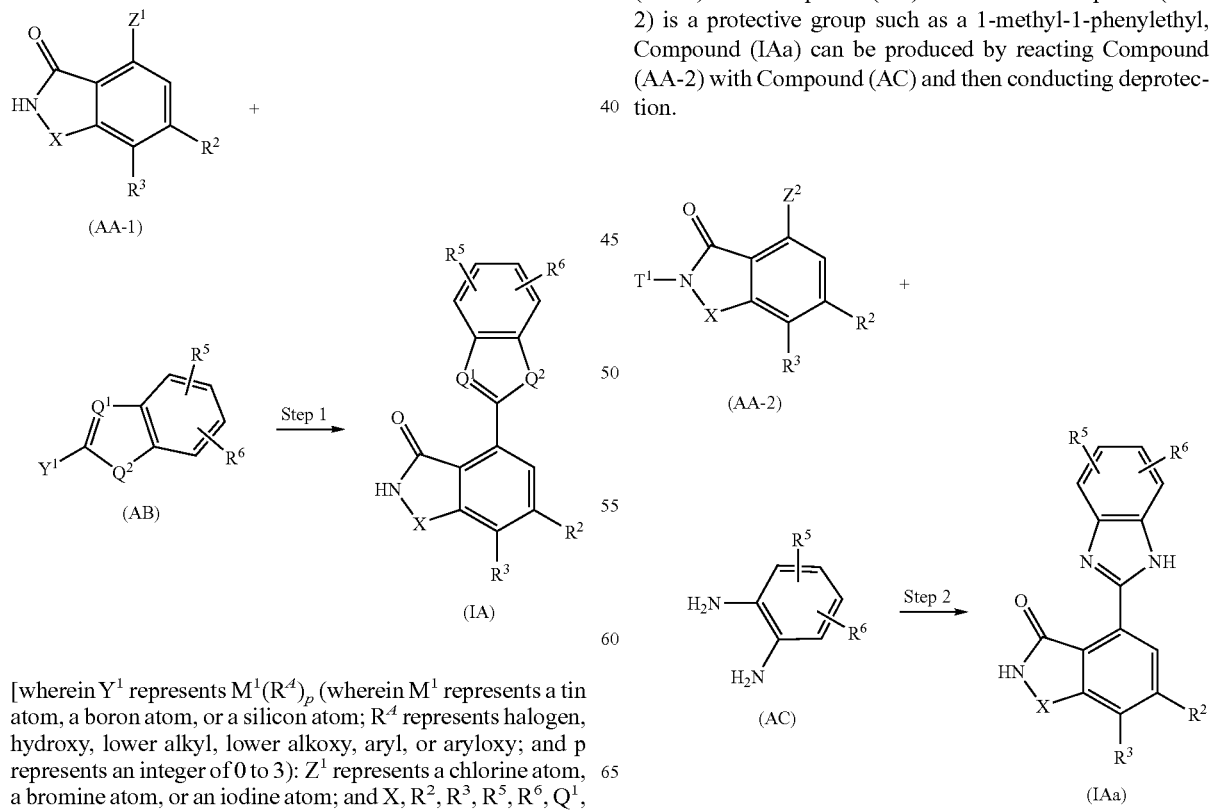

[wherein $Y^1$ represents $M^1(R^A)_p$ (wherein $M^1$ represents a tin atom, a boron atom, or a silicon atom; $R^A$ represents halogen, hydroxy, lower alkyl, lower alkoxy, aryl, or aryloxy; and p represents an integer of 0 to 3): $Z^1$ represents a chlorine atom, a bromine atom, or an iodine atom; and X, $R^2$, $R^3$, $R^5$, $R^6$, $Q^1$, and $Q^2$ are the same as those defined above, respectively]

(wherein $Z^2$ represents formyl or carboxy, $T^1$ represents a hydrogen atom or a protective group such as 1-methyl-1-phenylethyl, and X, $R^2$, $R^3$, $R^5$, and $R^6$ are the same as those defined above, respectively)

Step 2

Compound (IAa) can be synthesized by reacting Compound (AA-2) with 1 to 30 equivalents of Compound (AC) in the presence of 0.001 to 100 equivalents of an oxidizing agent and 0.001 to 100 equivalents of a dehydrating agent, or in the presence of 0.001 to 100 equivalents of a dehydrating agent, in a solvent at a temperature in the range of −50° C. to 200° C. for 5 minutes to 100 hours. When $T^1$ of Compound (AA-2) is a protective group, Compound (IAa) is obtained by subsequent proper deprotection.

Examples of the solvent include methanol, ethanol, dichloromethane, acetonitrile, toluene, ethyl acetate, THF, 1,4-dioxane, DMF, NMP, acetic acid, water and the like. These may be used alone or in combinations.

Examples of the oxidizing agent include oxygen, sulfur dioxide, 2,3-dichloro-5,6-dicyano-1,4-benzoquinone (DDQ), nitrobenzene, Oxone (registered trademark), benzofuroxan and the like. These may be used alone or in combinations.

Examples of the dehydrating agent include iron trichloride, zinc dichloride, tin dichloride, titanium tetrabutoxide, sulfuric acid, p-toluenesulfonic acid, thionyl chloride and the like. These may be used alone or in combinations.

Compound (AA-2) can be produced by reacting Compound (AK) obtained by a method similar to a known method [Organic Letters, Vol. 1, p. 1183 (1999)] with 1 to 5 equivalents of a lithium reagent in a solvent at a temperature in the range of −90° C. to room temperature for 5 minutes to 50 hours, followed by a reaction with 1 to 30 equivalents of DMF or carbon dioxide gas at a temperature in the range of −90° C. to 100° C. In this step, 0.01 to 30 equivalents of an additive may be added so as to accelerate the reaction.

Examples of the solvent include toluene, diethyl ether, THF, 1,4-dioxane and the like. These may be used alone or in combinations.

Examples of the lithium reagent include n-butyllithium, sec-butyllithium, tert-butyllithium, lithium diisopropylamide (LDA) and the like.

Examples of the additive include N,N,N',N'-tetramethylethylenediamine (TMEDA) and the like.

Instead of carbon dioxide gas, dry ice can also be used.

Production Method 3

Among compounds belonging to Compound (I), Compound (Ia-2) having specific functional groups at $R^{2b}$, $R^{3b}$, $R^{5b}$, $R^{6b}$, and $R^{8b}$, or Compound (Ia-1) having specific functional groups at $R^{2b}$, $R^{3b}$, $R^{5b}$, and $R^{6b}$ can also be produced by a step described below using Compound (AD-2) having other functional groups at $R^{2a}$, $R^{3a}$, $R^{5a}$, $R^{6a}$, and $R^{8a}$, or Compound (AD-1) having other functional groups at $R^{2a}$, $R^{3a}$, $R^{5a}$, and $R^{6a}$ obtained by a method similar to Production method 1 or 2.

In Steps 3 to 9 described below, some of the compounds denoted as Compound (AD-1) or Compound (AD-2) are included in Compound (I).

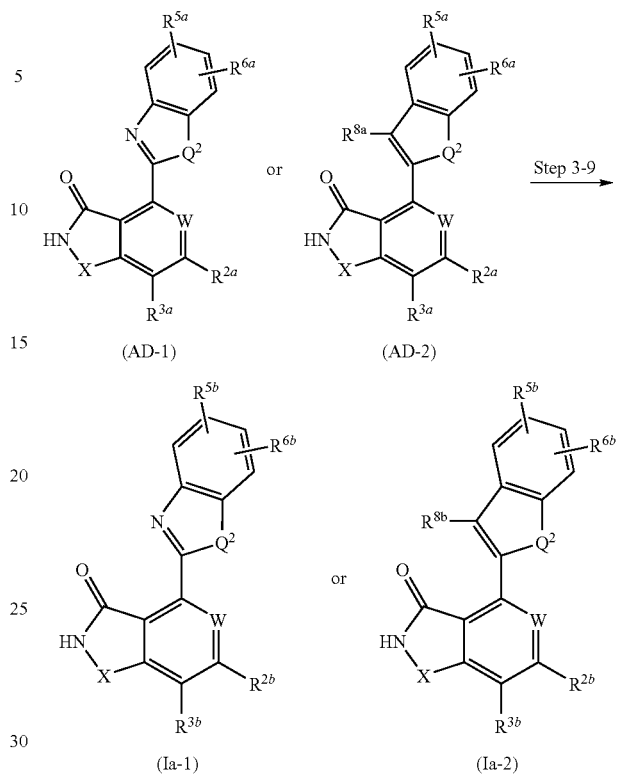

(wherein $R^{2a}$, $R^{3a}$, $R^{5a}$, $R^{6a}$, and $R^{8a}$ and $R^{2b}$, $R^{3b}$, $R^{5b}$, $R^{6b}$, and $R^{8b}$ each represents a group defined in Steps 3 to 9 described below, and W, X, and $Q^2$ are the same as those defined above, respectively)

Step 3

[In step 3, at least one of $R^{3a}$, $R^{5a}$, $R^{6a}$, and $R^{8a}$ is carboxy and at least one of $R^{3b}$, $R^{5b}$, $R^{6b}$, and $R^{8b}$ is —$CONR^9R^{10}$ (wherein $R^9$ and $R^{10}$ are the same as those defined above, respectively)]

Compound (Ia-1) or Compound (Ia-2) can be synthesized by reacting Compound (AD-1) or Compound (AD-2) with Compound (II) represented by $HNR^9R^{10}$ (wherein $R^9$ and $R^{10}$ are the same as those defined above, respectively) in the presence of a condensing agent and an activating agent, in a solvent.

Examples of the solvent include dichloromethane, THF, 1,4-dioxane, acetonitrile, DMF, NMP and the like. These may be used alone or in combinations.

Examples of the condensing agent include di(cyclohexyl)carbodiimide, 1-ethyl-3-(3-dimethylaminopropyl)carbodiimide (EDCI) and a hydrochloride thereof, polymer bound-1-ethyl-3-(3-dimethylaminopropyl)carbodiimide, triphenylphosphine oxide-trifluoromethanesulfonic acid anhydride and the like.

Examples of the activating agent include 4-dimethylaminopyridine (DMAP), 1-hydroxybenzotriazole (HOBt), N-hydroxysuccinimide and the like.

Each of the condensing agent, the activating agent, and Compound (II) is preferably used in an amount of 1 to 20 equivalents relative to the amount of Compound (AD-1) or Compound (AD-2). The reaction is normally performed at a temperature in the range of −20° C. to 80° C. and is finished within the range of 30 minutes to 48 hours.

Step 4

[In step 4, at least one of $R^{3a}$, $R^{5a}$, $R^{6a}$, and $R^{8a}$ is formyl and at least one of $R^{3b}$, $R^{5b}$, $R^{6b}$, and $R^{8b}$ is —CH$_2$NR$^{35}$R$^{36}$ (wherein $R^{35}$ and $R^{36}$ are the same as those defined above, respectively)]

Compound (Ia-1) or Compound (Ia-2) can be synthesized by reacting Compound (AD-1) or Compound (AD-2) with Compound (II) represented by HNR$^{35}$R$^{36}$ (wherein $R^{35}$ and $R^{36}$ are the same as those defined above, respectively) in the presence of a reducing agent, in a solvent. In this step, 0.01 to 30 equivalents of an appropriate additive may be added so as to accelerate the reaction.

Examples of the solvent include methanol, ethanol, acetonitrile, dichloromethane, THF, 1,4-dioxane, DMF, NMP, acetic acid and the like. These may be used alone or in combinations.

Examples of the reducing agent include sodium borohydride, sodium cyanotrihydroborate, sodium triacetoxyborohydride, pyridine-borane complex and the like.

Examples of the additive include acetic acid, molecular sieves, magnesium sulfate and the like.

Each of the reducing agent and Compound (II) is preferably used in an amount of 1 to 20 equivalents relative to the amount of Compound (AD-1) or Compound (AD-2). The reaction is normally performed at a temperature in the range of −20° C. to 80° C. and is finished within the range of 30 minutes to 100 hours.

Step 5

{In step 5, at least one of $R^{2a}$, $R^{3a}$, $R^{5a}$, $R^{6a}$, and $R^{8a}$ is a chlorine atom, a bromine atom, an iodine atom, —OSO$_2$CF$_3$, or —OTs (p-toluenesulfonyl), and at least one of $R^{2b}$, $R^{3b}$, $R^{5b}$, $R^{6b}$, and $R^{8b}$ is cyano, substituted or unsubstituted lower alkyl, substituted or unsubstituted cycloalkyl, Ar$^{1b}$ [wherein Ar$^{1b}$ represents substituted or unsubstituted aryl, or a substituted or unsubstituted aromatic heterocyclic group], HC=CHR$^B$ [wherein R$^B$ represents carboxy, substituted or unsubstituted lower alkyl, substituted or unsubstituted aryl, substituted or unsubstituted aralkyl, a substituted or unsubstituted heterocyclic group, substituted or unsubstituted lower alkanoyl, substituted or unsubstituted aroyl, substituted or unsubstituted heteroaroyl, substituted or unsubstituted lower alkoxycarbonyl, or —CONR$^9$R$^{10}$ (wherein R$^9$ and R$^{10}$ are the same as those defined above, respectively)] or C=CR$^B$ (wherein R$^B$ is the same as defined above)}

Compound (Ia-1) or Compound (Ia-2) can be produced by reacting Compound (AD-1) or Compound (AD-2) with 1 to 30 equivalents of (Ar$^{1b}$)$_q$M$^2_r$(R$^A$)$_s$, (R$^B$HC=CH)$_q$M$^2_r$(R$^A$)$_s$, (R$^B$C=C)$_q$M$^2_r$(R$^A$)$_s$, (R$^C$)$_q$M$^2_r$(R$^A$)$_s$, R$^B$HC=CH$_2$, or R$^B$C=CH (wherein Ar$^{1b}$, R$^A$, and R$^B$ are the same as those defined above, respectively; R$^C$ represents cyano, substituted or unsubstituted lower alkyl, or substituted or unsubstituted cycloalkyl; M$^2$ represents a tin atom, a zinc atom, a boron atom, a silicon atom, an aluminum atom, a zirconium atom, a copper atom, or a mercury atom; q and r may be the same or different and each represents 1 or 2; and s represents an integer of 0 to 3) in the presence of 0.001 to 1 equivalent of a transition metal catalyst, in a solvent at a temperature in the range of −5° C. to 200° C. for 5 minutes to 80 hours. In this step, 0.01 to 30 equivalents of an additive may be added so as to accelerate the reaction.

Examples of the solvent include methanol, ethanol, dichloromethane, chloroform, acetonitrile, toluene, ethyl acetate, THF, 1,4-dioxane, DMF, NMP, water and the like. These may be used alone or in combinations.

Examples of the transition metal catalyst include palladium catalysts such as palladium acetate, tetrakis(triphenylphosphine)palladium, palladium chloride, palladium bromide, bis(triphenylphosphine)palladium chloride, and dichlorobis(acetonitrile)palladium; and nickel catalysts such as nickel chloride, nickel acetylacetonate, bis(1,5-cyclooctadiene)nickel and nickel bromide; and the like.

Examples of the additive include triphenylphosphine, tri(o-tolyl)phosphine, 1,1'-bis(diphenylphosphino)ferrocene, 1,2-bis(diphenylphosphino)propane, 2,2'-bis(diphenylphosphino)-1,1'-binaphthyl, 1,2-bis(diphenylphosphino)ethane, silver oxide, copper iodide, lithium chloride, cesium fluoride, triethylamine, diethylamine, sodium hydroxide, potassium hydroxide, sodium carbonate, cesium carbonate and the like. These may be used alone or in combinations.

Step 6

{In step 6, at least one of $R^{2a}$, $R^{3a}$, $R^{5a}$, $R^{6a}$, and $R^{8a}$ is hydroxy, and at least one of $R^{2b}$, $R^{3b}$, $R^{5b}$, $R^{6b}$, and $R^{8b}$ is —O(C=O)R$^D$ or —OSO$_2$R$^D$ (wherein R$^D$ represents a hydrogen atom, substituted or unsubstituted lower alkyl, substituted or unsubstituted cycloalkyl, substituted or unsubstituted aryl, substituted or unsubstituted aralkyl, a substituted or unsubstituted heterocyclic group, or —NR$_{D1}$R$^{D2}$ [wherein R$^{D1}$ and R$^{D2}$ are the same as R$^9$ and R$^{10}$, respectively)]}

Compound (Ia-1) or Compound (Ia-2) can be synthesized by reacting Compound (AD-1) or Compound (AD-2) with Compound (III) represented by R$^D$COX$^1$ or R$^D$SO$_2$X$^1$ (wherein X$^1$ represents a chlorine atom, a bromine atom, or an iodine atom; and R$^D$ is the same as defined above) or (R$^D$CO)$_2$O or (R$^D$SO$_2$)$_2$O (wherein R$^D$ is the same as defined above) in the presence of a base, in a solvent.

Examples of the solvent include dichloromethane, THF, 1,4-dioxane, acetonitrile, DMF, NMP, and the like. These may be used alone or in combinations.

Examples of the base include DMAP, triethylamine, diisopropylethylamine, pyridine, sodium carbonate, sodium hydrogencarbonate, potassium carbonate, sodium hydroxide, potassium hydroxide, sodium hydride and the like.

Each of the base and Compound (III) is preferably used in an amount of 1 to 20 equivalents relative to the amount of Compound (AD-1) or Compound (AD-2). The reaction is normally performed at a temperature in the range of −20° C. to 80° C. and is finished within the range of 30 minutes to 24 hours. Regarding some types of Compound (III), a salt of Compound (III) may be prepared in advance by mixing with an activating agent, and the salt may then be used for the reaction.

Step 7

{In step 7, at least one of $R^{3a}$, $R^{5a}$, $R^{6a}$, and $R^{8a}$ is —NHR$^{11}$ (wherein R$^{11}$ is the same as defined above), and at least one of $R^{3b}$, $R^{5b}$, $R^{6b}$, and $R_{8b}$ is —NR$^{11}$(C=O)R$^D$ or —NR$^{11}$SO$_2$R$^D$ [wherein R$^{11}$ is the same as defined above; and R$^D$ represents a hydrogen atom, substituted or unsubstituted lower alkyl, substituted or unsubstituted cycloalkyl, substituted or unsubstituted aryl, substituted or unsubstituted aralkyl, a substituted or unsubstituted heterocyclic group, or —NR$^{D1}$R$^{D2}$ (wherein R$^{D1}$ and R$^{D2}$ are the same as R$^9$ and R$^{10}$ defined above, respectively)]}

Compound (Ia-1) or Compound (Ia-2) can be synthesized by reacting Compound (AD-1) or Compound (AD-2) with Compound (III) represented by R$^D$COX$^1$ or R$^D$SO$_2$X$^1$ (wherein X and R$^D$ are the same as those defined above, respectively) or (R$^D$CO)$_2$O or (R$^D$SO$_2$)$_2$O (wherein R$^D$ is the same as defined above) in the presence of a base, in a solvent.

Examples of the solvent include dichloromethane, THF, 1,4-dioxane, acetonitrile, DMF, NMP and the like. These may be used alone or in combinations.

Examples of the base include DMAP, triethylamine, diisopropylethylamine, pyridine, sodium carbonate, sodium hydrogencarbonate, potassium carbonate, sodium hydroxide, potassium hydroxide, sodium hydride and the like.

Each of the base and Compound (III) is preferably used in an amount of 1 to 20 equivalents relative to the amount of Compound (AD-1) or Compound (AD-2). The reaction is normally performed at a temperature in the range of −20° C. to 80° C. and is finished within the range of 30 minutes to 24 hours. Regarding some types of Compound (III), a salt of Compound (III) may be prepared in advance by mixing with an activating agent, and the salt may then be used for the reaction.

Step 8

[In step 8, at least one of $R^{2a}$, $R^{3a}$, $R^{5a}$, $R^{6a}$, and $R^{8a}$ is hydroxy, and at least one of $R^{2b}$, $R^{3b}$, $R^{5b}$, $R^{6b}$ and $R^{8b}$ is —$OR^E$ (wherein $R^E$ represents substituted or unsubstituted lower alkyl, or substituted or unsubstituted aralkyl)]

Compound (Ia-1) or Compound (Ia-2) can be synthesized by reacting Compound (AD-1) or Compound (AD-21 with Compound (IV) represented by $HOR^E$ (wherein $R^E$ is the same as defined above) in the presence of a condensing agent, in a solvent.

Examples of the solvent include THF, ether, toluene and the like. These may be used alone or in combinations.

Examples of the condensing agent include mixtures of trivalent phosphorus compounds such as triphenylphosphine and tributylphosphine, and azo compounds such as diethyl azodicarboxylate (DEAD) and 1,1-(azodicarbinyl)dipiperidine and the like.

Each of Compound (IV) and the condensing agent is preferably used in an amount of 1 equivalent or more, preferably in the range of 1 to 5 equivalents relative to the amount of Compound (AD-1) or Compound (AD-2).

The reaction is normally performed at a temperature in the range of −20° C. to 80° C., preferably 0° C. to 30° C., and is finished within the range of 5 minutes to 48 hours.

Step 9

[In step 9, at least one of $R^{2a}$, $R^{3a}$, $R^{5a}$, $R^{6a}$, and $R^{8a}$ is hydroxy, and at least one of $R^{2b}$, $R^{3b}$, $R^{5b}$, $R^{6b}$, and $R^{8b}$ is —$OR^F$ (wherein $R^F$ represents substituted or unsubstituted lower alkyl or substituted or unsubstituted aralkyl)]

Compound (Ia-1) or Compound (Ia-2) can be synthesized by reacting Compound (AD-1) or Compound (AD-2) with Compound (V) represented by $X^1R^F$ (wherein $X^1$ and $R^F$ are the same as those defined above, respectively) in the presence of a base, in a solvent.

Examples of the solvent include dichloromethane, THF, 1,4-dioxane, acetonitrile, DMF, NMP and the like. These may be used alone or in combinations.

Examples of the base include DMAP, triethylamine, diisopropylethylamine, pyridine, sodium carbonate, sodium hydrogencarbonate, potassium carbonate, sodium hydroxide, potassium hydroxide, sodium hydride and the like.

Each of the base and Compound (V) is preferably used in an amount of 1 to 20 equivalents relative to the amount of Compound (AD-1) or Compound (AD-2). The reaction is normally performed at a temperature in the range of −20° C. to 80° C. and is finished within the range of 30 minutes to 24 hours.

Production Method 4

Compound (I) can also be produced by a method similar to Production method 1 or Production method 2 using Compound (AF), Compound (AH), Compound (AI), Compound (AJ), Compound, (AL), Compound (AM), Compound (AN), Compound (AP), Compound (AQ), Compound (AR), Compound (AS), Compound (AT), and Compound (AV) obtained by Steps 10 to 14 described below. Substituents $R^{2c}$, $R^{2d}$, $R^{2e}$, $R^{2f}$, $R^{3c}$, $R^{3d}$, $R^{3e}$, and $R^{3f}$ of Compound (AF), Compound (AH), Compound (AI), Compound (AJ), Compound, (AL), Compound (AM), Compound (AN), Compound (AP), Compound (AQ), Compound (AR), Compound (AS), Compound (AT), and Compound (AV) obtained by Steps 10 to 14 described below can be converted to desired substituents by a method similar to Steps 3 to 9 of Production method 3.

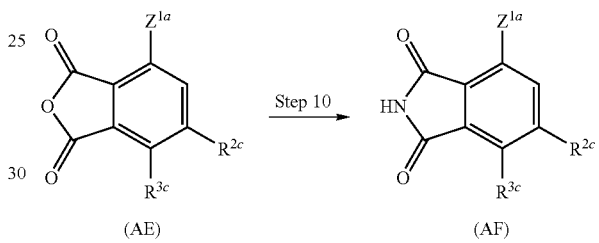

(wherein $Z^{1a}$, $R^{2c}$ and $R^{3c}$ are the same as $Z^1$, $R^2$ and $R^3$, defined above, respectively)

Step 10

Compound (AF) can be produced by reacting Compound (AE) obtained by a method similar to a known method [for example, Tetrahedron Letters, Vol. 23, p. 371 (1982); or Journal of Chemical Society Perkin Transaction I, Vol. 19, p. 2755 (1999)] with 1 to 30 equivalents of an imidizing agent in the presence or absence of a solvent at a temperature in the range of −50° C. to 250° C. for 5 minutes to 100 hours.

Examples of the solvent include methanol, ethanol, dichloromethane, acetonitrile, toluene, ethyl acetate, THF, 1,4-dioxane, DMF, NMP, water, acetic acid and the like. These may be used alone or in combinations.

Examples of the imidizing agent include ammonia; ammonium salts such as ammonium carbonate and ammonium acetate; urea; hexamethyldisilazane (HMDS) and the like.

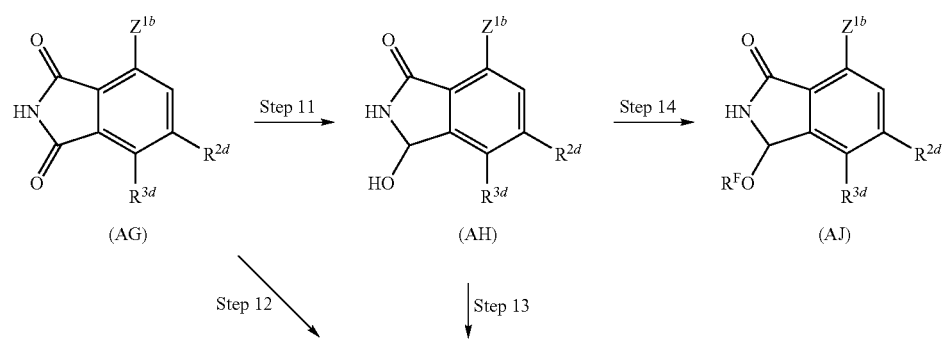

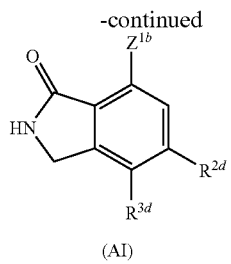

(AI)

(wherein $R^F$ represents substituted or unsubstituted lower alkyl, and $Z^{1b}$, $R^{2d}$ and $R^{3d}$ are the same as $Z^1$, $R^2$ and $R^3$ defined above, respectively)

Step 11

Compound (AH) can be produced by reacting Compound (AG) obtained by a method similar to a known method [Journal of the American Chemical Society, Vol. 78, p. 1631 (1956); or HETEROCYCLES, Vol. 45, p. 2217 (1997)] with 1 to 30 equivalents of a reducing reagent in a solvent at a temperature in the range of −90° C. to 200° C. for 5 minutes to 100 hours. In this step, 0.01 to 30 equivalents of an appropriate additive may be added so as to accelerate the reaction.

Examples of the solvent include methanol; ethanol; dichloromethane; acetonitrile; toluene; ethyl acetate; THF; 1,4-dioxane: DMF; NMP; buffer solutions such as sodium acetate-hydrochloric acid, acetic acid-sodium acetate, and citric acid-disodium hydrogenphosphate and the like. These may be used alone or in combinations.

Examples of the reducing agent include diisobutylaluminum hydride, sodium borohydride, lithium aluminum hydride, lithium borohydride, sodium trimethoxyborohydride, sodium borohydride cyanide, sodium triacetoxyborohydride and the like.

Examples of the additive include trifluoroborane-diethyl ether complex, titanium tetrachloride, methanesulfonic acid, cobalt dichloride and the like.

Step 12

Compound (AI) can be produced by reducing Compound (AG) using 1 to 30 equivalents of borane or a borane compound in a solvent at a temperature in the range of −90° C. to 200° C. for 5 minutes to 100 hours.

Examples of the solvent include methanol, ethanol, dichloromethane, acetonitrile, toluene, ethyl acetate, THF, 1,4-dioxane, DMF, NMP, water and the like. These may be used alone or in combinations.

Examples of the borane compound include borane-THF complex, borane-dimethyl sulfide complex, diborane and the like.

Step 13

Compound (AI) can also be produced by reducing Compound (AH) obtained in Step 11 using 1 to 30 equivalents of a hydrosilane compound in a solvent at a temperature in the range of −90° C. to 200° C. for 5 minutes to 100 hours. In this step, 0.01 to 30 equivalents of an additive may be added so as to accelerate the reaction.

Examples of the solvent include methanol, ethanol, dichloromethane, chloroform, acetonitrile, toluene, ethyl acetate, THF, 1,4-dioxane, acetic acid, trifluoroacetic acid and the like. These may be used alone or in combinations.

Examples of the hydrosilane compound include triethylsilane, trichlorosilane and the like.

Examples of the additive include trifluoroborane-diethyl ether complex, titanium tetrachloride and the like.

Step 14

Compound (AJ) can be produced by reacting Compound (AH) obtained in Step 11 with 1 equivalent to the amount of solvent of $R^FOH$ (wherein $R^F$ is the same as defined above) in the presence of an acid and in the presence or absence of a solvent at a temperature in the range of −90° C. to 200° C. for 5 minutes to 100 hours.

Examples of the solvent include dichloromethane, chloroform, acetonitrile, toluene, ethyl acetate, THF, 1,4-dioxane, DMF, NMP and the like. These may be used alone or in combinations.

Examples of the acid include concentrated hydrochloric acid, concentrated sulfuric acid, DL-10-camphorsulfonic acid, p-toluenesulfonic acid, aluminum chloride, boron trifluoride and the like.

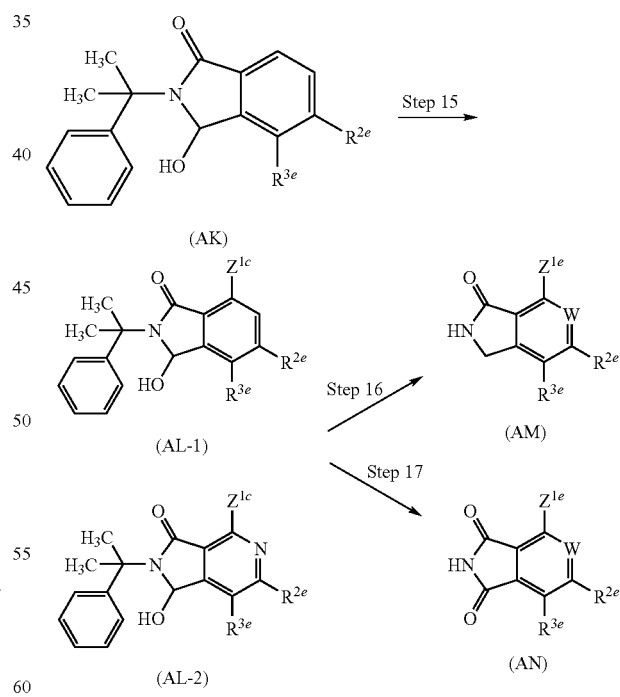

(wherein $Z^{1c}$ represents formyl or a halogen atom selected from a chlorine atom, a bromine atom, and an iodine atom: $Z^{1d}$ and $Z^{1e}$ each represents a chlorine atom, a bromine atom, or an iodine atom; and W, $R^{2e}$, and $R^{3e}$ are the same as W, $R^2$, and $R^3$ defined above, respectively)

Step 15

Compound (AL-1) can be produced by ortho-lithiation of Compound (AK), followed by halogenation or formylation of the resulting product Compound (AL-2) can be obtained by a method similar to a known method [Tetrahedron Letters, Vol. 32, p. 4883 (1991) or Tetrahedron, Vol. 49, p. 2885 (1993)].

Compound (AL-1) can be produced by reacting Compound (AK) obtained by a method similar to a known method [Organic Letters, Vol. 1, p. 1183 (1999)] with 1 to 5 equivalents of a lithium reagent in a solvent at a temperature in the range of −90° C. to room temperature for 5 minutes to 50 hours, followed by reacting with 1 to 30 equivalents of a halogenating agent or DMF at a temperature in the range of −90° C. to 100° C. In this step, 0.01 to 30 equivalents of an additive may be added so as to accelerate the reaction.

Examples of the solvent include toluene, diethyl ether, THF, 1,4-dioxane and the like. These may be used alone or in combinations.

Examples of the lithium reagent include n-butyllithium, sec-butyllithium, tert-butyllithium, lithium diisopropylamide (LDA) and the like.

Examples of the additive include N,N,N',N'-tetramethylethylenediamine (TMEDA) and the like.

Examples of the halogenating agent include 2,2,2-trifluoroiodomethane, iodine monochloride, iodine, bromine, hexachloroethane, and the like.

Step 16

Compound (AM) can be synthesized by reducing Compound (AL-1) or Compound (AL-2) using triethylsilane in the presence of trifluoroacetic acid, by a method similar to the method described in the document of [Organic Letters, Vol. 1, p. 1183 (1999)].

Step 17

Compound (AN) can be synthesized by oxidizing Compound (AL-1) or Compound (AL-2) using pyridinium dichromate (PDC), and deprotecting the resulting product using trifluoroacetic acid by a method similar to the method described in the document of [Organic Letters, Vol. 1, p. 1183 (1999)].

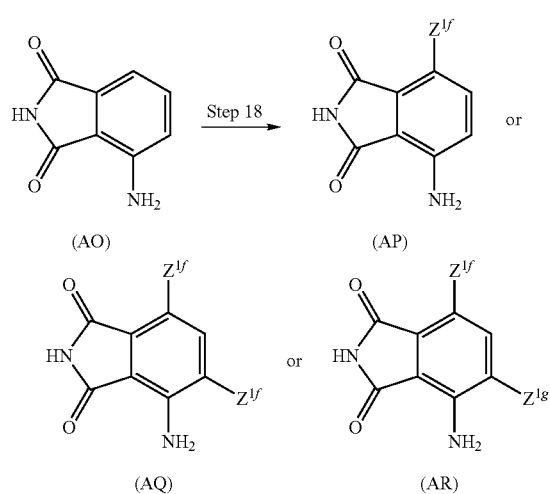

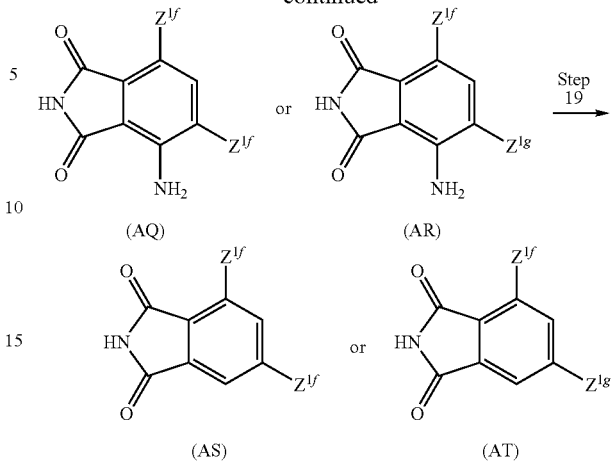

(wherein each of $Z^{1f}$ and $Z^{1g}$ is the same as $Z^1$ defined above)

Step 18

Compound (AP), Compound (AQ), or Compound (AR) can be synthesized by halogenating Compound (AO).

Compound (AP) can be synthesized by reacting Compound (AO) with 1 equivalent of a halogenating agent in a solvent at a temperature in the range of −50° C. to 200° C. for 5 minutes to 100 hours. When 2 equivalents or more of the halogenating agent is used, Compound (AQ) can be synthesized. Alternatively, when different types of halogenating agents are used for Compound (AP), Compound (AR) can be synthesized. In this step, 0.01 to 30 equivalents of an additive may be added so as to accelerate the reaction.

Examples of the solvent include methanol, ethanol, dichloromethane, chloroform, carbon tetrachloride, acetonitrile, toluene, ethyl acetate, THF, 1,4-dioxane, acetic acid, trifluoroacetic acid and the like. These may be used alone or in combinations.

Examples of the halogenating agent include chlorine, gaseous hydrogen chloride, concentrated hydrochloric acid, hydrobromic acid, tetra-n-butylammonium tribromide, bromine, iodine, N-chlorosuccinimide (NCS), N-bromosuccinimide (NBS), N-iodosuccinimide (NIS), iodine monochloride and the like.

Examples of the additive include silver sulfate, copper acetate, calcium carbonate, zinc chloride and the like.

Step 19

Compound (AS) can be produced using Compound (AQ) synthesized in Step 18, and Compound (AT) can be produced using Compound (AR) synthesized in Step 16, by a method similar to the method described in the document of [J. Chem. Soc. Perkin Transaction 1, p. 873 (1986)]. More specifically, Compound (AS) or Compound (AT) can be synthesized by reacting Compound (AQ) or Compound (AR) with a nitrite compound in a solvent containing 1 to 30 equivalents of formamide at a temperature in the range of −50° C. to 100° C. for 5 minutes to 100 hours, and then adding triethylamine.

Examples of the solvent include methanol, ethanol, dichloromethane, chloroform, acetonitrile, toluene, ethyl acetate, THF, 1,4-dioxane, water, acetic acid, trifluoroacetic acid and the like. These may be used alone or in combinations.

Examples of the nitrite compound include sodium nitrite, tert-butyl nitrite and the like.

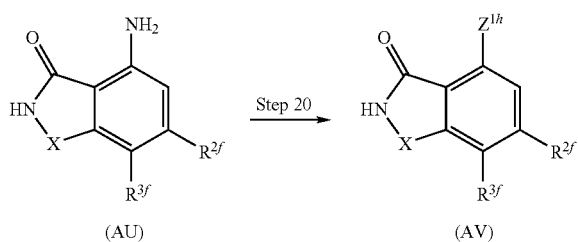

(wherein X is the same as defined above; and $Z^{1h}$, $R^{2f}$, and $R^{3f}$ are the same as $Z^1$, $R^2$, and $R^3$ defined above, respectively.)

Step 20

Compound (AV) can be produced by reacting a diazonium salt with a halogenating agent, and the diazonium salt capable of being prepared by reacting Compound (AU) obtained by Step 18 or a method similar to a known method [Bioorganic & Medicinal Chemistry Letters, Vol. 14, p. 4505 (2004)] with a nitrite compound.

Compound (AU) is reacting with 1 to 30 equivalents of a nitrite compound in the presence or absence of a solvent at a temperature in the range of −50° C. to 100° C. for 5 minutes to 48 hours to prepare its corresponding diazonium salt. The diazonium salt is then reacted with 1 to 30 equivalents of a halogenating agent in a solvent at a temperature in the range of −50° C. to 200° C. for 5 minutes to 48 hours to produce Compound (AV) can be produced.

Examples of the solvent include methanol, ethanol, dichloromethane, acetonitrile, toluene, ethyl acetate, THF, 1,4-dioxane, DMF, NMP, water and the like. These may be used alone or in combinations.

Examples of the halogenating agent include iodine, copper chloride, copper bromide, copper iodide and the like. Among these, copper halides can be prepared by adding sodium chloride, sodium bromide, or the like to an aqueous copper sulfate solution, and then reducing the mixture with sodium nitrite. The copper halides thus prepared may be used for the above step without isolation.

By conducting the above-described methods in combinations as needed, Compound (I) having desired functional groups at desired positions can be obtained.

The conversion of functional groups contained in the substituents of Compound (I) and starting material can be performed not only by the above-described steps but also by other known methods [for example, Comprehensive Organic Transformations, written by R. C. Larock (1989)].

Isolation and purification of the products obtained by the above-described production methods can be performed by appropriately combining methods that are generally used in organic synthesis, for example, filtration, extraction, washing, drying, concentration, crystallization, various types of chromatography and the like. Intermediates may be used in subsequent reactions without purification.

Isomers of Compound (I) such as stereoisomers, regioisomers, geometrical isomers, and optical isomers of Compound (I) can be present. The present invention also includes these isomers and mixtures containing these isomers in any ratio.

In order to produce a salt of Compound (I), when Compound (I) is obtained in the form of a salt, the salt can be purified without further treatment. On the other hand, when Compound (I) is obtained in the free form, Compound (I) is dissolved or suspended in an appropriate solvent, and an acid, a base, or the like is then added to the solution or the suspension to form a salt.

Compound (I) or a pharmaceutically acceptable salt thereof can be present in the form of an adduct of water or a solvent. The present invention also includes such adducts.

Table 1, Tables 2-1 to 2-9, Tables 3-1 to 3-3, Tables 4-1 to 4-10, Tables 5-1 to 5-6, Table 6, Tables 7-1 to 7-3, Table 8, and Table 9 show specific examples of the compounds of the present invention, but these compounds do not limit the scope of the present invention.

In the tables below, Me, Et, and Ph represent methyl, ethyl, and phenyl, respectively.

TABLE 1

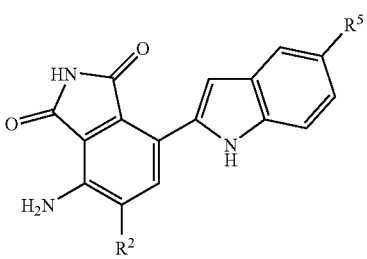

| Example No. | Compound No. | $R^5$ | $R^2$ |
|---|---|---|---|
| 1 | 1 | H | H |
| 2 | 2 | ![structure with NMe sulfonyl piperazine] | Ph |

TABLE 1-continued
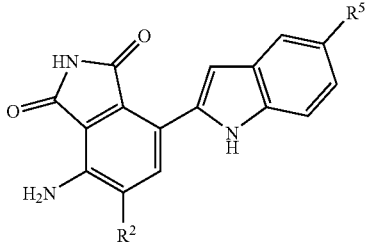
| Example No. | Compound No. | R⁵ | R² |
|---|---|---|---|
| 3 | 3 | 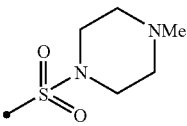 | 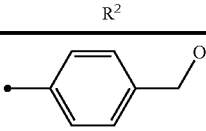 |
| 4 | 4 | 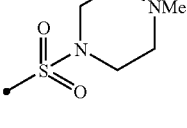 | H |
| 5 | 5 | 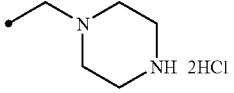 2HCl | H |
| 6 | 6 | 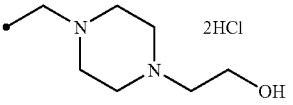 2HCl | H |
| 7 | 7 | 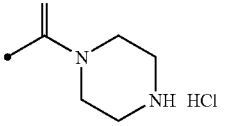 HCl | H |
| 8 | 8 | 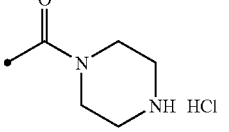 HCl | Ph |
| 9 | 9 | 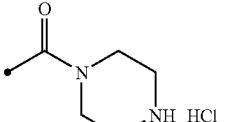 HCl | 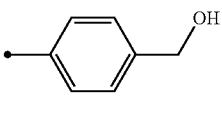 |
| 10 | 10 | 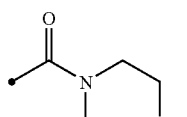 | 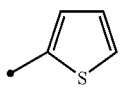 |
| 11 | 11 | 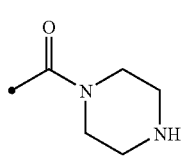 | 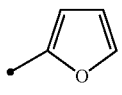 |

TABLE 1-continued

Structure: Isoindoline-1,3-dione core with R⁵-substituted indol-2-yl at position 7, H₂N at position 4, R² at position 5.

| Example No. | Compound No. | R⁵ | R² |
|---|---|---|---|
| 12 | 12 | -CH₂-(piperazin-1-yl), 2HCl | 2-thienyl |
| 13 | 13 | -CH₂-(piperazin-1-yl), 2HCl | 2-furyl |
| 14 | 14 | -CH₂-(piperidin-1-yl), HCl | 2-furyl |
| 15 | 15 | -C(O)-(piperazin-1-yl) | -CH=CH-CO₂Me (trans) |

TABLE 2-1

Structure: Isoindolin-1-one core with R⁵-substituted indol-2-yl at position 7 and R³ at position 4.

| Example No. | Compound No. | R⁵ | R³ |
|---|---|---|---|
| 16 | 16 | H | Cl |
| 17 | 17 | -C(O)-(4-methylpiperazin-1-yl) | Cl |
| 18 | 18 | Br | Cl |
| 19 | 19 | CO₂H | Cl |
| 20 | 20 | -C(O)-(4-acetylpiperazin-1-yl) | Cl |
| 21 | 21 | -C(O)-(4-methanesulfonylpiperazin-1-yl) | Cl |

TABLE 2-1-continued

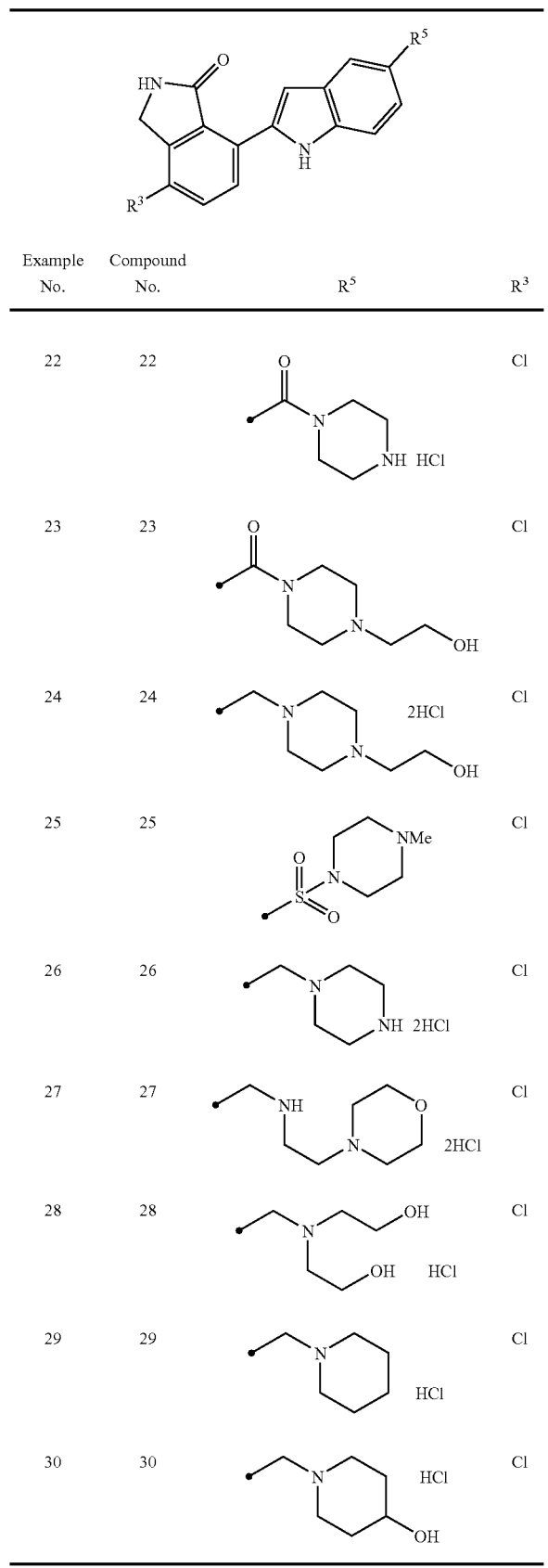

| Example No. | Compound No. | R⁵ | R³ |
|---|---|---|---|
| 22 | 22 | piperazine-C(O)- · HCl | Cl |
| 23 | 23 | 4-(2-hydroxyethyl)piperazine-C(O)- | Cl |
| 24 | 24 | -CH2-[4-(2-hydroxyethyl)piperazin-1-yl] · 2HCl | Cl |
| 25 | 25 | 4-methylpiperazine-1-sulfonyl | Cl |
| 26 | 26 | -CH2-piperazin-1-yl · 2HCl | Cl |
| 27 | 27 | -CH2-NH-CH2CH2-morpholino · 2HCl | Cl |
| 28 | 28 | -CH2-N(CH2CH2OH)2 · HCl | Cl |
| 29 | 29 | -CH2-piperidin-1-yl · HCl | Cl |
| 30 | 30 | -CH2-(4-hydroxypiperidin-1-yl) · HCl | Cl |

TABLE 2-2

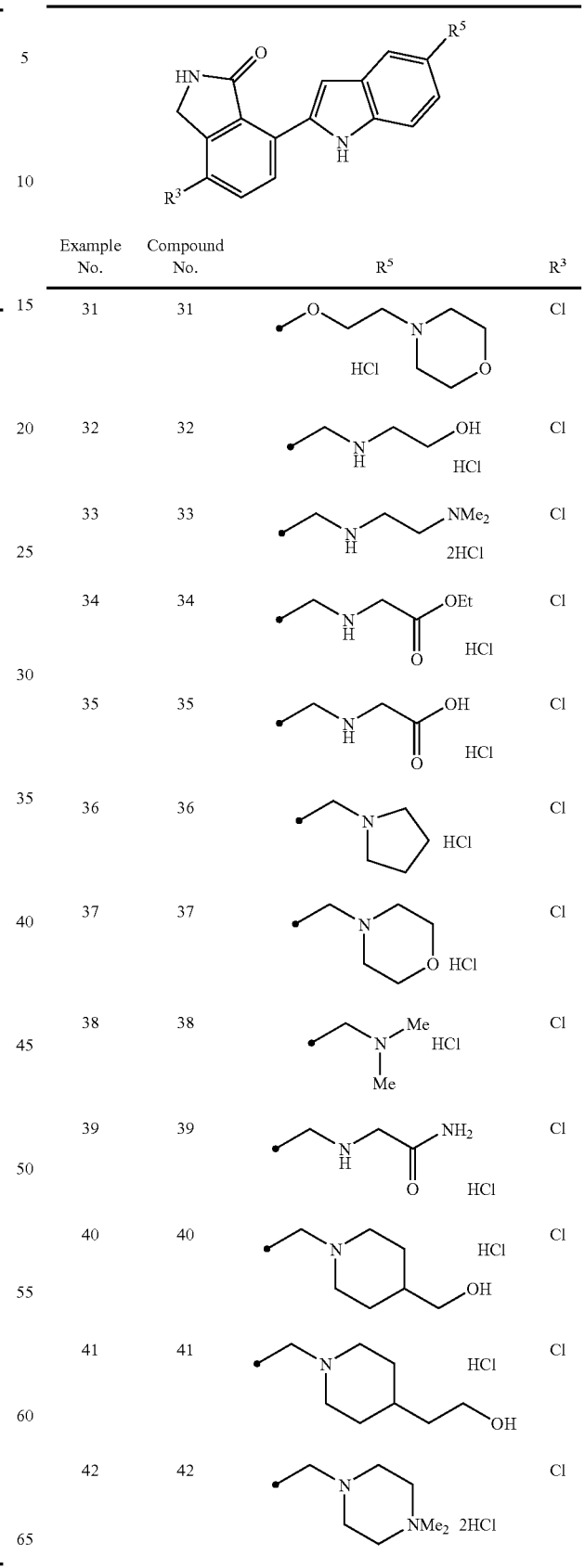

| Example No. | Compound No. | R⁵ | R³ |
|---|---|---|---|
| 31 | 31 | -O-CH2CH2-morpholino · HCl | Cl |
| 32 | 32 | -CH2-NH-CH2CH2OH · HCl | Cl |
| 33 | 33 | -CH2-NH-CH2CH2-NMe2 · 2HCl | Cl |
| 34 | 34 | -CH2-NH-CH2-C(O)OEt · HCl | Cl |
| 35 | 35 | -CH2-NH-CH2-C(O)OH · HCl | Cl |
| 36 | 36 | -CH2-pyrrolidin-1-yl · HCl | Cl |
| 37 | 37 | -CH2-morpholino · HCl | Cl |
| 38 | 38 | -CH2-NMe2 · HCl | Cl |
| 39 | 39 | -CH2-NH-CH2-C(O)NH2 · HCl | Cl |
| 40 | 40 | -CH2-[4-(hydroxymethyl)piperidin-1-yl] · HCl | Cl |
| 41 | 41 | -CH2-[4-(2-hydroxyethyl)piperidin-1-yl] · HCl | Cl |
| 42 | 42 | -CH2-(4-dimethylaminopiperazin-1-yl) · 2HCl | Cl |

TABLE 2-2-continued

[Structure: isoindolinone with R⁵-substituted indole, R³ substituent]

| Example No. | Compound No. | R⁵ | R³ |
|---|---|---|---|
| 43 | 43 | piperazin-2-one-N-CH₂- , HCl | Cl |
| 44 | 44 | 4-(methoxycarbonyl)piperidin-1-yl-CH₂- , HCl | Cl |
| 45 | 45 | 3-hydroxypiperidin-1-yl-CH₂- , HCl | Cl |

TABLE 2-3

[Structure: isoindolinone with R⁵-substituted indole, R³ substituent]

| Example No. | Compound No. | R⁵ | R³ |
|---|---|---|---|
| 46 | 46 | piperidin-1-yl-C(=O)- | Cl |
| 47 | 47 | -CH₂-NH-Et , HCl | Cl |
| 48 | 48 | -CH₂-NH-cyclohexyl , HCl | Cl |
| 49 | 49 | 2-(hydroxymethyl)piperidin-1-yl-CH₂- , HCl | Cl |

TABLE 2-3-continued

| Example No. | Compound No. | R⁵ | R³ |
|---|---|---|---|
| 50 | 50 | 4-methylpiperidin-1-yl-CH₂- , HCl | Cl |
| 51 | 51 | -C(=O)-NH-CH₂CH₂-OH | Cl |
| 52 | 52 | -C(=O)-NH-CH₂CH₂-NMe₂ | Cl |
| 53 | 53 | 4-bromopiperidin-1-yl-CH₂- , HCl | Cl |
| 54 | 54 | 4-(methanesulfonyl)piperazin-1-yl-CH₂- , HCl | Cl |
| 55 | 55 | 4-acetylpiperazin-1-yl-CH₂- , HCl | Cl |
| 56 | 56 | -CH₂-NH-CH₂-Ph , HCl | Cl |
| 57 | 57 | -C(=O)-NH-CH₂-Ph | Cl |
| 58 | 58 | -C(=O)-NH-CH₂CH₂-(2-pyridyl) | Cl |
| 59 | 59 | -C(=O)-NH-CH₂CH₂-(3-pyridyl) | Cl |

TABLE 2-3-continued

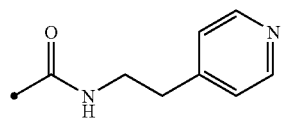

| Example No. | Compound No. | R⁵ | R³ |
|---|---|---|---|
| 60 | 60 | ![pyridin-3-ylethylamide] | Cl |

TABLE 2-4

| Example No. | Compound No. | R⁵ | R³ |
|---|---|---|---|
| 61 | 61 | (1-(hydroxymethyl)cyclopentyl)aminomethyl | Cl |
| 62 | 62 | (1-hydroxypropan-2-yl)aminomethyl | Cl |
| 63 | 63 | ((1-hydroxycyclohexyl)methyl)aminomethyl | Cl |
| 64 | 64 | (pyridin-2-ylmethyl)aminomethyl | Cl |
| 65 | 65 | (2-(pyridin-2-yl)ethyl)aminomethyl | Cl |
| 66 | 66 | (2-(2-hydroxyethoxy)ethyl)aminomethyl | Cl |

TABLE 2-4-continued

| Example No. | Compound No. | R⁵ | R³ |
|---|---|---|---|
| 67 | 67 | (pyridin-4-ylmethyl)aminomethyl | Cl |
| 68 | 68 | (2-(pyridin-4-yl)ethyl)aminomethyl | Cl |
| 69 | 69 | (2-(pyridin-3-yl)ethyl)aminomethyl | Cl |
| 70 | 70 | (pyridin-3-ylmethyl)aminomethyl | Cl |
| 71 | 71 | (3-hydroxy-2,2-dimethylpropyl)aminomethyl | Cl |
| 72 | 72 | N-((1-hydroxycyclohexyl)methyl)acetamide | Cl |
| 73 | 73 | N-(pyridin-2-ylmethyl)acetamide | Cl |
| 74 | 74 | N-(pyridin-4-ylmethyl)acetamide | Cl |
| 75 | 75 | tert-butyl (2-acetamidoethyl)carbamate | Cl |

TABLE 2-5
| Example No. | Compound No. | R⁵ | R³ |
|---|---|---|---|
| 76 | 76 | 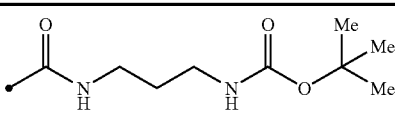 | Cl |
| 77 | 77 | 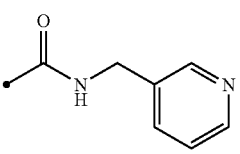 | Cl |
| 78 | 78 | 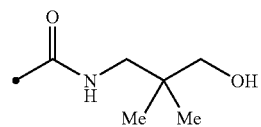 | Cl |
| 79 | 79 | 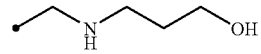 | Cl |
| 80 | 80 | 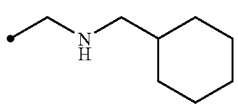 | Cl |
| 81 | 81 | 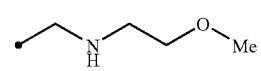 | Cl |
| 82 | 82 | 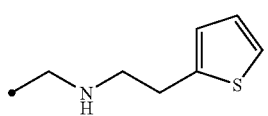 | Cl |
| 83 | 83 | 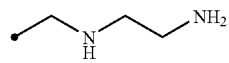 | Cl |
| 84 | 84 | 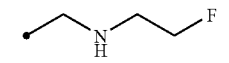 | Cl |
| 85 | 85 | 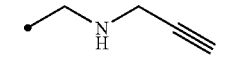 | Cl |
| 86 | 86 | 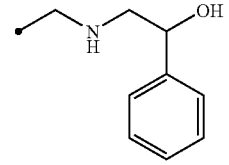 | Cl |
| 87 | 87 | 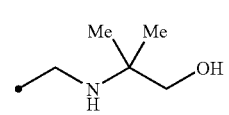 | Cl |

TABLE 2-5-continued
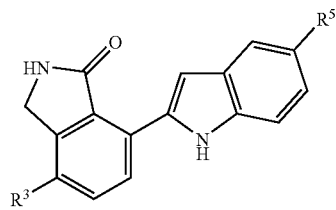
| Example No. | Compound No. | R⁵ | R³ |
|---|---|---|---|
| 88 | 88 | (azepan-1-ylmethyl) | Cl |
| 89 | 89 | (thiomorpholin-4-ylmethyl) | Cl |
| 90 | 90 | (4-(pyridin-2-yl)piperazin-1-ylmethyl) | Cl |
TABLE 2-6
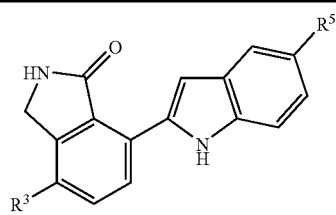
| Example No. | Compound No. | R⁵ | R³ |
|---|---|---|---|
| 91 | 91 | (4-phenylpiperidin-1-ylmethyl) | Cl |
| 92 | 92 | (4-hydroxy-4-phenylpiperidin-1-ylmethyl) | Cl |
| 93 | 93 | (4-(2-(2-hydroxyethoxy)ethyl)piperazin-1-ylmethyl) | Cl |
| 94 | 94 | (3-(hydroxymethyl)piperidin-1-ylmethyl) | Cl |
| 95 | 95 | (4-(pyridin-4-yl)piperazin-1-ylmethyl) | Cl |

TABLE 2-6-continued
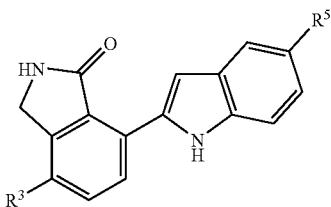
| Example No. | Compound No. | R⁵ | R³ |
|---|---|---|---|
| 96 | 96 | 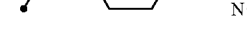 | Cl |
| 97 | 97 |  | Cl |
| 98 | 98 |  | Cl |
| 99 | 99 | 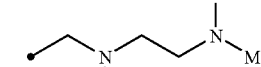 | Cl |
| 100 | 100 | 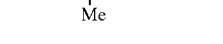 | Cl |
| 100 | 101 | 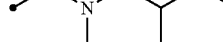 | Cl |
| 102 | 102 | 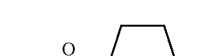 | Cl |
| 103 | 103 | 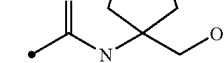 | Cl |
| 104 | 104 |  | Cl |
| 105 | 105 | 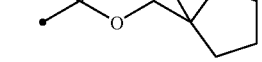 | Cl |

TABLE 2-7

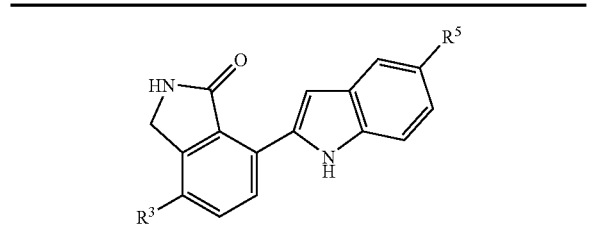

| Example No. | Compound No. | R⁵ | R³ |
|---|---|---|---|
| 106 | 106 | 1-(thiomorpholinyl)carbonyl | Cl |
| 107 | 107 | 4-(2-pyridyl)piperazin-1-yl-carbonyl | Cl |
| 108 | 108 | 2-(2-hydroxyethyl)piperidin-1-yl-carbonyl | Cl |
| 109 | 109 | 4-[2-(2-hydroxyethoxy)ethyl]piperazin-1-yl-carbonyl | Cl |
| 110 | 110 | 3-(hydroxymethyl)piperidin-1-yl-carbonyl | Cl |
| 111 | 111 | 4-(4-pyridyl)piperazin-1-yl-carbonyl | Cl |
| 112 | 112 | 4-(2-dimethylaminoethyl)piperazin-1-yl-carbonyl | Cl |
| 113 | 113 | 4-(2-pyrimidinyl)piperazin-1-yl-carbonyl | Cl |
| 114 | 114 | 4-(2-methoxyethyl)piperazin-1-yl-carbonyl | Cl |
| 115 | 115 | 4-(2-cyanoethyl)piperazin-1-yl-carbonyl | Cl |
| 116 | 116 | N-methyl-N-(2-dimethylaminoethyl)carbamoyl | Cl |
| 117 | 117 | N-methyl-N-(2,3-dihydroxypropyl)carbamoyl | Cl |
| 118 | 118 | phenylcarbamoyl | Cl |
| 119 | 119 | 4-(acetylamino)phenylcarbamoyl | Cl |
| 120 | 120 | 4-(hydroxymethyl)phenylcarbamoyl | Cl |

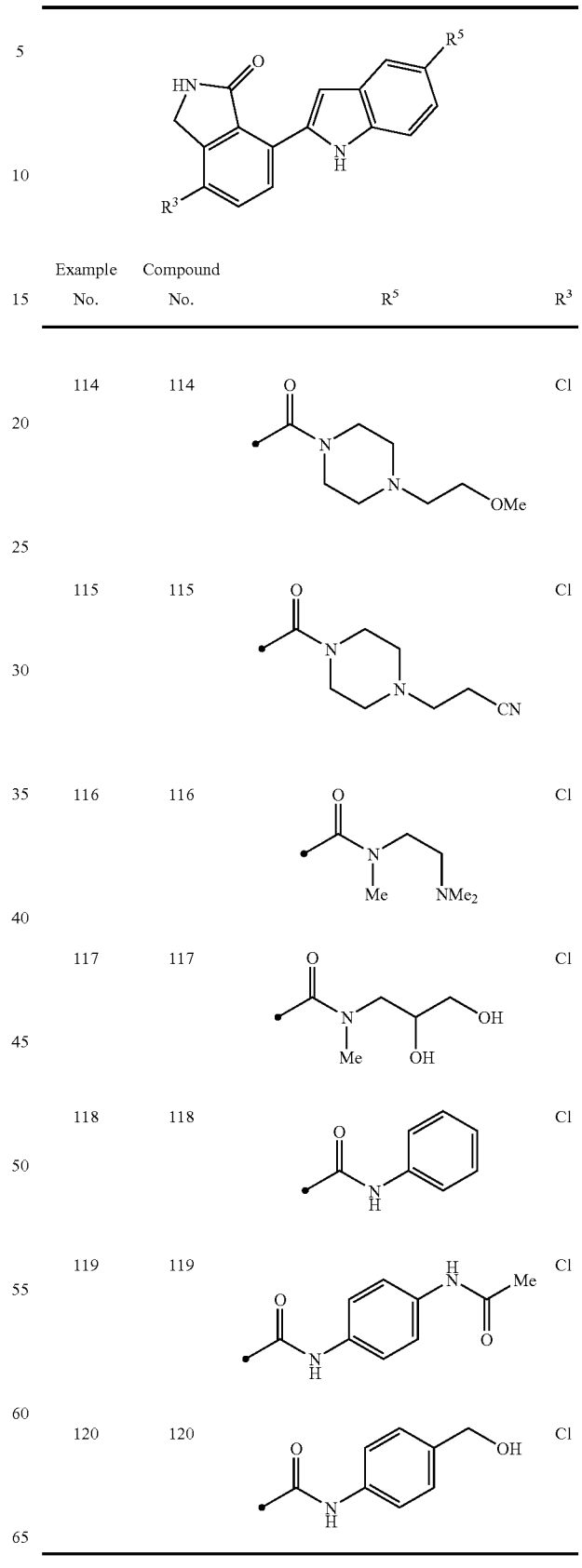

TABLE 2-8
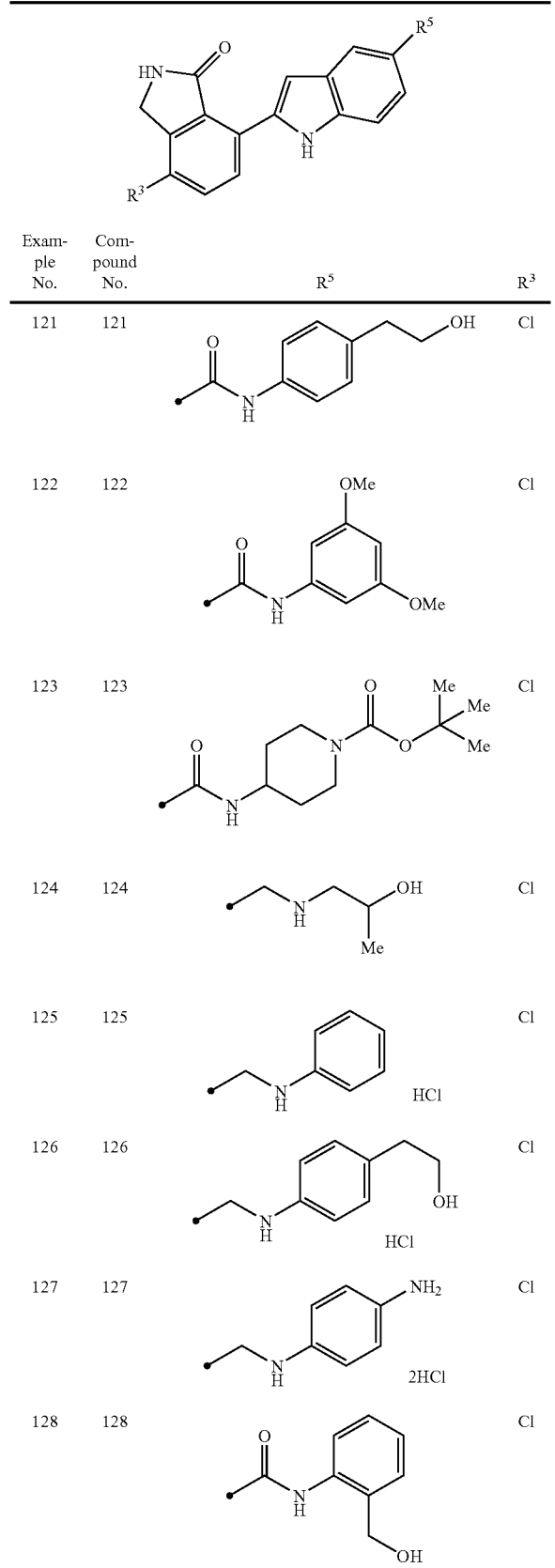
TABLE 2-8-continued
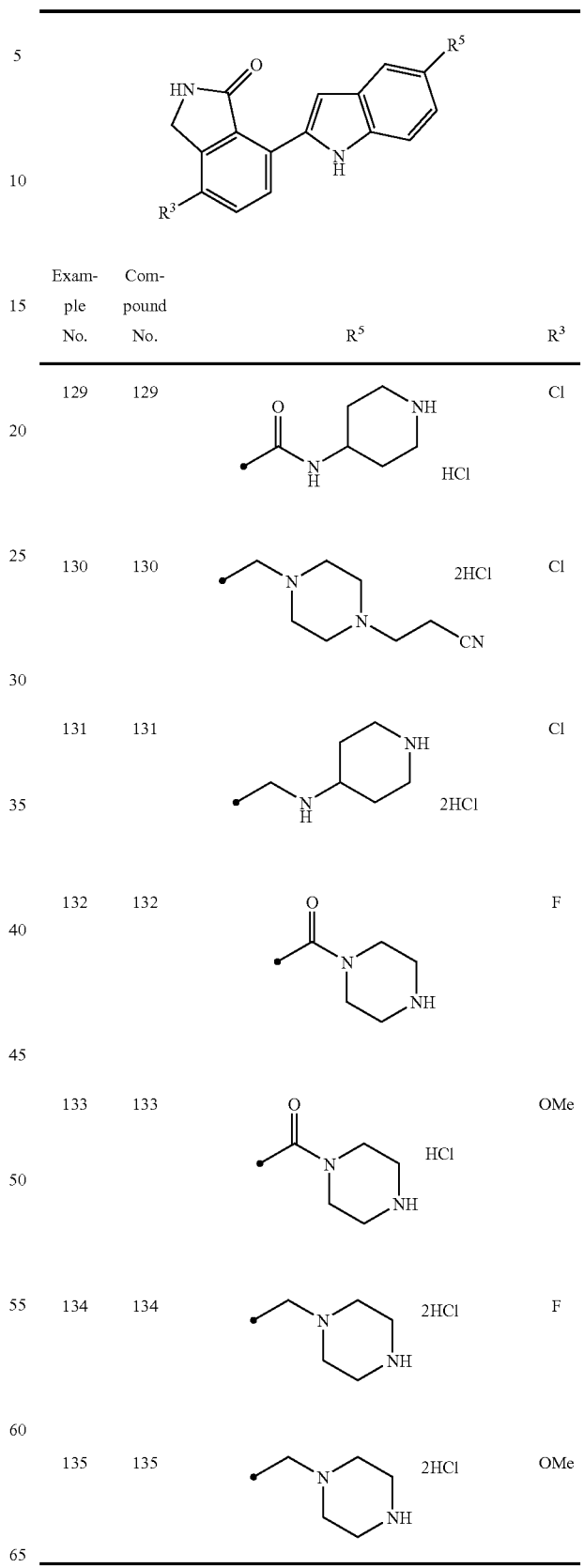

TABLE 2-9
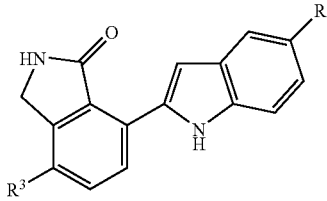
| Example No. | Compound No. | R⁵ | R³ |
|---|---|---|---|
| 136 | 136 | 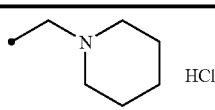 HCl | OMe |
| 137 | 137 | 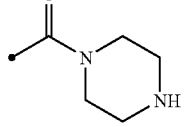 | OPh |
| 138 | 138 | 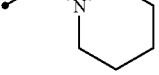 | OPh |
| 139 | 139 | 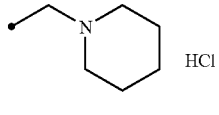 HCl | OH |
| 140 | 140 | 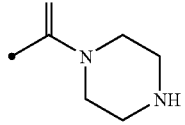 | Ph |
| 141 | 141 | 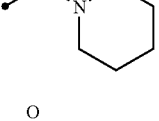 | Ph |
| 142 | 142 | 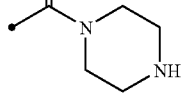 | 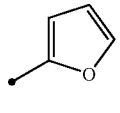 |
| 143 | 143 | 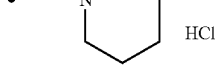 HCl | 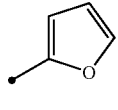 |
| 144 | 144 | 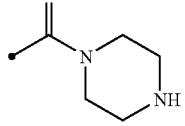 | OH |
| 145 | 145 | 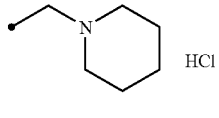 HCl | 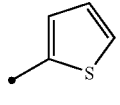 |

TABLE 2-9-continued
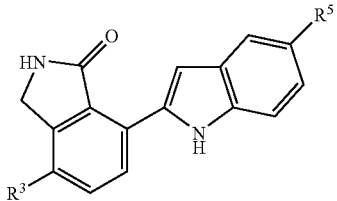
| Example No. | Compound No. | R⁵ | R³ |
|---|---|---|---|
| 146 | 146 | 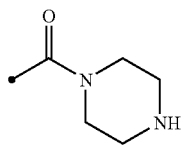 | 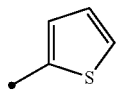 |
| 147 | 147 | 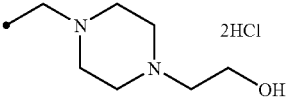 2HCl | OH |
| 148 | 148 | 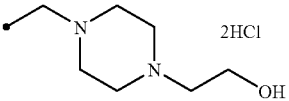 2HCl | 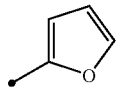 |
| 149 | 149 | 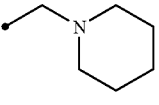 |  |
| 150 | 150 | 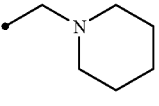 | 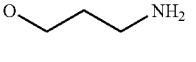 |
| 151 | 151 | 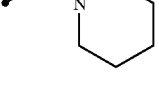 | 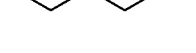 |
| 152 | 152 | 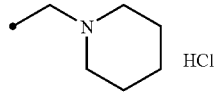 HCl | 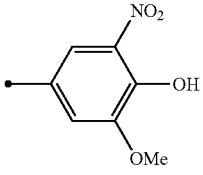 |
| 153 | 153 | 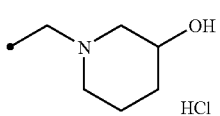 HCl | OH |

TABLE 3-1
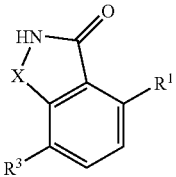
| Example No. | Compound No. | X | R¹ | R³ |
|---|---|---|---|---|
| 154 | 154 | C=O | 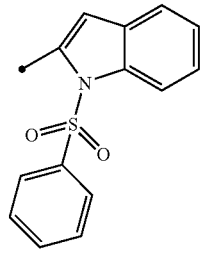 | $NH_2$ |
| 155 | 155 | $CH_2$ | 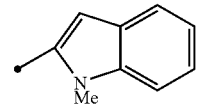 | Cl |
| 156 | 156 | $CH_2$ | 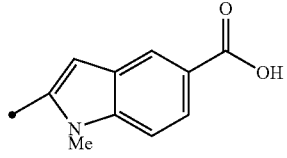 | Cl |
| 157 | 157 | $CH_2$ | 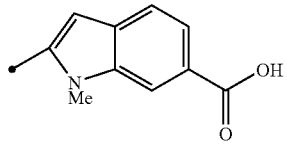 | Cl |
| 158 | 158 | $CH_2$ | 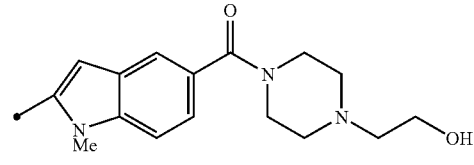 | Cl |
| 159 | 159 | $CH_2$ | 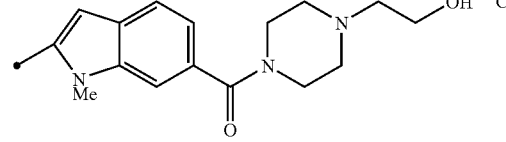 | Cl |
| 160 | 160 | $CH_2$ |  | Cl |

TABLE 3-1-continued
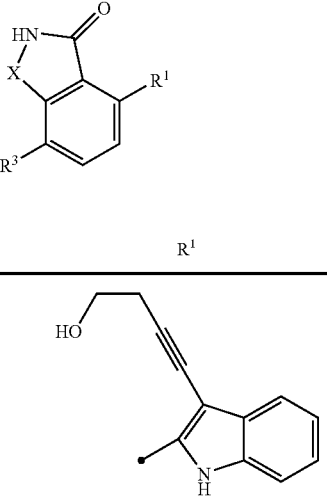
| Example No. | Compound No. | X | R¹ | R³ |
|---|---|---|---|---|
| 161 | 161 | C=O | 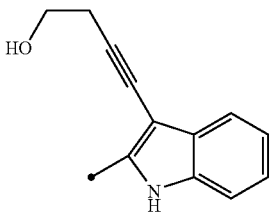 | NH₂ |
| 162 | 162 | CH₂ | 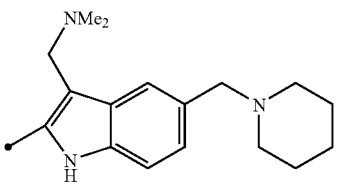 | Cl |
| 163 | 163 | CH₂ | 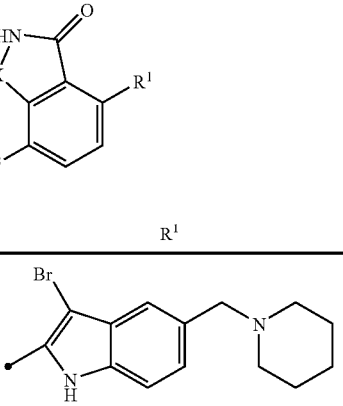 | Cl |
TABLE 3-2
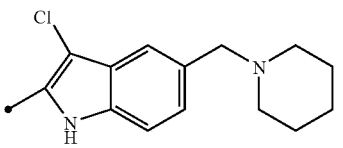
| Example No. | Compound No. | X | R¹ | R³ |
|---|---|---|---|---|
| 164 | 164 | CH₂ | (Br-substituted indole with piperidinylmethyl) | Cl |
| 165 | 165 | CH₂ | (Cl-substituted indole with piperidinylmethyl) | Cl |

TABLE 3-2-continued
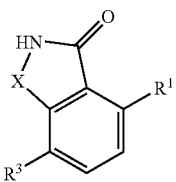
| Example No. | Compound No. | X | R¹ | R³ |
|---|---|---|---|---|
| 166 | 166 | C=O | 2-(6-(piperazine-1-carbonyl)-1H-indolyl) · HCl | NH₂ |
| 167 | 167 | CH₂ | 2-(6-(piperazine-1-carbonyl)-1H-indolyl) · HCl | Cl |
| 168 | 168 | C=O | 2-benzo[b]thienyl | H |
| 169 | 169 | C=O | 2-benzofuranyl | H |
| 170 | 170 | CH₂ | 2-benzofuranyl | Cl |
| 171 | 171 | C=O | 2-benzofuranyl | NH₂ |
| 172 | 172 | CH₂ | 2-(5-carboxybenzo[b]thienyl) | Cl |
| 173 | 173 | CH₂ | 2-(5-(4-(2-hydroxyethyl)piperazine-1-carbonyl)benzo[b]thienyl) | Cl |
| 174 | 174 | CH₂ | 2-(1H-benzimidazolyl) | Cl |

TABLE 3-2-continued

| Example No. | Compound No. | X | R¹ | R³ |
|---|---|---|---|---|
| 175 | 175 | CH₂ | benzimidazole-piperazine-NMe | Cl |
| 176 | 176 | CH₂ | benzimidazole-C(O)-piperazine-NMe | Cl |
| 177 | 177 | C=O | benzimidazole-C(O)-piperazine-NMe | Cl |
| 178 | 178 | CH₂ | benzimidazole-COOH | Cl |

TABLE 3-3

| Example No. | Compound No. | X | R¹ | R³ |
|---|---|---|---|---|
| 179 | 179 | CH₂ | benzimidazole-C(O)-piperazine-C(O)Me | Cl |

TABLE 3-3-continued

| Example No. | Compound No. | X | R¹ | R³ |
|---|---|---|---|---|
| 180 | 180 | CH₂ | benzimidazol-5-yl-C(O)-piperazine-N-C(O)O-C(Me)₃ | Cl |
| 181 | 181 | CH₂ | benzimidazol-5-yl-C(O)-piperazine·HCl | Cl |
| 182 | 182 | CH₂ | benzimidazol-5-yl-C(O)NMe₂ | Cl |
| 183 | 183 | CH₂ | benzimidazol-5-yl-C(O)-piperazine-N-(2-pyridyl) | Cl |
| 184 | 184 | CH₂ | benzimidazol-5-yl-C(O)-piperazine-N-CH₂CH₂OH | Cl |
| 185 | 185 | CH₂ | benzimidazol-5-yl-C(O)NH-CH₂CH₂OH | Cl |
| 186 | 186 | CH₂ | benzimidazol-5-yl-C(O)NH-CH₂-(2-pyridyl) | Cl |

TABLE 3-3-continued
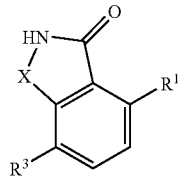
| Example No. | Compound No. | X | R¹ | R³ |
|---|---|---|---|---|
| 187 | 187 | CH₂ |  | Cl |
TABLE 4-1
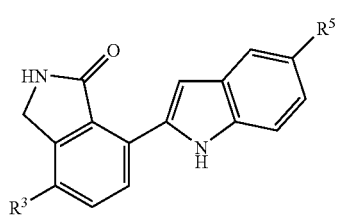
| Example No. | Compound No. | R⁵ | R³ |
|---|---|---|---|
| 188 | 188 | 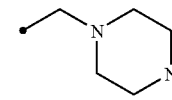 3HCl | Cl |
| 189 | 189 | 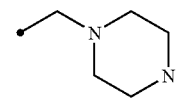 2HCl | Cl |
| 190 | 190 | 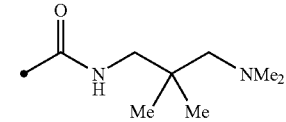 | Cl |
| 191 | 191 | 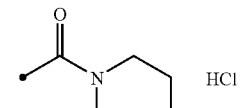 HCl | Cl |
| 192 | 192 | 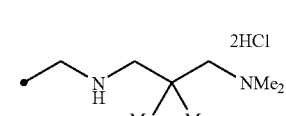 2HCl | Cl |
TABLE 4-1-continued
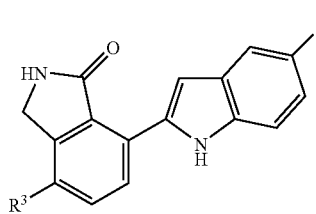
| Example No. | Compound No. | R⁵ | R³ |
|---|---|---|---|
| 193 | 193 | | Cl |
| 194 | 194 | 2HCl | Cl |
| 195 | 195 | 2HCl | Cl |
| 196 | 196 | | Cl |
| 197 | 197 | | Cl |

TABLE 4-1-continued

| Example No. | Compound No. | R⁵ | R³ |
|---|---|---|---|
| 198 | 198 | -CH₂-NH-CH₂-(3-pyridyl) · 2HCl | Cl |
| 199 | 199 | -C(=O)-N(piperidin-1-yl)-4-OH | Cl |
| 200 | 200 | -C(=O)-N(piperidin-1-yl)-4-CH₂CH₂OH | Cl |
| 201 | 201 | -C(=O)-N(piperidin-1-yl)-4-(CH₂)₃OH | Cl |
| 202 | 202 | -NH-C(=O)-(piperidin-4-yl) · HCl | Cl |

TABLE 4-2

| Example No. | Compound No. | R⁵ | R³ |
|---|---|---|---|
| 203 | 203 | NH₂ · HCl | Cl |
| 204 | 204 | -NH-(piperidin-4-yl) · 2HCl | Cl |
| 205 | 205 | OH | Cl |
| 206 | 206 | CN | Cl |
| 207 | 207 | -NH-C(=O)-piperazin-1-yl · HCl | Cl |
| 208 | 208 | -CH₂-N(4,4-dimethoxypiperidin-1-yl) · HCl | Cl |
| 209 | 209 | -CH₂-N(4-oxopiperidin-1-yl) · HCl | Cl |
| 210 | 210 | -O-CH₂CH₂-(piperidin-1-yl) · HCl | Cl |
| 211 | 211 | CO₂H | OH |
| 212 | 212 | -C(=O)-N(piperazin-1-yl)-4-CH₂CH₂CN | OH |
| 213 | 213 | -C(=O)-N(piperazin-1-yl)-4-(4-pyridyl) | OH |
| 214 | 214 | -CH₂-NH-CH₂-(3-pyridyl) · 2HCl | OH |
| 215 | 215 | -CH₂-NH-CH₂CH₂OH · HCl | OH |

TABLE 4-2-continued

Structure: isoindolinone-indole core with R5 at indole 5-position and R3 on benzene ring.

| Example No. | Compound No. | R5 | R3 |
|---|---|---|---|
| 216 | 216 | -CH2-NH-C(Me)2-CH2-NMe2 · 2HCl | OH |
| 217 | 217 | -CH2-(N-piperidinyl-4-carboxamide) · HCl | OH |

TABLE 4-3

Structure: isoindolinone-indole core with R5 at indole 5-position and R3 on benzene ring.

| Example No. | Compound No. | R5 | R3 |
|---|---|---|---|
| 218 | 218 | -CH2-(N-piperidinyl-4-CO2Me) · HCl | OH |
| 219 | 219 | -CH2-(N-piperidinyl) | -O-CH2-CH(OH)-CH2OH |
| 220 | 220 | -CH2-(N-piperazinyl-N'-CH2CH2OH) · 3HCl | -O-CH2CH2CH2-NH2 |
| 221 | 221 | -CH2-(N-(3-hydroxy)piperidinyl) | -O-CH2CH2CH2-NH2 |
| 222 | 222 | -CH2-(N-piperidinyl) · HCl | -O-CH2-C6H5 |

TABLE 4-3-continued

[Structure: isoindolinone with R3 substituent, connected to indole with R5 substituent]

| Example No. | Compound No. | R⁵ | R³ |
|---|---|---|---|
| 223 | 223 | piperidin-1-ylmethyl · HCl | -O-CH₂CH₂-O-CH(Me)₂ (1-methoxyethoxy ethyl ether) |
| 224 | 224 | piperidin-1-ylmethyl · 2HCl | -O-CH₂CH₂CH₂-NMe₂ |
| 225 | 225 | piperidin-1-ylmethyl · 3HCl | -O-CH₂CH₂CH₂-N(4-methylpiperazin-1-yl) |
| 226 | 226 | piperidin-1-ylmethyl · 2HCl | -O-CH₂CH₂-NH₂ |
| 227 | 227 | piperidin-1-ylmethyl · HCl | -O-S(=O)₂-Me |
| 228 | 228 | piperidin-1-ylmethyl · HCl | -O-S(=O)₂-CH₂-Ph |
| 229 | 229 | piperidin-1-ylmethyl · HCl | -O-S(=O)₂-Ph |
| 230 | 230 | piperidin-1-ylmethyl · HCl | -O-S(=O)₂-CH₂-Me |
| 231 | 231 | piperidin-1-ylmethyl · HCl | -O-S(=O)₂-NH₂ |
| 232 | 232 | piperidin-1-ylmethyl | -O-S(=O)₂-CH₂CH₂-NH-Et |

TABLE 4-4
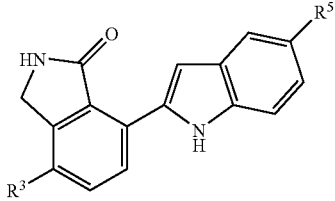
| Example No. | Compound No. | R⁵ | R³ |
|---|---|---|---|
| 233 | 233 | 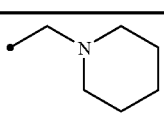 | 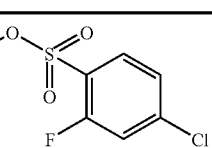 |
| 234 | 234 | 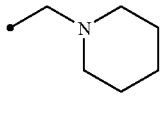 | 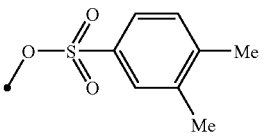 |
| 235 | 235 | 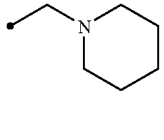 | 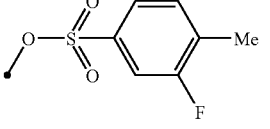 |
| 236 | 236 | 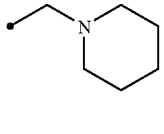 | 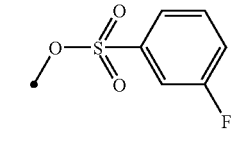 |
| 237 | 237 | 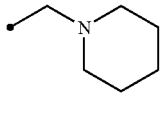 | 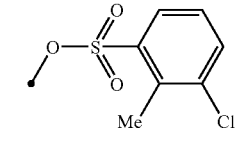 |
| 238 | 238 | 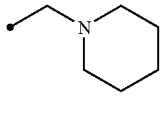 | 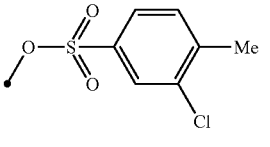 |
| 239 | 239 | 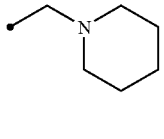 | 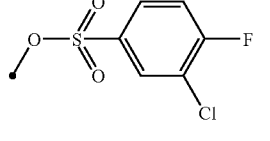 |
| 240 | 240 | 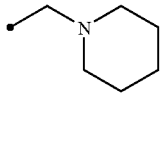 | 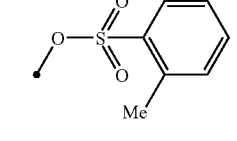 |
| 241 | 241 | 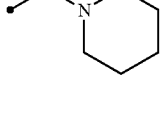 | 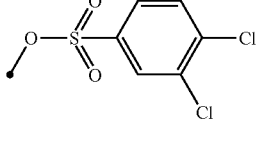 |

TABLE 4-4-continued

| Example No. | Compound No. | R⁵ | R³ |
|---|---|---|---|
| 242 | 242 | CH₂-piperidinyl | -O-SO₂-C₆H₄-4-CF₃ |
| 243 | 243 | CH₂-piperidinyl · HCl | -O-SO₂-C₆H₄-2-Cl |
| 244 | 244 | CH₂-piperidinyl | -O-SO₂-C₆H₄-2-CF₃ |
| 245 | 245 | CH₂-piperidinyl | -O-SO₂-C₆H₄-3-Cl |
| 246 | 246 | CH₂-piperidinyl | -O-SO₂-C₆H₃-2,6-Cl₂ |
| 247 | 247 | CH₂-piperidinyl | -O-SO₂-C₆H₃-2,3-Cl₂ |

TABLE 4-5

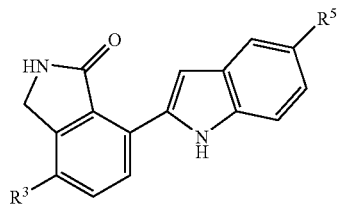

| Example No. | Compound No. | R⁵ | R³ |
|---|---|---|---|
| 248 | 248 | piperidinylmethyl | 5-fluoro-2-methylphenylsulfonyloxy |
| 249 | 249 | piperidinylmethyl | 3-methoxyphenylsulfonyloxy |
| 250 | 250 | piperidinylmethyl | 4-chloro-2,5-difluorophenylsulfonyloxy |
| 251 | 251 | piperidinylmethyl | 2-chloro-4-fluorophenylsulfonyloxy |
| 252 | 252 | piperidinylmethyl | 5-chloro-2,4-difluorophenylsulfonyloxy |
| 253 | 253 | piperidinylmethyl | 2,4-dimethoxyphenylsulfonyloxy |
| 254 | 254 | piperidinylmethyl | 5-chloro-2-methoxyphenylsulfonyloxy |
| 255 | 255 | piperidinylmethyl | 3,5-dimethylisoxazol-4-ylsulfonyloxy |

TABLE 4-5-continued

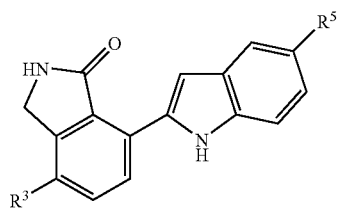

| Example No. | Compound No. | R⁵ | R³ |
|---|---|---|---|
| 256 | 256 | piperidinylmethyl | 2-CF₃-5-Me-furan-3-sulfonyloxy |
| 257 | 257 | piperidinylmethyl HCl | thiophene-3-sulfonyloxy |
| 258 | 258 | piperidinylmethyl | benzothiophene-2-sulfonyloxy |
| 259 | 259 | piperidinylmethyl | 5-Cl-1-Me-3-Me-pyrazole-4-sulfonyloxy |
| 260 | 260 | piperidinylmethyl | 1,3,5-triMe-pyrazole-4-sulfonyloxy |
| 261 | 261 | piperidinylmethyl HCl | pyridine-2-sulfonyloxy |
| 262 | 262 | piperidinylmethyl HCl | $-OSO_2NMe_2$ |

TABLE 4-6

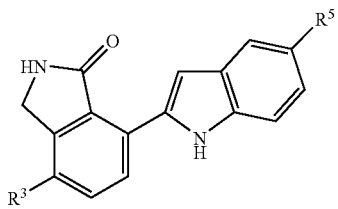

| Example No. | Compound No. | R⁵ | R³ |
|---|---|---|---|
| 263 | 263 | CH₂-piperidine | 4-methoxyphenylsulfonyloxy |
| 264 | 264 | CH₂-piperidine | 4-chlorophenylsulfonyloxy |
| 265 | 265 | CH₂-piperidine | 4-methylphenylsulfonyloxy |
| 266 | 266 | CH₂-piperidine | 3,5-dichlorophenylsulfonyloxy |
| 267 | 267 | CH₂-piperidine | 4-trifluoromethoxyphenylsulfonyloxy |
| 268 | 268 | CH₂-piperidine | 4-tert-butylphenylsulfonyloxy |
| 269 | 269 | CH₂-piperidine | quinolin-8-ylsulfonyloxy |
| 270 | 270 | CH₂-piperidine | 3-trifluoromethylphenylsulfonyloxy |

TABLE 4-6-continued

| Example No. | Compound No. | R⁵ | R³ |
|---|---|---|---|
| 271 | 271 | CH₂-piperidinyl | -O-SO₂-(naphthalen-1-yl) |
| 272 | 272 | CH₂-piperidinyl | -O-SO₂-CH(Me)₂ |
| 273 | 273 | CH₂-piperidinyl | -O-SO₂-(4-bromophenyl) |
| 274 | 274 | CH₂-piperidinyl | -O-SO₂-CH₂-(2-chlorophenyl) |
| 275 | 275 | CH₂-piperidinyl | -O-SO₂-(2-methoxy-4-methylphenyl) |
| 276 | 276 | CH₂-piperidinyl | -O-SO₂-CH=CH-phenyl |
| 277 | 277 | CH₂-piperidinyl | -O-SO₂-(4-methyl-3,4-dihydro-2H-benzo[1,4]oxazin-7-yl) |

TABLE 4-7
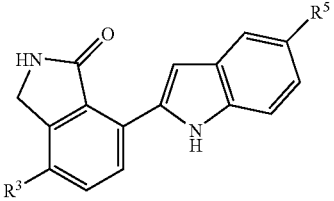
| Example No. | Compound No. | R⁵ | R³ |
|---|---|---|---|
| 278 | 278 | 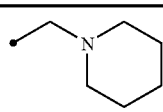 | 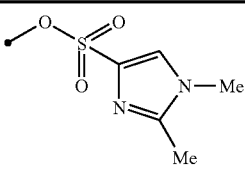 |
| 279 | 279 | 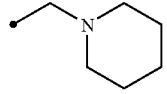 | 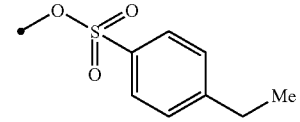 |
| 280 | 280 | 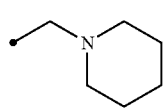 | 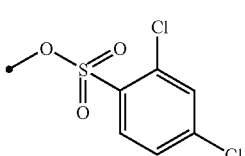 |
| 281 | 281 | 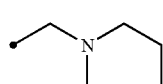 | 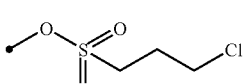 |
| 282 | 282 | 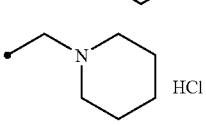 | 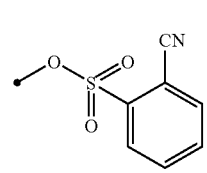 |
| 283 | 283 | 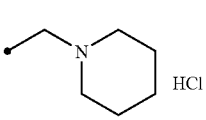 | 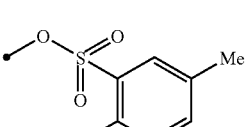 |
| 284 | 284 | 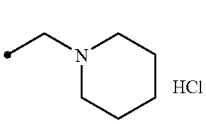 | 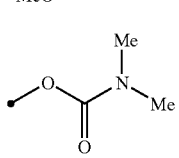 |
| 285 | 285 | 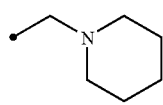 | 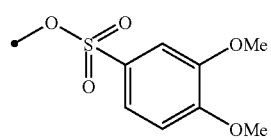 |
| 286 | 286 | 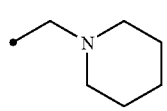 | 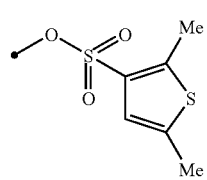 |

TABLE 4-7-continued
| Example No. | Compound No. | R⁵ | R³ |
|---|---|---|---|
| 287 | 287 | 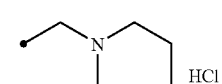 HCl | 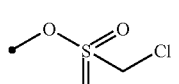 |
| 288 | 288 | 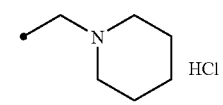 HCl | 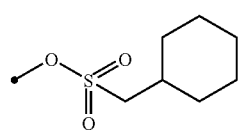 |
| 289 | 289 | 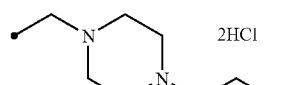 2HCl | 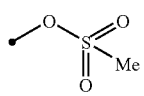 |
| 290 | 290 | 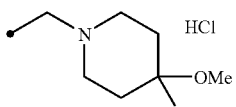 HCl | 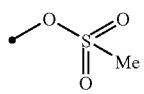 |
| 291 | 291 | 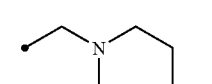 | 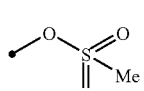 |
| 292 | 292 | 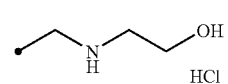 HCl | 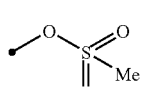 |
TABLE 4-8
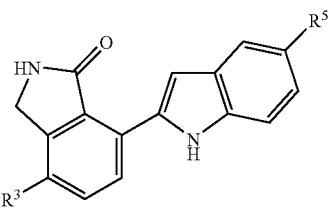
| Example No. | Compound No. | R⁵ | R³ |
|---|---|---|---|
| 293 | 293 | 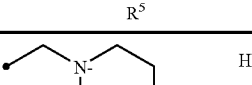 HCl | 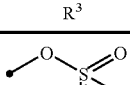 |
| 294 | 294 | 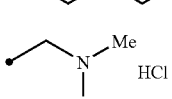 HCl | 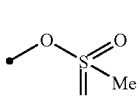 |

TABLE 4-8-continued
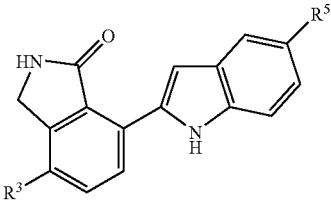
| Example No. | Compound No. | R⁵ | R³ |
|---|---|---|---|
| 295 | 295 | 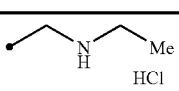 | 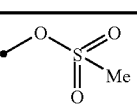 |
| 296 | 296 | 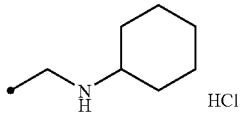 | 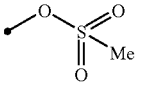 |
| 297 | 297 | 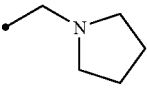 | 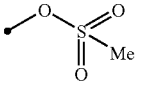 |
| 298 | 298 | 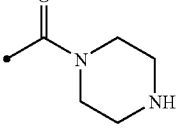 | 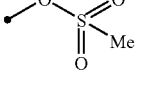 |
| 299 | 299 | 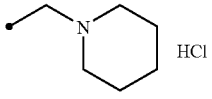 | 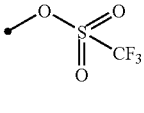 |
| 300 | 300 | 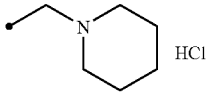 | Et |
| 301 | 301 | 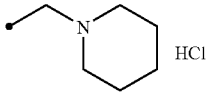 | Me |
| 302 | 302 | 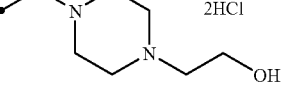 | Et |
| 303 | 303 | 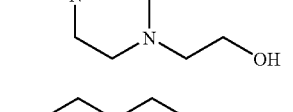 | Me |
| 304 | 304 | 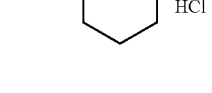 | 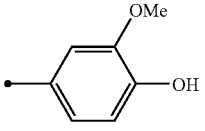 |
| 305 | 305 | 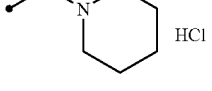 | 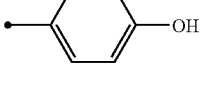 |

TABLE 4-8-continued

[Structure: isoindolinone-indole core with R5 on indole 5-position and R3 on isoindolinone]

| Example No. | Compound No. | R⁵ | R³ |
|---|---|---|---|
| 306 | 306 | piperidin-1-ylmethyl · HCl | 3-hydroxyphenyl |
| 307 | 307 | piperidin-1-ylmethyl · HCl | 4-(acetylamino)phenyl |

TABLE 4-9

[Structure: isoindolinone-indole core with R5 on indole 5-position and R3 on isoindolinone]

| Example No. | Compound No. | R⁵ | R³ |
|---|---|---|---|
| 308 | 308 | piperidin-1-ylmethyl · HCl | 4-(hydroxymethyl)phenyl |
| 309 | 309 | piperidin-1-ylmethyl · HCl | 3,5-dimethyl-4-hydroxyphenyl |
| 310 | 310 | piperidin-1-ylmethyl · HCl | 4-(methylsulfonylamino)phenyl |
| 311 | 311 | piperidin-1-ylmethyl · HCl | 3-acetylphenyl |

TABLE 4-9-continued
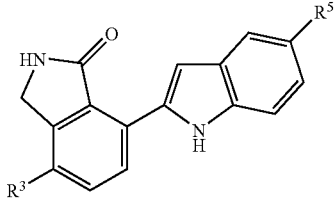
| Example No. | Compound No. | R⁵ | R³ |
|---|---|---|---|
| 312 | 312 |  HCl | 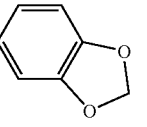 |
| 313 | 313 | 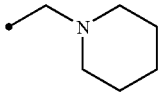 HCl | 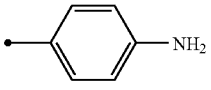 |
| 314 | 314 |  HCl | 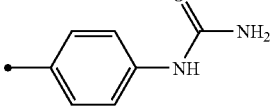 |
| 315 | 315 | 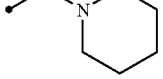 HCl | 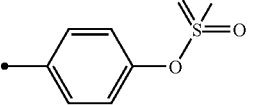 |
| 316 | 316 |  HCl | 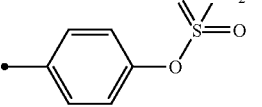 |
| 317 | 317 | 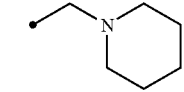 | 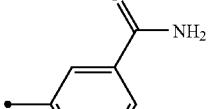 |
| 318 | 318 | 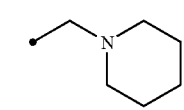 | 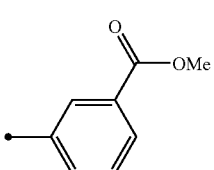 |
| 319 | 319 | 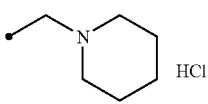 HCl | 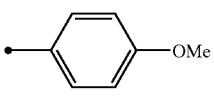 |
| 320 | 320 | 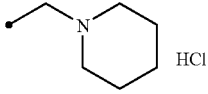 HCl | 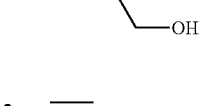 |
| 321 | 321 | 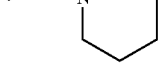 HCl |  |

TABLE 4-9-continued

[Structure: isoindolinone with R3 substituent, connected to indole with R5 substituent at 5-position]

| Example No. | Compound No. | R⁵ | R³ |
|---|---|---|---|
| 322 | 322 | piperidin-1-ylmethyl, 2HCl | -C≡C-CH₂-NHMe |

TABLE 4-10

[Structure: isoindolinone with R3 substituent, connected to indole with R5 substituent at 5-position]

| Example No. | Compound No. | R⁵ | R³ |
|---|---|---|---|
| 323 | 323 | piperidin-1-ylmethyl, HCl | vinyl (-CH=CH₂) |
| 324 | 324 | -CH₂-NH-CH₂CH₂-OH, HCl | Et |
| 325 | 325 | -CH₂-NH-CH₂CH₂-OH, HCl | Me |
| 326 | 326 | 4-(2-hydroxyethyl)piperazin-1-ylmethyl, 2HCl | vinyl (-CH=CH₂) |
| 327 | 327 | 4-(2-hydroxyethyl)piperazin-1-ylmethyl, 2HCl | cyclopropyl |
| 328 | 328 | piperidin-1-ylmethyl, HCl | -CH₂CH₂CH₂-OH |
| 329 | 329 | piperidin-1-ylmethyl, HCl | -C≡C-CH₂-OMe |

TABLE 4-10-continued
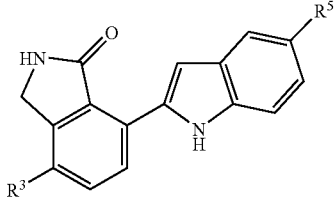
| Example No. | Compound No. | R⁵ | R³ |
|---|---|---|---|
| 330 | 330 | 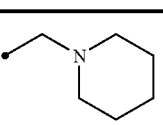 | 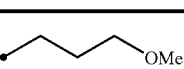 |
| 331 | 331 | 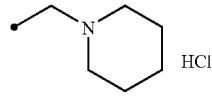 HCl |  |
| 332 | 332 | 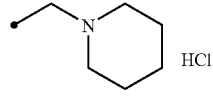 HCl | CN |
| 333 | 333 | 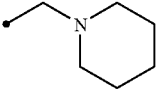 | NH₂ |
| 334 | 334 | 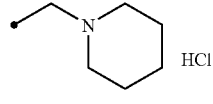 HCl | 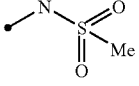 |
| 335 | 335 | 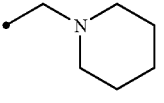 | 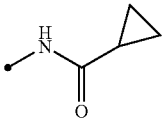 |
| 336 | 336 | 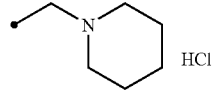 HCl | H |
| 337 | 337 | 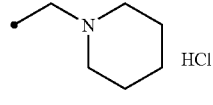 HCl | F |

TABLE 5-1

| Example No. | Compound No. | R² | R³ | R⁵ |
|---|---|---|---|---|
| 338 | 338 | Cl | Cl | CH₂-piperidine · HCl |
| 339 | 339 | Cl | Cl | CH₂-N(piperazine)-CH₂CH₂OH · 2HCl |
| 340 | 340 | F | Cl | CH₂-piperidine · HCl |
| 341 | 341 | OMe | Cl | CH₂-piperidine · HCl |
| 342 | 342 | Me | Cl | CH₂-piperidine · HCl |
| 343 | 343 | OMe | Cl | CH₂-N(piperazine)-CH₂CH₂OH · 2HCl |
| 344 | 344 | OMe | Cl | CH₂NH-C(Me)(Me)-CH₂-NMe₂ · 2HCl |
| 345 | 345 | Me | Cl | CH₂-N(piperazine)-CH₂CH₂OH · 2HCl |
| 346 | 346 | CH₂OMe | OH | CH₂-piperidine · HCl |
| 347 | 347 | OH | Cl | CH₂-piperidine · HCl |
| 348 | 348 | CH₂OMe | OS(O)₂Me | CH₂-piperidine · HCl |

TABLE 5-1-continued

[Structure: 7-(1H-indol-2-yl)-2,3-dihydro-1H-isoindol-1-one core with R² and R³ substituents on the isoindolinone ring and R⁵ on the indole 5-position]

| Example No. | Compound No. | R² | R³ | R⁵ |
|---|---|---|---|---|
| 349 | 349 | CH₂OMe | -O-S(=O)₂-Me | -CH₂-N(Me)Me · HCl |
| 350 | 350 | -O-S(=O)₂-Me | Cl | -CH₂-N(piperazinyl)-CH₂CH₂OH · 2HCl |
| 351 | 351 | OMe | OH | -CH₂-(piperidin-1-yl) · HCl |
| 352 | 352 | OMe | -O-S(=O)₂-Me | -CH₂-(piperidin-1-yl) · HCl |

TABLE 5-2

[Structure: same isoindolinone–indole core with R², R³, R⁵ substituents]

| Example No. | Compound No. | R² | R³ | R⁵ |
|---|---|---|---|---|
| 353 | 353 | Me | OH | -CH₂-(piperidin-1-yl) · HCl |
| 354 | 354 | Me | -O-S(=O)₂-Me | -CH₂-(piperidin-1-yl) · HCl |
| 355 | 355 | OMe | OMe | -CH₂-(piperidin-1-yl) · HCl |
| 356 | 356 | Me | -O-S(=O)₂-Me | -CH₂-N(piperazinyl)-CH₂CH₂OH · 2HCl |

TABLE 5-2-continued
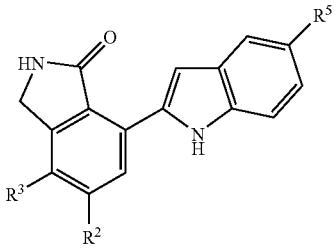
| Example No. | Compound No. | R² | R³ | R⁵ |
|---|---|---|---|---|
| 357 | 357 | OMe | OH | CH₂N(Me)₂ · HCl |
| 358 | 358 | OMe | OH | CH₂-pyrrolidinyl · HCl |
| 359 | 359 | OMe | OH | CH₂N(Et)Me · HCl |
| 360 | 360 | OMe | OH | CH₂NHMe · HCl |
| 361 | 361 | OMe | OS(O)₂Me | CH₂-N(piperazinyl)CH₂CH₂OH · 2HCl |
| 362 | 362 | OMe | OS(O)₂Me | CH₂N(Me)₂ |
| 363 | 363 | OMe | OS(O)₂Me | CH₂NH-cyclopropyl · HCl |
| 364 | 364 | OMe | OS(O)₂Me | CH₂NHEt · HCl |
| 365 | 365 | OMe | OS(O)₂Me | CH₂NH-cyclohexyl |
| 366 | 366 | OMe | OS(O)₂Me | CH₂-pyrrolidinyl |
| 367 | 367 | OMe | OS(O)₂Me | C(O)-piperazinyl-NH |

TABLE 5-3

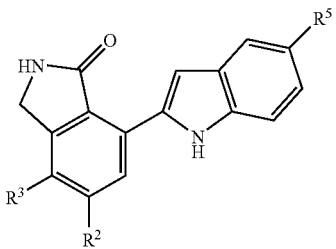

| Example No. | Compound No. | R² | R³ | R⁵ |
|---|---|---|---|---|
| 368 | 368 | OMe | -O-S(=O)₂-Me | 4-methylpiperazin-1-ylmethyl, 2HCl |
| 369 | 369 | OMe | -O-S(=O)₂-Me | -CH₂-NH-C(Me)₂-Me, HCl |
| 370 | 370 | OMe | -O-S(=O)₂-Me | NH₂, HCl |
| 371 | 371 | OMe | -O-S(=O)₂-Me | [1,4'-bipiperidin]-1'-ylmethyl, 2HCl |
| 372 | 372 | OMe | -O-S(=O)₂-Me | (3,5-dimethylpiperidin-1-yl)methyl, HCl |
| 373 | 373 | OMe | -O-S(=O)₂-Me | -CH₂-NH-CH₂-CH₂-Me, HCl |
| 374 | 374 | OMe | -O-S(=O)₂-Me | -CH₂-NH-CH₂-CH₂-OMe, HCl |
| 375 | 375 | OMe | -O-S(=O)₂-Me | -CH₂-NH-Me, HCl |
| 376 | 376 | OMe | -O-S(=O)₂-Me | -CH₂-N(Et)(Me), HCl |
| 377 | 377 | OMe | -O-S(=O)₂-Me | morpholin-4-ylmethyl, HCl |

TABLE 5-3-continued

[Structure: isoindolinone with R³, R² substituents on fused benzene ring, connected to indole bearing R⁵]

| Example No. | Compound No. | R² | R³ | R⁵ |
|---|---|---|---|---|
| 378 | 378 | OMe | -O-S(=O)₂-Me | -CH₂-NH₂ · HCl |
| 379 | 379 | OMe | -O-S(=O)₂-Me | Br |
| 380 | 380 | OMe | -O-S(=O)₂-Me | OH |
| 381 | 381 | OMe | -O-S(=O)₂-Me | H |
| 382 | 382 | OMe | -O-S(=O)₂-Me | -CH₂-NH-C(Me)₂-CH₂-N(Me)Me · 2HCl |

TABLE 5-4

[Structure: isoindolinone with R³, R² substituents, connected to indole bearing R⁵]

| Example No. | Compound No. | R² | R³ | R⁵ |
|---|---|---|---|---|
| 383 | 383 | OMe | -O-S(=O)₂-Me | -CH₂-NH-(CH₂)₃-N(Me)Me · 2HCl |
| 384 | 384 | OMe | -O-S(=O)₂-Me | -CH₂-NH-(4-(2,2,6,6-tetramethylpiperidinyl)) · 2HCl |

TABLE 5-4-continued

[Structure: isoindolin-1-one with R³, R² substituents on one ring and linked to 2-position of indole with R⁵ at 5-position]

| Example No. | Compound No. | R² | R³ | R⁵ |
|---|---|---|---|---|
| 385 | 385 | OMe | -O-S(=O)₂-Me | -CH₂-N(CH₂CH₂OMe)₂ · HCl |
| 386 | 386 | OMe | -O-S(=O)₂-Me | -CH₂-NH-CH₂-(3-pyridyl) · 2HCl |
| 387 | 387 | OMe | -O-S(=O)₂-Me | -CH₂-NH-CH₂-(1-ethylpyrrolidin-2-yl) · 2HCl |
| 388 | 388 | OMe | -O-S(=O)₂-Me | -CH₂-NH-CH₂CH₂-NMe₂ · 2HCl |
| 389 | 389 | OMe | -O-S(=O)₂-Me | -CH₂-N(CH₂CH₂OH)₂ · HCl |
| 390 | 390 | OMe | -O-S(=O)₂-Me | -CH₂-N(Me)-CH₂CH₂-NMe₂ · 2HCl |
| 391 | 391 | OMe | -O-S(=O)₂-Me | -CH₂-N(Me)-CH₂CH₂-NEt₂ · 2HCl |
| 392 | 392 | OMe | -O-S(=O)₂-Me | -CH₂-NH-CH₂CH₂CH₂-NEt₂ · 2HCl |
| 393 | 393 | OMe | -O-S(=O)₂-Me | -CH₂-N(Et)-CH₂CH₂-OH · HCl |
| 394 | 394 | OMe | -O-S(=O)₂-Me | -CH₂-NH-CH₂-Ph · HCl |

TABLE 5-4-continued
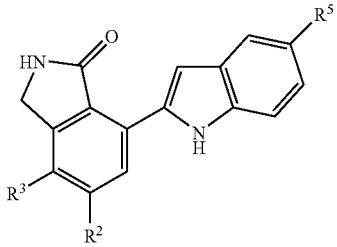
| Example No. | Compound No. | R² | R³ | R⁵ |
|---|---|---|---|---|
| 395 | 395 | OMe | 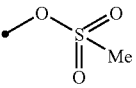 | 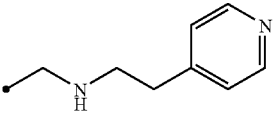<br>2HCl |
| 396 | 396 | OMe | 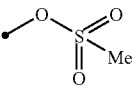 | 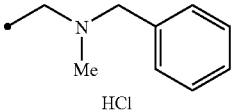<br>HCl |
| 397 | 397 | OMe | 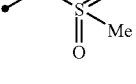 | 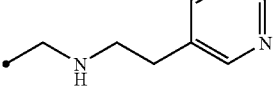<br>2HCl |
TABLE 5-5
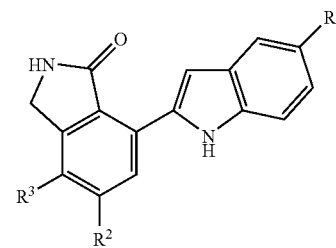
| Example No. | Compound No. | R² | R³ | R⁵ |
|---|---|---|---|---|
| 398 | 398 | OMe | 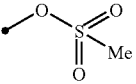 | 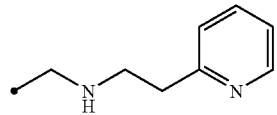<br>2HCl |
| 399 | 399 | OMe | 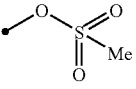 | 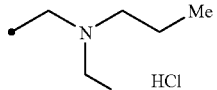<br>HCl |
| 400 | 400 | OMe | 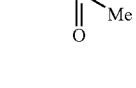 | 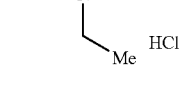<br>HCl |

TABLE 5-5-continued
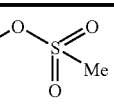
| Example No. | Compound No. | R² | R³ | R⁵ |
|---|---|---|---|---|
| 401 | 401 | OMe | 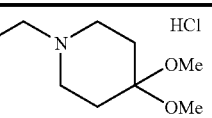 | 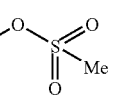 HCl |
| 402 | 402 | OMe | 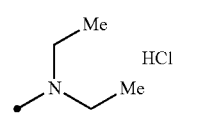 | 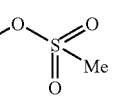 HCl |
| 403 | 403 | OMe | 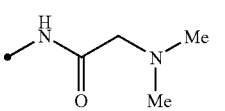 | 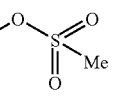 |
| 404 | 404 | OMe | 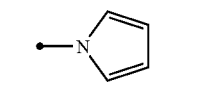 | 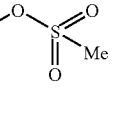 |
| 405 | 405 | OMe | 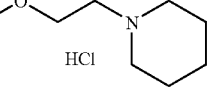 | 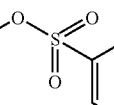 HCl |
| 406 | 406 | OMe | 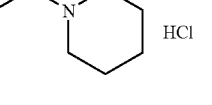 | 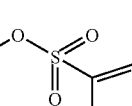 HCl |
| 407 | 407 | OMe | 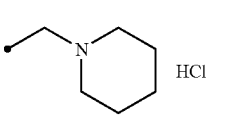 | 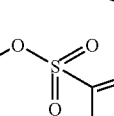 HCl |
| 408 | 408 | OMe | 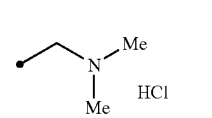 | 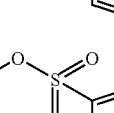 HCl |
| 409 | 409 | OMe | 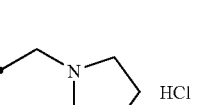 | 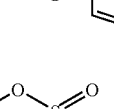 HCl |
| 410 | 410 | OMe | 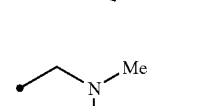 |  HCl |

TABLE 5-5-continued

| Example No. | Compound No. | R² | R³ | R⁵ |
|---|---|---|---|---|
| 411 | 411 | OMe | -O-SO₂-(2-cyanophenyl) | -CH₂-pyrrolidinyl · HCl |
| 412 | 412 | OMe | -O-SO₂-(2-pyridyl) | -CH₂-N(Me)₂ · HCl |

TABLE 5-6

| Example No. | Compound No. | R² | R³ | R⁵ |
|---|---|---|---|---|
| 413 | 413 | OMe | -O-SO₂-(2-pyridyl) | -CH₂-pyrrolidinyl · HCl |
| 414 | 414 | OMe | -O-SO₂-(2-pyridyl) | -CH₂-piperidinyl · HCl |
| 415 | 415 | OMe | -O-SO₂-(3-fluoro-4-methylphenyl) | -CH₂-piperidinyl · HCl |

TABLE 5-6-continued
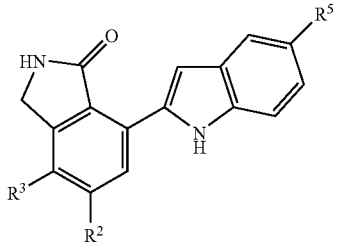
| Example No. | Compound No. | R² | R³ | R⁵ | |
|---|---|---|---|---|---|
| 416 | 416 | OMe | —O—S(=O)₂—NH₂ | pyrrolidinylmethyl | HCl |
| 417 | 417 | OMe | —O—S(=O)₂—NMe₂ | pyrrolidinylmethyl | HCl |
| 418 | 418 | OMe | —O—S(=O)₂—NH₂ | —CH₂—N(Et)(Et) | |
TABLE 6
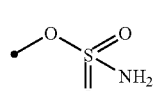
| Example No. | Compound No. | R² | R³ | R⁵ | |
|---|---|---|---|---|---|
| 419 | 419 | OMe | —O—S(=O)₂—Me | —CH₂—NMe₂ | HCl |
| 420 | 420 | OMe | —O—S(=O)₂—Me | —CH₂—N(Et)(Et) | HCl |
| 421 | 421 | OMe | —O—S(=O)₂—Me | —CH₂—NH—CH₂CH₂—OMe | HCl |
| 422 | 422 | OMe | —O—S(=O)₂—Me | pyrrolidinylmethyl | HCl |

TABLE 7-1

[Structure: isoindolin-1-one core with R³ and R² substituents on the benzo ring, linked at the 7-position to a 2-indolyl group bearing R⁵ at the 5-position]

| Example No. | Compound No. | R² | R³ | R⁵ | |
|---|---|---|---|---|---|
| 423 | 423 | vinyl (–CH=CH₂) | Cl | piperidin-1-ylmethyl | HCl |
| 424 | 424 | phenyl | Cl | piperidin-1-ylmethyl | HCl |
| 425 | 425 | furan-2-yl | Cl | piperidin-1-ylmethyl | HCl |
| 426 | 426 | Et | Cl | piperidin-1-ylmethyl | HCl |
| 427 | 427 | 4-(hydroxymethyl)phenyl | Cl | piperidin-1-ylmethyl | HCl |
| 428 | 428 | –OCH₂CH₂CH₂OH | Cl | piperidin-1-ylmethyl | HCl |
| 429 | 429 | –OCH₂CH₂OH | Cl | piperidin-1-ylmethyl | HCl |
| 430 | 430 | –OCH₂CH₂CH₂NHS(O)₂Me | Cl | piperidin-1-ylmethyl | HCl |
| 431 | 431 | –OCH₂CH₂CH₂OH | Cl | –CH₂N(Me)₂ | HCl |
| 432 | 432 | –OCH₂CH₂CH₂OH | Cl | pyrrolidin-1-ylmethyl | HCl |
| 433 | 433 | –OCH₂-(pyridin-3-yl) | Cl | piperidin-1-ylmethyl | 2HCl |

TABLE 7-1-continued
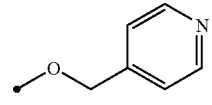
| Example No. | Compound No. | R² | R³ | R⁵ | |
|---|---|---|---|---|---|
| 434 | 434 | 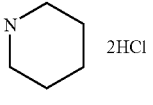 | Cl | 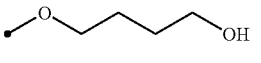 | 2HCl |
| 435 | 435 | 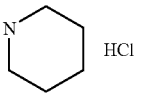 | Cl | 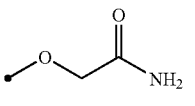 | HCl |
| 436 | 436 | 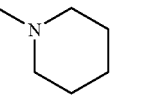 | Cl | 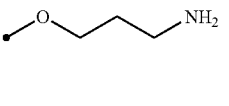 | |
| 437 | 437 | 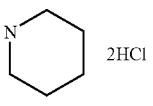 | Cl | 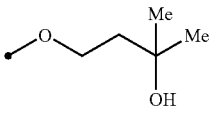 | 2HCl |
TABLE 7-2
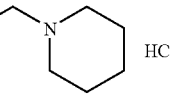
| Example No. | Compound No. | R² | R³ | R⁵ | |
|---|---|---|---|---|---|
| 438 | 438 | 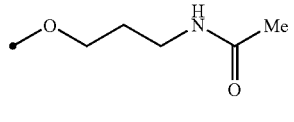 | Cl | 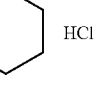 | HCl |
| 439 | 439 | 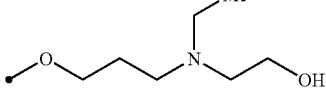 | Cl | 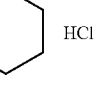 | HCl |
| 440 | 440 | 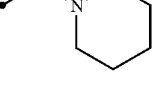 | Cl | 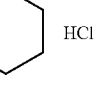 | 2HCl |

TABLE 7-2-continued

| Example No. | Compound No. | R² | R³ | R⁵ | |
|---|---|---|---|---|---|
| 441 | 441 | –O-CH₂-CH(OH)-CH₂-N(piperidine) | Cl | –CH₂-N(piperidine) | 2HCl |
| 442 | 442 | –O-(CH₂)₃-NH-C(O)-NH-Et | Cl | –CH₂-N(piperidine) | HCl |
| 443 | 443 | –O-(CH₂)₃-N(2-(hydroxymethyl)pyrrolidinyl) | Cl | –CH₂-N(piperidine) | 2HCl |
| 444 | 444 | –O-(CH₂)₃-N(4-(hydroxymethyl)piperidinyl) | Cl | –CH₂-N(piperidine) | 2HCl |
| 445 | 445 | –O-(CH₂)₃-N(4-hydroxypiperidinyl) | Cl | –CH₂-N(piperidine) | 2HCl |
| 446 | 446 | –O-(CH₂)₃-NH-C(Me)₂-CH₂OH | Cl | –CH₂-N(piperidine) | 2HCl |
| 447 | 447 | –O-(CH₂)₃-N(morpholinyl) | Cl | –CH₂-N(piperidine) | 2HCl |
| 448 | 448 | –O-(CH₂)₃-N(4-methylpiperazinyl) | Cl | –CH₂-N(piperidine) | 3HCl |
| 449 | 449 | –O-(CH₂)₃-Cl | Cl | –CH₂-N(piperidine) | 3HCl |

TABLE 7-2-continued
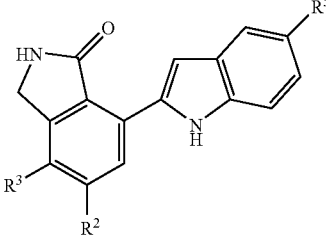
| Example No. | Compound No. | R² | R³ | R⁵ |
|---|---|---|---|---|
| 450 | 450 | OMe | 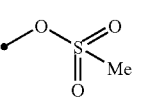 | 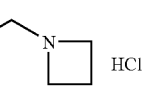 HCl |
| 451 | 451 | OMe | 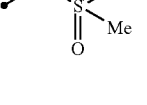 | 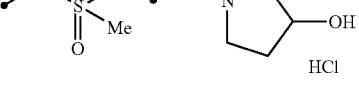 HCl |
| 452 | 452 | OMe | 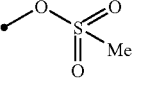 | 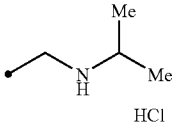 HCl |
TABLE 7-3
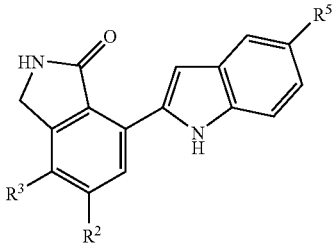
| Example No. | Compound No. | R² | R³ | R⁵ |
|---|---|---|---|---|
| 453 | 453 | OMe | 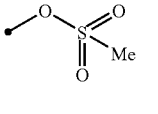 | 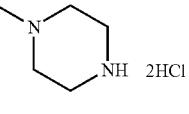 2HCl |
| 454 | 454 | OMe | 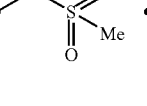 | 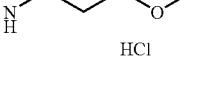 HCl |
| 455 | 455 | OMe | 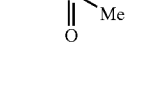 | 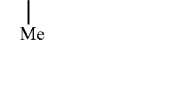 |

TABLE 7-3-continued

| Example No. | Compound No. | R² | R³ | R⁵ |
|---|---|---|---|---|
| 456 | 456 | OMe | –O–S(=O)₂–Me | CO₂H |
| 457 | 457 | OMe | –O–S(=O)₂–Me | 4-methylpiperazin-1-yl (2HCl) |
| 458 | 458 | F | Cl | 4-(2-hydroxyethyl)piperazin-1-ylmethyl (2HCl) |
| 459 | 459 | OMe | –O–S(=O)₂–Me | –(CH₂)₃N(Me)₂ · HCl |
| 460 | 460 | OMe | –O–S(=O)₂–Me | –OCH₂CH(OH)CH₂N(Et)(CH₂CH₂OH) · HCl |

TABLE 8

| Example No. | Compound No. | Structure |
|---|---|---|
| 461 | 461 | (isoindolinone-indole with 5-OH, 6-OMe, 7-OMs substituents) |

TABLE 9

| Example No. | Compound No. | R² | R³ | R⁵ |
|---|---|---|---|---|
| 462 | 462 | H | H | piperidin-1-ylmethyl |

TABLE 9-continued

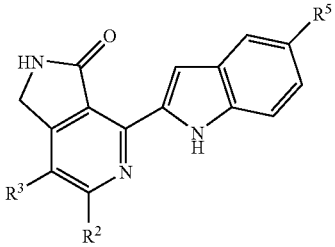

| Example No. | Compound No. | R² | R³ | R⁵ |
|---|---|---|---|---|
| 463 | 463 | H | H | 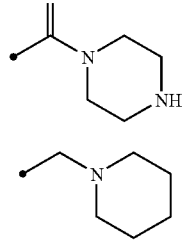 |
| 464 | 464 | H | Cl | 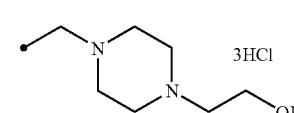 |
| 465 | 465 | H | Cl | 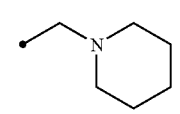 3HCl |
| 466 | 466 | Me | H | 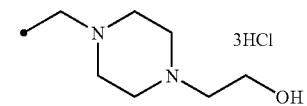 |
| 467 | 467 | Me | H | 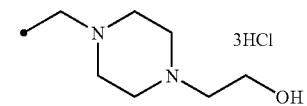 3HCl |

Next, pharmacological actions of Compound (I) will now be described using test examples.

TEST EXAMPLE 1

Fibroblast Growth Factor Receptor 3 (FGFR3) Inhibitory Activity

In order to determine FGFR3 inhibitory activity, the following method was employed. FGFR3 was prepared by allowing baculovirus that expresses a protein in which glutathione S-transferase (GST) was fused to the N-terminal of the intracellular domain (448-759 amino acids) of human FGFR3 to infect insect cells. Biotinylated polyglutamic acid-tyrosine peptide (Nihon Schering K.K., Catalogue No. 61GT0BAA) used as a substrate was immobilized on a 96-well plate coated with NeutroAvidin (Pierce, Catalogue No. 31000) and was then blocked with 0.25% gelatin to yield a plate for the determination of kinase reaction A solution containing, at final concentrations, 8 µg/L GST-fused FGFR3 protein, 20 mmol/L Tris-Cl (pH 7.5), 0.04% 2-mercaptoethanol, 0.04 mmol/L $Na_3VO_4$, 20 mmol/L $MgCl_2$, 5 mmol/L $MnCl_2$, 10 mmol/L ATP, 0.1% bovine serum albumin (BSA; Sigma Corporation, Catalogue No. A4503), 0.1% dimethyl sulfoxide (DMSO), and 10 µmol/L test compound was prepared. Subsequently, 50 µL of the solution was placed in each of the wells of the plate for the determination of kinase reaction, followed by enzymatic reaction at 24° C. for 60 minutes. The plate was washed with TBS-T [10 mM Tris-Cl (pH 7.5), 150 mmol/L NaCl, and 0.05% Tween 20 (Bio-Rad Laboratories Inc., Catalogue No. 170-6531)] four times, and allowed to react with europium-labeled anti-phosphotyrosine antibody (PerkinElmer Inc. Catalogue No. AD0160) at room temperature for 60 minutes. The plate was further washed with TBS-T four times. Subsequently, DELFIA. Enhancement Solution (PerkinElmer Inc. Catalogue No. 1244-105) was added to the plate, and time-resolved fluoroimmunoassay was performed (excitation wavelength: 340 nm, measuring wavelength: 615 nm). The relative activity (%) of a well in which the test compound was added was calculated using the value of a well containing the enzyme and 0.1% DMSO being 100% and the value of a well not containing the enzyme being 0%. The FGFR3 inhibitory activity (%) of the test compound was determined by subtracting the relative activity (%) from 100.

Compounds 22, 24, 29, 32, 139, 143, 231, 321, 357, 362, 366, 374, 375, 376, 407, 412, 417, 431, 454, 455, and 457 exhibited an FGFR3 inhibitory activity of 50% or more at a concentration of 10 µmol/L. This result shows that Compound (I) of the present invention exhibits effective FGFR3 inhibitory activity.

TEST EXAMPLE 2

Aurora Inhibitory Activity Using Western Blotting Method

It is known that Aurora phosphorylates Ser10 of histone H3 in the G2/M phase during the cell cycle [Molecular and Cellular Biology, Vol. 22, p. 874 (2002)]. Consequently, the inhibition of phosphorylation of histone H3 Ser10 in cells was detected by a Western blotting method using human colon cancer cell line HCT116 cells accumulated in the M phase. McCoy's 5A culture medium (GIBCO, Catalogue No. 16600-082) containing 10% bovine fetus serum (GIBCO, Catalogue No. 10099-141) was used for the cultivation of the cells. The HCT116 cells were inoculated and then treated with Nocodazole (Sigma Corporation, Catalogue No. M-1404) so that the cell cycle was accumulated to the M phase. A test compound (final concentration: 10 µmol/L) was added thereto, and the cells were incubated at 37° C. for 30 minutes. The cells were then recovered and washed with a phosphate buffered saline (PBS) once. The cells were suspended in a cell-solubilizing solution (50 mmol/L 2-[4-(2-hydroxyethyl)-1-piperazinyl]ethanesulfonic acid (HEPES) (pH 7.4), 150 mmol/L NaCl, 1 mmol/L ethylenediamine-N,N,N',N'-tetraacetic acid disodium salt dihydrate (EDTA), 2.5 mmol/L ethylene glycol bis(2-aminoethylether)-N,N,N',N'-tetraacetic acid (EGTA), 0.1% Tween-20 (Bio-Rad Laboratories Inc., Catalogue No. 170-6531), 10% β-glycerophosphate, 1 mmol/L NaF, 0.1 mmol/L $Na_3VO_4$, 1 mmol/L Pefabloc SC (Roche Diagnostics K.K., Catalogue No. 1 429 868), and Complete EDTA-free (Roche Diagnostics K.K., Catalogue No. 1 873 580)}, and the suspension was frozen and thawed. Subsequently, the supernatant obtained by centrifugal separation was used as a cell extraction solution. SDS-PAGE was performed using a 12.5% polyacrylamide gel under the condition that the amount of protein per sample was 30 µg in accordance with the method used by Laemmli et al. The protein was transferred onto a PVDF membrane (Millipore Corporation, Catalogue No. IPVH304F0) by a semi-dry method. The membrane was allowed to react with anti-phosphorylated histone H3 Ser10 antibody (Upstate Inc., Catalogue No. 06-570) used as a primary antibody, and an HRP-labeled anti-rabbit IgG antibody (Amersham biosciences, Catalogue No. NA934V) used as a secondary antibody. Subsequently, fluorescence was detected using a SuperSignal West Pico chemiluminescence substrate (Pierce, Catalogue No. 34077). In this test, the weaker the fluorescence intensity, the higher the test compound exhibits Aurora inhibitory activity.

Compounds 22, 24, 29, 32, 139, 143, 231, 321, 357, 362, 366, 374, 375, 376, 407, 412, 417, 431, 454, 455, and 457 almost completely suppressed the phosphorylation of histone H3 Ser10 in HCT116 cells at a concentration of 10 μmol/L. This result shows that Compound (I) of the present invention inhibits Aurora that phosphorylates histone H3 Ser10.

TEST EXAMPLE 3

Evaluation of Aurora Inhibitory Activity by Analysis of Nuclear Morphology

It has been reported that nuclei of cells exhibit a characteristic nuclear phenotype (enlarged lobed nuclei) by inhibiting the function of Aurora [Journal of Cell Biology, Vol. 161, p. 281 (2003)]. Consequently, enlarged lobed nuclei-inducibility of test compounds for HCT116 cells was evaluated. McCoy's 5A culture medium (GIBCO, Catalogue No. 16600-082) containing 10% bovine fetus serum (GIBCO, Catalogue No. 10099-141) was used for the cultivation of the cells. HCT116 cells were inoculated and, 24 hours later, each test compound was added thereto. The cells were in contact with the test compound for 17 hours, and the nuclei of the cells were then stained with Hoechst 33342 (Sigma Corporation, Catalogue No. B-2261) with a final concentration of 10 μmol/L. The karyotype was observed with a fluorescence microscope.

According to the results, it was confirmed that Compounds 22, 24, 29, 32, 139, 143, 231, 321, 357, 362, 366, 374, 375, 376, 407, 412, 417, 431, 454, 455, and 457 show ability of inducing enlarged lobed nuclei for HCT116 cells by treating the HCT116 cells with each of the compounds at a concentration in the range of 0.1 to 1 μmol/L, although the optimal concentration was different in each of the compounds. This result and the result shown in Test Example 2 show that Compound (I) of the present invention has Aurora inhibitory activity in cells.

TEST EXAMPLE 4

Flt-3 Inhibitory Activity

Flt-3 inhibitory activity was determined by a method described below.

Biotinylated polyglutamic acid-tyrosine peptide (Nihon Schering K.K., Catalogue No. 61GT0BAA) used as a substrate was immobilized on a 96-well plate (FIA-PLATE BLACK 96 well FALT-BOTTOM HIGH BINDING, Greiner Bio-one Co., Ltd., Catalogue No. 655077) coated with NeutroAvidin (Pierce, Catalogue No. 31000) and was then blocked with 0.25% gelatin to yield a plate for the determination of kinase reaction. A solution containing, at final concentrations, 8 μg/L His-tagged protein-fused Flt-3 (Upstate Inc., Catalogue No. 14-500), 20 mmol/L Tris-Cl (pH 7.5), 0.04% 2-mercaptoethanol, 0.04 mmol/L $Na_3VO_4$, 20 mmol/L $MgCl_2$, 5 mmol/L $MnCl_2$, 10 μmol/L ATP, 0.1% BSA, 0.1% DMSO, and 10 mol/L test compound was prepared. Subsequently, 50 μL of the solution was placed in each of the wells of the plate for the determination of kinase reaction, followed by enzymatic reaction at 24° C. for 60 minutes. The plate was washed with TBS-T [10 mmol/L Tris-Cl (pH 7.5), 150 mmol/L NaCl, and 0.05% Tween 20 (Bio-Rad Laboratories Inc., Catalogue No. 170-6531)] four times, and allowed to react with europium-labeled anti-phosphotyrosine antibody (PerkinElmer Inc. Catalogue No. AD0160) at room temperature for 60 minutes. The plate was further washed with TBS-T four times. Subsequently, time-resolved fluoroimmunoassay was performed (excitation wavelength: 340 nm, measuring wavelength: 615 nm). The relative activity (%) of a well to which the enzyme and the test compound were added was calculated using the value of a well to which the test compound was not added being 100% and the value of a well to which the enzyme and the test compound were not added being 0%. The Flt-3 inhibitory activity (%) of the test compound was determined by subtracting the relative activity (%) from 100.

Compounds 22, 24, 29, 32, 139, 143, 231, 321, 357, 362, 366, 374, 375, 376, 407, 412, 417, 431, 454, 455, and 457 exhibited an Flt-3 inhibitory activity of 50% or more at a concentration of 10 μmol/L. This result shows that Compound (I) of the present invention exhibits effective Flt-3 inhibitory activity.

TEST EXAMPLE 5

Cytostatic Activity Against Human Multiple Myeloma and Human Stomach Cancer Cell Line The cytostatic rates of test compounds on human multiple myeloma (KMS-11) and human stomach cancer cell line (KATO-III) were determined by a method described below.

Roswell Park Memorial Institute Medium (RPMI) 1640 culture medium (GIBCO, Catalogue No. 11875-093) containing 10% bovine fetus serum (GIBCO, Catalogue No. 10437-028) was used for the cultivation of the cells. Subsequently, an 80 μL of solution of the KMS-11 cells having a concentration of $7.5 \times 10^4$ cells/mL ($2.5 \times 10^4$ cells/mL in the case of the KATO-III cells) was inoculated in each wells of a TC MICROWELL 96U plate (Nalgene Nunc, Catalogue No. 163320). The cells were cultured at 37° C. for 24 hours in a 5% carbon dioxide gas incubator. Subsequently, 20 μL of a DMSO solution of each test compound having a final concentration of 10 μmol/L was added to each of the wells including the KMS-11 cells or the KATO-III cells. The cells were again cultured at 37° C. for 72 hours in a 5% carbon dioxide gas incubator. Subsequently, 20 μL of WST-1 reagent {4-[3-(4-iodophenyl)-2-(4-nitrophenyl)-2H-5-tetrazolio]-1,3-benzene disulfonate sodium salt} (Roche Diagnostics K.K., Catalogue No. 1644807) that was diluted to 50% with the above culture medium was added to each wells, and the mixtures were incubated at 37° C. for 2 hours. Subsequently, the absorbance at 450 nm (reference wavelength: 690 nm) was determined using a microplate spectrophotometer (SPECTRA max 340PC. Molecular Devices Corporation). The cytostatic rate was calculated according to the following formula using the value in a well to which the solvent of the compound solution was added and cultured in the same manner being 100%. A blank sample was prepared by adding WST-1 immediately after the addition of the solvent, and the absorbance of this sample was used as a blank.

$$\text{Cytostatic rate (\%)} = 100 - 100 \times \left(\frac{A - C}{B - C}\right)$$

A: Absorbance measured after treatment with test compound followed by culturing for 72 hours B: Absorbance measured after addition of solvent followed by culturing for 72 hours C: Absorbance measured immediately after addition of solvent The higher the cytostatic rate, the stronger the test compound exhibits a cytostatic activity against the cells.

Compounds 22, 24, 29, 32, 139, and 143 exhibited a cytostatic activity of 50% or more against human multiple myeloma KMS-11 and human stomach cancer cell line KATO-III at a concentration of 10 µmol/L. This result shows that Compound (I) of the present invention exhibits cytostatic activity against human multiple myeloma KMS-11 and human stomach cancer cell line KATO-III.

TEST EXAMPLE 6

Cytostatic Activity Against Human Colon Cancer Cell Line

The cytostatic rates of test compounds on human colon cancer cell lines (HCT116 and COLO205) were determined by a method described below.

McCoy's 5A culture medium (GIBCO, Catalogue No. 16600-082) containing 10% bovine fetus serum (GIBCO, Catalogue No. 10099-141) was used for the cultivation of HCT116 cells. Roswell Park Memorial Institute Medium (RPMI) 1640 culture medium (GIBCO, Catalogue No. 11875-119) containing 10% bovine fetus serum (GIBCO, Catalogue No. 10099-141), 1 mmol/L sodium pyruvate (GIBCO, Catalogue No. 11360-070), 10 mmol/L HEPES (GIBCO, Catalogue No. 15630-080), and 4.5 g/L D-glucose (Sigma Corporation, Catalogue No. G8769) was used for the cultivation of COLO205 cells. Subsequently, a 60 µL solution of HCT116 cells and a 60 µL solution of COLO205 cells each having a concentration of $1.7 \times 10^4$ cells/mL were inoculated in each wells of a TC MICROWELL 96U plate (Nalgene Nunc, Catalogue No. 163320). The cells were cultured at 37° C. for 24 hours in a 5% carbon dioxide gas incubator. Subsequently, 40 µL of a diluent of a test compound having a final concentration of 10 µmol/L was added to each of the wells including the cells. The cells were again cultured at 37° C. for 72 hours in a 5% carbon dioxide gas incubator. Subsequently, 20 µL of WST-1 reagent {4-[3-(4-iodophenyl)-2-(4-nitrophenyl)-2H-5-tetrazolio]-1,3-benzene disulfonate sodium salt} (Roche Diagnostics K.K., Catalogue No. 1644807) that was diluted to 50% with the above culture medium was added to each wells, and the mixtures were incubated at 37° C. for two hours. Subsequently, the absorbance at 450 nm (reference wavelength: 690 nm) was determined using a microplate spectrophotometer (SPECTRA max 340PC, Molecular Devices Corporation). The cytostatic rate was calculated according to the following formula using the value in a well to which the solvent of the compound solution was added and cultured in the same manner being 100%. A blank sample was prepared by adding WST-1 immediately after the addition of the solvent, and the absorbance of this sample was used as a blank.

$$\text{Cytostatic rate (\%)} = 100 - 100 \times \left(\frac{A-C}{B-C}\right)$$

A: Absorbance measured after treatment with test compound followed by culturing for 72 hours B: Absorbance measured after addition of solvent followed by culturing for 72 hours C: Absorbance measured immediately after addition of solvent The higher the cytostatic rate, the stronger the test compound exhibits a cytostatic activity against the cells.

Compounds 22, 24, 29, 32, 139, and 143 exhibited a cytostatic activity of 50% or more against human colon cancer cell lines (HCT 116 and COLO205) at a concentration of 10 µmol/L. This result shows that Compound (I) of the present invention exhibits cytostatic activity against human colon cancer cell lines (HCT 116 and COLO205).

Compound (I) or a pharmaceutically acceptable salt thereof can be used as it is or in various pharmaceutical forms in accordance with the pharmacological action, the purpose of administration, or the like. A pharmaceutical composition of the present invention can be produced by homogeneously mixing Compound (I) or a pharmaceutically acceptable salt thereof in an amount that is effective as an active ingredient with a pharmaceutically acceptable carrier. The forms of this carrier can be in a wide range in accordance with the drug formulation desirable for the administration. The pharmaceutical composition is preferably in a unit dosage form suitable for oral administration or parenteral administration such as injection.

In the preparation of tablets, for example, excipients such as lactose and mannitol, disintegrators such as starch, lubricants such as magnesium stearate, binders such as polyvinyl alcohol and hydroxypropyl cellulose, surfactants such as sucrose fatty acid esters and sorbitol fatty acid esters and the like may be used in accordance with a known procedure. Tablets containing 1 to 200 mg of an active ingredient per tablet are preferred.

In the preparation of injections, water; physiological saline; vegetable oil such as olive oil and peanut oil; solvents such as ethyl oleate and propylene glycol; solubilizing agents such as sodium benzoate, sodium salicylate, and urethane; isotonizing agents such as sodium chloride and glucose; preservatives such as phenol, cresol, p-hydroxybenzoates, and chlorobutanol; and antioxidants such as ascorbic acid and sodium pyrosulfite and the like may be used by a known procedure.

Compound (I) or a pharmaceutically acceptable salt thereof can be administered either orally or parenterally in the form of an injection solution or the like. The effective dose and frequency of administration are different depending on, for example, the dosage form, the age, the weight, and the symptom of a patient. In general, Compound (I) or a pharmaceutically acceptable salt thereof is preferably administered in an amount in the range of 0.01 to 100 mg/kg per day.

The present invention will now be described in further detail using examples and reference examples, but the present invention is not limited thereto.

In proton nuclear magnetic resonance spectra ($^1$H-NMR), exchangeable hydrogen may not be clearly observed in some compounds and under some measuring conditions. With regard to indication of multiplicity of signals, commonly used notation is used here, and br denotes a broad signal when visually observed.

Equipment data of each compound in the examples below was measured using the following analytical instruments.

$^1$H-NMR: JEOL JNM-EX270 (270 MHz) or JEOL JNM-AL300 (300 MHz)

MS: JEOL SX-102AQQ (FAB method) or Micromass Quattro (APCI method)

REFERENCE EXAMPLE 1

Compound BA

Step 1

5-Formylindole (200 mg, 1.38 mmol) was dissolved in acetonitrile (2 mL), and the solution was added with di-tert-butyldicarbonate (0.349 mL, 1.52 mmol) and DMAP (1.7 mg, 0.014 mmol), followed by stirring at room temperature for 1 hour. The solvent was evaporated under reduced pressure, and the residue was dissolved in methanol (2 mL). Trimethyl orthoformate (0.300 mL, 2.75 mmol) and p-toluenesulfonic acid monohydrate (5.2 mg, 0.027 mmol) were added thereto, and the mixture was stirred at room temperature for one hour. An aqueous saturated sodium hydrogen carbonate solution and water were added to the reaction mixture, and the mixture was then extracted with ethyl acetate. The organic layer was washed with saturated brine and then dried over anhydrous sodium sulfate. The solvent was evaporated under reduced pressure to obtain 1-(tert-butoxycarbonyl)-5-(dimethoxymethyl)indole (396 mg, yield 99%).

ESI-MS m/z: 260 [M−CH$_3$O]$^+$; $^1$H-NMR (CDCl$_3$) δ(ppm): 1.67 (s, 9H), 3.34 (s, 6H), 5.50 (s, 1H), 6.57 (d, J=3.7 Hz, 1H), 7.40 (dd, J=1.5, 8.4 Hz, 1H), 7.60 (d, J=3.7 Hz, 1H), 7.66 (d, J=1.5 Hz, 1H), 8.13 (d, J=8.4 Hz, 1H).

Step 2

1-(tert-Butoxycarbonyl)-5-(dimethoxymethyl)indole (396 mg, 1.36 mmol) was dissolved in THF (2 mL), and the solution was added with triisopropyl borate (0.478 mL, 2.07 mmol).

In an argon atmosphere, an LDA-heptane/THF/ethylbenzene solution (2.0 mol/L, 1.73 mL, and 3.5 mmol) was added dropwise at 0° C. over a period of 10 minutes, followed by stirring at the same temperature for 30 minutes. An aqueous saturated ammonium chloride solution (4 mL) and a 10% aqueous potassium hydrogensulfate solution (10 mL) were added to the reaction mixture. The pH of the reaction mixture was adjusted to 2, and the mixture was then stirred at room temperature for 2 hours. The reaction mixture was extracted with ethyl acetate. The organic layer was washed with saturated brine and then dried over anhydrous sodium sulfate. The solvent was then evaporated under reduced pressure. The residue was suspended in diisopropyl ether/hexane (1/1), and the suspension was stirred under ice cooling for 30 minutes. The solid was collected by filtration and washed with diisopropyl ether/hexane (1/1). The product was then dried under reduced pressure to obtain Compound BA (303 mg, yield 77%).

ESI-MS m/z: 288 [M−H]$^−$; $^1$H-NMR (CDCl$_3$) δ(ppm): 1.77 (s, 9H), 6.69 (s, 2H), 7.57 (s, 1H), 7.90 (dd, J=1.8, 8.8 Hz, 1H), 8.13 (d, J=1.8 Hz, 1H), 8.14 (d, J=8.8 Hz, 1H), 10.08 (s, 1H).

REFERENCE EXAMPLE 2

Compound BB

Step 1

Indole-5-carboxylic acid (1.00 g, 6.21 mmol) was dissolved in DMF (10 mL) and the solution was added with EDCI (2.38 g, 12.4 mmol), HOBT monohydrate (839 mg, 6.21 mmol) and 1-(tert-butoxycarbonyl)piperazine (1.73 g, 9.29 mmol), followed by stirring at room temperature for 3.5 hours. The reaction mixture was added with water and extracted with ethyl acetate. The organic layer was washed with saturated aqueous sodium hydrogencarbonate solution, 1 mol/L hydrochloric acid, and saturated brine, and was dried over anhydrous sodium sulfate. The solvent was evaporated under reduced pressure to obtain 5-[4-(tert-butoxycarbonyl)piperazin-1-ylcarbonyl]indole (2.26 g).

Step 2

5-[4-(tert-Butoxycarbonyl)piperazin-1-ylcarbonyl]indole (2.26 g) was dissolved in acetonitrile (20 mL) and the solution was added with di-tert-butyldicarbonate (3.15 mL, 13.7 mmol) and DMAP (84 mg, 0.69 mmol), followed by stirring at room temperature for 1 hour. The solvent was evaporated under reduced pressure, and the residue was purified by flash column chromatography (chloroform/methanol=19/1, 4/1). The obtained solid was dissolved in chloroform, and the solution was added with diisopropyl ether and then stirred under ice-cooling for 1 hour. The obtained solid was collected by filtration, washed with hexane and then dried under reduced pressure to obtain 5-[4-(tert-butoxycarbonyl)piperazin-1-ylcarbonyl]-1-(tert-butoxycarbonyl)indole (1.63 g, yield 61%, 2 steps).

APCI-MS m/z: 430 [M+H]$^+$; $^1$H-NMR (DMSO-d$_6$) δ(ppm): 1.41 (s, 9H), 1.64 (s, 9H), 3.32-3.60 (m, 8H), 6.77 (d, J=3.7 Hz, 1H), 7.37 (dd, J=1.3, 8.4 Hz, 1H), 7.69 (d, J=1.3 Hz, 1H), 7.75 (d, J=3.7 Hz, 1H), 8.09 (d, J=8.4 Hz, 1H).

Step 3

In a similar manner to Step 2 of Reference Example 1, 5-[4-(tert-butoxycarbonyl)piperazin-1-ylcarbonyl]-1-(tert-butoxycarbonyl)indole (200 mg, 0.466 mmol) was dissolved in THF (2 mL), and the solution was treated with triisopropyl borate (0.161 mL, 0.698 mmol) and LDA-heptane/THF/ethylbenzene solution (2.0 mol/L, 0.58 mL, 1.2 mmol). Then, the reaction mixture was added with saturated aqueous ammonium chloride solution (2 mL) and 10% aqueous potassium hydrogensulfate solution (10 mL) to adjust the pH to 2, followed by stirring at room temperature for 20 minutes. The reaction mixture was extracted with ethyl acetate. The organic layer was washed with saturated brine and dried over anhydrous sodium sulfate. The solvent was evaporated under reduced pressure, and the residue was suspended in chloroform/diisopropyl ether/hexane (1/10/10), followed by stirring under ice-cooling for 30 minutes. The solid was collected by filtration, washed with diisopropyl ether and then dried under reduced pressure to obtain Compound BB (201 mg, yield 91%).

ESI-MS m/z: 474 [M+H]$^+$; $^1$H-NMR (CDCl$_3$) δ(ppm): 1.47 (s, 9H), 1.57 (s, 9H), 3.30-3.85 (m, 8H), 6.78 (s, 2H), 7.40 (dd, J=1.7, 8.6 Hz, 1H), 7.48 (s, 1H), 7.67 (d, J=1.7 Hz, 1H), 8.04 (d, J=8.6 Hz, 1H).

REFERENCE EXAMPLE 3

Compound BC

Step 1

5-Formylindole (500 mg, 3.44 mmol) was dissolved in acetonitrile (10 mL), and the solution was added with 1-(tert-butoxycarbonyl)piperazine (961 mg, 5.16 mmol), acetic acid (3.90 mL, 68.1 mmol) and sodium triacetoxyborohydride (3.65 g, 17.2 mmol) little by little, followed by stirring at room temperature for 2 hours. The reaction mixture was added with water and sodium carbonate to adjust the pH to 9, followed by extracting with ethyl acetate. The organic layer was washed with saturated brine and dried over anhydrous sodium sulfate. The solvent was evaporated under reduced pressure and the residue was purified by flash column chromatography (hexane/ethyl acetate=19/1, 7/3, 1/1) to obtain 5-[4-(tert-butoxycarbonyl)piperazin-1-ylmethyl]indole (505 mg, yield 47%).

APCI-MS m/z: 316 [M+H]$^+$; $^1$H-NMR (CDCl$_3$) δ(ppm): 1.44 (s, 9H), 2.42-2.51 (m, 4H), 3.40-3.49 (m, 4H), 3.66 (s, 2H), 6.52 (m, 1H), 7.16 (dd, J=1.6, 8.4 Hz, 1H), 7.21 (m, 1H), 7.35 (d, J=8.4 Hz, 1H), 7.54 (br s, 1H), 8.25 (br s, 1H).

Step 2

In a similar manner to Step 2 of Reference Example 2, 5-[4-(tert-butoxycarbonyl)piperazin-1-ylmethyl]indole (495 mg, 1.57 mmol) was dissolved in acetonitrile (5.0 mL), and the solution was treated with di-tert-butyldicarbonate (1.19 mL, 5.19 mmol) and DMAP (19.2 mg, 0.157 mmol). The reaction mixture was purified by flash column chromatography (hexane/ethyl acetate=19/1, 9/1, 17/3, 7/3, 1/1) to obtain 5-[4-(tert-butoxycarbonyl)piperazin-1-ylmethyl]-1-(tert-butoxycarbonyl)indole (346 mg, yield 53%).

ESI-MS m/z: 416 [M+H]$^+$; $^1$H-NMR (CDCl$_3$) δ(ppm): 1.45 (s, 9H), 1.67 (s, 9H), 2.35-2.46 (m, 4H), 3.37-3.48 (m, 4H), 4.11 (s, 2H), 6.53 (d, J=3.7 Hz, 1H), 7.27 (dd, J=1.8, 8.5 Hz, 1H), 7.48 (br s, 1H), 7.58 (d, J=3.7 Hz, 1H), 8.07 (br d, J=8.5 Hz, 1H).

Step 3

In a similar manner to Step 2 of Reference Example 1, 5-[4-(tert-butoxycarbonyl)piperazin-1-ylmethyl]-1-(tert-butoxycarbonyl)indole (336 mg, 0.809 mmol) was dissolved in THF (2 mL), and the solution was treated with triisopropyl borate (0.280 mL, 1.21 mmol) and LDA-heptane/THF/ethylbenzene solution (2.0 mol/L, 1.01 mL, 2.0 mmol). Then, the reaction mixture was added with saturated aqueous ammonium chloride solution (2 mL) and 10% aqueous potassium hydrogensulfate solution (10 mL) to adjust the pH to 2, followed by stirring at room temperature for 30 minutes. The reaction mixture was added with saturated aqueous sodium hydrogencarbonate solution to adjust the pH to 9, followed by extracting with ethyl acetate. After washing with saturated brine, the organic layer was dried over anhydrous sodium sulfate. The solvent was evaporated under reduced pressure and the residue was suspended in diisopropyl ether/hexane (2/5), followed by stirring at room temperature for 30 minutes. The solid was collected by filtration, washed with hexane and dried under reduced pressure to obtain Compound BC (209 mg, yield 56%).

APCI-MS m/z: 460 [M+H]$^+$; $^1$H-NMR (CDCl$_3$) δ(ppm): 1.45 (s, 9H), 1.74 (s, 9H), 2.37-2.44 (m, 4H), 3.40-3.48 (m, 4H), 3.59 (s, 2H), 6.80 (br s, 2H), 7.33 (dd, J=1.6, 8.6 Hz, 1H), 7.45 (br s, 1H), 7.52 (d, J=1.6 Hz, 1H), 7.96 (d, J=8.6 Hz, 1H).

REFERENCE EXAMPLE 4

Compound BD

Step 1

5-Formylindole (5.50 g, 37.9 mmol) was dissolved in acetonitrile (100 mL), and the solution was added with di-tert-butyldicarbonate (9.60 mL, 41.8 mmol) and DMAP (46.0 mg, 0.377 mmol), followed by stirring at room temperature for 2 hours. The reaction mixture was added with piperidine (13.6 mL, 137 mmol) and acetic acid (39.4 mL, 688 mmol), and then sodium triacetoxyborohydride (36.5 g, 172 mmol) was added thereto little by little, followed by stirring at room temperature for 3 hours. The reaction mixture was added with water and sodium carbonate to adjust the pH to 9, followed by extracting with ethyl acetate. The organic layer was washed with saturated brine and dried over anhydrous sodium sulfate. The solvent was evaporated under reduced pressure and the residue was purified by flash column chromatography (hexane/ethyl acetate=19/1 to 4/1 to 7/3 to 3/2 to 1/1 to 2/3) to obtain 5-(piperidinomethyl)-1-(tert-butoxycarbonyl)indole (7.91 g, yield 66%).

ESI-MS m/z: 315 [M+H]$^+$; $^1$H-NMR (CDCl$_3$) δ(ppm): 1.37-1.48 (m, 2H), 1.54-1.62 (m, 4H), 1.66 (s, 9H), 2.33-2.45 (m, 4H), 3.56 (s, 2H), 6.53 (d, J=3.7 Hz, 1H), 7.27 (dd, J=1.5, 8.4 Hz, 1H), 7.49 (d, J=1.5 Hz, 1H), 7.58 (d, J=3.7 Hz, 1H), 8.05 (d, J=8.4 Hz, 1H).

Step 2

In a similar manner to Step 2 of Reference Example 1, 5-(piperidinomethyl)-1-(tert-butoxycarbonyl)indole (7.91 g, 25.2 mmol) was dissolved in THF (80 mL), and the solution was treated with triisopropyl borate (8.72 mL, 37.8 mmol) and LDA-heptane/THF/ethylbenzene solution (2.0 mol/L, 31.5 mL, 63 mmol). The reaction mixture was added with saturated aqueous ammonium chloride solution (80 mL) and 10% aqueous potassium hydrogensulfate solution (300 mL) to adjust the pH to 2, followed by stirring at room temperature for 2 hours. The reaction mixture was added with saturated aqueous sodium hydrogencarbonate solution to adjust the pH to 9, followed by extracting with ethyl acetate. The organic layer was washed with saturated brine and dried over anhydrous sodium sulfate. The solvent was evaporated under reduced pressure and the residue was suspended in hexane, followed by stirring at room temperature for 30 minutes. The solid was collected by filtration, washed with hexane and dried under reduced pressure to obtain Compound BD (6.59 g, yield 73%).

ESI-MS m/z: 359 [M+H]$^+$; $^1$H-NMR (CDCl$_3$) δ(ppm): 1.32-1.48 (m, 2H), 1.52-1.76 (m, 4H), 1.73 (s, 9H), 2.33-2.45 (m, 4H), 3.56 (s, 2H), 6.91 (br s, 2H), 7.34 (dd, J=1.7, 8.6 Hz, 1H), 744 (s, 1H), 7.52 (d, J=1.7 Hz, 1H), 7.94 (d, J=8.6 Hz, 1H).

REFERENCE EXAMPLE 5

Compound BE

Step 1

Indole-5-carboxylic acid (4.09 g, 25.4 mmol) was dissolved in DMF (200 mL), and the solution was added with EDCI (9.74 g, 50.8 mmol) and HOBT monohydrate (1.95 g, 12.7 mmol) under ice-cooling, followed by stirring at the same temperature for 10 minutes. Then, the reaction mixture was added with N-methylpiperazine (8.45 mL, 76.2 mmol), followed by stirring at room temperature for 3.7 hours. The reaction mixture was added with water and extracted with ethyl acetate and chloroform. The organic layer was washed with saturated brine and was dried over anhydrous sodium sulfate. The solvent was evaporated under reduced pressure and the residue was purified by flash column chromatography (chloroform/methanol=100/0, 90/10) to obtain 5-(4-methylpiperazin-1-ylcarbonyl)indole (5.81 g, yield 94%).

APCI-MS m/z: 244 [M+H]$^+$; $^1$H-NMR (CDCl$_3$) δ(ppm): 2.33 (s, 3H), 2.43 (m, 4H), 3.69 (m, 4H), 6.58 (m, 1H), 7.24-7.28 (m, 2H), 7.38 (d, J=8.4 Hz, 1H), 7.73 (s, 1H), 8.48 (s, 1H).

Step 2

5-(4-Methylpiperazin-1-ylcarbonyl)indol (5.80 g, 23.8 mmol) was dissolved in acetonitrile (170 mL), and the solution was added with di-tert-butyldicarbonate (15.6 g, 71.4 mmol) and DMAP (2.91 g, 23.8 mmol), followed by stirring at room temperature for 230 minutes. The reaction mixture was added with water and extracted with ethyl acetate. The organic layer was washed with saturated brine and was dried over anhydrous sodium sulfate. The solvent was evaporated under reduced pressure and the residue was purified by silica gel column chromatography (chloroform/methanol=95/5, 90/10) to obtain 5-(4-methylpiperazin-1-ylcarbonyl)-1-(tert-butoxycarbonyl)indole (7.83 g, yield 96%).

APCI-MS m/z: 344 [M+H]$^+$; $^1$H-NMR (CDCl$_3$) δ(ppm): 1.68 (s, 9H), 2.32 (s, 3H), 2.42 (m, 4H), 3.68 (m, 4H), 6.59 (dd, J=0.7, 3.7 Hz, 1H), 7.35 (dd, J=1.7, 8.5 Hz, 1H), 7.64 (m, 2H), 8.16 (d, J=8.6 Hz, 1H).

Step 3

5-(4-Methylpiperazin-1-ylcarbonyl)-1-(tert-butoxycarbonyl)indole (545 mg, 1.59 mmol) was dissolved in THF (27 mL), and the solution was added with tert-butyllithium-pentane solution (1.44 mol/L, 2.43 mL, 3.50 mmol) by drops for 5 minutes at −78° C., followed by stirring at the same temperature for 2 hours. Then, the solution was added with trimethyl borate (0.281 mL, 2.39 mmol), and the mixture was warmed from −78° C. to room temperature for 4.7 hours. The reaction mixture was added with 4 mol/L hydrochloric acid (3.98 mL), stirred for 10 minutes and then added with saturated aqueous sodium hydrogencarbonate solution, followed by extracting with ethyl acetate. The organic layer was washed with saturated brine and dried over anhydrous sodium sulfate. The solvent was evaporated under reduced pressure. The residue was purified by slurry using diisopropyl ether, then purified by preparative thin-layer chromatography (chloroform/methanol 12/5) to obtain Compound BE (107 mg, yield 17%).

APCI-MS m/z: 388 [M+H]$^+$; $^1$H-NMR (CDCl$_3$) δ(ppm): 1.75 (s, 9H), 2.33 (s, 3H), 2.43 (m, 4H), 3.49-3.76 (m, 4H), 7.41 (dd, J=1.7, 8.7 Hz, 1H), 7.48 (s, 1H), 7.67 (d, J=1.1 Hz, 1H), 8.03 (d, J=8.8 Hz, 1H).

REFERENCE EXAMPLE 6

Compound BF

In a similar manner to Step 2 of Reference Example 1, 5-bromo-1-(tert-butoxycarbonyl)indole (1.00 g, 3.38 mmol) was dissolved in THF (5 mL), and the solution was treated with triisopropyl borate (1.17 mL, 5.07 mmol) and LDA-heptane/THF/ethylbenzene solution (2.0 mol/L, 2.54 mL, 5.1 mmol). The reaction mixture was added with 2 mol/L hydrochloric acid (10 mL), followed by stirring under ice-cooling for 2 hours. The reaction mixture was extracted with ethyl acetate. The organic layer was washed with saturated brine and dried over anhydrous sodium sulfate. The solvent was evaporated under reduced pressure. The residue was suspended in hexane/diisopropyl ether (5/1), then the solid was collected by filtration and washed with hexane, followed by drying under reduced pressure to obtain Compound BF (1.02 g, yield 89%).

APCI-MS m/z: 340 [M+H]$^+$; $^1$H-NMR (CDCl$_3$) δ(ppm): 1.74 (s, 9H), 6.92 (s, 2H), 7.40 (s, 1H), 7.43 (dd, J=1.8, 9.2 Hz, 1H), 7.73 (d, J=1.8 Hz, 1H), 7.87 (d, J=9.2 Hz, 1H).

REFERENCE EXAMPLE 7

Compound BG

5-Bromo-1-(tert-butoxycarbonyl)indole (10.0 g, 33.8 mmol) was dissolved in THF (100 mL), and the residue was added with n-butyllithium-hexane solution (2.71 mol/L, 13.7 mL, 37.1 mmol) by drops to the solution for 10 minutes at −78° C., followed by stirring at the same temperature for 20 minutes. The mixture was added with triisopropyl borate (8.58 mL, 37.2 mmol) at −78° C., followed by stirring at the same temperature for 45 minutes. The mixture was added with n-butyllithium-hexane solution (2.71 mol/L, 13.7 mL, 37.1 mmol) by drops for 10 minutes at −78° C., followed by stirring at the same temperature for 10 minutes. The atmosphere in the reaction vessel was substituted with carbon dioxide, followed by stirring at 78° C. for 1 hour, then the mixture was warmed to room temperature, followed by stirring at the same temperature for 1 hour. The reaction mixture was added with saturated aqueous ammonium chloride solution (20 mL) and 10% aqueous potassium hydrogensulfate solution (120 mL) to adjust the pH to 2, followed by stirring at room temperature for 1 hour. The mixture was extracted with ethyl acetate. The organic layer was washed with saturated brine and dried over anhydrous sodium sulfate. The solvent was evaporated under reduced pressure. The residue was suspended in hexane/chloroform (2/1), and the suspenton was stirred under ice-cooling for 1 hour. The solid was collected by filtration and washed with hexane, followed by drying under reduced pressure to obtain Compound BG (4.45 g, yield 43%).

ESI-MS m/z: 304 [M−H]$^−$; $^1$H-NMR (DMSO-d$_6$) δ(ppm): 1.60 (s, 9H), 6.74 (s, 1H), 7.87 (dd, J=1.8, 8.8 Hz, 1H), 8.13 (d, J=8.8 Hz, 1H), 8.18 (d, J=1.8 Hz, 1H), 8.27 (s, 2H).

REFERENCE EXAMPLE 8

Compound BH

Step 1

In a similar manner to Step 1 of Reference Example 2, indole-6-carboxylic acid (200 mg, 1.24 mmol) was dissolved in DMF (2 mL), and the solution was treated with EDCI (475 mg, 2.48 mmol), HOBT monohydrate (168 mg, 1.24 mmol) and 1-(tert-butoxycarbonyl)piperazine (461 mg, 2.48 mmol) to obtain 6-[4-(tert-butoxycarbonyl)piperazin-1-ylcarbonyl]indole (529 mg).

Step 2

In a similar manner to Step 2 of Reference Example 2, 6-[4-(tert-butoxycarbonyl)piperazin-1-ylcarbonyl]indole (529 mg) was dissolved in acetonitrile (5 mL), and the solution was treated with di-tert-butyldicarbonate (0.740 mL, 3.22 mmol) and DMAP (20 mg, 0.16 mmol), followed by purification by flash column chromatography (hexane/ethyl acetate=19/1, 9/1, 4/1) to obtain 6-[4-(tert-butoxycarbonyl)piperazin-1-ylcarbonyl]-1-(tert-butoxycarbonyl)indole (518 mg, yield 97%, 2 Steps).

APCI-MS m/z: 430 [M+H]$^+$; $^1$H-NMR (CDCl$_3$) δ(ppm): 1.47 (s, 9H), 1.67 (s, 9H), 3.24-3.93 (m, 8H), 6.59 (d, J=3.5 Hz, 1H), 7.29 (dd, J=1.5, 8.1 Hz, 1H), 7.59 (d, J=8.1 Hz, 1H), 7.66 (d, J=3.5 Hz, 1H), 8.26 (br s, 1H).

Step 3

In a similar manner to Step 2 of Reference Example 1, 6-[4-(tert-butoxycarbonyl)piperazin-1-ylcarbonyl]-1-(tert-butoxycarbonyl)indole (224 mg, 0.522 mmol) was dissolved in THF (2 mL), and the solution was treated with triisopropyl borate (0.181 mL, 0.784 mmol) and LDA-heptane/THF/ethylbenzene solution (2.0 mol/L, 0.652 mL, 1.3 mmol). Then, the reaction mixture was added with saturated aqueous ammonium chloride solution (2 mL) and 10% aqueous potassium hydrogensulfate solution (5 mL) to adjust the pH to 2, followed by stirring at room temperature for 30 minutes. The reaction mixture was extracted with ethyl acetate. The organic layer was washed with saturated brine and dried over anhydrous sodium sulfate. The solvent was evaporated under reduced pressure. The residue was dissolved in chloroform, and the solution was added with diisopropyl ether and stirred under ice-cooling for 30 minutes. The solid was collected by filtration, washed with diisopropyl ether and then dried under reduced pressure to obtain Compound BH (95.7 mg, yield 39%).

ESI-MS m/z: 474 [M+H]$^+$; $^1$H-NMR (DMSO-d$_6$) δ(ppm): 1.40 (s, 9H), 1.59 (s, 9H), 3.33-3.57 (m, 8H), 6.67 (s, 1H), 7.24 (dd, J=1.1, 7.9 Hz, 1H), 7.61 (d, J=7.9 Hz, 1H), 8.12 (s, 1H), 8.26 (s, 2H).

REFERENCE EXAMPLE 9

Compound BI

Step 1

5-Hydroxyindole (200 mg, 1.50 mmol) was dissolved in DMF (2.0 mL), and the solution was added with potassium carbonate (622 mg, 4.50 mmol) and 4-(2-chloroethyl)morpholine hydrochloride (335 mg, 1.80 mmol), followed by stirring at 60° C. for 3 hours. Then, the mixture was added with potassium carbonate (622 mg, 4.50 mmol) and 4-(2-chloroethyl)morpholine hydrochloride (223 mg, 1.20 mmol), followed by stirring at 60° C. 5 hours. The reaction mixture was added with water and extracted with ethyl acetate. The organic layer was washed with saturated brine and dried over anhydrous sodium sulfate. The solvent was evaporated under reduced pressure. The residue was dissolved in acetonitrile (2.0 mL), and the solution was added with di-tert-butyldicarbonate (0.494 mL, 2.15 mmol) and DMAP (1.8 mg, 0.015 mmol), followed by stirring at room temperature for 20 hours. The solvent was evaporated under reduced pressure and the residue was purified by flash column chromatography (hexane/ethyl acetate=19/1, 4/1, 7/3, 3/2) to obtain 5-[2-(morpholin-4-yl)ethoxy]-1-(tert-butoxycarbonyl)indole (369 mg, yield 71%).

ESI-MS m/z: 347 [M+H]$^+$; $^1$H-NMR (CDCl$_3$) δ(ppm): 1.66 (s, 9H), 2.47-2.55 (m, 4H), 2.83 (t, J=5.5 Hz, 2H), 3.79-3.80 (m, 4H), 4.16 (t, J=5.5 Hz, 2H), 6.48 (d, J=3.7 Hz, 1H), 6.83 (dd, J=2.6, 8.8 Hz, 1H), 7.03 (d, J=2.6 Hz, 1H), 7.56 (d, J=3.7 Hz, 1H), 8.01 (d, J=8.8 Hz, 1H).

Step 2

In a similar manner to Step 2 of Reference Example 1, 5-[2-(morpholin-4-yl)ethoxy]-1-(tert-butoxycarbonyl)indole (359 mg, 1.04 mmol) was dissolved in THF (10 mL), and the solution was treated with triisopropyl borate (0.360 mL, 1.56 mmol) and LDA-heptane/THF/ethylbenzene solution (2.0 mol/L, 1.30 mL, 2.6 mmol). The reaction mixture was added with saturated aqueous ammonium chloride solution (3 mL) and 10% aqueous potassium hydrogensulfate solution (15 mL) to adjust the pH to 2, followed by stirring at room temperature for 30 minutes. The reaction mixture was added with saturated aqueous sodium hydrogencarbonate solution to adjust the pH to 9, followed by extracting with ethyl acetate. The organic layer was washed with saturated brine and dried over anhydrous sodium sulfate. The solvent was evaporated under reduced pressure. The residue was dissolved in chloroform, and the solution was added with diisopropyl ether under ice-cooling and stirred for 30 minutes. The solid was collected by filtration, washed with diisopropyl ether and then dried under reduced pressure to obtain Compound BI (347 mg, yield 86%).

APCI-MS m/z: 391 [M+H]$^+$; $^1$H-NMR (CDCl$_3$) δ(ppm): 1.73 (s, 9H), 2.56-2.61 (m, 4H), 2.84 (t, J=5.8 Hz, 2H), 3.70-3.80 (m, 4H), 4.17 (t, J=5.8 Hz, 2H), 6.84 (br s, 2H), 6.97 (dd, J=2.6, 9.1 Hz, 1H), 7.04 (d, J=2.6 Hz, 1H), 7.39 (s, 1H), 7.88 (d, J=9.1 Hz, 1H).

REFERENCE EXAMPLE 10

Compound BJ

Step 1

5-Formylindole (2.00 g, 13.8 mmol) was dissolved in acetonitrile (40 mL), and the solution was added with di-tert-butyldicarbonate (3.31 g, 15.2 mmol) and DMAP (16.8 mg, 0.138 mmol), followed by stirring at room temperature for 2.7 hours. The solution was added with a solution of N-(2-hydroxyethyl)piperazine (6.46 g, 49.6 mmol) in acetonitrile (15 mL), and acetic acid (14.2 mL, 248 mmol), then sodium triacetoxyborohydride (13.1 g, 62.0 mmol) was added thereto little by little, followed by stirring at room temperature for 2.5 hours. The reaction mixture was added with water and sodium carbonate to adjust the pH to 9, and extracted with ethyl acetate. The organic layer was washed with saturated brine and dried over anhydrous sodium sulfate. The solvent was evaporated under reduced pressure. The residue was purified by flash column chromatography (chloroform/methanol=9/1, 4/1) to obtain 5-[4-(2-hydroxyethyl)piperazin-1-ylmethyl]indole (4.73 g, yield 95%).

APCI-MS m/z: 360 [M+H]$^+$; $^1$H-NMR (CDCl$_3$) δ(ppm): 1.67 (s, 9H), 2.06-2.63 (m, 10H), 3.63 (m, 4H), 6.54 (d, J=3.8 Hz, 1H), 7.28 (m, 1H), 7.50 (s, 1H), 7.58 (d, J=3.6 Hz, 1H), 8.08 (d, J=8.6 Hz, 1H).

Step 2

In a similar manner to Step 2 of Reference Example 1, 5-[4-(2-hydroxyethyl)piperazin-1-ylmethyl]indole (956 mg, 2.66 mmol) was dissolved in THF (29 mL), and the solution was treated with triisopropyl borate (1.23 mL, 5.32 mmol) and LDA (2 mol/L, 6.65 mL, 13.3 mmol), followed by purification by slurry using hexane to obtain Compound BJ (663 mg, yield 62%).

ESI-MS m/z: 404 [M+H]$^+$; $^1$H-NMR (CDCl$_3$) δ(ppm): 1.72 (s, 9H), 2.54 (m, 10H), 3.60 (m, 4H), 7.15-7.32 (m, 2H), 7.51 (m, 1H), 7.95 (d, J=8.6 Hz, 1H).

REFERENCE EXAMPLE 11

Compound BK

1-Methylindole (200 mg, 1.52 mmol) was dissolved in THF (5 mL), and the solution was added with tert-butyl-lithium-pentane solution (1.48 mol/L, 1.23 mL, 1.82 mmol) by drops at −78° C. for 5 minutes under argon atmosphere. The mixture was warmed to room temperature, followed by stirring for 30 minutes. The mixture was cooled to −78° C. again, added with triisopropyl borate (0.526 mL, 2.28 mmol) and warmed from −78° C. to room temperature for 1 hour. The reaction mixture was added with saturated aqueous ammonium chloride solution (5 mL) and 10% aqueous potassium hydrogensulfate solution (5 mL) to adjust the pH to 2, followed by stirring at room temperature for 30 minutes. The mixture was extracted with ethyl acetate. The organic layer was washed with saturated brine and dried over anhydrous sodium sulfate. The solvent was evaporated under reduced pressure. The residue was suspended in diisopropyl ether, then the solid was collected by filtration, washed with diisopropyl ether and then dried under reduced pressure to obtain Compound BK (144 mg, yield 54%).

ESI-MS m/z: 174 [M−H]−; $^1$H-NMR (CDCl$_3$) δ(ppm): 4.01 (s, 3H), 4.73 (br s, 2H), 6.97 (d, J=0.7 Hz, 1H), 7.17 (m, 1H), 7.27-7.42 (m, 3H).

REFERENCE EXAMPLE 12

Compound BL

Step 1

Indole-5-carboxylic acid (200 mg, 1.24 mmol) was dissolved in DMF (2 mL), and the solution was added with 60% sodium hydride-mineral oil dispersant (164 mg, 4.1 mmol), followed by stirring at room temperature for 10 minutes. The mixture was added with methyl iodide (0.258 mL, 0.410 mmol), stirred at room temperature for 3 hours and then added with 4 mol/L aqueous potassium hydroxide solution (2 mL), followed by stirring at 80° C. for 5 hours. The reaction mixture was added with water, and the organic layer was separated from aqueous layer. The aqueous layer was added with 1 mol/L hydrochloric acid to adjust the pH to 1, followed by stirring at room temperature for 1 hour. The obtained solid was collected by filtration and dried under reduced pressure to obtain 1-methylindole-5-carboxylic acid (142 mg, yield 65%).

APCI-MS m/z: 174 [M−H]−; $^1$H-NMR (DMSO-d$_6$) δ(ppm): 3.83 (s, 3H), 6.57 (d, J=3.0 Hz, 1H), 7.43 (d, J=3.0 Hz, 1H), 7.50 (d, J=8.6 Hz, 1H), 7.76 (dd, J=1.6, 8.6 Hz, 1H), 8.22 (d, J=1.6 Hz, 1H), 12.49 (br s, 1H).

Step 2

In a similar manner to Reference Example 11, 1-methylindole-5-carboxylic acid (100 mg, 0.571 mmol) was dissolved in THF (5 mL), and the solution was treated with tert-butyllithium-pentane solution (1.48 mol/L, 0.970 mL, 1.44 mmol) and triisopropylborate (0.198 mL, 0.858 mmol). The reaction mixture was added with saturated aqueous ammonium chloride solution (5 mL) and 10% aqueous potassium hydrogensulfate solution (5 mL) to adjust the pH to 2, and the mixture was stirred at room temperature for 30 minutes, followed by extracting with ethyl acetate. The organic layer was washed with saturated brine and dried over anhydrous sodium sulfate. The solvent was evaporated under reduced pressure. The residue was suspended in diisopropyl ether, and the solid was collected by filtration, washed with diisopropyl ether and then dried under reduced pressure to obtain Compound BL (75.0 mg, yield 60%).

APCI-MS m/z: 220 [M+H]+; $^1$H-NMR (DMSO-d$_6$) δ(ppm): 3.96 (s, 3H), 7.19 (s, 1H), 7.49 (d, J=8.9 Hz, 1H), 7.77 (dd, J=1.7, 8.9 Hz, 1H), 8.23 (d, J=1.7 Hz, 1H), 8.40 (br s, 2H), 12.42 (br s, 1H).

REFERENCE EXAMPLE 13

Compound BM

Step 1

In a similar manner to Step 1 of Reference Example 12, indole-6-carboxylic acid (200 mg, 1.24 mmol) was dissolved in DMF (2 mL), and the solution was treated with 60% sodium hydride-mineral oil dispersant (109 mg, 2.71 mmol), methyl iodide (0.258 mL, 0.410 mmol) and 4 mol/L aqueous potassium hydroxide solution (2 mL). The reaction mixture was added with water and separated into aqueous layer and organic layer, and the organic layer was removed. The aqueous layer was added with 1 mol/L hydrochloric acid to adjust the pH to 1, followed by stirring at room temperature for 1 hour. The obtained solid was collected by filtration and dried under reduced pressure to obtain 1-methylindole-6-carboxylic acid (154 mg, yield 71%).

APCI-MS m/z: 174 [M−H]−; $^1$H-NMR (DMSO-d$_6$) δ(ppm): 3.86 (s, 3H), 6.50 (dd, J=0.7, 3.1 Hz, 1H), 7.54 (d; J=3.1 Hz, 1H), 7.60 (dd, J=0.7, 8.4 Hz, 1H), 7.64 (dd, J=1.3, 8.4 Hz, 1H), 8.07 (d, J=1.3 Hz, 1H), 12.59 (br s, 1H).

Step 2

In a similar manner to Reference Example 11, 1-methylindole-6-carboxylic acid (100 mg, 0.571 mmol) was dissolved in THF (5 mL), and the solution was treated with tert-butyllithium-pentane solution (1.48 mol/L, 0.970 mL, 1.44 mmol) and triisopropyl borate (0.198 mL, 0.858 mmol). The reaction mixture was added with saturated aqueous ammonium chloride solution (5 mL) and 10% aqueous potassium hydrogensulfate solution (5 mL) to adjust the pH to 2, followed by stirring at room temperature for 30 minutes. The reaction mixture was extracted with ethyl acetate. The organic layer was washed with saturated brine and dried over anhydrous sodium sulfate. The solvent was evaporated under reduced pressure. The residue was suspended in diisopropyl ether, the solid was collected by filtration, washed with diisopropyl ether and then dried under reduced pressure to obtain Compound BM (23.4 mg, yield 19%).

APCI-MS m/z: 220 [M+H]+; $^1$H-NMR (DMSO-d$_6$) δ(ppm): 3.99 (s, 3H), 7.10 (s, 1H), 7.61 (s, 2H), 8.06 (s, 1H), 8.46 (s, 2H), 12.57 (br s, 1H).

REFERENCE EXAMPLE 14

Compound BN

In a similar manner to Reference Example 11, benzothiophene-5-carboxylic acid (200 mg, 1.12 mmol) was dissolved in THF (5 mL), and the solution was treated with tert-butyllithium-pentane solution (1.48 mol/L, 1.89 mL, 2.80 mmol) and triisopropyl borate (0.388 mL, 1.68 mmol). The reaction mixture was added with saturated aqueous ammonium chloride solution (5 mL) and 10% aqueous potassium hydrogensulfate solution (5 mL) to adjust the pH to 2, followed by stirring at room temperature for 30 minutes. The mixture was extracted with ethyl acetate. The organic layer was washed with saturated brine and dried over anhydrous sodium sulfate. The solvent was evaporated under reduced pressure. The residue was suspended in hexane/chloroform/methanol (40/4/1), and the solid was collected by filtration, washed with hexane and dried under reduced pressure to obtain Compound BN (179 mg, yield-72%).

ESI-MS m/z: 221 [M−H]−; $^1$H-NMR (DMSO-d$_6$) δ(ppm): 7.90 (dd, J=1.5, 8.8 Hz, 1H), 8.06 (s, 1H), 8.08 (d, J=8.8 Hz, 1H), 8.49 (d, J=1.5 Hz, 1H), 8.59 (s, 2H), 12.93 (s, 1H).

REFERENCE EXAMPLE 15

Compound BO

Step 1

5-Aminoindole (100 mg, 0.757 mmol) was dissolved in DMF (2 mL), and the solution was added with EDCI (290 mg, 1.51 mmol), HOBT monohydrate (102 mg, 0.755 mmol) and 1-(tert-butoxycarbonyl)piperidine-4-carboxylic acid (208 mg, 0.907 mmol), followed by stirring at room temperature for 2 hours. The reaction mixture was added with water and extracted with ethyl acetate. The organic layer was washed with 1 mol/L hydrochloric acid, saturated aqueous sodium hydrogencarbonate solution and saturated brine, and dried over anhydrous sodium sulfate. The solvent was evaporated under reduced pressure and the residue was purified by slurry using acetonitrile to obtain 5-[1-(tert-butoxycarbonyl)piperidine-4-carbonylamino]indole (142 mg, yield 55%).

ESI-MS m/z: 344 [M+H]$^+$.

Step 2

In a similar manner to Step 2 of Reference Example 2, 5-[1-(tert-butoxycarbonyl)piperidine-4-carbonylamino]indole (140 mg, 0.408 mmol) was dissolved in acetonitrile (6 mL), and the solution was treated with di-tert-butyldicarbonate (0.103 mL, 0.448 mmol) and DMAP (1.0 mg, 0.0082 mmol), followed by purification by flash column chromatography (hexane/ethyl acetate=95/5 to 90/10 to 80/20 to 70/30 to 60/40 to 50/50) to obtain 5-[1-(tert-butoxycarbonyl)piperidine-4-carbonylamino]-1-(tert-butoxycarbonyl)indole (117 mg, yield 65%).

ESI-MS m/z: 444 [M+H]$^+$; $^1$H-NMR (CDCl$_3$) δ(ppm): 1.46 (s, 9H), 1.65 (s, 9H), 1.68-1.83 (m, 2H), 1.84-1.96 (m, 2H), 2.39 (m, 1H), 2.70-2.87 (m, 2H), 4.10-4.26 (m, 2H), 6.50 (s, 1H), 7.22 (d, J=8.7 Hz, 1H), 7.45-7.60 (m, 2H), 7.92 (s, 1H), 8.04 (d. J=8.7 Hz, 1H).

Step 3

In a similar manner to Step 2 of Reference Example 1, 5-[1-(tert-butoxycarbonyl)piperidine-4-carbonylamino]-1-(tert-butoxycarbonyl)indole (115 mg, 0.259 mmol) was dissolved in THF (3 mL), and the solution was treated with triisopropyl borate (0.090 mL, 0.39 mmol) and LDA-heptane/THF/ethylbenzene solution (2.0 mol/L, 0.45 mL, 0.90 mmol), followed by purification by slurry using diisopropyl ether and hexane to obtain Compound BO (116 mg, yield 92%).

ESI-MS m/z: 488 [M+H]$^+$; $^1$H-NMR (CDCl$_3$) δ(ppm): 1.47 (s, 9H), 1.71-1.85 (m, 2H), 1.73 (s, 9H), 1.88-1.99 (m, 2H), 2.27 (m, 1H), 2.74-2.88 (m, 2H), 4.10-4.30 (m, 2H), 6.83 (s, 2H), 7.40 (dd, J=2.2, 9.0 Hz, 1H), 7.41 (s, 1H), 7.83 (d, J=2.2 Hz, 1H), 7.94 (d, J=9.0 Hz, 1H).

REFERENCE EXAMPLE 16

Compound BP

Step 1

5-Aminoindole (100 mg, 0.757 mmol) was dissolved in acetonitrile (2 mL), and the solution was added with di-tert-butyldicarbonate (0.350 mL, 1.52 mmol), followed by stirring at room temperature for 1 hour. The reaction mixture was added with DMAP (1.0 mg, 0.0082 mmol), stirred at room temperature for 20 hours and then, the solvent was evaporated under reduced pressure. The residue was purified by flash column chromatography (hexane/ethyl acetate=95/5 to 90/10 to 80/20 to 70/30) to obtain 5-(tert-butoxycarbonylamino)-1-(tert-butoxycarbonyl)indole (236 mg, yield 94%).

ESI-MS m/z: 333 [M+H]$^+$; $^1$H-NMR (CDCl$_3$) δ(ppm): 1.53 (s, 9H), 1.66 (s, 9H), 6.49 (s, 1H), 6.50 (s, 1H), 7.12 (dd, J=2.9, 8.8 Hz, 1H), 7.55 (d, J=2.9 Hz, 1H), 7.73 (s, 1H), 8.02 (d, J=8.8 Hz, 1H).

Step 2

In a similar manner to Step 2 of Reference Example 1, 5-(tert-butoxycarbonylamino)-1-(tert-butoxycarbonyl)indole (230 mg, 0.692 mmol) was dissolved in THF (5 mL), and the solution was treated with triisopropyl borate (0.240 mL, 1.04 mmol) and LDA-heptane/THF/ethylbenzene solution (2.0 mol/L, 1.21 mL, 2.42 mmol), followed by purification by slurry using hexane to obtain Compound BP (210 mg, yield 81%).

ESI-MS m/z: 377 [M+H]$^+$; $^1$H-NMR (CDCl$_3$) δ(ppm): 1.54 (s, 9H), 1.72 (s, 9H), 6.55 (br s, 1H), 7.10 (s, 2H), 7.26 (dd, J=2.1, 8.9 Hz, 1H), 7.40 (s, 1H), 7.68 (d, J=2.1 Hz, 1H), 7.90 (d, J=8.9 Hz, 1H).

REFERENCE EXAMPLE 17

Compound BQ

Step 1

5-Aminoindole (100 mg, 0.757 mmol) was dissolved in acetonitrile (2 mL), and the solution was added with 1-(tert-butoxycarbonyl)-4-piperidinone (181 mg, 0.908 mmol), acetic acid (0.870 mL, 15.2 mmol) and sodium triacetoxyborohydride (160 mg, 0.755 mmol) little by little, followed by stirring at room temperature for 1 hour. The reaction mixture was added with water and sodium carbonate to adjust the pH to 9. The mixture was extracted with ethyl acetate. The organic layer was washed with saturated brine and dried over anhydrous sodium sulfate. The solvent was evaporated to obtain 5-[1-(tert-butoxycarbonyl)-4-piperidylamino]indole (300 mg).

5-[1-(tert-butoxycarbonyl)-4-piperidylamino]indole

APCI-MS m/z: 316 [M+H]$^+$; $^1$H-NMR (CDCl$_3$) δ(ppm): 1.21-1.42 (m, 2H), 1.47 (s, 9H), 2.03-2.14 (m, 2H), 2.86-2.98 (m, 2H), 3.43 (m, 1H), 3.97-4.13 (m, 2H), 6.39 (m, 1H), 6.62 (dd, J=2.2, 8.6 Hz, 1H), 6.88 (d, J=2.2 Hz, 1H), 7.13 (dd, J=2.7, 2.8 Hz, 1H), 7.21 (d, J=8.6 Hz, 1H), 7.96 (br s, 1H).

Step 2

In a similar manner to Step 2 of Reference Example 2, 5-[1-(tert-butoxycarbonyl)-4-piperidylamino]indole (300 mg) was dissolved in acetonitrile (6 mL), and the solution was treated with di-tert-butyldicarbonate (0.348 mL, 1.51 mmol), triethylamine (0.106 mL, 0.760 mmol) and DMAP (3.0 mg, 0.025 mmol), followed by purification by flash column chromatography (hexane/ethyl acetate=95/5 to 90/10 to 80/20 to 70/30) to obtain 5-[1-(tert-butoxycarbonyl)-4-piperidyl-N-(tert-butoxycarbonyl)amino]-1-(tert-butoxycarbonyl)indole (326 mg, yield 84%, 2 steps).

ESI-MS m/z: 516 [M+H]$^+$; $^1$H-NMR (CDCl$_3$) δ(ppm): 1.30-1.40 (m, 2H), 1.37 (s, 18H), 1.68 (s, 9H), 1.87-1.98 (m, 2H), 2.70-2.84 (m, 2H), 4.00-4.22 (m, 2H), 4.39 (m, 1H), 6.56 (d, J=3.7 Hz, 1H), 7.05 (dd, J=1.9, 8.7 Hz, 1H), 7.31 (d, J=1.9 Hz, 1H), 7.65 (d. J=3.7 Hz, 1H), 8.14 (d, J=8.7 Hz, 1H).

Step 3

In a similar manner to Step 2 of Reference Example 1, 5-[1-(tert-butoxycarbonyl)-4-piperidyl-N-(tert-butoxycarbonyl)amino]-1-(tert-butoxycarbonyl)indole (320 mg, 0.621 mmol) was dissolved in THF (5 mL), and the solution was treated with triisopropyl borate (0.215 mL, 0.932 mmol) and LDA-heptane/THF/ethylbenzene solution (2.0 mol/L, 0.776 mL, 1.55 mmol), followed by purification by slurry using hexane to obtain Compound BQ (177 mg, yield 62%).

ESI-MS m/z: 460 [M+H]$^+$; $^1$H-NMR (CDCl$_3$) δ(ppm): 1.20-1.42 (m, 2H), 1.47 (s, 9H), 1.72 (s, 9H), 2.02-2.13 (m, 2H), 2.86-3.00 (m, 2H), 3.46 (m, 1H), 4.00-4.17 (m, 2H), 6.68

REFERENCE EXAMPLE 18

Compound BR

Step 1

5-Hydroxyindole (209 mg, 1.57 mmol) was dissolved in DMF (6 mL), and the solution was added with imidazole (132 mg, 1.93 mmol) and tert-butyldimethylsilyl chloride (333 mg, 2.21 mmol) at 0° C. followed by stirring at room temperature for 3.5 hours. The reaction mixture was added with saturated aqueous sodium hydrogencarbonate solution at 0° C. and extracted with ethyl acetate. The organic layer was washed with saturated brine and dried over anhydrous sodium sulfate. The solvent was evaporated to obtain 5-(tert-butyldimethylsilyloxy)indole (517 mg).

Step 2

In a similar manner to Step 2 of Reference Example 2, 5-(tert-butyldimethylsilyloxy)indole (510 mg) was dissolved in acetonitrile (2 mL), and the solution was treated with di-tert-butyldicarbonate (0.510 mL, 2.22 mmol) and DMAP (10.1 mg, 0.0827 mmol), followed by purification by flash column chromatography (hexane/ethyl acetate=100/0 to 95/5) to obtain 5-(tert-butyldimethylsilyloxy)-1-(tert-butoxycarbonyl)indole (549 mg).

Step 3

In a similar manner to Step 2 of Reference Example 1, 5-(tert-butyldimethylsilyloxy)-1-(tert-butoxycarbonyl)indole (549 mg) was dissolved in THF (10 mL), and the solution was treated with triisopropyl borate (0.547 mL, 2.37 mmol) and LDA-heptane/THF/ethylbenzene solution (2.0 mol/L, 2.00 mL, 4.00 mmol), followed by purification by slurry using hexane to obtain Compound BR (431 mg, yield 70%, 3 steps).

ESI-MS m/z: 392 [M+H]$^+$; $^1$H-NMR (CDCl$_3$) δ(ppm): 0.20 (s, 6H), 1.00 (s, 9H), 1.72 (s, 9H), 6.88 (dd, J=2.6, 9.0 Hz, 1H), 6.97 (br s, 2H), 7.00 (d, J=2.6 Hz, 1H), 7.37 (s, 1H), 7.84 (d, J=9.0 Hz, 1H).

REFERENCE EXAMPLE 19

Compound BS

Step 1

In a similar manner to Step 1 of Reference Example 9, 5-hydroxyindole (200 mg, 1.50 mmol) was dissolved in DMF (2 mL), and the solution was treated with 1-(2-chloroethyl)piperidine (553 mg, 3.00 mmol) and potassium carbonate (1.25 g, 9.00 mmol). The reaction mixture was added with water and extracted with ethyl acetate. The organic layer was washed with saturated brine and dried over anhydrous sodium sulfate. The solvent was evaporated under reduced pressure. The residue was dissolved in acetonitrile (2.0 mL), and the solution was treated with di-tert-butyldicarbonate (0.483 mL, 2.10 mmol) and DMAP (1.8 mg, 0.015 mmol), followed by purification by flash column chromatography (hexane/ethyl acetate=7/3 to 1/1) to obtain 5-[2-(1-piperidino)ethoxy]-1-(tert-butoxycarbonyl)indole (348 mg, yield 67%).

ESI-MS m/z: 345 [M+H]$^+$; $^1$H-NMR (CDCl$_3$) δ(ppm): 1.50-1.62 (m, 2H), 1.62-1.73 (m, 4H), 1.66 (s, 9H), 2.45-2.60 (m, 4H), 2.79 (t, J=5.1 Hz, 2H), 4.15 (t, J=6.1 Hz, 2H), 6.48 (d, J=3.6 Hz, 1H), 6.93 (dd, J=2.5, 9.0 Hz, 1H), 7.03 (d, J=2.5 Hz, 1H), 7.55 (d, J=3.6 Hz, 1H), 7.99 (d, J=9.0 Hz, 1H).

Step 2

In a similar manner to Step 2 of Reference Example 1, 5-[2-(1-piperidino)ethoxy]-1-(tert-butoxycarbonyl)indole (346 mg, 1.00 mmol) was dissolved in THF (1.7 mL), and the solution was treated with triisopropyl borate (0.346 mL, 1.50 mmol) and LDA-heptane/THF/ethylbenzene solution (2.0 mol/L, 1.25 mL, 2.50 mmol), followed by purification by slurry using diisopropyl ether and hexane to obtain Compound BS (200 mg, yield 52%).

ESI-MS m/z: 389 [M+H]$^+$; $^1$H-NMR (CDCl$_3$) δ(ppm): 1.43-1.50 (m, 2H), 1.51-1.72 (m, 4H), 1.73 (s, 9H), 2.45-2.64 (m, 4H), 2.81 (t, J=6.0 Hz, 2H), 4.16 (t, J=6.0 Hz, 2H), 6.97 (dd, J=2.5, 9.2 Hz, 1H), 7.04 (d, J=2.5 Hz, 1H), 7.39 (s, 1H), 7.88 (d, J=9.2 Hz, 1H).

REFERENCE EXAMPLE 20

Compound BT

Step 1

1-(tert-Butoxycarbonyl)-4-piperidinone (400 mg, 2.01 mmol) was dissolved in methanol (4 mL), and the solution was added with 10% hydrogen chloride-methanol solution (4 mL), followed by stirring at 50° C. for 2 hours. The reaction mixture was added with diisopropyl ether and the precipitated solid was collected by filtration, washed with diisopropyl ether and then dried under reduced pressure to obtain 4,4-dimethoxypiperidine hydrochloride (238 mg, yield 65%).

ESI-MS m/z: 182 [M+H]$^+$; $^1$H-NMR (DMSO-d$_6$) δ(ppm): 1.83-1.90 (m, 4H), 2.96-3.05 (m, 4H), 3.11 (s, 6H), 8.71 (brs, 2H).

Step 2

In a similar manner to Step 1 of Reference Example 4, 5-formylindole (1.20 g, 8.27 mmol) was dissolved in acetonitrile (24 mL), and the solution was treated with di-tert-butyldicarbonate (2.09 mL, 9.10 mmol) and DMAP (10.1 mg, 0.0827 mmol), and then the mixture was treated with 4,4-dimethoxypiperidine hydrochloride (3.00 g, 16.5 mmol), triethylamine (2.53 mL, 18.2 mmol), acetic acid (4.73 mL, 82.6 mmol) and sodium triacetoxyborohydride (5.25 g, 24.8 mmol), followed by purification by flash column chromatography (hexane/ethyl acetate=95/5 to 90/10 to 85/15) to obtain 5-(4,4-dimethoxypiperidinomethyl)-1-(tert-butoxycarbonyl)indole (1.20 g, yield 39%).

APCI-MS m/z: 375 [M+H]$^+$; $^1$H-NMR (CDCl$_3$) δ(ppm): 1.67 (s, 9H), 1.74-1.82 (m, 4H), 2.41-2.49 (m, 4H), 3.18 (s, 6H), 3.59 (s, 2H), 6.53 (d, J=3.5 Hz, 1H), 7.28 (dd, J=1.5, 8.4 Hz, 1H), 7.49 (d, J=1.5 Hz, 1H), 7.57 (d, J=3.5 Hz, 1H), 8.06 (d, J=8.4 Hz, 1H).

Step 3

In a similar manner to Step 2 of Reference Example 1, 5-(4,4-dimethoxypiperidinomethyl)-1-(tert-butoxycarbonyl)indole (1.20 g, 3.21 mmol) was dissolved in THF (24 mL), and the solution was treated with triisopropyl borate (1.11 mL, 4.81 mmol) and LDA-heptane/THF/ethylbenzene solution (2.0 mol/L, 4.01 mL, 8.02 mmol) followed by purification by slurry using diisopropyl ether and hexane to obtain Compound BT (753 mg, yield 56%).

APCI-MS m/z: 419 [M+H]$^+$; $^1$H-NMR-(CDCl$_3$) δ(ppm): 1.73 (s, 9H), 1.75-1.81 (m, 4H), 2.40-2.48 (m, 4H), 3.18 (s, 6H), 3.59 (s, 2H), 6.80 (br s, 2H), 7.34 (dd, J=1.3, 8.8 Hz, 1H), 7.44 (s, 1H), 7.52 (d, J=1.3 Hz, 1H), 7.95 (d, J=8.8 Hz, 1H).

REFERENCE EXAMPLE 21

Compound BU

Step 1

In a similar manner to Step 1 of Reference Example 18, 5-[4-(2-hydroxyethyl)-1-piperazinylmethyl]-1-(tert-butoxycarbonyl)indole (5.02 g, 14.0 mmol) was dissolved in DMF (50 mL), and the solution was treated with imidazole (1.43 g, 21.0 mmol) and tert-butyldimethylsilyl chloride (3.16 g, 21.0 mmol) to obtain 5-(4-[2-(tert-butyldimethylsilyloxy)ethyl]-1-piperazinylmethyl)-1-(tert-butoxycarbonyl)indole (5.97 g, yield 90%).

APCI-MS m/z: 474 [M+H]$^+$; $^1$H-NMR (CDCl$_3$) δ(ppm): 0.06 (s, 6H), 0.87 (s, 9H), 1.67 (s, 9H), 2.80-3.15 (m, 10H), 2.80-3.15 (m, 2H), 3.70-3.85 (m, 2H), 6.56 (d, J=3.6 Hz, 1H), 7.32 (m, 1H), 7.58 (m, 1H), 7.61 (d, J=3.6 Hz, 1H), 8.12 (d, J=8.6 Hz, 1H).

Step 2

In a similar manner to Step 2 of Reference Example 1, 5-{4-[2-(tert-butyldimethylsilyloxy)ethyl]-1-piperazinylmethyl}-1-(tert-butoxycarbonyl)indole (5.00 g, 10.6 mmol) was dissolved in THF (50 mL), and the solution was treated with triisopropyl borate (3.67 mL, 15.9 mmol) and LDA-heptane/THF/ethylbenzene solution (2.0 mol/L, 13.3 mL, 26.6 mmol), followed by purification by flash column chromatography (hexane/ethyl acetate=50/50 to 20/80 to 0/100) to obtain Compound BU (3.16 g, yield 58%).

ESI-MS m/z: 518 [M+H]$^+$; $^1$H-NMR (CDCl$_3$) δ(ppm): 0.04 (s, 6H), 0.88 (s, 9H), 1.73 (s, 9H), 2.44-2.61 (m, 8H), 2.52 (t, J=6.5 Hz, 2H), 3.58 (s, 2H), 3.75 (t, J=6.5 Hz, 2H), 6.85 (br s, 2H), 7.34 (d, J=8.7 Hz, 1H), 7.44 (s, 1H), 7.53 (s, 1H), 7.95 (d, J=8.7 Hz, 1H).

REFERENCE EXAMPLE 22

Compound BV

Step 1

In a similar manner to Step 1 of Reference Example 4, 5-formylindole (2.00 g, 13.8 mmol) was dissolved in acetonitrile (20 mL), and the solution was treated with di-tert-butyldicarbonate (3.49 mL, 15.2 mmol) and DMAP (17.0 mg, 0.139 mmol), then the mixture was treated with 4-piperidinemethanol (6.36 g, 55.2 mmol), acetic acid (15.8 mL, 276 mmol) and sodium triacetoxyborohydride (8.77 g, 41.4 mmol) to obtain 5-(4-hydroxymethylpiperidinomethyl)-1-(tert-butoxycarbonyl)indole (2.85 g, yield 60%).

ESI-MS m/z: 345 [M+H]$^+$; $^1$H-NMR (CDCl$_3$) δ(ppm): 1.24-1.36 (m, 2H), 1.44-1.74 (m, 3H), 1.67 (s, 9H), 1.91-2.02 (m, 2H), 2.89-2.97 (m, 2H), 3.49 (d, J=6.4 Hz, 2H), 3.58 (s, 2H), 6.53 (dd, J=0.7, 3.7 Hz, 1H), 7.27 (dd, J=1.5, 8.6 Hz, 1H), 7.49 (dd, J=0.7, 1.5 Hz, 1H), 7.57 (d, J=3.7 Hz, 1H), 8.06 (d, J=8.6 Hz, 1H).

Step 2

In a similar manner to Step 1 of Reference Example 18, 5-(4-hydroxymethylpiperidinomethyl)-1-(tert-butoxycarbonyl)indole (2.85 g, 8.27 mmol) was dissolved in DMF (50 mL), and the solution was treated with imidazole (619 mg, 9.09 mmol and tert-butyldimethylsilyl chloride (1.37 g, 9.09 mmol), followed by purification by flash column chromatography (hexane/ethyl acetate=95/5 to 80/20) to obtain 5-[4-(tert-butyldimethylsilyloxy)methylpiperidinomethyl]-1-(tert-butoxycarbonyl)indole (2.90 g, yield 76%).

ESI-MS m/z: 459 [M+H]$^+$; $^1$H-NMR (CDCl$_3$) δ(ppm): 0.02 (s, 6H), 0.88 (s, 9H), 1.14-1.40 (m, 2H), 1.59-1.74 (m, 3H), 1.66 (s, 9H), 1.88-2.00 (m, 2H), 2.86-2.95 (m, 2H), 3.41 (d, J=6.4 Hz, 2H), 3.56 (s, 2H), 6.50 (dd, J=0.6, 3.7 Hz, 1H), 7.25 (dd, J=1.7, 8.3 Hz, 1H), 7.46 (dd, J=0.6, 1.7 Hz, 1H), 7.55 (d, J=3.7 Hz, 1H), 8.03 (d, J=8.3 Hz, 1H).

Step 3

In a similar manner to Step 2 of Reference Example 1, 5-[4-(tert-butyldimethylsilyloxy)methylpiperidinomethyl]-1-(tert-butoxycarbonyl)indole (2.90 g, 6.32 mmol) was dissolved in THF (30 mL), and the solution was treated with triisopropyl borate (1.51 mL, 6.54 mmol) and LDA-heptane/THF/ethylbenzene solution (2.0 mol/L, 5.45 mL, 10.9 mmol), followed by purification by flash column chromatography (hexane/ethyl acetate=50/50 to 20/80) to obtain Compound BV (1.91 g, yield 60%).

ESI-MS m/z: 503 [M+H]$^+$; $^1$H-NMR (CDCl$_3$) δ(ppm) 0.02 (s, 6H), 0.88 (s, 9H), 1.15-1.31 (m, 2H), 1.47 (m, 1H), 1.62-1.77 (m, 2H), 1.73 (s, 9H), 1.89-2.01 (m, 2H), 2.90 (d, J=11.5 Hz, 2H), 3.43 (d, J=6.4 Hz, 2H), 3.58 (s, 2H), 7.02 (br s, 2H), 7.33 (dd, J=1.4, 8.7 Hz, 1H), 7.44 (s, 1H), 7.52 (d, J=1.4 Hz, 1H), 7.94 (d, J=8.7 Hz, 1H).

REFERENCE EXAMPLE 23

Compound BW

Step 1

In a similar manner to Step. 1 of Reference Example 4, 5-formylindole (2.00 g, 13.8 mmol) was dissolved in acetonitrile (20 mL), and the solution was treated with di-tert-butyldicarbonate (3.49 mL, 15.2 mmol) and DMAP (17.0 mg, 0.139 mmol), then the mixture was treated with N,N,2,2-tetramethyl-1,3-propanediamine (8.79 mL, 55.2 mmol), acetic acid (15.8 mL, 276 mmol) and sodium triacetoxyborohydride (8.76 g, 41.3 mmol) to obtain 5-(N,N,2,2-tetramethyl-1,3-propanediaminomethyl)-1-(tert-butoxycarbonyl)indole (10.2 g).

Step 2

In a similar manner to Step 2 of Reference Example 1, 5-(N,N,2,2-tetramethyl-1,3-propanediaminomethyl)-1-(tert-butoxycarbonyl)indole (10.2 g) was dissolved in THF (50 mL), and the solution was treated with triisopropyl borate (6.37 mL, 27.6 mmol) and LDA-heptane/THF/ethylbenzene solution (2.0 mol/L, 17.3 mL, 34.6 mmol), followed by purification by slurry using ethyl acetate and hexane to obtain Compound BW (2.52 g, yield 45%, 2 steps).

ESI-MS m/z: 404 [M+H]$^+$; $^1$H-NMR (CDCl$_3$) δ(ppm): 0.90 (s, 6H), 1.73 (s, 9H), 2.16 (s, 2H), 2.25 (s, 6H), 2.47 (s, 2H), 3.88 (s, 2H), 7.33 (d, J=8.5 Hz, 1H), 7.42 (br s, 1H), 7.52 (s, 1H), 7.95 (d. J=8.5 Hz, 1H).

REFERENCE EXAMPLE 24

Compound BX

Step 1

In a similar manner to Step 1 of Reference Example 4, 5-formylindole (2.00 g, 13.8 mmol) was dissolved in acetonitrile (20 mL), and the solution was treated with di-tert-butyldicarbonate (3.49 mL, 15.2 mmol) and DMAP (17.0 mg, 0.139 mmol), then the mixture was treated with ethanolamine (8.33 mL, 138 mmol), acetic acid (15.8 mL, 276 mmol) and sodium triacetoxyborohydride (4.80 g, 22.6 mmol) to obtain 5-[(2-hydroxyethyl)aminomethyl]-1-(tert-butoxycarbonyl)indole (5.40 g).

Step 2

In a similar manner to Step 1 of Reference Example 18, 5-[(2-hydroxyethyl)aminomethyl]-1-(tert-butoxycarbonyl)indole (5.40 g) was dissolved in DMF (50 mL) and the solution was treated with imidazole (940 mg, 13.8 mmol) and tert-butyl dimethylsilylchloride (2.08 g, 13.8 mmol), followed by purification by slurry using diisopropyl ether and hexane to obtain 5-{[2-(tert-butyldimethylsilyloxy)ethyl]aminomethyl}-1-(tert-butoxycarbonyl)indole (4.80 g, yield 86%, 2 steps).

ESI-MS m/z: 291 [M+H]$^+$; $^1$H-NMR (CDCl$_3$) δ(ppm): 0.07 (s, 6H), 0.86 (s, 9H), 1.65 (s, 9H), 3.00 (t, J=5.2 Hz, 2H), 3.95 (t, J=5.2 Hz, 2H), 4.24 (s, 2H), 6.57 (d, J=3.6 Hz, 1H), 7.43 (d, J=8.4 Hz, 1H), 7.60 (d, J=3.6 Hz, 1H), 7.75 (s, 1H), 8.13 (d, J=8.1 Hz, 1H).

Step 3

In a similar manner to Step 2 of Reference Example 1, 5-{[2-(tert-butyldimethylsilyloxy)ethyl]aminomethyl}-1-(tert-butoxycarbonyl)indole (4.70 g, 11.6 mmol) was dissolved in THF (50 mL), and the solution was treated with triisopropyl borate (4.02 mL, 17.4 mmol) and LDA-heptane/THF/ethylbenzene solution (2.0 mol/L, 14.5 mL, 29.0 mmol), followed by purification by flash column chromatography (chloroform/methanol=95/5 to 20/80) to obtain Compound BX (1.09 g, yield 21%).

ESI-MS m/z: 449 [M+H]$^+$; $^1$H-NMR (CDCl$_3$) δ(ppm): 0.06 (s, 6H), 0.89 (s, 9H), 1.73 (s, 9H), 2.77 (t, J=5.2 Hz, 2H), 3.76 (t, J=5.2 Hz, 2H), 3.92 (s, 2H), 7.34 (d, J=8.8 Hz, 1H), 7.42 (s, 1H), 7.54 (s, 1H), 7.95 (d, J=8.8 Hz, 1H).

REFERENCE EXAMPLE 25

Compound BY

Step 1

In a similar manner to Step 1 of Reference Example 1, 5-formylindole (1.00 g, 6.89 mmol) was treated with di-tert-butyldicarbonate (2.40 mL, 10.3 mmol) and DMAP (0.00840 g, 0.0688 mmol). Then, the mixture was treated with trimethyl orthoformate (1.50 mL, 13.8 mmol) and p-toluenesulfonic acid monohydrate (0.00260 g, 0.138 mmol) to obtain 1-(tert-butoxycarbonyl)-4-(dimethoxymethyl)indole (2.00 g, yield 99%).

ESI-MS m/z: 292 [M−CH$_3$O]$^+$; $^1$H-NMR (CDCl$_3$) δ(ppm): 1.53 (s, 9H), 3.35 (s, 6H), 5.68 (s, 1H), 6.82 (d. J=3.8 Hz, 1H), 7.26-7.39 (m, 2H), 7.61 (d, J=3.8 Hz, 1H), 8.15 (d, J=7.9. Hz, 1H).

Step 2

In a similar manner to Step 2 of Reference Example 1, Compound BY (1.40 g, yield 70%) was obtained by treating 1-(tert-butoxycarbonyl)-5-(dimethoxymethyl)indole (2.00 g, 6.89 mmol) with triisopropyl borate (2.40 mL, 10.3 mmol) and LDA-heptane/THF/ethylbenzene solution (2.0 mol/L, 10.3 mL, 20.7 mmol).

ESI-MS m/z: 288 [M−H]$^−$; $^1$H-NMR (CDCl$_3$) δ(ppm): 1.62 (s, 9H), 7.29 (d, J=0.8 Hz, 1H), 7.52 (dd, J=7.4, 8.2 Hz, 1H), 7.84 (dd, J=0.8, 7.4 Hz, 1H), 8.43 (d, J=8.2 Hz, 1H), 10.3 (s, 1H).

REFERENCE EXAMPLE 26

Compound BZ

Step 1

In a similar manner to Step 1 of Reference Example 4, 5-formylindole (5.27 g, 36.3 mmol) was dissolved in acetonitrile (100 mL), and the solution was treated with di-tert-butyldicarbonate (9.17 mL, 39.9 mmol) and DMAP (44.0 mg, 0.360 mmol), then the mixture was treated with 51% aqueous dimethylamine solution (72.0 mL, 724 mmol), acetic acid (41.6 mL, 727 mmol) and sodium triacetoxyborohydride (46.2 g, 218 mmol), followed by purification by slurry using diisopropyl ether to obtain 5-(dimethylaminomethyl)-1-(tert-butoxycarbonyl)indole (3.61 g, yield 36%).

ESI-MS m/z: 275 [M+H]$^+$; $^1$H-NMR (CDCl$_3$) δ(ppm): 1.68 (s, 9H), 2.72 (s, 6H), 4.23 (s, 2H), 6.62 (d, J=3.7 Hz, 1H), 7.46 (dd, J=1.4, 8.5 Hz, 1H), 7.67 (d, J=3.7 Hz, 1H), 7.80 (d, J=1.4 Hz, 1H), 8.21 (d, J=8.5 Hz, 1H).

Step 2

In a similar manner to; Step 2 of Reference Example 1, 5-(dimethylaminomethyl)-1-(tert-butoxycarbonyl)indole (7.30 g, 26.6 mmol) was dissolved in THF (80 mL), and the solution was treated with triisopropyl borate (9.21 mL, 39.9 mmol) and LDA-heptane/THF/ethylbenzene solution (2.0 mol/L, 33.3 mL, 66.6 mmol), followed by purification by slurry using hexane to obtain Compound BZ (4.92 g, yield 58%).

ESI-MS m/z: 319 [M+H]$^+$; $^1$H-NMR (CDCl$_3$) δ(ppm): 1.73 (s, 9H), 2.26 (s, 6H), 3.52 (s, 2H), 7.32 (dd, J=1.4, 8.8 Hz, 1H), 7.43 (s, 1H), 7.52 (d, J=1.4 Hz, 1H), 7.95 (d, J=8.8 Hz, 1H).

REFERENCE EXAMPLE 27

Compound CA

Step 1

In a similar manner to Step 2 of Reference Example 2, 5-iodoindole (1.16 g, 4.78 mmol) was dissolved in acetonitrile (20 mL), and the solution was treated with di-tert-butyldicarbonate (1.32 mL, 5.73 mmol) and DMAP (5.8 mg, 0.0477 mmol), followed by purification by flash column chromatography (hexane/ethyl acetate=1/0 to 9/1) to obtain 1-(tert-butoxycarbonyl)-5-iodoindole (1.64 g, yield 99%).

ESI-MS m/z: 344 [M+H]$^+$; $^1$H-NMR (CDCl$_3$) δ(ppm): 1.66 (s, 9H), 6.48 (d, J=3.8 Hz, 1H), 7.52-7.62 (m, 2H), 7.87-7.94 (d, 1H).

Step 2

1-(tert-Butoxycarbonyl)-5-iodoindole (3.46 g, 10.1 mmol) was dissolved in toluene (45.0 mL), and the solution was added with 4-methylpiperazine (2.24 mL, 20.2 mmol), 2,2'-(diphenylphosphino)-1,1'-binaphthyl (1.26 g, 2.02 mmol), cesium carbonate (4.94 mg, 15.2 mmol) and palladium acetate (226 mg, 1.01 mmol), followed by stirring under reflux for 24 hours. The mixture was added with water and extracted with ethyl acetate. The organic layer was washed with saturated brine and dried over anhydrous sodium sulfate. The solvent was evaporated under reduced pressure. The residue was purified by flash column chromatography (chloroform/methanol=9/1) to obtain 1-(tert-butoxycarbonyl)-5-(4-methylpiperazino)indole (887 mg, 28%).

ESI-MS m/z: 316 [M+H]$^+$; $^1$H-NMR (CDCl$_3$) δ(ppm): 1.46 (s, 9H), 2.29 (s, 3H), 2.33-2.38 (m, 4H), 2.55-2.61 (m, 4H), 6.50 (d, J=3.6 Hz, 1H), 6.82-6.88 (m, 1H), 6.99-7.05 (m, 1H), 7.53 (d, J=3.6 Hz, 1H), 7.88 (d. J=9.2 Hz, 1H).

Step 3

In a similar manner to Step 2 of Reference Example 1, 1-(tert-butoxycarbonyl)-5-(4-methylpiperazino)indole (880 mg, 2.79 mmol) was dissolved in THF (2.0 mL), and the solution was treated with triisopropyl borate (0.966 mL, 4.19 mmol) and LDA-heptane/THF/ethylbenzene solution (2.0 mol/L, 4.19 mL, 8.37 mmol), then the mixture was purified by slurry using diisopropyl ether and hexane to obtain Compound CA (738 mg, yield 74%).

ESI-MS m/z: 360 [M+H]$^+$; $^1$H-NMR (CDCl$_3$) δ(ppm): 1.48 (s, 9H), 2.31 (s, 3H), 2.36-2.46 (m, 4H), 2.58-2.65 (m, 4H), 6.55 (s, 1H), 6.82-6.88 (m, 1H), 6.99-7.05 (m, 1H), 7.88 (d, J=9.2 Hz, 1H).

REFERENCE EXAMPLE 28

Compound CB

Step 1

1-(tert-Butoxycarbonyl)-5-iodoindole (1.00 g, 2.91 mmol) was dissolved in diethylamine (20 mL), and the solution was added with bis(triphenylphosphine)dichloropalladium (163 mg, 0.233 mmol), cuprous iodide (44.4 mg, 0.233 mmol) and 1-dimethylamino-2-propyne (0.628 mL, 5.82 mmol), followed by stirring at 80° C. for 7.0 hours. The reaction mixture was added with water and extracted with ethyl acetate. The organic layer was washed with saturated brine and dried over anhydrous sodium sulfate. The solvent was evaporated under reduced pressure. The residue was purified by preparative thin-layer chromatography (chloroform/methanol=19/1) to obtain 1-(tert-butoxycarbonyl)-5-(3-dimethylamino-2-propyn-1-yl)indole (0.78 g, yield 90%).

ESI-MS m/z: 299 [M+H]$^+$; $^1$H-NMR (CDCl$_3$) δ(ppm): 1.67 (s, 9H), 2.39 (s, 6H), 3.48 (s, 2H), 6.52 (d, J=3.8 Hz, 1H), 7.38 (dd, J=1.6, 8.4 Hz, 1H), 7.59 (d, J=3.8 Hz, 1H), 7.65 (d, J=1.6 Hz, 1H), 8.06 (d, J=8.4 Hz, 1H).

Step 2

1-(tert-Butoxycarbonyl)-5-(3-dimethylamino-2-propynlyl)indole (0.78 g, 2.61 mmol) was dissolved in ethanol (78 mL), and the solution was added with 10% Pd/C (39.0 mg) under hydrogen atmosphere, followed by stirring at room temperature for 2 days. The reaction mixture was filtered using Celite, then the filtrate was concentrated. The residue was purified by preparative thin-layer chromatography (chloroform/methanol=19/1, 4/1) to obtain 1-(tert-butoxycarbonyl)-5-(3-dimethylamino)propylindole (645 mg, yield 82%).

ESI-MS m/z: 303 [M+H]$^+$; $^1$H-NMR (CDCl$_3$) δ(ppm): 1.67 (s, 9H), 1.80-1.90 (m, 2H), 2.25 (s, 6H), 2.34 (t, J=7.8 Hz, 2H), 2.73 (t, J=7.8 Hz, 2H), 6.51 (dd, J=0.6, 3.9 Hz, 1H), 7.19 (dd, J=1.8, 8.7 Hz, 1H), 7.36 (d, J=1.8 Hz, 1H), 7.56 (d, J=3.9 Hz, 1H), 8.03 (d, J=8.7 Hz, 1H).

Step 3

1-(tert-Butoxycarbonyl)-5-(3-dimethylamino)propylindole (645 mg, 2.13 mmol) was dissolved in THF (6.5 mL), and the solution was added with triisopropyl borate (0.729 mL, 0.825 mmol). The mixture was cooled to 0° C. and added with LDA-heptane/THF/ethylbenzene solution (2.98 mL, 2.0 mol/L, 5.96 mmol), followed by stirring at 0° C. for 3.0 hours. The reaction mixture was added with 1 mol/L hydrochloric acid (25 mL) and stirred at room temperature for 1.0 hour. The mixture was added with a saturated aqueous sodium carbonate solution by drops until the pH of the mixture is adjusted to 8, then extracted with ethyl acetate. The organic layer was washed with saturated brine and dried over anhydrous sodium sulfate. The solvent was evaporated under reduced pressure. The residue was purified by slurry using diisopropyl ether and hexane to obtain Compound CB (486 mg, yield 66%).

$^1$H-NMR (DMSO-d$_6$) δ(ppm): 1.59 (s, 9H), 1.69-1.79 (m, 2H), 2.18 (s, 6H), 2.27 (t, J=6.9 Hz, 2H), 2.65 (t. J=7.5 Hz, 2H), 6.56 (s, 1H), 7.12 (dd, J=1.5, 8.4 Hz, 1H), 7.36 (d, J=1.5 Hz, 1H), 7.96 (d, J=8.4 Hz, 1H), 8.17 (br s, 2H).

REFERENCE EXAMPLE 29

Compound CC

Step 1

5-Hydroxyindole (3.49 g, 26.2 mmol) was dissolved in acetonitrile (35.0 mL), and the solution was added with di-tert-butyldicarbonate (18.1 mL, 78.6 mmol) and DMAP (294 mg, 2.62 mmol), followed by stirring at room temperature for 4 hours. The reaction mixture was concentrated under reduced pressure, and the residue was dissolved in methanol (130 mL) and added with potassium carbonate (18.1 g, 131 mmol) followed by stirring at room temperature for 4 hours. The mixture was added with acetic acid (7.50 mL) to neutralize, then added with water, followed by extracting with ethyl acetate. The organic layer was washed with saturated brine and dried over anhydrous sodium sulfate. The solvent was evaporated under reduced pressure. The residue was purified by flash column chromatography (hexane/ethyl acetate=2/1) to obtain 1-(tert-butoxycarbonyl)-5-hydroxyindole (5.74 g, 94%).

ESI-MS m/z: 234 [M+H]$^+$; $^1$H-NMR (CDCl$_3$) δ(ppm): 1.66 (s, 9H), 4.68 (s, 1H), 6.45 (d, J=3.8 Hz, 1H), 6.83 (dd, J=2.6, 8.9 Hz, 1H), 6.97 (d, J=2.6 Hz, 1H), 7.56 (d, J=3.8 Hz, 1H), 7.98 (d, J=8.9 Hz, 1H).

Step 2

1-(tert-Butoxycarbonyl)-5-hydroxyindole (2.33 g, 10.0 mmol) and triphenylphosphine 5.25 g, 20.0 mmol) were dissolved in toluene (46.0 mL), and the solution was added with glycidol (1.32 mL, 20.0 mmol) and 40% DEAD-toluene solution (9.10 mL, 20 mmol) at room temperature, followed by stirring at 80° C. for 4 hours. The solvent was evaporated under reduced pressure and the residue was purified by flash column chromatography (hexane/ethyl acetate=4/1). A crude product (1.28 g) of 1-(tert-butoxycarbonyl)-5-hydroxyindole (1.28 g) was obtained. The obtained crude product was dissolved in N,N-dimethylacetoamide (20.0 mL), and the solution was added with 2-(ethylamino)ethanol (8.60 mL, 87.8 mmol), followed by stirring at 80° C. for 4 hours. The reaction mixture was added with water and extracted with ethyl acetate. The organic layer was washed with saturated brine and dried over anhydrous sodium sulfate. The solvent was evaporated under reduced pressure and the residue was purified by flash column chromatography (chloroform/methanol=9/1) to obtain 1-(tert-butoxycarbonyl)-5-{3-[N-ethyl(2-hydroxyethyl)amino]-2-hydroxypropoxy}indole (1.53 g, 40%).

ESI-MS m/z: 379 [M+H]$^+$; $^1$H-NMR (CDCl$_3$) δ(ppm): 1.07 (t, J=7.2 Hz, 3H), 1.66 (s, 9H), 2.61-2.80 (m, 6H), 3.61-3.68 (m, 2H), 3.99-4.14 (m, 3H), 6.48 (d, J=3.9 Hz, 1H), 6.94 (dd, J=2.6, 8.7 Hz, 1H), 7.04 (d, J=2.6 Hz, 1H), 7.56 (d, J=3.9 Hz, 1H), 8.01 (d, J=8.7 Hz, 1H).

Step 3

1-(tert-Butoxycarbonyl)-5-{3-[N-ethyl(2-hydroxyethyl) amino]-2-hydroxypropoxy}indole (1.53 g, 4.04 mmol) was dissolved in acetonitrile (20.0 mL), and the solution was added with imidazole (1.10 g, 16.2 mmol) and tert-butyldimethylsilyl chloride (1.83 g, 12.1 mmol), followed by stirring at room temperature for 2 hours. The reaction mixture was added with water and extracted with ethyl acetate. The organic layer was washed with saturated brine and dried over anhydrous sodium sulfate. The solvent was evaporated under reduced pressure and the residue was purified by flash column chromatography (hexane/ethyl acetate=85/15) to obtain 1-(tert-butoxycarbonyl)-5-{3-[N-ethyl(2-(tert-butyldimethylsilyl oxy)ethyl)amino]-2-(tert-butyldimethylsilyloxy) propoxy}indole (2.34 g, 96%).

ESI-MS m/z: 607 [M+H]$^+$.

Step 4

In a similar manner to Step 2 of Reference Example 1, 1-(tert-butoxycarbonyl)-5-{3-[N-ethyl(2-(tert-butyldimethylsilyl oxy)ethyl)amino]-2-(tert-butyldimethylsilyloxy) propoxy}indole (2.34 g, 3.86 mmol) was dissolved in THF (46.0 mL), and the solution was treated with triisopropyl borate (1.33 mL, 5.78 mmol) and LDA-heptane/THF/ethylbenzene solution (2.0 mol/L, 5.78 mL, 11.6 mmol) to obtain Compound CC (1.89 g, yield 75%).

ESI-MS m/z: 651 [M+H]$^+$; $^1$H-NMR (CDCl$_3$) δ(ppm): 0.04 (s, 6H), 0.10 (s, 3H), 0.12 (s, 3H), 0.88 (s, 9H), 0.90 (s, 9H), 1.02 (t, J=6.7 Hz, 3H), 1.73 (s, 9H), 2.51-2.70 (m, 6H), 3.66 (t, J=6.7 Hz, 2H), 3.82-3.92 (m, 1H), 4.01-4.22 (m, 2H), 6.90-6.74 (m, 3H), 7.87 (dd, J=3.1, 9.4 Hz, 1H).

REFERENCE EXAMPLE 30

Compound CD

Step 1

4-Hydroxyindole (831 mg, 6.24 mmol) was dissolved in DMF (8.0 mL), and the solution was added with imidazole (510 mg, 7.49 mmol) and tert-butyldimethylsilyl chloride (1.03 g, 6.86 mmol), followed by stirring at room temperature for 5 hours. The reaction mixture was added with water and extracted with ethyl acetate. The organic layer was washed with saturated brine and dried over anhydrous sodium sulfate. The solvent was evaporated under reduced pressure and the residue was purified by flash column chromatography (hexane/ethyl acetate=85/15) to obtain 4-(tert-butyldimethylsilyloxy)indole (1.53 g, 99%).

ESI-MS m/z: 248 [M+H]$^+$; $^1$H-NMR (CDCl$_3$) δ(ppm): 0.24 (s, 6H), 1.06 (s, 9H), 6.52 (dd, J=2.8, 5.4. Hz, 1H), 6.59 (dd, J=2.3, 2.8 Hz, 1H), 7.01-7.08 (m, 1H), 7.09 (dd, J=2.3, 3.3 Hz, 1H), 7.25 (s, 1H), 8.09 (br s, 1H).

Step 2

In a similar manner to Step 2 of Reference Example 1, 4-(tert-butyldimethylsilyloxy)indole (1.53 g, 6.23 mmol) was treated with di-tert-butyldicarbonate (2.15 mL, 9.36 mmol) and DMAP (7.60 mg, 0.0624 mmol), then the residue was purified by flash column chromatography (hexane/ethyl acetate=10/1) to obtain 1-(tert-butoxycarbonyl)-4-(tert-butyldimethylsilyloxy)indole (2.17 g, 99%).

ESI-MS m/z: 348 [M+H]$^+$; $^1$H-NMR (CDCl$_3$) δ(ppm): 0.22 (s, 6H), 1.04 (s, 9H), 1.67 (s, 9H), 6.62 (dd, J=0.8, 3.6 Hz, 1H), 6.65 (dd, J=0.8, 8.2 Hz, 1H), 7.15 (dd, J=8.2, 8.2 Hz, 1H), 7.49 (d, J=3.6 Hz, 1H), 7.75 (d, J=8.2 Hz, 1H).

Step 3

In a similar manner to Step 2 of Reference Example 1, Compound CD (645 mg, yield 46%) was obtained by treating 1-(tert-butoxycarbonyl)-4-(tert-butyldimethylsilyloxy)indole (1.25 g, 3.60 mmol) with triisopropyl borate (1.25 mL, 5.40 mmol) and LDA-heptane/THF/ethylbenzene solution (2.0 mol/L, 5.40 mL, 10.8 mmol).

ESI-MS m/z: 392 [M+H]$^+$; $^1$H-NMR (DMSO-d$_6$) δ(ppm): 0.01 (s, 6H), 0.82 (s, 9H), 1.40 (s, 9H), 6.34 (d, J=7.7 Hz, 1H), 6.46 (d, J=7.7 Hz, 1H), 6.96 (dd, J=7.7, 7.7 Hz, 1H), 7.52 (d, J=7.7 Hz, 1H), 7.99 (s, 2H).

Hereinafter, structures of Compounds BA to BZ obtained in Reference Examples 1 to 26 will be described in Tables 10-1 to 10-3. In addition, Me, TBS and Boc respectively represents methyl, tert-butyldimethylsilyl and tert-butoxycarbonyl in the following tables.

TABLE 10-1

(HO)$_2$B—R$^{1B}$

| Ref. Example No. | Compound No. | R$^{1B}$ |
|---|---|---|
| 1 | BA | 2-methyl-1-Boc-indol-5-yl with CHO substituent |
| 2 | BB | 2-methyl-1-Boc-indol-5-yl C(O)–(4-Boc-piperazin-1-yl) |
| 3 | BC | 2-methyl-1-Boc-indol-5-yl CH$_2$–(4-Boc-piperazin-1-yl) |

TABLE 10-1-continued (HO)₂B—R^(1B)

| Ref. Example No. | Compound No. | R^(1B) |
|---|---|---|
| 4 | BD | 2-indolyl(N-Boc)-5-CH₂-piperidine |
| 5 | BE | 2-indolyl(N-Boc)-5-C(O)-N-(4-methylpiperazine) |
| 6 | BF | 2-indolyl(N-Boc)-5-Br |
| 7 | BG | 2-indolyl(N-Boc)-5-CO₂H |
| 8 | BH | 2-indolyl(N-Boc)-6-C(O)-N-piperazine-NBoc |
| 9 | BI | 2-indolyl(N-Boc)-5-O-CH₂CH₂-morpholine |
| 10 | BJ | 2-indolyl(N-Boc)-5-CH₂-N-piperazine-N-CH₂CH₂OH |
| 11 | BK | 2-indolyl(N-Me) |
| 12 | BL | 2-indolyl(N-Me)-5-CO₂H |
| 13 | BM | 2-indolyl(N-Me)-6-CO₂H |
| 14 | BN | 2-benzothiophene-5-CO₂H |

TABLE 10-2
(HO)₂B—R^{1B}
| Ref. Example No. | Compound No. | R^{1B} |
|---|---|---|
| 15 | BO | 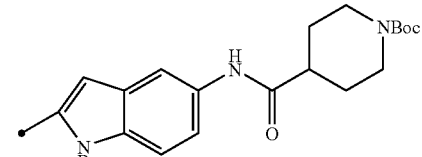 |
| 16 | BP | 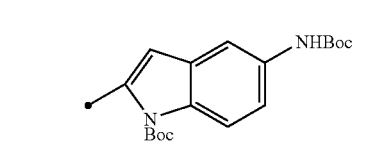 |
| 17 | BQ | 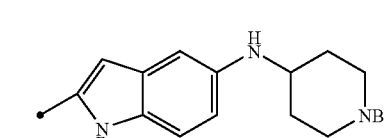 |
| 18 | BR | 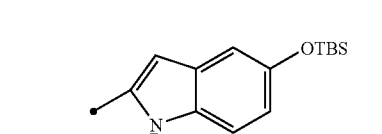 |
| 19 | BS | 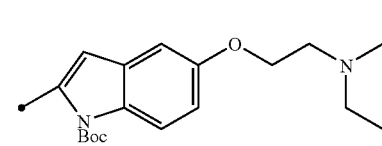 |
| 20 | BT | 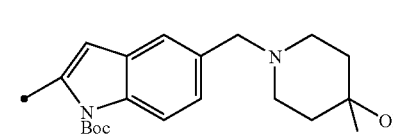 |
| 21 | BU | 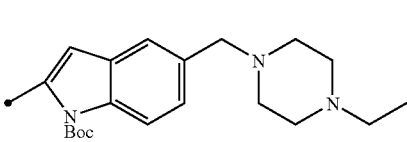 |
| 22 | BV | 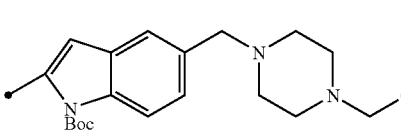 |
| 23 | BW | 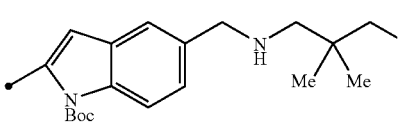 |
| 24 | BX | 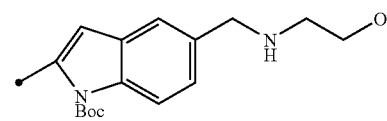 |

TABLE 10-2-continued (HO)₂B—R^{1B}

| Ref. Example No. | Compound No. | R^{1B} |
|---|---|---|
| 25 | BY | 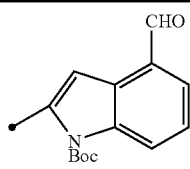 |
| 26 | BZ | 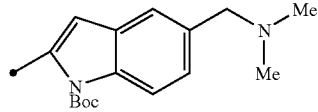 |

TABLE 10-3

(HO)₂B—R^{1B}

| Ref. Example No. | Compound No. | R^{1B} |
|---|---|---|
| 27 | CA | 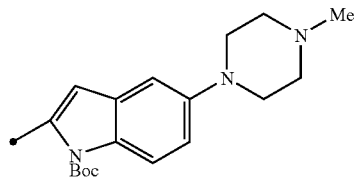 |
| 28 | CB | 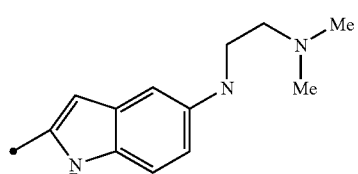 |
| 29 | CC | 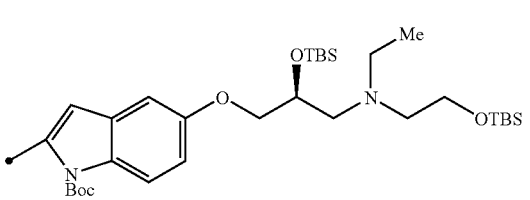 |
| 30 | CD | 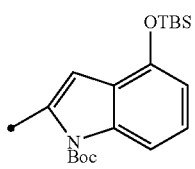 |

EXAMPLE 1

3-Amino-6-(1H-indol-2-yl)phthalimide (Compound 1)

Step 1

3-Aminophthalimide (2.00 g, 12.3 mmol) was dissolved in methanol (200 mL), and the solution was added with N-bromosuccinimide (2.19 g, 12.3 mmol), followed by stirring at room temperature for 50 minutes. The obtained solid was collected by filtration and washed with methanol to obtain 3-amino-6-bromophthalimide (2.21 g, yield 74%).

APCI-MS m/z: 241 [M−H]⁻; ¹H-NMR (DMSO-d₆) δ(ppm): 6.53 (br s, 2H), 6.88 (d, J=8.9 Hz, 1H), 7.49 (d, J=8.9 Hz, 1H), 11.07 (br s, 1H).

Step 2

3-Amino-6-bromophthalimide (100 mg, 0.415 mmol) was dissolved in acetonitrile (7 mL), and the solution was added with 1-(tert-butoxycarbonyl)indole-2-boronic acid (217 mg, 0.830 mmol), palladium acetate (7.5 mg, 0.033 mmol), tri(o-tolyl)phosphine (20 mg, 0.066 mmol) and triethylamine (0.578 mL, 4.15 mmol), followed by stirring under reflux for 7.5 hours under argon atmosphere. The reaction mixture was added with water and extracted with ethyl acetate. The organic layer was washed with saturated brine and dried over anhydrous sodium sulfate. The solvent was evaporated under reduced pressure and the residue was purified by preparative thin-layer chromatography (chloroform/methanol=20/1, chloroform/acetonitrile=15/1) to obtain 3-amino-6-[1-(tert-butoxycarbonyl)indol-2-yl]phthalimide (106 mg, yield 67%).

APCI-MS m/z: 376 [M−H]$^-$; $^1$H-NMR (DMSO-d$_6$) δ(ppm): 1.27 (s, 9H), 6.55 (s, 2H), 6.65 (s, 1H), 7.02 (d, J=8.4 Hz, 1H), 7.24 (dd, J=6.8, 7.5 Hz, 1H), 7.33 (dd, J=7.2, 7.2 Hz, 1H), 7.43 (d, J=8.4 Hz, 1H), 7.59 (d, J=7.7 Hz, 1H), 8.13 (d, J=8.1 Hz, 1H), 10.96 (s, 1H).

Step 3

3-Amino-6-[1-(tert-butoxycarbonyl)indol-2-yl]phthalimide (21.8 mg, 0.0578 mmol) was dissolved in methanol (2.2 mL), and the solution was added with 10% hydrogen chloride-methanol solution (2.2 mL), followed by stirring at 70° C. for 1.3 hours. The reaction mixture was added with saturated aqueous sodium hydrogencarbonate solution, extracted with ethyl acetate. The organic layer was washed with saturated brine and dried over anhydrous sodium sulfate. The solvent was evaporated under reduced pressure and the residue was purified by preparative thin-layer chromatography (chloroform/acetone=6/1, chloroform/methanol=12/1) to obtain Compound 1 (14 mg, yield 87%).

APCI-MS m/z: 276 [M−H]$^-$; $^1$H-NMR (DMSO-d$_6$) δ(ppm): 6.71 (s, 2H), 7.00-7.09 (m, 4H), 7.46 (d, J=7.9 Hz, 1H), 7.54 (d, J=7.6 Hz, 1H), 8.03 (d, J=8.8 Hz, 1H), 11.31 (s, 1H), 12.09 (s, 1H).

EXAMPLE 2

3-Amino-4-phenyl-6-[1H-5-(4-methylpiperazin-1-ylsulfonyl)indol-2-yl]phthalimide (Compound 2)

Step 1

Iodine (6.29 g, 24.8 mmol) was dissolved in ethanol (225 mL), and the solution was added with silver sulfate (3.87 g, 12.4 mmol) and 3-amino-6-bromophthalimide (3.00 g, 12.4 mmol), followed by stirring at room temperature for 23 hours. The reaction mixture was added with 10% aqueous sodium thiosulfate solution and extracted with ethyl acetate. The organic layer was washed with 0.5 mol/L hydrochloric acid and saturated brine and dried over anhydrous sodium sulfate. The solvent was evaporated under reduced pressure, the residue was purified by slurry using hexane and methanol to obtain 3-amino-4-iodo-6-bromophthalimide (4.3 g. yield 96%).

APCI-MS m/z: 365 [M−H]$^-$, $^1$H-NMR (DMSO-d$_6$) δ(ppm): 6.34 (s, 2H), 8.10 (s, 1H), 11.23 (s, 1H).

Step 2

3-Amino-4-iodo-6-bromophthalimide (80.0 mg, 0.218 mmol) was dissolved in THF (5.6 mL), and the solution was added with phenylboronic acid (80 mg, 0.65 mmol), tetrakis(triphenylphosphine)palladium (20 mg, 0.017 mmol) and copper(I) thiophene-2-carboxylate (125 mg, 0.65 mmol), followed by stirring at room temperature for 14 hours under argon atmosphere. The reaction mixture was added with saturated aqueous ammonium chloride solution and extracted with ethyl acetate. The organic layer was washed with saturated aqueous sodium hydrogencarbonate solution and saturated brine and dried over anhydrous sodium sulfate. The solvent was evaporated under reduced pressure. The residue was purified by slurry using isopropylether, then by preparative thin-layer chromatography (chloroform/methanol=60/1) to obtain 3-amino-4-phenyl-6-bromophthalimide (46 mg, yield 66%) and 3-amino-4,6-diphenylphthalimide (7.6 mg, yield 11%).

3-amino-4-phenyl-6-bromophthalimide

APCI-MS m/z: 315 [M−H]$^-$; $^1$H-NMR (DMSO-d$_6$) δ(ppm): 6.10 (s, 2H), 7.45-7.53 (m, 6H), 11.24 (s, 1H).

3-amino-4,6-diphenylphthalimide

APCI-MS m/z: 313 [M−H]$^-$; $^1$H-NMR (DMSO-d$_6$) δ(ppm): 5.58 (s, 2H), 7.27-7.58 (m, 11H), 7.63 (br s, 1H).

Step 3

In a similar manner to Step 2 of Example 1, 3-amino-4-phenyl-6-bromophthalimide (70.0 mg, 0.221 mmol) was dissolved in acetonitrile (5.6 mL), and the solution was treated with a mixture (281 mg) of 1-(tert-butoxycarbonyl)-5-(4-methylpiperazin-1-ylsulfonyl)indol-2-boronic acid synthesized in a similar manner to the literature [Bioorganic & Medicinal Chemistry Letters, 2004, vol. 14, p. 351] and 5-(4-methylpiperazin-1-ylsulfonyl)-1H-indol-2-boronic acid, palladium acetate (4.0 mg, 0.018 mmol), tri(o-tolyl)phosphine (11 mg, 0.035 mmol) and triethylamine (0.308 mL, 2.21 mmol), followed by purification by preparative thin-layer chromatography (ethyl acetate/methanol=20/1) to obtain Compound 2 (21 mg, yield 19%) and 3-amino-4-phenyl-6-[1-(tert-butoxycarbonyl)-5-(4-methylpiperazin-1-ylsulfonyl)indol-2-yl]phthalimide (28 mg, yield 20%).

Compound 2

ESI-MS m/z: 516 [M+H]$^+$; $^1$H-NMR (DMSO-d$_6$) δ(ppm): 2.18 (br s, 3H), 2.45 (br s, 4H), 2.88 (br s, 4H), 6.32 (s, 2H), 7.40-7.57 (m, 7H), 7.68 (d, J=8.6 Hz, 1H), 7.88 (s, 1H), 7.95 (s, 1H), 11.43 (s, 1H), 12.35 (s, 1H).

3-amino-4-phenyl-6-[1-(tert-butoxycarbonyl)-5-(4-methylpiperazine-1-ylsulfonyl)indol-2-yl]phthalimide ESI-MS m/z: 616 [M+H]$^+$; $^1$H-NMR (DMSO-d$_6$) δ(ppm): 1.32 (s, 9H), 2.12 (s, 3H), 2.35 (br s, 4H), 2.89 (br s, 4H), 6.97 (s, 2H), 7.41 (s, 1H), 7.45-7.53 (m, 5H), 7.68 (dd, J=1.9, 8.8 Hz, 1H), 8.01 (d, J=1.6 Hz, 1H), 8.32 (d, J=8.9 Hz, 1H), 11.18 (s, 1H).

EXAMPLE 3

3-Amino-4-[4-(hydroxymethyl)phenyl]-6-[1H-5-(4-methylpiperazin-1-ylsulfonyl)indol-2-yl]phthalimide (Compound 3)

Step 1

In a similar manner to Step 2 of Example 2, 3-amino-4-iodo-6-bromophthalimide (100 mg, 0.273 mmol) was dissolved in THF (7 mL), and the solution was treated with 4-hydroxymethylphenylboronic acid (83 mg, 0.55 mmol), tetrakis(triphenylphosphine)palladium (25 mg, 0.022 mmol) and copper(I)thiophene-2-carboxylate (104 mg, 0.546 mmol), followed by purification by preparative thin-layer chromatography (chloroform/methanol=15/1) to obtain 3-amino-4-(hydroxymethylphenyl)-6-bromophthalimide (61 mg, yield 64%) and 3-amino-4,6-di(4-hydroxymethylphenyl)phthalimide (29 mg, yield 29%).

3-amino-4-(hydroxymethylphenyl)-6-bromophthalimide

APCI-MS m/z: 345 [M−H]$^-$; $^1$H-NMR (DMSO-d$_6$) δ(ppm): 4.56 (d, J=5.6 Hz, 2H), 5.28 (t, J=5.7 Hz, 1H), 6.07 (s, 2H), 7.43 (m, 5H), 11.22 (s, 1H).

3-amino-4,6-di(4-hydroxymethylphenyl)phthalimide

APCI-MS m/z: 373 [M−H]$^-$: $^1$H-NMR (DMSO-d$_6$) δ(ppm): 4.47-4.57 (m, 4H), 5.19 (t, J=5.8 Hz, 1H), 5.27 (t, J=5.7 Hz, 1H), 6.07 (s, 2H), 7.25-7.95 (m, 9H), 10.99 (s, 1H).

Step 2

In a similar manner to Step 2 of Example 1, 3-amino-4-(hydroxymethylphenyl)-6-bromophthalimide (70.0 mg, 0.200 mmol) was dissolved in acetonitrile (5.6 mL), and the solution was treated with a mixture (212 mg) of 1-(tert-butoxycarbonyl)-5-(4-methylpiperazin-1-ylsulfonyl)indol-2-boronic acid synthesized in a similar manner to the literature [Bioorganic & Medicinal Chemistry Letters, 2004, vol. 14, p. 351] and 5-(4-methylpiperazin-1-ylsulfonyl)-1H-indol-2-boronic acid, palladium acetate (3.6 mg, 0.016 mmol), tri(o-tolyl)phosphine (9.7 mg, 0.032 mmol) and triethylamine (0.279 mL, 2.00 mmol), followed by purification by preparative thin-layer chromatography (ethyl acetate/methanol=50/1) to obtain Compound 3 (44 mg, yield 40%) and 3-amino-4-[4-(hydroxymethyl)phenyl]-6-[1-(tert-butoxycarbonyl)-5-(4-methylpiperazin-1-ylsulfonyl)indol-2-yl]phthalimide (70 mg, yield 54%).

3-amino-4-[4-(hydroxymethyl)phenyl]-6-[1-(tert-butoxycarbonyl)-5-(4-methylpiperazin-1-ylsulfonyl)indol-2-yl]phthalimide ESI-MS m/z: 646 [M+H]$^+$; $^1$H-NMR (DMSO-d$_6$) δ(ppm): 1.32 (s, 9H), 2.12 (s, 3H), 2.35 (br s, 4H), 2.89 (br s, 4H), 4.57 (d, J=5.5 Hz, 2H), 5.29 (t, J=5.7 Hz, 1H), 6.17 (s, 2H), 6.96 (s, 1H), 7.39 (s, 1H), 7.47 (m, 4H), 7.68 (dd, J=1.8, 8.8 Hz, 4H), 8.01 (d, J=1.8 Hz, 1H), 8.32 (d, J=9.5 Hz, 1H), 11.17 (s, 1H).

Compound 3

ESI-MS m/z: 546 [M+H]$^+$; $^1$H-NMR (DMSO-d$_6$) δ(ppm): 2.14 (br s, 3H), 2.37 (br s, 4H), 3.30 (br s, 4H), 4.59 (d, J=5.9 Hz, 2H), 5.31 (t, J=5.7 Hz, 1H), 6.32 (s, 2H), 7.38 (s, 1H), 7.43 (dd, J=1.7, 8.6 Hz, 1H), 7.51 (m, 4H), 7.68 (d, J=8.8 Hz, 1H), 7.87 (s, 1H), 7.95 (s, 1H), 11.43 (s, 1H), 12.35 (s, 1H).

EXAMPLE 4

3-Amino-6-[1H-5-(4-methylpiperazin-1-ylsulfonyl)indol-2-yl]phthalimide (Compound 4)

In a similar manner to Step 2 of Example 1, 3-amino-6-bromophthalimide (60.0 mg, 0.249 mmol) was dissolved in acetonitrile (3 mL), and the solution was treated with a mixture (228 mg) of 1-(tert-butoxycarbonyl)-5-(4-methylpiperazin-1-sulfonyl)indole-2-boronic acid synthesized in a similar manner to the literature [Bioorganic & Medicinal Chemistry Letters, 2004, vol. 14, p. 351] and 5-(4-methylpiperazin-1-sulfonyl)-1H-indol-2-boronic acid, palladium acetate (4.5 mg, 0.020 mmol), tri(o-tolyl)phosphine (12 mg, 0.040 mmol) and triethylamine (0.347 mL, 2.49 mmol). The reaction mixture was added with water and the precipitated solid was collected by filtration, washed with water and then dried under reduced pressure to obtain Compound 4 (39.8 mg, yield 36%).

ESI-MS m/z: 440 [M+H]$^+$; $^1$H-NMR (DMSO-d$_6$) δ(ppm): 2.10 (s, 3H), 2.30-2.40 (m, 4H), 2.82-2.92 (m, 4H), 6.77 (br s, 2H), 7.10 (d, J=8.8 Hz, 1H), 7.23 (d, J=1.5 Hz, 1H), 7.42 (dd, J=1.5, 8.4 Hz, 1H), 7.69 (d, J=8.4 Hz, 1H), 7.96 (br s, 1H), 7.99 (d, J=8.8 Hz, 1H), 11.32 (br s, 1H), 12.45 (s, 1H).

EXAMPLE 5

3-Amino-6-[1H-5-(piperazin-1-ylmethyl)indol-2-yl]phthalimide dihydrochloride (Compound 5)

Step 1

In a similar manner to Step 2 of Example 1, 3-amino-6-bromophthalimide (30.0 mg, 0.124 mmol) was dissolved in acetonitrile (2 mL), and the solution was treated with Compound BC (85.0 mg, 0.185 mmol), palladium acetate (2.2 mg, 0.0098 mmol), tri(o-tolyl)phosphine (6.0 mg, 0.020 mmol) and triethylamine (0.169 mL, 1.24 mmol), followed by purification by flash column chromatography (hexane/ethyl acetate=4/1, 3/2, 1/1, 2/3) to obtain 3-amino-6-[1-(tert-butoxycarbonyl)-5-(piperazin-1-ylmethyl)indol-2-yl]phthalimide (26.7 mg, yield 37%).

ESI-MS m/z: 576 [M+H]$^+$; $^1$H-NMR (CDCl$_3$) δ(ppm): 1.43 (s, 9H), 1.45 (s, 9H), 2.36-2.46 (m, 4H), 3.48-3.58 (m, 4H), 3.60 (s, 2H), 5.37 (s, 2H), 6.54 (s, 1H), 6.90 (d, J=8.4 Hz, 1H), 7.29 (dd, J=3.8, 8.6 Hz, 1H), 7.44 (d, J=8.4 Hz, 1H), 7.47 (br s, 1H), 7.50 (m, 1H), 8.11 (d, J=8.6 Hz, 1H).

Step 2

3-Amino-6-[1-(tert-butoxycarbonyl)-5-(piperazin-1-ylmethyl)indol-2-yl]phthalimide (26.0 mg, 0.045 mmol) was dissolved in 4 mol/L hydrogen chloride-ethyl acetate solution (2 mL), followed by stirring at 50° C. for 9 hours The reaction mixture was cooled to room temperature, then the precipitated solid was collected by filtration, washed with ethyl acetate and then dried under reduced pressure to obtain Compound 5 (21.0 mg, yield 100%).

ESI-MS m/z: 376 [M+H]$^+$; $^1$H-NMR (DMSO-d$_6$) δ(ppm): 3.15-3.70 (m, 8H), 4.44 (s, 2H), 6.76 (s, 2H), 7.09 (d, J=8.8 Hz, 1H), 7.11 (s, 1H), 7.31 (d, J=8.4 Hz, 1H), 7.55 (d, J=8.4 Hz, 1H), 7.76 (br s, 1H), 8.03 (d, J=8.8 Hz, 1H), 9.30 (br s, 1H), 9.40 (br s, 1H), 11.33 (s, 1H), 11.45 (br s, 1H), 12.20 (br s, 1H).

EXAMPLE 6

3-Amino-6-{1H-5-[4-(2-hydroxyethyl)piperazin-1-ylmethyl]indol-2-yl}phthalimide dihydrochloride (Compound 6)

Step 1

In a similar manner to Step 2 of Example 1, 3-amino-6-bromophthalimide (83.0 mg, 0.344 mmol) was dissolved in acetonitrile (5 mL), and the solution was treated with Compound BA (150 mg, 0.519 mmol), palladium acetate (6.2 mg, 0.028 mmol), tri(o-tolyl)phosphine (17 mg, 0.055 mmol) and triethylamine (0.480 mL, 3.44 mmol), followed by purification by flash column chromatography (hexane/ethyl acetate=4/1, 3/2, 1/1, 2/3) to obtain 3-amino-6-[1-(tert-butoxycarbonyl)-5-formylindol-2-yl]phthalimide (74.1 mg, yield 53%).

ESI-MS m/z: 404 [M−H]−; $^1$H-NMR (CDCl$_3$) δ(ppm): 1.44 (s, 9H), 5.41 (br s, 2H), 6.69 (s, 1H), 6.93 (d, J=8.4 Hz, 1H), 7.41 (br s, 1H), 7.47 (d, J=8.4 Hz, 1H), 7.87 (dd, J=1.7, 8.8 Hz, 1H), 8.09 (d, J=1.7 Hz, 1H), 8.32 (d, J=8.8 Hz, 1H), 10.07 (s, 1H).

Step 2

3-Amino-6-[1-(tert-butoxycarbonyl)-5-formylindol-2-yl]phthalimide (45.0 mg, 0.111 mmol) was dissolved in acetonitrile (2 mL), and the solution was added with 1-(2-hydroxyethyl)piperazine (57 mg, 0.440 mmol), acetic acid (0.508 mL, 8.87 mmol) and sodium triacetoxyborohydride (118 mg, 0.557 mmol), followed by stirring at room temperature for 2.5 hours. The reaction mixture was added with water and sodium carbonate, extracted with ethyl acetate. The organic layer was washed with saturated brine and dried over anhydrous sodium sulfate. The solvent was evaporated under reduced pressure and the residue was purified by flash column chromatography (hexane/ethyl acetate=4/1, 1/1) to obtain 3-amino-6-{1-(tert-butoxycarbonyl)-5-[4-(2-hydroxyethyl)piperazin-1-ylmethyl]indol-2-yl}phthalimide (22.2 mg, yield 38%).

ESI-MS m/z: 520 [M+H]$^+$; $^1$H-NMR (CDCl$_3$) δ(ppm): 1.43 (s, 9H), 2.48-2.65 (m, 10H), 3.59-3.68 (m, 4H), 5.38 (s, 2H), 6.54 (s, 2H), 6.89 (d, J=8.4 Hz, 1H), 7.29 (dd, J=1.5, 8.4 Hz, 1H), 7.43 (d, J=8.4 Hz, 1H), 7.48 (br s, 1H), 8.11 (d, J=8.4 Hz, 1H).

Step 3

In a similar manner to Step 2 of Example 5, 3-amino-6-{1-(tert-butoxycarbonyl)-5-[4-(2-hydroxyethyl)piperazin-1-ylmethyl]indol-2-yl}phthalimide (22.0 mg, 0.043 mmol) was treated with 4 mol/L hydrogen chloride-ethyl acetate solution (2 mL), then the obtained solid was collected by filtration, washed with ethyl acetate and dried under reduced pressure to obtain Compound 6 (21.0 mg, yield 100%).

ESI-MS m/z: 470 [M+H]$^+$; $^1$H-NMR (DMSO-d$_6$) δ(ppm): 3.15-3.60 (m, 10H), 3.64-3.85 (m, 4H), 4.45 (br s, 2H), 7.09 (d, J=9.0 Hz, 1H), 7.12 (m, 1H), 7.34 (d, J=8.4 Hz, 1H), 7.55 (d, J=8.4 Hz, 1H), 7.79 (s, 1H), 8.03 (d, J=9.0 Hz, 1H), 11.02 (br s, 1H), 11.34 (s, 1H), 11.72 (br s, 1H), 12.22 (s, 1H).

EXAMPLE 7

3-Amino-6-[(1H-5-(piperazin-1-ylcarbonyl)indol-2-yl]phthalimide hydrochloride (Compound 7)

Step 1

In a similar manner to Step 2 of Example 1, 3-amino-6-bromophthalimide (30.0 mg, 0.124 mmol) was dissolved in acetonitrile (2-mL), and the solution was treated with Compound BB (88 mg, 0.186 mmol), palladium acetate (2.2 mg, 0.010 mmol), tri(o-tolyl)phosphine (6.0 mg, 0.020 mmol) and triethylamine (0.169 mL, 1.24 mmol), followed by purification by flash column chromatography (hexane/ethyl acetate=4/1, 3/2, 1/1, 2/3) to obtain 3-amino-6-[(1-(tert-butoxycarbonyl)-5-(4-(tert-butoxycarbonyl)piperazin-1-ylcarbonyl]indol-2-yl)phthalimide (22.8 mg, yield 31%).

ESI-MS m/z: 590 [M+H]$^+$; $^1$H-NMR (CDCl$_3$) δ(ppm): 1.27 (s, 9H), 1.42 (s, 9H), 3.35-3.90 (m, 8H), 5.44 (s, 2H), 6.70 (s, 1H), 6.90 (d, J=8.6 Hz, 1H), 7.32-7.50 (m, 2H), 7.62-7.77 (m, 2H), 8.34 (d, J=8.6 Hz, 1H).

Step 2

In a similar manner to Step 2 of Example 5, 3-amino-6-{1-(tert-butoxycarbonyl)-5-[(4-(tert-butoxycarbonyl)piperazin-1-ylcarbonyl]indol-2-yl}phthalimide (22.0 mg, 0.037 mmol) was treated with 4 mol/L hydrogen chloride-ethyl acetate solution (2 mL), then the obtained solid was collected by filtration and washed with ethyl acetate, followed by drying under reduced pressure to obtain Compound 7 (14.9 mg, yield 94%).

ESI-MS m/z: 390 [M+H]$^+$; $^1$H-NMR (DMSO-d$_6$) δ(ppm): 3.10-3.22 (m, 4H), 3.69-3.80 (m, 4H), 6.78 (br s, 2H), 7.09 (d, J=8.4 Hz, 1H), 7.13 (s, 1H), 7.22 (dd, J=0.8, 8.4 Hz, 1H), 7.53 (d, J=8.4 Hz, 1H), 7.69 (s, 1H), 8.01 (d, J=8.4 Hz, 1H), 9.09 (br s, 2H), 11.34 (s, 1H), 12.23 (br s, 1H).

EXAMPLE 8

3-Amino-4-phenyl-6-[1H-5-(piperazin-1-ylcarbonyl)indol-2-yl]phthalimide hydrochloride (Compound 8)

Step 1

In a similar manner to Step 2 of Example 1, 3-amino-4-phenyl-6-bromophthalimide (100 mg, 0.315 mmol) was dissolved in acetonitrile (7 mL), and the solution was treated with Compound BB (298 mg, 0.630 mmol), palladium acetate (5.7 mg, 0.025 mmol), tri(o-tolyl)phosphine (15 mg, 0.050 mmol) and triethylamine (0.439 mL, 3.15 mmol), followed by purification by preparative thin-layer chromatography (chloroform/acetonitrile=7/1, hexane/ethyl acetate=1/1) to obtain 3-amino-4-phenyl-6-{1-(tert-butoxycarbonyl)-5-[4-(tert-butoxycarbonyl)piperazin-1-ylcarbonyl]indol-2-yl}phthalimide (29 mg).

Step 2

3-Amino-4-phenyl-6-{1-(tert-butoxycarbonyl)-5-[4-(tert-butoxycarbonyl)piperazin-1-ylcarbonyl]indol-2-yl}phthalimide (29.0 mg) was dissolved in methanol (2.3 mL), and the solution was added with 10% hydrogen chloride-methanol solution (2.3 mL), followed by stirring at 70° C. for 1.3 hours. The reaction mixture was cooled to room temperature, then the obtained solid was collected by filtration, washed with methanol and then dried under reduced pressure to obtain Compound 8 (12 mg, yield 7.4%, 2 Steps).

APCI-MS m/z: 466 [M+H]$^+$; $^1$H-NMR (DMSO-d$_6$) δ(ppm): 3.16 (br s, 4H), 3.74 (br s, 4H), 6.28 (br s, 2H), 7.22 (dd, J=1.6, 8.3 Hz, 1H), 7.30 (s, 1H), 7.47-7.57 (m, 6H), 7.68 (s, 1H), 7.90 (s, 1H), 9.04 (br s, 2H), 11.42 (s, 1H), 12.13 (s, 1H).

EXAMPLE 9

3-Amino-4-[4-(hydroxymethyl)phenyl]-6-[1H-5-(piperazin-1-ylcarbonyl)indol-2-yl-]phthalimide hydrochloride (Compound 9)

Step 1

In a similar manner to Step 2 of Example 1, 3-amino-4-(4-hydroxymethylphenyl)-6-bromophthalimide (100 mg, 0.288 mmol) was dissolved in acetonitrile (7 mL), and the solution was treated with Compound BB (341 mg, 0.720 mmol), palladium acetate (5.2 mg, 0.023 mmol), tri(o-tolyl)phosphine (14 mg, 0.046 mmol) and triethylamine (0.401 mL, 2.88 mmol), followed by purification by preparative thin-layer chromatography (chloroform/acetonitrile=7/1, 5/1) to obtain 3-amino-4-[4-(hydroxymethyl)phenyl]-6-{1-(tert-butoxycarbonyl)-5-[4-(tert-butoxycarbonyl)piperazin-1-ylcarbonyl]indol-2-yl}phthalimide (103 mg, yield 51%).

ESI-MS m/z: 696 [M+H]$^+$; $^1$H-NMR (CDCl$_3$) δ(ppm): 1.48 (s, 9H), 1.49 (s, 9H), 3.47 (br s, 4H), 3.61 (br s, 4H), 4.79 (d, J=3.8 Hz, 2H), 5.58 (s, 1H), 6.64 (s, 1H), 7.35-7.69 (m, 8H), 8.19 (d, J=8.7 Hz, 1H).

Step 2

In a similar manner to Step 2 of Example 8, 3-amino-4-[4-(hydroxymethyl)phenyl]-6-(1-(tert-butoxycarbonyl)-5-[(4-(tert-butoxycarbonyl)piperazin-1-ylcarbonyl]indol-2-yl)phthalimide (99 mg, 0.143 mmol) was dissolved in methanol (4.0 mL), and the solution was treated with 10% hydrogen chloride-methanol solution (4.0 mL), then the obtained solid was collected by filtration, washed with methanol and then dried under reduced pressure to obtain Compound 9 (43 mg, yield 57%).

mp >295° C.; APCI-MS m/z: 496 [M+H]$^+$; $^1$H-NMR (DMSO-d$_6$) δ(ppm): 3.16 (br s, 4H), 3.74 (br s, 4H), 4.59 (s, 2H), 6.28 (s, 2H), 7.22 (dd, J=1.5, 8.4 Hz, 1H), 7.28 (s, 1H), 7.47-7.54 (m, 6H), 7.68 (s, 1H), 7.88 (s, 1H), 9.08 (br s, 2H), 11.41 (s, 1H), 12.13 (s, 1H).

EXAMPLE 10

3-Amino-4-(thiophen-2-yl)-6-[1H-5-(piperazin-1-ylcarbonyl)indol-2-yl]phthalimide (Compound 10)

Step 1

3-Amino-4-iodo-6-bromophthalimide (100 mg, 0.273 mmol) was dissolved in THF (5 mL), and the solution was added with 2-(tributylstannyl)thiophene (0.173 mL, 0.546 mmol) and bis(triphenylphosphine)dichloropalladium (15 mg, 0.022 mmol), followed by stirring under reflux for 12.5 hours under argon atmosphere. The reaction mixture was added with 10% aqueous ammonium fluoride solution, extracted with ethyl acetate. The organic layer was washed with saturated brine and dried over sodium sulfate. The solvent was evaporated under reduced pressure. The residue was purified by slurry using hexane, then purified by preparative thin-layer chromatography (chloroform/acetonitrile=30/1) to obtain 3-amino-4-(thiophen-2-yl)-6-bromophthalimide (77 mg, yield 87%).

APCI-MS m/z: 321 [M−H]$^-$; $^1$H-NMR (DMSO-d$_6$) δ(ppm): 6.31 (s, 2H), 7.23 (dd, J=3.6, 5.3 Hz, 1H), 7.43 (dd, J=1.2, 3.6 Hz, 1H), 7.59 (s, 1H), 7.75 (dd, J=1.2, 5.1 Hz, 1H), 11.26 (s, 1H).

Step 2

In a similar manner to Step 2 of Example 1, 3-amino-4-(thiophen-2-yl)-6-bromophthalimide (100 mg, 0.309 mmol) was dissolved in acetonitrile (7 mL), and the solution was treated with Compound BB (293 mg, 0.618 mmol), palladium acetate (5.5 mg, 0.025 mmol), tri(o-tolyl)phosphine (15 mg, 0.049 mmol) and triethylamine (0.431 mL, 3.09 mmol), followed by purification by preparative thin-layer chromatography (chloroform/acetonitrile=7/1) to obtain 3-amino-4-(thiophen-2-yl)-6-{1-(tert-butoxycarbonyl)-5-[4-(tert-butoxycarbonyl)piperazin-1-ylcarbonyl]indol-2-yl}phthalimide (152 mg, yield 73%).

ESI-MS m/z: 672 [M+H]$^+$; $^1$H-NMR (CDCl$_3$) δ(ppm): 1.48 (s, 18H), 3.47 (br s, 4H), 3.60 (br s, 4H), 5.86 (s, 1H), 7.19 (dd, J=3.6, 5.1 Hz, 1H), 7.33 (d, J=3.6 Hz, 1H), 7.37 (dd, J=1.6, 8.7 Hz, 1H), 7.47 (m, 2H), 7.58 (s, 1H), 7.69 (s, 1H), 8.20 (d, J=8.7 Hz, 1H).

Step 3

In a similar manner to Step 3 of Example 1, 3-amino-4-(thiophen-2-yl)-6-(1-(tert-butoxycarbonyl)-5-[4-(tert-butoxycarbonyl)piperazin-1-ylcarbonyl]indol-2-yl)phthalimide (146 mg, 0.218 mmol) was dissolved in methanol (4.4 mL), and the solution was treated with 10% hydrogen chloride-methanol solution (4.4 mL), followed by purification by preparative thin-layer chromatography (chloroform/methanol=5/1) to obtain Compound 10 (46 mg, yield 45%).

APCI-MS m/z: 472 [M+H]$^+$; $^1$H-NMR (DMSO-d$_6$) δ(ppm): 2.69 (br s, 4H), 3.44 (br s, 4H), 6.48 (s, 2H), 7.14 (dd, J=1.6, 8.5 Hz, 1H), 7.23 (s, 1H), 7.28 (dd, J=3.5, 5.2 Hz, 1H), 7.48-7.51 (m, 2H), 7.58 (s, 1H), 7.78 (dd, J=1.1, 5.2 Hz, 1H), 8.01 (s, 1H), 12.10 (s, 1H).

EXAMPLE 11

3-Amino-4-(furan-2-yl)-6-[1H-5-(piperazin-1-ylcarbonyl)indol-2-yl]phthalimide (Compound 11)

Step 1

In a similar manner to Step 1 of Example 10, 3-amino-4-iodo-6-bromophthalimide (100 mg, 0.273 mmol) was dissolved in THF (5 mL), and the solution was treated with 2-(tributylstannyl)furan (0.129 mL, 0.410 mmol) and bis(triphenylphosphine)dichloropalladium (15 mg, 0.022 mmol), followed by purification by preparative thin-layer chromatography (chloroform/acetonitrile=50/1, 40/1) to obtain 3-amino-4-(furan-2-yl)-6-bromophthalimide (44 mg, yield 52%).

APCI-MS m/z: 305 [M−H]$^-$; $^1$H-NMR (DMSO-d$_6$) δ(ppm): 6.56 (s, 2H), 6.73 (m, 1H), 7.16 (d, J=3.5 Hz, 1H), 7.89 (br s, 2H), 11.27 (s, 1H).

Step 2

In a similar manner to Step 2 of Example 1, 3-amino-4-(furan-2-yl)-6-bromophthalimide (100 mg, 0.326 mmol) was dissolved in acetonitrile (7 mL), and the solution was treated with Compound BB (309 mg, 0.652 mmol), palladium acetate (5.9 mg, 0.026 mmol), tri(o-tolyl)phosphine (16 mg, 0.052 mmol) and triethylamine (0.454 mL, 3.26 mmol), followed by purification by preparative thin-layer chromatography (chloroform/acetonitrile=6/1) to obtain 3-amino-4-(furan-2-yl)-6-{1-(tert-butoxycarbonyl)-5-[4-(tert-butoxycarbonyl)piperazin-1-ylcarbonyl]indol-2-yl}phthalimide (114 mg, yield 53%).

ESI-MS m/z: 656 [M+H]$^+$; $^1$H-NMR (CDCl$_3$) δ(ppm): 1.46 (s, 9H), 1.48 (s, 9H), 3.48 (br s, 4H), 3.64 (br s, 4H), 6.33 (s, 1H), 6.59 (dd, J=1.5, 3.3 Hz, 1H), 6.66 (s, 1H), 6.79 (d, J=3.5 Hz, 1H), 7.33 (s, 1H), 7.38 (dd, J=1.4, 8.8 Hz, 1H), 7.60-7.65 (m, 2H), 7.76 (s, 1H), 8.22 (d, J=8.4 Hz, 1H).

Step 3

In a similar manner to Step 3 of Example 1, 3-amino-4-(furan-2-yl)-6-(1-(tert-butoxycarbonyl)-5-[4-(tert-butoxycarbonyl)piperazin-1-ylcarbonyl]indol-2-yl)phthalimide (111 mg, 0.169 mmol) was dissolved in methanol (3.3 mL), and the solution was treated with 10% hydrogen chloride-methanol solution (3.3 mL), followed by purification by preparative thin-layer chromatography (chloroform/methanol/7 mol/L ammonia-methanol solution=16/2.2/1, chloroform/methanol=3/1) to obtain Compound 11 (21 mg, yield 28%).

APCI-MS m/z: 456 [M+H]$^+$; $^1$H-NMR (DMSO-d$_6$) δ(ppm): 2.69 (br s, 4H), 3.45 (br s, 4H), 6.73 (s, 2H), 6.76 (dd, J=1.9, 3.5 Hz, 1H), 7.15 (dd, J=1.6, 8.3 Hz, 1H), 7.23 (d, J=3.5 Hz, 1H), 7.27 (s, 1H), 7.51 (d, J=8.4 Hz, 1H), 7.60 (s, 1H), 7.92 (d, J=1.3 Hz, 1H), 8.28 (s, 1H), 12.13 (s, 1H).

EXAMPLE 12

3-Amino-4-(thiophen-2-yl)-6-[1H-5-(piperazin-1-ylmethyl)indol-2-yl]phthalimide dihydrochloride (Compound 12)

Step 1

In a similar manner to Step 2 of Example 1, 3-amino-4-(thiophen-2-yl)-6-bromophthalimide (100 mg, 0.309 mmol) was dissolved in acetonitrile (7 mL), and the solution was treated with Compound BC (284 mg, 0.618 mmol), palladium acetate (8.3 mg, 0.037 mmol), tri(o-tolyl)phosphine (23 mg, 0.074 mmol) and triethylamine (0.431 mL, 3.09 mmol), followed by purification by preparative thin-layer chromatography (chloroform/acetonitrile=6/1) to obtain 3-amino-4-(thiophen-2-yl)-6-(1-(tert-butoxycarbonyl)-5-[4-(tert-butoxycarbonyl)piperazin-1-ylmethyl]indol-2-yl)phthalimide (92 mg, yield 45%).

ESI-MS m/z: 658 [M+H]$^+$; $^1$H-NMR (CDCl$_3$) δ(ppm): 1.46 (s, 9H), 1.48 (s, 9H), 2.41 (br s, 4H), 3.43 (br s, 4H), 3.60 (s, 2H), 5.84 (s, 2H), 6.61 (s, 1H), 7.19 (dd, J=3.6, 5.2 Hz, 1H), 7.28-7.33 (m, 2H), 7.38 (s, 1H), 7.46 (dd, J=1.0, 5.1 Hz, 1H), 7.48 (s, 1H), 7.57 (s, 1H), 8.10 (d, J=8.6 Hz, 1H).

Step 2

In a similar manner to Step 2 of Example 8, 3-amino-4-(thiophen-2-yl)-6-{1-(tert-butoxycarbonyl)-5-[4-(tert-butoxycarbonyl)piperazin-1-ylmethyl]indol-2-yl}phthalimide (86.8 mg, 0.132 mmol) was dissolved in methanol (2.6 mL), and the solution was treated with 10% hydrogen chloride-methanol solution (2.6 mL). The obtained solid was collected by filtration, washed with methanol and then dried under reduced pressure to obtain Compound 12 (57 mg, yield 82%).

mp 238-240° C.; APCI-MS m/z: 458 [M+H]$^+$; $^1$H-NMR (DMSO-d$_6$) δ(ppm): 3.50 (br s, 8H), 4.45 (br s, 2H), 6.48 (s, 2H), 7.25 (s, 1H), 7.28 (dd, J=3.5, 5.5 Hz, 1H), 7.31 (m, 1H), 7.49 (dd, J=1.2, 3.6 Hz, 1H), 7.54 (d, J=8.6 Hz, 1H), 7.78 (br s, 1H), 7.79 (dd, J=1.2, 5.1 Hz, 1H), 8.02 (s, 1H), 9.28 (br s, 2H), 11.45 (br s, 2H), 12.07 (s, 1H).

EXAMPLE 13

3-Amino-4-(furan-2-yl)-6-[1H-5-(piperazin-1-ylmethyl)indol-2-yl]phthalimide dihydrochloride (Compound 13)

Step 1

In a similar manner to Step 2 of Example 1, 3-amino-4-(furan-2-yl)-6-bromophthalimide (94.5 mg, 0.308 mmol) was dissolved in acetonitrile (7 mL), and the solution was treated with Compound BC (283 mg, 0.616 mmol), palladium acetate (5.5 mg, 0.025 mmol), tri(o-tolyl)phosphine (15 mg, 0.050 mmol) and triethylamine (0.429 mL, 3.08 mmol), followed by purification by preparative thin-layer chromatography (chloroform/acetonitrile=5/1) to obtain 3-amino-4-(furan-2-yl)-6-{1-(tert-butoxycarbonyl)-5-[4-(tert-butoxycarbonyl)piperazin-1-ylmethyl]indol-2-yl}phthalimide (80 mg, yield 40%).

ESI-MS m/z: 642 [M+H]$^+$; $^1$H-NMR (CDCl$_3$) δ(ppm): 1.45 (s, 9H), 1.46 (s, 9H), 2.42 (br s, 4H), 3.44 (br s, 4H), 3.61 (s, 2H), 6.30 (s, 2H), 6.58 (dd, J=1.9, 3.5 Hz, 1H), 6.60 (s, 1H), 6.77 (d, J=3.5 Hz, 1H), 7.30 (dd, J=1.6, 8.6 Hz, 1H), 7.40 (s, 1H), 7.49 (br s, 1H), 7.60 (d, J=1.3 Hz, 1H), 7.75 (s, 1H), 8.12 (d, J=8.6 Hz, 1H).

Step 2

In a similar manner to Step 2 of Example 8, 3-amino-4-(furan-2-yl)-6-(1-(tert-butoxycarbonyl)-5-[4-(tert-butoxycarbonyl)piperazin-1-ylmethyl]indol-2-yl)phthalimide (76.9 mg, 0.120 mmol) was dissolved in methanol (2.3 mL), and the solution was treated with 10% hydrogen chloride-methanol solution (2.3 mL). The obtained solid was collected by filtration, washed with methanol and then dried under reduced pressure to obtain Compound 13 (48 mg, yield 77%).

mp >295° C.; APCI-MS m/z: 442 [M+H]$^+$; $^1$H-NMR (DMSO-d$_6$) δ(ppm): 3.50 (br s, 8H), 4.44 (br s, 2H), 6.75 (br s, 2H), 6.76 (dd, J=1.8, 3.5 Hz, 1H), 7.25 (d, J=3.6 Hz, 1H), 7.29 (br s, 1H), 7.34 (d, J=8.7 Hz, 1H), 7.55 (d, J=8.4 Hz, 1H), 7.81 (s, 1H), 7.92 (d, J=1.5 Hz, 1H), 8.28 (s, 1H), 9.49 (br s, 2H), 11.44 (s, 1H), 11.70 (br s, 1H), 12.11 (s, 1H)

EXAMPLE 14

3-Amino-4-(furan-2-yl)-6-[1H-5-(piperidinomethyl)indol-2-yl]phthalimide hydrochloride (Compound 14)

Step 1

In a similar manner to Step 2 of Example 1, 3-amino-4-(furan-2-yl)-6-bromophthalimide (100 mg, 0.326 mmol) was dissolved in acetonitrile (7 mL), and the solution was treated with Compound BD (234 mg, 0.652 mmol), palladium acetate (5.9 mg, 0.026 mmol), tri(o-tolyl)phosphine (16 mg, 0.052 mmol) and triethylamine (0.454 mL, 3.26 mmol), followed by purification by preparative thin-layer chromatography (chloroform/methanol=12/1, 8/1) to obtain 3-amino-4-(furan-2-yl)-6-[(1-(tert-butoxycarbonyl)-5-(piperidinomethyl)indol-2-yl]phthalimide (101 mg, yield 57%).

APCI-MS m/z: 541 [M+H]$^+$; $^1$H-NMR (CDCl$_3$) δ(ppm): 1.45 (s, 9H), 1.45 (br s, 2H), 1.60 (br s, 4H), 2.42 (br s, 4H), 3.60 (s, 2H), 6.30 (s, 2H), 6.58 (dd, J=1.8, 3.3 Hz, 1H), 6.60 (s, 1H), 6.76 (d, J=3.5 Hz, 1H), 7.26-7.32 (m, 2H), 7.50 (s, 1H), 7.60 (d, J=1.6 Hz, 1H), 7.75 (s, 1H), 8.11 (d, J=8.7 Hz, 1H).

Step 2

In a similar manner to Step 2 of Example 8, 3-amino-4-(furan-2-yl)-6-[1-(tert-butoxycarbonyl)-5-(piperidinomethyl)indol-2-yl]phthalimide (99.4 mg, 0.184 mmol) was dissolved in methanol (3 mL), and the solution was treated with 10% hydrogen chloride-methanol solution (5 mL). The obtained solid was collected by filtration, washed with methanol and then dried under reduced pressure to obtain Compound 14 (75 mg, yield 85%).

mp >295° C.; APCI-MS m/z: 441 [M+H]$^+$; $^1$H-NMR (DMSO-d$_6$) δ(ppm): 1.66-1.77 (m, 6H), 2.87 (m, 2H), 3.30 (br s, 2H), 4.32 (s, 2H), 6.74 (s, 2H), 6.76 (dd, J=1.8, 3.5 Hz, 1H), 7.23-7.30 (m, 3H), 7.55 (d, J=8.2 Hz, 1H), 7.75 (s, 1H), 7.93 (d, J=1.6 Hz, 1H), 8.28 (s, 1H), 9.79 (br s, 1H), 11.44 (s, 1H), 12.11 (s, 1H).

EXAMPLE 15

(E)-3-amino-4-(2-methoxycarbonylvinyl)-6-[1H-5-(piperazin-1-ylcarbonyl)indol-2-yl]phthalimide (Compound 15)

Step 1

3-Amino-4-iodo-6-bromophthalimide (500 mg, 1.36 mmol) was dissolved in acetonitrile (25 mL), and the solution was added with methyl acrylate (0.245 mL, 2.72 mmol), palladium acetate (24 mg, 0.11 mmol) and triethylamine (1.90 mL, 13.6 mmol), followed by stirring under reflux for 5 hours under argon atmosphere. The mixture was added with methyl acrylate (0.122 mL, 1.36 mmol), palladium acetate (24 mg, 0.11 mmol) and triethylamine (1.90 mL, 13.6 mmol) and further stirred for 142 hours. The mixture was added with methyl acrylate (0.245 mL, 2.72 mmol), palladium acetate (24 mg, 0.11 mmol) and triethylamine (0.95 mL, 6.8 mmol) and further stirred for 20 hours. The reaction mixture was added with water, extracted with ethyl acetate. The organic layer was washed with saturated brine and dried over sodium sulfate. The solvent was evaporated under reduced pressure and the residue was purified by slurry using chloroform to obtain (E)-3-amino-4-(2-methoxycarbonylvinyl)-6-bromophthalimide (313 mg, yield 71%).

APCI-MS m/z: 323 [M−H]$^-$; $^1$H-NMR (DMSO-d$_6$) δ(ppm): 3.73 (s, 3H), 6.71 (d, J=15.8 Hz, 1H), 6.84 (s, 2H), 7.86 (d, J=15.8 Hz, 1H), 8.01 (s, 1H), 11.24 (s, 1H).

Step 2

In a similar manner to Step 2 of Example 1, (E)-3-amino-4-(2-methoxycarbonylvinyl)-6-bromophthalimide (100 mg, 0.308 mmol) was dissolved in acetonitrile (7 mL), and the solution was treated with Compound BB (292 mg, 0.616 mmol), palladium acetate (5.5 mg, 0.025 mmol), tri(o-tolyl)phosphine (15 mg, 0.049 mmol) and triethylamine (0.429 mL, 3.08 mmol), followed by purification by preparative thin-layer chromatography (chloroform/acetonitrile=6/1) to obtain (E)-3-amino-4-(2-methoxycarbonylvinyl)-6-(tert-butoxycarbonyl)-5-[4-(tert-butoxycarbonyl)piperazin-1-ylcarbonyl]indol-2-yl)phthalimide (102 mg, yield 49%).

ESI-MS m/z: 674 [M+H]$^+$; $^1$H-NMR (CDCl$_3$) δ(ppm): 1.47 (s, 9H), 1.48 (s, 9H), 3.16-3.49 (m, 8H), 3.84 (s, 3H), 5.78 (s, 2H), 6.50 (d, J=15.5 Hz, 1H), 6.64 (s, 1H), 7.44 (m, 1H), 7.55 (s, 1H), 7.67 (d, J=9.2 Hz, 1H), 7.69 (s, 1H), 7.79 (d, J=15.9 Hz, 1H), 8.19 (d, J=8.6 Hz, 1H).

Step 3

In a similar manner to Step 3 of Example 1, (E)-3-amino-4-(2-methoxycarbonylvinyl)-6-{1-(tert-butoxycarbonyl)-5-[4-(tert-butoxycarbonyl)piperazin-1-ylcarbonyl]indol-2-yl}phthalimide (97.7 mg, 0.145 mmol) was dissolved in methanol (2.9 mL), and the solution was treated with 10% hydrogen chloride-methanol solution (2.9 mL), followed by purification by preparative thin-layer chromatography (chloroform/methanol/7 mol/L ammonia-methanol solution=10/0-0.8/0.2) to obtain Compound 15 (18 mg, yield 26%).

ESI-MS m/z: 474 [M+H]$^+$; $^1$H-NMR (DMSO-d$_6$) δ(ppm): 2.70 (br s, 4H), 3.45 (br s, 4H), 3.77 (s, 3H), 6.92 (d, J=15.5 Hz, 1H), 7.01 (s, 2H), 7.14 (d, J=8.4 Hz, 1H), 7.40 (s, 1H), 7.50 (d, J=8.4 Hz, 1H), 7.58 (s, 1H), 7.97 (d, J=15.5 Hz, 1H), 8.36 (s, 1H), 12.06 (s, 1H).

EXAMPLE 16

4-Chloro-7-(1H-indol-2-yl)isoindolinone (Compound 16)

Step 1

3-Chlorobenzoylchloride (110.0 g, 57.1 mmol) was dissolved in dichloromethane (200 mL), and the solution was added with cumylamine (9.04 mL, 62.9 mmol), triethylamine (12.0 mL, 85.7 mmol) and DMAP (698 mg, 5.71 mmol), followed by stirring at room temperature for 3 hours. The reaction mixture was added with water, extracted with ethyl acetate. The organic layer was washed with saturated brine and dried over anhydrous sodium sulfate. The solvent was evaporated under reduced pressure and the residue was purified by slurry using diisopropyl ether to obtain 3-chloro-N-(1-methyl-1-phenylethyl)benzamide (15.0 g, yield 96%).

APCI-MS m/z: 274 [M+H]$^+$; $^1$H-NMR (CDCl$_3$) δ(ppm): 1.83 (s, 6H), 6.35 (br s, 1H), 7.24 (m, 1H), 7.28-7.38 (m, 3H), 7.44-7.47 (m, 3H), 7.62 (d, J=7.6 Hz, 1H), 7.73 (br s, 1H).

Step 2

3-Chloro-N-(1-methyl-1-phenylethyl)benzamide (7.00 g, 25.6 mmol) was dissolved in THF (280 mL), and the solution was added with TMEDA (12.4 mL, 81.9 mmol), then added with sec-butyllithium-hexane solution (0.99 mol/L, 82.7 mL, 81.9 mmol) by drops at −78° C. for 40 minutes under argon atmosphere, followed by stirring at the same temperature for 2.5 hours. Then, the mixture was added with DMF (4.36 mL, 56.3 mmol) and warmed from −78° C. to room temperature over 2 hours. The reaction mixture was added with water, extracted with ethyl acetate. The organic layer was washed with saturated brine and dried over anhydrous sodium sulfate. The solvent was evaporated under reduced pressure and the residue was purified by slurry using diisopropyl ether to obtain 4-chloro-3-hydroxy-2-(1-methyl-1-phenylethyl)isoindolinone (6.86 g, yield 89%).

APCI-MS m/z: 302 [M+H]$^+$; $^1$H-NMR (CDCl$_3$) δ(ppm): 1.94 (s, 3H), 1.98 (s, 3H), 6.26 (br s, 1H), 7.21-7.35 (m, 4H), 7.39-7.51 (m, 4H), 7.58 (d, J=7.3 Hz, 1H).

Step 3

4-Chloro-3-hydroxy-2-(1-methyl-1-phenylethyl)isoindolinone (6.86 g, 22.7 mmol) was dissolved in THF (274 mL), and the solution was added with TMEDA (7.55 mL, 50.0 mmol), then added with sec-butyllithium-hexane solution (0.99 mol/L, 50.5 mL, 50.0 mmol) by drops at −78° C. over 20 minutes under argon atmosphere, followed by stirring at the same temperature for 2 hours. Then, the mixture was added with iodine (6.92 g, 27.3 mmol) and warmed from −78° C. to room temperature for 2.5 hours. The reaction mixture was added with 10% aqueous sodium thiosulfate solution and extracted with ethyl acetate. The organic layer was washed with saturated brine and dried over anhydrous sodium sulfate. The solvent was evaporated under reduced pressure and the residue was purified by flash column chromatography (chloroform/methanol=100/0, 85/15) to obtain 4-chloro-3-hydroxy-7-iodo-2-(1-methyl-1-phenylethyl)isoindolinone (8.22 g, yield 85%).

APCI-MS m/z: 428 [M+H]$^+$; $^1$H-NMR (CDCl$_3$) δ(ppm): 1.96 (s, 3H), 2.00 (s, 3H), 2.44 (d, J=7.9 Hz, 1H), 6.69 (d, J=8.1 Hz, 1H), 7.20 (d, J=8.4 Hz, 1H), 7.23-7.28 (m, 1H), 7.32-7.37 (m, 2H), 7.44-7.47 (m, 2H), 7.85 (d, J=8.3 Hz, 1H).

Step 4

4-Chloro-3-hydroxy-7-iodo-2-(1-methyl-1-phenylethyl)isoindolinone (6.94 g, 16.2 mmol) was dissolved in nitromethane (280 mL), and the solution was added with trifluoroacetic acid (17.7 mL, 230 mmol) and triethylsilane (7.35 mL, 46.1 mmol), followed by stirring at room temperature for 23 hours. The reaction mixture was added with water and extracted with ethyl acetate. The organic layer was washed with saturated brine and dried over anhydrous sodium sulfate. The solvent was evaporated under reduced pressure and the residue was purified by slurry using diisopropyl ether to obtain 4-chloro-7-iodoisoindolinone (4.73 g, yield 99%).

APCI-MS m/z: 294 [M+H]$^+$; $^1$H-NMR (DMSO-d$_6$) δ(ppm): 4.28 (s, 2H), 7.41 (d, J=8.2 Hz, 1H), 7.91 (d, J=8.1 Hz, 1H), 8.96 (br s, 1H).

Step 5

In a similar manner to Step 2 of Example 1, 4-chloro-7-iodoisoindolinone (100 mg, 0.341 mmol) was dissolved in acetonitrile (7 mL), and the solution was treated with 1-(tert-butoxycarbonyl)indol-2-boronic acid (178 mg, 0.682 mmol), palladium acetate (6.1 mg, 0.027 mmol), tri(o-tolyl)phosphine (17 mg, 0.055 mmol) and triethylamine (0.475-mL, 3.41 mmol), followed by purification by preparative thin-layer chromatography (chloroform/methanol=30/1) to obtain 4-chloro-7-(1-(tert-butoxycarbonyl)indol-2-yl)isoindolinone (57 mg, yield 44%).

APCI-MS m/z: 383 [M+H]$^+$; $^1$H-NMR (CDCl$_3$) δ(ppm): 1.38 (s, 9H), 4.42 (s, 2H), 6.59 (br s, 2H), 7.23 (m, 1H), 7.34 (dd, J=7.1, 8.1 Hz, 1H), 7.44 (d, J=8.1 Hz, 1H), 7.56 (d, J=7.9 Hz, 4H), 8.22 (d, J=8.4 Hz, 1H).

Step 6

In a similar manner to Step 3 of Example 1, 4-chloro-7-(1-(tert-butoxycarbonyl)indol-2-yl)isoindolinone (39.3 mg, 0.103 mmol) was dissolved in methanol (3.9 mL), and the solution was treated with 10% hydrogen chloride-methanol solution (3.9 mL), followed by purification by preparative thin-layer chromatography (chloroform/acetone=12/1) to obtain Compound 16 (24 mg, yield 83%).

APCI-MS m/z: 281 [M−H]$^−$; $^1$H-NMR (DMSO-d$_6$) δ(ppm): 4.50 (s, 2H), 7.03 (dd, J=7.1, 7.9 Hz, 1H), 7.14 (dd, J=7.4, 7.8 Hz, 1H), 7.27 (s, 1H), 7.47 (d, J=8.1 Hz, 1H), 7.58 (d, J=7.8 Hz, 1H), 7.73 (d, J=8.3 Hz, 1H), 8.21 (d, J=8.6 Hz, 1H), 9.52 (s, 1H), 13.72 (s, 1H).

EXAMPLE 17

4-Chloro-7-[1H-5-(4-methylpiperazin-1-ylcarbonyl)indol-2-yl]isoindolinone (Compound 17)

Step 1

In a similar manner to Step 2 of Example 1, 4-chloro-7-iodoisoindolinone (53.7 mg, 0.183 mmol) was dissolved in acetonitrile (4.3 mL), and the solution was treated with Compound BE (106 mg, 0.275 mmol), palladium acetate (3.3 mg, 0.015 mmol), tri(o-tolyl)phosphine (8.9 mg, 0.029 mmol) and triethylamine (0.255 mL, 1.83 mmol), followed by purification by preparative thin-layer chromatography (chloroform/methanol=15/1, ethyl acetate/methanol=2/1) to obtain 4-chloro-7-[1-(tert-butoxycarbonyl)-5-(4-methylpiperazin-1-ylcarbonyl)indol-2-yl]isoindolinone (40 mg, yield 43%).

APCI-MS m/z: 509 [M+H]$^+$; $^1$H-NMR (CDCl$_3$) δ(ppm): 1.33 (s, 9H), 2.33 (s, 3H), 2.43 (m, 4H), 3.69 (m, 4H), 4.40 (s, 2H), 6.60 (s, 1H), 7.39 (dd, J=1.7, 8.6 Hz, 1H), 7.43 (d, J=8.1 Hz, 1H), 7.56 (d, J=8.1 Hz, 1H), 7.64 (d, J=0.8 Hz, 1H), 7.75 (s, 1H), 8.26 (d, J=8.6 Hz, 1H).

Step 2

In a similar manner to Step 3 of Example 1, 4-chloro-7-[1-(tert-butoxycarbonyl)-5-(4-methylpiperazin-1-ylcarbonyl)indol-2-yl]isoindolinone (27.7 mg, 0.0544 mmol) was dissolved in methanol (2.8 mL), and the solution was treated with 10% hydrogen chloride-methanol solution (4.2 mL), followed by purification by preparative thin-layer chromatography (chloroform/methanol=12/1) to obtain Compound 17 (13 mg, yield 60%).

APCI-MS m/z: 409 [M+H]$^+$; $^1$H-NMR (CDCl$_3$+CD$_3$OD) δ(ppm): 2.36 (s, 3H), 2.50 (m, 4H), 3.72 (m, 4H), 4.48 (s, 2H), 7.12 (s, 1H), 7.23 (dd, J=1.7, 8.4 Hz, 1H), 7.50 (d, J=8.4 Hz, 1H), 7.57 (d, J=8.4 Hz, 1H), 7.70 (s, 1H), 8.08 (d, J=8.6 Hz, 1H).

EXAMPLE 18

7-(1H-5-bromoindol-2-yl)-4-chloroisoindolinone (Compound 18)

Step 1

In a similar manner to Step 2 of Example 1, 4-chloro-7-iodoisoindolinone (50.0 mg, 0.183 mmol) was dissolved in acetonitrile (4 mL), and the solution was treated with Compound BF (116 mg, 0.341 mmol), palladium acetate (3.1 mg, 0.014 mmol), tri(o-tolyl)phosphine (8.3 mg, 0.027 mmol) and triethylamine (0.240 mL, 1.72 mmol), followed by purification by preparative thin-layer chromatography (hexane/ethyl acetate=1/1, chloroform/methanol=30/1) to obtain 7-[(1-(tert-butoxycarbonyl)-5-bromoindol-2-yl]-4-chloroisoindolinone (50.5 mg, yield 64%).

APCI-MS m/z: 461 [M+H]$^+$; $^1$H-NMR (CDCl$_3$) δ(ppm): 1.31 (s, 9H), 4.38 (s, 2H), 6.51 (s, 1H), 7.37-7.45 (m, 2H), 7.49 (br s, 1H), 7.55 (d, J=7.7 Hz, 1H), 7.68 (d, J=1.8 Hz, 1H), 8.12 (d, J=8.8 Hz, 1H).

Step 2

In a similar manner to Step 2 of Example 5, 7-[1-(tert-butoxycarbonyl)-5-bromoindol-2-yl]-4-chloroisoindolinone (20.0 mg, 0.043 mmol) was treated with 4 mol/L hydrogen chloride-ethyl acetate solution (2 mL), then the solvent was evaporated under reduced pressure. The residue was added with water and sodium hydrogen carbonate, followed by extracting with ethyl acetate. The organic layer was washed with saturated brine and dried over anhydrous sodium sulfate. The solvent was evaporated under reduced pressure and the residue was dissolved in methanol. Then, the solution was added with chloroform and diisopropyl ether. The precipitated solid was collected by filtration, washed with diisopropyl ether and then dried under reduced pressure to obtain Compound 18 (10.9 mg, yield 69%).

ESI-MS m/z: 361 [M+H]$^+$; $^1$H-NMR (DMSO-d$_6$) δ(ppm): 4.51 (s, 2H), 7.24 (dd, J=1.8, 8.6 Hz, 1H), 7.25 (s, 1H), 7.48 (d, J=8.6 Hz, 1H), 7.75 (d, J=8.4 Hz, 1H), 7.78 (d, J=1.8 Hz, 1H), 8.20 (d, J=8.4 Hz, 1H), 9.57 (s, 1H), 13.91 (s, 1H).

EXAMPLE 19

7-(1H-5-carboxyindol-2-yl)-4-chloroisoindolinone (Compound 19)

Step 1

4-Chloro-7-iodoisoindolinone (1.61 g, 5.49 mmol) was dissolved in DMF (50 mL), and the solution was added with Compound BG (2.51 g, 8.23 mmol), palladium acetate (99 mg, 0.441 mmol) and triethylamine (7.65 mL, 54.9 mmol), followed by stirring at 60° C. for 4 hours under argon atmosphere. The reaction mixture was added with water, extracted with ethyl acetate. The organic layer was washed with saturated brine and dried over anhydrous sodium sulfate. The solvent was evaporated under reduced pressure and the residue was dissolved in ethyl acetate. The solution was added with diisopropyl ether and stirred under ice-cooling for 1 hour. The precipitated solid was collected by filtration, washed with diisopropyl ether and then dried under reduced pressure to obtain 7-[1-(tert-butoxycarbonyl)-5-carboxyindol-2-yl]-4-chloroisoindolinone (1.72 g, yield 74%).

ESI-MS m/z: 425 [M−H]$^−$; $^1$H-NMR (DMSO-d$_6$) δ(ppm): 1.18 (s, 9H), 4.41 (s, 2H), 6.81 (s, 1H), 7.52 (d, J=8.0 Hz, 1H), 7.74 (d, J=8.0 Hz, 1H), 7.93 (dd, J=1.7, 8.8 Hz, 1H), 8.21 (d, J=8.8 Hz, 1H), 8.24 (d, J=1.7 Hz, 1H), 8.88 (s, 1H).

Step 2

In a similar manner to Step 2 of Example 5, 7-[1-(tert-butoxycarbonyl)-5-carboxyindol-2-yl]-4-chloroisoindolinone (1.71 g, 4.01 mmol) was treated with 4 mol/L hydrogen chloride-ethyl acetate (70 mL), then the obtained solid was collected by filtration, washed with hexane and then dried under reduced pressure to obtain Compound 19 (1.13 g, yield 86%).

APCI-MS m/z: 327 [M+H]$^+$; $^1$H-NMR (DMSO-d$_6$) δ(ppm): 4.52 (s, 2H), 7.43 (s, 1H), 7.55 (d, J=8.8 Hz, 1H), 7.75 (dd, J=1.5, 8.8 Hz, 1H), 7.77 (d, J=8.4 Hz, 1H), 8.24 (d, J=8.4 Hz, 1H), 8.27 (br s, 1H), 9.59 (s, 1H), 12.49 (br s, 1H), 14.00 (s, 1H).

EXAMPLE 20

4-Chloro-7-[1H-5-(4-acetylpiperazin-1-ylcarbonyl)indol-2-yl]isoindolinone (Compound 20)

Compound 19 (30.0 mg, 0.0918 mmol) was dissolved in DMF (1 mL), and the solution was added with EDCI (35 mg, 0.18 mmol), HOBT monohydrate (12 mg, 0.089 mmol) and 1-acetylpiperazine (47 mg, 0.37 mmol), followed by stirring at 60° C. for 2 hours. The reaction mixture was added with water and the precipitated solid was collected by filtration and washed with water, followed by drying under reduced pressure to obtain Compound 20 (23.2 mg, yield 58%).

APCI-MS m/z: 437 [M+H]$^+$; $^1$H-NMR (DMSO-d$_6$) δ(ppm): 2.02 (s, 3H), 3.45-3.60 (m, 8H), 4.51 (s, 2H), 7.20 (d, J=8.4 Hz, 1H), 7.34 (s, 1H), 7.54 (d, J=8.4 Hz, 1H), 7.68 (br s, 1H), 7.74 (d, J=8.4 Hz, 1H), 8.22 (d, J=8.4 Hz, 1H), 9.55 (br s, 1H), 13.91 (br s, 1H).

EXAMPLE 21

4-Chloro-7-[1H-5-(4-methylsulfonylpiperazin-1-ylcarbonyl)indol-2-yl]isoindolinone (Compound 21)

In a similar manner to Example 20, Compound 19 (30.0 mg, 0.0918 mmol) was dissolved in DMF (1 mL), and the solution was treated with EDCI (35 mg, 0.18 mmol), HOBT monohydrate (12 mg, 0.089 mmol) and 1-(methylsulfonyl)piperazine hydrochloride (74 mg, 0.37 mmol). The mixture was added with water and extracted with chloroform. The organic layer was washed with 1 mol/L hydrochloric acid, saturated aqueous sodium hydrogencarbonate solution and saturated brine, and dried over anhydrous sodium sulfate. The solvent was evaporated under reduced pressure and the residue was suspended in chloroform. The suspension was added with hexane and stirred for 10 minutes. The solid was collected by filtration, washed with hexane/chloroform (1/1) and then dried under reduced pressure to obtain Compound 21 (28.9 mg, yield 67%).

ESI-MS m/z: 473 [M+H]$^+$; $^1$H-NMR (DMSO-d$_6$) δ(ppm): 2.91 (s, 3H), 3.11-3.21 (m, 4H), 3.54-3.70 (m, 4H), 4.51 (s, 2H), 7.21 (dd, J=1.7, 8.4 Hz, 1H), 7.34 (br s, 1H), 7.54 (d, J=8.4 Hz, 1H), 7.68 (br s, 1H), 7.74 (d, J=8.6 Hz, 1H), 8.22 (d, J=8.6 Hz, 1H), 9.56 (s, 1H), 13.92 (s, 1H).

EXAMPLE 22

4-Chloro-7-[(1H-5-(piperazin-1-ylcarbonyl)indol-2-yl]isoindolinone hydrochloride (Compound 22)

Step 1

In a similar manner to Example 20, 7-[1-(tert-butoxycarbonyl)-5-carboxyindol-2-yl]-4-chloroisoindolinone (37.8 mg, 0.0886 mmol) was dissolved in DMF (1 mL), and the solution was treated with EDCI (34 mg, 0.18 mmol), HOBT monohydrate (12 mg, 0.089 mmol) and 1-(tert-butoxycarbonyl)piperazine (66 mg, 0.35 mmol). The mixture was added with water and the precipitated solid was collected by filtration, washed with water and then dried under reduced pressure to obtain 4-chloro-7-(1-(tert-butoxycarbonyl)-5-[4-(tert-butoxycarbonyl)piperazin-1-ylcarbonyl]indol-2-yl)isoindolinone (43.5 mg, yield 83%).

ESI-MS m/z: 595 [M+H]$^+$; $^1$H-NMR (DMSO-d$_6$) δ(ppm): 1.19 (s, 9H), 1.40 (s, 9H), 3.40-3.60 (m, 8H), 4.41 (s, 2H), 6.73 (s, 1H), 7.39 (dd, J=1.5, 8.2 Hz, 1H), 7.51 (d, J=8.2 Hz, 1H), 7.69 (br s, 1H), 7.74 (d, J=8.2 Hz, 1H), 8.18 (d, J=8.2 Hz, 1H), 8.88 (s, 1H).

Step 2

In a similar manner to Step 2 of Example 5, 4-chloro-7-(1-(tert-butoxycarbonyl)-5-[4-(tert-butoxycarbonyl)piperazin-1-ylcarbonyl]indol-2-yl)isoindolinone (42.0 mg, 0.0707 mmol) was treated with 4 mol/L hydrogen chloride-ethyl acetate (4 mL). The obtained solid was collected by filtration, washed with ethyl acetate and dried under reduced pressure to obtain Compound 22 (29.0 mg, yield 95%).

mp >295° C.: ESI-MS m/z: 395 [M+H]$^+$; $^1$H-NMR (DMSO-d$_6$) δ(ppm): 3.12-3.20 (m, 4H), 3.69-3.78 (m, 4H), 4.51 (s, 2H), 7.24 (dd, J=1.5, 8.4 Hz, 1H), 7.34 (br s, 1H), 7.55 (d, J=8.4 Hz, 1H), 7.74 (s, 1H), 7.75 (d, J=8.6 Hz, 1H), 8.22 (d, J=8.6 Hz, 1H), 9.10 (br s, 2H), 9.57 (s, 1H), 13.93 (s, 1H).

EXAMPLE 23

4-Chloro-7-{1H-5-[4-(2-hydroxyethyl)piperazin-1-ylcarbonyl]indol-2-yl}isoindolinone (Compound 23)

In a similar manner to Example 20, Compound 19 (14.0 mg, 0.0428 mmol) was dissolved in DMF (0.5 mL), and the solution was treated with EDCI (16 mg, 0.084 mmol), HOBT monohydrate (6.0 mg, 0.044 mmol) and 1-(2-hydroxyethyl)piperazine (22 mg, 0.17 mmol). The mixture was added with water and extracted with ethyl acetate. The organic layer was washed with saturated aqueous sodium hydrogencarbonate solution and saturated brine, and dried over anhydrous sodium sulfate. The solvent was evaporated under reduced pressure and the residue was suspended in chloroform. Then, the suspension was added with diisopropyl ether and stirred for 1 hour. The solid was collected by filtration, washed with diisopropyl ether and then dried under reduced pressure to obtain Compound 23 (10.2 mg, yield 54%).

mp >295° C.: ESI-MS m/z: 439 [M+H]$^+$; $^1$H-NMR (DMSO-d$_6$) δ(ppm): 2.39-2.48 (m, 6H), 3.47-3.59 (m, 6H), 4.43 (t, J=5.5 Hz, 1H), 4.51 (s, 2H), 7.17 (dd, J=1.5, 8.4 Hz, 1H), 7.34 (br s, 1H), 7.53 (d, J=8.4 Hz, 1H), 7.64 (br s, 1H), 7.75 (d, J=8.4 Hz, 1H), 8.22 (d, J=8.4 Hz, 1H), 9.56 (s, 1H), 13.90 (s, 1H).

EXAMPLE 24

4-Chloro-7-{1H-5-[4-(2-hydroxyethyl)piperazin-1-ylmethyl]indol-2-yl}isoindolinone dihydrochloride (Compound 24)

Step 1

In a similar manner to Step 2 of Example 1, 4-chloro-7-iodoisoindolinone (500 mg, 1.70 mmol) was dissolved in acetonitrile (10 mL), and the solution was treated with Compound BA (737 mg, 2.55 mmol), palladium acetate (31 mg, 0.14 mmol) and triethylamine (2.37 mL, 17.0 mmol), followed by purification by flash column chromatography (hexane/ethyl acetate=4/1, 7/3, 3/2) to obtain 4-chloro-7-[1-(tert-butoxycarbonyl)-5-formylindol-2-yl]isoindolinone (498 mg, yield 71%).

APCI-MS m/z: 411 [M+H]$^+$; $^1$H-NMR (CDCl$_3$) δ(ppm): 1.34 (s, 9H), 4.43 (s, 2H), 6.70 (s, 1H), 7.33 (s, 1H), 7.47 (d, J=8.1 Hz, 1H), 7.61 (d, J=8.1 Hz, 1H), 7.88 (dd, J=1.5, 8.8 Hz, 1H), 8.11 (d, J=1.5 Hz, 1H), 8.37 (d, J=8.8 Hz, 1H), 10.04 (s, 1H).

Step 2

In a similar manner to Step 2 of Example 6, 4-chloro-7-[1-(tert-butoxycarbonyl)-5-formylindol-2-yl]isoindolinone (20.7 mg, 0.0504 mmol) was dissolved in acetonitrile (1 mL), and the solution was treated with 1-(2-hydroxyethyl)piperazine (28 mg, 0.22 mmol), acetic acid (0.232 mL, 4.05 mmol) and sodium triacetoxyborohydride (116 mg, 0.547 mmol). The reaction mixture was added with water and sodium carbonate, followed by extracting with ethyl acetate. The organic layer was washed with saturated brine and dried over anhydrous sodium sulfate. The solvent was evaporated under reduced pressure to obtain 4-chloro-7-(1-(tert-butoxycarbonyl)-5-[4-(2-hydroxyethyl)piperazin-1-ylmethyl]indol-2-yl)isoindolinone (29.6 mg).

Step 3

In a similar manner to Step 2 of Example 5, 4-chloro-7-(1-(tert-butoxycarbonyl)-5-[4-(2-hydroxyethyl)piperazine-1-ylmethyl]indol-2-yl)isoindolinone (29.6 mg) was treated with 4 mol/L hydrogen chloride-ethyl acetate solution (4 mL). The obtained solid was collected by filtration and washed with ethyl acetate, followed by drying under reduced pressure to obtain Compound 24 (17.8 mg, yield 71%, 2 Steps).

mp 232-243° C.; ESI-MS m/z: 425 [M+H]$^+$: $^1$H-NMR (DMSO-d$_6$) δ(ppm): 3.10-3.90 (m, 14H), 4.44 (br s, 1H), 4.52 (s, 2H), 7.30-7.42 (m, 2H), 7.58 (d, J=8.4 Hz, 1H), 7.76 (d, J=8.6 Hz, 1H), 7.82 (br s, 1H), 8.26 (d, J=8.6 Hz, 1H), 9.58 (s, 1H), 10.90 (br s, 1H), 11.61 (br s, 1H), 13.90 (s, 1H).

EXAMPLE 25

4-Chloro-7-[1H-5-(4-methylpiperazin-1-ylsulfonyl)indol-2-yl]isoindolinone (Compound 25)

In a similar manner to Step 2 of Example 1, 4-chloro-7-iodoisoindolinone (60.0 mg, 0.204 mmol) was dissolved in acetonitrile (2 mL), and the solution was treated with a mixture (259 mg) of 1-(tert-butoxycarbonyl)-5-(4-methylpiperazin-1-ylsulfonyl)indol-2-boronic acid and 5-(4-methylpiperazin-1-ylsulfonyl)-1H-indol-2-boronic acid synthesized in a similar manner to the literature [Bioorganic & Medicinal Chemistry Letters, 2004, vol. 14, p. 351], palladium acetate (3.7 mg, 0.017 mmol) and triethylamine (0.284 mL, 2.04 mmol). The reaction mixture was added with water. The precipitated solid was collected by filtration and washed with water, followed by drying under reduced pressure to obtain Compound 25 (28.4 mg, yield 31%).

ESI-MS m/z: 445 [M+H]$^+$; $^1$H-NMR (DMSO-d$_6$) δ(ppm): 2.11 (s, 3H), 2.31-2.38 (m, 4H), 2.85-2.94 (m, 4H), 4.52 (s, 2H), 7.45 (d, J=8.8 Hz, 1H), 7.48 (s, 1H), 7.72 (d, J=8.8 Hz, 1H), 7.79 (d, J=8.4 Hz, 1H), 8.02 (s, 1H), 8.23 (d, J=8.4 Hz, 1H), 9.60 (s, 1H), 14.18 (s, 1H).

EXAMPLE 26

4-Chloro-7-[1H-5-(piperazin-1-ylmethyl)indol-2-yl]isoindolinone dihydrochloride (Compound 26)

Step 1

In a similar manner to Step 2 of Example 1, 4-chloro-7-iodoisoindolinone (53.3 mg, 0.181 mmol) was dissolved in acetonitrile (2 mL), and the solution was treated with Compound BC (100 mg, 218 mmol), palladium acetate (3.3 mg, 0.015 mmol) and triethylamine (0.126 mL, 0.904 mmol), followed by purification by flash column chromatography (hexane/ethyl acetate=4/1, 1/1, 3/7) to obtain 4-chloro-7-(1-(tert-butoxycarbonyl)-5-[4-(tert-butoxycarbonyl)piperazin-1-ylmethyl]indol-2-yl)isoindolinone (75.2 mg, yield 71%).

APCI-MS m/z: 581 [M+H]$^+$; $^1$H-NMR (CDCl$_3$) δ(ppm): 1.38 (s, 9H), 1.45 (s, 9H), 2.35-2.46 (m, 4H), 3.38-3.47 (m, 4H), 3.60 (s, 2H), 4.42 (s, 2H), 6.40 (br s, 1H), 6.55 (s, 1H), 7.29 (dd, J=1.7, 8.6 Hz, 1H), 7.43 (d, J=8.1 Hz, 1H), 7.48 (d, J=1.7 Hz, 1H), 7.56 (d, J=8.1 Hz, 1H), 8.14 (d, J=8.6 Hz, 1H).

Step 2

In a similar manner to Step 2 of Example 5, 4-chloro-7-{1-(tert-butoxycarbonyl)-5-[4-(tert-butoxycarbonyl)piperazin-1-ylmethyl]indol-2-yl}isoindolinone (70 mg, 0.120 mmol) was treated with 4 mol/L hydrogen chloride-ethyl acetate solution (6 mL). The precipitated solid was collected by filtration, washed with ethyl acetate and then dried under reduced pressure to obtain Compound 26 (50.7 mg, yield 93%).

mp >295° C.; ESI-MS m/z: 381 [M+H]$^+$; $^1$H-NMR (DMSO-d$_6$) δ(ppm): 3.10-3.65 (m, 8H), 4.30-4.55 (m, 2H), 4.43 (s, 2H), 7.33 (s, 1H), 7.35 (m, 1H), 7.56 (d, J=8.4 Hz, 1H), 7.74 (d, J=8.4 Hz, 1H), 7.82 (s, 1H), 8.24 (d, J=8.4 Hz, 1H), 9.45 (br s, 2H), 9.56 (s, 1H), 11.62 (br s, 1H), 13.88 (s, 1H).

EXAMPLE 27

4-Chloro-7-{1H-5-[(2-morpholinoethyl)aminomethyl]indol-2-yl}isoindolinone dihydrochloride (Compound 27)

Step 1

In a similar manner to Step 2 of Example 6, 4-chloro-7-[1-(tert-butoxycarbonyl)-5-formylindol-2-yl]isoindolinone (37.6 mg, 0.0915 mmol) was dissolved in acetonitrile (2 mL), and the solution was treated with 4-(2-aminoethyl)morpholine (0.048 mL, 0.37 mmol), acetic acid (0.105 mL, 1.83 mmol) and sodium triacetoxyborohydride (97 mg, 0.46 mmol). The reaction mixture was added with water and sodium carbonate, followed by extracting with ethyl acetate. The organic layer was washed with saturated brine and dried over anhydrous sodium sulfate and the solvent was evaporated under reduced pressure to obtain 4-chloro-7-(1-(tert-butoxycarbonyl)-5-[(2-morpholinoethyl)aminomethyl]indol-2-yl)isoindolinone (51.7 mg).

Step 2

In a similar manner to Step 2 of Example 5, 4-chloro-7-{1-(tert-butoxycarbonyl)-5-[(2-morpholinoethyl)aminomethyl]indol-2-yl}isoindolinone (50.7 mg) was treated with 4 mol/L hydrogen chloride-ethyl acetate solution (2 mL). The precipitated solid was collected by filtration, washed with ethyl acetate and then dried under reduced pressure to obtain Compound 27 (28.3 mg, yield 62%, 2 Steps).

ESI-MS m/z: 425 [M+H]$^+$; $^1$H-NMR (DMSO-d$_6$) δ(ppm): 3.00-3.63 (m, 8H), 3.65-4.10 (m, 4H), 4.26 (br s, 2H), 4.50 (s, 2H), 7.33 (d, J=8.3 Hz, 1H), 7.34 (s, 1H), 7.56 (d, J=8.3 Hz, 1H), 7.74 (d, J=8.6 Hz, 1H), 7.82 (s, 1H), 8.24 (d, J=8.6 Hz, 1H), 9.40 (br s, 2H), 9.56 (s, 1H), 11.17 (br s, 1H), 13.88 (s, 1H).

EXAMPLE 28

4-Chloro-7-{1H-5-[di(2-hydroxyethyl)aminomethyl]indol-2-yl}isoindolinone hydrochloride (Compound 28)

Step 1

In a similar manner to Step 2 of Example 6, 4-chloro-7-[1-(tert-butoxycarbonyl)-5-formylindol-2-yl]isoindolinone (37.6 mg, 0.0922 mmol) was dissolved in acetonitrile (2 mL), and the solution was treated with diethanolamine (0.035 mL, 0.37 mmol), acetic acid (0.106 mL, 1.85 mmol) and sodium triacetoxyborohydride (98 mg, 0.46 mmol), followed by purification by preparative thin-layer chromatography (hexane/ethyl acetate=1/2) to obtain 4-chloro-7-(1-(tert-butoxycarbonyl)-5-[di(2-hydroxyethyl)aminomethyl]indol-2-yl) isoindolinone (29.2 mg, yield 64%).

ESI-MS m/z: 500 [M+H]$^+$; $^1$H-NMR (CDCl$_3$) δ(ppm): 1.33 (s, 9H), 2.49 (br s, 2H), 2.72 (t, J=5.4 Hz, 4H), 3.62 (t, J=5.4 Hz, 4H), 3.76 (s, 2H), 4.37 (s, 2H), 6.53 (s, 1H), 7.26 (dd, J=1.8, 8.6 Hz, 1H), 7.41 (d, J=8.1 Hz, 1H), 7.45 (d, J=1.8 Hz, 1H), 7.54 (d, J=8.1 Hz, 1H), 7.76 (br s, 1H), 8.17 (d, J=8.6 Hz, 1H).

Step 2

In a similar manner to Step 2 of Example 5, 4-chloro-7-{1-(tert-butoxycarbonyl)-5-[di(2-hydroxyethyl)aminomethyl]indol-2-yl}isoindolinone (28.0 mg, 0.0560 mmol) was treated with 4 mol/L hydrogen chloride-ethyl acetate solution (2 mL). The precipitated solid was collected by filtration, washed with ethyl acetate and then dried under reduced pressure to obtain Compound 28 (21.6 mg, yield 89%).

ESI-MS m/z: 400 [M+H]$^+$; $^1$H-NMR (DMSO-d$_6$) δ(ppm): 3.16-3.28 (m, 4H), 3.72-3.86 (m, 4H), 4.45-4.54 (m, 2H), 4.50 (s, 2H), 5.31 (br s, 2H), 7.33 (dd, J=1.3, 8.6 Hz, 1H), 7.34 (s, 1H), 7.56 (d, J=8.6 Hz, 1H), 7.75 (d, J=8.6 Hz, 1H), 7.81 (s, 1H), 8.23 (d, J=8.6 Hz, 1H), 9.47 (s, 1H), 9.55 (s, 1H), 13.87 (s, 1H).

EXAMPLE 29

4-Chloro-7-[1H-5-(piperidinomethyl)indol-2-yl]isoindolinone hydrochloride (Compound 29)

Step 1

In a similar manner to Step 2 of Example 6, 4-chloro-7-[1-(tert-butoxycarbonyl)-5-formylindol-2-yl]isoindolinone (36.2 mg, 0.0881 mmol) was dissolved in acetonitrile (2 mL), and the solution was treated with piperidine (0.035 mL, 0.35 mmol), acetic acid (0.101 mL, 1.76 mmol) and sodium triacetoxyborohydride (93 mg, 0.44 mmol), followed by purification by preparative thin-layer chromatography (hexane/ethyl acetate=1/2) to obtain 4-chloro-7-[1-(tert-butoxycarbonyl)-5-(piperidinomethyl)indol-2-yl]isoindolinone (31.2 mg, yield 74%).

ESI-MS m/z: 480 [M+H]$^+$; $^1$H-NMR (CDCl$_3$) δ(ppm): 1.34 (s, 9H), 1.40-1.52 (m, 2H), 1.52-1.62 (m, 4H), 2.34-2.50 (m, 4H), 3.59 (s, 2H), 4.38 (s, 2H), 6.54 (s, 1H), 7.30 (dd, J=1.5, 8.8 Hz, 1H), 7.42 (d, J=8.1 Hz, 1H), 7.49 (d, J=1.5 Hz, 1H), 7.54 (d, J=8.1 Hz, 1H), 7.64 (s, 1H), 8.15 (d, J=8.8 Hz, 1H).

Step 2

In a similar manner to Step 2 of Example 5, 4-chloro-7-[1-(tert-butoxycarbonyl)-5-(piperidinomethyl)indol-2-yl]isoindolinone (30.0 mg, 0.0629 mmol) was treated with 4 mol/L hydrogen chloride-ethyl acetate solution (2 mL). The mixture was added with diisopropyl ether. The precipitated solid was collected by filtration, washed with diisopropyl ether and then dried under reduced pressure to obtain Compound 29 (11.2 mg, yield 43%).

mp >295° C.; ESI-MS m/z: 380 [M+H]$^+$; $^1$H-NMR (DMSO-d$_6$) δ(ppm): 1.45 (m, 1H), 1.59-1.74 (m, 3H), 1.75-1.89 (m, 2H), 2.40-2.58 (m, 2H), 2.80-2.95 (m, 2H), 4.33 (d, J=4.6 Hz, 2H), 4.52 (s, 2H), 7.28 (dd, J=1.0, 5.4 Hz, 1H), 7.36 (d, J=1.0 Hz, 1H), 7.58 (d, J=8.4 Hz, 1H), 7.75 (s, 1H), 7.76 (d, J=8.6 Hz, 1H), 8.25 (d. J=8.6 Hz, 1H), 9.44 (br s, 1H), 9.57 (s, 1H), 13.90 (s, 1H).

EXAMPLE 30

4-Chloro-7-(1H-5-[(4-hydroxypiperidino)methyl]indol-2-yl)isoindolinone hydrochloride (Compound 30)

Step 1

In a similar manner to Step 2 of Example 6, 4-chloro-7-[1-(tert-butoxycarbonyl)-5-formyl]indolylisoindolinone (39.0 mg, 0.0949 mmol) was dissolved in acetonitrile (2 mL), and the solution was treated with 4-hydroxypiperidine (38 mg, 0.38 mmol), acetic acid (0.109 mL, 1.90 mmol) and sodium triacetoxyborohydride (101 mg, 0.477 mmol), followed by purification by preparative thin-layer chromatography (hexane/ethyl acetate=1/2) to obtain 4-chloro-7-{1-(tert-butoxycarbonyl)-5-[(4-hydroxypiperidino)methyl]indol-2-yl}isoindolinone (30.1 mg, yield 64%).

ESI-MS m/z: 496 [M+H]$^+$; $^1$H-NMR (CDCl$_3$) δ(ppm): 1.34 (s, 9H), 1.50-1.68 (m, 2H), 1.82-2.02 (m, 2H), 2.10-2.22 (m, 2H), 2.73-2.88 (m, 2H), 3.58-3.75 (m, 2H), 3.60 (s, 2H), 4.39 (s, 2H), 6.54 (s, 1H), 7.29 (dd, J=1.8, 8.8 Hz, 1H), 7.42 (d, J=8.1 Hz, 1H), 7.44-7.51 (m, 2H), 7.55 (d, J=8.1 Hz, 1H), 8.15 (d, J=8.8 Hz, 1H).

Step 2

In a similar manner to Step 2 of Example 5, 4-chloro-7-{1-(tert-butoxycarbonyl)-5-[(4-hydroxypiperidino)methyl]indol-2-yl}isoindolinone (29.0 mg, 0.0584 mmol) was treated with 4 mol/L hydrogen chloride-ethyl acetate solution (2 mL). The mixture was added with diisopropyl ether. The precipitated solid was collected by filtration, washed with diisopropyl ether and then dried under reduced pressure to obtain Compound 30 (14.6 mg, yield 58%).

ESI-MS m/z: 396 [M+H]$^+$; $^1$H-NMR (DMSO-d$_6$) δ(ppm): 1.62-1.74 (m, 2H), 1.85-2.00 (m, 2H), 2.85-3.40 (m, 4H), 3.92 (m, 1H), 4.35 (d, J=5.0 Hz, 2H), 4.52 (s, 2H), 7.29-7.40 (m, 2H), 7.57 (d, J=8.4 Hz, 1H), 7.76 (d, J=8.6 Hz, 1H), 7.77 (s, 1H), 8.25 (d, J=8.6 Hz, 1H), 9.58 (s, 1H), 10.01 (br s, 1H), 13.89 (s, 1H).

EXAMPLE 31

4-Chloro-7-[1H-5-(2-morpholinoethoxy)indol-2-yl]isoindolinone hydrochloride (Compound 31)

Step 1

In a similar manner to Step 2 of Example 1, 4-chloro-7-iodoisoindolinone (50.0 mg, 0.170 mmol) was dissolved in acetonitrile (2 mL), and the solution was treated with Compound BI (100 mg, 256 mmol), palladium acetate (3.1 mg, 0.014 mmol) and triethylamine (0.237 mL, 1.70 mmol), followed by purification by flash column chromatography (hexane/ethyl acetate=4/1, 1/1, 3/7) to obtain 4-chloro-7-[1-(tert-butoxycarbonyl)-5-(2-morpholinoethoxy)indol-2-yl]isoindolinone (71.4 mg, yield 82%).

ESI-MS m/z: 512 [M+H]$^+$; $^1$H-NMR (CDCl$_3$) δ(ppm): 1.30 (s, 9H), 2.55-2.65 (m, 4H), 2.83 (t, J=5.7 Hz, 2H), 3.72-3.80 (m, 4H), 4.17 (t, J=5.7 Hz, 2H), 4.35 (s, 2H), 6.49 (s, 1H), 6.97 (dd, J=2.6, 9.1 Hz, 1H), 7.03 (d, J=2.6 Hz, 1H), 7.40 (d, J=8.0 Hz, 1H), 7.53 (d, J=8.0 Hz, 1H), 7.98 (s, 1H), 8.13 (d, J=9.1 Hz, 1H).

Step 2

In a similar manner to Step 2 of Example 8, 4-chloro-7-[1-(tert-butoxycarbonyl)-5-(2-morpholinoethoxy)indol-2-yl]isoindolinone (70.0 mg, 0.137 mmol) was dissolved in methanol (1 mL), and the solution was treated with 10% hydrogen chloride-methanol solution (1 mL). The mixture was added with ethyl acetate. The precipitated solid was collected by filtration, washed with ethyl acetate and then dried under reduced pressure to obtain Compound 31 (50.3 mg, yield 80%).

APCI-MS m/z: 412 [M+H]$^+$; $^1$H-NMR (DMSO-d$_6$) δ(ppm): 3.16-3.30 (m, 2H), 3.48-3.62 (m, 4H), 3.92-4.06 (m, 4H), 4.35-4.45 (m, 2H), 4.50 (s, 2H), 6.88 (dd, J=2.2, 8.8 Hz, 1H), 7.17 (d, J=2.2 Hz, 1H), 7.20 (br s, 1H), 7.44 (d, J=8.8 Hz, 1H), 7.73 (d, J=8.4 Hz, 1H), 8.19 (d, J=8.4 Hz, 1H), 9.53 (s, 1H), 10.63 (br s, 1H), 13.68 (s, 1H).

EXAMPLE 32

4-Chloro-7-{1H-5-[(2-hydroxyethyl)aminomethyl]indol-2-yl}isoindolinone hydrochloride
(Compound 32)

Step 1

In a similar manner to Step 2 of Example 6, 4-chloro-7-[1-(tert-butoxycarbonyl)-5-formylindol-2-yl]isoindolinone (40.0 mg, 0.0974 mmol) was dissolved in acetonitrile (2 mL), and the solution was treated with 2-aminoethanol (0.024 mL, 0.39 mmol), acetic acid (0.112 mL, 1.96 mmol) and sodium triacetoxyborohydride (103 mg, 0.486 mmol), followed by purification by preparative thin-layer chromatography (hexane/ethyl acetate=1/2) to obtain 4-chloro-7-(1-(tert-butoxycarbonyl)-5-[(2-hydroxyethyl)aminomethyl]indol-2-yl)isoindolinone (39.4 mg, yield 871).

APCI-MS m/z: 456 [M+H]$^+$; $^1$H-NMR (CDCl$_3$) δ(ppm): 1.32 (s, 9H), 2.80 (t, J=5.2 Hz, 2H), 3.65 (t, J=5.2 Hz, 2H), 3.88 (s, 2H), 4.35 (s, 2H), 6.53 (s, 1H), 7.27 (d, J=8.6 Hz, 1H), 7.38 (d, J=8.0 Hz, 1H), 7.42 (br s, 1H), 7.53 (d, J=8.0 Hz, 1H), 7.86 (br s, 1H), 8.18 (d, J=8.6 Hz, 1H).

Step 2

In a similar manner to Step 2 of Example 8, 4-chloro-7-{1-(tert-butoxycarbonyl)-5-[(2-hydroxyethyl)aminomethyl]indol-2-yl}isoindolinone (39.0 mg, 0.0855 mmol) was dissolved in methanol (1 mL), and the solution was treated with 10% hydrogen chloride-methanol solution (1 mL). The mixture was added with ethyl acetate. The precipitated solid was collected by filtration, washed with ethyl acetate and then dried under reduced pressure to obtain Compound 32 (10.7 mg, yield 32%).

mp >295° C.: APCI-MS m/z: 356 [M+H]$^+$; $^1$H-NMR (DMSO-d$_6$) δ(ppm); 2.90-3.00 (m, 2H), 3.66 (dt, J=5.1, 5.3 Hz, 2H), 4.19-4.27 (m, 2H), 4.52 (s, 2H), 5.21 (t, J=5.1 Hz, 1H), 7.29 (dd, J=1.3, 8.6 Hz, 1H), 7.35 (s, 1H), 7.56 (d, J=8.4 Hz, 1H), 7.74 (d, J=1.3 Hz, 1H), 7.75 (d, J=8.4 Hz, 1H), 8.25 (d, J=8.4 Hz, 1H), 8.85 (br s, 2H), 9.57 (s, 1H), 13.87 (s, 1H).

EXAMPLE 33

4-Chloro-7-(1H-5-[(2-dimethylaminoethyl)aminomethyl]indol-2-yl)isoindolinone dihydrochloride
(Compound 33)

Step 1

In a similar manner to Step 2 of Example 6, 4-chloro-7-[1-(tert-butoxycarbonyl)-5-formylindol-2-yl]isoindolinone (40.0 mg, 0.0974 mmol) was dissolved in acetonitrile (2 mL), and the solution was treated with N,N-dimethylethylenediamine (0.043 mL, 0.39 mmol), acetic acid (0.112 mL, 1.96 mmol) and sodium triacetoxyborohydride (103 mg, 0.486 mmol). The reaction mixture was added with water and sodium carbonate to adjust the pH to 9, followed by extracting with ethyl acetate. The organic layer was washed with saturated brine and dried over anhydrous sodium sulfate. The solvent was evaporated under reduced pressure to obtain 4-chloro-7-(1-(tert-butoxycarbonyl)-5-[(2-dimethylaminoethyl)aminomethyl]indol-2-yl)isoindolinone (51.5 mg).

Step 2

In a similar manner to Step 2 of Example 8, 4-chloro-7-{1-(tert-butoxycarbonyl)-5-[(2-dimethylaminoethyl)aminomethyl]indol-2-yl}isoindolinone (51.0 mg) was dissolved in methanol (1 mL), and the solution was treated with 10% hydrogen chloride-methanol solution (1 mL). The mixture was added with diisopropyl ether. The precipitated solid was collected by filtration, washed with diisopropyl ether and then dried under reduced pressure to obtain Compound 33 (37.6 mg, yield 85%, 2 Steps).

APCI-MS m/z: 383 [M+H]$^+$; $^1$H-NMR (DMSO-d$_6$) δ(ppm): 2.83 (s, 6H), 3.38-3.50 (m, 4H), 4.27 (s, 2H), 4.52 (s, 2H), 7.34 (d, J=8.4 Hz, 1H), 7.36 (s, 1H), 7.57 (d, J=8.4 Hz, 1H), 7.76 (d, J=8.4 Hz, 1H), 7.80 (s, 1H), 8.26 (d, J=8.4 Hz, 1H), 9.41 (br s, 2H), 9.58 (s, 1H), 10.70 (br s, 1H), 13.90 (s, 1H).

EXAMPLE 34

4-Chloro-7-[1H-5-(ethoxycarbonylmethylaminomethyl)indol-2-yl]isoindolinone hydrochloride
(Compound 34)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with glycine ethylester hydrochloride (41.0 mg, 0.294 mmol), triethylamine (0.081 mL, 0.58 mmol), acetic acid (0.084 mL, 1.5 mmol) and sodium triacetoxyborohydride (77.0 mg, 0.360 mmol). The reaction mixture was added with water and sodium hydrogen carbonate, followed by extracting with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(ethoxycarbonylmethylaminomethyl)indol-2-yl]isoindolinone (39.2 mg).

Step 2

In a similar manner to Step 2 of Example 5, 4-chloro-7-[1-(tert-butoxycarbonyl)-5-(ethoxycarbonylmethylaminomethyl)indol-2-yl]isoindolinone (39.2 mg) was treated with 4 mol/L hydrogen chloride-ethyl acetate solution (2 mL). The precipitated solid was collected by filtration, washed with ethyl acetate and then dried under reduced pressure to obtain Compound 34 (27.9 mg, yield 88%, 2 Steps).

ESI-MS m/z: 398 [M+H]$^+$; $^1$H-NMR (DMSO-d$_6$) δ(ppm): 1.22 (t, J=7.1 Hz, 3H), 3.95 (d, J=5.8 Hz, 2H), 4.20 (q, J=7.1 Hz, 2H), 4.24 (s, 2H), 4.52 (s, 2H), 7.26 (dd, J=1.4, 8.3 Hz, 1H), 7.35 (d, J=1.4 Hz, 1H), 7.56 (d, J=8.3 Hz, 1H), 7.72 (s, 1H), 7.76 (d, J=8.6 Hz, 1H), 8.25 (d, J=8.6 Hz, 1H), 9.38 (br s, 2H), 9.57 (s, 1H), 13.89 (s, 1H).

EXAMPLE 35

4-Chloro-7-[1H-5-(carboxymethylaminomethyl)indol-2-yl]isoindolinone hydrochloride (Compound 35)

Step 1

Compound 34 (20.0 mg, 46.0 mmol) was dissolved in acetonitrile (1 mL), and the solution was treated with di-tert-butyldicarbonate (0.012 mL, 0.052 mmol) and triethylamine (0.026 mL, 0.19 mmol), followed by stirring at room temperature for 1 hour. The reaction mixture was added with water, extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(ethoxycarbonylmethylaminomethyl)indol-2-yl]isoindolinone (43.4 mg).

Step 2

4-Chloro-7-[1-(tert-butoxycarbonyl)-5-(ethoxycarbonylmethylaminomethyl)indol-2-yl]isoindolinone (43.4 mg) was dissolved in DMF (2 mL), and the solution was added with 4 mol/L aqueous lithium hydroxide solution (1 mL), followed by stirring at room temperature for 1 hour. The reaction mixture was added with 1 mol/L hydrochloric acid, extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(carboxymethylaminomethyl)indol-2-yl]isoindolinone (25.0 mg).

Step 3

In a similar manner to Step 2 of Example 5, 4-chloro-7-[1-(tert-butoxycarbonyl)-5-(carboxymethylaminomethyl)indol-2-yl]isoindolinone (25.0 mg) was treated with 4 mol/L hydrogen chloride-ethyl acetate solution (1 mL). The precipitated solid was collected by filtration, washed with ethyl acetate and then dried under reduced pressure to obtain Compound 35 (16.8 mg, yield 90%, 3 Steps).

ESI-MS m/z: 367 [M−H]$^-$; $^1$H-NMR (DMSO-d$_6$) δ(ppm): 3.84 (br s, 2H), 4.23 (br s, 2H), 4.52 (s, 2H), 7.27 (dd, J=1.3, 8.4 Hz, 1H), 7.35 (br s, 1H), 7.56 (d, J=8.4 Hz, 1H), 7.73 (s, 1H), 7.76 (d, J=8.4 Hz, 1H), 8.25 (d, J=8.4 Hz, 1H), 9.31 (br s, 2H), 9.58 (s, 1H), 13.70 (br s, 1H), 13.89 (s, 1H).

EXAMPLE 36

4-Chloro-7-[1H-5-(pyrrolidin-1-ylmethyl)indol-2-yl]isoindolinone hydrochloride (Compound 36)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with pyrrolidine (0.096 mL, 1.2 mmol), acetic acid (0.084 mL, 1.5 mmol) and sodium triacetoxyborohydride (77 mg, 0.36 mmol). The reaction mixture was added with 1 mol/L hydrochloric acid and ethyl acetate, followed by extracting with 1 mol/L hydrochloric acid. The aqueous layer was added with sodium carbonate to adjust the pH to 9, then extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(pyrrolidin-1-ylmethyl)indol-2-yl]isoindolinone (35.3 mg).

Step 2

In a similar manner to Step 2 of Example 8, 4-chloro-7-[1-(tert-butoxycarbonyl)-5-(pyrrolidin-1-ylmethyl)indol-2-yl]isoindolinone (35.0 mg) was dissolved in methanol (1 mL), and the solution was treated with 10% hydrogen chloride-methanol solution (1 mL). The mixture was added with diisopropyl ether. The precipitated solid was collected by filtration, washed with diisopropyl ether and then dried under reduced pressure to obtain Compound 36 (15.6 mg, yield 53%, 2 Steps).

ESI-MS m/z: 366 [M+H]$^+$; $^1$H-NMR (DMSO-d$_6$) δ(ppm): 1.80-2.12 (m, 4H), 3.03-3.21 (m, 2H), 3.30-3.45 (m, 2H), 4.38 (br s, 2H), 4.52 (s, 2H), 7.31 (dd, J=1.2, 8.3 Hz, 1H), 7.35 (br s, 1H), 7.57 (d, J=8.3 Hz, 1H), 7.76 (d, J=8.4 Hz, 1H), 7.77 (s, 1H), 8.25 (d, J=8.4 Hz, 1H), 9.57 (s, 1H), 10.08 (br s, 1H), 13.88 (s, 1H).

EXAMPLE 37

4-Chloro-7-[1H-5-(morpholinomethyl)indol-2-yl]isoindolinone hydrochloride (Compound 37)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with morpholine (0.100 mL, 1.15 mmol), acetic acid (0.084 mL, 1.5 mmol) and sodium triacetoxyborohydride (154 mg, 0.727 mmol). The reaction mixture was added with 1 mol/L hydrochloric acid and ethyl acetate, followed by extracting with 1 mol/L hydrochloric acid. The aqueous layer was added with sodium carbonate to adjust the pH to 9, followed by extracting with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(morpholinomethyl)indol-2-yl]isoindolinone (36.5 mg).

Step 2

In a similar manner to Step 2 of Example 8, 4-chloro-7-[1-(tert-butoxycarbonyl)-5-(morpholinomethyl)indol-2-yl]isoindolinone (36.0 mg) was dissolved in methanol (1 mL), and the solution was treated with 10% hydrogen chloride-methanol solution (1 mL). The mixture was added with diisopropyl ether. The precipitated solid was collected by filtration, washed with diisopropyl ether and then dried under reduced pressure to obtain Compound 37 (12.7 mg, yield 42%, 2 Steps).

ESI-MS m/z: 382 [M+H]$^+$; $^1$H-NMR (DMSO-d$_6$) δ(ppm): 3.04-3.20 (m, 2H), 3.22-3.40 (m, 2H), 3.60-3.74 (m, 2H), 3.90-4.02 (m, 2H), 4.41 (d, J=4.6 Hz, 2H), 4.52 (s, 2H), 7.30 (d, J=8.4 Hz, 1H), 7.36 (br s, 1H), 7.59 (d, J=8.4 Hz, 1H), 7.76

(d, J=8.6 Hz, 1H), 7.78 (s, 1H), 8.25 (d, J=8.6 Hz, 1H), 9.57 (s, 1H), 10.12 (br s, 1H), 13.92 (s, 1H).

EXAMPLE 38

4-Chloro-7-[1H-5-(dimethylaminomethyl)indol-2-yl]isoindolinone hydrochloride (Compound 38)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with N,N-dimethylamine hydrochloride (120 mg, 1.47 mmol), triethylamine (0.162 mL, 1.17 mmol), acetic acid (0.084 mL, 1.5 mmol) and sodium triacetoxyborohydride (154 mg, 0.727 mmol). The reaction mixture was added with water and ethyl acetate. The mixture was added with sodium carbonate to adjust the pH to 9. Then, the mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(dimethylaminomethyl)indol-2-yl]isoindolinone (37.8 mg).

Step 2

In a similar manner to Step 2 of Example 8, 4-chloro-7-[1-(tert-butoxycarbonyl)-5-(dimethylaminomethyl)indol-2-yl]isoindolinone (37.0 mg) was dissolved in methanol (1 mL), and the solution was treated with 10% hydrogen chloride-methanol solution (1 mL). The mixture was added with diisopropyl ether. The precipitated solid was collected by filtration, washed with diisopropyl ether and then dried under reduced pressure to obtain Compound 38 (21.4 mg, yield 78%, 2 Steps).

ESI-MS m/z: 340 [M+H]$^+$; $^1$H-NMR (DMSO-d$_6$) δ(ppm): 2.71 (s, 6H), 4.30 (s, 2H), 4.52 (s, 2H), 7.27 (dd, J=0.8, 8.6 Hz, 1H), 7.36 (d, J=0.8 Hz, 1H), 7.58 (d, J=8.4 Hz, 1H), 7.74 (s, 1H), 7.76 (d, J=8.4 Hz, 1H), 8.25 (d, J=8.6 Hz, 1H), 9.57 (s, 1H), 9.82 (br s, 1H), 13.89 (s, 1H).

EXAMPLE 39

4-Chloro-7-{1H-5-[(aminocarbonylmethyl)aminomethyl]indol-2-yl}isoindolinone hydrochloride (Compound 39)

Step 1

In a similar manner to Step 2 of Example 6, 4-chloro-7-[1-(tert.-butoxycarbonyl)-5-formylindol-2-yl]isoindolinone (30.0 mg, 0.0730 mmol) was dissolved in acetonitrile (2 mL), and the solution was treated with glycineamide hydrochloride (96 mg, 0.87 mmol), triethylamine (0.243 mL, 1.74 mmol), acetic acid (0.252 mL, 4.40 mmol) and sodium triacetoxyborohydride (231 mg, 1.09 mmol). The reaction mixture was added with 1 mol/L hydrochloric acid and ethyl acetate, followed by extracting with 1 mol/L hydrochloric acid. The aqueous layer was added with sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-{1-(tert-butoxycarbonyl)-5-[(aminocarbonylmethyl)aminomethyl]indol-2-yl}isoindolinone (41.3 mg).

Step 2

In a similar manner to Step 2 of Example 5, 4-chloro-7-{1-(tert-butoxycarbonyl)-5-[(aminocarbonylmethyl)aminomethyl]indol-2-yl}isoindolinone (41.0 mg) was treated with 4 mol/L hydrogen chloride-ethyl acetate solution (2 mL). The mixture was added with diisopropyl ether. The obtained solid was collected by filtration, washed with diisopropyl ether and then dried under reduced pressure to obtain Compound 39 (21.4 mg, yield 72%, 2 Steps).

ESI-MS m/z: 369 [M+H]$^+$; $^1$H-NMR (DMSO-d$_6$) δ(ppm): 3.58 (s, 2H), 4.22 (s, 2H), 4.52 (s, 2H), 7.26 (dd, J=1.2, 8.3 Hz, 1H), 7.35 (s, 1H), 7.54 (s, 1H), 7.56 (d, J=8.3 Hz, 1H), 7.72 (s, 1H), 7.76 (d, J=8.4 Hz, 1H), 7.81 (s, 1H), 8.25 (d, J=8.4 Hz, 1H), 9.10 (br s, 2H), 9.57 (s, 1H), 13.88 (s, 1H).

EXAMPLE 40

4-Chloro-7-[1H-5-[4-(hydroxymethyl)piperidinomethyl]indol-2-yl]isoindolinone hydrochloride (Compound 40)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with 4-piperidine methanol (84 mg, 0.729 mmol), acetic acid (0.168 mL, 2.93 mmol) and sodium triacetoxyborohydride (54 mg, 0.26 mmol). The reaction mixture was added with 1 mol/L hydrochloric acid and ethyl acetate, followed by extracting with 1 mol/L hydrochloric acid. The aqueous layer was added with sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-[4-(hydroxymethyl)piperidinomethyl]indol-2-yl]isoindolinone (39.7 mg).

Step 2

In a similar manner to Step 2 of Example 8, 4-chloro-7-[1-(tert-butoxycarbonyl)-5-[4-(hydroxymethyl)piperidinomethyl]indol-2-yl]isoindolinone (39.0 mg) was dissolved in methanol (1 mL), and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 40 (27.9 mg, yield 86%, 2 Steps).

APCI-MS m/z: 410 [M+H]$^+$; $^1$H-NMR (DMSO-d$_6$) δ(ppm): 1.30-1.69 (m, 3H), 1.71-1.90 (m, 2H), 2.81-2.99 (m, 2H), 3.25 (dd, J=5.2, 5.5 Hz, 2H), 3.30-3.47 (m, 2H), 4.32 (br d, J=3.5 Hz, 2H), 4.52 (s, 2H), 4.64 (t, J=5.2 Hz, 1H), 7.30 (d, J=8.4 Hz, 1H), 7.35 (s, 1H), 7.57 (d, J=8.4 Hz, 1H), 7.75 (d, J=8.4 Hz, 1H), 7.76 (s, 1H), 8.25 (d, J=8.4 Hz, 1H), 9.57 (s, 1H), 9.64 (br s, 1H), 13.88 (s, 1H).

EXAMPLE 41

4-Chloro-7-{1H-5-[4-(2-hydroxyethyl)piperidinomethyl]indol-2-yl}isoindolinone hydrochloride (Compound 41)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with 4-piperidineethanol (94 mg, 0.73 mmol), acetic acid (0.168 mL, 2.93 mmol) and sodium triacetoxyborohydride (54 mg, 0.26 mmol). The reaction mixture was added with 1 mol/L hydrochloric acid and ethyl acetate, followed by extracting with 1 mol/L hydrochloric acid. The aqueous layer was added with sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-{1-(tert-butoxycarbonyl)-5-[4-(2-hydroxyethyl)piperidinomethyl]indol-2-yl}isoindolinone (42.2 mg).

Step 2

In a similar manner to Step 2 of Example 8, 4-chloro-7-{1-(tert-butoxycarbonyl)-5-[4-(2-hydroxyethyl)piperidinomethyl]indol-2-yl}isoindolinone (41.0 mg) was dissolved in methanol (1 mL), and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 41 (25.9 mg, yield 77%, 2 Steps).

APCI-MS m/z: 424 [M+H]$^+$; $^1$H-NMR (DMSO-d$_6$) δ(ppm): 1.30-1.70 (m, 5H), 1.77-1.88 (m, 2H), 2.80-2.98 (m, 2H), 3.27-3.40 (m, 2H), 3.42 (dt, J=5.1, 6.1 Hz, 2H), 4.31 (br d, J=2.9 Hz, 2H), 4.42 (t, J=5.1 Hz, 1H), 4.52 (s, 2H), 7.31 (dd, J=0.8, 8.4 Hz, 1H), 7.35 (d, J=0.8 Hz, 1H), 7.57 (d, J=8.4 Hz, 1H), 7.75 (d, J=8.6 Hz, 1H), 7.77 (s, 1H), 8.25 (d, J=8.6 Hz, 1H), 9.57 (s, 1H), 9.77 (br s, 1H), 13.89 (s, 1H).

EXAMPLE 42

4-Chloro-7-[1H-5-(4-methylpiperazin-1-ylmethyl)indol-2-yl]isoindolinone dihydrochloride (Compound 42)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with 1-methylpiperazine (0.081 mL, 0.73 mmol), acetic acid (0.168 mL, 2.93 mmol) and sodium triacetoxyborohydride (60 mg, 0.28 mmol). The reaction mixture was added with 1 mol/L hydrochloric acid and ethyl acetate, followed by extracting with 1 mol/L hydrochloric acid. The aqueous layer was added with sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl-5-(4-methylpiperazin-1-ylmethyl)indol-2-yl]isoindolinone (35.8 mg).

Step 2

In a similar manner to Step 2 of Example 8, 4-chloro-7-[1-(tert-butoxycarbonyl)-5-(4-methylpiperazin-1-ylmethyl)indol-2-yl]isoindolinone (35.0 mg) was dissolved in methanol (1 mL) and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 42 (29.5 mg, yield 86%, 2 Steps), APCI-MS m/z: 395 [M+H]$^+$; $^1$H-NMR (DMSO-d$_6$) δ(ppm): 2.79 (br s, 3H), 3.20-3.80 (m, BH), 4.18-4.60 (m, 2H), 4.52 (s, 2H), 7.28-7.42 (m, 2H), 7.57 (d, J=8.4 Hz, 1H), 7.75 (d, J=8.7 Hz, 1H), 7.81 (br s, 1H), 8.25 (d, J=8.7 Hz, 1H), 9.56 (s, 1H), 11.53 (br s, 2H), 13.88 (s, 1H).

EXAMPLE 43

4-Chloro-7-[1H-5-(3-oxopiperazin-1-ylmethyl)indol-2-yl]isoindolinone hydrochloride (Compound 43)

Step 1

In a similar manner to Step 2 of Example 6, 4-chloro-7-[1-(tert-butoxycarbonyl)-5-formylindol-2-yl]isoindolinone (42.6 mg, 0.104 mmol) was dissolved in acetonitrile (2 mL), and the solution was treated with 2-piperadinone (42 mg, 0.42 mmol), acetic acid (0.120 mL, 2.10 mmol) and sodium triacetoxyborohydride (46 mg, 0.22 mmol). The reaction mixture was added with water and sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(3-oxopiperazin-1-ylmethyl)indol-2-yl]isoindolinone (55.6 mg).

Step 2

In a similar manner to Step 2 of Example 8, 4-chloro-7-[1-(tert-butoxycarbonyl)-5-(3-oxopiperazin-1-ylmethyl)indol-2-yl]isoindolinone (54.1 mg) was dissolved in methanol (2 mL), and the solution was treated with 10% hydrogen chloride-methanol solution (2 mL). The mixture was added with diisopropyl ether. The obtained solid was collected by filtration, washed with diisopropyl ether and then dried under reduced pressure to obtain. Compound 43 (34.9 mg, yield 78%, 2 Steps).

ESI-MS m/z: 393 [M−H]$^-$; $^1$H-NMR (DMSO-d$_6$) δ(ppm): 2.90-3.18 (m, 4H), 3.65 (s, 2H), 3.90-4.10 (m, 2H), 4.51 (s, 2H), 7.23 (m, 1H), 7.27 (m, 1H), 7.49 (d, J=8.4 Hz, 1H), 7.61 (m, 1H), 7.74 (d, J=8.6 Hz, 1H), 7.77-7.93 (m, 2H), 8.22 (d, J=8.6 Hz, 1H), 9.53 (s, 1H), 13.76 (s, 1H).

EXAMPLE 44

4-Chloro-7-[1H-5-(4-methoxycarbonylpiperidinomethyl)indol-2-yl]isoindolinone hydrochloride (Compound 44)

Step 1

In a similar manner to Step 2 of Example 6, 4-chloro-7-[1-(tert-butoxycarbonyl)-5-formylindol-2-yl]isoindolinone (40.0 mg, 0.0974 mmol) was dissolved in acetonitrile (3 mL), and the solution was treated with isonipecotamide (154 mg, 1.20 mmol), acetic acid (0.896 mL, 15.7 mmol) and sodium triacetoxyborohydride (188 mg, 0.887 mmol). The reaction mixture was added with water and sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(4-methoxycarbonylpiperidinomethyl)indol-2-yl]isoindolinone (35.5 mg, yield 70%).

ESI-MS m/z: 523 [M+H]$^+$; $^1$H-NMR (CDCl$_3$) δ(ppm): 1.37 (s, 9H), 1.78-1.95 (m, 4H), 2.17 (m, 1H), 2.36-2.59 (m, 4H), 3.67 (s, 2H), 4.42 (s, 2H), 5.66 (br s, 2H), 6.55 (s, 1H), 7.01 (br s, 1H), 7.28 (m, 1H), 7.43 (d, J=8.1 Hz, 1H), 7.49 (m, 1H), 7.56 (d, J=8.1 Hz, 1H), 8.14 (d, J=8.4 Hz, 1H).

Step 2

In a similar manner to Step 2 of Example 8, 4-chloro-7-[1-(tert-butoxycarbonyl)-5-(4-methoxycarbonylpiperidinomethyl)indol-2-yl]isoindolinone (34.5 mg, 0.0660 mmol) was dissolved in methanol (1 mL), and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 44 (22.0 mg, yield 49%).

ESI-MS m/z: 438 [M+H]$^+$; $^1$H-NMR (DMSO-d$_6$) δ(ppm): 1.79-2.13 (m, 4H), 2.60 (m, 1H), 2.83-3.02 (m, 2H), 3.20-3.45 (m, 2H), 3.61 (s, 3H), 4.31 (br s, 2H), 4.51 (s, 2H), 7.29-7.38 (m, 2H), 7.56 (d. J=8.1 Hz, 1H), 7.75 (d, J=8.5 Hz, 1H), 7.79 (s, 1H), 8.24 (d, J=8.5 Hz, 1H), 9.56 (s, 1H), 10.40 (m, 1H), 13.87 (s, 1H).

EXAMPLE 45

4-Chloro-7-[1H-5-(3-hydroxypiperidinomethyl)indol-2-yl]isoindolinone hydrochloride (Compound 45)

Step 1

In a similar manner to Step 2 of Example 6, 4-chloro-7-[1-(tert-butoxycarbonyl)-5-formylindol-2-yl]isoindolinone (40.0 mg, 0.0974 mmol) was dissolved in acetonitrile (3 mL), and the solution was treated with 3-hydroxypiperidine hydrochloride (181 mg, 1.32 mmol), triethylamine (0.220 mL, 1.58 mmol), acetic acid (0.896 mL, 15.7 mmol) and sodium triacetoxyborohydride (188 mg, 0.887 mmol). The reaction mixture was added with water and sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[(1-(tert-butoxycarbonyl)-5-(3-hydroxypiperidinomethyl)indol-2-yl]isoindolinone (41.8 mg, yield 87%).

ESI-MS m/z: 496 [M+H]$^+$: $^1$H-NMR (CDCl$_3$) δ(ppm): 1.34 (s, 9H), 1.46-1.70 (m, 3H), 1.82 (m, 1H), 2.31 (m, 1H), 2.42-2.68 (m, 4H), 3.67 (s, 2H), 3.84 (m, 1H), 4.42 (s, 2H), 6.54 (s, 1H), 7.28 (m, 1H), 7.42 (d, J=8.1 Hz, 1H), 7.47 (m, 1H), 7.50 (br s, 1H), 7.55 (d, J=8.1 Hz, 1H), 8.16 (d, J=8.6 Hz, 1H).

Step 2

In a similar manner to Step 2 of Example 8, 4-chloro-7-[1-(tert-butoxycarbonyl)-5-(3-hydroxypiperidinomethyl)indol-2-yl]isoindolinone (40.8 mg, 0.0823 mmol) was dissolved in methanol (1 mL), and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 45 (27.1 mg, yield 76%).

mp >295° C.; APCI-MS m/z: 396 [M+H]$^+$; $^1$H-NMR (DMSO-d$_6$) δ(ppm): 1.50-2.15 (m, 4H), 2.70-3.08 (m, 2H), 3.18-3.44 (m, 2H), 3.80 (m, 1H), 4.15-4.46 (m, 2H), 4.51 (s, 2H), 5.35 (m, 1H), 7.30 (d, J=8.9 Hz, 1H), 7.35 (s, 1H), 7.57 (d, J=8.4 Hz, 1H), 7.76 (d, J=8.6 Hz, 1H), 7.75-7.82 (m, 1H), 8.24 (d, J=8.4 Hz, 1H), 10.41 (br s, 1H), 9.56 (s, 1H), 13.88 (s, 1H).

EXAMPLE 46

4-Chloro-7-[1H-5-(piperidinocarbonyl)indol-2-yl]isoindolinone (Compound 46)

In a similar manner to Example 20, Compound 19 (30.0 mg, 0.0918 mmol) was dissolved in DMF (2 mL), and the solution was treated with EDCI (35 mg, 0.18 mmol), HOBT monohydrate (12 mg, 0.089 mmol) and piperidine (0.036 mL, 0.37 mmol). The mixture was added with water. The precipitated solid was collected by filtration and washed with water, followed by drying under reduced pressure to obtain Compound 46 (30.1 mg, yield 83%).

APCI-MS m/z: 394 [M+H]$^+$; $^1$H-NMR (DMSO-d$_6$) δ(ppm): 1.45-1.70 (m, 6H). 3.40-3.58 (m, 4H), 4.51 (s, 2H), 7.16 (d, J=8.4 Hz, 1H), 7.33 (s, 1H), 7.52 (d, J=8.4 Hz, 1H), 7.62 (br s, 1H), 7.75 (d, J=8.3 Hz, 1H), 8.22 (d, J=8.3 Hz, 1H), 9.56 (br s, 1H), 13.88 (s, 1H).

EXAMPLE 47

4-Chloro-7-[1H-5-(ethylaminomethyl)indol-2-yl]isoindolinone hydrochloride (Compound 47)

Step 1

In a similar manner to Step 2 of Example 6, 4-chloro-7-[1-(tert-butoxycarbonyl)-5-formylindol-2-yl]isoindolinone (41.2 mg, 0.100 mmol) was dissolved in acetonitrile (2 mL), and the solution was treated with 70% aqueous ethylamine-solution (0.192 mL, 2.42 mmol), acetic acid (0.345 mL, 6.03 mmol) and sodium triacetoxyborohydride (170 mg, 0.802 mmol). The reaction mixture was added with 1 mol/L hydrochloric acid and ethyl acetate, followed by extracting with 1 mol/L hydrochloric acid. The aqueous layer was added with sodium hydrogen carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(ethylaminomethyl)indol-2-yl]isoindolinone (36.4 mg, yield 83%).

APCI-MS m/z: 440 [M+H]$^+$; $^1$H-NMR (CDCl$_3$) δ(ppm): 1.12 (t, J=7.2 Hz, 3H), 1.32 (s, 9H), 2.67 (q, J=7.2 Hz, 2H), 3.52 (br s, 1H), 3.97 (br s, 2H), 4.42 (s, 2H), 6.50 (s, 1H), 7.28 (m, 1H), 7.40 (d. J=8.1 Hz, 1H), 7.48 (s, 1H), 7.55 (d, J=8.1 Hz, 1H), 7.85 (br s, s, 1H), 8.21 (d, J=8.6 Hz, 1H).

Step 2

In a similar manner to Step 2 of Example 8, 4-chloro-7-[1-(tert-butoxycarbonyl)-5-(ethylaminomethyl)indol-2-yl]isoindolinone (36.4 mg, 0.0827 mmol) was dissolved in methanol (1 mL), and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 47 (25.0 mg, yield 80%).

APCI-MS m/z: 340 [M+H]$^+$; $^1$H-NMR (DMSO-d$_6$) δ(ppm): 1.23 (t, J=7.2 Hz, 3H), 2.96 (q, J=7.2 Hz, 2H), 4.18 (s, 2H), 4.51 (s, 2H), 7.28 (dd, J=1.4, 8.6 Hz, 1H), 7.34 (d, J=1.4 Hz, 1H), 7.56 (d, J=8.6 Hz, 1H), 7.74 (s, 1H), 7.75 (d, J=8.6 Hz, 1H), 8.25 (d, J=8.6 Hz, 1H), 8.83 (br s, 2H), 9.56 (s, 1H), 13.87 (s, 1H).

EXAMPLE 48

4-Chloro-7-[1H-5-(cyclohexylaminomethyl)indol-2-yl]isoindolinone hydrochloride (Compound 48)

Step 1

In a similar manner to Step 2 of Example 6, 4-chloro-7-[1-(tert-butoxycarbonyl)-5-formylindol-2-yl]isoindolinone (42.6 mg, 0.104 mmol) was dissolved in acetonitrile (2 mL), and the solution was treated with cyclohexylamine (0.150 mL, 1.31 mmol), acetic acid (0.345 mL, 6.03 mmol) and sodium triacetoxyborohydride (170 mg, 0.802 mmol). The reaction mixture was added with 1 mol/L hydrochloric acid and ethyl acetate, followed by extracting with 1 mol/L hydrochloric acid. The aqueous layer was added with sodium hydrogen carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[(1-(tert-butoxycarbonyl)-5-(cyclohexylaminomethyl)indol-2-yl]isoindolinone (24.2 mg, yield 47%).

APCI-MS m/z: 494 [M+H]$^+$; $^1$H-NMR (CDCl$_3$) δ(ppm): 1.10-1.44 (m, 6H), 1.34 (s, 9H), 1.52-1.76 (m, 2H), 1.82-1.98 (m, 2H), 2.43-2.59 (m, 2H), 3.96 (s, 2H), 4.42 (s, 2H), 6.52 (s, 1H), 7.30 (dd, J=1.6, 8.6 Hz, 1H), 7.41 (d, J=8.1 Hz, 1H), 7.46 (br s, 1H), 7.50 (d, J=1.6 Hz, 1H), 7.55 (d, J=8.1 Hz, 1H), 8.19 (d, J=8.6 Hz, 1H)

Step 2

In a similar manner to Step 2 of Example 8, 4-chloro-7-[1-(tert-butoxycarbonyl)-5-(cyclohexylaminomethyl)indol-2-yl]isoindolinone (24.2 mg, 0.0490 mmol) was dissolved in methanol (1 mL), and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 48 (10.4 mg, yield 49%).

APCI-MS m/z: 394 [M+H]$^+$; $^1$H-NMR (DMSO-d$_6$) δ(ppm): 1.13-1.45 (m, 5H), 1.61 (m, 1H), 1.73-1.83 (m, 2H), 2.07-2.18 (m, 2H), 2.98 (m, 1H), 4.21 (s, 2H), 4.51 (s, 2H), 7.30 (d, J=8.6 Hz, 1H), 7.34 (s, 1H), 7.56 (d, J=8.6 Hz, 1H), 7.75 (d, J=8.6 Hz, 1H), 7.76 (s, 1H), 8.25 (d, J=8.6 Hz, 1H), 8.74 (br s, 2H), 9.56 (s, 1H), 13.87 (s, 1H).

EXAMPLE 49

4-Chloro-7-{1H-5-[2-(hydroxymethyl)piperidinomethyl]indol-2-yl}isoindolinone hydrochloride (Compound 49)

Step 1

In a similar manner to Step 2 of Example 6, 4-chloro-7-[1-(tert-butoxycarbonyl)-5-formylindol-2-yl]isoindolinone (50.9 mg, 0.124 mmol) was dissolved in acetonitrile (2 mL), and the solution was treated with 2-piperidine methanol (63.8 mg, 0.554 mmol), acetic acid (0.284 mL, 4.96 mmol) and sodium triacetoxyborohydride (158 mg, 0.745 mmol). The reaction mixture was added with 1 mol/L hydrochloric acid and ethyl acetate, followed by extracting with 1 mol/L hydrochloric acid. The aqueous layer was added with sodium hydrogen carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-{1-(tert-butoxycarbonyl)-5-[2-(hydroxymethyl)piperidinomethyl]indol-2-yl}isoindolinone (36.2 mg, yield 57%).

ESI-MS m/z: 510 [M+H]$^+$; $^1$H-NMR (CDCl$_3$) δ(ppm): 1.30-1.50 (m, 2H), 1.37 (s, 9H), 1.50-1.80 (m, 4H), 2.00-2.33 (m, 2H), 2.54 (m, 1H), 2.92 (m, 1H), 3.48-3.60 (m, 2H), 3.96 (m, 1H), 4.16 (m, 1H), 4.42 (s, 2H), 6.54 (s, 1H), 6.79 (br s, 1H), 7.28 (m, 1H), 7.43 (d, J=8.1 Hz, 1H), 7.48 (s, 1H), 7.56 (d, J=8.1 Hz, 1H), 8.15 (d, J=8.7 Hz, 1H).

Step 2

In a similar manner to Step 2 of Example 8, 4-chloro-7-{1-(tert-butoxycarbonyl)-5-[2-(hydroxymethyl)piperidinomethyl]indol-2-yl}isoindolinone (45.5 mg, 0.0892 mmol) was dissolved in methanol (1 mL), and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 49 (21.9 mg, yield 55%).

APCI-MS m/z: 410 [M+H]$^+$; $^1$H-NMR (DMSO-d$_6$) δ(ppm): 1.32-1.94 (m, 6H), 2.74-3.28 (m, 3H), 3.38-3.90 (m, 2H), 4.00-4.26 (m, 2H), 4.52 (s, 2H), 5.64 (m, 1H), 7.28 (d, J=8.4 Hz, 1H), 7.35 (s, 1H), 7.57 (d, J=8.4 Hz, 1H), 7.760 (d, J=8.4 Hz, 1H), 7.762 (s, 1H), 8.24 (d, J=8.4 Hz, 1H), 9.17 (br s, 1H), 9.55 (s, 1H), 13.88 (s, 1H).

EXAMPLE 50

4-Chloro-7-[1H-5-(4-methylpiperidinomethyl)indol-2-yl-]isoindolinone hydrochloride (Compound 50)

Step 1

In a similar manner to Step 2 of Example 6, 4-chloro-7-[1-(tert-butoxycarbonyl)-5-formylindol-2-yl]isoindolinone (41.0 mg, 0.0998 mmol) was dissolved in acetonitrile (2 mL), and the solution was treated with 4-methylpiperidine (0.048 mL, 0.41 mmol), acetic acid (0.345 mL, 6.03 mmol) and sodium triacetoxyborohydride (169 mg, 0.797 mmol). The reaction mixture was added with water and sodium hydrogen carbonate to adjust the pH of to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(4-methylpiperidinomethyl)indol-2-yl]isoindolinone (25.0 mg, yield 51%).

ESI-MS m/z: 494 [M+H]$^+$; $^1$H-NMR (CDCl$_3$) δ(ppm): 0.92 (d, J=5.6 Hz, 3H), 1.34 (m, 1H), 1.38 (s, 9H), 1.57-1.72 (m, 4H), 1.92-2.08 (m, 2H), 2.85-2.98 (m, 2H), 3.63 (br s, 2H), 4.42 (s, 2H), 6.39 (br s, 1H), 6.55 (s, 1H), 7.29 (m, 1H), 7.43 (d, J=8.1 Hz, 1H), 7.50 (br s, 1H), 7.56 (d. J=8.1 Hz, 1H), 8.13 (d, J=8.6 Hz, 1H).

Step 2

In a similar manner to Step 2 of Example 8, 4-chloro-7-[1-(tert-butoxycarbonyl)-5-(4-methylpiperidinomethyl)indol-2-yl]isoindolinone (25.0 mg, 0.0506 mmol) was dissolved in methanol (1 mL), and the solution was treated with 10% hydrogen chloride-methanol solution (1 mL). The mixture was added with diisopropyl ether. The obtained solid was collected by filtration, washed with diisopropyl ether and then dried under reduced pressure to obtain Compound 50 (13.0 mg, yield 60%).

APCI-MS m/z: 394 [M+H]$^+$; $^1$H-NMR (DMSO-d$_6$) δ(ppm): 0.90 (d, J=6.3 Hz, 3H), 1.20-1.90 (m, 5H), 2.70-3.20 (m, 4H), 4.31 (br s, 2H), 4.52 (s, 2H), 7.28 (d, J=8.6 Hz, 1H), 7.35 (s, 1H), 7.57 (d, J=8.6 Hz, 1H), 7.75 (s, 1H), 7.76 (d. J=8.6 Hz, 1H), 8.24 (d. J=8.6 Hz, 1H), 9.55 (br s, 2H), 13.88 (s, 1H).

EXAMPLE 51

4-Chloro-7-[1H-5-(2-hydroxyethylaminocarbonyl) indol-2-yl] isoindolinone (Compound 51)

In a similar manner to Step 1 of Example 20, Compound 19 (30.0 mg, 0.0918 mmol) was dissolved in DMF (2 mL), and the solution was treated with EDCI (35 mg, 0.18 mmol), HOBT monohydrate (12 mg, 0.089 mmol) and ethanolamine (0.022 mL, 0.37 mmol). The mixture was added with water. The precipitated solid was collected by filtration and washed with water, followed by drying under reduced pressure to obtain Compound 51 (28.2 mg, yield 83%).

APCI-MS m/z: 370 [M+H]$^+$; $^1$H-NMR (DMSO-d$_6$) δ(ppm): 3.28-3.40 (m, 2H), 3.53 (dt, J=5.5, 6.3 Hz, 2H), 4.51 (s, 2H), 4.72 (t, J=5.5 Hz, 1H), 7.38 (s, 1H), 7.52 (d, J=8.5 Hz, 1H), 7.69 (dd, J=1.7, 8.5 Hz, 1H), 7.75 (d, J=8.5 Hz, 1H), 8.17 (s, 1H), 8.26 (d, J=8.5 Hz, 1H), 8.32 (m, 1H), 9.57 (br s, 1H), 13.92 (s, 1H).

EXAMPLE 52

4-Chloro-7-[1H-5-(2-dimethylaminoethylaminocarbonyl)indol-2-yl]isoindolinone (Compound 52)

In a similar manner to Step 1 of Example 20, Compound 19 (30.0 mg, 0.0918 mmol) was dissolved in DMF (2 mL), and the solution was treated with EDCI (35 mg, 0.18 mmol), HOBT monohydrate (12 mg, 0.089 mmol) and N,N-dimethylethylenediamine (0.040 mL, 0.36 mmol). The mixture was added with water. The precipitated solid was collected by filtration and washed with water, followed by drying under reduced pressure to obtain Compound 52 (28.3 mg, yield 78%).

APCI-MS m/z: 397 [M+H]$^+$; $^1$H-NMR (DMSO-d$_6$) δ(ppm): 2.19 (s, 6H), 2.42 (t, J=7.0 Hz, 2H), 3.28-3.45 (m, 2H), 4.51 (s, 2H), 7.38 (s, 1H), 7.52 (d, J=8.6 Hz, 1H), 7.67 (dd, J=1.7, 8.6 Hz, 1H), 7.75 (d, J=8.6 Hz, 1H), 8.14 (s, 1H), 8.25 (d, J=8.6 Hz, 1H), 8.28 (br s, 1H), 9.57 (br s, 1H), 13.92 (s, 1H).

EXAMPLE 53

4-Chloro-7-[1H-5-(4-bromopiperidinomethyl)-indol-2-yl]isoindolinone hydrochloride (Compound 53)

Step 1

In a similar manner to Step 2 of Example 6, 4-chloro-7-[1-(tert-butoxycarbonyl)-5-formylindol-2-yl]isoindolinone (42.7 mg, 0.104 mmol) was dissolved in acetonitrile (2 mL), and the solution was treated with 4-bromopiperidine hydrobromide (105 mg, 0.428 mmol), acetic acid (0.120 mL, 2.10 mmol) and sodium triacetoxyborohydride (51.1 mg, 0.241 mmol). The reaction mixture was added with water and sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(4-bromopiperidinomethyl)indol-2-yl]isoindolinone (77.3 mg).

Step 2

In a similar manner to Step 2 of Example 8, 4-chloro-7-[1-(tert-butoxycarbonyl)-5-(4-bromopiperidinomethyl)indol-2-yl]isoindolinone (76.3 mg) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 53 (37.0 mg, yield 72%, 2 steps).

APCI-MS m/z: 458 [M+H]$^+$; $^1$H-NMR (DMSO-d$_6$) δ(ppm): 2.05-2.45 (m, 4H), 2.92-3.08 (m, 2H), 3.15-3.29 (m, 2H), 4.27-4.40 (m, 2H), 4.46 (m, 1H), 4.52 (s, 2H), 7.29 (d, J=8.6 Hz, 1H), 7.35 (s, 1H), 7.58 (d, J=8.6 Hz, 1H), 7.76 (d, J=8.6 Hz, 1H), 7.83 (s, 1H), 8.25 (d, J=8.6 Hz, 1H), 9.55 (s, 1H), 10.16 (br s, 1H), 13.89 (s, 1H).

EXAMPLE 54

4-Chloro-7-{1H-5-[4-(methylsulfonyl)piperazin-1-ylmethyl]indol-2-yl}isoindolinone hydrochloride (Compound 54)

Step 1

In a similar manner to Step 2 of Example 6, 4-chloro-7-[1-(tert-butoxycarbonyl)-5-formylindol-2-yl]isoindolinone (40.7 mg, 0.0991 mmol) was dissolved in acetonitrile (2 mL), and the solution was treated with 1-(methylsulfonyl)piperazine hydrochloride (80.0 mg, 0.399 mmol), triethylamine (0.110 mL, 0.789 mmol), acetic acid (0.115 mL, 2.01 mmol) and sodium triacetoxyborohydride (77.7 mg, 0.367 mmol). The reaction mixture was added with water and sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-{1-(tert-butoxycarbonyl)-5-[4-(methylsulfonyl)piperazin-1-ylmethyl]indol-2-yl}isoindolinone (67.2 mg).

Step 2

In a similar manner to Step 2 of Example 5, 4-chloro-7-{1-(tert-butoxycarbonyl)-5-[4-(methylsulfonyl)piperazin-1-ylmethyl]indol-2-yl}isoindolinone (66.2 mg) was treated with 4 mol/L hydrogen chloride-ethyl acetate solution (1 mL). The mixture was added with diisopropylether. The obtained solid was collected by filtration and washed with diisopropylether, followed by drying under reduced pressure to obtain Compound 54 (46.8 mg, yield 95%, 2 steps).

APCI-MS m/z; 459 [M+H]$^+$; $^1$H-NMR (DMSO-d$_6$) δ(ppm): 2.99 (s, 3H), 3.09-3.23 (m, 4H), 3.39-3.49 (m, 2H), 3.64-3.78 (m, 2H), 4.43 (br s, 2H), 4.52 (s, 2H), 7.33 (m, 1H), 7.36 (s, 1H), 7.59 (d, J=8.2 Hz, 1H), 7.76 (d, J=8.6 Hz, 1H), 7.79 (s, 1H), 8.25 (d, J=8.6 Hz, 1H), 9.56 (s, 1H), 10.50 (br s, 1H), 13.90 (s, 1H).

EXAMPLE 55

4-Chloro-7-[1H-5-(4-acetylpiperazin-1-ylmethyl)indol-2-yl]isoindolinone hydrochloride (Compound 55)

Step 1

In a similar manner to Step 2 of Example 6, 4-chloro-7-[1-(tert-butoxycarbonyl)-5-formylindol-2-yl]isoindolinone (41.5 mg, 0.101 mmol) was dissolved in acetonitrile (2 mL), and the solution was treated with 1-acetylpiperazin (54 mg, 0.42 mmol), acetic acid (0.116 mL, 2.03 mmol) and sodium triacetoxyborohydride (51 mg, 0.25 mmol). The reaction mixture was added with water and sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(4-acetylpiperazin-1-ylmethyl)indol-2-yl]isoindolinone (64.7 mg).

Step 2

In a similar manner to Step 2 of Example 5, 4-chloro-7-[1-(tert-butoxycarbonyl)-5-(4-acetylpiperazin-1-ylmethyl)indol-2-yl]isoindolinone (63.7 mg) was treated with 4 mol/L hydrogen chloride-ethyl acetate solution (3 mL). The mixture was added with diisopropylether. The obtained solid was collected by filtration and washed with diisopropylether, followed by drying under reduced pressure to obtain Compound 55 (41.1 mg, yield 89%, 2 steps).

APCI-MS m/z: 423 [M+H]+; 1H-NMR (DMSO-d6) δ(ppm): 2.03 (s, 3H), 2.89-3.10 (m, 4H), 3.22-3.52 (m, 4H), 4.46-4.47 (m, 2H), 4.52 (s, 2H), 7.31 (d, J=8.4 Hz, 1H), 7.35 (s, 1H), 7.58 (d, J=8.4 Hz, 1H), 7.76 (d, J=8.6 Hz, 1H), 7.78 (s, 1H), 8.25 (d, J=8.6 Hz, 1H), 9.56 (s, 1H), 10.44 (br s, 1H), 13.90 (s, 1H).

EXAMPLE 56

4-Chloro-7-[1H-5-(benzylaminomethyl)indol-2-yl]isoindolinone hydrochloride (Compound 56)

Step 1

4-Chloro-7-[1-(tert-butoxycarbonyl)-5-formylindol-2-yl]isoindolinone (20.0 mg, 0.0487 mmol) was dissolved in dichloromethane (0.5 mL), and the solution was added with benzylamine (0.011 mL, 0.10 mmol) and sodium triacetoxyborohydride (32 mg, 0.15 mmol) followed by stirring at room temperature for 16 hours. The reaction mixture was added with 3 mol/L aqueous sodium hydroxide solution, extracted with dichloromethane. The organic layer was dried over anhydrous sodium sulfate. The mixture was added with aldehyde resin and stirred at room temperature for 16 hours. The resin was filtered off and the solvent of the filtrate was evaporated under reduced pressure. The residue was dissolved in chloroform, and the solution was filtered through a column filled with SCX (positive-ion-exchange resin). The resulting SCX was washed with 7 mol/L ammonia-methanol solution and the solvent of the filtrate was evaporated under reduced pressure to obtain 4-chloro-7-[1-(tert-butoxycarbonyl)-5-(benzylaminomethyl)indol-2-yl]isoindolinone.

Step 2

4-Chloro-7-[(1-(tert-butoxycarbonyl)-5-(benzylaminomethyl)indol-2-yl]isoindolinone was dissolved in 10% hydrogen chloride-methanol solution (0.5 mL) followed by stirring at 55° C. for 12 hours. The solvent of the reaction mixture was evaporated under reduced pressure. The residue was added with 3 mol/L sodium hydroxide solution followed by stirring for 30 minutes. The obtained solid was collected by filtration and washed with water, followed by drying under reduced pressure to obtain Compound 56 (9.90 mg, yield 49%, 2 steps).

APCI-MS m/z: 402 [M+H]+; 1H-NMR (DMSO-d6) δ(ppm): 4.17 (br s, 2H), 4.23 (br s, 2H), 4.52 (s, 2H), 7.29 (dd, J=1.2, 8.4 Hz, 1H), 7.35 (d, J=1.2 Hz, 1H), 7.40-7.62 (m, 6H), 7.56 (d, J=8.6 Hz, 1H), 7.74 (s, 1H), 7.75 (d, J=8.6 Hz, 1H), 8.25 (d, J=8.4 Hz, 1H), 9.35 (br s, 1H), 9.56 (s, 1H), 13.89 (s, 1H).

EXAMPLE 57

4-Chloro-7-[1H-5-(benzylaminocarbonyl)indol-2-yl]isoindolinone (Compound 57)

In a similar manner to Step 1 of Example 20, Compound 19 (30.2 mg, 0.0924 mmol) was dissolved in DMF (2 mL), and the solution was treated with EDCI (38.5 mg, 0.201 mmol), HOBT monohydrate (16.9 mg, 0.110 mmol) and benzylamine (0.040 mL, 0.37 mmol). The mixture was added with water. The precipitated solid was collected by filtration, washed with water and dried under reduced pressure to obtain Compound 57 (31.1 mg, yield 81%).

mp 246° C. APCI-MS m/z: 416 [M+H]+; 1H-NMR (DMSO-d6) δ(ppm): 4.51 (d, J=5.9 Hz, 2H), 4.52 (s, 2H), 7.19-7.41 (m, 5H), 7.37 (d, J=1.6 Hz, 1H), 7.54 (d, J=8.6 Hz, 1H), 7.73 (dd, J=1.6, 8.6 Hz, 1H), 7.75 (d, J=8.6 Hz, 1H), 8.23 (br s, 1H), 8.26 (d, J=8.6 Hz, 1H), 8.94 (t, J=5.9 Hz, 1H), 9.56 (s, 1H), 13.94 (s, 1H).

EXAMPLE 58

4-Chloro-7-{1H-5-[(2-(pyridin-2-yl)ethyl)aminocarbonyl]indol-2-yl}isoindolinone (Compound 58)

In a similar manner to Step 1 of Example 20, Compound 19 (30.5 mg, 0.0933 mmol) was dissolved in DMF (2 mL), and the solution was treated with EDCI (39.6 mg, 0.207 mmol). HOBT monohydrate (16.0 mg, 0.104 mmol) and 2-(2-aminoethyl)pyridine (0.045 mL, 0.38 mmol). The mixture was added with water. The precipitated solid was collected by filtration and washed with water, followed by drying under reduced pressure to obtain Compound 58 (22.5 mg, yield 56%).

APCI-MS m/z: 431 [M+H]+; 1H-NMR (DMSO-d6) δ(ppm): 3.03 (t, J=7.7 Hz, 2H), 3.64 (dt, J=5.7, 7.7 Hz, 2H), 4.51 (s, 2H), 7.23 (m, 1H), 7.30 (d, J=8.6 Hz, 1H), 7.38 (s, 1H), 7.51 (d, J=8.6 Hz, 1H), 7.60 (m, 1H), 7.70 (m, 1H), 7.75 (d, J=8.6 Hz, 1H), 8.14 (s, 1H), 8.26 (d, J=8.6 Hz, 1H), 8.47 (t, J=5.7 Hz, 1H), 8.52 (m, 1H), 9.56 (s, 1H), 13.92 (s, 1H).

EXAMPLE 59

4-Chloro-7-{1H-5-[(2-(pyridin-3-yl)ethyl)aminocarbonyl]indol-2-yl}isoindolinone (Compound 59)

In a similar manner to Step 1 of Example 20, Compound 19 (30.5 mg, 0.0933 mmol) was dissolved in DMF (2 mL), and the solution was treated with EDCI (36.2 mg, 0.189 mmol), HOBT monohydrate (17.6 mg, 0.115 mmol) and 3-(2-aminoethyl)pyridine (0.045 mL, 0.38 mmol). The mixture was added with water. The precipitated solid was collected by filtration and washed with water, followed by drying under reduced pressure to obtain Compound 59 (23.3 mg, yield 58%).

APCI-MS m/z: 431 [M+H]+; 1H-NMR (DMSO-d6) δ(ppm): 2.90 (t, J=7.1 Hz, 2H), 3.54 (m, 2H), 4.51 (s, 2H), 7.32 (dd. J=4.8, 7.7 Hz, 1H), 7.38 (s, 1H), 7.52 (d, J=8.6 Hz, 1H), 7.62-7.72 (m, 2H), 7.75 (d, J=8.4 Hz, 1H), 8.12 (s, 1H), 8.26 (d, J=8.6 Hz, 1H), 8.42 (dd, J=1.6, 4.8 Hz, 1H), 8.44-8.51 (m, 2H), 9.56 (s, 1H), 13.93 (s, 1H).

EXAMPLE 60

4-Chloro-7-{1H-5-[(2-(pyridin-4-yl)ethyl)aminocarbonyl]indol-2-yl}isoindolinone (Compound 60)

In a similar manner to Step 1 of Example 20, Compound 19 (30.4 mg, 0.0930 mmol) was dissolved in DMF (2 mL), and the solution was treated with EDCI (38.2 mg, 0.199 mmol), HOBT monohydrate (18.2 mg, 0.119 mmol) and 4-(2-aminoethyl)pyridine (0.045 mL, 0.38 mmol). The mixture was added with water. The precipitated solid was collected by filtration and washed with water, followed by drying under reduced pressure to obtain Compound 60 (23.8 mg, yield 72%).

APCI-MS m/z: 431 [M+H]+; 1H-NMR (DMSO-d6) δ(ppm): 2.91 (t, J=7.2 Hz, 2H), 3.56 (m, 2H), 4.51 (s, 2H), 7.26-7.32 (m, 2H), 7.38 (s, 1H), 7.52 (d. J=8.6 Hz, 1H), 7.65 (dd, J=1.3, 8.6 Hz, 1H), 7.75 (d, J=8.6 Hz, 1H), 8.12 (s, 1H), 8.26 (d, J=8.6 Hz, 1H), 8.44-8.50 (m, 3H), 9.56 (s, 1H), 13.93 (s, 1H).

EXAMPLE 61

4-Chloro-7-{1H-5-[(1-hydroxymethylcyclopentyl)aminomethyl]indol-2-yl}isoindolinone (Compound 61)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL), and the solution was treated with 1-amino-1-cyclopentanemethanol (23 mg, 0.20 mmol) and sodium triacetoxyborohydride (48 mg, 0.23 mmol) to obtain 4-chloro-7-{1-(tert-butoxycarbonyl)-5-[(1-hydroxymethylcyclopentyl)aminomethyl]indol-2-yl}isoindolinone was obtained.

Step 2

In a similar manner to Step 2 of Example 56, 4-chloro-7-{1-(tert-butoxycarbonyl)-5-[(1-hydroxymethylcyclopentyl)aminomethyl]indol-2-yl}isoindolinone was treated with 10% hydrogen chloride-methanol solution (0.5 mL) to obtain Compound 61 (4.71 mg, yield 23%, 2 steps).

ESI-MS m/z: 410 [M+H]$^+$.

EXAMPLE 62

4-Chloro-7-{1H-5-[(2-hydroxy-1-methylethyl)aminomethyl]indol-2-yl}isoindolinone (Compound 62)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL), and the solution was treated with 2-amino-1 propanol (0.0080 mL, 0.10 mmol) and sodium triacetoxyborohydride (32 mg, 0.15 mmol) to obtain 4-chloro-7-{1-(tert-butoxycarbonyl)-5-[(2-hydroxy-1-methylethyl)aminomethyl]indol-2-yl}isoindolinone.

Step 2

In a similar manner to Step 2 of Example 56, 4-chloro-7-{1-(tert-butoxycarbonyl)-5-[(2-hydroxy-1-methylethyl)aminomethyl]indol-2-yl}isoindolinone was treated with 10% hydrogen chloride-methanol solution (0.5 mL) to obtain Compound 62 (1.92 mg, yield-10%, 2 steps).

ESI-MS m/z: 370 [M+H]$^+$.

EXAMPLE 63

4-Chloro-7-{1H-5-[(1-hydroxycyclohexyl)methylaminomethyl]indol-2-yl}isoindolinone (Compound 63)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 1-aminomethyl-1-cyclohexanol hydrochloride (13 mg, 0.10 mmol) and sodium triacetoxyborohydride (32 mg, 0.15 mmol) to obtain 4-chloro-7-{1-(tert-butoxycarbonyl)-5-[(1-hydroxycyclohexyl)methylaminomethyl]indol-2-yl}isoindolinone.

Step 2

In a similar manner to Step 2 of Example 56, 4-chloro-7-(1-(tert-butoxycarbonyl)-5-[(1-hydroxycyclohexyl)methylaminomethyl]indol-2-yl)isoindolinone was treated with 10% hydrogen chloride-methanol solution (0.5 mL) to obtain Compound 63 (2.65 mg, yield 13%, 2 steps).

ESI-MS m/z: 424 [M+H]$^+$.

EXAMPLE 64

4-Chloro-7-{1H-5-[(pyridin-2-ylmethyl)aminomethyl]indol-2-yl}isoindolinone (Compound 64)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 2-(aminomethyl)pyridine (0.010 mL, 0.097 mmol) and sodium triacetoxyborohydride (32 mg, 0.15 mmol) to obtain 4-chloro-7-(1-(tert-butoxycarbonyl)-5-[(pyridin-2-ylmethyl)aminomethyl]indol-2-yl)isoindolinone.

Step 2

In a similar manner to Step 2 of Example 56, 4-chloro-7-(1-(tert-butoxycarbonyl)-5-[(pyridin-2-ylmethyl)aminomethyl]indol-2-yl)isoindolinone was treated with 10% hydrogen chloride-methanol solution (0.5 mL) to obtain Compound 64 (3.49 mg, yield 17%, 2 steps).

ESI-MS m/z: 403 [M+H]$^+$.

EXAMPLE 65

4-Chloro-7-{1H-5-[(2-(pyridin-2-yl)ethyl)aminomethyl]indol-2-y}isoindolinone (Compound 65)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 2-(2-aminoethyl)pyridine (0.012 mL, 0.10 mmol) and sodium triacetoxyborohydride (32 mg, 0.15 mmol) to obtain 4-chloro-7-{1-(tert-butoxycarbonyl)-5-[(2-(pyridin-2-yl)ethyl)aminomethyl]indol-2-yl}isoindolinone.

Step 2

In a similar manner to Step 2 of Example 56, 4-chloro-7-(1-(tert-butoxycarbonyl)-5-[(2-(pyridin-2-yl)ethyl)aminomethyl]indol-2-yl)isoindolinone was treated with 10% hydrogen chloride-methanol solution (0.5 mL) to obtain Compound 65 (10.4 mg, yield 50%, 2 steps).

ESI-MS m/z: 417 [M+H]$^+$.

EXAMPLE 66

4-Chloro-7-{1H-5-[2-(2-hydroxyethoxy)ethylaminomethyl]indol-2-yl}isoindolinone (Compound 66)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 2-(2-aminoethoxy)ethanol (0.010 mL, 0.10 mmol) and sodium triacetoxyborohydride (48 mg, 0.23 mmol) to obtain 4-chloro-7-{1-(tert-butoxycarbonyl)-5-[2-(2-hydroxyethoxy)ethylaminomethyl]indol-2-yl}isoindolinone.

Step 2

In a similar manner to Step 2 of Example 56, 4-chloro-7-{1-(tert-butoxycarbonyl)-5-[2-(2-hydroxyethoxy)ethylaminomethyl]indol-2-yl}isoindolinone was treated with 10% hydrogen chloride-methanol solution (0.5 mL) to obtain Compound 66 (6.05 mg, yield 30%, 2 steps).

ESI-MS m/z: 400 [M+H]$^+$.

EXAMPLE 67

4-Chloro-7-{1H-5-[(pyridin-4-ylmethyl)aminomethyl]indol-2-yl}isoindolinone (Compound 67)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 4-(aminomethyl) pyridine (0.010 mL, 0.099 mmol) and sodium triacetoxyborohydride (32 mg, 0.15 mmol) to obtain 4-chloro-7-{1-(tert-butoxycarbonyl)-5-[(pyridin-4-ylmethyl)amino methyl]indol-2-yl}isoindolinone.

Step 2

In a similar manner to Step 2 of Example 56, 4-chloro-7-{1-(tert-butoxycarbonyl)-5-[(pyridin-4-ylmethyl)aminomethyl]indol-2-yl}isoindolinone was treated with 10% hydrogen chloride-methanol solution (0.5 mL) to obtain Compound 67 (7.58 mg, yield 38%, 2 steps).

ESI-MS m/z: 403 [M+H]$^+$.

EXAMPLE 68

4-Chloro-7-{1H-5-[(2-(pyridin-4-yl)ethyl)aminomethyl]indol-2-yl}isoindolinone (Compound 68)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 4-(2-aminoethyl) pyridine (0.012 mL, 0.10 mmol) and sodium triacetoxyborohydride (32 mg, 0.15 mmol) to obtain 4-chloro-7-(1-(tert-butoxycarbonyl)-5-[(2-(pyridin-4-yl)ethyl)aminomethyl]indol-2-yl)isoindolinone.

Step 2

In a similar manner to Step 2 of Example 56, 4-chloro-7-(1-(tert-butoxycarbonyl)-5-[(2-(pyridin-4-yl)ethyl)aminomethyl]indol-2-yl)isoindolinone was treated with 10% hydrogen chloride-methanol solution (0.5 mL) to obtain Compound 68 (17.5 mg, yield 84%, 2 steps).

ESI-MS m/z: 417 [M+H]$^+$.

EXAMPLE 69

4-Chloro-7-{1H-5-[(2-(pyridin-3-yl)ethyl)aminomethyl]indol-2-yl}isoindolinone (Compound 69)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL) and the solution was treated with 3-(2-aminoethyl) pyridine (0.012 mL, 0.10 mmol) and sodium triacetoxyborohydride (32 mg, 0.15 mmol) to obtain 4-chloro-7-{1-(tert-butoxycarbonyl)-5-[(2-(pyridin-3-yl)ethyl)aminomethyl] indol-2-yl}isoindolinone.

Step 2

In a similar manner to Step 2 of Example 56, 4-chloro-7-(1-(tert-butoxycarbonyl)-5-[(2-(pyridin-3-yl)ethyl)aminomethyl]indol-2-yl)isoindolinone was treated with 10% hydrogen chloride-methanol solution (0.5 mL) to obtain Compound 69 (11.2 mg, yield 54%, 2 steps).

ESI-MS m/z: 417 [M+H]$^+$.

EXAMPLE 70

4-Chloro-7-{1H-5-[(pyridin-3-ylmethyl)aminomethyl]indol-2-yl}isoindolinone (Compound 70)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 3-aminomethylpyridine (0.010 mL, 0.098 mmol) and sodium triacetoxyborohydride (32 mg, 0.15 mmol) to obtain 4-chloro-7-(1-(tert-butoxycarbonyl)-5-[(pyridin-3-ylmethyl)amino methyl]indol-2-yl)isoindolinone.

Step 2

In a similar manner to Step 2 of Example 56, 4-chloro-7-(1-(tert-butoxycarbonyl)-5-[(pyridin-3-ylmethyl)aminomethyl]indol-2-yl)isoindolinone was treated with 10% hydrogen chloride-methanol solution (0.5 mL) to obtain Compound 70 (9.08 mg, yield 45%, 2 steps).

ESI-MS m/z: 403 [M+H]$^+$.

EXAMPLE 71

4-Chloro-7-{1H-5-[(3-hydroxy-2,2-dimethylpropyl) aminomethyl]indol-2-yl}isoindolinone (Compound 71)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 3-amino-2,2-dimethylpropanol (10 mg, 0.10 mmol) and sodium triacetoxyborohydride (32 mg, 0.15 mmol) to obtain 4-chloro-7-{1-(tert-butoxycarbonyl)-5-[(3-hydroxy-2,2-dimethylpropyl) aminomethyl]indol-2-yl}isoindolinone.

Step 2

In a similar manner to Step 2 of Example 56, 4-chloro-7-{1-(tert-butoxycarbonyl)-5-[(3-hydroxy-2,2-dimethylpropyl)aminomethyl]indol-2-yl}isoindolinone was treated with 10% hydrogen chloride-methanol solution (0.5 mL) to obtain Compound 71 (5.49 mg, yield 28%, 2 steps).

ESI-MS m/z: 403 [M+H]$^+$.

EXAMPLE 72

4-Chloro-7-{1H-5-[(1-hydroxycyclohexylmethyl) aminocarbonyl]indol-2-yl}isoindolinone (Compound 72)

In a similar manner to Step 1 of Example 20, Compound 19 (30.5 mg, 0.0933 mmol) was dissolved in DMF (2 mL), and the solution was treated with EDCI (73.4 mg, 0.383 mmol), HOBT monohydrate (35.3 mg, 0.231 mmol) and 1-aminomethyl-1-cyclohexanol hydrochloride (102 mg, 0.789 mmol). The mixture was added with water. The precipitated solid was collected by filtration and washed with water, followed by drying under reduced pressure to obtain Compound 72 (33.2 mg, yield 81%).

APCI-MS m/z: 438 [M+H]$^+$; $^1$H-NMR (DMSO-d$_6$) δ(ppm): 1.15-1.64 (m, 10H), 3.27-3.31 (m, 2H), 4.47 (s, 1H), 4.52 (s, 2H), 7.39 (s, 1H), 7.53 (d, J=8.6 Hz, 1H), 7.69 (dd, J=1.5, 8.6 Hz, 1H), 7.76 (d, J=8.6 Hz, 1H), 8.08 (t, J=5.9 Hz, 1H), 8.18 (s, 1H), 8.25 (d, J=8.6 Hz, 1H), 9.57 (s, 1H), 13.94 (s, 1H).

EXAMPLE 73

4-Chloro-7-{1H-5-[(pyridin-2-ylmethyl)aminocarbonyl]indol-2-yl}isoindolinone (Compound 73)

In a similar manner to Step 1 of Example 20, Compound 19 (30.4 mg, 0.0930 mmol) was dissolved in DMF (2 mL), and the solution was treated with EDCI (74.2 mg, 0.387 mmol), HOBT monohydrate (35.9 mg, 0.235 mmol) and 2-(aminomethyl)pyridine (0.080 mL, 0.78 mmol). The mixture was added with water. The precipitated solid was collected by filtration and washed with water, followed by drying under reduced pressure to obtain Compound 73 (33.5 mg, yield 86%).

APCI-MS m/z: 417 [M+H]$^+$; $^1$H-NMR (DMSO-d$_6$) δ(ppm): 4.52 (s, 2H), 4.60 (d, J=5.8 Hz, 2H), 7.26 (m, 1H), 7.35 (d, J=7.9 Hz, 1H), 7.41 (s, 1H), 7.55 (d, J=8.6 Hz, 1H), 7.74-7.79 (m, 3H), 8.25 (s, 1H), 8.27 (m, 1H), 8.52 (d, J=4.8 Hz, 1H), 9.01 (t, J=5.8 Hz, 1H), 9.57 (s, 1H), 13.96 (s, 1H).

EXAMPLE 74

4-Chloro-7-{1H-5-[(pyridin-4-ylmethyl)aminocarbonyl]indol-2-yl}isoindolinone (Compound 74)

In a similar manner to Step 1 of Example 20, Compound 19 (31.0 mg, 0.0949 mmol) was dissolved in DMF (2 mL), and the solution was treated with EDCI (38.2 mg, 0.199 mmol), HOBT monohydrate (19.3 mg, 0.126 mmol) and 4-aminomethylpyridine (0.040 mL, 0.40 mmol). The mixture was added with water. The precipitated solid was collected by filtration and washed with water, followed by drying under reduced pressure to obtain Compound 74 (38.6 mg, yield 98%).

APCI-MS m/z: 417 [M+H]$^+$; $^1$H-NMR (DMSO-d$_6$) δ(ppm): 4.52 (s, 4H), 7.30-7.36 (m, 2H), 7.41 (s, 1H), 7.56 (d, J=8.6 Hz, 1H), 7.74 (dd, J=1.4, 8.6 Hz, 1H), 7.76 (d, J=8.6 Hz, 1H), 8.25 (s, 1H), 8.28 (s, 1H), 8.49-8.52 (m, 2H), 9.03 (t, J=5.9 Hz, 1H), 9.57 (s, 1H), 13.97 (s, 1H).

EXAMPLE 75

4-Chloro-7-{1H-5-[2-((2,2-dimethylethoxy)carbonylamino)ethylaminocarbonyl]indol-2-yl}isoindolinone (Compound 75)

In a similar manner to Step 1 of Example 20, Compound 19 (31.6 mg, 0.0967 mmol) was dissolved in DMF (2 mL), and the solution was treated with EDCI (38.6 mg, 0.201 mmol), HOBT monohydrate (18.9 mg, 0.123 mmol) and N-(2-aminoethyl)carbamic acid tert-butyl (0.061 mL, 0.39 mmol). The mixture was added with water. The precipitated solid was collected by filtration and washed with water, followed by drying under reduced pressure to obtain Compound 75 (40.8 mg, yield 90%).

ESI-MS m/z: 469 [M+H]$^+$; $^1$H-NMR (DMSO-d$_6$) δ(ppm): 1.39 (s, 9H), 3.08-3.19 (m, 2H), 3.28-3.41 (m, 2H), 4.52 (s, 2H), 6.91 (m, 1H), 7.38 (s, 1H), 7.52 (d, J=8.6 Hz, 1H), 7.67 (m, 1H), 7.75 (d, J=8.6 Hz, 1H), 8.15 (s, 1H), 8.26 (d, J=28.6 Hz, 1H), 8.34 (m, 1H), 9.56 (s, 1H), 13.93 (s, 1H).

EXAMPLE 76

4-Chloro-7-{1H-5-[3-((2,2-dimethylethoxy)carbonylamino)propylaminocarbonyl]indol-2-yl}isoindolinone (Compound 76)

In a similar manner to Step 1 of Example 20, Compound 19 (31.6 mg, 0.0967 mmol) was dissolved in DMF (2 mL), and the solution was treated with EDCI (39.0 mg, 0.203 mmol), HOBT monohydrate (18.2 mg, 0.119 mmol) and N-(3-aminopropyl)carbamic acid tert-butyl (0.084 mL, 0.48 mmol). The mixture was added with water. The precipitated solid was collected by filtration and washed with water, followed by drying under reduced pressure to obtain Compound 76 (44.1 mg, yield 94%).

ESI-MS m/z: 483 [M+H]$^+$, $^1$H-NMR (DMSO-d$_6$) δ(ppm): 1.38 (s, 9H), 1.64 (m, 2H), 2.94-3.45 (m, 2H), 3.23-3.31 (m, 2H), 4.52 (s, 2H), 6.82 (m, 1H), 7.39 (s, 1H), 7.52 (d, J=8.6 Hz, 1H), 7.67 (dd, J=1.5, 8.6 Hz, 1H), 7.75 (d, J=8.6 Hz, 1H), 8.15 (s, 1H), 8.26 (d, J=8.6 Hz, 1H), 8.33 (t, J=5.4 Hz, 1H), 9.56 (s, 1H), 13.93 (s, 1H).

EXAMPLE 77

4-Chloro-7-{1H-5-[(pyridin-3-ylmethyl)aminocarbonyl]indol-2-yl}isoindolinone (Compound 77)

In a similar manner to Step 1 of Example 20, Compound 19 (30.7 mg, 0.0940 mmol) was dissolved in DMF (2 mL), and the solution was treated with EDCI (38.8 mg, 0.202 mmol), HOBT monohydrate (19.9 mg, 0.130 mmol) and 3-(aminomethyl)pyridine (0.040 mL, 0.39 mmol). The mixture was added with water. The precipitated solid was collected by filtration and washed with water, followed by drying under reduced pressure to obtain Compound 77 (35.9 mg, yield 92%).

APCI-MS m/z: 417 [M+H]$^+$; $^1$H-NMR (DMSO-d$_6$) δ(ppm): 4.52 (s, 2H), 4.53 (s, 2H), 7.37 (m, 1H), 7.40 (s, 1H), 7.54 (d, J=8.4 Hz, 1H), 7.69-7.79 (m, 3H), 8.22 (s, 1H), 8.26 (d, J=8.6 Hz, 1H), 8.46 (dd, J=1.6, 4.8 Hz, 1H), 8.58 (d, J=2.0 Hz, 1H), 9.00 (t, J=5.9 Hz, 1H), 9.57 (s, 1H), 13.96 (s, 1H).

EXAMPLE 78

4-Chloro-7-{1H-5-[(3-hydroxy-2,2-dimethylpropyl)aminocarbonyl]indol-2-yl}isoindolinone (Compound 78)

In a similar manner to Step 1 of Example 20, Compound 19 (31.2 mg, 0.0955 mmol) was dissolved in DMF (2 mL), and the solution was treated with EDCI (41.0 mg, 0.214 mmol), HOBT monohydrate (16.9 mg, 0.110 mmol) and, 3-amino-2,2-dimethylpropanol (42.2 mg, 0.409 mmol). The mixture was added with water. The precipitated solid was collected by filtration and washed with water, followed by drying under reduced pressure to obtain Compound 78 (34.2 mg, yield 87%).

APCI-MS m/z: 412 [M+H]$^+$; $^1$H-NMR (DMSO-d$_6$) δ(ppm): 0.86 (s, 6H), 3.14 (d, J=6.3 Hz, 2H), 3.18 (d, J=6.3 Hz, 2H), 4.52 (s, 2H), 4.70 (t, J=6.3 Hz, 1H), 7.40 (s, 1H), 7.53 (d, J=8.6 Hz, 1H), 7.67 (dd, J=1.6, 8.6 Hz, 1H), 7.76 (d, J=8.6 Hz, 1H), 8.16 (s, 1H), 8.26 (d, J=8.6 Hz, 1H), 8.34 (t, J=6.3 Hz, 1H), 9.57 (s, 1H), 13.95 (s, 1H).

EXAMPLE 79

4-Chloro-7-[1H-5-(3-hydroxypropylaminomethyl)indol-2-yl]isoindolinone (Compound 79)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 3-amino-1-propanol (0.015 mL, 0.20 mmol) and sodium triacetoxyborohydride (32 mg, 0.15 mmol) to obtain 4-chloro-7-[1-(tert-butoxycarbonyl)-5-(3-hydroxypropylaminomethyl)indol-2-yl]isoindolinone.

Step 2

In a similar manner to Step 2 of Example 56, 4-chloro-7-[1-(tert-butoxycarbonyl)-5-(3-hydroxypropylaminomethyl)indol-2-yl]isoindolinone was treated with 10% hydrogen chloride-methanol solution (0.5 mL) to obtain Compound 79 (5.14 mg, yield 28%, 2 steps).

ESI-MS m/z: 370 [M+H]$^+$.

EXAMPLE 80

4-Chloro-7-[1H-5-(cyclohexylmethylaminomethyl)indol-2-yl]isoindolinone (Compound 80)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with cyclohexanemethylamine (0.026 mL, 0.20 mmol) and sodium triacetoxyborohydride (32 mg, 0.15 mmol) to obtain 4-chloro-7-[1-(tert-butoxycarbonyl)-5-(cyclohexylmethylaminomethyl)indol-2-yl]isoindolinone.

Step 2

In a similar manner to Step 2 of Example 56, 4-chloro-7-[1-(tert-butoxycarbonyl)-5-(cyclohexylmethylaminomethyl)indol-2-yl]isoindolinone was treated with 10% hydrogen chloride-methanol solution (0.5 mL) to obtain Compound 80 (4.01 mg, yield 20%, 2 steps).

ESI-MS m/z: 408 [M+H]$^+$.

EXAMPLE 81

4-Chloro-7-[1H-5-[(2-methoxyethyl)aminomethyl]indol-2-yl]isoindolinone (Compound 81)

Step 1

In a similar manner to Step. 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 2-methoxyethylamine (0.017 mL, 0.20 mmol) and sodium triacetoxyborohydride (32 mg, 0.15 mmol) to obtain 4-chloro-7-[1-(tert-butoxycarbonyl)-5-[(2-methoxyethyl)aminomethyl]indol-2-yl]isoindolinone.

Step 2

In a similar manner to Step 2 of Example 56, 4-chloro-7-[1-(tert-butoxycarbonyl)-5-[(2-methoxyethyl)aminomethyl]indol-2-yl]isoindolinone was treated with 10% hydrogen chloride-methanol solution (0.5 mL) to obtain Compound 81 (7.99 mg, yield 43%, 2 steps).

ESI-MS m/z: 370 [M+H]$^+$.

EXAMPLE 82

4-Chloro-7-{1H-5-[2-(thiophen-2-yl)ethylaminomethyl]indol-2-yl}isoindolinone (Compound 82)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with thiophene-2-ethylamine (0.023 mL, 0.20 mmol) and sodium triacetoxyborohydride (32 mg, 0.15 mmol) to obtain 4-chloro-7-[1-(tert-butoxycarbonyl)-5-(2-(thiophen-2-yl)ethylaminomethyl]indol-2-yl)isoindolinone.

Step 2

In a similar manner to Step 2 of Example 56, 4-chloro-7-{1-(tert-butoxycarbonyl)-5-[2-(thiophen-2-yl)ethylaminomethyl]indol-2-yl}isoindolinone was treated with 10% hydrogen chloride-methanol solution (0.5 mL) to obtain Compound 82 (5.28 mg, yield 25%, 2 steps).

ESI-MS m/z: 422 [M+H]$^+$.

EXAMPLE 83

4-Chloro-7-{1H-5-[(2-aminoethyl)aminomethyl]indol-2-yl}isoindolinone (Compound 83)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with N-(2-aminoethyl)carbamic acid tert-butyl (0.032 mL, 0.20 mmol) and sodium triacetoxyborohydride (32 mg, 0.15 mmol) to obtain 4-chloro-7-{1-(tert-butoxycarbonyl)-5-[(2-(tert-butoxycarbonyl)aminoethyl)aminomethyl]indol-2-yl}isoindolinone.

Step 2

In a similar manner to Step 2 of Example 56, 4-chloro-7-{1-(tert-butoxycarbonyl)-5-[(2-(tert-butoxycarbonyl)aminoethyl)aminomethyl]indol-2-yl}isoindolinone was treated with 10% hydrogen chloride-methanol solution (0.5 mL) to obtain Compound 83 (4.43 mg, yield 25%, 2 steps).

ESI-MS m/z: 355 [M+H]$^+$.

EXAMPLE 84

4-Chloro-7-{1H-5-[(2-fluoroethyl)aminomethyl]indol-2-yl}isoindolinone (Compound 84)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 2-fluoroethylamine hydrochloride (20 mg, 0.20 mmol) and sodium triacetoxyborohydride (32 mg, 0.15 mmol) to obtain 4-chloro-7-{1-(tert-butoxycarbonyl)-5-[(2-fluoroethyl)aminomethyl]indol-2-yl}isoindolinone.

Step 2

In a similar manner to Step 2 of Example 56, 4-chloro-7-{1-(tert-butoxycarbonyl)-5-[(2-fluoroethyl)aminomethyl]indol-2-yl}isoindolinone was treated with 10% hydrogen chloride-methanol solution (0.5 mL) to obtain Compound 84 (3.87 mg, yield 22%, 2 steps).

ESI-MS m/z: 358 [M+H]$^+$.

EXAMPLE 85

4-Chloro-7-[1H-5-(2-propynylaminomethyl)indol-2-yl]isoindolinone (Compound 85)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with propargylamine (0.013 mL, 0.19 mmol) and sodium triacetoxyborohydride (32 mg, 0.15 mmol) to obtain 4-chloro-7-[1-(tert-butoxycarbonyl)-5-(2-propynylaminomethyl)indol-2-yl]isoindolinone.

Step 2

In a similar manner to Step 2 of Example 56, 4-chloro-7-[1-(tert-butoxycarbonyl)-5-(2-propynylaminomethyl)indol-2-yl]isoindolinone was treated with 10% hydrogen chloride-methanol solution (0.5 mL) to obtain Compound 85 (3.06 mg, yield 18%, 2 steps).

ESI-MS m/z: 350 [M+H]$^+$.

EXAMPLE 86

4-Chloro-7-[1H-5-[(2-hydroxy-2-phenylethyl)aminomethyl]indol-2-yl]isoindolinone (Compound 86)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 2-amino-1-phenylethanol (27 mg, 0.20 mmol) and sodium triacetoxyborohydride (32 mg, 0.15 mmol) to obtain 4-chloro-7-[1-(tert-butoxycarbonyl)-5-[(2-hydroxy-2-phenylethyl)aminomethyl]indol-2-yl]isoindolinone.

Step 2

In a similar manner to Step 2 of Example 56, 4-chloro-7-[1-(tert-butoxycarbonyl)-5-[(2-hydroxy-2-phenylethyl)aminomethyl]indol-2-yl]isoindolinone was treated with 10% hydrogen chloride-methanol solution (0.5 mL) to obtain Compound 86 (4.47 mg, yield 21%, 2 steps).

ESI-MS m/z: 432 [M+H]$^+$.

EXAMPLE 87

4-Chloro-7-{1H-5-[(2-hydroxy-1,1-dimethylethyl)aminomethyl]indol-2-yl}isoindolinone (Compound 87)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 2-amino-2-methyl-1-propanol (18 mg, 0.20 mmol) and sodium triacetoxyborohydride (32 mg, 0.15 mmol) to obtain 4-chloro-7-(1-(tert-butoxycarbonyl)-5-[(2-hydroxy-1,1-dimethylethyl)aminomethyl]indol-2-yl)isoindolinone.

Step 2

In a similar manner to Step 2 of Example 56, 4-chloro-7-{1-(tert-butoxycarbonyl)-5-[(2-hydroxy-1,1-dimethylethyl)aminomethyl]indol-2-yl}isoindolinone was treated with 10% hydrogen chloride-methanol solution (0.5 mL) to obtain Compound 87 (3.85 mg, yield 20%, 2 steps).

ESI-MS m/z: 384 [M+H]$^+$.

EXAMPLE 88

4-Chloro-7-[1H-5-(azepan-1-ylaminomethyl)indol-2-yl]isoindolinone (Compound 88)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with homopiperidine (0.023 mL, 0.20 mmol) and sodium triacetoxyborohydride (32 mg, 0.15 mmol) to obtain 4-chloro-7-[1-(tert-butoxycarbonyl)-5-(azepan-1-ylaminomethyl)indol-2-yl]isoindolinone.

Step 2

In a similar manner to Step 2 of Example 56, 4-chloro-7-[1-(tert-butoxycarbonyl)-5-(azepan-1-ylaminomethyl)indol-2-yl]isoindolinone was treated with 10% hydrogen chloride-methanol solution (0.5 mL) to obtain Compound 88 (2.90 mg, yield 15%, 2 steps).

ESI-MS m/z: 394 [M+H]$^+$.

EXAMPLE 89

4-Chloro-7-[1H-5-(thiomorpholinomethyl)indol-2-yl]isoindolinone (Compound 89)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with thiomorpholine (0.020 mL, 0.20 mmol) and sodium triacetoxyborohydride (32 mg, 0.15 mmol) to obtain 4-chloro-7-[1-(tert-butoxycarbonyl)-5-(thiomorpholinomethyl)indol-2-yl]isoindolinone.

Step 2

In a similar manner to Step 2 of Example 56, 4-chloro-7-[1-(tert-butoxycarbonyl)-5-(thiomorpholinomethyl)indol-2-yl]isoindolinone was treated with 10% hydrogen chloride-methanol solution (0.5 mL) to obtain Compound 89 (5.13 mg, yield 26%, 2 steps).

ESI-MS m/z: 398 [M+H]$^+$.

EXAMPLE 90

4-Chloro-7-{1H-5-[4-(pyridin-2-yl)piperazin-1-ylmethyl]indol-2-yl}isoindolinone (Compound 90)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 1-(pyridin-2-yl)piperazine (0.030 mL, 0.20 mmol) and sodium triacetoxyborohydride (32 mg, 0.15 mmol) to obtain 4-chloro-7-{1-(tert-butoxycarbonyl)-5-[4-(pyridin-2-yl)piperazin-1-ylmethyl]indol-2-yl}isoindolinone.

Step 2

In a similar manner to Step 2 of Example 56, 4-chloro-7-{1-(tert-butoxycarbonyl)-5-[4-(pyridin-2-yl)piperazin-1-ylmethyl]indol-2-yl}isoindolinone was treated with 10% hydrogen chloride-methanol solution (0.5 mL) to obtain Compound 90 (4.37 mg, yield 19%, 2 steps).

ESI-MS m/z: 458 [M+H]$^+$.

EXAMPLE 91

4-Chloro-7-[1H-5-(4-phenylpiperidinomethyl)indol-2-yl]isoindolinone (Compound 91)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 4-phenylpiperidine (32 mg, 0.20 mmol) and sodium triacetoxyborohydride (32 mg, 0.15 mmol) to obtain 4-chloro-7-[1-(tert-butoxycarbonyl)-5-(4-phenylpiperidinomethyl)indo-2-yl]isoindolinone.

Step 2

In a similar manner to Step 2 of Example 56, 4-chloro-7-[1-(tert-butoxycarbonyl)-5-(4-phenylpiperidinomethyl)indol-2-yl]isoindolinone was treated with 10% hydrogen chloride-methanol solution (0.5 mL) to obtain Compound 91 (3.27 mg, yield 14%, 2 steps).

ESI-MS m/z: 456 [M+H]$^+$.

EXAMPLE 92

4-Chloro-7-[1H-5-(4-hydroxy-4-phenylpiperidinomethyl)indol-2-yl]isoindolinone (Compound 92)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 4-hydroxy-4-phenylpiperidine (35 mg, 0.20 mmol) and sodium triacetoxyborohydride (32 mg, 0.15 mmol) to obtain 4-chloro-7-[1-(tert-butoxycarbonyl)-5-(4-hydroxy-4-phenylpiperidinomethyl)indol-2-yl]isoindolinone.

Step 2

In a similar manner to Step 2 of Example 56, 4-chloro-7-[1-(tert-butoxycarbonyl)-5-(4-hydroxy-4-phenylpiperidinomethyl)indol-2-yl]isoindolinone was treated with 10% hydrogen chloride-methanol solution (0.5 mL) to obtain Compound 92 (7.03 mg, yield 30%, 2 steps).

ESI-MS m/z: 472 [M+H]$^-$.

EXAMPLE 93

4-Chloro-7-{1H-5-[4-(2-(2-hydroxyethoxy)ethyl)piperazin-1-ylmethyl]indol-2-yl}isoindolinone (Compound 93)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 1-[2-(2-hydroxyethoxy)ethyl]piperazine (35 mg, 0.20 mmol) and sodium triacetoxyborohydride (32 mg, 0.15 mmol) to obtain 4-chloro-7-{1-(tert-butoxycarbonyl)-5-[4-(2-(2-hydroxyethoxy)ethyl)piperazin-1-ylmethyl]indol-2-yl}isoindolinone.

Step 2

In a similar manner to Step 2 of Example 56, 4-chloro-7-{1-(tert-butoxycarbonyl)-5-[4-(2-(2-hydroxyethoxy)ethyl)piperazin-1-ylmethyl]indol-2-yl}isoindolinone was treated with 10% hydrogen chloride-methanol solution (0.5 mL) to obtain Compound 93 (4.14 mg, yield 18%, 2 steps).

ESI-MS m/z: 469 [M+H]$^+$.

EXAMPLE 94

4-Chloro-7-{1H-5-[3-(hydroxymethyl)piperidinomethyl]indol-2-yl}isoindolinone (Compound 94)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 3-piperidine methanol (0.022 mL, 0.20 mmol) and sodium triacetoxyborohydride (32 mg, 0.15 mmol) to obtain 4-chloro-7-(1-(tert-butoxycarbonyl)-5-[3-(hydroxymethyl)piperidinomethyl]indol-2-yl)isoindolinone.

Step 2

In a similar manner to Step 2 of Example 56, 4-chloro-7-{1-(tert-butoxycarbonyl)-5-[(3-(hydroxymethyl)piperidinomethyl]indol-2-yl}isoindolinone was treated with 10% hydrogen chloride-methanol solution (0.5 mL) to obtain Compound 94 (4.95 mg, yield 24%, 2 steps).

ESI-MS m/z: 410 [M+H]$^+$.

EXAMPLE 95

4-Chloro-7-{1H-5-[(4-(pyridin-4-yl)piperazin-1-ylmethyl]indol-2-yl}isoindolinone (Compound 95)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 1-(pyridin-4-yl)piperazine (32 mg, 0.20 mmol) and sodium triacetoxyborohydride (32 mg, 0.15 mmol) to obtain 4-chloro-7-(1-(tert-butoxycarbonyl)-5-[4-(pyridin-4-yl)piperazin-1-ylmethyl]indol-2-yl)isoindolinone.

Step 2

In a similar manner to Step 2 of Example 56, 4-chloro-7-{1-(tert-butoxycarbonyl)-5-[4-(pyridin-4-yl)piperazin-1-ylmethyl]indol-2-yl}isoindolinone was treated with 10% hydrogen chloride-methanol solution (0.5 mL) to obtain Compound 95 (4.51 mg, yield 20%, 2 steps).

ESI-MS m/z: 458 [M+H]$^+$.

EXAMPLE 96

4-Chloro-7-{1H-5-[4-(pyrimidin-2-yl)piperazin-1-ylmethyl]indol-2-yl}isoindolinone (Compound 96)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 1-(2-pyrimidyl)piperazine (33 mg, 0.20 mmol) and sodium triacetoxyborohydride (32 mg, 0.15 mmol) to obtain 4-chloro-7-(1-(tert-butoxycarbonyl)-5-[4-(pyrimidin-2-yl)piperazin-1-ylmethyl]indol-2-yl)isoindolinone.

Step 2

In a similar manner to Step 2 of Example 56, 4-chloro-7-{1-(tert-butoxycarbonyl)-5-[4-(pyrimidin-2-yl)piperazin-1-ylmethyl]indol-2-yl}isoindolinone was treated with 10% hydrogen chloride-methanol solution (0.5 mL) to obtain Compound 96 (6.91 mg, yield 30%, 2 steps).

ESI-MS m/z: 459 [M+H]$^+$.

EXAMPLE 97

4-Chloro-7-{1H-5-[4-(2-methoxyethyl)piperazin-1-ylmethyl]indol-2-yl}isoindolinone (Compound 97)

Step 1

In a similar manner to Step 1, of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 1-(2-methoxyethyl)piperazine (29 mg, 0.20 mmol) and sodium triacetoxyborohydride (32 mg, 0.15 mmol) to obtain 4-chloro-7-{1-(tert-butoxycarbonyl)-5-[4-(2-methoxyethyl)piperazin-1-ylmethyl]indol-2-yl}isoindolinone.

Step 2

In a similar manner to Step 2 of Example 56, 4-chloro-7-(1-(tert-butoxycarbonyl)-5-[4-(2-methoxyethyl)piperazin-1-ylmethyl]indol-2-yl)isoindolinone was treated with 10% hydrogen chloride-methanol solution (0.5 mL) to obtain Compound 97 (9.62 mg, yield 44%, 2 steps).

ESI-MS m/z: 439 [M+H]$^+$.

EXAMPLE 98

4-Chloro-7-{1H-5-[N-(2-(dimethylamino)ethyl)-N-methylaminomethyl]indol-2-yl}isoindolinone (Compound 98)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with N,N,N'-trimethylethylenediamine (32 mg, 0.20 mmol) and sodium triacetoxyborohydride (32 mg, 0.15 mmol) to obtain 4-chloro-7-(1-(tert-butoxycarbonyl)-5-[N-(2-(dimethylamino)ethyl)-N-methylaminomethyl]indol-2-yl)isoindolinone.

Step 2

In a similar manner to Step 2 of Example 56, 4-chloro-7-{1-(tert-butoxycarbonyl)-5-[N-(2-(dimethylamino)ethyl)-N-methylaminomethyl]indol-2-yl}isoindolinone was treated with 10% hydrogen chloride-methanol solution (0.5 mL) to obtain Compound 98 (5.46 mg, yield 28%, 2 steps).

ESI-MS m/z: 397 [M+H]$^+$.

EXAMPLE 99

4-Chloro-7-{1H-5-[N-(2,3-dihydroxypropyl)-N-methylaminomethyl]indol-2-yl}isoindolinone (Compound 99)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 3-methylamino-1,2-propanediol (21 mg, 0.20 mmol) and sodium triacetoxyborohydride (32 mg, 0.15 mmol) to obtain 4-chloro-7-{1-(tert-butoxycarbonyl)-5-[N-(2,3-dihydroxypropyl)-N-methylaminomethyl]indol-2-yl}isoindolinone.

Step 2

In a similar manner to Step 2 of Example 56, 4-chloro-7-{1-(tert-butoxycarbonyl)-5-[N-(2,3-dihydroxypropyl)-N-methylaminomethyl]indol-2-yl}isoindolinone was treated with 10% hydrogen chloride-methanol solution (0.5 mL) to obtain Compound 99 (9.32 mg, yield 48%, 2 steps).

ESI-MS m/z: 386 [M+H]$^+$.

EXAMPLE 100

4-Chloro-7-{1H-5-[1-(hydroxymethyl)cyclopentylaminocarbonyl]indol-2-yl}isoindolinone (Compound 100)

In a similar manner to Step 1 of Example 20, Compound 19 (30.7 mg, 0.0940 mmol) was dissolved in DMF (2 mL), and the solution was treated with EDCI (35.4 mg, 0.185 mmol), HOBT monohydrate (17.8 mg, 0.116 mmol) and 1-amino-1-cyclopentanemethanol (46.0 mg, 0.399 mmol). The mixture was added with water. The precipitated solid was collected by filtration, washed with water and dried under reduced pressure. The solid was suspended in ethyl acetate and the suspension was collected by filtration, washed with ethyl acetate, followed by drying under reduced pressure. The solid was suspended in methanol. The suspension was filtered to collect the solid. The solid was washed with methanol, followed by drying under reduced pressure to obtain Compound 100 (11.8 mg, yield 30%) and Compound 101 (6.9 mg, yield 17%).

Compound 100

APCI-MS m/z: 424 [M+H]$^+$; $^1$H-NMR (DMSO-d$_6$) δ(ppm): 1.30-1.80 (m, 8H), 3.27 (s, 2H), 4.51 (s, 2H), 7.38 (s, 1H), 7.47 (d, J=8.6 Hz, 1H), 7.75 (d, J=8.4 Hz, 1H), 7.76 (d, J=8.6 Hz, 1H), 8.228 (s, 1H), 8.229 (d, J=8.4 Hz, 1H), 9.58 (br s, 1H), 13.91 (s, 1H).

EXAMPLE 101

4-Chloro-7-{1H-5-[(1-aminocyclopentyl)methoxycarbonyl]indol-2-yl}isoindolinone (Compound 101)

As described above, Compound 101 was obtained by the method described in Example 100.

Compound 101

APCI-MS m/z: 424 [M+H]$^+$; $^1$H-NMR (DMSO-d$_6$) δ(ppm); 1.59-1.71 (m, 8H), 3.60 (d, J=5.8 Hz, 2H), 4.52 (s, 2H), 4.93 (t, J=5.8 Hz, 1H), 7.38 (s, 1H), 7.50 (d, J=8.6 Hz, 1H), 7.65 (dd, J=1.6, 8.6 Hz, 1H), 7.62-7.68 (m, 1H), 7.75 (d, J=8.6 Hz, 1H), 8.14 (s, 1H), 8.25 (d, J=8.6 Hz, 1H), 9.56 (s, 1H), 13.91 (s, 1H).

EXAMPLE 102

4-Chloro-7-{1H-5-[(2-hydroxy-1-(hydroxymethyl)ethyl)aminocarbonyl]indol-2-yl}isoindolinone (Compound 102)

In a similar manner to Step 1 of Example 20, Compound 19 (31.0 mg, 0.0949 mmol) was dissolved in DMF (2 mL), and the solution was treated with EDCI (73.4 mg, 0.383 mmol), HOBT monohydrate (35.2 mg, 0.230 mmol) and 2-amino-1,3-propanediol hydrochloride (73.4 mg, 0.569 mmol). The mixture was added with water. The precipitated solid was collected by filtration, washed with water and dried under reduced pressure. The solid was suspended in methanol. The suspension was filtered to collect the solid. The solid was washed with methanol, followed by drying under reduced pressure to obtain Compound 102 (11.0 mg, yield 29%).

APCI-MS m/z: 400 [M+H]$^+$; $^1$H-NMR (DMSO-d$_6$) δ(ppm): 3.55 (dd, J=5.8, 5.8 Hz, 4H), 3.99 (m, 1H), 4.52 (s, 2H), 4.65 (t, J=5.8 Hz, 2H), 7.38 (s, 1H), 7.52 (d, J=8.6 Hz, 1H), 7.70 (dd, J=1.6, 8.6 Hz, 1H), 7.75 (d, J=8.6 Hz, 1H), 7.83 (d, J=8.1 Hz, 1H), 8.18 (s, 1H), 8.26 (d, J=8.6 Hz, 1H), 9.57 (s, 1H), 13.93 (s, 1H).

EXAMPLE 103

4-Chloro-7-{1H-5-[(2-aminoethyl)aminocarbonyl]indol-2-yl}isoindolinone hydrochloride (Compound 103)

In a similar manner to Step 2 of Example 8, Compound 75 (30.0 mg, 0.0640 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 103 (24.7 mg, yield 95%).

APCI-MS m/z: 369 [M+H]$^+$; $^1$H-NMR (DMSO-d$_6$) δ(ppm): 2.95-3.07 (m, 2H), 3.54 (dt, J=5.4, 5.9 Hz, 2H), 4.52 (s, 2H), 7.40 (s, 1H), 7.55 (d, J=8.6 Hz, 1H), 7.73 (d, J=8.6 Hz, 1H), 7.76 (d, J=8.6 Hz, 1H), 7.92 (br s, 3H), 8.22 (s, 1H), 8.26 (d, J=8.6 Hz, 1H), 8.58 (t, J=5.4 Hz, 1H), 9.57 (s, 1H), 13.96 (s, 1H).

EXAMPLE 104

4-Chloro-7-{1H-5-[(3-aminopropyl)aminocarbonyl]indol-2-yl}isoindolinone hydrochloride (Compound 104)

In a similar manner to Step 2 of Example 8, Compound 76 (30.0 mg, 0.0621 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 104 (22.8 mg, yield 88%).

APCI-MS m/z: 383 [M+H]$^+$; $^1$H-NMR (DMSO-d$_6$) δ(ppm): 1.78-1.88 (m, 2H), 2.80-2.92 (m, 2H), 3.25-3.50 (m, 2H), 4.52 (s, 2H), 7.39 (s, 1H), 7.54 (d, J=8.4 Hz, 1H), 7.69 (dd, J=1.3, 8.6 Hz, 1H), 7.76 (d, J=8.6 Hz, 1H), 7.81 (br s, 3H), 8.18 (s, 1H), 8.26 (d, J=8.6 Hz, 1H), 8.57 (t, J=5.6 Hz, 1H), 9.57 (s, 1H), 13.95 (s, 1H).

EXAMPLE 105

4-Chloro-7-{1H-5-[(3-hydroxypropyl)aminocarbonyl]indol-2-yl}isoindolinone (Compound 105)

In a similar manner to Step 1 of Example 20, Compound 19 (31.5 mg, 0.0964 mmol) was dissolved in DMF (1 mL), and the solution was treated with EDCI (37.3 mg, 0.195 mmol), HOBT monohydrate (15.2 mg, 0.0990 mmol) and 3-amino-1-propanol (0.030 mL, 0.39 mmol). The mixture was added with water. The precipitated solid was collected by filtration, washed with water, and dried under reduced pressure. The solid was suspended in methanol. The suspension was filtered to collect the solid. The solid was washed with methanol, followed by drying under reduced pressure. The solid was suspended in chloroform and methanol. The suspension was filtered to collect the solid. The solid was washed with methanol, followed by drying under reduced pressure to obtain Compound 105 (14.0 mg, yield 38%).

ESI-MS m/z: 384 [M+H]$^+$; $^1$H-NMR (DMSO-d$_6$) δ(ppm): 1.59 (quint, J=6.6 Hz, 2H), 2.73 (t, J=6.7 Hz, 2H), 3.45-3.51 (m, 2H), 4.51 (s, 2H), 7.36 (s, 1H), 7.44 (d, J=8.6 Hz, 1H), 7.74 (d, J=8.4 Hz, 1H), 7.76 (d, J=8.6 Hz, 1H), 8.21 (s, 1H), 8.23 (d, J=8.4 Hz, 1H), 13.86 (s, 1H).

EXAMPLE 106

4-Chloro-7-[1H-5-(thiomorpholinocarbonyl)indol-2-yl]isoindolinone (Compound 106)

In a similar manner to Step 1 of Example 20. Compound 19 (32.1 mg, 0.0982 mmol) was dissolved in DMF (1 mL), and the solution was treated with EDCI (37.3 mg, 0.195 mmol), HOBT monohydrate (16.5 mg, 0.108 mmol) and thiomorpholine (0.040 mL, 0.40 mmol). The mixture was added with water. The precipitated solid was collected by filtration and washed with water, followed by drying under reduced pressure to obtain Compound 106 (36.6 mg, yield 90%).

APCI-MS m/z: 412 [M+H]$^+$; $^1$H-NMR (DMSO-d$_6$) δ(ppm): 2.66 (m, 4H), 3.78 (m, 4H), 4.51 (s, 2H), 7.17 (dd, J=1.6, 8.4 Hz, 1H), 7.33 (s, 1H), 7.53 (d, J=8.4 Hz, 1H), 7.65 (s, 1H), 7.75 (d, J=8.6 Hz, 1H), 8.22 (d, J=8.6 Hz, 1H), 9.55 (s, 1H), 13.89 (s, 1H).

EXAMPLE 107

4-Chloro-7-{1H-5-[4-(pyridin-2-yl)piperazin-1-ylcarbonyl]indol-2-yl}isoindolinone (Compound 107)

In a similar manner to Step 1 of Example 20, Compound 19 (31.6 mg, 0.0967 mmol) was dissolved in DMF (1 mL), and the solution was treated with EDCI (39.4 mg, 0.206 mmol), HOBT monohydrate (16.7 mg, 0.109 mmol) and 1-(2-pyridyl)piperazine (66.0 mg, 0.404 mmol). The mixture was added with water. The precipitated solid was collected by filtration and washed with water, followed by drying under reduced pressure to obtain Compound 107 (41.6 mg, yield 91%).

mp >295° C.; APCI-MS m/z: 472 [M+H]$^+$; $^1$H-NMR (DMSO-d$_6$) δ(ppm): 3.50-3.72 (m, 8H), 4.52 (s, 2H), 6.67 (m, 1H), 6.85 (d, J=8.6 Hz, 1H), 7.24 (d, J=8.6 Hz, 1H), 7.35 (m, 1H), 7.50-7.58 (m, 2H), 7.71 (m, 1H), 7.76 (d, J=8.7 Hz, 1H), 8.13 (m, 1H), 8.23 (d, J=8.7 Hz, 1H), 9.56 (s, 1H), 13.91 (s, 1H).

EXAMPLE 108

4-Chloro-7-{1H-5-[2-(2-hydroxyethyl)piperidinocarbonyl]indol-2-yl}isoindolinone (Compound 108)

In a similar manner to Step 1 of Example 20, Compound 19 (30.6 mg, 0.0937 mmol) was dissolved in DMF (1 mL), and the solution was treated with EDCI (37.9 mg, 0.198 mmol), HOBT monohydrate (15.5 mg, 0.101 mmol) and 2-(2-hydroxyethyl)piperidine (56.4 mg, 0.437 mmol). The mixture was added with water. The precipitated solid was collected by filtration and washed with water, followed by drying under reduced pressure to obtain Compound 108 (42.7 mg, yield 100%). APCI-MS m/z: 438 [M+H]$^+$; $^1$H-NMR (DMSO-d$_6$) δ(ppm): 1.32-1.80 (m, 8H), 3.22-3.56 (m, 5H), 4.38 (m, 1H), 4.51 (s, 2H), 7.13 (d, J=8.7 Hz, 1H), 7.33 (s, 1H), 7.51 (d, J=8.7 Hz, 1H), 7.59 (s, 1H), 7.75 (d, J=8.7 Hz, 1H), 8.22 (d, J=8.7 Hz, 1H), 9.55 (s, 1H), 13.86 (s, 1H).

EXAMPLE 109

4-Chloro-7-{1H-5-[4-(2-(2-hydroxyethoxy)ethyl) piperazin-1-ylcarbonyl]indol-2-yl}isoindolinone (Compound 109)

In a similar manner to Step 1 of Example 20, Compound 19 (31.7 mg, 0.0970 mmol) was dissolved in DMF (1 mL), and the solution was treated with EDCI (36.5 mg, 0.190 mmol), HOBT monohydrate (19.0 mg, 0.124 mmol) and 1-[2-(2-hydroxyethoxy)ethyl]piperazine (79.9 mg, 0.459 mmol). The mixture was added with water. The precipitated solid was collected by filtration and washed with water, followed by drying under reduced pressure to obtain Compound 109 (30.0 mg, yield 64%).

mp 255° C.; APCI-MS m/z: 483 [M+H]$^+$; $^1$H-NMR (DMSO-d$_6$) δ(ppm): 2.40-2.58 (m, 6H), 3.27-3.60 (m, 10H), 4.51 (s, 2H), 4.59 (m, 1H), 7.17 (dd, J=1.2, 8.6 Hz, 1H), 7.34 (s, 1H), 7.53 (d, J=8.6 Hz, 1H), 7.64 (s, 1H), 7.75 (d, J=8.6 Hz, 1H), 8.22 (d, J=8.6 Hz, 1H), 9.55 (s, 1H), 13.89 (s, 1H).

EXAMPLE 110

4-Chloro-7-{1H-5-[3-(hydroxymethyl)piperidinocarbonyl]indol-2-yl}isoindolinone (Compound 110)

In a similar manner to Step 1 of Example 20, Compound 19 (30.7 mg, 0.0940 mmol) was dissolved in DMF (1 mL), and the solution was treated with EDCI (38.0 mg, 0.198 mmol), HOBT monohydrate (18.5 mg, 0.121 mmol) and 3-piperidine methanol (49.0 mg, 0.425 mmol). The mixture was added with water. The precipitated solid was collected by filtration and washed with water, followed by drying under reduced pressure to obtain Compound 110 (39.4 mg, yield 99%).

APCI-MS m/z: 424 [M+H]$^+$; $^1$H-NMR (DMSO-d$_6$) δ(ppm): 1.10-1.80 (m, 5H), 3.15-3.40 (m, 6H), 4.51 (s, 3H), 7.16 (m, 1H), 7.33 (s, 1H), 7.52 (d, J=8.6 Hz, 1H), 7.62 (s, 1H), 7.75 (d, J=8.6 Hz, 1H), 8.22 (d, J=8.6 Hz, 1H), 9.55 (s, 1H), 13.87 (s, 1H).

EXAMPLE 111

4-Chloro-7-{1H-5-[4-(pyridin-4-yl)piperazin-1-ylcarbonyl]indol-2-yl}isoindolinone (Compound 111)

In a similar manner to Step 1 of Example 20, Compound 19 (31.3 mg, 0.0958 mmol) was dissolved in DMF (1 mL), and the solution was treated with EDCI (39.0 mg, 0.203 mmol), HOBT monohydrate (15.7 mg, 0.103 mmol) and 1-(pyridin-4-yl)piperazine (66.9 mg, 0.410 mmol). The mixture was added with water. The precipitated solid was collected by filtration and washed with water, followed by drying under reduced pressure to obtain Compound III (40.9 mg, yield 90%).

APCI-MS m/z: 472 [M+H]$^+$; $^1$H-NMR (DMSO-d$_6$) δ(ppm): 3.25-3.48 (m, 4H), 3.60-3.74 (m, 4H), 4.52 (s, 2H), 6.80-6.85 (m, 2H), 7.24 (dd, J=1.7, 8.2 Hz, 1H), 7.36 (s, 1H), 7.56 (d, J=8.2 Hz, 1H), 7.72 (s, 1H), 7.76 (d, J=8.6 Hz, 1H), 8.15-8.20 (m, 2H), 8.23 (d, J=8.6 Hz, 1H), 9.56 (s, 1H), 13.93 (s, 1H).

EXAMPLE 112

4-Chloro-7-{1H-5-[4-(2-dimethylaminoethyl)piperazin-1-ylcarbonyl]indol-2-yl}isoindolinone (Compound 112)

In a similar manner to Step. 1 of Example 20, Compound 19 (31.7 mg, 0.0970 mmol) was dissolved in DMF (1 mL), and the solution was treated with EDCI (39.7 mg, 0.207 mmol), HOBT monohydrate (18.8 mg, 0.123 mmol) and 1-[2-(2-dimethylamino)ethyl]piperazine (62.0 mg, 0.394 mmol). The mixture was added with water. The precipitated solid was collected by filtration and washed with water, followed by drying under reduced pressure to obtain Compound 112 (38.1 mg, yield 84%).

mp 271-272° C.; APCI-MS m/z: 466 [M+H]$^+$; $^1$H-NMR (DMSO-d$_6$) δ(ppm): 2.13 (s, 6H), 2.30-2.55 (m, 8H), 3.45-3.57 (m, 4H), 4.51 (s, 2H), 7.17 (m, 1H), 7.34 (s, 1H), 7.53 (d, J=8.6 Hz, 1H), 7.63 (s, 1H), 7.75 (d, J=8.6 Hz, 1H), 8.22 (d, J=8.6 Hz, 1H), 9.55 (s, 1H), 13.89 (s, 1H).

EXAMPLE 113

4-Chloro-7-{1H-5-[4-(pyrimidin-2-yl)piperazin-1-ylcarbonyl]indol-2'-yl}isoindolinone (Compound 113)

In a similar manner to Step 1 of Example 20, Compound 19 (31.4 mg, 0.0961 mmol) was dissolved in DMF (1 mL), and the solution was treated with EDCI (40.2 mg, 0.210 mmol), HOBT monohydrate (18.4 mg, 0.120 mmol) and 1-(pyrimidin-2-yl)piperazine (66.6 mg, 0.406 mmol). The mixture was added with water. The precipitated solid was collected by filtration and washed with water, followed by drying under reduced pressure to obtain Compound 113 (40.0 mg, yield 88%).

APCI-MS m/z: 473 [M+H]$^+$; $^1$H-NMR (DMSO-d$_6$) δ(ppm): 3.58-3.68 (m, 4H) 3.77-3.85 (m, 4H), 4.52 (s, 2H), 6.67 (t, J=4.8 Hz, 1H), 7.24 (dd, J=1.3, 8.6 Hz, 1H), 7.36 (s, 1H), 7.56 (d, J=8.6 Hz, 1H), 7.72 (s, 1H), 7.76 (d, J=8.6 Hz, 1H), 8.23 (d, J=8.6 Hz, 1H), 8.39 (d, J=4.8 Hz, 2H), 9.56 (s, 1H), 13.91 (s, 1H).

EXAMPLE 114

4-Chloro-7-{1H-5-[4-(2-methoxyethyl)piperazin-1-ylcarbonyl]indol-2-yl}isoindolinone (Compound 114)

In a similar manner to Step 1 of Example 20, Compound 19 (31.0 mg, 0.0949 mmol) was dissolved in DMF (1 mL), and the solution was treated with EDCI (38.7 mg, 0.202 mmol), HOBT monohydrate (18.2 mg, 0.119 mmol) and 1-(2-methoxyethyl)piperazine (62.2 mg, 0.431 mmol). The mixture was added with water. The precipitated solid was collected by filtration and washed with water, followed by drying under reduced pressure to obtain Compound 114 (35.6 mg, yield 83%).

APCI-MS m/z: 453 [M+H]$^+$; $^1$H-NMR (DMSO-d$_6$) δ(ppm): 2.41-2.56 (m, 6H), 3.23 (s, 3H), 3.25-3.40 (m, 2H), 3.44 (t, J=5.9 Hz, 2H), 3.48-3.56 (m, 2H), 4.51 (s, 2H), 7.17 (m, 1H), 7.34 (s, 1H), 7.53 (d, J=8.4 Hz, 1H), 7.64 (s, 1H), 7.75 (d, J=8.0 Hz, 1H), 8.22 (d, J=8.0 Hz, 1H), 9.55 (s, 1H), 13.89 (s, 1H).

EXAMPLE 115

4-Chloro-7-{1H-5-[4-(2-cyanoethyl)piperazin-1-ylcarbonyl]indol-2-yl}isoindolinone (Compound 115)

In a similar manner to Step 1 of Example 20, Compound 19 (31.8 mg, 0.0973 mmol) was dissolved in DMF (1 mL), and the solution was treated with EDCI (39.4 mg, 0.206 mmol), HOBT monohydrate (17.6 mg, 0.115 mmol) and 1-(2-cyanoethyl)piperazine (64.0 mg, 0.460 mmol). The mixture was added with water. The precipitated solid was collected by filtration and washed with water, followed by drying under reduced pressure to obtain Compound 115 (38.7 mg, yield 89%).

ESI-MS m/z: 448 [M+H]$^+$; $^1$H-NMR (DMSO-d$_6$) δ(ppm): 2.43-2.56 (m, 4H), 2.58-2.73 (m, 4H), 3.50-3.59 (m, 4H), 4.51 (s, 2H), 7.18 (m, 1H), 7.34 (s, 1H), 7.53 (d, J=8.4 Hz, 1H), 7.65 (s, 1H), 7.75 (d, J=8.4 Hz, 1H), 8.22 (d, J=8.4 Hz, 1H), 9.55 (s, 1H), 13.90 (s, 1H).

EXAMPLE 116

4-Chloro-7-{1H-5-[N-(2-dimethylaminoethyl)-N-methylaminocarbonyl]indol-2-yl}isoindolinone (Compound 116)

In a similar manner to Step 1 of Example 20, Compound 19 (30.9 mg, 0.0946 mmol) was dissolved in DMF (1 mL), and the solution was treated with EDCI (39.7 mg, 0.207 mmol), HOBT monohydrate (18.4 mg, 0.120 mmol) and N,N,N'-trimethylethylenediamine (0.050 mL, 0.39 mmol). The mixture was added with water. The precipitated solid was collected by filtration and washed with water, followed by drying under reduced pressure to obtain Compound 116 (30.2 mg, yield 78%).

APCI-MS m/z: 411 [M+H]$^+$; $^1$H-NMR (DMSO-d$_6$) δ(ppm): 2.38-2.45 (m, 2H), 2.50 (s, 6H), 2.98 (s, 3H), 3.35-3.55 (m, 2H), 4.51 (s, 2H), 7.16 (dd, J=1.7, 8.6 Hz, 1H), 7.33 (s, 1H), 7.52 (d, J=8.6 Hz, 1H), 7.63 (s, 1H), 7.75 (d, J=8.4 Hz, 1H), 8.22 (d, J=8.4 Hz, 1H), 9.55 (s, 1H), 13.87 (s, 1H).

EXAMPLE 117

4-Chloro-7-{1H-5-[N-(2,3-dihydroxypropyl)-N-methylaminocarbonyl]indol-2-yl}isoindolinone (Compound 117)

In a similar manner to Step 1 of Example 20, Compound 19 (31.5 mg, 0.0964 mmol) was dissolved in DMF (1 mL), and the solution was treated with EDCI (38.9 mg, 0.203 mmol), HOBT monohydrate (18.4 mg, 0.120 mmol) and 3-methylamino-1,2-propanediol (44.0 mg, 0.418 mmol). The mixture was added with water. The precipitated solid was collected by filtration, washed with water and dried under reduced pressure. The solid was suspended in methanol, collected by filtration and washed with methanol, followed by drying under reduced pressure to obtain Compound 117 (18.2 mg, yield 46%).

APCI-MS m/z: 414 [M+H]$^+$; $^1$H-NMR (DMSO-d$_6$) δ(ppm): 3.04 (s, 3H), 3.20-3.45 (m, 5H), 4.51 (s, 2H), 4.55 (m, 1H), 4.88 (d, J=5.3 Hz, 1H), 7.21 (d, J=8.6 Hz, 1H), 7.32 (s, 1H), 7.51 (m, 1H), 7.67 (s, 1H), 7.75 (d, J=8.6 Hz, 1H), 8.22 (d, J=8.6 Hz, 1H), 9.55 (s, 1H), 13.86 (s, 1H).

EXAMPLE 118

4-Chloro-7-[1H-5-(phenylaminocarbonyl)indol-2-yl]isoindolinone (Compound 118)

In a similar manner to Step 1 of Example 20, Compound 19 (31.2 mg, 0.0955 mmol) was dissolved in DMF (1 mL), and the solution was treated with EDCI (42.1 mg, 0.220 mmol), HOBT monohydrate (15.3 mg, 0.100 mmol) and aniline (0.035 mL, 0.40 mmol). The mixture was added with water. The precipitated solid was collected by filtration and washed with water, followed by drying under reduced pressure to obtain Compound 118 (35.7 mg, yield 93%).

APCI-MS m/z: 402 [M+H]$^+$; $^1$H-NMR (DMSO-d$_6$) δ(ppm): 4.53 (s, 2H), 7.08 (m, 1H), 7.30-7.39 (m, 2H), 7.45 (m, 1H), 7.60 (d, J=8.6 Hz, 1H), 7.75-7.85 (m, 4H), 8.28 (d, J=8.6 Hz, 1H), 8.31 (m, 1H), 9.58 (s, 1H), 10.16 (s, 1H), 14.00 (5, 1H).

EXAMPLE 119

4-Chloro-7-{1H-5-[4-(acetylamino)phenylaminocarbonyl]indol-2-yl}isoindolinone (Compound 119)

In a similar manner to Step 1 of Example 20, Compound 19 (31.3 mg, 0.0958 mmol) was dissolved in DMF (1 mL), and the solution was treated with EDCI (39.7 mg, 0.207 mmol), HOBT monohydrate (16.0 mg, 0.104 mmol) and 4'-aminoacetanilide (59.3 mg, 0.395 mmol). The mixture was added with water. The precipitated solid was collected by filtration and washed with water, followed by drying under reduced pressure to obtain Compound 119 (40.5 mg, yield 92%).

APCI-MS m/z: 459 [M+H]$^+$; $^1$H-NMR (DMSO-d$_6$) δ(ppm): 2.04 (s, 3H), 4.52 (s, 2H), 7.44 (m, 1H), 7.50-7.63 (m, 3H), 7.68-7.82 (m, 4H), 8.26 (m, 1H), 8.29 (s, 1H), 9.58 (s, 1H), 9.88 (s, 1H), 10.11 (s, 1H), 14.00 (s, 1H).

EXAMPLE 120

4-Chloro-7-{1H-5-[4-(hydroxymethyl)phenylaminocarbonyl]indol-2-yl}isoindolinone (Compound 120)

In a similar manner to Step 1 of Example 20, Compound 19 (30.6 mg, 0.0937 mmol) was dissolved in DMF (1 mL), and the solution was treated with EDCI (39.2 mg, 0.204 mmol), HOBT monohydrate (17.4 mg, 0.114 mmol) and 4-aminobenzyl alcohol (51.8 mg, 0.421 mmol). The mixture was added with water. The precipitated solid was collected by filtration and washed with water, followed by drying under reduced pressure to obtain Compound 120 (37.4 mg, yield 92%).

APCI-MS m/z: 432 [M+H]$^+$; $^1$H-NMR (DMSO-d$_6$) δ(ppm): 4.46 (d, J=5.4 Hz, 2H), 4.51 (s, 2H), 5.09 (t, J=5.4 Hz, 1H), 7.25-7.30 (m, 2H), 7.43 (s, 1H), 7.59 (d, J=8.6 Hz, 1H), 7.73-7.81 (m, 4H), 8.27 (d, J=8.6 Hz, 1H), 8.30 (m, 1H), 9.57 (s, 1H), 10.13 (s, 1H), 13.98 (s, 1H).

EXAMPLE 121

4-Chloro-7-{1H-5-[4-(2-hydroxyethyl)phenylaminocarbonyl]indol-2-yl}isoindolinone (Compound 121)

In a similar manner to Step 1 of Example 20, Compound 19 (313 mg, 0.0958 mmol) was dissolved in DMF (1 mL), and the solution was treated with EDCI (39.4 mg, 0.206 mmol), HOBT monohydrate (16.9 mg, 0.110 mmol) and 4-aminophenethyl alcohol (57.3 mg, 0.418 mmol). The mixture was added with water. The precipitated solid was collected by filtration and washed with water, followed by drying under reduced pressure to obtain Compound 121 (40.0 mg, yield 94%).

APCI-MS m/z: 446 [M+H]$^+$; $^1$H-NMR (DMSO-d$_6$) δ(ppm): 2.66-2.74 (m, 2H), 3.55-3.61 (m, 2H), 4.51 (s, 2H), 4.61 (m, 1H), 7.14-7.20 (m, 2H), 7.43 (s, 1H), 7.58 (d, J=8.6 Hz, 1H), 7.66-7.80 (m, 4H), 8.27 (d, J=8.2 Hz, 1H), 8.28 (s, 1H), 9.57 (s, 1H), 10.08 (s, 1H), 13.98 (s, 1H).

EXAMPLE 122

4-Chloro-7-[1H-5-(3,5-dimethoxyphenylaminocarbonyl)indol-2-yl]isoindolinone (Compound 122)

In a similar manner to Step 1 of Example 20, Compound 19 (31.7 mg, 0.0970 mmol) was dissolved in DMF (1 mL), and the solution was treated with EDCI (39.5 mg, 0.206 mmol), HOBT monohydrate (18.9 mg, 0.123 mmol) and 3,5-dimethoxyaniline (64.9 mg, 0.424 mmol). The mixture was added with water. The precipitated solid was collected by filtration and washed with water, followed by drying under reduced pressure to obtain Compound 121 (42.4 mg, yield 95%).

APCI-MS m/z: 462 [M+H]$^+$; $^1$H-NMR (DMSO-d$_6$) δ(ppm): 3.74 (s, 6H), 4.51 (s, 2H), 6.24 (t, J=2.1 Hz, 1H), 7.14 (d, J=2.1 Hz, 2H), 7.43 (s, 1H), 7.59 (d, J=8.6 Hz, 1H), 7.76 (d, J=8.4 Hz, 1H), 7.77 (d, J=8.6 Hz, 1H), 8.27 (d, J=8.4 Hz, 1H), 8.28 (s, 1H), 9.57 (s, 1H), 10.08 (s, 1H), 14.00 (s, 1H).

EXAMPLE 123

4-Chloro-7-{1H-5-[1-(1,1-dimethylethoxycarbonyl)piperidin-4-ylaminocarbonyl]indol-2-yl}isoindolinone (Compound 123)

In a similar manner to Step 1 of Example 20, Compound 19 (30.4 mg, 0.0930 mmol) was dissolved in DMF (1 mL), and the solution was treated with EDCI (41.2 mg, 0.215 mmol), HOBT monohydrate (18.2 mg, 0.119 mmol) and 4-amino-1-(tert-butoxycarbonyl)piperidine (85.9 mg, 0.429 mmol). The mixture was added with water. The precipitated solid was collected by filtration and washed with water, followed by drying under reduced pressure to obtain Compound 123 (45.2 mg, yield 95%).

APCI-MS m/z: 509 [M+H]$^+$; $^1$H-NMR (DMSO-d$_6$) δ(ppm): 1.30-1.40 (m, 2H), 1.41 (s, 9H), 1.75-1.84 (m, 2H), 2.71-2.90 (m, 2H), 3.90-4.03 (m, 3H), 4.50 (s, 2H), 7.37 (s, 1H), 7.51 (d, J=8.4 Hz, 1H), 7.67 (d, J=8.4 Hz, 1H), 7.74 (d, J=8.7 Hz, 1H), 8.15 (s, 1H), 8.17 (m, 1H), 8.24 (d, J=8.7 Hz, 1H), 9.56 (s, 1H), 13.91 (s, 1H).

EXAMPLE 124

4-Chloro-7-[1H-5-(2-hydroxypropylaminomethyl)indol-2-yl]isoindolinone (Compound 124)

Step 1

In a similar manner to Step 1 of Example 56, 4-chloro-7-[1-(tert-butoxycarbonyl)-5-formylindol-2-yl]isoindolinone (20.0 mg, 0.0487 mmol) was dissolved in dichloromethane (0.5 mL). The solution was treated with 1-amino-2-propanol (0.015 mL, 0.19 mmol) and sodium triacetoxyborohydride (32 mg, 0.15 mmol) to obtain 4-chloro-7-[1-(tert-butoxycarbonyl)-5-(2-hydroxypropylaminomethyl)indol-2-yl]isoindolinone.

Step 2

In a similar manner to Step 2 of Example 56, 4-chloro-7-[1-(tert-butoxycarbonyl)-5-(2-hydroxypropylaminomethyl)indol-2-yl]isoindolinone was treated with 10% hydrogen chloride-methanol solution (0.5 mL) to obtain Compound 124 (6.32 mg, yield 34%, 2 steps).

ESI-MS m/z: 370 [M+H]$^+$.

EXAMPLE 125

4-Chloro-7-(1H-5-(phenylaminomethyl)indol-2-yl)isoindolinone hydrochloride (Compound 125)

Step 1

In a similar manner to Step 2 of Example 6, 4-chloro-7-[1-(tert-butoxycarbonyl)-5-formylindol-2-yl]isoindolinone (57.5 mg, 0.140 mmol) was dissolved in acetonitrile (3 mL), and the solution was treated with aniline (0.051 mL, 0.56 mmol), acetic acid (0.160 mL, 2.80 mmol) and sodium triacetoxyborohydride (89 mg, 0.42 mmol). The reaction mixture was added with 1 mol/L hydrochloric acid and extracted with ethyl acetate. The organic layer was washed with saturated aqueous sodium hydrogencarbonate solution and saturated brine, and dried over anhydrous sodium sulfate. The solvent was evaporated under reduced pressure to obtain 4-chloro-7-(1-(tert-butoxycarbonyl)-5-(phenylaminomethyl)indol-2-yl)isoindolinone (63.0 mg, yield 92%).

APCI-MS m/z: 488 [M+H]$^+$; $^1$H-NMR (CDCl$_3$) δ(ppm): 1.36 (s, 9H), 4.40 (s, 2H), 4.41 (s, 2H), 6.54 (s, 1H), 6.63-6.72 (m, 3H), 6.97 (br s, 1H), 7.13-7.22 (m, 2H), 7.34 (dd, J=1.5; 8.6 Hz, 1H), 7.42 (d, J=8.1 Hz, 1H), 7.54 (d, J=8.1 Hz, 1H), 7.55 (d, J=1.5 Hz, 1H), 8.18 (d, J=8.6 Hz, 1H).

Step 2

In a similar manner to Step 2 of Example 8, 4-chloro-7-(1-(tert-butoxycarbonyl)-5-(phenylaminomethyl)indol-2-yl)isoindolinone (63.0 mg, 0.129 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 125 (38.9 mg, yield 71%).

ESI-MS m/z: 386 [M–H]$^-$; $^1$H-NMR (DMSO-d$_6$) δ(ppm): 4.45 (s, 2H), 4.56 (s, 2H), 6.84-7.10 (m, 3H), 7.17-7.30 (m, 2H), 7.21 (d, J=8.4 Hz, 1H), 7.26 (s, 1H), 7.46 (d, J=8.4 Hz, 1H), 7.62 (s, 1H), 7.73 (d, J=8.6 Hz, 1H), 8.21 (d, J=8.6 Hz, 1H), 9.53 (s, 1H), 13.76 (s, 1H).

EXAMPLE 126

4-Chloro-7-{1H-5-[4-(2-hydroxyethyl)phenylaminomethyl]indol-2-yl}isoindolinone hydrochloride (Compound 126)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with 4-aminophenethyl alcohol (40 mg, 0.29 mmol), acetic acid (0.084 mL, 1.5 mmol) and sodium triacetoxyborohydride (46 mg, 0.22 mmol). The reaction mixture was added with 1 mol/L hydrochloric acid and extracted with ethyl acetate. The organic layer was washed with saturated aqueous sodium hydrogencarbonate solution and saturated brine, followed by drying over anhydrous sodium sulfate. The solvent was evaporated under reduced pressure to obtain Compound 4-chloro-7-{1-(tert-butoxycarbonyl)-5-[4-(2-hydroxyethyl)phenylaminomethyl]indol-2-yl}isoindolinone (38.8 mg, yield 100%).

APCI-MS m/z: 532 [M+H]$^+$; $^1$H-NMR (CDCl$_3$) δ(ppm): 1.35 (s, 9H), 2.75 (t, J=6.4 Hz, 2H), 3.78 (t, J=6.4 Hz, 2H), 4.39 (br s, 4H), 6.53 (s, 1H), 6.59-6.66 (m, 2H), 6.99-7.07 (m, 2H), 7.15 (br s, 1H), 7.33 (dd, J=1.5, 8.6 Hz, 1H), 7.41 (d, J=8.1 Hz, 1H), 7.537 (d, J=1.5 Hz, 1H), 7.544 (d, J=8.1 Hz, 1H), 8.18 (d, J=8.6 Hz, 1H).

Step 2

In a similar manner to Step 2 of Example 8, 4-chloro-7-{1-(tert-butoxycarbonyl)-5-[4-(2-hydroxyethyl)phenylaminomethyl]indol-2-yl}isoindolinone (38.8 mg, 0.0730 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 126 (24.7 mg, yield 72%).

ESI-MS m/z: 432 [M+H]$^+$; $^1$H-NMR (DMSO-d$_6$) δ(ppm): 2.66 (t, J=6.9 Hz, 2H), 3.55 (t, J=6.9 Hz, 2H), 4.48 (s, 2H), 4.51 (s, 2H), 7.01-7.27 (m, 4H), 7.23 (dd, J=1.6, 8.1 Hz, 1H), 7.28 (br s, 1H), 7.49 (d, J=8.1 Hz, 1H), 7.66 (s, 1H), 7.73 (d, J=8.5 Hz, 1H), 8.22 (d, J=8.5 Hz, 1H), 9.54 (s, 1H), 13.19 (s, 1H).

EXAMPLE 127

4-Chloro-7-[1H-5-(4-aminophenylaminomethyl)indol-2-yl]isoindolinone dihydrochloride (Compound 127)

Step 1

In a similar manner to Step 2 of Example 6, 4-chloro-7-[1-(tert-butoxycarbonyl)-5-formylindol-2-yl]isoindolinone (30.0 mg, 0.0730 mmol) was dissolved in acetonitrile (2 mL), and the solution was treated with 4'-aminoacetanilide (44 mg, 0.29 mmol), acetic acid (0.084 mL, 1.5 mmol) and sodium triacetoxyborohydride (46 mg, 0.22 mmol). The reaction mixture was added with 1 mol/L hydrochloric acid and extracted with ethyl acetate. The organic layer was washed with saturated aqueous sodium hydrogencarbonate solution and saturated brine, followed by drying over anhydrous sodium sulfate. The solvent was evaporated under reduced pressure to obtain 4-chloro-7-[1-(tert-butoxycarbonyl)-5-(4-aminophenylaminomethyl)indol-2-yl]isoindolinone (35.2 mg, yield 88%).

APCI-MS m/z: 545 [M+H]$^+$; $^1$H-NMR (DMSO-d$_6$) δ(ppm): 1.16 (s, 9H), 1.98 (s, 3H), 4.39 (s, 2H), 4.47 (br s, 2H), 6.66 (s, 1H), 6.82-7.07 (m, 2H), 7.33-7.51 (m, 2H), 7.36 (dd, J=1.3, 8.6 Hz, 1H), 7.48 (d, J=8.0 Hz, 1H), 7.61 (br s, 1H), 7.72 (d, J=8.0 Hz, 1H), 8.09 (d, J=8.6 Hz, 1H), 8.83 (s, 1H), 9.82 (br s, 1H).

Step 2

In a similar manner to Step 2 of Example 8, 4-chloro-7-[1-(tert-butoxycarbonyl)-5-(4-aminophenylaminomethyl)indol-2-yl]isoindolinone (35.2 mg, 0.0646 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 127 (29.7 mg, yield 97%).

ESI-MS m/z: 403 [M+H]$^+$; $^1$H-NMR (DMSO-d$_6$) δ(ppm): 4.36 (s, 2H), 4.50 (s, 2H), 6.69-6.80 (m, 2H), 6.94-7.06 (m, 2H), 7.16 (dd, J=1.3, 8.3 Hz, 1H), 7.24 (d, J=1.3 Hz, 1H), 7.44 (d, J=8.3 Hz, 1H), 7.56 (s, 1H), 7.72 (d, J=8.5 Hz, 1H), 8.20 (d, J=8.5 Hz, 1H), 9.53 (s, 1H), 13.71 (s, 1H).

EXAMPLE 128

4-Chloro-7-{1H-5-[2-(hydroxymethyl)phenylaminocarbonyl]indol-2-yl}isoindolinone (Compound 128)

In a similar manner to Step 1 of Example 20, Compound 19 (32.2 mg, 0.0986 mmol) was dissolved in DMF (1 mL), and the solution was treated with EDCI (39.5 mg, 0.206 mmol), HOBT monohydrate (18.5 mg, 0.121 mmol) and 2-aminobenzyl alcohol (52.2 mg, 0.424 mmol). The mixture was added with water. The precipitated solid was collected by filtration and washed with water and dried under reduced pressure. The solid was suspended in methanol, collected by filtration and then washed with methanol, followed by drying under reduced pressure. The solid was purified by preparative thin-layer chromatography (chloroform/methanol=9/1) to obtain Compound 128 (12.3 mg, yield 29%).

APCI-MS m/z: 432 [M+H]$^+$; $^1$H-NMR (DMSO-d$_6$) δ(ppm): 4.53 (s, 2H), 4.65 (d, J=5.3 Hz, 2H), 5.67 (t, J=5.3 Hz, 1H), 7.16 (m, 1H), 7.31 (m, 1H), 7.41 (m, 1H), 7.45 (s, 1H), 7.62 (d, J=8.9 Hz, 1H), 7.75 (d, J=8.7 Hz, 1H), 7.77 (d, J=8.7 Hz, 1H), 7.86 (d, J=7.9 Hz, 1H), 8.26 (s, 1H), 8.27 (d, J=7.9 Hz, 1H), 9.58 (s, 1H), 10.10 (s, 1H), 14.02 (s, 1H).

EXAMPLE 129

4-Chloro-7-[1H-5-(piperidin-4-ylaminocarbonyl)indol-2-yl]isoindolinone hydrochloride (Compound 129)

In a similar manner to Step 2 of Example 8, Compound 123 (30.1 mg, 0.0591 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 129 (21.0 mg, yield 74%).

ESI-MS m/z: 409 [M+H]$^+$; $^1$H-NMR (DMSO-d$_6$) δ(ppm): 1.74-1.87 (m, 2H), 1.94-2.05 (m, 2H), 2.99-3.10 (m, 2H), 3.28-3.42 (m, 2H), 4.09 (m, 1H), 4.52 (s, 2H), 7.38 (s, 1H), 7.53 (d, J=8.4 Hz, 1H), 7.71 (d, J=8.4 Hz, 1H), 7.76 (d, J=8.4 Hz, 1H), 8.19 (s, 1H), 8.25 (d, J=8.4 Hz, 1H), 8.38 (d, J=7.4 Hz, 1H), 8.61 (m, 1H), 8.72 (m, 1H), 9.57 (s, 1H), 13.94 (s, 1H).

EXAMPLE 130

4-Chloro-7-{1H-5-[4-(2-cyanoethyl)piperazin-1-ylmethyl]indol-2-yl}isoindolinone dihydrochloride (Compound 130)

Step 1

In a similar manner to Step 2 of Example 6, 4-chloro-7-[1-(tert-butoxycarbonyl)-5-formylindol-2-yl]isoindolinone (40.8 mg, 0.0993 mmol) was dissolved in acetonitrile (2 mL), and the solution was treated with 1-(2-cyanoethyl)piperazine (59.8 mg, 0.430 mmol), acetic acid (0.115 mL, 2.01 mmol) and sodium triacetoxyborohydride (74.3 mg, 0.351 mmol). The reaction mixture was added with water and sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-{1-(tert-butoxycarbonyl)-5-[4-(2-cyanoethyl)piperazin-1-ylmethyl]indol-2-yl}isoindolinone (53.0 mg, yield 100%).

ESI-MS m/z: 534 [M+H]$^+$; $^1$H-NMR (CDCl$_3$) δ(ppm): 1.37 (s, 9H), 2.47-2.58 (m, 10H), 2.70 (t, J=7.0 Hz, 2H), 3.59 (s, 2H), 4.42 (s, 2H), 6.42 (br s, 1H), 6.54 (s, 1H), 7.29 (dd, J=1.7, 8.6 Hz, 1H), 7.43 (d, J=8.1 Hz, 1H), 7.48 (m, 1H), 7.56 (d, J=8.1 Hz, 1H), 8.14 (d, J=8.6 Hz, 1H).

Step 2

In a similar manner to Step 2 of Example 8, 4-chloro-7-(1-(tert-butoxycarbonyl)-5-[4-(2-cyanoethyl)piperazin-1-ylmethyl]indol-2-yl)isoindolinone (53.0 mg, 0.0993 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure. The solid was suspended in methanol, collected by filtration and washed with methanol, followed by drying under reduced pressure to obtain Compound 130 (29.7 mg, yield 97%).

ESI-MS m/z: 434 [M+H]$^+$; $^1$H-NMR (DMSO-d$_6$) δ(ppm): 2.74-2.85 (m, 4H), 3.08-3.22 (m, 4H), 3.32-3.43 (m, 2H), 3.50-3.80 (m, 2H), 4.39 (br s, 2H), 4.52 (s, 2H), 7.31 (m, 1H), 7.35 (m, 1H), 7.58 (d, J=8.7 Hz, 1H), 7.76 (d, J=8.7 Hz, 1H), 7.79 (m, 1H), 8.25 (d, J=8.7 Hz, 1H), 9.56 (s, 1H), 13.89 (s, 1H).

EXAMPLE 131

4-Chloro-7-[1H-5-(piperidin-4-ylaminomethyl)indol-2-yl]isoindolinone dihydrochloride (Compound 131)

Step 1

In a similar manner to Step 2 of Example 6, 4-chloro-7-[1-(tert-butoxycarbonyl)-5-formylindol-2-yl]isoindolinone (34.5 mg, 0.0840 mmol) was dissolved in acetonitrile (1 mL), and the solution was treated with 4-amino-1-(tert-butoxycarbonyl)piperidine (70.1 mg, 0.350 mmol), acetic acid (0.100 mL, 1.74 mmol) and sodium triacetoxyborohydride (44.0 mg, 0.208 mmol). The reaction mixture was added with water and sodium carbonate to adjust the pH to 9. The mixture was extracted with ethyl acetate. The organic layer was washed with saturated brine and dried over anhydrous sodium sulfate. The solvent was evaporated under reduced pressure to obtain 4-chloro-7-[1-(tert-butoxycarbonyl)-5-(piperidin-4-ylaminomethyl)indol-2-yl]isoindolinone (80.8 mg).

Step 2

In a similar manner to Step 2 of Example 8, 4-chloro-7-[1-(tert-butoxycarbonyl)-5-(piperidin-4-ylaminomethyl)indol-2-yl]isoindolinone (79.3 mg) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure. The solid was suspended in methanol, collected by filtration and washed with methanol, followed by drying under reduced pressure to obtain Compound 131 (28.7 mg, yield 73%, 2 steps).

ESI-MS m/z: 393 [M−H]$^−$, 395 [M+H]$^+$; $^1$H-NMR (DMSO-d$_6$) δ(ppm): 1.84-2.00 (m, 2H), 2.23-2.34 (m, 2H), 2.85-2.99 (m, 2H), 3.25-3.45 (m, 2H), 4.22 (s, 2H), 4.51 (s, 2H), 7.32-7.39 (m, 1H), 7.34 (s, 1H), 7.56 (d, J=8.4 Hz, 1H), 7.75 (d, J=8.6 Hz, 1H), 7.81 (s, 1H), 8.25 (d, J=8.4 Hz, 1H), 8.40-9.50 (m, 4H), 9.56 (s, 1H), 13.87 (s, 1H).

EXAMPLE 132

4-Fluoro-7-[1H-5-(piperazin-1-ylcarbonyl)indol-2-yl]isoindolinone (Compound 132)

Step 1

In a similar manner to Step 1 of Example 16, 3-fluorobenzoyl chloride (2.00 g, 12.6 mmol) was dissolved in dichloromethane (40 mL), and the solution was treated with cumylamine (1.99 mL, 13.9 mmol), triethylamine (2.63 mL, 18.9 mmol) and DMAP (154 mg, 1.26 mmol). The mixture was purified by slurry using diisopropylether to obtain 3-fluoro-N-(1-methyl-1-phenylethyl)benzamide (3.09 g, yield 95%).

APCI-MS m/z: 258 [M+H]$^+$; $^1$H-NMR (CDCl$_3$) δ(ppm): 1.82 (s, 6H), 6.39 (s, 1H), 7.18 (m, 1H), 7.25 (m, 1H), 7.32-7.40 (m, 3H), 7.42-7.53 (m, 4H).

Step 2

In a similar manner to Step 2 of Example 16, 3-fluoro-N-(1-methyl-1-phenylethyl)benzamide (2.00 g, 7.77 mmol) was dissolved in THF (80 mL), and the solution was treated with TMEDA (3.8 mL, 24.9 mmol), sec-butyllithium-hexane solution (1.01 mol/L, 24.6 mL, 24.9 mmol) and DMF (1.30 mL, 17.1 mmol). The mixture was purified by slurry using diisopropylether to obtain 4-fluoro-3-hydroxy-2-(1-methyl-1-phenylethyl)isoindolinone (2.07 g, yield 93%).

APCI-MS m/z: 286 [M+H]$^+$; $^1$H-NMR (CDCl$_3$) δ(ppm): 1.93 (s, 3H), 1.97 (s, 3H), 2.73 (d, J=8.1 Hz, 1H), 6.32 (d, J=7.3 Hz, 1H), 7.18-7.26 (m, 2H), 7.30-7.35 (m, 2H), 7.41-7.49 (m, 4H).

Step 3

In a similar manner to Step 3 of Example 16, 4-fluoro-3-hydroxy-2-(1-methyl-1-phenylethyl)isoindolinone (2.06 g, 7.22 mmol) was dissolved in THF (80 mL), and the solution was treated with TMEDA (2.40 mL, 15.9 mmol), sec-butyllithium-hexane solution (0.99 mol/L, 16.0 mL, 15.9 mmol) and iodine (2.20 g, 8.66 mmol), followed by purification by flash column chromatography (chloroform/methanol=100/0, 85/15) to obtain 4-fluoro-3-hydroxy-7-iodo-2-(1-methyl-1-phenylethyl)isoindolinone (1.19 g, yield 40%) and 1-(1-methyl-1-phenylethyl)-3-fluoro-6-iodophtalimide (425 mg, yield 14%).

APCI-MS m/z: 412 [M+H]$^+$; $^1$H-NMR (CDCl$_3$) δ(ppm): 1.96 (s, 3H), 2.00 (s, 3H), 2.02 (d, J=8.7 Hz, 1H), 6.15 (d, J=8.7 Hz, 1H), 6.98 (dd, J=8.4, 8.4 Hz, 1H), 7.26 (m, 1H), 7.35 (m, 2H), 7.45 (m, 2H), 7.88 (dd, J=4.4, 8.7 Hz, 1H).

Step 4

In a similar manner to Step 4 of Example 16, 4-fluoro-3-hydroxy-7-iodo-2-(1-methyl-1-phenylethyl)isoindolinone (1.17 g, 2.86 mmol) was dissolved in nitromethane (46 mL), and the solution was treated with trifluoroacetic acid (2.20 mL, 28.6 mmol) and triethylsilane (0.914 mL, 5.72 mmol), followed by purification by flash column chromatography (chloroform/methanol=100/0, 85/15) to obtain 4-fluoro-7-iodoisoindolinone (586 mg, yield 74%).

APCI-MS m/z: 276 [M−H]⁻; ¹H-NMR (DMSO-d₆) δ(ppm): 4.23 (s, 2H), 7.12 (dd, J=8.6, 8.7 Hz, 1H), 7.79 (dd, J=4.7, 8.5 Hz, 1H), 8.80 (s, 1H).

Step 5

In a similar manner to Step 2 of Example 1, 4-fluoro-7-iodoisoindolinone (80.0 mg, 0.289 mmol) was dissolved in acetonitrile (5.6 mL), and the solution was treated with Compound BB (274 mg, 0.578 mmol), palladium acetate (5.2 mg, 0.023 mmol), tri(o-tolyl)phosphine (14 mg, 0.046 mmol) and triethylamine (0.403 mL, 2.89 mmol), followed by purification by preparative thin-layer chromatography (chloroform/acetonitrile=4/1, ethyl acetate/methanol=100/1, chloroform/methanol=15/1) to obtain 4-fluoro-7-{1-(tert-butoxycarbonyl)-5-[4-(tert-butoxycarbonyl)piperazin-1-ylcarbonyl]indol-2-yl}isoindolinone (85.8 mg, yield 51%).

ESI-MS m/z: 579 [M+H]⁺; ¹H-NMR (CDCl₃) δ(ppm): 1.36 (s, 9H), 1.48 (s, 9H), 3.48 (br s, 4H), 3.63 (br s, 4H), 4.50 (s, 2H), 6.58 (s, 1H), 6.65 (s, 1H), 7.31 (d, J=8.4 Hz, 1H), 7.37 (dd, J=1.7, 8.6 Hz, 1H), 7.47 (dd, J=4.5, 8.3 Hz, 1H), 7.64 (d, J=1.0 Hz, 1H), 8.26 (d, J=8.6 Hz, 1H).

Step 6

In a similar manner to Step 3 of Example 1, 4-fluoro-7-{1-(tert-butoxycarbonyl)-5-[4-(tert-butoxycarbonyl)piperazin-1-ylcarbonyl]indol-2-yl}isoindolinone (85.0 mg, 0.147 mmol) was dissolved in methanol (3.4 mL), and the solution was treated with 10% hydrogen chloride-methanol solution (3.4 mL), followed by purification by preparative thin-layer chromatography (chloroform/methanol=5/1) to obtain Compound 132 (27.9 mg, yield 50%).

APCI-MS m/z: 379 [M+H]⁺; ¹H-NMR (DMSO-d₆) δ(ppm): 2.69 (br s, 4H), 3.44 (br s, 4H), 4.58 (s, 2H), 7.14 (d, J=8.2 Hz, 1H), 7.24 (s, 1H), 7.48-7.60 (m, 3H), 8.22 (dd, J=4.9, 8.8 Hz, 1H), 9.49 (s, 1H), 13.78+(s, 1H).

EXAMPLE 133

4-Methoxy-7-[1H-5-(piperazin-1-ylcarbonyl)indol-2-yl]isoindolinone hydrochloride (Compound 133)

Step 1

In a similar manner to Step 1 of Example 16, 3-methoxybenzoylchloride (8.00 g, 46.9 mmol) was dissolved in dichloromethane (160 mL), and the solution was treated with cumylamine (7.40 mL, 51.6 mmol), triethylamine (9.80 mL, 70.4 mmol) and DMAP (573 mg, 4.69 mmol), followed by purification by slurry using diisopropylether to obtain 3-methoxy-N-(1-methyl-1-phenylethyl)benzamide (12.4 g, yield 98%).

APCI-MS m/z: 270 [M+H]⁺; ¹H-NMR (CDCl₃) δ(ppm): 1.82 (s, 18H), 3.83 (s, 3H), 6.41 (s, 2H), 7.01-7.04 (m, 1H), 7.22-7.38 (m, 6H), 7.44-7.47 (m, 2H).

Step 2

In a similar manner to Step 2 of Example 16, 3-methoxy-N-(1-methyl-1-phenylethyl)benzamide (6.00 g, 22.3 mmol) was dissolved in THF (240 mL), and the solution was treated with TMEDA (10.8 mL, 71.3 mmol), sec-butyllithium-hexane solution (0.99 mol/L, 72.0 mL, 71.3 mmol) and DMF (3.80 mL, 49.0 mmol), followed by purification by flash column chromatography (hexane/ethyl acetate=2/1, 1/1) to obtain 4-methoxy-3-hydroxy-2-(1-methyl-1-phenylethyl)isoindolinone (4.36 g, yield 66%) and 6-methoxy-3-hydroxy-2-(1-methyl-1-phenylethyl)isoindolinone (1.12 g, yield 17%).

4-methoxy-3-hydroxy-2-(1-methyl-1-phenylethyl)isoindolinone

APCI-MS m/z: 298 [M+H]⁺; ¹H-NMR (CDCl₃) d (ppm): 1.92 (s, 3H), 1.98 (s, 3H), 2.49 (d, J=7.3 Hz, 1H), 3.94 (s, 3H), 6.29 (d, J=7.7 Hz, 1H), 7.03 (d, J=8.1 Hz, 1H), 7.19-7.34 (m, 4H), 7.41-7.47 (m, 3H), 6-methoxy-3-hydroxy-2-(1-methyl-1-phenylethyl)isoindolinone APCI-MS m/z: 298 [M+H]⁺; ¹H-NMR (CDCl₃) δ(ppm): 1.90 (s, 3H), 1.94 (s, 3H), 2.84 (d, J=10.6 Hz, 1H), 3.78 (s, 3H), 6.08 (d, J=10.6 Hz, 1H), 7.05 (dd, J=2.4, 8.3 Hz, 1H), 7.09 (d, J=2.2 Hz, 1H), 7.18-7.33 (m, 3H), 7.38-7.41 (m, 3H).

Step 3

In a similar manner to Step 3 of Example 16, 4-methoxy-3-hydroxy-2-(1-methyl-1-phenylethyl)isoindolinone (3.55 g, 11.9 mmol) was dissolved in THF (140 mL), and the solution was treated with TMEDA (4.00 mL, 26.2 mmol), sec-butyllithium-hexane solution (0.99 mol/L, 26.4 mL, 26.2 mmol) and iodine (3.62 g, 14.3 mmol), followed by purification by flash column chromatography (hexane/ethyl acetate=9/1, 7/3) to obtain 4-methoxy-3-hydroxy-7-iodo-2-(1-methyl-1-phenylethyl)isoindolinone (3.88 g, yield 77%).

APCI-MS m/z: 422 [M−H]⁻; ¹H-NMR (CDCl₃) δ(ppm) 1.94 (s, 3H), 1.98 (s, 3H), 2.43 (d, J=7.0 Hz, 1H), 3.92 (s, 3H), 6.12 (d, J=7.0 Hz, 1H), 6.80 (d, J=8.6 Hz, 1H), 7.23 (m, 1H), 7.32 (m, 2H), 7.43 (m, 2H), 7.83 (d, J=8.6 Hz, 1H).

Step 4

In a similar manner to Step 4 of Example 16, 4-methoxy-3-hydroxy-7-iodo-2-(1-methyl-1-phenylethyl)isoindolinone (2.50 g, 5.91 mmol) was dissolved in nitromethane (100 mL), and the solution was treated with trifluoroacetic acid (4.50 mL, 59.1 mmol) and triethylsilane (1.90 mL, 11.8 mmol). The obtained solid was collected by filtration and washed with ethyl acetate. The obtained solid was dried under reduced pressure to obtain 4-methoxy-7-iodoisoindolinone (1.32 g, yield 78%).

APCI-MS m/z: 290 [M+H]⁺; ¹H-NMR (DMSO-d₆) δ(ppm): 3.85 (s, 3H), 4.16 (s, 2H), 6.99 (d, J=8.4 Hz, 1H), 7.81 (d, J=8.4 Hz, 1H), 8.72 (s, 1H).

Step 5

In a similar manner to Step 2 of Example 1, 4-methoxy-7-iodoisoindolinone (80.0 mg, 0.277 mmol) was dissolved in acetonitrile (5.6 mL), and the solution was treated with Compound BB (262 mg, 0.554 mmol), palladium acetate (5.0 mg, 0.022 mmol), tri(o-tolyl)phosphine (14 mg, 0.044 mmol) and triethylamine (0.386 mL, 2.77 mmol), followed by purification by preparative thin-layer chromatography (chloroform/acetonitrile=4/1, hexane/ethyl acetate=1/1) to obtain 4-methoxy-7-{1-(tert-butoxycarbonyl)-5-[4-(tert-butoxycarbonyl)piperazin-1-ylcarbonyl]indol-2-yl}isoindolinone (91.3 mg, yield 56%).

ESI-MS m/z: 591 [M+H]⁺; ¹H-NMR (CDCl₃) δ(ppm): 1.34 (s, 9H), 1.48 (s, 9H), 3.47 (br s, 4H), 3.50 (br s, 4H), 3.95 (s, 3H), 4.37 (s, 2H), 6.55 (s, 1H), 6.72 (s, 1H), 7.04 (d, J=8.4 Hz, 1H), 7.34 (dd, J=1.6, 8.7 Hz, 1H), 7.43 (d, J=8.2 Hz, 1H), 7.62 (s, 1H), 8.25 (d, J=8.7 Hz, 1H).

Step 6

In a similar manner to Step 2 of Example 8, 4-methoxy-7-(1-(tert-butoxycarbonyl)-5-[4-(tert-butoxycarbonyl)piperazin-1-ylcarbonyl]indol-2-yl)isoindolinone (80.9 mg, 0.137 mmol) was dissolved in methanol (2.0 mL), and the solution was treated with 10% hydrochloric acid-methanol solution (2.0 mL). The obtained solid was collected by filtration and washed with methanol, followed by drying under reduced pressure to obtain Compound 133 (48.8 mg, yield 83%).

mp >295° C.; APCI-MS m/z: 391 [M+H]⁺; ¹H-NMR (DMSO-d₆) δ(ppm): 3.16 (br s, 4H), 3.75 (br s, 4H), 3.94 (s, 3H), 4.40 (s, 2H), 7.16 (s, 1H), 7.19 (dd, J=1.6, 8.3 Hz, 1H), 7.34 (d, J=8.9 Hz, 1H), 7.50 (d, J=8.4 Hz, 1H), 7.68 (s, 1H) 8.17 (d, J=8.7 Hz, 1H), 9.15 (br s, 2H), 9.34 (s, 1H), 13.86 (s, 1H).

EXAMPLE 134

4-Fluoro-7-[1H-5-(piperazin-1-ylmethyl)indol-2-yl]isoindolinone dihydrochloride (Compound 134)

Step 1

In a similar manner to Step 2 of Example 1, 4-fluoro-7-iodoisoindolinone (80.0 mg, 0.289 mmol) was dissolved in acetonitrile (5.6 mL), and the solution was treated with Compound BC (265 mg, 0.578 mmol), palladium acetate (5.2 mg, 0.023 mmol), tri(o-tolyl)phosphine (14 mg, 0.046 mmol) and triethylamine (0.403 mL, 2.89 mmol), followed by purification by preparative thin-layer chromatography (chloroform/methanol=15/1, chloroform/acetone=5/1) to obtain 4-fluoro-7-{1-(tert-butoxycarbonyl)-5-[4-(tert-butoxycarbonyl)piperazin-1-ylmethyl]indol-2-yl}isoindolinone (131 mg, yield 80%).

APCI-MS m/z: 565 [M+H]⁺; ¹H-NMR (CDCl₃) δ(ppm): 1.35 (s, 9H), 1.46 (s, 9H), 2.42 (br s, 4H), 3.43 (br s, 4H), 3.61 (s, 2H), 4.47 (s, 2H), 6.53 (s, 1H), 7.04 (s, 1H), 7.23-7.31 (m, 2H), 7.44 (dd, J=4.5, 8.3 Hz, 1H), 7.49 (br s, 1H), 8.17 (d, J=8.6 Hz, 1H).

Step 2

In a similar manner to Step 2 of Example 8, 4-fluoro-7-{1-(tert-butoxycarbonyl)-5-[4-(tert-butoxycarbonyl)piperazin-1-ylmethyl]indol-2-yl}isoindolinone (122 mg, 0.217 mmol) was dissolved in methanol (3.7 mL), and the solution was treated with 10% hydrogen chloride-methanol solution (3.7 mL). The obtained solid was collected by filtration and washed with methanol, followed by drying under reduced pressure to obtain Compound 134 (77.0 mg, yield 81%).

mp >295° C.; APCI-MS m/z: 365 [M+H]⁺; ¹H-NMR (DMSO-d₆) δ(ppm): 3.44 (br s, 8H), 4.44 (br s, 2H), 4.58 (s, 2H), 7.26 (s, 1H), 7.34 (d, J=8.4 Hz, 1H), 7.53-7.59 (m, 2H), 7.82 (s, 1H), 8.25 (dd, J=4.7, 8.8 Hz, 1H), 9.50 (br s, 3H), 11.73 (br s, 1H), 13.78 (s, 1H).

EXAMPLE 135

4-Methoxy-7-[1H-5-(piperazin-1-ylmethyl)indol-2-yl]isoindolinone dihydrochloride (Compound 135)

Step 1

In a similar manner to Step 2 of Example 1, 4-methoxy-7-iodoisoindolinone (80.0 mg, 0.277 mmol) was dissolved in acetonitrile (5.6 mL), and the solution was treated with Compound BC (254 mg, 0.554 mmol), palladium acetate (5.0 mg, 0.022 mmol), tri(o-tolyl)phosphine (14 mg, 0.044 mmol) and triethylamine (0.386 mL, 2.77 mmol), followed by purification by preparative thin-layer chromatography (chloroform/methanol=30/1, chloroform/acetone=5/1) to obtain 4-methoxy-7-(1-(tert-butoxycarbonyl)-5-[(4-(tert-butoxycarbonyl)piperazin-1-ylmethyl]indol-2-yl)isoindolinone (98.6 mg, yield 62%).

ESI-MS m/z: 577 [M+H]⁺; ¹H-NMR (CDCl₃) δ(ppm): 1.36 (s, 9H), 1.46 (s, 9H), 2.41 (br s, 4H), 3.43 (br s, 4H), 3.60 (s, 2H), 4.37 (s, 2H), 6.21 (br s, 1H), 6.50 (d, J=0.7 Hz, 1H), 7.04 (d, J=8.2 Hz, 1H), 7.26 (dd, J=1.5, 8.6 Hz, 1H), 7.42 (d, J=8.2 Hz, 1H), 7.47 (s, 1H), 8.15 (d, J=8.6 Hz, 1H).

Step 2

In a similar manner to Step 2 of Example 8, 4-methoxy-7-{1-(tert-butoxycarbonyl)-5-[4-(tert-butoxycarbonyl)piperazin-1-ylmethyl]indol-2-yl}isoindolinone (90.6 mg, 0.157 mmol) was dissolved in methanol (2.7 mL), and the solution was treated with 10% hydrogen chloride-methanol solution (2.7 mL). The obtained solid was collected by filtration and washed with methanol, followed by drying under reduced pressure to obtain Compound 135 (56.0 mg, yield 79%).

mp >295° C.: APCI-MS m/z: 377 [M+H]⁺; ¹H-NMR (DMSO-d₆) δ(ppm): 3.34 (br s, 8H), 3.93 (s, 3H), 4.40 (br s, 4H), 7.14 (s, 1H), 7.31 (m, 2H), 7.51 (d, J=8.4 Hz, 1H), 7.78 (s, 1H), 8.19 (d, J=8.9 Hz, 1H), 9.33 (s, 1H), 9.52 (br s, 2H), 11.70 (br s, 1H), 13.82 (s, 1H).

EXAMPLE 136

4-Methoxy-7-[1H-5-(piperidinomethyl)indol-2-yl]isoindolinone hydrochloride (Compound 136)

Step 1

In a similar manner to Step 2 of Example 1, 4-methoxy-7-iodoisoindolinone (80.0 mg, 0.277 mmol) was dissolved in acetonitrile (5.6 mL), and the solution was treated with Compound BD (198 mg, 0.554 mmol), palladium acetate (5.0 mg, 0.022 mmol), tri(o-tolyl)phosphine (14 mg, 0.044 mmol) and triethylamine (0.386 mL, 2.77 mmol), followed by purification by preparative thin-layer chromatography (chloroform/methanol=12/1) to obtain 4-methoxy-7-[1-(tert-butoxycarbonyl)-5-(piperidinomethyl)indol-2-yl]isoindolinone (119 mg, yield 90%).

APCI-MS m/z: 476 [M+H]⁺; ¹H-NMR (CDCl₃) δ(ppm): 1.36 (s, 9H), 1.44 (br s, 2H), 1.59 (br s, 4H), 2.42 (br s, 4H), 3.60 (s, 2H), 3.94 (s, 3H), 4.37 (s, 2H), 6.50 (s, 1H), 6.73 (br s, 1H), 7.03 (d, J=8.3 Hz, 1H), 7.27 (d, J=8.3 Hz, 1H), 7.42 (d, J=8.3 Hz, 1H), 7.48 (s, 1H), 8.15 (d, J=8.6 Hz, 1H).

Step 2

In a similar manner to Step 2 of Example 8, 4-methoxy-7-[1-(tert-butoxycarbonyl)-5-(piperidinomethyl)indol-2-yl]isoindolinone (110 mg, 0.232 mmol) was dissolved in methanol (3.3 mL), and the solution was treated with 10% hydrogen chloride-methanol solution (3.3 mL). The obtained solid was collected by filtration and washed with methanol, followed by drying under reduced pressure to obtain Compound 136 (57.5 mg, yield-60%).

mp >295° C.; APCI-MS m/z: 376 [M+H]⁺; ¹H-NMR (DMSO-d₆) δ(ppm): 1.35-1.77 (m, 6H), 2.82-3.15 (m, 2H), 3.32 (br s, 2H), 3.93 (s, 3H), 4.29 (br s, 2H), 4.40 (s, 2H), 7.15 (s, 1H), 7.24 (d, J=8.3 Hz, 1H), 7.33 (d, J=8.6 Hz, 1H), 7.51 (d, J=8.3 Hz, 1H), 7.72 (s, 1H), 8.18 (d, J=8.6 Hz, 1H), 9.34 (s, 1H), 9.86 (br s, 1H), 13.81 (s, 1H).

EXAMPLE 137

4-Phenoxy-7-[1H-5-(piperazin-1-ylcarbonyl)indol-2-yl]isoindolinone (Compound 137)

Step 1

3-Phenoxybenzoic acid (3.00 g, 14.0 mmol) was dissolved in DMF (45 mL), and the solution was added with EDCI (4.03 g, 21.0 mmol) and HOBT monohydrate (1.07 g, 7.00 mmol) under ice-cooling, followed by stirring at the same temperature for 5 minutes. Then, the mixture was added with cumylamine (4.03 mL, 28.0 mmol) and stirred at room temperature for 2 hours. The reaction mixture was added with water and extracted with ethyl acetate. The organic layer was washed with saturated brine and dried over anhydrous sodium sulfate. The solvent was evaporated under reduced pressure. The residue was purified by slurry using hexane to obtain 3-phenoxy-N-(1-methyl-1-phenylethyl)benzamide (4.51 g, yield 97%).

APCI-MS m/z: 332 [M+H]$^+$; $^1$H-NMR (CDCl$_3$) δ(ppm): 1.81 (m, 6H), 6.36 (s, 1H), 7.01 (m, 2H), 7.12 (m, 2H), 7.21-7.46 (m, 10H).

Step 2

In a similar manner to Step 2 of Example 16, 3-phenoxy-N-(1-methyl-1-phenylethyl)benzamide (4.00 g, 12.1 mmol) was dissolved in THF (160 mL), and the solution was treated with TMEDA (5.80 mL, 38.7 mmol), sec-butyllithium-hexane solution (0.99 mol/L, 39.0 mL, 38.7 mmol) and DMF (2.10 mL, 26.6 mmol), followed by purification by slurry using diisopropylether to obtain 4-phenoxy-3-hydroxy-2-(1-methyl-1-phenylethyl)isoindolinone (3.92 g, yield 90%).

APCI-MS m/z: 360 [M+H]$^+$; $^1$H-NMR (CDCl$_3$) δ(ppm): 1.93 (s, 3H), 1.97 (s, 3H), 2.55 (d, J=7.6 Hz, 1H), 6.31 (d, J=7.6 Hz, 1H), 6.94-7.47 (m, 13H).

Step 3

In a similar manner to Step 3 of Example 16, 4-phenoxy-3-hydroxy-2-(1-methyl-1-phenylethyl)isoindolinone (700 mg, 1.95 mmol) was dissolved in THF (28 mL), and the solution was treated with TMEDA (0.94 mL, 6.2 mmol), sec-butyllithium-hexane solution (1.01 mol/L, 6.20 mL, 6.24 mmol) and iodine (594 mg, 2.34 mmol), followed by purification by flash column chromatography (chloroform/methanol=100/0, 99/1) to obtain 4-phenoxy-3-hydroxy-7-iodo-2-(1-methyl-1-phenylethyl)isoindolinone (708 mg, yield 75%).

ESI-MS m/z: 486 [M+H]$^+$; $^1$H-NMR (CDCl$_3$) δ(ppm): 1.95 (s, 3H), 1.98 (s, 3H), 2.46 (d, J=6.9 Hz, 1H), 6.16 (d, J=6.9 Hz, 1H), 6.69 (d, J=8.6 Hz, 1H), 7.06 (m, 2H), 7.17-7.48 (m, 8H), 7.77 (d, J=8.6 Hz, 1H).

Step 4

In a similar manner to Step 4 of Example 16, 4-phenoxy-3-hydroxy-7-iodo-2-(1-methyl-1-phenylethyl)isoindolinone (700 mg, 1.44 mmol) was dissolved in nitromethane (28 mL), and the solution was treated with trifluoroacetic acid (1.10 mL, 14.4 mmol) and triethylsilane (0.460 mL, 2.88 mmol), followed by purification by slurry using diisopropylether to obtain 4-phenoxy-7-iodoisoindolinone (369 mg, yield 73%).

APCI-MS m/z: 352 [M+H]$^+$; $^1$H-NMR (CDCl$_3$) δ(ppm): 4.31 (s, 2H), 6.78 (d, J=8.4 Hz, 1H), 7.01-7.05 (m, 3H), 7.18 (m, 1H), 7.35-7.41 (m, 2H), 7.81 (d, J=8.6 Hz, 1H).

Step 5

In a similar manner to Step 2 of Example 1, 4-phenoxy-7-iodoisoindolinone (80.0 mg, 0.228 mmol) was dissolved in acetonitrile (5.6 mL), and the solution was treated with Compound BB (216 mg, 0.456 mmol), palladium acetate (4.1 mg, 0.018 mmol), tri(o-tolyl)phosphine (11 mg, 0.036 mmol) and triethylamine (0.318 mL, 2.28 mmol), followed by purification by preparative thin-layer chromatography (chloroform/acetonitrile=4/1) to obtain 4-phenoxy-7-[1-(tert-butoxycarbonyl)-5-(piperazin-1-ylcarbonyl)indol-2-yl]isoindolinone (81.1 mg, yield 54%).

ESI-MS m/z: 653 [M+H]$^+$; $^1$H-NMR (CDCl$_3$) δ(ppm): 1.41 (s, 9H), 1.51 (s, 9H), 3.50 (m, 8H), 4.44 (s, 2H), 6.37 (s, 1H), 6.61 (s, 1H), 7.08-7.47 (m, 8H), 7.65 (s, 1H), 8.30 (d, J=8.6 Hz, 1H).

Step 6

In a similar manner to Step 3 of Example 1, 4-phenoxy-7-[1-(tert-butoxycarbonyl)-5-(piperazin-1-ylcarbonyl)indol-2-yl]isoindolinone (77.5 mg, 0.119 mmol) was dissolved in methanol (2.3 mL), and the solution was treated with 10% hydrogen chloride-methanol solution (2.3 mL), followed by purification by preparative thin-layer chromatography (chloroform/methanol=8/1) to obtain Compound 137 (30.7 mg, yield 57%).

APCI-MS m/z: 453 [M+H]$^+$; $^1$H-NMR (DMSO-d$_6$) δ(ppm): 2.69 (m, 4H), 3.44 (m, 4H), 4.45 (s, 2H), 7.11-7.25 (m, 6H), 7.42-7.51 (m, 3H), 7.59 (s, 1H), 8.16 (d, J=8.7 Hz, 1H), 9.41 (s, 1H), 13.86 (s, 1H).

EXAMPLE 138

4-Phenoxy-7-[1H-5-(piperidinomethyl)indol-2-yl]isoindolinone (Compound 138)

Step 1

In a similar manner to Step 2 of Example 1, 4-phenoxy-7-iodoisoindolinone (80.0 mg, 0.228 mmol) was dissolved in acetonitrile (5.6 mL), and the solution was treated with Compound BD (163 mg, 0.456 mmol), palladium acetate (4.1 mg, 0.018 mmol), tri(o-tolyl)phosphine (11 mg, 0.036 mmol) and triethylamine (60.318 mL, 2.28 mmol), followed by purification by preparative thin-layer chromatography (chloroform/methanol=12/1) to obtain 4-phenoxy-7-[1-(tert-butoxycarbonyl)-5-(piperidinomethyl)indol-2-yl]isoindolinone (114 mg, yield 93%).

APCI-MS m/z: 538 [M+H]$^+$; $^1$H-NMR (CDCl$_3$) δ(ppm): 1.37 (s, 9H), 1.43 (m, 2H), 1.73 (m, 4H), 2.43 (m, 4H), 3.60 (s, 2H), 4.38 (s, 2H), 6.53 (s, 1H), 6.71 (s, 1H), 7.03-7.22 (m, 4H), 7.26-7.49 (m, 5H), 8.16 (d. J=8.6 Hz, 1H).

Step 2

In a similar manner to Step 3 of Example 1, 4-phenoxy-7-[1-(tert-butoxycarbonyl)-5-(piperidinomethyl)indol-2-yl]isoindolinone (111 mg, 0.207 mmol) was dissolved in methanol (3.3 mL), and the solution was treated with 10% hydrogen chloride-methanol solution (3.3 mL), followed by purification by preparative thin-layer chromatography (chloroform/methanol=8/1) to obtain Compound 138 (63.3 mg, yield 70%).

APCI-MS m/z: 438 [M+H]$^+$; $^1$H-NMR (DMSO-d$_6$) δ(ppm): 1.39-1.49 (m, 6H), 2.36 (m, 4H), 3.49 (s, 2H), 4.43 (s, 2H), 7.07-7.23 (m, 6H), 7.37-7.47 (m, 4H), 8.14 (d, J=8.6 Hz, 1H), 9.36 (s, 1H), 13.65 (s, 1H).

EXAMPLE 139

4-Hydroxy-7-[1H-5-(piperidinomethyl)indol-2-yl]isoindolinone hydrochloride (Compound 139)

Step 1

In a similar manner to Step 1 of Example 137, 3-acetoxybenzoic acid (7.92 g, 44.0 mmol) was dissolved in DMF (45 mL), and the solution was treated with EDCI (12.7 g, 66.0 mmol), HOBT monohydrate (3.37 g, 22.0 mmol) and cumylamine (14.2 mL, 96.8 mmol), followed by purification by slurry using diisopropylether to obtain 3-acetoxy-N-(1-methyl-1-phenylethyl)benzamide (9.57 g, yield 73%).

Step 2

3-Acetoxy-N-(1-methyl-1-phenylethyl)benzamide (9.57 g, 32.2 mmol) was dissolved in methanol (190 mL), and the solution was added with 4 mol/L sodium hydroxide solution (32.2 mL), followed by stirring at room temperature for 20 minutes. The reaction mixture was added with 1 mol/L hydrochloric acid water to adjust the pH to 7, and extracted with ethyl acetate. The organic layer was washed with saturated brine and dried over anhydrous sodium sulfate. The solvent was evaporated under reduced pressure. The residue was dissolved in dichloromethane (190 mL), and the solution was added with diisopropylethylamine (16.8 mL, 96.6 mmol) and chloromethyl methyl ether (3.70 mL, 48.3 mmol) under ice-cooling. Then, the reaction mixture was warmed to room temperature and stirred for 2 hours. The mixture was added with diisopropylethylamine (5.60 mL, 32.2 mmol) and chloromethyl methyl ether (1.20 mL, 15.8 mmol), followed by further stirring for 2 hours. The reaction mixture was added with water and extracted with chloroform. The organic layer was washed with saturated brine and dried over anhydrous sodium sulfate. The solvent was evaporated under reduced pressure. The residue was purified by flash column chromatography (chloroform/methanol=100/0, 99/1) to obtain 3-methoxymethoxy-N-(1-methyl-1-phenylethyl)benzamide (8.09 g, yield 84%).

APCI-MS m/z: 298 [M+H]$^+$; $^1$H-NMR (CDCl$_3$) δ(ppm): 1.81 (s, 6H), 2.31 (s, 3H), 6.39 (s, 1H), 7.20-7.27 (m, 2H), 7.32-7.48 (m, 6H), 7.61 (ddd, J=1.2, 1.5, 7.9 Hz, 1H).

Step 3

In a similar manner to Step 2 of Example 16, 3-methoxymethoxy-N-(1-methyl-1-phenylethyl)benzamide (8.07 g, 27.0 mmol) was dissolved in THF (320 mL), and the solution was treated with TMEDA (13.0 mL, 85.4 mmol), sec-butyllithium-hexane solution (0.99 mol/L, 87.1 mL, 86.3 mmol) and DMF (4.60 mL, 59.3 mmol), followed by purification by slurry using hexane to obtain 4-methoxymethoxy-3-hydroxy-2-(1-methyl-1-phenylethyl)isoindolinone (8.50 g, yield 96%).

APCI-MS m/z: 300 [M+H]$^+$; $^1$H-NMR (CDCl$_3$) δ(ppm): 1.82 (s, 6H), 3.47 (s, 3H), 5.19 (s, 2H), 6.40 (s, 1H), 7.14-7.27 (m, 2H), 7.30-7.37 (m, 4H), 7.44-7.47 (m, 3H).

Step 4

In a similar manner to Step 3 of Example 16, 4-methoxymethoxy-3-hydroxy-2-(1-methyl-1-phenylethyl)isoindolinone (8.50 mg, 26.0 mmol) was dissolved in THF (340 mL), and the solution was treated with TMEDA (12.5 mL, 83.1 mmol), sec-butyllithium-hexane solution (0.99 mol/L, 8.4.0 mL, 83.1 mmol) and iodine (7.91 g, 31.2 mmol), followed by purification by flash column chromatography (hexane/ethyl acetate=90/10, 70/30) to obtain 4-methoxymethoxy-3-hydroxy-7-iodo-2-(1-methyl-1-phenylethyl)isoindolinone (7.65 g, yield 65%).

APCI-MS m/z: 328 [M+H]$^+$; $^1$H-NMR (CDCl$_3$) δ(ppm): 1.93 (s, 3H), 1.98 (s, 3H), 2.66 (d, J=7.9 Hz, 1H), 3.52 (s, 3H), 5.30 (s, 2H), 6.31 (d, J=7.9 Hz, 1H), 7.19-7.45 (m, 8H).

Step 5

In a similar manner to Step 4 of Example 16, 4-methoxymethoxy-3-hydroxy-7-iodo-2-(1-methyl-1-phenylethyl)isoindolinone (1.15 g, 2.54 mmol) was dissolved in nitromethane (58 mL), and the solution was added with trifluoroacetic acid (1.20 mL, 7.62 mmol) and triethylsilane (0.587 mL, 7.62 mmol), followed by stirring at room temperature for 30 minutes. The reaction mixture was added with water and extracted with ethyl acetate. The organic layer was washed with saturated aqueous sodium hydrogencarbonate solution and saturated brine, and dried over anhydrous sodium sulfate. The solvent was evaporated under reduced pressure. The residue was purified by flash column chromatography (chloroform/methanol=100/0, 99/1, hexane/ethyl acetate=80/20, 60/40) to obtain 4-methoxymethoxy-7-iodo-2-(1-methyl-1-phenylethyl)isoindolinone (935 mg, yield 84%).

ESI-MS m/z: 454 [M+H]$^+$; $^1$H-NMR (CDCl$_3$) δ(ppm): 1.94 (s, 3H), 1.98 (s, 3H), 2.50 (d, J=7.4 Hz, 1H), 3.50 (s, 3H), 5.27 (s, 2H), 6.13 (d, J=7.3 Hz, 1H), 7.02 (d, J=8.8 Hz, 1H), 7.23-7.35 (m, 4H), 7.43-7.46 (m, 2H), 7.81 (d, J=8.6 Hz, 1H).

Step 6

4-Methoxymethoxy-7-iodo-2-(1-methyl-1-phenylethyl)isoindolinone (463 mg, 1.06 mmol) was dissolved in 10% hydrogen chloride-methanol solution (14 mL), and the solution was stirred at 70° C. for 2.5 hours. Then, the solution was added with 10% hydrogen chloride-methanol solution (4.3 mL) and further stirred at 2.5 hours. The reaction mixture was added with chloroform and purified by slurry. The solid was collected by filtration and washed with chloroform/methanol (9/1). The obtained solid was dried under reduced pressure to obtain 4-hydroxy-7-iodoisoindolinone (248 mg, yield 85%).

APCI-MS m/z: 276 [M+H]$^+$; $^1$H-NMR (DMSO-d$_6$) δ(ppm): 4.12 (s, 2H), 6.77 (d, J=8.2 Hz, 1H), 7.64 (d, J=8.2 Hz, 1H), 8.65 (s, 1H), 10.21 (s, 1H).

Step 7

In a similar manner to Step 2 of Example 1, 4-hydroxy-7-iodoisoindolinone (220 mg, 0.800 mmol) was dissolved in acetonitrile (13.2 mL), and the solution was treated with Compound BD (573 mg, 1.60 mmol), palladium acetate (14.4 mg, 0.064 mmol), tri(o-tolyl)phosphine (39.0 mg, 0.128 mmol) and triethylamine (1.12 mL, 8.00 mmol), followed by purification by preparative thin-layer chromatography (chloroform/methanol=7/1) to obtain 4-hydroxy-7-[1-(tert-butoxycarbonyl)-5-(piperidinomethyl)indol-2-yl]isoindolinone (294 mg, yield 80%).

ESI-MS m/z: 462 [M+H]$^+$; $^1$H-NMR (CDCl$_3$) δ(ppm): 1.26 (s, 9H), 1.49 (m, 2H), 1.67 (m, 4H), 2.55 (m, 4H), 3.62 (s, 2H), 4.11 (m, 2H), 6.03 (s, 1H), 6.11 (s, 1H), 6.59 (d, J=8.3 Hz, 1H), 7.04 (d, J=8.1 Hz, 1H), 7.15 (d, J=8.4 Hz, 1H), 7.26 (m, 1H), 8.14 (d, J=8.4 Hz, 1H).

Step 8

In a similar manner to Step 2 of Example 8, 4-hydroxy-7-[1-(tert-butoxycarbonyl)-5-(piperidinomethyl)indol-2-yl]isoindolinone (284 mg, 0.616 mmol) was dissolved in methanol (7.1 mL), and the solution was treated with 10% hydrogen chloride-methanol solution (7.1 mL). The obtained solid was collected by filtration and washed with methanol, followed by drying under reduced pressure to obtain Compound 139 (189 mg, yield 77%).

mp 253-256° C.; APCI-MS m/z: 362 [M+H]$^+$; $^1$H-NMR (DMSO-d$_6$) δ(ppm): 1.65-1.76 (m, 6H), 2.82-2.86 (m, 2H), 3.32 (m, 2H), 4.29 (m, 2H), 4.37 (s, 2H), 7.05 (s, 1H), 7.11 (d, J=8.4 Hz, 1H), 7.21 (d. J=8.3 Hz, 1H), 7.49 (d. J=8.3 Hz, 1H), 7.69 (s, 1H), 8.03 (d, J=8.4 Hz, 1H), 9.27 (s, 1H), 9.71 (br s, 1H), 10.40 (s, 1H), 13.85 (s, 1H).

EXAMPLE 140

4-Phenyl-7-[1H-5-(piperazin-1-ylcarbonyl)indol-2-yl]isoindolinone (Compound 140)

Step 1

3-Amino-6-bromophthalimide (3.10 g, 12.9 mmol) was dissolved in THF (240 mL), and the solution was added with diisobutylaluminiumhydride (0.94 mol/L, 68.6 mL, 64.5 mmol) by drops at −78° C. for 25 minutes, then the reaction mixture was warmed to room temperature, followed by stirring for 1.5 hours. Then, the reaction mixture was ice-cooled, added with water and filtered using Celite. The filtrate was extracted with ethyl acetate. The organic layer was dried over anhydrous sodium sulfate. The solvent was evaporated under reduced pressure. The residue was purified by slurry using chloroform to obtain 7-amino-4-bromo-3-hydroxyisoindolinone (2.26 g, yield 72%).

APCI-MS m/z: 243 [M+H]$^+$; $^1$H-NMR (DMSO-d$_6$) δ(ppm): 5.64 (d, J=9.5 Hz, 1H), 6.16 (s, 2H), 6.21 (d, J=9.5 Hz, 1H), 6.58 (d, J=8.6 Hz, 1H), 7.30 (d, J=8.6 Hz, 1H), 8.65 (s, 1H).

Step 2

7-Amino-4-bromo-3-hydroxyisoindolinone (3.11 g, 12.8 mmol) was dissolved in nitromethane (125 mL), and the solution was added with trifluoroacetic acid (9.90 mL, 128 mmol) and triethylsilane (4.10 mL, 25.6 mmol), followed by stirring at room temperature for 2 hours. The reaction mixture was added with water, extracted with ethyl acetate. The organic layer was washed with saturated aqueous sodium hydrogencarbonate solution and saturated brine, and dried over anhydrous sodium sulfate. The solvent was evaporated under reduced pressure and the residue was purified by slurry using chloroform to obtain 7-amino-4-bromoisoindolinone (2.16 g, yield 74%).

APCI-MS m/z: 227 [M+H]$^+$; $^1$H-NMR (CDCl$_3$+CD$_3$OD) δ(ppm): 4.25 (s, 2H), 6.56 (d, J=8.6 Hz, 1H), 7.33 (d, J=8.6 Hz, 1H).

Step 3

In a similar manner to Step 2 of Example 1, 7-amino-4-bromoisoindolinone (250 mg, 1.10 mmol) was dissolved in acetonitrile (15 mL), and the solution was treated with phenylboronic acid (402 mg, 3.30 mmol), palladium acetate (20 mg, 0.088 mmol), tri(o-tolyl)phosphine (53.6 mg, 0.176 mmol) and triethylamine (1.53 mL, 11.0 mmol), followed by purification by preparative thin-layer chromatography (chloroform/methanol=15/1, chloroform/acetonitrile=6/1) to obtain 7-amino-4-phenylisoindolinone (219 mg, yield 89%).

APCI-MS m/z: 225 [M+H]$^+$; $^1$H-NMR (CDCl$_3$) δ(ppm): 4.47 (s, 2H), 5.32 (s, 2H), 6.01 (s, 1H), 6.68 (d, J=8.3 Hz, 1H), 7.29-7.45 (m, 6H).

Step 4

7-Amino-4-phenylisoindolinone (80.0 mg, 0.357 mmol) was dissolved in acetonitrile (4.8 mL), and the solution was added with potassium iodide (71.0 mg, 0.428 mmol), copper iodide (82.0 mg, 0.428 mmol), iodine (109 mg, 0.428 mmol) and tert-butyl nitrite (0.068 mL, 0.57 mmol), followed by stirring under ice-cooling for 1.5 hours. Then, the reaction mixture was warmed to room temperature and further added with tert-butyl nitrite (0.068 mL, 0.57 mmol), followed by stirring at 50° C. for 1.5 hours. The reaction mixture was added with 10% aqueous sodium thiosulfate solution and extracted with ethyl acetate. The organic layer was washed with saturated brine and dried over anhydrous sodium sulfate. The solvent was evaporated under reduced pressure and the residue was purified by preparative thin-layer chromatography (chloroform/acetonitrile=6/1) to obtain 7-iodo-4-phenylisoindolinone (72.6 mg, yield 61%).

ESI-MS m/z: 336 [M+H]$^+$; $^1$H-NMR (CDCl$_3$) δ(ppm): 4.40 (s, 2H), 6.58 (s, 1H), 7.36-7.54 (m, 5H), 8.01 (d, J=7.9 Hz, 1H), 8.25 (d, J=7.9 Hz, 1H).

Step 5

In a similar manner to Step 2 of Example 1, 7-iodo-4-phenylisoindolinone (69.0 mg, 0.206 mmol) was dissolved in acetonitrile (5.5 mL), and the solution was treated with Compound BB (195 mg, 0.412 mmol), palladium acetate (3.7 mg, 0.016 mmol), tri(o-tolyl)phosphine (10 mg, 0.032 mmol) and triethylamine (0.287 mL, 2.06 mmol), followed by purification by preparative thin-layer chromatography (chloroform/methanol=12/1, chloroform/acetonitrile=6/1) to obtain 4-phenyl-7-{1-(tert-butoxycarbonyl)-5-[4-(tert-butoxycarbonyl)piperazin-1-ylcarbonyl]indol-2-yl}isoindolinone (49.5 mg, yield 38%).

ESI-MS m/z: 637 [M+H]$^+$; $^1$H-NMR (DMSO-d$_6$) δ(ppm): 1.35 (s, 9H), 1.48 (s, 9H), 3.47 (m, 8H), 4.51 (s, 2H), 6.63 (s, 1H), 6.64 (s, 1H), 7.35-7.73 (m, 9H), 8.28 (d, J=8.4 Hz, 1H).

Step 6

In a similar manner to Step 3 of Example 1, 4-phenyl-7-{1-(tert-butoxycarbonyl)-5-[4-(tert-butoxycarbonyl)piperazin-1-ylcarbonyl]indol-2-yl}isoindolinone (49.0 mg, 0.0770 mmol) was dissolved in methanol (1.5 mL), and the solution was treated with 10% hydrogen chloride-methanol solution (1.5 mL), followed by purification by preparative thin-layer chromatography (chloroform/methanol=4/1) to obtain Compound 140 (15.4 mg, yield 46%).

APCI-MS m/z: 437 [M+H]$^+$; $^1$H-NMR (DMSO-d$_6$) δ(ppm): 2.70 (m, 4H), 3.46 (m, 4H), 4.61 (s, 2H), 7.15 (d, J=8.6 Hz, 1H), 7.33 (s, 1H), 7.44-7.65 (m, 7H), 7.69 (d, J=8.3 Hz, 1H), 8.29 (d, J=7.9 Hz, 1H), 9.42 (s, 1H), 14.16 (s, 1H).

EXAMPLE 141

4-Phenyl-7-[1H-5-(piperidinomethyl)indol-2-yl]isoindolinone (Compound 141)

Step 1

In a similar manner to Step 2 of Example 1, 7-iodo-4-phenylisoindolinone (127 mg, 0.379 mmol) was dissolved in acetonitrile (7.6 mL), and the solution was treated with Compound BD (272 mg, 0.758 mmol), palladium acetate (6.8 mg, 0.030 mmol), tri(o-tolyl)phosphine (19 mg, 0.061 mmol) and triethylamine (0.528 mL, 3.79 mmol), followed by purification by preparative thin-layer chromatography (chloroform/methanol=7/1) to obtain 4-phenyl-7-[1-(tert-butoxycarbonyl)-5-(piperidinomethyl)indol-2-yl]isoindolinone (146 mg, yield 74%).

ESI-MS m/z: 522 [M+H]$^+$; $^1$H-NMR (CDCl$_3$) δ(ppm): 1.24-1.61 (m, 6H), 1.34 (s, 9H), 2.44 (m, 4H), 3.61 (m, 2H), 4.48 (s, 2H), 6.57 (s, 1H), 6.75 (s, 1H), 7.30-7.61 (m, 9H), 8.17 (d, J=8.6 Hz, 1H).

Step 2

In a similar manner to Step 3 of Example 1, 4-phenyl-7-[1-(tert-butoxycarbonyl)-5-(piperidinomethyl)indol-2-yl]isoindolinone (136 mg, 0.260 mmol) was dissolved in methanol (3.4 mL), and the solution was treated with 10% hydrogen chloride-methanol solution (3.4 mL), followed by purification by preparative thin-layer chromatography (chloroform/methanol=10/1) to obtain Compound 141 (41.6 mg, yield 38%).

APCI-MS m/z: 422 [M+H]$^+$; $^1$H-NMR (DMSO-d$_6$) δ(ppm): 1.40-1.49 (m, 6H), 2.37 (m, 4H), 3.51 (s, 2H), 4.60 (s, 2H), 7.08 (d, J=7.6 Hz, 1H), 7.22 (s, 1H), 7.39-7.54 (m, 5H), 7.62-7.65 (m, 2H), 7.67 (d, J=8.3 Hz, 1H), 8.26 (d, J=8.3 Hz, 1H), 9.38 (s, 1H), 13.93 (s, 1H).

EXAMPLE 142

4-(Furan-2-yl)-7-[1H-5-(piperazin-1-ylcarbonyl)indol-2-yl]isoindolinone (Compound 142)

Step 1

In a similar manner to Step 1 of Example 10, 7-amino-4-bromoisoindolinone (234 mg, 1.03 mmol) was dissolved in THF (11.6 mL), and the solution was treated with 2-(tributylstannyl)furane (0.649 mL, 2.06 mmol) and bis(triphenylphosphine)dichloropalladium (58 mg, 0.082 mmol), followed by purification by preparative thin-layer chromatography (chloroform/acetone=4/1, chloroform/methanol=12/1) to obtain 7-amino-4-(furan-2-yl)isoindolinone (121 mg, yield 55%).

APCI-MS m/z: 215 [M+H]$^+$; $^1$H-NMR (CDCl$_3$) δ(ppm): 4.61 (s, 2H), 5.37 (s, 2H), 6.14 (s, 1H), 6.38 (d, J=3.5 Hz, 1H), 6.50 (m, 1H), 6.64 (d, J=8.4 Hz, 1H), 7.45 (m, 1H), 7.62 (d, J=8.4 Hz, 1H).

Step 2

In a similar manner to Step 4 of Example 140, 7-amino-4-(furan-2-yl)isoindolinone (43.0 mg, 0.201 mmol) was dissolved in acetonitrile (4.3 mL), and the solution was treated with potassium iodide (40.0 mg, 0.241 mmol), copper iodide (46.0 mg, 0.241 mmol), iodine (61.0 mg, 0.241 mmol) and tert-butyl nitrite (0.072 mL, 0.60 mmol), followed by purification by preparative thin-layer chromatography (chloroform/acetonitrile=6/1) to obtain 7-iodo-4-(furan-2-yl)isoindolinone (37.8 mg, yield 58%).

APCI-MS m/z: 326 [M+H]$^+$; $^1$H-NMR (CDCl$_3$) δ(ppm): 4.61 (s, 2H), 6.56 (dd, J=1.9, 3.5 Hz, 1H), 6.70 (d, J=3.5 Hz, 1H), 6.72 (s, 1H), 7.55 (d, J=8.2 Hz, 1H), 7.57 (d, J=1.9 Hz, 1H), 7.96 (d, J=8.2 Hz, 1H).

Step 3

In a similar manner to Step 2 of Example 11, 7-iodo-4-(furan-2-yl)isoindolinone (157 mg, 0.484 mmol) was dissolved in acetonitrile (11 mL), and the solution was treated with Compound BB (458 mg, 0.968 mmol), palladium acetate (8.7 mg, 0.039 mmol), tri(o-tolyl)phosphine (24 mg, 0.077 mmol) and triethylamine (0.675 mL, 4.84 mmol), followed by purification by preparative thin-layer chromatography (chloroform/methanol=12/1) to obtain 4-(furan-2-yl)-7-(1-(tert-butoxycarbonyl)-5-[4-(tert-butoxycarbonyl)piperazin-1-ylcarbonyl]indol-2-yl)isoindolinone (186 mg, yield 61%).

ESI-MS m/z: 627 [M+H]$^+$; $^1$H-NMR (CDCl$_3$) δ(ppm): 1.33 (s, 9H), 1.48 (s, 9H), 3.47-3.60 (m, 8H), 4.71 (s, 2H), 6.58-6.62 (m, 3H), 6.72 (d, J=3.3 Hz, 1H), 7.37 (d, J=8.4 Hz, 1H), 7.52 (d, J=7.9 Hz, 1H), 7.58 (s, 1H), 7.64 (s, 1H), 7.91 (d, J=8.1 Hz, 1H), 8.28 (d, J=8.4 Hz, 1H).

Step 4

In a similar manner to Step 2 of Example 8, 4-(furan-2-yl)-7-(1-(tert-butoxycarbonyl)-5-[4-(tert-butoxycarbonyl)piperazin-1-ylcarbonyl]indol-2-yl)isoindolinone (186 mg, 0.297 mmol) was dissolved in methanol (7.4 mL), and the solution was treated with 10% hydrogen chloride-methanol solution (7.4 mL). The obtained solid was collected by filtration and washed with methanol, followed by drying under reduced pressure. The obtained solid was purified by preparative thin-layer chromatography (chloroform/methanol/7 mol/L ammonia-methanol solution=12/0.5/0.5) to obtain Compound 142 (60.4 mg, yield 48%).

APCI-MS m/z: 427 [M+H]$^+$: $^1$H-NMR (DMSO-d$_6$) δ(ppm): 2.70 (m, 4H), 3.45 (m, 4H), 4.74 (s, 2H), 6.72 (dd, J=2.0, 3.6 Hz, 1H), 7.04 (d, J=2.6 Hz, 1H), 7.15 (d, J=8.6 Hz, 1H), 7.34 (s, 1H), 7.52 (d, J=8.9 Hz, 1H), 7.62 (s, 1H), 7.90 (s, 1H), 8.02 (d, J=8.9 Hz, 1H), 8.27 (d, J=7.9 Hz, 1H), 9.45 (s, 1H), 14.15 (s, 1H).

EXAMPLE 143

4-(Furan-2-yl)-7-[1H-5-(piperidinomethyl)indol-2-yl]isoindolinone hydrochloride (Compound 143)

Step 1

In a similar manner to Step 2 of Example 1, 7-iodo-4-(furan-2-yl)isoindolinone (37.8 mg, 0.116 mmol) was dissolved in acetonitrile (3.0 mL), and the solution was treated with Compound BD (83.0 mg, 0.232 mmol), palladium acetate (2.1 mg, 0.0093 mmol), tri(o-tolyl)phosphine (5.6 mg, 0.019 mmol) and triethylamine (0.162 mL, 1.1.6 mmol), followed by purification by preparative thin-layer chromatography (chloroform/methanol=12/1) to obtain 4-(furan-2-yl)-[1-(tert-butoxycarbonyl)-5-(piperidinomethyl)indol-2-yl]isoindolinone (36.7 mg, yield 62%).

ESI-MS m/z: 512 [M+H]$^+$; $^1$H-NMR (CDCl$_3$) δ(ppm): 1.23-1.43 (m, 6H), 1.33 (s, 9H), 2.44 (s, 4H), 3.62 (s, 2H), 4.69 (s, 2H), 6.57 (m, 2H), 6.65 (s, 1H), 6.70 (d, J=3.5 Hz, 1H), 7.29 (m, 1H), 7.50 (m, 2H), 7.58 (br s, 1H), 7.89 (d, J=7.9 Hz, 1H), 8.18 (d, J=8.3 Hz, 1H).

Step 2

In a similar manner to Step 2 of Example 8, 4-(furan-2-yl)-7-[1-(tert-butoxycarbonyl)-5-(piperidinomethyl)indol-2-yl]isoindolinone (36.7 mg, 0.0717 mmol) was dissolved in methanol (1.1 mL), and the solution was treated with 10% hydrogen chloride-methanol solution (1.1 mL). The obtained solid was collected by filtration and washed with methanol, followed by drying under reduced pressure to obtain Compound 143 (23.7 mg, yield 74%).

mp >295° C.; APCI-MS m/z: 412 [M+H]$^+$; $^1$H-NMR (DMSO-d$_6$) δ(ppm) 1.66-1.77 (m, 6H), 2.87 (m, 2H), 3.31 (m, 2H), 4.32 (s, 2H), 4.73 (s, 2H), 6.72 (m, 1H), 7.04 (d, J=3.5 Hz, 1H), 7.28 (d, J=8.9 Hz, 1H), 7.35 (s, 1H), 7.56 (d, J=8.6 Hz, 1H), 7.76 (s, 1H), 7.90 (br s, 1H), 8.02 (d, J=8.4 Hz, 1H), 8.29 (d, J=8.6 Hz, 1H), 9.54 (s, 1H), 9.73 (br s, 1H), 14.16 (s, 1H).

EXAMPLE 144

4-Hydroxy-7-[1H-5-(piperazin-1-ylcarbonyl)indol-2-yl]isoindolinone (Compound 144)

Step 1

In a similar manner to Step 4 of Example 16, 4-methoxymethoxy-3-hydroxy-7-iodo-2-(1-methyl-1-phenylethyl)isoindolinone (500 mg, 1.10 mmol) was dissolved in nitromethane (25 mL), and the solution was treated with trifluoroacetic acid (0.525 mL, 6.82 mmol) and triethylsilane (0.527 mL, 3.30 mmol), followed by purification by flash column chromatography (chloroform/methanol=100/0, 99/1) to obtain 4-hydroxy-7-iodo-2-(1-methyl-1-phenylethyl)isoindolinone (257 mg, yield 59%) and 4-methoxymethoxy-7-iodo-2-(1-methyl-1-phenylethyl)isoindolinone (131 mg, yield 27%).

4-hydroxy-7-iodo-2'-(1-methyl-1-phenylethyl)isoindolinone

APCI-MS m/z: 394 [M+H]$^+$; $^1$H-NMR (CDCl$_3$+CD$_3$OD) δ(ppm): 1.91 (s 6H), 4.27 (s, 1H), 6.67 (d, J=8.4 Hz, 1H), 7.21-7.34 (m, 5H), 7.63 (d, J=8.4 Hz, 1H).

4-methoxymethoxy-7-iodo-2-(1-methyl-1-phenylethyl)isoindolinone

APCI-MS m/z: 438 [M+H]$^+$; $^1$H-NMR (CDCl$_3$) δ(ppm): 1.95 (s 6H), 3.46 (s, 3H), 4.22 (s, 2H), 5.20 (s, 2H), 6.97 (d, J=8.6 Hz, 1H), 7.26-7.36 (m, 5H), 7.78 (d, J=8.6 Hz, 1H).

Step 2

In a similar manner to Step 2 of Example 1, 4-hydroxy-7-iodo-2-(1-methyl-1-phenylethyl)isoindolinone (133 mg, 0.338 mmol) was dissolved in acetonitrile (8.0 mL), and the solution was treated with Compound BB (320 mg, 0.676 mmol), palladium acetate (6.1 mg, 0.027 mmol), tri(o-tolyl)phosphine (17 mg, 0.054 mmol) and triethylamine (0.471 mL, 3.38 mmol), followed by purification by preparative thin-layer chromatography (chloroform/methanol=20/1, chloroform/acetonitrile=7/1) to obtain 4-hydroxy-2-(1-methyl-1-phenylethyl)-7-(1-(tert-butoxycarbonyl)-5-[4-(tert-butoxycarbonyl)piperazin-1-ylcarbonyl]indol-2-yl)isoindolinone (111 mg, yield 47%).

ESI-MS m/z: 695 [M+H]$^+$; $^1$H-NMR (CDCl$_3$) δ(ppm): 1.33 (s 9H), 1.48 (s, 9H), 1.81 (s, 6H), 3.50 (m, 8H), 4.27 (br s, 2H), 6.37 (s, 1H), 6.63 (d, J=7.3 Hz 1H), 7.06 (d, J=7.9 Hz, 1H), 7.17-7.34 (m, 7H), 7.47 (s, 1H), 8.18 (d, J=8.6 Hz, 1H).

Step 3

4-Hydroxy-2-(1-methyl-1-phenylethyl)-7-{1-(tert-butoxycarbonyl)-5-[4-(tert-butoxycarbonyl)piperazin-1-ylcarbonyl]indol-2-yl}isoindolinone (111 mg, 0.160 mmol) was dissolved in methanol (3.3 mL) and the solution was added with 10% hydrogen chloride-methanol solution (3.3 mL), followed by stirring at 70° C. for 5.7 hours. The reaction mixture was added with trifluoroacetic acid (0.123 mL, 1.60 mmol) and stirred at 50° C. for 6 hours, and then at room temperature for 12 hours. The reaction mixture was added with saturated aqueous sodium hydrogencarbonate solution and extracted with ethyl acetate. The organic layer was washed with saturated brine and dried over anhydrous sodium sulfate. The solvent was evaporated under reduced pressure and the residue was purified by preparative thin-layer chromatography (chloroform/methanol=4/1, chloroform/methanol/7 mol/L ammonia-methanol solution=8/0.7/0.3) to obtain Compound 144 (5.7 mg, yield 9.5%).

ESI-MS m/z: 377 [M+H]$^+$; $^1$H-NMR (DMSO-d$_6$) δ(ppm): 2.69 (m, 4H), 3.44 (m, 4H), 4.36 (s, 2H), 7.04-7.10 (m, 3H), 7.44 (d, J=7.9 Hz, 1H), 7.55 (s, 1H), 8.01 (d, J=8.6 Hz, 1H), 9.25 (s, 1H), 13.84 (s, 1H).

EXAMPLE 145

4-(Thiophen-2-yl)-7-[1H-5-(piperidinomethyl)indol-2-yl]isoindolinone hydrochloride (Compound 145)

Step 1

In a similar manner to Step 1 of Example 10, 7-amino-4-bromoisoindolinone (404 mg, 1.78 mmol) was dissolved in THF (20 mL), and the solution was treated with 2-(tributylstannyl)thiophene (1.13 mL, 3.56 mmol) and bis(triphenylphosphine)dichloropalladium (100 mg, 0.142 mmol), followed by purification by preparative thin-layer chromatography (chloroform/methanol=12/1) to obtain 7-amino-4-(thiophen-2-yl)isoindolinone (220 mg, yield 54%).

APCI-MS m/z: 231 [M+H]$^+$; $^1$H-NMR (DMSO-d$_6$) δ(ppm): 4.44 (s, 2H), 6.30 (s, 2H), 6.64 (d, J=8.2 Hz, 1H), 7.10 (dd, J=3.6, 5.1 Hz, 1H), 7.20 (d, J=3.6 Hz, 1H), 7.45 (d, J=5.1 Hz, 1H), 7.49 (d, J=8.6 Hz, 1H), 8.36 (s, 1H).

Step 2

In a similar manner to Step 4 of Example 140, 7-amino-4-(thiophen-2-yl)isoindolinone (212 mg, 0.920 mmol) was dissolved in acetonitrile (14.8 mL), and the solution was treated with potassium iodide (183 mg, 1.10 mmol), copper iodide (210 mg, 1.10 mmol), iodine (280 mg, 1.10 mmol) and tert-butyl nitrite (0.382 mL, 2.76 mmol), followed by purification by preparative thin-layer chromatography (chloroform/acetonitrile=6/1, chloroform/methanol=10/1) to obtain 7-iodo-4-(thiophen-2-yl)isoindolinone (138 mg, yield 44%).

APCI-MS m/z: 342 [M+H]$^+$; $^1$H-NMR (DMSO-d$_6$) δ(ppm): 4.50 (s, 2H), 7.22 (dd, J=3.8, 4.9 Hz, 1H), 7.54-7.57 (m, 2H), 7.71 (d, J=5.1 Hz, 1H), 7.95 (d, J=8.1 Hz, 1H), 8.93 (s, 1H).

Step 3

In a similar manner to Step 2 of Example 1, 7-iodo-4-(thiophen-2-yl)isoindolinone (50.0 mg, 0.147 mmol) was dissolved in acetonitrile (4.0 mL), and the solution was treated with Compound BD (105 mg, 0.294 mmol), palladium acetate (2.6 mg, 0.012 mmol), tri(o-tolyl)phosphine (7.2 mg, 0.024 mmol) and triethylamine (0.205 mL, 1.47 mmol), followed by purification by preparative thin-layer chromatography (chloroform/methanol=12/1) to obtain 4-(thiophen-2-yl)-7-[1-(tert-butoxycarbonyl)-5-(piperidinomethyl)indol-2-yl]isoindolinone (70.3 mg, yield 91%).

APCI-MS m/z: 528 [M+H]$^+$; $^1$H-NMR (CDCl$_3$) δ(ppm): 1.36 (s, 9H), 1.43 (m, 2H), 1.60 (m, 4H), 2.44 (br s, 4H), 3.62 (s, 2H), 4.64 (s, 2H), 6.58 (s, 1H), 6.68 (s, 1H), 7.18 (dd, J=3.8, 4.9 Hz, 1H), 7.28-7.32 (m, 2H), 7.43 (dd, J=0.7, 5.1 Hz, 1H), 7.51 (d, J=7.7 Hz, 1H), 7.51 (s, 1H), 7.81 (d, J=7.9 Hz, 1H), 8.17 (d, J=8.6 Hz, 1H).

Step 4

In a similar manner to Step 2 of Example 8, 4-(thiophen-2-yl)-7-[(1-(tert-butoxycarbonyl)-5-(piperidinomethyl)indol-2-yl]isoindolinone (66.8 mg, 0.127 mmol) was dissolved in methanol (2.0 mL), and the solution was treated with 10% hydrogen chloride-methanol solution (2.0 mL). The obtained solid was collected by filtration and washed with methanol, followed by drying under reduced pressure to obtain Compound 145 (35.2 mg, yield 60%).

mp >295° C.; APCI-MS m/z: 428 [M+H]$^+$; $^1$H-NMR (DMSO-d$_6$) δ(ppm): 1.66-1.77 (m, 6H), 2.88 (m, 2H), 3.30 (m, 2H), 4.33 (s, 2H), 4.75 (s, 2H), 7.24-7.30 (m, 2H), 7.34 (s, 1H), 7.56-7.60 (m, 2H), 7.74 (d, J=5.3 Hz, 1H), 7.77 (s, 1H), 7.92 (d, J=8.4 Hz, 1H), 8.28 (d, J=7.6 Hz, 1H), 9.54 (s, 1H), 9.68 (br s, 1H), 14.13 (s, 1H).

EXAMPLE 146

4-(Thiophen-2-yl)-7-[1H-5-(piperazin-1-ylcarbonyl)indol-2-yl]isoindolinone (Compound 146)

Step 1

In a similar manner to Step 2 of Example 1, 7-iodo-4-(thiophen-2-yl)isoindolinone (82.1 mg, 0.241 mmol) was dissolved in acetonitrile (5.7 mL), and the solution was treated with Compound BB (228 mg, 0.482 mmol), palladium acetate (4.3 mg, 0.019 mmol), tri(o-tolyl)phosphine (12 mg, 0.039 mmol) and triethylamine (0.336 mL, 4.84 mmol), followed by purification by preparative thin-layer chromatography (chloroform/methanol=12/1) to obtain 4-(thiophen-2-yl)-7-{1-(tert-butoxycarbonyl)-5-[(4-(tert-butoxycarbonyl)piperazin-1-ylcarbonyl]indol-2-yl}isoindolinone (96.0 mg, yield 62%).

ESI-MS m/z: 643 [M+H]$^+$; $^1$H-NMR (CDCl$_3$) δ(ppm): 1.36 (s, 9H), 1.48 (s, 9H), 3.47-3.60 (m, 8H), 4.66 (s, 2H), 6.60 (br s, 1H), 6.63 (s, 1H), 7.19 (dd, J=3.6, 5.3 Hz, 1H), 7.33 (d, J=3.6 Hz, 1H), 7.37 (dd, J=1.8, 8.6 Hz, 1H), 7.45 (d, J=5.0 Hz, 1H), 7.53 (d, J=7.9 Hz, 1H), 7.64 (s, 1H), 7.84 (d, J=7.9 Hz, 1H), 8.27 (d, J=8.6 Hz, 1H).

Step 2

In a similar manner to Step 2 of Example 8, 4-(thiophen-2-yl)-7-(1-(tert-butoxycarbonyl)-5-[4-(tert-butoxycarbonyl)piperazin-1-ylcarbonyl]indol-2-yl)isoindolinone (92.0 mg, 0.143 mmol) was dissolved in methanol (2.8 mL), and the solution was treated with 10% hydrogen chloride-methanol solution (2.8 mL). The obtained solid was collected by filtration and washed with methanol, followed by drying under reduced pressure. The obtained solid was purified by preparative thin-layer chromatography (chloroform/methanol=3/1) to obtain Compound 146 (27.8 mg, yield 44%).

APCI-MS m/z: 443 [M+H]$^+$; $^1$H-NMR (DMSO-d$_6$) δ(ppm): 2.69 (m, 4H), 3.45 (m, 4H), 4.74 (s, 2H), 7.15 (d, J=8.4 Hz, 1H), 7.25 (dd, J=3.9, 4.8 Hz, 1H), 7.33 (s, 1H), 7.52 (d, J=8.4 Hz, 1H), 7.59 (d, J=3.8 Hz, 1H), 7.63 (s, 1H), 7.73 (d, J=5.1 Hz, 1H), 7.92 (d, J=8.4 Hz, 1H), 8.25 (d, J=8.2 Hz, 1H), 9.53 (s, 1H), 14.12 (s, 1H).

EXAMPLE 147

4-Hydroxy-7-{1H-5-[4-(2-hydroxyethyl)piperazin-1-ylmethyl]indol-2-yl}isoindolinone dihydrochloride (Compound 147)

Step 1

In a similar manner to Step 2 of Example 1, 7-iodo-4-hydroxyisoindolinone (300 mg, 1.09 mmol) was dissolved in acetonitrile (18 mL), and the solution was treated with Compound BA (630 mg, 2.18 mmol), palladium acetate (20.0 mg, 0.0872 mmol), tri(o-tolyl)phosphine (53.0 mg, 0.174 mmol) and triethylamine (1.52 mL, 10.9 mmol), followed by purification by slurry using chloroform to obtain 4-hydroxy-7-[1-(tert-butoxycarbonyl)-5-formylindol-2-yl]isoindolinone (389 mg, yield 91%).

APCI-MS m/z: 393 [M+H]$^+$; $^1$H-NMR (DMSO-d$_6$) δ(ppm): 1.17 (s, 9H), 4.26 (s, 2H), 6.72 (s, 1H), 7.02 (d, J=7.9 Hz, 1H), 7.29 (d, J=7.7 Hz, 1H), 7.84 (d, J=8.9 Hz, 1H), 8.17 (s, 1H), 8.30 (d, J=8.6 Hz, 1H), 8.56 (s, 1H), 10.05 (s, 1H), 10.23 (s, 1H).

Step 2

4-Hydroxy-7-[1-(tert-butoxycarbonyl)-5-formylindol-2-yl]isoindolinone (140 mg, 0.357 mmol) was dissolved in acetonitrile (7 mL), and the solution was added with 1-(2-hydroxyethyl)piperazine (186 mg, 1.43 mmol), acetic acid (0.409 mL, 7.14 mmol) and sodium triacetoxyborohydride (151 mg, 0.714 mmol), followed by stirring at room temperature for 1.3 hours. The mixture was added with sodium triacetoxyborohydride (151 mg, 0.714 mmol) and further stirred for 3.8 hours. Further, the mixture was added with sodium triacetoxyborohydride (76.0 mg, 0.357 mmol) and stirred for 0.6 hours. The reaction mixture was added with 1 mol/L hydrochloric acid and extracted with ethyl acetate. The organic layer was washed with saturated aqueous sodium carbonate solution and saturated brine, and dried over anhydrous sodium sulfate. The solvent was evaporated under reduced pressure to obtain 4-hydroxy-7-{1-(tert-butoxycarbonyl)-5-[4-(2-hydroxyethyl)piperazin-1-ylmethyl]indol-2-yl}isoindolinone (143 mg, yield 79%).

APCI-MS m/z: 507 [M+H]$^+$; $^1$H-NMR (DMSO-d$_6$) δ(ppm): 1.16 (m, 9H), 2.40 (m, 10H), 3.46-3.53 (m, 4H), 4.24 (s, 2H), 6.47 (s, 1H), 6.99 (d, J=8.1 Hz, 1H), 7.20-7.29 (m, 2H), 7.45 (s, 1H), 8.06 (d, J=8.2 Hz, 1H), 8.50 (s, 1H), 10.14 (s, 1H).

Step 3

In a similar manner to Step 2 of Example 8, 4-hydroxy-7-{1-(tert-butoxycarbonyl)-5-[4-(2-hydroxyethyl)piperazin-1-ylmethyl]indol-2-yl}isoindolinone (143 mg, 0.283 mmol) was dissolved in methanol (3.6 mL), and the solution was treated with 10% hydrogen chloride-methanol solution (3.6 mL). The obtained solid was collected by filtration and washed with methanol, followed by drying under reduced pressure to obtain Compound 147 (115 mg, yield 85%).

mp >295° C.; APCI-MS m/z: 407 [M+H]$^+$; $^1$H-NMR (DMSO-d$_6$) δ(ppm): 2.74-3.72 (m, 12H), 4.37 (m, 4H), 7.05 (s, 1H), 7.11 (d, J=8.4 Hz, 1H), 7.25 (d, J=7.2 Hz, 1H), 7.50 (d, J=8.4 Hz, 1H), 7.72 (s, 1H), 8.04 (d, J=8.6 Hz, 1H), 9.25 (s, 1H), 10.39 (s, 1H), 11.00-11.80 (br s, 2H), 13.85 (s, 1H).

EXAMPLE 148

4-(Furan-2-yl)-7-{1H-5-[4-(2-hydroxyethyl)piperazin-1-ylmethyl]indol-2-yl}isoindolinone dihydrochloride (Compound 148)

Step 1

In a similar manner to Step 2 of Example 1, 7-iodo-4-(furan-2-yl)isoindolinone (60.0 mg, 0.185 mmol) was dissolved in acetonitrile (4.2 mL), and the solution was treated with Compound BJ (149 mg, 0.370 mmol), palladium acetate (5.0 mg, 0.022 mmol), tri(o-tolyl)phosphine (13.5 mg, 0.044 mmol) and triethylamine (0.774 mL, 5.55 mmol), followed by purification by preparative thin-layer chromatography (chloroform/methanol=6/1) to obtain 4-(furan-2-yl)-7-{1-(tert-butoxycarbonyl)-5-[4-(2-hydroxyethyl)piperazin-1-ylmethyl]indol-2-yl}isoindolinone (30.4 mg, yield 30%).

APCI-MS m/z: 557 [M+H]$^+$; $^1$H-NMR (CDCl$_3$) δ(ppm): 1.34 (s, 9H), 2.55 (m, 10H), 3.61 (m, 4H), 4.70 (s, 2H), 6.39 (s, 1H), 6.57 (m, 2H), 6.71 (d, J=3.3 Hz, 1H), 7.28 (m, 1H), 7.49 (s, 1H), 7.50 (d, J=7.6 Hz, 1H), 7.58 (s, 1H), 7.90 (d, J=7.8 Hz, 1H), 8.18 (d, J=9.1 Hz, 1H).

Step 2

In a similar manner to Step 2 of Example 8, 4-(furan-2-yl)-7-(1-(tert-butoxycarbonyl)-5-[4-(2-hydroxyethyl)piperazin-1-ylmethyl]indol-2-yl)isoindolinone (22.7 mg, 0.0448 mmol) was dissolved in methanol (0.91 mL), and the solution was treated with 10% hydrogen chloride-methanol solution (1.36 mL). The obtained solid was collected by filtration and washed with methanol, followed by drying under reduced pressure to obtain Compound 148 (12.2 mg, yield 57%).

mp >295° C.; APCI-MS m/z: 457 [M+H]$^+$; $^1$H-NMR (DMSO-d$_6$) δ(ppm): 2.23-3.73 (m, 12H), 4.43 (m, 2H), 4.73 (s, 2H), 6.72 (dd; J=1.5, 3.5 Hz, 1H), 7.04 (d, J=3.1 Hz, 1H), 7.34 (m, 2H), 7.57 (d, J=8.7 Hz, 1H), 7.80 (s, 1H), 7.90 (s, 1H), 8.02 (d, J=8.2 Hz, 1H), 8.29 (d, J=8.2 Hz, 1H), 9.54 (s, 1H), 11.00-11.80 (br s, 2H), 14.15 (s, 1H).

EXAMPLE 149

4-[2-(Dimethylamino)ethoxy]-7-[1H-5-(piperidinomethyl)indol-2-yl]isoindolinone (Compound 149)

Step 1

4-Hydroxy-7-[1-(tert-butoxycarbonyl)-5-(piperidinomethyl)indol-2-yl]isoindolinone (60.0 mg, 0.130 mmol) was dissolved in THF (3.6 mL), and the solution was added with triphenylphosphine (68 mg, 0.26 mmol), 2-dimethylaminoethanol (0.026 mL, 0.26 mmol) and 40% DEAD-toluene solution (0.118 mL) under ice-cooling, followed by stirring for 20 minutes. The reaction mixture was warmed to room temperature and stirred for 14 hours. The mixture was added with triphenylphosphine (68 mg, 0.26 mmol), 2-dimethylaminoethanol (0.026 mL, 0.26 mmol) and 40% DEAD-toluene solution (0.118 mL) and stirred for 1.7 hours. Then, the mixture was further added with triphenylphosphine (34 mg, 0.13 mmol), 2-dimethylaminoethanol (0.026 mL, 0.26 mmol) and 40% DEAD-toluene solution (0.059 mL), followed by stirring for 1.3 hours. The reaction mixture was added with water and extracted with ethyl acetate. The organic layer was washed with saturated brine and dried over anhydrous sodium sulfate. The solvent was evaporated under reduced pressure and the residue was purified by preparative thin-layer chromatography (chloroform/methanol/7 mol/L ammonia-methanol solution=12/0.5/0.5, chloroform/methanol=3/1) to obtain 4-[2-(dimethylamino)ethoxy]-7-[1-(tert-butoxycarbonyl)-5-(piperidinomethyl)indol-2-yl]isoindolinone (36.9 mg, yield 53%).

ESI-MS m/z: 533 [M+H]$^+$; $^1$H-NMR (CDCl$_3$) δ(ppm): 1.32 (s, 9H), 1.42 (m, 2H), 1.59 (m, 4H), 2.37 (s, 6H), 2.42 (m, 4H), 2.79 (t, J=5.6 Hz, 2H), 3.59 (s, 2H), 4.21 (t, J=5.6 Hz, 2H), 4.36 (s, 2H), 6.49 (s, 1H), 7.01 (d, J=8.2 Hz, 1H), 7.27 (m, 1H), 7.33 (s, 1H), 7.38 (d, J=8.1 Hz, 1H), 7.47 (s, 1H), 8.16 (d, J=8.6 Hz, 1H).

Step 2

In a similar manner to Step 2 of Example 8, 4-[2-(dimethylamino)ethoxy]-7-[1-(tert-butoxycarbonyl)-5-(piperidinomethyl)indol-2-yl]isoindolinone (58.9 mg, 0.111 mmol) was dissolved in methanol (1.8 mL), and the solution was treated with 10% hydrogen chloride-methanol solution (1.8 mL). The solvent was evaporated under reduced pressure and the residue was purified by preparative thin-layer chromatography (chloroform/methanol/7 mol/L ammonia-methanol solution=12/0.5/0.5) to obtain Compound 149 (35.7 mg, yield 74%).

APCI-MS m/z: 433 [M+H]$^+$; $^1$H-NMR (DMSO-d$_6$) δ(ppm): 1.39 (m, 2H), 1.48 (m, 4H), 2.23 (s, 6H), 2.33 (m, 4H), 2.67 (t, J=5.6 Hz, 2H), 3.45 (s, 2H), 4.23 (t, J=5.8 Hz, 2H), 4.36 (s, 2H), 7.02 (m, 2H), 7.33 (d, J=8.6 Hz, 1H), 7.34 (d, J=8.4 Hz, 1H), 7.39 (s, 1H), 8.10 (d, J=8.7 Hz, 1H), 9.25 (s, 1H), 13.56 (s, 1H).

EXAMPLE 150

4-(3-Aminopropoxy)-7-[1H-5-(piperidinomethyl)indol-2-yl]isoindolinone (Compound 150)

Step 1

In a similar manner to Step 1 of Example 149, 4-hydroxy-7-[1-(tert-butoxycarbonyl)-5-(piperidinomethyl)indol-2-yl]isoindolinone (60.0 mg, 0.130 mmol) was dissolved in THF (3.6 mL), and the solution was treated with triphenylphosphine (136 mg, 0.78 mmol), tert-butyl N-(3-hydroxypropyl)carbamate (92 mg, 0.52 mmol) and 40% DEAD-toluene solution (0.236 mL), followed by purification by preparative thin-layer chromatography (chloroform/methanol=4/1) to obtain 4-[(3-(tert-butoxycarbonylamino)propoxy]-7-[1-(tert-butoxycarbonyl)-5-(piperidinomethyl)indol-2-yl]isoindolinone (70.5 mg, yield 88%).

APCI-MS m/z: 619 [M+H]$^+$; $^1$H-NMR (CDCl$_3$) δ(ppm): 1.37 (s, 9H), 1.43 (m, 2H), 1.45 (s, 9H), 2.04 (m, 2H), 2.40 (m, 4H), 3.35 (m, 2H), 3.58 (s, 2H), 4.17 (t, J=5.9 Hz, 2H), 4.37 (s, 2H), 4.75 (br s, 1H), 6.33 (s, 1H), 6.49 (d, J=0.7 Hz, 1H), 7.01 (d, J=8.3 Hz, 1H), 7.25 (m, 1H), 7.39 (d, J=8.3 Hz, 1H), 7.46 (s, 1H), 8.12 (d, J=8.4 Hz, 1H).

Step 2

In a similar manner to Step 3 of Example 1, 4-[3-(tert-butoxycarbonylamino)propoxy]-7-[1-(tert-butoxycarbonyl)-5-(piperidinomethyl)indol-2-yl]isoindolinone (70.0 mg, 0.113 mmol) was dissolved in methanol (2.1 mL), and the solution was treated with 10% hydrogen chloride-methanol solution (2.1 mL), followed by purification by preparative thin-layer chromatography (chloroform/methanol/7 mol/L ammonia-methanol solution=15/0.5/0.5) to obtain Compound 150 (22.4 mg, yield 47%).

APCI-MS m/z: 419 [M+H]$^+$; $^1$H-NMR (DMSO-d$_6$) δ(ppm): 1.39 (m, 2H), 1.47 (m, 4H), 1.81 (m, 2H), 2.32 (m, 4H), 2.71 (t, J=6.6 Hz, 2H), 3.45 (s, 2H), 4.22 (t, J=6.3 Hz, 2H), 4.37 (s, 2H), 7.00 (s, 1H), 7.02 (d, J=8.1 Hz, 1H), 7.31 (d, J=8.2 Hz, 1H), 7.34 (d, J=7.9 Hz, 1H), 7.39 (s, 1H), 8.10 (d, J=8.7 Hz, 1H), 9.26 (br s, 1H), 13.57 (s, 1H).

EXAMPLE 151

4-(3-Hydroxypropoxy)-7-[1H-5-(piperidinomethyl)indol-2-yl]isoindolinone (Compound 151)

Step 1

In a similar manner to Step 1 of Example 149, 4-hydroxy-7-[1-(tert-butoxycarbonyl)-5-(piperidinomethyl)indol-2-yl]isoindolinone (80.0 mg, 0.173 mmol) was dissolved in THF (4.0 mL), and the solution was treated with triphenylphosphine (136 mg, 0.519 mmol), 3-(tert-butyldimethylsilyloxy)propanol (0.111 mL, 0.519 mmol) and 40% DEAD-toluene solution (0.237 mL), followed by purification by preparative thin-layer chromatography (chloroform/methanol=4/1) to obtain 4-[3-(tert-butyldimethylsilyloxy)propoxy]-7-[1-(tert-butoxycarbonyl)-5-(piperidinomethyl)indol-2-yl]isoindolinone (58.6 mg, yield 53%).

APCI-MS m/z: 634 [M+H]$^+$; $^1$H-NMR (CDCl$_3$) δ(ppm): 0.06 (s, 6H), 0.90 (s, 9H), 1.31 (s, 9H), 1.47 (m, 2H), 1.74 (m, 4H), 2.03 (m, 2H), 2.64 (m, 4H), 3.82 (t, J=6.0 Hz, 2H), 3.84 (s, 2H), 4.21 (t, J=6.2 Hz, 2H), 4.36 (s, 2H), 6.51 (s, 1H), 7.04 (d, J=8.3 Hz, 1H), 7.28-7.42 (m, 3H), 7.55 (s, 1H), 8.20 (d, J=8.4 Hz, 1H).

Step 2

In a similar manner to Step 2 of Example 8, 4-[3-(tert-butyldimethylsilyloxy)propoxy]-7-[1-(tert-butoxycarbonyl)-5-(piperidinomethyl)indol-2-yl]isoindolinone (58.6 mg, 0.0924 mmol) was dissolved in methanol (1.8 mL), and the solution was treated with 10% hydrogen chloride-methanol solution (1.8 mL). The solvent was evaporated under reduced pressure and the residue was purified by preparative thin-layer chromatography (chloroform/methanol/7 mol/L ammonia-methanol solution=15/0.5/0.5) to obtain Compound 151 (13.7 mg, yield 35%).

APCI-MS m/z: 420 [M+H]$^+$; $^1$H-NMR (DMSO-d$_6$) δ(ppm): 1.39-1.51 (m, 6H), 1.90 (m, 2H), 2.48 (m, 4H), 3.31-3.59 (m, 4H), 4.22 (t, J=6.2 Hz, 2H), 4.37 (s, 2H), 4.58 (br s, 1H), 7.02 (s, 1H), 7.04 (d, J=8.6 Hz, 1H), 7.31 (d, J=8.6 Hz, 1H), 7.36 (d, J=8.3 Hz, 1H), 7.43 (s, 1H), 8.11 (d, J=8.4 Hz, 1H), 9.27 (s, 1H), 13.60 (s, 1H).

EXAMPLE 152

4-(4-Hydroxy-3-methoxy-5-nitrophenyl)-7-[1H-5-(piperidinomethyl)indol-2-yl]isoindolinone hydrochloride (Compound 152)

Step 1

7-Amino-4-bromoisoindolinone (150 mg, 0.661 mmol) was dissolved in dimethoxythane (10.5 mL), and the solution was added with 2-methoxy-4-(4,4,5,5-tetramethyl-1,3,2-dioxaboran-2-yl)phenol (331 mg, 1.32 mmol), [bis(diphenylphosphino)ferrocene]dichloropalladium (43.2 mg, 0.0529 mmol) and potassium carbonate (456 mg, 3.31 mmol), and stirred at 90° C. for 4.3 hours under argon atmosphere. The reaction mixture was added with water and extracted with ethyl acetate. The organic layer was washed with saturated brine and dried over anhydrous sodium sulfate. The solvent was evaporated under reduced pressure and the residue was purified by preparative thin-layer chromatography (chloroform/acetonitrile=4/1, chloroform/methanol=10/1) to obtain 7-amino-4-(4-hydroxy-3-methoxyphenyl)isoindolinone (169 mg, yield 94%).

APCI-MS m/z: 271 [M+H]$^+$; $^1$H-NMR (DMSO-d$_6$) δ(ppm): 3.79 (s, 3H), 4.37 (s, 2H), 6.10 (s, 2H), 6.63 (d, J=+8.4 Hz, 1H), 6.78 (d, J=8.1 Hz, 1H), 6.85 (d, J=8.2 Hz, 1H), 6.97 (s, 1H), 7.27 (d, J=8.2 Hz, 1H), 8.21 (s, 1H), 8.93 (s, 1H).

Step 2

In a similar manner to Step 4 of Example 140, 7-amino-4-(4-hydroxy-3-methoxyphenyl)isoindolinone (202 mg, 0.747 mmol) was dissolved in acetonitrile (10.1 mL), and the solution was treated with potassium iodide (149 mg, 0.896 mmol), copper iodide (171 mg, 0.896 mmol), iodine (228 mg, 0.896 mmol) and tert-butyl nitrite (0.266 mL, 0.896 mmol), followed by purification by preparative thin-layer chromatography (chloroform/methanol=15/1) to obtain 7-iodo-4-(4-hydroxy-3-methoxy-5-nitrophenyl)isoindolinone (100 mg, yield 31%).

APCI-MS m/z: 427 [M+H]$^+$; $^1$H-NMR (DMSO-d$_6$) δ(ppm): 3.93 (s, 3H), 4.42 (s, 2H), 7.40 (d, J=8.1 Hz, 1H), 7.44 (d, J=1.6 Hz, 1H), 7.60 (d, J=1.5 Hz, 1H), 7.99 (d, J=8.1 Hz, 1H), 8.30 (s, 1H), 8.85 (s, 1H).

Step 3

In a similar manner to Step 2 of Example 1, 7-iodo-4-(4-hydroxy-3-methoxy-5-nitrophenyl)isoindolinone (40.0 mg, 0.0939 mmol) was dissolved in acetonitrile (2.8 mL), and the solution was treated with Compound BD (75.0 mg, 0.207 mmol), palladium acetate (1.9 mg, 0.0085 mmol), tri(o-tolyl)phosphine (5.1 mg, 0.017 mmol) and triethylamine (0.146 mL, 1.05 mmol), followed by purification by preparative thin-layer chromatography (chloroform/methanol=4/1) to obtain 4-(4-hydroxy-3-methoxy-5-nitrophenyl)-7-[1-(tert-butoxycarbonyl)-5-(piperidinomethyl)indol-2-yl]isoindolinone (29.8 mg, yield 52%).

ESI-MS m/z: 613 [M+H]$^+$; $^1$H-NMR (DMSO-d$_6$) δ(ppm): 1.20 (s, 9H), 1.35 (m, 2H), 1.41 (m, 4H), 2.55 (m, 4H), 3.73 (s, 2H), 3.85 (s, 3H), 4.54 (s, 2H), 6.58 (s, 1H), 7.25 (s, 1H), 7.30 (d, J=8.4 Hz, 1H), 7.48 (d, J=7.9 Hz, 1H), 7.52 (s, 1H), 7.62 (s, 1H), 7.70 (d, J=7.6 Hz, 1H), 8.10 (d, J=8.6 Hz, 1H), 8.30 (s, 1H), 8.67 (s, 1H).

Step 4

In a similar manner to Step 2 of Example 8, 4-(4-hydroxy-3-methoxy-5-nitrophenyl)-7-[1-(tert-butoxycarbonyl)-5-(piperidinomethyl)indol-2-yl]isoindolinone (26.5 mg, 0.0432 mmol) was dissolved in methanol (1.1 mL), and the solution was treated with 10% hydrogen chloride-methanol solution (1.1 mL). The obtained solid was collected by filtration and washed with methanol, followed by drying under reduced pressure to obtain Compound 152 (13.1 mg, yield 55%).

ESI-MS m/z: 513 [M+H]$^+$; $^1$H-NMR (DMSO-d$_6$) δ(ppm): 1.53-1.74 (m, 6H), 3.07 (m, 2H), 3.95 (s, 3H), 4.31 (s, 2H), 4.66 (s, 2H), 7.27 (d, J=8.7 Hz, 1H), 7.36 (s, 1H), 7.49 (d, J=1.8 Hz, 1H), 7.57 (d, J=8.2 Hz, 1H), 7.65 (d, J=2.0 Hz, 1H), 7.57 (m, 2H), 8.31 (d, J=8.4 Hz, 1H), 9.45 (s, 1H), 10.20 (br s, 1H), 14.15 (s, 1H).

EXAMPLE 153

4-Hydroxy-7-[1H-5-(3-hydroxypiperidinomethyl)indol-2-yl]isoindolinone (Compound 153)

Step 1

In a similar manner to Step 2 of Example 147, 4-hydroxy-7-[(1-(tert-butoxycarbonyl)-5-formylindol-2-yl]isoindolinone (60.0 mg, 0.153 mmol) was dissolved in acetonitrile (3 mL), and the solution was treated with 3-hydroxypiperidine (62.0 mg, 0.612 mmol), acetic acid (0.175 mL, 3.06 mmol) and sodium triacetoxyborohydride (151 mg, 0.714 mmol), and then with sodium triacetoxyborohydride (260 mg, 1.22 mmol). The reaction mixture was added with 1 mol/L hydrochloric acid and extracted with ethyl acetate. The organic layer was washed with saturated sodium carbonate and saturated brine, and dried over anhydrous sodium sulfate. The solvent was evaporated under reduced pressure to obtain 4-hydroxy-7-[1-(tert-butoxycarbonyl)-5-(3-hydroxypiperidinomethyl)indol-2-yl]isoindolinone (59.4 mg, yield 81%).

APCI-MS m/z: 478 [M+H]$^+$; $^1$H-NMR (DMSO-d$_6$) δ(ppm): 1.16 (s, 9H), 1.32-1.90 (m, 4H), 2.65-2.81 (m, 2H), 3.28-3.42 (m, 2H), 3.45 (d, J=12.5 Hz, 1H), 3.60 (d, J=12.7 Hz, 1H), 4.24 (s, 2H), 4.50 (d, J=4.9 Hz, 1H), 6.48 (s, 1H), 6.99 (d, J=8.1 Hz, 1H), 7.22 (m, 2H), 7.45 (s, 1H), 8.06 (d, J=8.4 Hz, 1H), 8.51 (s, 1H), 10.17 (br s, 1H).

Step 2

In a similar manner to Step 2 of Example 8, 4-hydroxy-7-[1-(tert-butoxycarbonyl)-5-(3-hydroxypiperidinomethyl)indol-2-yl]isoindolinone (57.4 mg, 0.120 mmol) was dissolved in methanol (1.7 mL), and the solution was treated with 10% hydrogen chloride-methanol solution (2.6 mL). The reaction mixture was added with diisopropylether and purified by slurry to obtain Compound 153 (21 mg, yield 42%).

APCI-MS m/z: 378 [M+H]$^+$; $^1$H-NMR (DMSO-d$_6$) δ(ppm): 1.01-2.23 (m, 4H), 2.75-3.59 (m, 4H), 4.00-4.20 (m, 3H), 4.37 (s, 2H), 7.06 (s, 1H), 7.12 (d, J=8.4 Hz, 1H), 7.22 (m, 1H), 7.50 (d, J=8.2 Hz, 1H), 7.70 (s, 1H), 8.03 (d, J=8.2 Hz, 1H), 9.26 (s, 1H), 10.10 (br s, 1H), 10.41 (br. s, 1H), 13.85 (s, 1H).

EXAMPLE 154

3-Amino-6-[1-(phenylsulfonyl)indol-2-yl]phtalimide (Compound 154)

In a similar manner to Step 2 of Example 1, 3-amino-6-bromophthalimide (50.0 mg, 0.207 mmol) was dissolved in acetonitrile (3.5 mL), and the solution was treated with 1-(phenylsulfonyl)-1H-indolyl-2-boronic acid (125 mg, 0.414 mmol), palladium acetate (3.7 mg, 0.017 mmol), tri(o-tolyl)phosphine (10 mg, 0.033 mmol) and triethylamine (0.289 mL, 2.07 mmol), followed by purification by preparative thin-layer chromatography (chloroform/methanol=9/1) to obtain Compound 154 (32.9 mg, yield 38%).

APCI-MS m/z: 416 [M−H]$^-$; $^1$H-NMR (DMSO-d$_6$) δ(ppm): 6.65 (s, 2H), 6.77 (s, 1H), 6.99 (d, J=8.6 Hz, 1H), 7.26 (dd, J=7.1, 7.2 Hz, 1H), 7.36 (m, 2H), 7.43-7.47 (m, 4H), 7.53-7.61 (m, 2H), 8.07 (d, J=8.2 Hz, 1H), 10.89 (s, 1H).

EXAMPLE 155

4-Chloro-7-[1-(phenylsulfonyl)indol-2-yl]isoindolinone (Compound 155)

In a similar manner to Step 2 of Example 1, 4-chloro-7-iodoisoindolinone (50.0 mg, 0.170 mmol) was dissolved in acetonitrile (3.5 mL), and the solution was treated with 1-(phenylsulfonyl)-1H-indolyl-2-boronic acid (102 mg, 0.340 mmol), palladium acetate (3.1 mg, 0.014 mmol), tri(o-tolyl)phosphine (8.3 mg, 0.027 mmol) and triethylamine (0.047 mL, 0.34 mmol), followed by purification by preparative thin-layer chromatography (chloroform/methanol=60/1) to obtain Compound 155 (69 mg, yield 96%).

APCI-MS m/z: 423 [M+H]$^+$; $^1$H-NMR (DMSO-d$_6$) δ(ppm): 4.37 (d, J=17.1 Hz, 1H), 4.44 (d, J=17.1 Hz, 1H), 6.79 (s, 1H), 7.27 (dd, J=7.2, 7.9 Hz, 1H), 7.35 (ddd, J=1.3, 7.2, 8.3 Hz, 1H), 7.43-7.62 (m, 7H), 7.75 (d, J=8.1 Hz, 1H), 8.00 (d, J=8.1 Hz, 1H), 8.78 (s, 1H).

EXAMPLE 156

4-Chloro-7-(1-methylindol-2-yl)isoindolinone (Compound 156)

In a similar manner to Step 2 of Example 1, 4-chloro-7-iodoisoindolinone (84.0 mg, 0.286 mmol) was dissolved in acetonitrile (3 mL), and the solution was treated with Compound BK (100 mg, 0.571 mmol), palladium acetate (5.2 mg, 0.023 mmol) and triethylamine (0.400 mL, 2.87 mmol), followed by purification by flash column chromatography (hexane/ethyl acetate=7/3, 3/2, 1/1) to obtain Compound 156 (69.7 mg, yield 82%).

APCI-MS m/z: 297. [M+H]$^+$; $^1$H-NMR (DMSO-d$_6$) δ(ppm): 3.51 (s, 3H), 4.43 (s, 2H), 6.48 (s, 1H), 7.07 (m, 1H), 7.19 (m, 1H), 7.46 (m, 1H), 7.49 (d, J=8.1 Hz, 1H), 7.57 (d, J=7.9 Hz, 1H), 7.78 (d, J=8.1 Hz, 1H), 8.87 (br s, 1H).

EXAMPLE 157

4-Chloro-7-(5-carboxy-1-methylindol-2-yl)isoindolinone (Compound 157)

In a similar manner to Step 1 of Example 19, 4-chloro-7-iodoisoindolinone (47.0 mg, 0.160 mmol) was dissolved in DMF (2 mL), and the solution was treated with Compound BL (70.0 mg, 0.320 mmol), palladium acetate (2.9 mg, 0.013 mmol) and triethylamine (0.223 mL, 1.60 mmol). The reaction mixture was added with 1 mol/L hydrochloric acid and extracted with ethyl acetate. The organic layer was washed with saturated brine and dried over anhydrous sodium sulfate. The solvent was evaporated under reduced pressure. The residue was dissolved in methanol, and the solution was added with diisopropylether and stirred for 1 hour. The obtained solid was collected by filtration and washed with diisopropylether, followed by drying under reduced pressure to obtain Compound 157 (31.7 mg, yield 58%).

APCI-MS m/z: 341 [M+H]$^+$; $^1$H-NMR (DMSO-d$_6$) δ(ppm): 3.54 (s, 3H), 4.44 (s, 2H), 6.64 (s, 1H), 7.52 (d, J=8.1 Hz, 1H), 7.55 (d, J=8.8 Hz, 1H), 7.80 (d, J=8.1 Hz, 1H), 7.81 (dd, J=1.5, 8.8 Hz, 1H), 8.26 (d, J=1.5 Hz, 1H), 8.90 (s, 1H), 12.47 (br s, 1H).

EXAMPLE 158

4-Chloro-7-(6-carboxy-1-methylindol-2-yl)isoindolinone (Compound 158)

In a similar manner to Step 1 of Example 19, 4-chloro-7-iodoisoindolinone (47.0 mg, 0.160 mmol) was dissolved in DMF (2 mL), and the solution was treated with Compound BM (70.0 mg, 0.320 mmol), palladium acetate (2.9 mg, 0.013 mmol) and triethylamine (0.223 mL, 1.60 mmol). The reaction mixture was added with water and ethyl acetate. The obtained solid was collected by filtration and washed with water and ethyl acetate, followed by drying under reduced pressure to obtain Compound 158 (34.7 mg, yield 63%).

APCI-MS m/z: 341 [M+H]$^+$; $^1$H-NMR (DMSO-d$_6$) δ(ppm): 3.57 (s, 3H), 4.44 (s, 2H), 6.58 (s, 1H), 7.52 (d, J=8.1 Hz, 1H), 7.63 (d, J=8.3 Hz, 1H), 7.69 (dd, J=1.3, 8.3 Hz, 1H), 7.81 (d, J=8.1 Hz, 1H), 8.10 (s, 1H), 8.90 (s, 1H), 12.62 (br s, 1H).

EXAMPLE 159

4-Chloro-7-{5-[4-(2-hydroxyethyl)piperazin-1-ylcarbonyl]-1-methylindol-2-yl}isoindolinone (Compound 159)

In a similar manner to Step 1 of Example 20, Compound 157 (20.0 mg, 0.0587 mmol) was dissolved in DMF (1 mL), and the solution was treated with EDCI (23 mg, 0.12 mmol), HOBT monohydrate (7.9 mg, 0.059 mmol) and 1-(2-hydroxyethyl)piperazine (31 mg, 0.24 mmol). The mixture was added with water and ethyl acetate and extracted with 1 mol/L hydrochloric acid. The aqueous layer was added with sodium carbonate to adjust the pH to 9 and extracted with ethyl acetate. The organic layer was washed with saturated brine and dried over anhydrous sodium sulfate. The solvent was evaporated under reduced pressure. The residue was dissolved in chloroform, and the solution was added with hexane and stirred for 30 minutes. The solid was collected by filtration and washed with hexane, followed by drying under reduced pressure to obtain Compound 159 (18.5 mg, yield 70%).

APCI-MS m/z: 453 [M+H]$^+$; $^1$H-NMR (DMSO-d$_6$) δ(ppm): 2.37-2.46 (m, 6H), 3.46-3.62 (m, 6H), 3.52 (s, 3H), 4.42 (m, 1H), 4.44 (s, 2H), 6.55 (s, 1H), 7.22 (dd, J=1.3, 8.4 Hz, 1H), 7.50 (d, J=8.1 Hz, 1H), 7.52 (d, J=8.4 Hz, 1H), 7.62 (d, J=11.3 Hz, 1H), 7.79 (d, J=8.1 Hz, 1H), 8.89 (br s, 1H).

EXAMPLE 160

4-Chloro-7-{6-[4-(2-hydroxyethyl)piperazin-1-ylcarbonyl]-1-methylindol-2-yl}isoindolinone (Compound 160)

In a similar manner to Step 1 of Example 20, Compound 158 (20.0 mg, 0.0587 mmol) was dissolved in DMF (1 mL), and the solution was treated with EDCI (23 mg, 0.12 mmol), HOBT monohydrate (7.9 mg, 0.059 mmol) and 1-(2-hydroxyethyl)piperazine (31 mg, 0.24 mmol). The mixture was added with water and ethyl acetate, and then extracted with 1 mol/L hydrochloric acid. The aqueous layer was added with sodium carbonate to adjust the pH to 9 and extracted with ethyl acetate. The organic layer was washed with saturated brine and dried over anhydrous sodium sulfate. The solvent was evaporated under reduced pressure. The residue was dissolved in chloroform, and the solution was added with hexane and stirred for 30 minutes. The solid was collected by filtration, washed with hexane and dried under reduced pressure to obtain Compound 160 (16.6 mg, yield 62%).

APCI-MS m/z: 453 [M+H]$^+$; $^1$H-NMR (DMSO-d$_6$) δ(ppm): 2.39-2.48 (m, 6H), 3.47-3.60 (m, 6H), 3.52 (s, 3H), 4.44 (br s, 3H), 6.53 (s, 1H), 7.09 (dd, J=1.1, 8.1 Hz, 1H), 7.49 (br s, 1H), 7.52 (d, J=8.1 Hz, 1H), 7.60 (d, J=8.1 Hz, 1H), 7.79 (d, J=8.1 Hz, 1H), 8.89 (s, 1H).

EXAMPLE 161

3-Amino-6-[1H-3-(4-hydroxy-1-butynyl)indol-2-yl] phtalimide (Compound 161)

Step 1

3-Amino-6-[1-(tert-butoxycarbonyl)indol-2-yl]phtalimide (300 mg, 0.795 mmol) was dissolved in ethanol (21 mL), and the solution was added with iodine (242 mg, 0.954 mmol) and silver sulfate (248 mg, 0.795 mmol), followed by stirring at room temperature for 1.3 hours. The reaction mixture was added with water and extracted with ethyl acetate. The organic layer was washed with saturated brine and dried over anhydrous sodium sulfate. The solvent was evaporated under reduced pressure and the residue was purified by slurry using chloroform to obtain 3-amino-6-[1-(tert-butoxycarbonyl)-3-iodoindol-2-yl]phtalimide (326 mg, yield 82%).

APCI-MS m/z: 502 [M–H]$^-$; $^1$H-NMR (DMSO-d$_6$) δ(ppm): 1.21 (s, 9H), 6.64 (s, 2H), 7.05 (d, J=8.4 Hz, 1H), 7.32-7.45 (m, 4H), 8.13 (d, J=7.9 Hz, 1H), 10.98 (s, 1H).

Step 2

3-Amino-6-[1-(tert-butoxycarbonyl)-3-iodoindol-2-yl] phtalimide (150 mg, 0.298 mmol) was dissolved in diethylamine (7.5 mL), and the solution was added with bis(triphenylphosphine)dichloropalladium (16.7 mg, 0.0234 mmol), copper iodide (11.4 mg, 0.0596 mmol) and 3-butyn-1-ol (0.226 mL, 2.98 mmol), followed by stirring at 50° C. for 3.7 hours under argon atmosphere. The reaction mixture was added with water and extracted with ethyl acetate. The organic layer was washed with saturated brine and dried over anhydrous sodium sulfate. The solvent was evaporated under reduced pressure and the residue was purified by preparative thin-layer chromatography (chloroform/methanol=10/1) to obtain 3-amino-6-[1-(tert-butoxycarbonyl)-3-(4-hydroxy-1-butynyl)indol-2-yl]phtalimide (115 mg, yield 87%).

APCI-MS m/z: 444 [M–H]$^-$; $^1$H-NMR (CDCl$_3$+CD$_3$OD) δ(ppm): 2.62 (t, J=6.8 Hz, 2H), 3.70 (t, J=6.8 Hz, 2H), 6.96 (d, J=8.6 Hz, 1H), 7.26-7.39 (m, 2H), 7.57 (d, J=8.4 Hz, 1H), 7.65 (d, J=7.3 Hz, 1H), 8.17 (d, J=8.3 Hz, 1H).

Step 3

3-Amino-6-[1-(tert-butoxycarbonyl)-3-(4-hydroxy-1-butynyl)indol-2-yl]phtalimide (40.0 mg, 0.0898 mmol) was dissolved in dichloromethane (2.0 mL). The solution was treated with trifluoroacetic acid (1 mL) and stirred at room temperature for 1 hour. The reaction mixture was added with saturated aqueous sodium hydrogencarbonate solution and extracted with ethyl acetate. The organic layer was washed with saturated brine and dried over anhydrous sodium sulfate. The solvent was evaporated under reduced pressure and the residue was purified by preparative thin-layer chromatography (chloroform/methanol=6/1) to obtain Compound 161 (19 mg, yield 61%).

APCI-MS m/z: 346 [M+H]$^-$; $^1$H-NMR (DMSO-d$_6$) δ(ppm): 2.46 (m, 2H), 3.21 (m, 2H), 4.31 (t, 34.8 Hz, 1H), 6.70 (s, 2H), 7.04 (d, J=8.6 Hz, 1H), 7.19 (m, 2H), 7.38 (m, 1H), 7.47 (d, J=8.6 Hz, 1H), 8.17 (m, 1H), 10.99 (s, 1H), 11.90 (s, 1H).

EXAMPLE 162

4-Chloro-7-[1H-3-(4-hydroxy-1-butynyl)indol-2-yl] isoindolinone (Compound 162)

Step 1

In a similar manner to Step 1 of Example 161, 4-chloro-7-(1-(tert-butoxycarbonyl)-indol-2-yl)isoindolinone (374 mg, 0.980 mmol) was dissolved in ethanol (26 mL), and the solution was treated with iodine (299 mg, 1.18 mmol) and silver sulfate (306 mg, 0.980 mmol), followed by purification by slurry using hexane and diisopropylether to obtain 4-chloro-7-[1-(tert-butoxycarbonyl)-3-iodoindol-2-yl]isoindolinone (179 mg, yield 36%).

APCI-MS m/z: 509 [M+H]$^+$; $^1$H-NMR (DMSO-d$_6$) δ(ppm): 1.13 (s, 9H), 4.39 (d, J=18.5 Hz, 1H), 4.48 (d, J=18.5 Hz, 1H), 7.34-7.46 (m, 3H), 7.49 (d, J=8.1 Hz, 1H), 7.80 (d, J=8.1 Hz, 1H), 8.16 (d, J=7.9 Hz, 1H), 8.87 (s, 1H).

Step 2

In a similar manner to Step 2 of Example 161, 4-chloro-7-[1-(tert-butoxycarbonyl)-3-iodoindol-2-yl]isoindolinone (148 mg, 0.291 mmol) was dissolved in diethylamine (7.4 mL), and the Solution was treated with bis(triphenylphosphine)dichloropalladium (16.3 mg, 0.0233 mmol), copper iodide (11.1 mg, 0.0582 mmol) and 3-butyn-1-ol (0.220 mL, 2.91 mmol), followed by purification by preparative thin-layer chromatography (chloroform/methanol=10/1) to obtain 4-chloro-7-[1-(tert-butoxycarbonyl)-3-(4-hydroxy-1-butynyl)indol-2-yl]isoindolinone (114 mg, yield 87%).

APCI-MS m/z: 451 [M+H]$^+$; $^1$H-NMR (DMSO-d$_6$) δ(ppm): 1.17 (s, 9H), 2.46 (m, 2H), 3.48 (m, 2H), 4.38 (d, J=18.3 Hz, 1H), 4.46 (d. J=18.7 Hz, 1H), 4.83 (t, J=5.6 Hz, 1H), 7.33 (dd, J=6.2, 7.5 Hz, 1H), 7.41 (ddd, J=1.5, 7.0, 8.4 Hz, 1H), 7.59 (d, J=8.3 Hz, 1H), 7.62 (d, J=9.2 Hz, 1H), 7.77 (d, J=8.1 Hz, 1H), 8.16 (d, J=8.1 Hz. 1H), 8.89 (s, 1H).

Step 3

In a similar manner to Step 3 of Example 161, 4-chloro-7-[(1-(tert-butoxycarbonyl)-3-(4-hydroxy-1-butynyl)indol-2-yl]isoindolinone (82.4 mg, 0.183 mmol) was dissolved in dichloromethane (4.1 mL), and the solution was treated with trifluoroacetic acid (1 mL), followed by purification by preparative thin-layer chromatography (chloroform/methanol=10/1) to obtain Compound 162 (38.8 mg, yield 60%).

APCI-MS m/z: 351 [M+H]$^+$: $^1$H-NMR (DMSO-d$_6$) δ(ppm): 2.38 (t, J=7.2 Hz, 2H), 3.18 (m, 2H), 4.28 (t, J=5.2 Hz, 1H), 4.44 (s, 2H), 7.22 (m, 2H), 7.40 (m, 1H), 7.58 (d, J=8.1 Hz, 1H), 7.78 (d, J=8.1 Hz, 1H), 8.17 (m, 1H), 8.88 (s, 1H), 12.01 (s, 1H).

EXAMPLE 163

4-Chloro-7-[1H-3-dimethylaminomethyl-5-(piperidinomethyl)indol-2-yl]isoindolinone (Compound 163)

Compound 29 (25.0 mg, 0.0600 mmol) was suspended in acetic acid (0.5 mL), and the suspension was added with 50% aqueous dimethylamine solution (0.024 mL, 0.24 mmol) and 37% aqueous formamide solution (23 mg, 0.12 mmol), followed by stirring at room temperature for 10 hours. The reaction mixture was added with water and sodium carbonate to adjust the pH to 9, and extracted with ethyl acetate. The organic layer was washed with water and saturated brine and then dried over anhydrous sodium sulfate. The solvent was evaporated under reduced pressure. The residue was dissolved in ethyl acetate, and the solution was added with hexane and stirred for 30 minutes. The solid was collected by filtration and washed with hexane, followed by drying under reduced pressure to obtain Compound 163 (12.0 mg, yield 46%).

ESI-MS m/z: 437 [M+H]$^+$; $^1$H-NMR (DMSO-d$_6$) δ(ppm): 1.32-1.56 (m, 6H), 2.14 (s, 6H), 2.29-2.40 (m, 4H), 3.47 (s, 2H), 3.49 (s, 2H), 4.45 (s, 2H), 7.08 (d, J=8.4 Hz, 1H), 7.33 (d, J=8.4 Hz, 1H), 7.54 (s, 1H), 7.78 (d, J=8.1 Hz, 1H), 8.13 (d. J=8.1 Hz, 1H), 9.10 (s, 1H), 12.16 (s, 1H).

EXAMPLE 164

4-Chloro-7-[1H-3-bromo-5-(piperidinomethyl)indol-2-yl]isoindolinone (Compound 164)

Compound 29 (30.0 mg, 0.0721 mmol) was suspended in THF (2 mL), and the suspension was added with triethylamine (0.100 mL, 0.715 mmol), water (1 mL) and N-bromosuccineimide (12.8 mg, 0.719 mmol), followed by stirring at room temperature for 20 hours. The reaction mixture was added with water and extracted with ethyl acetate. The organic layer was washed with saturated brine, followed by drying over anhydrous sodium sulfate. The solvent was evaporated under reduced pressure. The residue was suspended in hexane, and the solid was collected by filtration and washed with hexane, followed by drying under reduced pressure to obtain Compound 164 (29.1 mg, yield 88%).

ESI-MS m/z: 458 [M+H]$^+$; $^1$H-NMR (DMSO-d$_6$) δ(ppm): 1.33-1.56 (m, 6H), 2.29-2.40 (m, 4H), 3.52 (s, 2H), 4.46 (s, 2H), 7.17 (d, J=8.2 Hz, 1H), 7.34 (s, 1H), 7.39 (d, J=8.2 Hz, 1H), 7.82 (d, J=8.4 Hz, 1H), 7.90 (d, J=8.4 Hz, 1H), 9.07 (br s, 1H), 12.24 (s, 1H).

EXAMPLE 165

4-Chloro-7-[1H-3-chloro-5-(piperidinomethyl)indol-2-yl]isoindolinone (Compound 165)

Compound 29 (30.0 mg, 0.0721 mmol) was dissolved in THF (4 mL), and the solution was added with triethylamine (0.100 mL, 0.715 mmol), water (2 mL) and N-chlorosuccineimide (9.6 mg, 0.72 mmol), followed by stirring at room temperature for 20 hours. The reaction mixture was added with water and extracted with ethyl acetate. The organic layer was washed with saturated brine and dried over anhydrous sodium sulfate. The solvent was evaporated under reduced pressure. The residue was suspended in hexane and the solid was collected by filtration and washed with hexane, followed by drying under reduced pressure to obtain Compound 165 (28.5 mg, yield 95%).

APCI-MS m/z: 414 [M+H]$^+$; $^1$H-NMR (CDCl$_3$) δ(ppm): 1.38-1.49 (m, 2H), 1.55-1.65 (m, 4H), 2.39-2.49 (m, 4H), 3.62 (s, 2H), 4.49 (s, 2H), 6.66 (br s, 1H), 7.27 (m, 1H), 7.41 (d, J=8.4 Hz, 1H), 7.55 (s, 1H), 7.62 (d, J=8.7 Hz, 1H), 8.80 (d, J=8.7 Hz, 1H), 13.17 (s, 1H).

EXAMPLE 166

3-Amino-6-[1H-6-(piperazin-1-ylcarbonyl)indol-2-yl]phtalimide hydrochloride (Compound 166)

Step 1

In a similar manner to Step 2 of Example 1, 3-amino-6-bromophthalimide (30.0 mg, 0.124 mmol) was dissolved in acetonitrile (2 mL), and the solution was treated with Compound BH (88.0 mg, 0.186 mmol), palladium acetate (2.2 mg, 0.0098 mmol), tri(o-tolyl)phosphine (6.0 mg, 0.020 mmol) and triethylamine (0.169 mL, 1.24 mmol), followed by purification by flash column chromatography (hexane/ethyl acetate=4/1, 3/2, 1/1, 2/3) to obtain 3-amino-6-{1-(tert-butoxycarbonyl)-6-[4-(tert-butoxycarbonyl)piperazin-1-ylcarbonyl]indol-2-yl}phtalimide (38.7 mg, yield 53%).

ESI-MS m/z: 590 [M+H]$^+$, $^1$H-NMR (CDCl$_3$) δ(ppm): 1.40 (s, 9H), 1.48 (s, 9H), 3.35-3.87 (m, 8H), 5.41 (s, 2H), 6.58 (s, 1H), 6.91 (d, J=8.4 Hz, 1H), 7.29 (dd, J=1.5, 7.9 Hz, 1H), 7.41 (m, 1H), 7.44 (d, J=8.4 Hz, 1H), 7.57 (d, J=7.9 Hz, 1H), 8.31 (s, 1H).

Step 2

In a similar manner to Step 2 of Example 5, 3-amino-6-{1-(tert-butoxycarbonyl)-6-[4-(tert-butoxycarbonyl)piperazin-1-ylcarbonyl]indol-2-yl}phtalimide (38.7 mg, 0.0656 mmol) was treated with 4 mol/L hydrogen chloride-ethyl acetate solution (2 mL). The obtained solid was collected by filtration and washed with ethyl acetate, followed by drying under reduced pressure to obtain Compound 166 (25.4 mg, yield 91%).

ESI-MS m/z: 390 [M+H]$^+$; $^1$H-NMR (DMSO-d$_6$) δ(ppm): 3.12-3.22 (m, 4H), 3.69-3.76 (m, 4H), 6.76 (br s, 2H), 7.06-7.14 (m, 3H), 7.60 (d, J=8.4 Hz, 1H), 7.63 (s, 1H), 8.04 (d, J=8.8 Hz, 1H), 8.98 (br s, 2H), 11.35 (s, 1H), 12.27 (s, 1H).

EXAMPLE 167

4-Chloro-7-[1H-6-(piperazin-1-ylcarbonyl)indol-2-yl]isoindolinone hydrochloride (Compound 167)

Step 1

In a similar manner to Step 2 of Example 1, 4-chloro-7-iodoisoindolinone (30.0 mg, 0.102 mmol) was dissolved in acetonitrile (2 mL), and the solution was treated with Compound BH (72.0 mg, 0.152 mmol), palladium acetate (1.8 mg, 0.0080 mmol) and triethylamine (0.142 mL, 1.02 mmol), followed by purification by flash column chromatography (hexane/ethyl acetate=4/1, 3/2, 1/1, 2/3, 7/3) to obtain 4-chloro-7-{1-(tert-butoxycarbonyl)-6-[4-(tert-butoxycarbonyl)piperazin-1-ylcarbonyl]indol-2-yl}isoindolinone (60.8 mg, yield 100%).

APCI-MS m/z: 595 [M+H]$^+$, $^1$H-NMR (CDCl$_3$) δ(ppm): 1.34 (s, 9H), 1.48 (s, 9H), 3.50-3.82 (m, 8H), 4.45 (s, 2H), 6.22 (br s, 1H), 6.59 (br s, 1H), 7.30 (m, 1H), 7.45 (d, J=8.1 Hz, 1H), 7.58 (dd, J=1.8, 8.1 Hz, 1H), 7.59 (m, 1H), 8.33 (br s, 1H).

Step 2

In a similar manner to Step 2 of Example 5, 4-chloro-7-(1-(tert-butoxycarbonyl)-6-[4-(tert-butoxycarbonyl)piperazin-1-ylcarbonyl]indol-2-yl)isoindolinone (60.8 mg, 0.102 mmol) was treated with 4 mol/L hydrogen chloride-ethyl acetate solution (2 mL). The obtained solid was collected by filtration and washed with ethyl acetate, followed by drying under reduced pressure to obtain Compound 167 (29.1 mg, yield 64%).

mp >295° C.; ESI-MS m/z: 395 [M+H]$^+$; $^1$H-NMR (DMSO-d$_6$) δ(ppm): 3.12-3.22 (m, 4H), 3.68-3.80 (m, 4H), 4.51 (s, 2H), 7.12 (d, J=8.4 Hz, 1H), 7.33 (br s, 1H), 7.63 (s, 1H), 7.65 (d, J=8.4 Hz, 1H), 7.76 (d, J=8.4 Hz, 1H), 8.24 (d, J=8.4 Hz, 1H), 8.94 (br s, 2H), 9.56 (s, 1H), 13.94 (s, 1H).

EXAMPLE 168

3-(Benzothiophen-2-yl)phtalimide (Compound 168)

Step 1

3-Aminophthalic acid (5.00 g, 27.6 mmol) was dissolved in 8.4 mol/L hydrochloric acid (60 mL), and the solution was added with an aqueous solution (10 mL) of sodium nitrate (2.0 g, 29 mmol) by drops under ice-cooling for 20 minutes, followed by stirring at the same temperature for 3 hours. Then, an aqueous solution (10 mL), in which potassium iodide (6.9 g, 41 mmol) and urea (291 mg) were dissolved, is added by drops to the mixture, followed by stirring at room temperature for 20 hours. The reaction mixture was added with 10% aqueous sodium thiosulfate solution and extracted with ethyl acetate. The organic layer was washed with saturated brine and dried over anhydrous sodium sulfate. The solvent was evaporated under reduced pressure and the residue was washed with chloroform to obtain 3-iodophthalic acid (5.0 g, yield 62%).

Step 2

3-Iodophthalic acid (4.00 g, 13.7 mmol) was dissolved in anhydrous acetic acid, and the solution was stirred at 145° C. for 1 hour. The solvent of the reaction mixture was evaporated under reduced pressure and the residue was purified by slurry using diisopropylether to obtain 3-iodophthalic acid anhydride (3.6 g, yield 96%).

FAB-MS m/z: 275 [M+H]$^+$; $^1$H-NMR (CDCl$_3$) δ(ppm): 7.56 (dd, J=7.6, 7.6 Hz, 1H), 8.01 (dd, J=0.8, 7.4 Hz, 1H), 8.30 (dd, J=0.7, 7.9 Hz, 1H).

Step 3

3-Iodophthalic anhydride (598 mg, 2.18 mmol) was dissolved in DMF (14 mL), and the solution was added with an aqueous solution (10 mL) of hexamethyldisilazane (HMDS) (4.6 mL, 22 mmol) and methanol (0.44 mL, 11 mmol), followed by stirring at room temperature for 18.5 hours. The reaction mixture was added with water and extracted with ethyl acetate. The organic layer was washed with saturated brine and dried over anhydrous sodium sulfate. The solvent was evaporated under reduced pressure a and the residue was purified by slurry using chloroform to obtain 3-iodophtalimide (403 mg, yield 68%).

APCI-MS m/z: 272 [M−H]$^-$; $^1$H-NMR (DMSO-d$_6$) δ(ppm): 7.53 (dd, J=7.4, 7.8 Hz, 1H), 7.84 (dd, J=0.6, 7.3 Hz, 1H), 8.22 (dd, J=0.6, 7.8 Hz, 1H), 11.52 (br s, 1H).

Step 4

In a similar manner to Step 2 of Example 1, 3-iodophtalimide (50.0 mg, 0.183 mmol) was dissolved in acetonitrile (2.5 mL), and the solution was treated with 2-benzothiopheneboronic acid (65.0 mg, 0.366 mmol), palladium acetate (2.0 mg, 0.0092 mmol), tri(o-tolyl)phosphine (5.6 mg, 0.018 mmol) and triethylamine (0.128 mL, 0.915 mmol), followed by purification by preparative thin-layer chromatography (chloroform/acetonitrile=30/1) to obtain Compound 168 (43.3 mg, yield 85%).

APCI-MS m/z: 278 [M−H]$^-$; $^1$H-NMR (DMSO-d$_6$) δ(ppm): 7.43-7.48 (m, 2H), 7.84-8.07 (m, 5H), 8.15 (s, 1H), 11.48 (br s, 1H).

EXAMPLE 169

3-(Benzofuran-2-yl)phtalimide (Compound 169)

In a similar manner to Step 2 of Example 1, 3-iodophtalimide (50.0 mg, 0.183 mmol) was dissolved in acetonitrile (2.5 mL), and the solution was treated with 2-benzofuraneboronic acid (59.0 mg, 0.366 mmol), palladium acetate (4.0 mg, 0.018 mmol), tri(o-tolyl)phosphine (11 mg, 0.036 mmol) and triethylamine (0.128 mL, 0.915 mmol), followed by purification by preparative thin-layer chromatography (chloroform/acetonitrile=30/1, chloroform/methanol=40/1) to obtain Compound 169 (16.3 mg, yield 34%).

APCI-MS m/z: 262 [M−H]$^-$; $^1$H-NMR (DMSO-d$_6$) δ(ppm): 7.32 (dd, J=7.4, 7.4 Hz, 1H), 7.43 (dd, J=7.1, 8.4 Hz, 1H), 7.68 (d, J=8.3 Hz, 1H), 7.82 (d, J=7.8 Hz, 1H), 7.85 (d, J=7.4 Hz, 1H), 7.96 (dd, J=7.6, 7.8 Hz, 1H), 8.31 (s, 1H), 8.38 (d, J=7.9 Hz, 1H), 11.55 (br s, 1H).

EXAMPLE 170

4-Chloro-7-(benzofuran-2-yl)isoindolinone (Compound 170)

In a similar manner to Step 2 of Example 1, 4-chloro-7-iodoisoindolinone (80.0 mg, 0.273 mmol) was dissolved in acetonitrile (4.0 mL), and the solution was treated with 2-benzofuraneboronic acid (133 mg, 0.819 mmol), palladium acetate (7.4 mg, 0.033 mmol), tri(o-tolyl)phosphine (20 mg, 0.066 mmol) and triethylamine (0.381 mL, 2.73 mmol), followed by purification by preparative thin-layer chromatography (chloroform/acetonitrile=15/1) to obtain Compound 170 (14.3 mg, yield 18%).

APCI-MS m/z: 284 [M+H]$^+$; $^1$H-NMR (CDCl$_3$+CD$_3$OD) δ(ppm): 4.44 (s, 2H), 7.24 (ddd, J=1.1, 7.2, 7.6 Hz, 1H), 7.33 (m, 1H), 7.52 (dd, J=0.9, 7.3 Hz, 1H), 7.62 (d, J=8.6 Hz, 1H), 7.66 (ddd, J=0.6, 0.7, 7.7 Hz, 1H), 8.16 (d, J=8.6 Hz, 1H), 8.36 (d, J=0.9 Hz, 1H).

EXAMPLE 171

3-Amino-6-(benzofuran-2-yl)phtalimide (Compound 171)

In a similar manner to Step 2 of Example 1, 3-amino-6-bromophthalimide (80.0 mg, 0.332 mmol) was dissolved in acetonitrile (4.0 mL), and, the solution was treated with 2-benzofuraneboronic acid (161 mg, 0.996 mmol), palladium acetate (9.0 mg, 0.040 mmol), tri(o-tolyl)phosphine (24.3 mg, 0.080 mmol) and triethylamine (0.463 mL, 3.32 mmol), followed by purification by preparative thin-layer chromatography (chloroform/acetonitrile=15/1) to obtain Compound 171 (30.1 mg, yield 33%).

APCI-MS m/z: 277 [M−H]$^-$; $^1$H-NMR (DMSO-d$_6$) δ(ppm): 6.78 (s, 2H), 7.11 (d, J=9.1 Hz, 1H), 7.24-7.32 (m, 2H), 7.58 (d, J=7.5 Hz, 1H), 7.70 (d, J=7.5 Hz, 1H), 8.02 (s, 1H), 8.04 (d, J=8.9 Hz, 1H), 11.13 (s, 1H).

EXAMPLE 172

4-Chloro-7-(5-carboxybenzothiophen-2-yl)isoindolinone (Compound 172)

In a similar manner to Step 1 of Example 19, 4-chloro-7-iodoisoindolinone (66.0 mg, 0.225 mmol) was dissolved in DMF 2 mL), and the solution was treated with Compound BN (100 mg, 0.450 mmol), palladium acetate (4.0 mg, 0.018 mmol) and triethylamine (0.314 mL, 2.25 mmol). The reaction mixture was added with water, ethyl acetate and 1 mol/L hydrochloric acid. The obtained solid was collected by filtration and washed with water, followed by drying under reduced pressure to obtain Compound 172 (57.7 mg, yield 57%).

ESI-MS m/z: 342 [M–H]⁻; ¹H-NMR (DMSO-d₆) δ(ppm): 4.40 (s, 2H), 7.69 (d, J=8.2 Hz, 1H), 7.78 (d, J=8.2 Hz, 1H), 7.92 (d, J=8.6 Hz, 1H), 8.11 (d, J=8.6 Hz, 1H), 8.12 (s, 1H), 8.47 (s, 1H), 8.94 (s, 1H), 13.03 (s, 1H).

EXAMPLE 173

4-Chloro-7-(5-[4-(2-hydroxyethyl)piperazin-1-ylcarbonyl]benzothiophen-2-yl)isoindolinone (Compound 173)

In a similar manner to Step 1 of Example 20, Compound 172 (25.0 mg, 0.0727 mmol) was dissolved in DMF (1 mL), and the solution was treated with EDCI (28 mg, 0.15 mmol), HOBT monohydrate (9.8 mg, 0.073 mmol) and 1-(2-hydroxyethyl)piperazine (38 mg, 0.29 mmol). The reaction mixture was added with water and ethyl acetate, and extracted with 1 mol/L hydrochloric acid. The aqueous layer was added with sodium carbonate to adjust the pH to 9 and extracted with ethyl acetate. The organic layer was washed with saturated brine and then dried over anhydrous sodium sulfate. The solvent was evaporated under reduced pressure. The residue was dissolved in chloroform, and the solution was added with diisopropylether and stirred for 30 minutes. The solid was collected by filtration, washed with diisopropylether and then dried under reduced pressure to obtain Compound 173 (22.9 mg, yield 69%).

APCI-MS m/z: 456 [M+H]⁺; ¹H-NMR (DMSO-d₆) δ(ppm): 2.40-2.49 (m, 4H), 2.42 (t, J=6.2 Hz, 2H), 3.35-3.78 (m, 4H), 3.51 (dt, J=5.3, 6.2 Hz, 2H), 4.41 (s, 2H), 4.43 (t, J=5.3 Hz, 1H), 7.38 (dd, J=1.5, 8.4 Hz, 1H), 7.67 (d, J=8.3 Hz, 1H), 7.77 (d, J=8.3 Hz, 1H), 7.91 (br s, 1H), 8.067 (s, 1H), 8.069 (d, J=8.4 Hz, 1H), 8.93 (s, 1H).

EXAMPLE 174

4-Chloro-7-(1H-benzoimidazol-2-yl)isoindolinone (Compound 174)

Step 1

4-Chloro-3-hydroxy-2-(1-methyl-1-phenylethyl)isoindolinone (1.00 g, 3.31 mmol) was dissolved in THF (40 mL), and the solution was added with TMEDA (1.10 mL, 7.28 mmol), and added with sec-butyllithium-hexane solution (0.99 mol/L, 7.36 mL, 7.28 mmol) by drops at −78° C. for 5 minutes under argon atmosphere, and the mixture was stirred for 2 hours at the same temperature. Then, the mixture was added with DMF (0.384 mL, 4.97 mmol) and warmed from −78° C. to room temperature for 3.5 hours. The reaction mixture was added with water and extracted with ethyl acetate. The organic layer was washed with saturated brine and dried over anhydrous sodium sulfate. The solvent was evaporated under reduced pressure and the residue was purified by flash column chromatography (hexane/ethyl acetate=95/5, 60/40) and preparative thin-layer chromatography (hexane/ethyl acetate=1/1) to obtain 4-chloro-3-hydroxy-7-formyl-2-(1-methyl-1-phenylethyl)isoindolinone (993 mg, yield 91%).

APCI-MS m/z: 330 [M+H]⁺; ¹H-NMR (CDCl₃) δ(ppm): 1.96 (s, 3H), 2.01 (s, 3H), 6.32 (d, J=8.4 Hz, 1H), 7.28 (m, 2H), 7.36 (m, 2H), 7.46 (m, 2H), 7.57 (dd, J=0.7, 8.3 Hz, 1H), 7.94 (d, J=8.3 Hz, 1H), 10.92 (s, 1H).

Step 2

4-Chloro-3-hydroxy-7-formyl-2-(1-methyl-1-phenylethyl)isoindolinone (100 mg, 0.303 mmol) was dissolved in nitrobenzene (2 mL), and the solution was added with o-phenylenediamine (49 mg, 0.45 mmol), followed by stirring at 130° C. for 5.2 hours. The reaction mixture was added with hexane and the obtained solid was collected by filtration and purified by preparative thin-layer chromatography (hexane/ethyl acetate=2/1, 1/1) to obtain 4-chloro-3-hydroxy-7-(1H-benzoimidazol-2-yl)-2-(1-methyl-1-phenylethyl)isoindolinone (42.8 mg, yield 34%).

APCI-MS m/z: 418 [M+H]⁺; ¹H-NMR (DMSO-d₆) δ(ppm): 1.90 (s, 3H), 1.92 (s, 3H), 6.52 (d, J=10.4 Hz, 1H), 6.99 (d, J=10.2 Hz, 1H), 7.16-7.22 (m, 3H), 7.30 (dd, J=7.1, 7.7 Hz, 2H), 7.48 (d, J=7.1 Hz, 2H), 7.66 (m, 2H), 7.88 (d, J=8.6 Hz, 1H), 8.72 (d, J=8.6 Hz, 1H), 14.03 (s, 1H).

Step 3

4-Chloro-3-hydroxy-7-(1H-benzoimidazol-2-yl)-2-(1-methyl-1-phenylethyl)isoindolinone (39.4 mg, 0.0943 mmol) was dissolved in nitromethane (2.8 mL), and the solution was added with trifluoroacetic acid (0.073 mL, 0.94 mmol) and triethylsilane (0.030 mL, 0.19 mmol), followed by stirring at room temperature for 23.5 hours. Then, the mixture was added with trifluoroacetic acid (0.146 mL, 1.89 mmol) and triethylsilane (0.045 mL, 0.28 mmol) and warmed to 70° C., followed by stirring for 7.5 hours. Further, the mixture was added with trifluoroacetic acid (1.00 mL) and triethylsilane (0.15 mL, 0.94 mmol), followed by stirring for 4 hours. The reaction mixture was added with saturated aqueous sodium hydrogencarbonate solution and extracted with ethyl acetate. The organic layer was washed with saturated brine and dried over anhydrous sodium sulfate. The solvent was evaporated under reduced pressure. The residue was purified by slurry using chloroform/methanol (9/1) and by preparative thin-layer chromatography (hexane/ethyl acetate=2/1, 1/1) to obtain Compound 174 (13.7 mg, yield 51%).

APCI-MS m/z: 284 [M+H]⁺; ¹H-NMR (DMSO-d₆) δ(ppm): 4.57 (s, 2H), 7.25 (m, 2H), 7.70 (m, 2H), 7.88 (d, J=8.4 Hz, 1H), 8.31 (s, 0.4H), 8.70 (d, J=8.4 Hz, 1H), 9.76 (s, 1H), 14.82 (s, 0.6H).

EXAMPLE 175

4-Chloro-7-[1H-5-(4-methylpiperazin-1-yl)benzoimidazol-2-yl]isoindolinone (Compound 175)

Step 1

In a similar manner to Step. 2 of Example 174, 4-chloro-3-hydroxy-7-formyl-2-(1-methyl-1-phenylethyl)isoindolinone (453 mg, 1.37 mmol) was dissolved in nitrobenzene (6.8 mL), and the solution was treated with 4-(4-methylpiperadino)-1,2-benzenediamine (424 mg, 2.06 mmol), followed by purification by preparative thin-layer chromatography (chloroform/methanol=6/1) to obtain 4-chloro-3-hydroxy-7-[1H-6-(4-methylpiperazin-1-yl)benzoimidazol-2-yl]-2-(1-methyl-1-phenylethyl)isoindolinone (184 mg, yield 26%).

APCI-MS m/z: 544 [M+H]⁺; ¹H-NMR (DMSO-d₆) δ(ppm): 2.01-2.12 (m, 6H), 2.34 (s, 3H), 2.43 (m, 4H), 3.54-4.20 (m, 4H), 6.27 (m, 1H), 7.11-7.69 (m, 10H), 8.57-8.69 (m, 1H), 13.78 (s, 1H).

Step 2

In a similar manner to Step 3 of Example 174, 4-chloro-3-hydroxy-7-[1H-6-(4-methylpiperazin-1-yl)benzoimidazol-2-yl]-2-(1-methyl-1-phenylethyl)isoindolinone (58.7 mg, 0.114 mmol) was dissolved in trifluoroacetic acid (1.17 mL), and the solution was treated with triethylsilane (0.091 mL, 0.57 mmol), followed by purification by preparative thin-layer chromatography (chloroform/methanol=6/1) to obtain Compound 175 (38.9 mg, yield 89%).

APCI-MS m/z: 382 [M+H]$^+$; $^1$H-NMR (DMSO-d$_6$) δ(ppm): 2.23 (s, 3H), 2.48 (m, 4H), 3.16 (m, 4H), 4.53 (s, 2H), 7.01 (m, 1H), 7.11 (m, 1H), 7.52 (d, J=8.8 Hz, 1H), 7.82 (m, 1H), 8.30 (s, 0.6H), 8.62 (m, 1H), 9.69 (br s, 1H), 14.52 (s, 0.4H).

EXAMPLE 176

4-Chloro-7-[1H-5-(4-methylpiperazin-1-ylcarbonyl) benzoimidazol-2-yl]isoindolinone (Compound 176)

Step 1

HOBT monohydrate (2.00 g, 13.1 mmol) was dissolved in DMF (20 mL), and the solution was added with triethylamine (2.54 mL, 18.2 mmol) and ethylchloroformate (1.24 mL, 13.0 mmol), followed by stirring at 0° C. for 3 hours. Then, the mixture was added with triethylamine (4.22 mL, 30.3 mmol) and 3,4-diaminobenzoic acid (1.86 g, 12.2 mmol), followed by stirring at the same temperature for 2 hours. The mixture was added with a solution of N-methylpiperazine (1.21 mL, 10.9 mmol) in DMF (20 mL), followed by further stirring for 30 minutes. The reaction mixture was added with water (2 mL) and the solvent was evaporated under reduced pressure. The residue was purified by silica gel column chromatography (chloroform/methanol/7 mol/L ammonia-methanol solution=50/0.5/0.5-7/0.5/0.5) and preparative thin-layer chromatography (chloroform/methanol/7 mol/L ammonia-methanol solution=4/0.5/0.5) to obtain (3,4-diaminophenyl) (4-methylpiperazin-1-yl)methanone (455 mg, yield 18%).

APCI-MS m/z: 235 [M+H]$^+$; $^1$H-NMR (CDCl$_3$) δ(ppm): 2.33 (s, 3H), 2.42 (br s, 4H), 3.50 (br s, 2H), 3.59 (br s, 2H), 3.66 (br s, 4H), 6.80 (d, J=7.9 Hz, 1H), 6.80 (dd, J=1.9, 7.8 Hz, 1H), 6.84 (d, J=1.8 Hz, 1H), Step 2

In a similar manner to Step 2 of Example 174, 4-chloro-3-hydroxy-7-formyl-2-(1-methyl-1-phenylethyl)isoindolinone (416 mg, 1.26 mmol) was dissolved in nitrobenzene (8.3 mL), and the solution was treated with (3,4-diaminophenyl)(4-methylpiperazin-1-yl)methanone (443 mg, 1.89 mmol), followed by purification by preparative thin-layer chromatography (chloroform/methanol=10/1, ethyl acetate/methanol=2/1) to obtain 4-chloro-3-hydroxy-7-[1H-6-(4-methylpiperazin-1-ylcarbonyl)benzoimidazol-2-yl]-2-(1-methyl-1-phenylethyl)isoindolinone (334 mg, yield 49%).

APCI-MS m/z: 516 [M+H]$^+$; $^1$H-NMR (DMSO-d$_6$) δ(ppm): 1.91 (s, 3H), 2.22 (s, 3H), 2.23 (s, 3H), 2.45 (m, 4H), 3.11 (m, 4H), 6.50 (m, 1H), 6.95 (m, 2H), 7.07 (m, 1H), 7.19 (m, 1H), 7.30 (m, 2H), 7.48 (m, 3H), 7.83 (m, 1H), 8.66 (m, 1H), 13.80 (m, 1H).

Step 3

In a similar manner to Step 3 of Example 174, 4-chloro-3-hydroxy-7-[1H-6-(4-methylpiperazin-1-ylcarbonyl)benzo imidazol-2-yl]-2-(1-methyl-1-phenylethyl)isoindolinone (80.0 mg, 0.147 mmol) was dissolved in trifluoroacetic acid (1.6 mL), and the solution was treated with triethylsilane (0.117 mL, 0.735 mmol), followed by purification by preparative thin-layer chromatography (ethyl acetate/methanol=1/1, chloroform/methanol=12/1) to obtain Compound 176 (50.8 mg, yield 84%).

APCI-MS m/z: 410 [M+H]$^+$; $^1$H-NMR (DMSO-d$_6$) δ(ppm): 2.21 (s, 3H), 2.34 (m, 4H), 3.52 (m, 4H), 4.56 (s, 2H), 7.26 (ddd, J=1.6, 8.3, 8.4 Hz, 1H), 7.70-7.76 (m, 2H), 7.88 (d, J=8.4 Hz, 1H), 8.68 (d, J=8.4 Hz, 1H), 9.76 (d, J=4.1 Hz, 1H).

EXAMPLE 177

3-Chloro-6-[1H-5-(4-methylpiperazin-1-ylcarbonyl) benzoimidazol-2-yl]phtalimide (Compound 177)

Step 1

4-Chloro-3-hydroxy-7-[1H-6-(4-methylpiperazin-1-ylcarbonyl)benzoimidazol-2-yl]-2-(1-methyl-1-phenylethyl) isoindolinone (113 mg, 0.208 mmol) was dissolved in DMF (3.4 mL), and the solution was added with PDC (235 mg, 0.624 mmol) under argon atmosphere and stirred from 0° C. to room temperature over 1.7 hours. The mixture was added with PDC (157 mg, 0.416 mmol) and stirred at 50° C. for 3 hours. Further, the mixture was added with PDC (157 mg, 0.416 mmol) and stirred at 50° C. for 3 hours. Further, the mixture was added with PDC (157 mg, 0.416 mmol) and stirred at 50° C. for 7 hours. Further, the mixture was added with PDC (235 mg, 0.624 mmol) and DMF (3 mL) and stirred at 50° C. for 6 hours. The reaction mixture was added with water and extracted with ethyl acetate. The organic layer was washed with saturated brine and dried over anhydrous sodium sulfate. The solvent was evaporated under reduced pressure and the residue was purified by preparative thin-layer chromatography (chloroform/methanol=10/1, 12/1) to obtain 3-chloro-6-[1H-6-(4-methylpiperazin-1-ylcarbonyl)benzoimidazol-2-yl]-1-(1-methyl-1-phenylethyl)phtalimide (12.7 mg, yield 11%).

APCI-MS m/z: 542 [M+H]$^+$; $^1$H-NMR (CDCl$_3$) δ(ppm): 2.12 (s, 6H), 2.33 (s, 3H), 2.44 (m, 4H), 3.71 (m, 4H), 7.26-7.43 (m, 6H), 7.59-7.66 (m, 1H), 7.77-7.84 (m, 2H), 9.05 (d, J=8.6 Hz, 1H), 13.23 (s, 1H).

Step 2

3-Chloro-6-[1H-6-(4-methylpiperazin-1-ylcarbonyl)benzoimidazol-2-yl]-1-(1-methyl-1-phenylethyl)phtalimide (16.1 mg, 0.0297 mmol) was dissolved in trifluoroacetic acid (3.6 mL), and the solution was stirred from room temperature to 70° C. for 72 hours. The reaction mixture was added with saturated aqueous sodium hydrogencarbonate solution and extracted with ethyl acetate. The organic layer was washed with saturated brine and then dried over anhydrous sodium sulfate. The solvent was evaporated under reduced pressure and the residue was purified by preparative thin-layer chromatography (chloroform/methanol=10/1) to obtain Compound 177 (10.6 mg, yield 84%).

APCI-MS m/z: 424 [M+H]$^+$; $^1$H-NMR (DMSO-d$_6$) δ(ppm): 2.21 (s, 3H), 3.34 (m, 4H), 3.52 (m, 4H), 7.28 (m, 1H), 7.58 (m, 1H), 7.74-7.83 (m, 2H), 7.97 (d, J=8.6 Hz, 1H), 8.68 (m, 1H), 13.46 (br s, 1H).

EXAMPLE 178

4-Chloro-7-(1H-5-carboxybenzimidazol-2-yl)isoindolinone (Compound 178)

Step 1

4-Chloro-3-hydroxy-7-formyl-2-(1-methyl-1-phenylethyl)isoindolinone (200 mg, 0.606 mmol) was suspended in acetonitrile (8 mL), and the suspension was added with 2,3-dichloro-5,6-dicyano-1,4-benzoquinone (151 mg, 0.665 mmol), followed by stirring at room temperature for 4 hours. The reaction mixture was added with water and stirred under ice-cooling for 1 hour. The obtained solid was collected by filtration, washed with water and dried under reduced pressure. The solid was suspended in methanol, and the suspetion was added with water and stirred at room temperature for 1 hour. The solid was collected by filtration, washed with water and dried under reduced pressure. The solid was suspended in methanol and added with diisopropylether, followed by stirring under ice-cooling for 30 minutes. The solid was collected by filtration and washed with diisopropylether/methanol (10/1), followed by drying under reduced pressure to obtain 4-chloro-3-hydroxy-7-(1H-5-carboxybenzoimidazol-2-yl)-2-(1-methyl-1-phenylethyl)isoindolinone (181 mg, yield 65%).

ESI-MS m/z: 462 [M+H]$^+$; $^1$H-NMR (DMSO-d$_6$) δ(ppm): 1.91 (s, 6H), 6.53 (d, J=10.3 Hz, 1H), 7.03 (d, J=10.3 Hz, 1H), 7.18 (m, 1H), 7.26-7.32 (m, 2H), 7.45-7.56 (m, 2H), 7.70-7.85 (m, 2H), 7.89 (d, J=8.4 Hz, 1H), 8.24 (s, 1H), 8.71 (d, J=8.4 Hz, 1H), 12.70 (br s, 1H), 14.24 (s, 1H).

Step 2

In a similar manner to Step 3 of Example 174, 4-chloro-3-hydroxy-7-(1H-5-carboxybenzoimidazol-2-yl)-2-(1-methyl-1-phenylethyl)isoindolinone (180 mg, 0.390 mmol) was dissolved in trifluoroacetic acid (3.6 mL), and the solution was treated with triethylsilane (0.187 mL, 1.17 mmol). The solvent was evaporated under reduced pressure. The residue was suspended in ethyl acetate and the solid was collected by filtration, washed with ethyl acetate and then dried under reduced pressure. The solid was suspended in methanol and stirred at room temperature for 30 minutes. Then, the solid was collected by filtration and washed with methanol, followed by drying under reduced pressure to obtain Compound 178 (62.2 mg, yield 49%).

ESI-MS m/z: 328 [M+H]$^+$; $^1$H-NMR (DMSO-d$_6$) δ(ppm): 4.58 (s, 2H), 7.78 (d, J=8.6 Hz, 1H), 7.87 (dd, J=1.5, 8.6 Hz, 1H), 7.91 (d, J=8.4 Hz, 1H), 8.29 (d, J=1.5 Hz, 1H), 8.67 (d, J=8.4 Hz, 1H), 9.84 (s, 1H).

EXAMPLE 179

4-Chloro-7-[1H-5-(4-acetylpiperazin-1-ylcarbonyl) benzimidazol-2-yl]isoindolinone (Compound 179)

Compound 178 (15.0 mg, 0.0458 mmol) was dissolved in DMF (0.5 mL), and the solution was added with EDCI (9.7 mg, 0.051 mmol), HOBT monohydrate (3.1 mg, 0.023 mmol) and 1-acetylpiperazin (7.0 mg, 0.055 mmol), followed by stirring at room temperature for 30 hours. The reaction mixture was added with water and extracted with ethyl acetate. The organic layer was washed with saturated brine and dried over anhydrous sodium sulfate. The solvent was evaporated under reduced pressure and the residue was purified by flash column chromatography (chloroform/methanol=9/1, 4/1). The obtained solid was suspended in chloroform, added with diisopropylether and stirred under ice-cooling for 30 minutes. The solid was collected by filtration, washed with diisopropylether and then dried under reduced pressure to obtain Compound 179 (11.5 mg, yield 58%).

APCI-MS m/z: 438 [M+H]$^+$; $^1$H-NMR (DMSO-d$_6$) δ(ppm): 2.03 (s, 3H), 3.45-3.60 (m, 8H), 4.58 (s, 2H), 7.30 (dd, J=1.5, 8.4 Hz, 1H), 7.78 (d, J=8.4 Hz, 1H), 7.82 (s, 1H), 7.90 (d, J=8.4 Hz, 1H), 8.70 (d, J=8.4 Hz, 1H), 9.81 (s, 1H), 15.00 (s, 1H).

EXAMPLE 180

4-Chloro-7-{1H-5-[4-(1,1-dimethylethoxycarbonyl) piperazin-1-ylcarbonyl]benzimidazol-2-yl}isoindolinone (Compound 180)

In a similar manner to Example 179, Compound 178 (50.7 mg, 0.155 mmol) was dissolved in DMF (1 mL), and the solution was treated with EDCI (32.7 mg, 0.171 mmol), HOBT monohydrate (10.5 mg, 0.0777 mmol) and 1-(tert-butoxycarbonyl)piperazine (34.6 mg, 0.186 mmol). The reaction mixture was added with water and extracted with chloroform. The organic layer was washed with 1 mol/L hydrochloric acid, saturated aqueous sodium hydrogencarbonate solution and saturated brine, and dried over anhydrous sodium sulfate. The solvent was evaporated under reduced pressure and the residue was purified by flash column chromatography (chloroform/methanol=19/1, 4/1) to obtain Compound 180 (18.8 mg, yield 25%).

ESI-MS m/z: 496 [M+H]$^+$; $^1$H-NMR (CDCl$_3$) δ(ppm): 1.48 (s, 9H), 3.40-3.80 (m, 8H), 4.57 (s, 2H), 6.70 (br s, 1H), 7.39 (dd, J=1.5, 8.4 Hz, 1H), 7.62 (d, J=8.4 Hz, 1H), 7.72 (d, J=8.4 Hz, 1H), 7.83 (br s, 1H), 8.86 (d, J=8.4 Hz, 1H), 14.52 (br s, 1H).

EXAMPLE 181

4-Chloro-7-[1H-5-(piperazin-1-ylcarbonyl)benzoimidazol-2-yl]isoindolinone hydrochloride (Compound 181)

Compound 180 (15.1 mg, 0.0304 mmol) was suspended in 4 mol/L hydrogen chloride-ethyl acetate solution (1 mL), and the suspension was added with methanol (1 mL), followed by stirring at room temperature for 30 minutes. The solvent was evaporated under reduced pressure. The residue was dissolved in methanol and added with diisopropylether, followed by stirring at room temperature for 30 minutes. The obtained solid was collected by filtration and washed with diisopropylether, followed by drying under reduced pressure to obtain Compound 181 (9.1 mg, yield 69%).

ESI-MS m/z: 396 [M+H]$^+$; $^1$H-NMR (DMSO-d$_6$) δ(ppm): 3.12-3.25 (m, 4H), 3.68-3.80 (m, 4H), 4.59 (s, 2H), 7.38 (dd, J=1.5, 8.4 Hz, 1H), 7.81 (d, J=8.4 Hz, 1H), 7.88 (br s, 1H), 7.93 (d, J=8.4 Hz, 1H), 8.68 (d, J=8.4 Hz, 1H), 9.09 (br s, 3H), 9.86 (br s, 1H).

EXAMPLE 182

4-Chloro-7-[1H-5-(dimethylaminocarbonyl)benzoimidazol-2-yl]isoindolinone (Compound 182)

In a similar manner to Example 179, Compound 178 (30.0 mg, 0.0915 mmol) was dissolved in DMF (1 mL), and the solution was treated with EDCI (19.3 mg, 0.101 mmol), HOBT monohydrate (6.2 mg, 0.046 mmol). N,N-dimethylamine hydrochloride (15 mg, 0.18 mmol) and triethylamine (0.051 mL, 0.37 mmol). The reaction mixture was added with water and 1 mol/L hydrochloric acid, followed by extracting with chloroform. The organic layer was washed with saturated aqueous sodium hydrogencarbonate solution and saturated brine, followed by drying over anhydrous sodium sulfate. The solvent was evaporated under reduced pressure. The residue was dissolved in chloroform and added with diisopropylether, followed by stirring at room temperature for 30 minutes. The obtained solid was collected by filtration and washed with diisopropylether, followed by drying under reduced pressure to obtain Compound 182 (7.8 mg, yield 24%).

APCI-MS m/z: 355 [M+H]$^+$; $^1$H-NMR (DMSO-d$_6$) δ(ppm): 3.00 (s, 6H), 4.58 (s, 2H), 7.29 (m, 1H), 7.71-7.79 (m, 2H), 7.90 (d, J=8.4 Hz, 1H), 8.70 (d, J=8.4 Hz, 1H), 9.81 (br s, 1H), 14.98 (br s, 1H).

EXAMPLE 183

4-Chloro-7-{1H-5-[4-(pyridin-2-yl)piperazin-1-ylcarbonyl]benzimidazol-2-yl}isoindolinone (Compound 183)

In a similar manner to Example 179, Compound 178 (30.0 mg, 0.0915 mmol) was dissolved in DMF (1 mL), and the solution was treated with EDCI (52.6 mg, 0.274 mmol), HOBT monohydrate (12.4 mg, 0.0918 mmol) and 1-(pyridin-2-yl)piperazine (0.056 mL, 0.37 mmol). The reaction mixture was added with water. The obtained solid was collected by filtration and washed with water, followed by drying under reduced pressure to obtain Compound 183 (16.3 mg, yield 38%).

APCI-MS-m/z: 473 [M+H]$^+$; $^1$H-NMR (DMSO-d$_6$) δ(ppm): 3.53-3.71 (m, 8H), 4.58 (s, 2H), 6.66 (m, 1H), 6.84 (d, J=8.4 Hz, 1H), 7.33 (m, 1H), 7.55 (m, 1H), 7.72-7.86 (m, 2H), 7.89 (d, J=8.4 Hz, 1H), 8.12 (m, 1H), 8.69 (d, J=8.4 Hz, 1H), 9.81 (br s, 1H), 14.98 (s, 1H).

EXAMPLE 184

4-Chloro-7-{1H-5-[4-(2-hydroxyethyl)piperazin-1-ylcarbonyl]benzimidazol-2-yl}isoindolinone (Compound 184)

Compound 178 (30.0 mg, 0.0915 mmol) was dissolved in DMF (1.0 mL), and the solution was added with thionyl chloride (0.020 mL, 0.27 mmol) under ice-cooling and stirred for 40 minutes. The mixture was added with 1-(2-hydroxyethyl)-piperazine (0.112 mL, 0.913 mmol) and stirred for 30 minutes under ice-cooling. The reaction mixture was added with water. The obtained solid was collected by filtration and washed with water, followed by drying under reduced pressure to obtain Compound 184 (20.8 mg, yield 52%).

APCI-MS m/z: 440 [M+H]$^+$; $^1$H-NMR (DMSO-d$_6$) δ(ppm): 2.38-2.50 (m, 4H), 3.44-3.68 (m, 8H), 4.44 (br s, 1H), 4.56 (s, 2H), 7.27 (dd, J=1.5, 8.3 Hz, 1H), 7.69-7.78 (m, 2H), 7.88 (d, J=8.6 Hz, 1H), 8.68 (d, J=8.6 Hz, 1H), 9.79 (br s, 1H), 14.94 (s, 1H).

EXAMPLE 185

4-Chloro-7-[1H-5-(2-hydroxyethylaminocarbonyl)benzoimidazol-2-yl ]isoindolinone (Compound 185)

In a similar manner to Example 184, Compound 178 (30.0 mg, 0.0915 mmol) was dissolved in DMF (1.0 mL), and the solution was treated with thionyl chloride (0.020 mL, 0.27 mmol) and 2-aminoethanol (0.055 mL, 0.91 mmol). The reaction mixture was added with water. The obtained solid was collected by filtration and washed with water, followed by drying under reduced pressure to obtain Compound 185 (18.8 mg, yield 58%).

ESI-MS m/z: 371 [M+H]$^+$; $^1$H-NMR (DMSO-d$_6$) δ(ppm): 3.35-3.42 (m, 2H), 3.53 (dt, J=5.6, 6.1 Hz, 2H), 4.57 (s, 2H), 4.74 (t, J=5.6 Hz, 1H), 7.70-7.83 (m, 2H), 7.89 (d, J=8.5 Hz, 1H), 8.25 (s, 1H), 8.43 (br s, 1H), 8.69 (d, J=8.5 Hz, 1H), 9.82 (br s, 1H), 15.00 (s, 1H).

EXAMPLE 186

4-Chloro-7-{1H-5-[(pyridin-2-ylmethyl)aminocarbonyl]benzoimidazol-2-ylcarbonyl}isoindolinone (Compound 186)

In a similar manner to Example 184, Compound 178 (30.0 mg, 0.0915 mmol) was dissolved in DMF (1.0 mL), and the solution was treated with thionyl chloride (0.020 mL, 0.27 mmol) and 2-picolylamine (0.094 mL, 0.91 mmol). The reaction mixture was added with water. The obtained solid was collected by filtration and washed with water, followed by drying under reduced pressure to obtain Compound 186 (29.1 mg, yield 76%).

ESI-MS m/z: 418 [M+H]$^+$; $^1$H-NMR (DMSO-d$_6$) δ(ppm): 4.58 (s, 2H), 4.59 (s, 2H), 7.26 (m, 1H), 7.35 (m, 1H), 7.72-7.95 (m, 4H), 8.31 (d, J=8.5 Hz, 1H), 8.51 (m, 1H), 8.70 (d, J=8.5 Hz, 1H), 9.13 (br s, 1H), 9.83 (br s, 1H), 15.14 (s, 1H).

EXAMPLE 187

4-Chloro-7-{1H-5-[4-(methylsulfonyl)piperazin-1-ylcarbonyl]benzoimidazol-2-yl}isoindolinone (Compound 187)

In a similar manner to Example 184, Compound 178 (30.0 mg, 0.0915 mmol) was dissolved in DMF (1.0 mL), and the solution was treated with thionyl chloride (0.020 mL, 0.27 mmol), 1-(methylsulfonyl)piperazine hydrochloride (73 mg, 0.36 mmol) and triethylamine (0.128 mL, 0.0918 mmol). The reaction mixture was added with water. The obtained solid was collected by filtration and washed with water, followed by drying under reduced pressure to obtain Compound 187 (35.8 mg, yield 83%).

APCI-MS m/z: 474 [M+H]$^+$; $^1$H-NMR (DMSO-d$_6$) δ(ppm): 2.91 (s, 3H), 3.12-3.24 (m, 4H), 3.54-3.75 (m, 4H), 4.57 (s, 2H), 7.32 (dd, J=1.3, 8.4 Hz, 1H), 7.73-7.83 (m, 2H), 7.89 (d, J=8.4 Hz, 1H), 8.69 (d, J=8.4 Hz, 1H), 9.80 (s, 1H), 15.00 (s, 1H).

EXAMPLE 188

4-Chloro-7-{1H-5-[4-(2-aminoethyl)piperazin-1-ylmethyl]indol-2-yl}isoindolinone trihydrochloride (Compound 188)

Step 1

Compound 26 (30.0 mg, 0.0719 mmol) was dissolved in DMF (1 mL), and the solution was added with potassium carbonate (40.0 mg, 0.289 mmol) and N-tert-butoxycarbonyl-2-bromoethylamine (64.0 mg, 0.286 mmol), followed by stirring at 50° C. for 8 hours. The reaction mixture was added with water and extracted with ethyl acetate. The organic layer was washed with saturated brine and dried over anhydrous sodium sulfate. The solvent was evaporated under reduced pressure and the residue was purified by slurry using diisopropylether to obtain 4-chloro-7-(5-(4-[2-(tert-butoxycarbonyl)aminoethyl]piperazin-1-ylmethyl)indol-2-yl)isoindolinone (19.9 mg, yield 53%).

ESI-MS m/z: 524 [M+H]$^+$; $^1$H-NMR (CDCl$_3$) δ(ppm): 1.45 (s, 9H), 2.35-2.60 (m, 10H), 3.12-3.38 (m, 2H), 3.60 (s, 2H), 4.50 (s, 2H), 4.98 (br s, 1H), 6.46 (s, 1H), 7.04 (s, 1H), 7.18 (d, J=8.4 Hz, 1H), 7.44 (d, J=8.4 Hz, 1H), 7.54 (d, J=8.5 Hz, 2H), 8.06 (d, J=8.5 Hz, 1H), 13.21 (s, 1H).

Step 2

In a similar manner to Step 2 of Example 8, 4-chloro-7-{5-[4-(2-tert-butoxycarbonylaminoethyl)piperazin-1-yl methyl]indol-2-yl}isoindolinone (19.9 mg, 0.0380 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 188 (18.8 mg, yield 93%).

ESI-MS m/z: 424 [M+H]$^+$; $^1$H-NMR (DMSO-d$_6$) δ(ppm): 2.70-3.80 (m, 12H), 4.40 (br s, 2H), 4.52 (s, 2H), 7.35 (s, 1H), 7.36 (d, J=8.3 Hz, 1H), 7.57 (d, J=8.3 Hz, 1H), 7.76 (d, J=8.4 Hz, 1H), 7.83 (s, 1H), 7.95 (br s, 3H), 8.25 (d, J=8.4 Hz, 1H), 9.57 (s, 1H), 13.88 (s, 1H).

EXAMPLE 189

4-Chloro-7-{1H-5-[4-(3-hydroxypropyl)piperazin-1-ylmethyl]indol-2-yl}isoindolinone dihydrochloride (Compound 189)

Step 1

Compound 26 (30.0 mg, 0.0719 mmol) was dissolved in DMF (1 mL), and the solution was added with potassium carbonate (40.0 mg, 0.289 mmol) and 3-bromopropoxy-tert-butyldimethylsilane (0.066 mL 0.29 mmol), followed by stirring at 60° C. for 4 hours. The reaction mixture was added with water and the precipitated solid was collected by filtration and washed with water, followed by drying under reduced pressure to obtain 4-chloro-7-(5-(4-[2-(tert-butyldimethylsilyloxy)ethyl]piperazin-1-ylmethyl)indol-2-yl)isoindolinone (53.5 mg).

Step 2

In a similar manner to Step 2 of Example 8, 4-chloro-7-(5-(4-[2-(tert-butyldimethylsilyloxy)ethyl]piperazin-1-ylmethyl)indol-2-yl)isoindolinone (53.5 mg) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 189 (16.0 mg, yield 43%, 2 steps).

APCI-MS m/z: 439 [M+H]$^+$; $^1$H-NMR (DMSO-d$_6$) δ(ppm): 1.70-1.88 (m, 2H), 3.00-3.70 (m, 12H), 4.43-4.48 (m, 2H), 4.51 (s, 2H), 7.25-7.38 (m, 2H), 7.55 (br s, 1H), 7.75 (d, J=8.6 Hz, 2H), 7.77 (s, 1H), 8.24 (d, J=8.6 Hz, 1H), 9.56 (s, 1H), 13.87 (s, 1H).

EXAMPLE 190

4-Chloro-7-{1H-5-[(2,2-dimethyl-3-(dimethylamino)propyl)aminocarbonyl]indol-2-yl}isoindolinone (Compound 190)

In a similar manner to Example 20, Compound 19 (30.0 mg, 0.0918 mmol) was dissolved in DMF (2 mL), and the solution was treated with EDCI (35.2 mg, 0.184 mmol), HOBT monohydrate (12.4 mg, 0.0918 mmol) and N,N,2,2-tetramethyl-1,3-propanediamine (0.058 mL, 0.36 mmol). The mixture was added with water. The precipitated solid was collected by filtration and washed with water, followed by drying under reduced pressure to obtain Compound 190 (37.1 mg, yield 92%).

APCI-MS m/z: 439 [M+H]$^+$; $^1$H-NMR (DMSO-d$_6$) δ(ppm): 0.91 (s, 6H), 2.20 (s, 2H), 2.28 (s, 6H), 3.21 (d, J=5.8 Hz, 2H), 4.51 (s, 2H), 7.40 (d, J=1.5 Hz, 1H), 7.53 (d, J=8.6 Hz, 1H), 7.64 (dd, J=1.5, 8.6 Hz, 1H), 7.75 (d, J=8.6 Hz, 1H), 8.11 (s, 1H), 8.25 (d, J=8.6 Hz, 1H), 8.42 (t, J=5.8 Hz, 1H), 9.57 (s, 1H), 13.93 (s, 1H).

EXAMPLE 191

4-Chloro-7-[1H-5-(4-aminopiperidinocarbonyl)indol-2-yl]isoindolinone hydrochloride (Compound 191)

Step 1

In a similar manner to Example 20, Compound 19 (30.0 mg, 0.0918 mmol) was dissolved in DMF (2 mL), and the solution was treated with EDCI (35.2 mg, 0.184 mmol), HOBT monohydrate (12.4 mg, 0.0918 mmol) and 4-(tert-butoxycarbonylamino)piperidine (74.0 mg, 0.369 mmol). The mixture was added with water. The precipitated solid was collected by filtration and washed with water, followed by drying under reduced pressure to obtain 4-chloro-7-[1H-5-(4-tert-butoxycarbonylaminopiperidinocarbonyl)indol-2-yl]isoindolinone (43.6 mg).

Step 2

In a similar manner to Step 2 of Example 8, 4-chloro-7-[1H-5-(4-tert-butoxycarbonylaminopiperidinocarbonyl)indol-2-yl]isoindolinone (43.6 mg) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 191 (16.1 mg, yield 39%, 2 steps).

ESI-MS m/z: 409 [M+H]$^+$; $^1$H-NMR (DMSO-d$_6$) δ(ppm): 1.38-1.60 (m, 2H), 1.87-2.03 (m, 2H), 2.90-3.10 (m, 2H), 3.20-3.50 (m, 3H), 4.52 (s, 2H), 7.16 (dd, J=1.0, 8.6 Hz, 1H), 7.35 (d, J=1.0 Hz, 1H), 7.55 (d, J=8.6 Hz, 1H), 7.63 (s, 1H), 7.76 (d, J=8.8 Hz, 1H), 8.03 (br s, 3H), 8.22 (d, J=8.8 Hz, 1H), 9.57 (s, 1H), 13.91 (s, 1H).

EXAMPLE 192

4-Chloro-7-{1H-5-[(2,2-dimethyl-3-(dimethylamino)propyl)aminomethyl]indol-2-yl}isoindolinone dihydrochloride (Compound 192)

Step 1

In a similar manner to Step 2 of Example 6, 4-chloro-7-[1-(tert-butoxycarbonyl)-5-formyl]indolylisoindolinone (30.0 mg, 0.0730 mmol) was dissolved in acetonitrile (2 mL), and the solution was treated with N,N,2,2-tetramethyl-1,3-propanediamine (0.046 mL, 0.29 mmol), acetic acid (0.084 mL, 1.5 mmol) and sodium triacetoxyborohydride (46.0 mg, 0.217 mmol) to obtain 4-chloro-7-{1-(tert-butoxycarbonyl)-5-[(2,2-dimethyl-3-(dimethylamino)propyl)aminomethyl]indol-2-yl}isoindolinone (38.9 mg).

Step 2

In a similar manner to Step 2 of Example 8, 4-chloro-7-{1-(tert-butoxycarbonyl)-5-[(2,2-dimethyl-3-(dimethylamino)propyl)aminomethyl]indol-2-yl}isoindolinone (38.9 mg) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 192 (27.5 mg, yield 76%, 2 steps).

ESI-MS m/z: 425 [M+H]$^+$, $^1$H-NMR (DMSO-d$_6$) δ(ppm): 1.16 (s, 6H), 2.78 (d, J=4.6 Hz, 6H), 2.94 (br s, 2H), 3.25 (d, J=3.8 Hz, 2H), 4.26 (br s, 2H), 4.52 (s, 2H), 7.34 (s, 1H), 7.41 (d, J=8.5 Hz, 1H), 7.56 (d, J=8.5 Hz, 1H), 7.75 (dd, J=0.8, 8.4 Hz, 1H), 7.84 (s, 1H), 8.25 (d, J=8.5 Hz, 1H), 9.17 (br s, 2H), 9.57 (s, 1H), 10.00 (br s, 1H), 13.86 (s, 1H).

EXAMPLE 193

4-Chloro-7-{1H-5-[(2-amino-2-methylpropyl)aminocarbonyl]indol-2-yl}isoindolinone (Compound 193)

In a similar manner to Example 20, Compound 19 (30.0 mg, 0.0918 mmol) was dissolved in DMF (2 mL), and the solution was treated with EDCI (35.2 mg, 0.184 mmol), HOBT monohydrate (12.4 mg, 0.0918 mmol) and 1,2-diamino-2-methylpropane (0.038 mL, 0.36 mmol). The reaction mixture was added with water and extracted with ethyl acetate. The organic layer was washed with saturated brine and dried over anhydrous sodium sulfate. The solvent was evaporated under reduced pressure and the residue was purified by slurry using chloroform and diisopropylether to obtain Compound 193 (19.5 mg, yield 54%).

ESI-MS m/z: 397 [M+H]$^+$; $^1$H-NMR (DMSO-d$_6$) δ(ppm): 1.03 (s, 6H), 3.21 (d, J=6.0 Hz, 2H), 4.52 (s, 2H), 7.39 (s, 1H), 7.53 (d, J=8.6 Hz, 1H), 7.69 (d, J=8.6 Hz, 1H), 7.76 (dd, J=1.0, 8.6 Hz, 1H), 8.14 (t, J=6.0 Hz, 1H), 8.18 (s, 1H), 8.26 (d, J=8.6 Hz, 1H), 9.58 (br s, 1H), 13.93 (s, 1H).

EXAMPLE 194

4-Chloro-7-[1H-5-(4-aminopiperidinomethyl)indol-2-yl]isoindolinone dihydrochloride (Compound 194)

Step 1

In a similar manner to Step 2 of Example 6, 4-chloro-7-[1-(tert-butoxycarbonyl)-5-formyl]indolylisoindolinone (30.0 mg, 0.0730 mmol) was dissolved in acetonitrile (2 mL), and the solution was treated with 4-(tert-butoxycarbonylamino)piperidine (58.0 mg, 0.290 mmol), acetic acid (0.084 mL, 1.5 mmol) and sodium triacetoxyborohydride (46.0 mg, 0.217 mmol) to obtain 4-chloro-7-[1-(tert-butoxycarbonyl)-5-(4-tert-butoxycarbonylaminopiperidinomethyl)indol-2-yl]isoindolinone (32.0 mg).

Step 2

In a similar manner to Step 2 of Example 8, 4-chloro-7-[1-(tert-butoxycarbonyl)-5-(4-tert-butoxycarbonylaminopiperidinomethyl)indol-2-yl]isoindolinone (32.0 mg) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 194 (6.5 mg, yield 18%, 2 steps).

ESI-MS m/z: 395 [M+H]$^+$; $^1$H-NMR (DMSO-d$_6$) δ(ppm): 1.78-2.20 (m, 4H), 2.80-3.10 (m, 2H), 3.25-3.50 (m, 3H), 4.32 (br s, 2H), 4.52 (s, 2H), 7.31 (d, J=8.7 Hz, 1H), 7.35 (s, 1H), 7.58 (d, J=8.7 Hz, 1H), 7.76 (d, J=8.5 Hz, 1H), 7.78 (s, 1H), 8.21 (br s, 3H), 8.25 (t, J=8.5 Hz, 1H), 9.56 (s, 1H), 10.34 (s, 1H), 13.89 (s, 1H).

EXAMPLE 195

4-Chloro-7-{1H-5-[(2-amino-2-methylpropyl)aminomethyl]indol-2-yl}isoindolinone dihydrochloride (Compound 195)

Step 1

In a similar manner to Step 2 of Example 6, 4-chloro-7-[1-(tert-butoxycarbonyl)-5-formyl]indolylisoindolinone (30.0 mg, 0.0730 mmol) was dissolved in acetonitrile (2 mL), and the solution was treated with 1,2-diamino-2-methylpropane (0.031 mL, 0.30 mmol), acetic acid (0.084 mL, 1.5 mmol) and sodium triacetoxyborohydride (46.0 mg, 0.217 mmol) to obtain 4-chloro-7-(1-(tert-butoxycarbonyl)-5-[(2-amino-2-methylpropyl)aminomethyl]indol-2-yl)isoindolinone (36.7 mg).

Step 2

In a similar manner to Step 2 of Example 8, 4-chloro-7-{1-(tert-butoxycarbonyl)-5-[(2-amino-2-methylpropyl)aminomethyl]indol-2-yl}isoindolinone (36.7 mg) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 195 (19.8 mg, yield 61%, 2 steps).

ESI-MS m/z: 383 [M+H]$^+$; $^1$H-NMR (DMSO-d$_6$) δ(ppm): 1.37 (s, 6H), 3.15 (br s, 2H), 4.29 (br s, 2H), 4.52 (s, 2H), 7.35 (s, 1H), 7.40 (d, J=8.4 Hz, 1H), 7.57 (d, J=8.4 Hz, 1H), 7.75 (d, J=8.6 Hz, 1H), 7.84 (s, 1H), 8.25 (d, J=8.6 Hz, 1H), 8.48 (br s, 3H), 9.56 (s, 1H), 9.60 (s, 2H), 13.87 (s, 1H).

EXAMPLE 196

4-Chloro-7-[1H-5-(3-hydroxypiperidinocarbonyl)indol-2-yl]isoindolinone (Compound 196)

In a similar manner to Example 20, Compound 19 (31.8 mg, 0.0973 mmol) was dissolved in DMF (1 mL), and the solution was treated with EDCI (38.5 mg, 0.201 mmol), HOBT monohydrate (18.6 mg, 0.121 mmol), 3-hydroxypiperidine hydrochloride (56.2 mg, 0.408 mmol) and triethylamine (0.055 mL, 0.403 mmol). The mixture was added with water. The precipitated solid was collected by filtration and washed with water, followed by drying under reduced pressure to obtain Compound 196 (24.5 mg, yield 61%).

ESI-MS m/z: 410 [M+H]$^+$; $^1$H-NMR (DMSO-d$_6$) δ(ppm): 1.36-1.46 (m, 2H), 1.69 (m, 1H), 1.88 (m, 1H), 2.70-3.15 (m, 4H), 3.13 (m, 1H), 4.51 (s, 2H), 4.88 (m, 1H), 7.17 (d, J=8.2 Hz, 1H), 7.33 (s, 1H), 7.52 (d, J=8.2 Hz, 1H) 7.63 (s, 1H), 7.75 (d, J=8.2 Hz, 1H), 8.22 (d, J=8.2 Hz, 1H), 9.55 (s, 1H), 13.88 (s, 1H).

EXAMPLE 197

4-Chloro-7-{1H-5-[4-(hydroxymethyl)piperidinocarbonyl]indol-2-yl}isoindolinone (Compound 197)

In a similar manner to Example 20, Compound 19 (33.0 mg, 0.101 mmol) was dissolved in DMF (1 mL), and the solution was treated with EDCI (42.0 mg, 0.219 mmol), HOBT monohydrate (19.7 mg, 0.129 mmol) and 4-piperidinemethanol (53.2 mg, 0.462 mmol). The mixture was added with water. The precipitated solid was collected by filtration and washed with water, followed by drying under reduced pressure to obtain Compound 197 (31.8 mg, yield 74%).

ESI-MS m/z: 424 [M+H]$^+$; $^1$H-NMR (DMSO-d$_6$) δ(ppm): 1.08-1.22 (m, 2H), 1.58-1.75 (m, 3H), 2.82-2.94 (m, 2H), 3.26-3.39 (m, 4H), 4.49 (m, 1H), 4.51 (s, 2H), 7.15 (dd, J=1.6, 8.6 Hz, 1H), 7.33 (s, 1H), 7.52 (d, J=8.6 Hz, 1H), 7.61 (s, 1H), 7.75 (d, J=8.6 Hz, 1H), 8.22 (d, J=8.6 Hz, 1H), 9.55 (s, 1H), 13.88 (s, 1H).

EXAMPLE 198

4-Chloro-7-{1H-5-[(pyridin-3-ylmethyl)aminomethyl]indol-2-yl}isoindolinone dihydrochloride (Compound 198)

Step 1

In a similar manner to Step 2 of Example 6, 4-chloro-7-[1-(tert-butoxycarbonyl)-5-formyl]indolylisoindolinone (32.7 mg, 0.0796 mmol) was dissolved in acetonitrile (1 mL), and the solution was treated with 3-(aminomethyl)pyridine (0.033 mL, 0.32 mmol), acetic acid (0.100 mL, 1.75 mmol) and sodium triacetoxyborohydride (24.2 mg, 0.114 mmol) to obtain 4-chloro-7-{1-(tert-butoxycarbonyl)-5-[(pyridin-3-ylmethyl)aminomethyl]indol-2-yl}isoindolinone (40.8 mg).

Step 2

In a similar manner to Step 2 of Example 8, 4-chloro-7-{1-(tert-butoxycarbonyl)-5-[(pyridin-3-ylmethyl)aminomethyl]indol-2-yl}isoindolinone (40.8 mg) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 198 (33.4 mg, yield 88%, 2 steps).

APCI-MS m/z: 403 [M+H]$^+$; $^1$H-NMR (DMSO-d$_6$) δ(ppm): 4.25-4.38 (m, 4H), 4.51 (s, 2H), 7.31-7.37 (m, 2H), 7.56 (d, J=8.2 Hz, 1H), 7.75 (d, J=8.6 Hz, 1H), 7.74-7.82 (m, 2H), 8.25 (d, J=8.6 Hz, 1H), 8.38 (d, J=8.6 Hz, 1H), 8.77 (m, 1H), 8.92 (s, 1H), 9.56 (s, 1H), 9.78 (br s, 2H), 9.55 (s, 1H), 13.87 (s, 1H).

EXAMPLE 199

4-Chloro-7-[1H-5-(4-hydroxypiperidinocarbonyl)indol-2-yl]isoindolinone (Compound 199)

In a similar manner to Example 20, Compound 19 (31.6 mg, 0.0967 mmol) was dissolved in DMF (1 mL), and the solution was treated with EDCI (38.9 mg, 0.203 mmol), HOBT monohydrate (17.2 mg, 0.112 mmol) and 4-hydroxypiperidine (41.4 mg, 0.409 mmol). The mixture was added with water. The precipitated solid was collected by filtration and washed with water, followed by drying under reduced pressure to obtain Compound 199 (34.8 mg, yield 88%).

ESI-MS m/z: 410 [M+H]$^+$; $^1$H-NMR (DMSO-d$_6$) δ(ppm): 1.30-1.50 (m, 2H), 1.70-1.85 (m, 2H), 3.14-3.28 (m, 2H), 3.72-3.80 (m, 3H), 4.51 (s, 2H), 4.77 (d, J=4.1 Hz, 1H), 7.16 (d, J=8.6 Hz, 1H), 7.34 (s, 1H), 7.52 (d, J=8.6 Hz, 1H), 7.62 (s, 1H), 7.75 (d, J=8.6 Hz, 1H), 8.22 (d, J=8.6 Hz, 1H), 9.55 (s, 1H), 13.88 (s, 1H).

EXAMPLE 200

4-Chloro-7-{1H-5-[4-(2-hydroxyethyl)piperidinocarbonyl]indol-2-yl}isoindolinone (Compound 200)

In a similar manner to Example 20, Compound 19 (31.8 mg, 0.0973 mmol) was dissolved in DMF (1 mL), and the solution was treated with EDCI (40.7 mg, 0.212 mmol), HOBT monohydrate (19.2 mg, 0.125 mmol) and 4-piperidineethanol (70.8 mg, 0.548 mmol). The mixture was added with water. The precipitated solid was collected by filtration and washed with water, followed by drying under reduced pressure to obtain Compound 200 (11.2 mg, yield 26%).

ESI-MS m/z: 438 [M+H]$^+$; $^1$H-NMR (DMSO-d$_6$) δ(ppm): 1.07-1.20 (m, 2H), 1.35-1.45 (m, 2H), 1.60-1.75 (m, 3H), 2.75-3.00 (m, 2H), 3.38-3.40 (m, 2H), 3.41-3.49 (m, 2H), 4.38 (t, J=5.2 Hz, 1H), 4.51 (s, 2H), 7.16 (d, J=8.4 Hz, 1H), 7.33 (s, 1H), 7.52 (d, J=8.4 Hz, 1H), 7.62 (s, 1H), 7.75 (d, J=8.4 Hz, 1H), 8.21 (d, J=8.4 Hz, 1H), 9.55 (s, 1H), 13.88 (s, 1H).

EXAMPLE 201

4-Chloro-7-{1H-5-[4-(3-hydroxypropyl)piperidinocarbonyl]indol-2-yl}isoindolinone (Compound 201)

In a similar manner to Example 20, Compound 19 (34.5 mg, 0.106 mmol) was dissolved in DMF (1 mL), and the solution was treated with EDCI (42.5 mg, 0.222 mmol), HOBT monohydrate (17.1 mg, 0.112 mmol) and 1-(3-hydroxypropyl)piperidine (92.0 mg, 0.424 mmol). The mixture was added with water. The precipitated solid was collected by filtration and washed with water, followed by drying under reduced pressure to obtain Compound 201 (40.4 mg, yield 84%).

ESI-MS m/z: 453 [M+H]$^+$; $^1$H-NMR (DMSO-d$_6$) δ(ppm): 1.57-1.71 (m, 2H), 2.40-2.65 (m, 6H), 3.20-3.65 (m, 7H), 4.51 (s, 2H), 7.19 (dd, J=1.5, 8.4 Hz, 1H), 7.34 (s, 1H), 7.54 (d, J=8.6 Hz, 1H), 7.66 (s, 1H), 7.75 (d, J=8.6 Hz, 1H), 8.21 (d, J=8.6 Hz, 1H), 9.56 (s, 1H), 13.90 (s, 1H).

EXAMPLE 202

4-Chloro-7-[1H-5-(piperidin-4-ylcarbonylamino)indol-2-yl]isoindolinone hydrochloride (Compound 202)

Step 1

In a similar manner to Step 2 of Example 1, 4-chloro-7-iodoisoindolinone (45.0 mg, 0.153 mmol) was dissolved in acetonitrile (2 mL), and the solution was treated with Compound BO (110 mg, 0.230 mmol), palladium acetate (3.4 mg, 0.015 mmol) and triethylamine (0.213 mL, 1.53 mmol), followed by purification by flash column chromatography (hexane/ethyl acetate=95/5 to 80/20 to 70/30 to 60/40 to 40/60) to obtain 4-chloro-7-{1-(tert-butoxycarbonyl)-5-[1-(tert-butoxycarbonyl)piperidin-4-ylcarbonylamino]indol-2-yl}isoindolinone (73.1 mg, yield 78%).

ESI-MS m/z: 609 [M+H]$^+$; $^1$H-NMR (CDCl$_3$) δ(ppm): 1.35 (s, 9H), 1.47 (s, 9H), 1.68-1.84 (m, 2H), 1.86-1.98 (m, 2H), 2.38 (m, 1H), 2.70-2.89 (m, 2H), 4.10-4.28 (m, 2H), 4.41 (s, 2H), 6.52 (s, 1H), 6.54 (br s, 1H), 7.19 (dd, J=1.8, 8.8 Hz, 1H), 7.32 (s, 1H), 7.43 (d, J=8.1 Hz, 1H), 7.56 (d, J=8.1 Hz, 1H), 7.90 (d, J=1.8 Hz, 1H), 8.11 (d, J=8.8 Hz, 1H).

Step 2

In a similar manner to Step 2 of Example 5, 4-chloro-7-(1-(tert-butoxycarbonyl)-5-[1-(tert-butoxycarbonyl)piperidin-4-ylcarbonylamino]indol-2-yl)isoindolinone (41.0 mg, 0.0673 mmol) was treated with 4 mol/L hydrogen chloride-ethyl acetate solution (2 mL). The obtained solid was collected by filtration and washed with ethyl acetate, followed by drying under reduced pressure to obtain Compound 202 (22.1 mg, yield 74%).

ESI-MS m/z: 409 [M+H]$^+$; $^1$H-NMR (DMSO-d$_6$) δ(ppm): 1.76-2.05 (m, 4H), 2.65 (m, 1H), 2.86-3.00 (m, 2H), 3.26-3.40 (m, 2H), 4.50 (s, 2H), 7.23 (s, 1H), 7.25 (dd, J=1.9, 8.9 Hz, 1H), 7.41 (d, J=8.9 Hz, 1H), 7.72 (d, J=8.5 Hz, 1H), 7.97 (d, J=1.9 Hz, 1H), 8.20 (d, J=8.5 Hz, 1H), 8.58 (br s, 2H), 9.53 (s, 1H), 9.91 (s, 1H), 13.69 (s, 1H).

EXAMPLE 203

4-Chloro-7-(1H-5-aminoindol-2-yl)isoindolinone hydrochloride (Compound 203)

Step 1

In a similar manner to Step 2 of Example 1, 4-chloro-7-iodoisoindolinone (104 mg, 0.354 mmol) was dissolved in acetonitrile (5 mL), and the solution was treated with Compound BP (200 mg, 0.532 mmol), palladium acetate (6.4 mg, 0.029 mmol) and triethylamine (0.493 mL, 3.54 mmol), followed by purification by flash column chromatography (hexane/ethyl acetate=95/5 to 80/20 to 70/30 to 60/40) to obtain 4-chloro-7-[1-(tert-butoxycarbonyl)-5-(tert-butoxycarbonyl)aminoindol-2-yl]isoindolinone (141 mg, yield 80%).

ESI-MS m/z: 498 [M+H]$^+$; $^1$H-NMR (CDCl$_3$) δ(ppm): 1.34 (s, 9H), 1.53 (s, 9H), 4.39 (s, 2H), 6.50 (s, 1H), 6.56 (br s, 1H), 7.11 (s, 1H), 7.13 (dd, J=2.3, 9.0 Hz, 1H), 7.42 (d, J=8.1 Hz, 1H), 7.54 (d, J=8.1 Hz, 1H), 7.72 (br s, 1H), 8.10 (d, J=9.0 Hz, 1H).

Step 2

In a similar manner to Step 2 of Example 8, 4-chloro-7-[1-(tert-butoxycarbonyl)-5-(tert-butoxycarbonyl)amino indol-2-yl]isoindolinone (140 mg, 0.281 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 203 (87.4 mg, yield 93%).

APCI-MS m/z: 298 [M+H]$^+$; $^1$H-NMR (DMSO-d$_6$) δ(ppm): 4.52 (s, 2H), 7.11 (dd, J=1.8, 8.4 Hz, 1H), 7.35 (s, 1H), 7.58 (d, J=1.8 Hz, 1H), 7.61 (d, J=8.4 Hz, 1H), 7.77 (d, J=8.4 Hz, 1H), 8.22 (d, J=8.4 Hz, 1H), 9.58 (s, 1H), 9.94 (br s, 3H), 13.96 (s, 1H).

EXAMPLE 204

4-Chloro-7-[1H-5-(4-piperidylamino)indol-2-yl]isoindolinone dihydrochloride (Compound 204)

Step 1

In a similar manner to Step 2 of Example 1, 4-chloro-7-iodoisoindolinone (64 mg, 0.218 mmol) was dissolved in acetonitrile (3 mL), and the solution was treated with Compound BQ (150 mg, 0.326 mmol), palladium acetate (3.9 mg, 0.017 mmol) and triethylamine (0.304 mL, 2.18 mmol), followed by purification by flash column chromatography (hexane/ethyl acetate=95/5 to 80/20 to 70/30 to 60/40 to 50/50 to 40/60) to obtain 4-chloro-7-{1-(tert-butoxycarbonyl)-5-[1-(tert-butoxycarbonyl)-4-piperidylamino]indol-2-yl}isoindolinone (73.3 mg, yield 58%).

APCI-MS m/z: 581 [M+H]$^+$; $^1$H-NMR (CDCl$_3$) δ(ppm): 1.25-1.45 (m, 2H), 1.33 (s, 9H), 1.47 (s, 9H), 2.03-2.15 (m, 2H), 2.86-3.01 (m, 2H), 3.46 (m, 1H), 3.88-4.19 (m, 2H), 4.39 (s, 2H), 6.42 (s, 1H), 6.68 (dd, J=2.3, 8.8 Hz, 1H), 6.75 (d, J=2.3 Hz, 1H), 7.32 (br s, 1H), 7.40 (d, J=8.1 Hz, 1H), 7.53 (d, J=8.1 Hz, 1H), 8.01 (d, J=8.8 Hz, 1H).

Step 2

In a similar manner to Step 2 of Example 8, 4-chloro-7-{1-(tert-butoxycarbonyl)-5-[1-(tert-butoxycarbonyl)-4-piperidylamino]indol-2-yl}isoindolinone (73.0 mg, 0.126 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 204 (38.2 mg, yield 67%).

APCI-MS m/z: 381 [M+H]$^+$; $^1$H-NMR (DMSO-d$_6$) δ(ppm): 1.84-2.05 (m, 2H), 2.06-2.20 (m, 2H), 2.82-3.00 (m, 2H), 3.25-3.40 (m, 2H), 3.74 (m, 1H), 4.52 (s, 2H), 7.24 (m, 1H), 7.37 (br s, 1H), 7.60-7.80 (m, 2H), 7.78 (d, J=8.6 Hz, 1H), 8.23 (d, J=8.6 Hz, 1H), 8.79 (br s, 1H), 8.98 (br s, 1H), 9.58 (s, 1H), 11.49 (br s, 2H), 13.97 (s, 1H).

EXAMPLE 205

4-Chloro-7-(1H-5-hydroxyindol-2-yl)isoindolinone (Compound 205)

Step 1

In a similar manner to Step 2 of Example 1, 4-chloro-7-iodoisoindolinone (150 mg, 0.511 mmol) was dissolved in acetonitrile (3 mL), and the solution was treated with Compound BR (300 mg, 0.767 mmol), palladium acetate (9.2 mg, 0.041 mmol) and triethylamine (0.712 mL, 5.11 mmol), followed by purification by flash column chromatography (hexane/ethyl acetate=95/5 to 80/20) to obtain 4-chloro-7-[1-(tert-butoxycarbonyl)-5-(tert-butyldimethylsilyloxy)indol-2-yl]isoindolinone (217 mg, yield 83%).

APCI-MS m/z: 513 [M+H]$^+$; $^1$H-NMR (CDCl$_3$) δ(ppm): 0.21 (s, 6H), 1.01 (s, 9H), 1.32 (s, 9H), 4.38 (s, 2H), 6.47 (s, 1H), 6.87 (dd, J=2.3, 9.0 Hz, 1H), 6.98 (d, J=2.3 Hz, 1H), 7.41 (d, J=8.1 Hz, 1H), 7.54 (d, J=8.1 Hz, 1H), 7.61 (br s, 1H), 8.07 (d, J=9.0 Hz, 1H).

Step 2

In a similar manner to Step 2 of Example 8, 4-chloro-7-[1-(tert-butoxycarbonyl)-5-(tert-butyldimethylsilyloxy)indol-2-yl]isoindolinone (216 mg, 0.421 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 205 (115 mg, yield 91%).

APCI-MS m/z: 299 [M+H]$^+$; $^1$H-NMR (DMSO-d$_6$) δ(ppm): 3.16 (s, 1H), 4.48 (s, 2H), 6.68 (dd, J=2.2, 8.7 Hz, 1H), 6.87 (d, J=2.2 Hz, 1H), 7.06 (s, 1H), 7.26 (d, J=8.7 Hz, 1H), 7.69 (d, J=8.5 Hz, 1H), 8.14 (d, J=8.5 Hz, 1H), 9.47 (s, 1H), 13.46 (s, 1H).

EXAMPLE 206

4-Chloro-7-(1H-5-cyanoindol-2-yl)isoindolinone (Compound 206)

Step 1

In a similar manner to Step 2 of Example 1, 4-chloro-7-iodoisoindolinone (68.4 mg, 0.230 mmol) was dissolved in acetonitrile (1.4 mL), and the solution was treated with 1-(tert-butoxycarbonyl)-5-cyanoindole-2-boronic acid (100 mg, 0.350 mmol) synthesized in a similar manner to the method described in Journal of Organic Chemistry, 2002, vol. 67, p. 7551, palladium acetate (4.1 mg, 0.018 mmol) and triethylamine (0.321 mL, 2.30 mmol), followed by purification by preparative thin-layer chromatography (hexane/ethyl acetate=1/1) to obtain 4-chloro-7-[1-(tert-butoxycarbonyl)-5-cyanoindol-2-yl]isoindolinone (40.2 mg).

Step 2

In a similar manner to Step 2 of Example 5, 4-chloro-7-[1-(tert-butoxycarbonyl)-5-cyanoindol-2-yl]isoindolinone (39.1 mg) was treated with 4 mol/L hydrochloric acid-ethyl acetate solution (2 mL). The mixture was added with diisopropylether. The obtained solid was collected by filtration and washed with diisopropylether, followed by drying under reduced pressure to obtain Compound 206 (12.1 mg, yield 17%, 2 steps).

ESI-MS m/z: 308 [M+H]$^+$; $^1$H-NMR (DMSO-$d_6$) δ(ppm): 4.50 (s, 2H), 7.39 (s, 1H), 7.45 (dd, J=1.6, 8.5 Hz, 1H), 7.67 (d, J=8.5 Hz, 1H), 7.76 (d, J=8.3 Hz, 1H), 8.11 (s, 1H), 8.23 (d, J=8.3 Hz, 1H), 9.58 (s, 1H), 14.17 (s, 1H).

EXAMPLE 207

4-Chloro-7-[1H-5-(piperazin-1-ylcarbonylamino)indol-2-yl]isoindolinone hydrochloride (Compound 207)

Step 1

Compound 203 (30.0 mg, 0.0898 mmol) was suspended in THF (2 mL), and the suspension was added with phenyl chlorocarbonate (0.012 mL, 0.096 mmol) and triethylamine (0.025 mL, 0.18 mmol), followed by stirring at room temperature for 30 minutes. The mixture was added with 1-(tert-butoxycarbonyl)piperazine (126 mg, 0.677 mmol) and triethylamine (0.039 mL, 0.28 mmol) and stirred at 60° C. for 14 hours. The reaction mixture was added with water and 1 mol/L hydrochloric acid, then added with ethyl acetate. The precipitated solid was collected by filtration and washed with hexane-ethyl acetate (1/1), followed by drying under reduced pressure to obtain 4-chloro-7-[1-(tert-butoxycarbonyl)-5-(piperazin-1-ylcarbonylamino)indol-2-yl]isoindolinone (36.1 mg, yield 79%).

APCI-MS m/z: 510 [M+H]$^+$; $^1$H-NMR (DMSO-$d_6$) δ(ppm): 1.43 (s, 9H), 3.30-3.38 (m, 4H), 3.39-3.48 (m, 4H), 4.49 (s, 2H), 7.14-7.21 (m, 2H), 7.35 (d, J=8.9 Hz, 1H), 7.66 (s, 1H), 7.71 (d, J=8.6 Hz, 1H), 8.19 (d, J=8.6 Hz, 1H), 8.41 (s, 1H), 9.50 (s, 1H), 13.60 (s, 1H).

Step 2

In a similar manner to Step 2 of Example 8, 4-chloro-7-[1-(tert-butoxycarbonyl)-5-(piperazin-1-ylcarbonylamino)indol-2-yl]isoindolinone (34.0 mg, 0.0667 mmol) was treated with 10% hydrogen chloride-methanol solution (2 mL). The mixture was added with diisopropylether. The obtained solid was collected by filtration and washed with diisopropylether, followed by drying under reduced pressure to obtain Compound 207 (27.6 mg, yield 93%).

ESI-MS m/z: 410 [M+H]$^+$; $^1$H-NMR (DMSO-$d_6$) δ(ppm): 3.10-3.20 (m, 4H), 3.64-3.72 (m, 4H), 4.50 (s, 2H), 7.15-7.23 (m, 2H), 7.37 (d, J=8.4 Hz, 1H), 7.67 (s, 1H), 7.72 (d, J=8.4 Hz, 1H), 8.19 (d, J=8.1 Hz, 1H), 8.59 (s, 1H), 8.94 (br s, 2H), 9.51 (s, 1H), 13.62 (s, 1H).

EXAMPLE 208

4-Chloro-7-[1H-5-(4,4-dimethoxypiperidinomethyl)indol-2-yl]isoindolinone hydrochloride (Compound 208)

Step 1

In a similar manner to Step 2 of Example 6, 4-chloro-7-[1-(tert-butoxycarbonyl)-5-formyl]indolylisoindolinone (60.0 mg, 0.146 mmol) was dissolved in acetonitrile (3 mL), and the solution was treated with 4,4-dimethoxypiperidine hydrochloride (106 mg, 0.584 mmol), acetic acid (0.167 mL, 2.92 mmol) and sodium triacetoxyborohydride (93.0 mg, 0.439 mmol) to obtain 4-chloro-7-[1-(tert-butoxycarbonyl)-5-(4,4-dimethoxypiperidinomethyl)indol-2-yl]isoindolinone (30.5 mg, yield 39%).

ESI-MS m/z: 540 [M+H]$^+$; $^1$H-NMR (CDCl$_3$) δ(ppm): 1.36 (s, 9H), 1.71-1.86 (m, 4H), 2.43-2.55 (m, 4H), 3.18 (s, 6H), 3.65 (s, 2H), 4.41 (s, 2H), 6.55 (s, 1H), 6.80 (br s, 1H), 7.31 (dd, J=1.5, 8.6 Hz, 1H), 7.43 (d, J=8.1 Hz, 1H), 7.51 (d, J=1.5 Hz, 1H), 7.55 (d, J=8.1 Hz, 1H), 8.14 (d, J=8.6 Hz, 1H).

Step 2

In a similar manner to Step 2 of Example 8, 4-chloro-7-[1-(tert-butoxycarbonyl)-5-(4,4-dimethoxypiperidinomethyl)indol-2-yl]isoindolinone (30.0 mg, 0.0556 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 208 (17.7 mg, yield 67%).

ESI-MS m/z: 440 [M+H]$^+$; $^1$H-NMR (DMSO-$d_6$) δ(ppm): 1.71-1.88 (m, 2H), 2.08-2.19 (m, 2H), 2.87-3.02 (m, 2H), 3.10 (s, 3H), 3.11 (s, 3H), 3.26-3.38 (m, 2H), 4.40 (d, J=4.8 Hz, 2H), 4.52 (s, 2H), 7.32 (dd, J=1.1, 8.5 Hz, 1H), 7.35 (d, J=1.1 Hz, 1H), 7.58 (d, J=8.4 Hz, 1H), 7.76 (d, J=8.6 Hz, 1H), 7.79 (s, 1H), 8.25 (d, J=8.6 Hz, 1H), 9.56 (s, 1H), 9.91 (br s, 1H), 13.89 (s, 1H).

EXAMPLE 209

4-Chloro-7-[1H-5-(4-oxopiperidinomethyl)indol-2-yl]isoindolinone hydrochloride (Compound 209)

In a similar manner to Step 2 of Example 5, Compound 208 (10.0 mg, 0.0210 mmol) was suspended in ethyl acetate (4 mL), and the suspension was treated with 4 mol/L hydrochloric acid-ethyl acetate solution (4 mL). The mixture was added with diisopropylether. The obtained solid was collected by filtration and washed with diisopropylether, followed by drying under reduced pressure to obtain Compound 209 (7.4 mg, yield 82%).

ESI-MS m/z: 394 [M+H]$^+$; $^1$H-NMR (DMSO-$d_6$) δ(ppm): 2.42-2.53 (m, 4H), 2.75-2.86 (m, 4H), 3.72 (s, 2H), 4.50 (s, 2H), 6.69 (br s, 1H), 7.05 (s, 1H), 7.22 (d, J=8.0 Hz, 1H), 7.47 (d, J=8.0 Hz, 1H), 7.54 (d, J=8.8 Hz, 1H), 7.56 (s, 1H), 8.06 (d, J=8.6 Hz, 1H), 13.29 (s, 1H).

EXAMPLE 210

4-Chloro-7-[1H-5-(2-piperidinoethoxy)indol-2-yl]isoindolinone hydrochloride (Compound 210)

Step 1

In a similar manner to Step 2 of Example 1, 4-chloro-7-iodoisoindolinone (40.0 mg, 0.136 mmol) was dissolved in acetonitrile (0.8 mL), and the solution was treated with Compound BS (106 mg, 0.272 mmol), palladium acetate (2.4 mg, 0.010 mmol) and triethylamine (0.190 mL, 1.36 mmol), followed by purification by flash column chromatography (hexane/ethyl acetate=4/6 to 3/7 to 2/8) to obtain 4-chloro-7-[1-(tert-butoxycarbonyl)-5-(2-piperidinoethoxy)indol-2-yl]isoindolinone (44.4 mg, yield 64%).

ESI-MS m/z: 510 [M+H]$^+$; $^1$H-NMR (CDCl$_3$) δ(ppm): 1.36 (s, 9H), 1.40-1.50 (m, 2H), 1.54-1.68 (m, 4H), 2.48-2.60 (m, 4H), 2.80 (t, J=6.2 Hz, 2H), 4.16 (t, J=6.2 Hz, 2H), 4.41 (s, 2H), 6.49 (s, 1H), 6.50 (br s, 1H), 6.96 (dd, J=2.6, 9.1 Hz, 1H), 7.02 (d, J=2.6 Hz, 1H), 7.42 (d, J=8.1 Hz, 1H), 7.55 (d. J=8.1 Hz, 1H), 8.08 (d, J=9.1 Hz, 1H).

Step 2

In a similar manner to Step 2 of Example 8, 4-chloro-7-[1-(tert-butoxycarbonyl)-5-(2-piperidinoethoxy)indol-2-yl]isoindolinone (42.2 mg, 0.0830 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 210 (32.4 mg, yield 88%).

APCI-MS m/z: 410 [M+H]$^+$; $^1$H-NMR (DMSO-d$_6$) δ(ppm): 1.39 (m, 1H), 1.61-1.89 (m, 5H), 2.95-3.05 (m, 2H), 3.40-3.60 (m, 4H), 4.38 (t, J=4.8 Hz, 2H), 4.49 (s, 2H), 6.86 (dd, J=2.3, 8.8 Hz, 1H), 7.15 (d, J=2.3 Hz, 1H), 7.19 (s, 1H), 7.43 (d, J=8.8 Hz, 1H), 7.72 (d, J=8.5 Hz, 1H), 8.17 (d, J=8.5 Hz, 1H), 9.51 (s, 1H), 10.00 (br s, 1H), 13.66 (s, 1H).

EXAMPLE 211

7-(1H-5-carboxyindol-2-yl)-4-hydroxyisoindolinone
(Compound 211)

Step 1

In a similar manner to Step 1 of Example 19, 4-hydroxy-7-iodoisoindolinone (200 mg, 0.727 mmol) was dissolved in DMF (4 mL), and the solution was treated with Compound BG (444 mg, 1.46 mmol), palladium acetate (13 mg, 0.058 mmol), tri(o-tolyl)phosphine (35 mg, 0.115 mmol) and triethylamine (1.01 mL, 7.25 mmol). The mixture was added with chloroform and methanol. The obtained solid was collected by filtration and washed with chloroform, followed by drying under reduced pressure to obtain 7-[1-(tert-butoxycarbonyl)-5-carboxyindol-2-yl]-4-hydroxyisoindolinone (71.0 mg, yield 24%).

APCI-MS m/z: 409 [M+H]$^+$; $^1$H-NMR (DMSO-d$_6$) δ(ppm): 1.17 (s, 9H), 4.26 (s, 2H), 6.66 (s, 1H), 7.02 (d, J=8.3 Hz, 1H), 7.28 (d, J=8.3 Hz, 1H), 7.90 (d, J=8.7 Hz, 1H), 8.202 (d, J=8.7 Hz, 1H), 8.203 (s, 1H), 8.56 (s, 1H).

Step 2

In a similar manner to Step 2 of Example 8, 7-[1-(tert-butoxycarbonyl)-5-carboxyindol-2-yl]-4-hydroxyisoindolinone (71.0 mg, 0.0174 mmol) was dissolved in methanol (1 mL), and the solution was treated with 10% hydrogen chloride-methanol solution (1 mL). The obtained solid was collected by filtration and washed with ethyl acetate, followed by drying under reduced pressure to obtain 7-[1H-5-methoxycarbonylindol-2-yl]-4-hydroxyisoindolinone (33.4 mg, yield 60%).

APCI-MS m/z: 323 [M+H]$^+$; $^1$H-NMR (DMSO-d$_6$) δ(ppm): 3.85 (s, 3H), 4.38 (s, 2H), 7.11 (d, J=8.7 Hz, 1H), 7.15 (d, J=1.3 Hz, 1H), 7.51 (d, J=8.6 Hz, 1H), 7.70 (dd, J=1.3, 8.6 Hz, 1H), 8.04 (d, J=8.7 Hz, 1H), 8.23 (s, 1H), 9.31 (s, 1H), 10.40 (s, 1H), 14.06 (s, 1H).

Step 3

7-[1H-5-methoxycarbonylindol-2-yl]-4-hydroxyisoindolinone (81.0 mg, 0.251 mmol) was dissolved in 4 mol/L aqueous potassium hydroxide solution (5 mL), and the solution was stirred at 50° C. for 0.5 hour. The reaction mixture was added with 1 mol/L hydrochloric acid and the precipitated solid was collected by filtration and washed with water, followed by drying under reduced pressure to obtain Compound 211 (77.5 mg, yield 100%).

APCI-MS m/z: 309 [M+H]$^+$; $^1$H-NMR (DMSO-d$_6$) δ(ppm): 4.38 (s, 2H), 7.12 (d, J=8.6 Hz, 1H), 7.14 (s, 1H), 7.48 (d, J=8.6 Hz, 1H), 7.69 (dd, J=1.7, 8.6 Hz, 1H), 8.04 (d, J=8.6 Hz, 1H), 8.20 (s, 1H), 9.30 (s, 1H), 10.40 (s, 1H), 12.38 (br s, 1H), 14.01 (s, 1H).

EXAMPLE 212

4-Hydroxy-7-{1H-5-[4-(2-cyanoethyl)piperazin-1-ylcarbonyl]indol-2-yl}isoindolinone
(Compound 212)

In a similar manner to Example 20, Compound 211 (20.0 mg, 0.0649 mmol) was dissolved in DMF (1 mL), and the solution was treated with EDCI (24.9 mg, 0.130 mmol), HOBt monohydrate (8.8 mg, 0.065 mmol) and 1-(2-cyanoethyl)piperazine (36.0 mg, 0.259 mmol). The reaction mixture was added with water and extracted with ethyl acetate. The organic layer was washed with saturated brine and dried over anhydrous sodium sulfate. The solvent was evaporated under reduced pressure and the residue was purified by slurry using chloroform and diisopropylether to obtain Compound 212 (15.8 mg, yield 57%).

APCI-MS m/z: 430 [M+H]$^+$; $^1$H-NMR (DMSO-d$_6$) δ(ppm): 2.42-2.53 (m, 4H), 2.57-2.74 (m, 4H), 3.49-3.60 (m, 4H), 4.37 (s, 2H), 7.06 (s, 1H), 7.11 (dd, J=1.7, 8.4 Hz, 1H), 7.12 (d, J=8.7 Hz, 1H), 7.46 (d, J=8.4 Hz, 1H), 7.58 (s, 1H), 8.02 (d, J=8.7 Hz, 1H), 9.27 (s, 1H), 10.39 (br s, 1H), 13.88 (s, 1H).

EXAMPLE 213

4-Hydroxy-7-{1H-5-[4-(pyridin-4-yl)piperazin-1-ylcarbonyl]indol-2-yl}isoindolinone
(Compound 213)

In a similar manner to Example 20, Compound 211 (20.0 mg, 0.0649 mmol) was dissolved in DMF (1 mL), and the solution was treated with EDCI (24.9 mg, 0.130 mmol), HOBT monohydrate (8.8 mg, 0.065 mmol) and 1-(pyridin-4-yl)piperazine (42.0 mg, 0.257 mmol). The mixture was added with water. The precipitated solid was collected by filtration and washed with water, followed by drying under reduced pressure to obtain Compound 213 (23.2 mg, yield 79%).

APCI-MS m/z: 454 [M+H]$^+$; $^1$H-NMR (DMSO-d$_6$) δ(ppm): 3.37-3.50 (m, 4H), 3.60-3.73 (m, 4H), 4.38 (s, 2H), 6.80-6.88 (m, 2H), 7.07 (d, J=1.4 Hz, 1H), 7.11 (d, J=8.4 Hz, 1H), 7.17 (dd, J=1.4, 8.4 Hz, 1H), 7.48 (d, J=8.4 Hz, 1H), 7.65 (s, 1H), 8.03 (d, J=8.4 Hz, 1H), 8.15-8.22 (m, 2H), 9.27 (s, 1H), 13.90 (s, 1H).

EXAMPLE 214

4-Hydroxy-7-{1H-5-[(pyridin-3-ylmethyl)aminomethyl]indol-2-yl}isoindolinone dihydrochloride (Compound 214)

Step 1

In a similar manner to Step 2 of Example 6, 4-hydroxy-7-[1-(tert-butoxycarbonyl)-5-formyl]indolylisoindolinone (40.3 mg, 0.103 mmol) was dissolved in acetonitrile (1 mL), and the solution was treated with 3-aminomethylpyridine (0.042 mL, 0.41 mmol), acetic acid (0.118 mL, 2.06 mmol) and sodium triacetoxyborohydride (43.6 mg, 0.206 mmol), to obtain 4-hydroxy-7-{1-(tert-butoxycarbonyl)-5-[(pyridin-3-ylmethyl)aminomethyl]indol-2-yl}isoindolinone (36.5 mg, yield 73%).

ESI-MS m/z: 485 [M+H]$^+$; $^1$H-NMR (CDCl$_3$) δ(ppm): 1.29 (s, 9H), 3.85 (s, 2H), 3.88 (s, 2H), 4.20 (br s, 2H), 6.32 (br s, 1H), 6.38 (s, 1H), 6.86 (d, J=8.3 Hz, 1H), 7.20 (d, J=8.3 Hz, 1H), 7.27 (m, 1H), 7.44 (s, 1H), 7.76 (d, J=7.6 Hz, 1H), 8.14 (d, J=8.3 Hz, 1H), 8.51 (d, J=5.0 Hz, 1H), 8.59 (s, 1H).

Step 2

In a similar manner to Step 2 of Example 8, 4-hydroxy-7-(1-(tert-butoxycarbonyl)-5-[(pyridin-3-ylmethyl)aminomethyl]indol-2-yl)isoindolinone (34.3 mg, 0.0710 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 214 (29.1 mg, yield 90%).

APCI-MS m/z: 385 [M+H]$^+$; $^1$H-NMR (DMSO-d$_6$) δ(ppm): 4.25 (br s, 2H), 4.33 (br s, 2H), 4.36 (s, 2H), 7.04 (s, 1H), 7.12 (d, J=8.7 Hz, 1H), 7.25 (dd, J=1.3, 8.4 Hz, 1H), 7.48 (d, J=8.4 Hz, 1H), 7.70 (s, 1H), 7.80 (dd, J=5.5, 7.7 Hz, 1H), 8.03 (d, J=8.7 Hz, 1H), 8.40 (d, J=8.1 Hz, 1H), 8.78 (dd, J=1.4, 5.4 Hz, 1H), 8.92 (s, 1H), 9.25 (s, 1H), 9.73 (br s, 2H), 10.42 (br s, 1H), 13.84 (s, 1H).

EXAMPLE 215

4-Hydroxy-7-{1H-5-[(2-hydroxyethyl)aminomethyl]indol-2-yl}isoindolinone hydrochloride (Compound 215)

Step 1

In a similar manner to Step 2 of Example 6, 4-hydroxy-7-[1-(tert-butoxycarbonyl)-5-formyl]indolylisoindolinone (40.4 mg, 0.103 mmol) was dissolved in acetonitrile (1 mL), and the solution was treated with 2-aminoethanol (0.025 mL, 0.41 mmol), acetic acid (0.118 mL, 2.06 mmol) and sodium triacetoxyborohydride (65.4 mg, 0.309 mmol) to obtain 4-hydroxy-7-{1-(tert-butoxycarbonyl)-5-[(2-hydroxyethyl)aminomethyl]indol-2-yl}isoindolinone (12.0 mg, yield 27%).

ESI-MS m/z: 438 [M+H]$^+$; $^1$H-NMR (CDCl$_3$) δ(ppm): 1.31 (s, 9H), 2.75-2.86 (m, 2H), 3.65-3.73 (m, 2H), 3.92 (s, 2H), 4.31 (br s, 2H), 6.37 (br s, 1H), 6.96 (d, J=7.9 Hz, 1H), 7.11-7.30 (m, 2H), 7.43 (br s, 1H), 8.13 (d, J=8.4 Hz, 1H).

Step 2

In a similar manner to Step 2 of Example 8, 4-hydroxy-7-(1-(tert-butoxycarbonyl)-5-[(2-hydroxyethyl)aminomethyl]indol-2-yl)isoindolinone (12.0 mg, 0.0270 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 215 (8.0 mg, yield 79%).

APCI-MS m/z: 336 [M−H]$^−$; $^1$H-NMR (DMSO-d$_6$) δ(ppm): 2.88-2.98 (m, 2H), 3.55 (m, 1H), 3.65 (t, J=5.3 Hz, 2H), 4.19 (s, 2H), 4.36 (s, 2H), 7.03 (s, 1H), 7.10 (d, J=8.3 Hz, 1H), 7.21 (d, J=8.8 Hz, 1H), 7.47 (d, J=8.3 Hz, 1H), 7.67 (s, 1H), 8.02 (d. J=8.8 Hz, 1H), 8.89 (br s, 2H), 9.25 (s, 1H), 10.38 (br s, 1H), 13.81 (s, 1H).

EXAMPLE 216

4-Hydroxy-7-{1H-5-[(2,2-dimethyl-3-(dimethylamino)propyl)aminomethyl]indol-2-yl}isoindolinone dihydrochloride (Compound 216)

Step 1

In a similar manner to Step 2 of Example 6, 4-hydroxy-7-[1-(tert-butoxycarbonyl)-5-formyl]indolylisoindolinone (40.0 mg, 0.102 mmol) was dissolved in acetonitrile (1 mL), and the solution was treated with N,N,2,2-tetramethyl-1,3-propanediamine (0.065 mL, 0.408 mmol), acetic acid (0.114 mL, 2.04 mmol) and sodium triacetoxyborohydride (64.8 mg, 0.306 mmol) to obtain 4-hydroxy-7-{1-(tert-butoxycarbonyl)-5-[(2,2-dimethyl-3-(dimethylamino)propyl)aminomethyl]indol-2-yl}isoindolinone (18.8 mg, yield 36%).

ESI-MS m/z: 507 [M+H]$^+$; $^1$H-NMR (CDCl$_3$) δ(ppm): 1.08 (s, 6H), 1.27 (s, 9H), 2.21 (s, 6H), 2.33 (s, 2H), 2.89 (s, 2H), 4.18 (s, 2H), 4.31 (s, 2H), 6.33 (s, 1H), 7.07 (d, J=8.6 Hz, 1H), 7.22 (d, J=8.3 Hz, 1H), 7.28 (m, 1H), 7.59 (s, 1H), 8.26 (d, J=8.6 Hz, 1H).

Step 2

In a similar manner to Step 2 of Example 8, 4-hydroxy-7-(1-(tert-butoxycarbonyl)-5-[(2,2-dimethyl-3-(dimethylamino)propyl)aminomethyl]indol-2-yl)isoindolinone (18.6 mg, 0.0370 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 216 (10.2 mg, yield 58%).

APCI-MS m/z: 407 [M+H]$^+$; $^1$H-NMR (DMSO-d$_6$) δ(ppm): 1.13 (s, 6H), 2.75 (s, 3H), 2.77 (s, 3H), 2.87-2.95 (m, 2H), 3.18-3.30 (m, 2H), 4.22 (s, 2H), 4.36 (s, 2H), 7.04 (s, 1H), 7.11 (d, J=8.6 Hz, 1H), 7.31 (d, J=8.3 Hz, 1H), 7.48 (d, J=8.3 Hz, 1H), 7.75 (s, 1H), 8.02 (d, J=8.6 Hz, 1H), 9.10 (br s, 2H), 9.24 (s, 1H), 9.95 (br s, 1H), 10.39 (br s, 1H), 13.80 (s, 1H).

EXAMPLE 217

4-Hydroxy-7-[1H-5-(4-carbamoylpiperidinomethyl)indol-2-yl]isoindolinone hydrochloride (Compound 217)

Step 1

In a similar manner to Step 2 of Example 6, 4-hydroxy-7-[1-(tert-butoxycarbonyl)-5-formyl]indolylisoindolinone (80.4 mg, 0.205 mmol) was dissolved in acetonitrile (2 mL), and the solution was treated with isonipecotamide (105 mg, 0.820 mmol), acetic acid (0.235 mL, 4.10 mmol) and sodium triacetoxyborohydride (130 mg, 0.615 mmol) to obtain 4-hydroxy-7-[1-(tert-butoxycarbonyl)-5-(4-carbamoylpiperidinomethyl)indol-2-yl]isoindolinone (68.8 mg, yield 67%).

ESI-MS m/z: 505 [M+H]+; 1H-NMR (CDCl3) δ(ppm): 1.31 (s, 9H), 1.41-1.92 (m, 9H), 2.95 (br s, 1H), 2.99 (br s, 1H), 3.60 (s, 2H), 4.31 (s, 2H), 6.43 (s, 1H), 6.93 (d, J=8.3 Hz, 1H), 7.18-7.28 (m, 2H), 7.43 (s, 1H), 8.14 (d, J=8.3 Hz, 1H).

Step 2

In a similar manner to Step 2 of Example 5, 4-hydroxy-7-[1-(tert-butoxycarbonyl)-5-(4-carbamoylpiperidinomethyl)indol-2-yl]isoindolinone (34.4 mg, 0.0682 mmol) was treated with 4 mol/L hydrogen chloride-ethyl acetate solution (2 mL). The obtained solid was collected by filtration and washed with ethyl acetate, followed by drying under reduced pressure to obtain Compound 217 (32.0 mg, yield 100%).

APCI-MS m/z: 405 [M+H]+; 1H-NMR (DMSO-d6) δ(ppm): 1.84-1.92 (m, 2H), 2.31 (m, 1H), 2.86-2.96 (m, 2H), 3.30-3.60 (m, 4H), 4.28-4.38 (m, 2H), 4.38 (s, 2H), 6.89 (br s, 1H), 7.07 (s, 1H), 7.14 (d, J=8.6 Hz, 1H), 7.23 (d, J=8.9 Hz, 1H), 7.36 (br s, 1H), 7.52 (d, J=8.9 Hz, 1H), 7.70 (s, 1H), 8.05 (d, J=8.6 Hz, 1H), 9.26 (br s, 1H), 9.68 (br s, 1H), 10.41 (br s, 1H), 13.86 (s, 1H).

EXAMPLE 218

4-Hydroxy-7-[1H-5-(4-methoxycarbonylpiperidinomethyl)indol-2-yl]isoindolinone hydrochloride (Compound 218)

In a similar manner to Step 2 of Example 8, 4-hydroxy-7-[1-(tert-butoxycarbonyl)-5-(4-carbamoylpiperidinomethyl)indol-2-yl]isoindolinone (34.1 mg, 0.0676 mmol) was treated with 10% hydrogen chloride-methanol solution (2 mL). The mixture was added with diisopropylether. The obtained solid was collected by filtration and washed with diisopropylether, followed by drying under reduced pressure to obtain Compound 218 (21.7 mg, yield 70%).

APCI-MS m/z: 420 [M+H]+; 1H-NMR (DMSO-d6) δ(ppm): 1.74-1.92 (m, 2H), 2.00-2.10 (m, 2H), 2.48 (m, 1H), 2.86-2.96 (m, 2H), 3.30-3.60 (m, 2H), 3.61 (s, 3H), 4.31 (br s, 2H), 4.37 (s, 2H), 7.05 (s, 1H), 7.12 (d, J=8.5 Hz, 1H), 7.22 (d, J=8.3 Hz, 1H), 7.50 (d, J=8.3 Hz, 1H), 7.70 (s, 1H), 8.04 (d, J=8.5 Hz, 1H), 9.26 (s, 1H), 10.03 (br s, 1H), 10.40 (br s, 1H), 13.84 (s, 1H).

EXAMPLE 219

4-(2,3-Dihydroxypropoxy)-7-[1H-5-(piperidinomethyl)indol-2-yl]isoindolinone (Compound 219)

Step 1

In a similar manner to Step 1 of Example 149, 4-hydroxy-7-[1-(tert-butoxycarbonyl)-5-(piperidinomethyl)indol-2-yl]isoindolinone (80.0 mg, 0.173 mmol) was dissolved in THF (4.0 mL), and the solution was treated with triphenylphosphine (181 mg, 0.692 mmol), Solketal (0.087 mL, 0.692 mmol) and 40% DEAD-toluene solution (0.316 mL), followed by purification by flash column chromatography (chloroform/methanol=9/1) to obtain 4-{2,2-dimethyl-[1,3]dioxoran-4-ylmethoxy}-7-[1-(tert-butoxycarbonyl)-5-(piperidinomethyl)indol-2-yl]isoindolinone (53.2 mg, yield 53%).

ESI-MS m/z: 576 [M+H]+; 1H-NMR (CDCl3) δ(ppm): 1.33 (s, 9H), 1.42 (s, 3H), 1.48 (s, 3H), 1.42-1.72 (m, 6H), 2.61 (br s, 4H), 3.81 (s, 2H), 3.94 (dd, J=5.6, 8.4 Hz, 1H), 4.07-4.22 (m, 3H), 4.38 (s, 2H), 4.51 (m, 1H), 6.50 (s, 1H), 7.04 (d, J=8.3 Hz, 1H), 7.30 (dd, J=1.5, 8.4 Hz, 1H), 7.35 (br s, 1H), 7.40 (d, J=8.3 Hz, 1H), 7.55 (s, 1H), 8.18 (d, J=8.4 Hz, 1H).

Step 2

In a similar manner to Step 2 of Example 8, 4-(2,2-dimethyl-[1,3]dioxoran-4-ylmethoxy)-7-[1-(tert-butoxycarbonyl)-5-(piperidinomethyl)indol-2-yl]isoindolinone (50.1 mg, 0.0892 mmol) was dissolved in methanol (1.5 mL), and the solution was treated with 10% hydrogen chloride-methanol solution (3 mL), the solvent was evaporated under reduced pressure and the residue was purified by preparative thin-layer chromatography (chloroform/methanol/7 mol/L ammonia-methanol solution=10/0.5/0.5) to obtain Compound 219 (11.9 mg, yield 31%).

ESI-MS m/z: 436 [M+H]+; 1H-NMR (CDCl3+CD3OD) δ(ppm): 1.47 (br s, 2H), 1.62 (br s, 4H), 2.53 (br s, 4H), 3.35-3.78 (m, 2H), 3.73 (s, 2H), 4.04-4.24 (m, 3H), 4.45 (s, 2H), 6.93 (s, 1H), 7.11 (d, J=8.4 Hz, 1H), 7.18 (d, J=8.8 Hz, 1H), 7.40 (d, J=8.4 Hz, 1H), 7.51 (s, 1H), 8.06 (d. J=8.8 Hz, 1H).

EXAMPLE 220

4-(3-Aminopropoxy)-7-{1H-5-[4-(2-hydroxyethyl)piperazin-1-ylmethyl]isoindolinone trihydrochloride (Compound 220)

Step 1

In a similar manner to Step 1 of Example 149, 4-hydroxy-7-[1-(tert-butoxycarbonyl)-5-formylindol-2-yl]isoindolinone (150 mg, 0.382 mmol) was dissolved in THF (7.5 mL), and the solution was treated with triphenylphosphine (200 mg, 0.764 mmol), tert-butyl N-(3-hydroxypropyl)carbamate (134 mg, 0.764 mmol) and 40% DEAD-toluene solution (0.348 mL), followed by purification by flash column chromatography (chloroform/methanol=100/0 to 95/5) to obtain 4-[3-(tert-butoxycarbonylamino)propoxy]-7-[1-(tert-butoxycarbonyl)-5-formylindol-2-yl]isoindolinone (208 mg, yield 99%).

ESI-MS m/z: 550 [M+H]+; 1H-NMR (CDCl3) δ(ppm): 1.37 (s, 9H), 1.45 (s, 9H), 2.05 (m, 2H), 3.66 (m, 2H), 4.19 (t, J=6.0 Hz, 2H), 4.40 (s, 2H), 4.74 (br s, 1H), 6.31 (s, 1H), 6.64 (s, 1H), 7.04 (d, J=8.3 Hz, 1H), 7.43 (d, J=8.3 Hz, 1H), 7.85 (dd, J=1.5, 8.7 Hz, 1H), 8.07 (d, J=1.7 Hz, 1H), 8.34 (d, J=8.6 Hz, 1H), 10.06 (s, 1H).

Step 2

In a similar manner to Step 2 of Example 6, 4-[3-(tert-butoxycarbonylamino)propoxy]-7-[1-(tert-butoxycarbonyl)-5-formylindol-2-yl]isoindolinone (104 mg, 0.189 mmol) was dissolved in acetonitrile (5.2 mL), and the solution was treated with 1-(2-hydroxyethyl)piperazine (98 mg, 0.756 mmol), acetic acid (0.216 mL, 3.78 mmol) and sodium triacetoxyborohydride (160 mg, 0.756 mmol). The reaction mixture was added with water and sodium carbonate, followed by extracting with ethyl acetate. The organic layer was washed with saturated brine and dried over anhydrous sodium sulfate. The solvent was evaporated under reduced pressure to obtain 4-[3-(tert-butoxycarbonylamino)propoxy]-7-{1-(tert-butoxycarbonyl)-5-[4-(2-hydroxyethyl)piperazin-1-ylmethyl]indol-2-yl}isoindolinone (86.5 mg, yield 69%).

ESI-MS m/z: 664 [M+H]+; 1H-NMR (CDCl3) δ(ppm): 1.37 (s, 9H), 1.44 (s, 9H), 2.05 (m, 2H), 2.53 (m, 10H), 3.28-3.37 (m, 2H), 3.60 (s, 2H), 3.65 (m, 2H), 4.17 (t, J=5.6 Hz, 2H), 4.38 (s, 2H), 4.75 (br s, 1H), 6.14 (s, 1H), 6.49 (s, 1H), 7.01 (d, J=8.3 Hz, 1H), 7.26 (m, 1H), 7.40 (d, J=7.8 Hz, 1H), 7.46 (s, 1H), 8.13 (d, J=8.3 Hz, 1H).

Step 3

In a similar manner to Step 2 of Example 8, 4-[3-(tert-butoxycarbonylamino)propoxy]-7-{1-(tert-butoxycarbonyl)-5-[4-(2-hydroxyethyl)piperazin-1-ylmethyl]indol-2-yl}isoindolinone (86.5 mg, 0.130 mmol) was dissolved in methanol (2.6 mL), and the solution was treated with 10% hydrogen chloride-methanol solution (2.6 mL). The precipitated solid was collected by filtration and washed with methanol, followed by drying under reduced pressure to obtain Compound 220 (40.4 mg, yield 54%).

ESI-MS m/z: 464 [M+H]$^+$; $^1$H-NMR (DMSO-d$_6$) δ(ppm): 2.06 (m, 2H), 2.97 (br s, 2H), 3.17-3.72 (m, 12H), 4.26 (t, J=5.8 Hz, 2H), 4.41 (br s, 4H), 7.14 (s, 1H), 7.27 (br s, 1H), 7.31 (d, J=8.8 Hz, 1H), 7.50 (d, J=8.3 Hz, 1H), 7.76 (s, 1H), 8.02 (br s, 3H), 8.17 (d, J=8.8 Hz, 1H), 9.35 (s, 1H), 13.80 (s, 1H).

EXAMPLE 221

4-(3-Aminopropoxy)-7-[1H-5-(3-hydroxypiperidinomethyl)indol-2-yl]isoindolinone (Compound 221)

Step 1

In a similar manner to Step 2 of Example 147, 4-[3-(tert-butoxycarbonylamino)propoxy]-7-[1-(tert-butoxycarbonyl)-5-formylindol-2-yl]isoindolinone (104 mg, 0.188 mmol) was dissolved in acetonitrile (5.2 mL), and the solution was treated with 3-hydroxypiperidine (76.0 mg, 0.752 mmol), acetic acid (0.215 mL, 3.76 mmol) and sodium triacetoxyborohydride (160 mg, 0.752 mmol). The reaction mixture was added with 1 mol/L hydrochloric acid and extracted with ethyl acetate. The organic layer was washed with saturated aqueous sodium carbonate solution and saturated brine, and dried over anhydrous sodium sulfate. The solvent was evaporated under reduced pressure to obtain 4-[3-(tert-butoxycarbonylamino)propoxy]-7-[1-(tert-butoxycarbonyl)-5-(3-hydroxypiperidinomethyl)indol-2-yl]isoindolinone (40.9 mg, yield 34%).

ESI-MS m/z: 635 [M+H]$^+$; $^1$H-NMR (CDCl$_3$) δ(ppm): 1.36 (s, 9H), 1.45 (s, 9H), 1.57-2.56 (m, 10H), 3.35 (m, 2H), 3.68 (s, 2H), 3.87 (br s, 1H), 4.17 (t, J=5.8 Hz, 2H), 4.38 (s, 2H), 4.77 (br s, 1H), 6.49 (s, 1H), 6.74 (br s, 1H), 7.02 (d, J=7.4 Hz, 1H), 7.24 (m, 1H), 7.40 (d, J=7.9 Hz, 1H), 7.44 (s, 1H), 8.15 (d, J=8.6 Hz, 1H).

Step 2

In a similar manner to Step 2 of Example 8, 4-[3-(tert-butoxycarbonylamino)propoxy]-7-[1-(tert-butoxycarbonyl)-5-(3-hydroxypiperidinomethyl)indol-2-yl]isoindolinone (40.2 mg, 0.0633 mmol) was dissolved in methanol (1.2 mL), and the solution was treated with 10% hydrogen chloride-methanol solution (2.4 mL). The solvent was evaporated under reduced pressure. The residue was purified by preparative thin-layer chromatography (chloroform/methanol/7 mol/L ammonia-methanol solution=6/0.5/0.5) to obtain Compound 221 (6.2 mg, yield 24%).

ESI-MS m/z: 435 [M+H]$^+$; $^1$H-NMR (DMSO-d$_6$) δ(ppm): 1.55-1.80 (m, 6H), 2.57-2.76 (m, 4H), 3.32-3.50 (m, 4H), 4.15 (t, J=5.7 Hz, 2H), 4.30 (s, 2H), 4.43 (br s, 1H), 6.94 (br s, 2H), 7.22-7.32 (m, 3H), 8.04 (d, J=8.8 Hz, 1H), 9.19 (s, 1H), 13.49 (s, 1H).

EXAMPLE 222

4-(2,3-Dihydroxypropoxy)-7-[1H-5-(piperidinomethyl)indol-2-yl]isoindolinone hydrochloride (Compound 222)

Step 1

In a similar manner to Step 1 of Example 149, 4-hydroxy-7-[1-(tert-butoxycarbonyl)-5-(piperidinomethyl)indol-2-yl]isoindolinone (80.0 mg, 0.173 mmol) was dissolved in THF (4.0 mL), and the solution was treated with triphenylphosphine (137 mg, 0.519 mmol), benzylalcohol (0.0534 mL, 0.519 mmol) and 40% DEAD-toluene solution (0.237 mL), followed by purification by flash column chromatography (chloroform/methanol=100/0 to 90/10) to obtain 4-benzyloxy-7-[1-(tert-butoxycarbonyl)-5-(piperidinomethyl)indol-2-yl]isoindolinone (70 mg, yield 73%).

ESI-MS m/z: 552 [M+H]$^+$; $^1$H-NMR (CDCl$_3$) δ(ppm): 1.34 (s, 9H), 1.43-1.58 (m, 6H), 2.43 (br s, 4H), 3.61 (br s, 2H), 4.41 (s, 2H), 5.21 (s, 2H), 6.32 (s, 1H), 6.49 (s, 1H), 7.08 (d, J=8.4 Hz, 1H), 7.27 (m, 1H), 7.37-7.48 (m, 7H), 8.14 (d, J=8.4 Hz, 1H).

Step 2

In a similar manner to Step 2 of Example 8, 4-benzyloxy-7-[(1-(tert-butoxycarbonyl)-5-(piperidinomethyl)indol-2-yl]isoindolinone (65.7 mg, 0.119 mmol) was dissolved in methanol (2.0 mL), and the solution was treated with 10% hydrogen chloride-methanol solution (2.0 mL). The precipitated solid was collected by filtration and washed with methanol, followed by drying under reduced pressure to obtain Compound 222 (42 mg, yield 72%).

ESI-MS m/z: 452 [M+H]$^+$; $^1$H-NMR (DMSO-d$_6$) δ(ppm): 1.65-1.77 (m, 6H), 2.84 (m, 2H), 3.31 (m, 2H), 4.29 (d, J=4.8 Hz, 2H), 4.46 (s, 2H), 5.32 (s, 2H), 7.14 (s, 1H), 7.23 (d, J=8.4 Hz, 1H), 7.31-7.44 (m, 4H), 7.51 (m, 3H), 7.70 (s, 1H), 8.15 (d, J=8.8 Hz, 1H), 9.35 (s, 1H), 9.70 (br s, 1H), 13.83 (s, 1H).

EXAMPLE 223

4-(2-Isopropoxyethoxy)-7-[(1-(tert-butoxycarbonyl)-5-(piperidinomethyl)indol-2-yl]isoindolinone hydrochloride (Compound 223)

Step 1

In a similar manner to Step 1 of Example 149, 4-hydroxy-7-[1-(tert-butoxycarbonyl)-5-(piperidinomethyl)indol-2-yl]isoindolinone (0.102 g, 0.221 mmol) was dissolved in THF (5.1 mL), and the solution was treated with triphenylphosphine (0.116 g, 0.442 mmol), 40% DEAD-toluene solution (0.201 mL, 0.442 mmol) and 2-isopropoxyethanol (0.126 mL, 1.10 mmol), followed by purification by flash column chromatography (chloroform/methanol=4/1) to obtain 4-(2-isopropoxyethoxy)-7-[1-(tert-butoxycarbonyl)-5-(piperidinomethyl)indol-2-yl]isoindolinone (0.0677 g, yield 59%).

ESI-MS m/z: 548 [M+H]$^+$; $^1$H-NMR (DMSO-d$_6$) δ(ppm): 1.20 (s, 3H), 1.22 (s, 3H), 1.33 (s, 9H), 1.38-1.47 (m, 2H), 1.54-1.63 (m, 4H), 2.37-2.45 (m, 4H), 3.61 (s, 2H), 3.82 (dd, J=4.8, 5.3 Hz, 2H), 4.24 (dd, J=4.8, 5.3 Hz, 2H), 4.37 (s, 2H), 6.49 (s, 1H), 7.02 (d, J=8.3 Hz, 1H), 7.26 (d. J=8.6 Hz, 1H), 7.38 (d, J=8.3 Hz, 1H), 7.47 (s, 1H), 8.31 (d, J=8.6 Hz, 1H).

Step 2

In a similar manner to Step 2 of Example 8, 4-(2-isopropoxyethoxy)-7-[1-(tert-butoxycarbonyl)-5-(piperidinomethyl)indol-2-yl]isoindolinone (0.0677 g, 0.124 mmol) was treated in 10% hydrogen chloride-methanol solution (5.0 mL). The obtained solid was collected by filtration to obtain Compound 223 (0.0559 g, yield 94%).

ESI-MS m/z: 448 [M+H]$^+$; $^1$H-NMR (DMSO-$d_6$) δ(ppm): 1.11 (s, 3H), 1.13 (s, 3H), 1.28-1.45 (m, 2H), 1.59-1.87 (m, 6H), 2.74-2.95 (m, 2H), 3.61-3.67 (m, 1H), 3.75 (m, 2H), 4.24-4.35 (m, 3H), 4.39 (m, 2H), 7.16 (s, 1H), 7.23 (d, J=8.3 Hz, 1H), 7.36 (d, J=8.9 Hz, 1H), 7.52 (d, J=8.3 Hz, 1H), 7.71 (s, 1H), 8.17 (d, J=8.9 Hz, 1H), 9.32 (s, 1H), 9.55 (br s, 1H), 13.8 (br s, 1H).

EXAMPLE 224

4-[3-(Dimethylamino)propoxy]-7-[1H-5-(piperidinomethyl)indol-2-yl]isoindolinone dihydrochloride (Compound 224)

Step 1

In a similar manner to Step 1 of Example 149, 4-hydroxy-7-[1-(tert-butoxycarbonyl)-5-(piperidinomethyl)indol-2-yl]isoindolinone (0.102 g, 0.221 mmol) was dissolved in THF (5.1 mL), and the solution was treated with triphenylphosphine (0.116 g, 0.442 mmol), 40% DEAD-toluene solution (0.201 mL, 0.442 mmol) and 3-(dimethylamino)propanol (0.130 mL, 1.10 mmol), followed by purification by flash column chromatography (chloroform/methanol=4/1) to obtain 4-[3-(dimethylamino)propoxy]-7-[1-(tert-butoxycarbonyl)-5-(piperidinomethyl)indol-2-yl]isoindolinone (0.0467 g, yield 39%).

ESI-MS m/z: 547 [M+H]$^+$; $^1$H-NMR (CDCl$_3$) δ(ppm): 1.34 (s, 9H), 1.53-1.63 (m, 4H), 1.64-1.73 (m, 1H), 1.76-1.87 (m, 1H), 1.94-2.06 (m, 2H), 2.27 (s, 6H), 2.33-2.58 (m, 6H), 3.59 (s, 2H), 4.12-4.24 (m, 2H), 4.35 (s, 2H), 6.48 (s, 1H), 7.02 (d, J=7.9 Hz, 1H), 7.22-7.30 (m, 2H), 7.38 (d, J=7.9 Hz, 1H), 7.46 (s, 1H), 8.14 (d, J=8.5 Hz, 1H).

Step 2

In a similar manner to Step 2 of Example 8, 4-[3-(dimethylamino)propoxy]-7-[1-(tert-butoxycarbonyl)-5-(piperidinomethyl)indol-2-yl]isoindolinone (0.0460 g, 0.0841 mmol) was treated with 10% hydrogen chloride-methanol solution (5.0 mL). The residue was purified by slurry using ethyl acetate and methanol to obtain Compound 224 (0.0116 g, yield 27%).

ESI-MS m/z: 447 [M+H]$^+$; $^1$H-NMR (DMSO-$d_6$) δ(ppm): 1.28-1.45 (m, 1H), 1.61-1.87 (m, 6H), 2.14-2.30 (m, 2H), 2.74-2.95 (m, 5H), 3.53-3.83 (m, 6H), 4.25-4.38 (m, 4H), 4.45 (s, 2H), 7.17 (s, 1H), 7.26 (d, J=8.4 Hz, 1H), 7.35 (d, J=8.7 Hz, 1H), 7.52 (d, J=8.3 Hz, 1H), 7.74 (s, 1H), 8.19 (d, J=8.7 Hz, 1H), 9.39 (s, 1H), 9.86 (br s, 1H), 13.8 (br s, 1H).

EXAMPLE 225

4-[3-(4-Methylpiperazin-1-yl)propoxy]-7-[1H-butoxycarbonyl]-5-(piperidinomethyl)indol-2-yl]isoindolinone trihydrochloride (Compound 225)

Step 1

In a similar manner to Step 1 of Example 149, 4-hydroxy-7-[1-(tert-butoxycarbonyl)-5-(piperidinomethyl)indol-2-yl]isoindolinone (0.0817 g, 0.177 mmol) was dissolved in THF (4.0 mL), and the solution was treated with triphenylphosphine (0.0930 g, 0.354 mmol), 40% DEAD-toluene solution (0.161 mL, 0.354 mmol) and 1-(3-hydroxypropyl)-4-methylpiperazine (0.140 g, 0.855 mmol), followed by purification by flash column chromatography (chloroform/methanol=7/3) to obtain 4-[3-(4-methylpiperazin-1-yl)propoxy]-7-[1-(tert-butoxycarbonyl)-5-(piperidinomethyl)indol-2-yl]isoindolinone (0.0617 g, yield 58%).

ESI-MS m/z: 602 [M+H]$^+$; $^1$H-NMR (CDCl$_3$) δ(ppm): 1.20-1.31 (m, 3H), 1.35 (s, 9H), 1.39-1.48 (m, 3H), 1.55-1.65 (m, 3H), 1.68-1.76 (m, 1H), 1.79-1.90 (m, 1H), 1.97-2.08 (m, 2H), 2.27-2.29 (m, 3H), 2.31 (s, 2H), 2.45-2.58 (m, 5H), 3.64 (s, 2H), 3.80 (dd, J=5.3 Hz, 1H), 4.11-4.23 (m, 3H), 4.35 (s, 2H), 6.49 (s, 1H), 7.02 (d, J=8.3 Hz, 1H), 7.23-7.29 (m, 2H), 7.38 (d, J=8.3 Hz, 1H), 7.48 (d, J=1.2 Hz, 1H), 8.14 (d, J=8.6 Hz, 1H).

Step 2

In a similar manner to Step 2 of Example 8, 4-[3-(4-methylpiperazin-1-yl)propoxy]7-[(1-(tert-butoxycarbonyl)-5-(piperidinomethyl)indol-2-yl]-isoindolinone (0.0617 g, 0.103 mmol) was treated with 10% hydrogen chloride-methanol solution (5 mL), followed by purification by slurry using ethyl acetate and methanol to obtain Compound 225 (0.0187 g, yield 30%).

ESI-MS m/z: 502 [M+H]$^+$; $^1$H-NMR (DMSO-$d_6$) δ(ppm): 1.30-1.43 (m, 1H), 1.62-1.87 (m, 7H), 2.12-2.25 (m, 3H), 2.74-2.94 (m, 12H), 3.15-3.83 (m, 2H), 4.23-4.54 (m, 5H), 4.45 (s, 2H), 7.17 (s, 1H), 7.26 (d, J=8.4 Hz, 1H), 7.35 (d, J=8.9 Hz, 1H), 7.53 (d, J=8.4 Hz, 1H), 7.73 (s, 1H), 8.19 (d, J=8.9 Hz, 1H), 9.40 (br s, 2H), 10.2 (br s, 1H), 13.8 (br s, 1H).

EXAMPLE 226

4-(2-Aminoethoxy)-7-[1H-5-(piperidinomethyl)indol-2-yl]isoindolinone dihydrochloride (Compound 226)

Step 1

In a similar manner to Step 1 of Example 149, 4-hydroxy-7-[(1-(tert-butoxycarbonyl)-5-(piperidinomethyl)indol-2-yl]isoindolinone (0.243 g, 0.526 mmol) was dissolved in THF (10.0 mL), and the solution was treated with triphenylphosphine (0.690 g, 2.63 mmol), 40% DEAD-toluene solution (1.20 mL, 2.63 mmol) and N-(tert-butoxycarbonyl)ethanolamine (0.424 g, 2.63 mmol), followed by purification by flash column chromatography (chloroform/methanol=85/15) to obtain 4-[2-(tert-butoxycarbonylamino)ethoxy]-7-[(1-(tert-butoxycarbonyl)-5-(piperidinomethyl)indol-2-yl]isoindolinone (0.191 g, yield 60%).

ESI-MS m/z: 605 [M+H]$^+$; $^1$H-NMR (CDCl$_3$) δ(ppm): 1.32 (s, 9H), 1.47 (s, 9H), 1.39-1.48 (m, 3H), 1.55-1.65 (m, 3H), 2.41-2.60 (m, 6H), 3.52-3.62 (m, 1H), 3.64 (s, 1H), 4.11-4.19 (m, 2H), 4.35 (s, 2H), 5.03 (t, J=6.3 Hz, 1H), 6.49 (s, 1H), 7.00 (d, J=8.3 Hz, 1H), 7.23-7.29 (m, 2H), 7.38 (d, J=8.3 Hz, 1H), 7.48 (d, J=1.2 Hz, 1H), 8.14 (d, J=8.6 Hz, 1H).

Step 2

In a similar manner to Step 2 of Example 8, 4-[2-(tert-butoxycarbonylamino)ethoxy]-7-[1-(tert-butoxycarbonyl)-5-(piperidinomethyl)indol-2-yl]isoindolinone (0.145 g, 0.240 mmol) was treated with 10% hydrogen chloride-methanol solution (5.0 mL). The residue was purified by slurry using diisopropylether and methanol to obtain Compound 226 (0.0386 g, yield 34%).

ESI-MS m/z: 502 [M+H]$^+$; $^1$H-NMR (DMSO-$d_6$) δ(ppm): 1.28-1.41 (m, 1H), 1.63-1.85 (m, 5H), 2.74-2.94 (m, 2H), 3.21-3.35 (m, 4H), 3.94-4.13 (m, 2H), 4.29 (d, J=4.7 Hz, 2H), 4.40 (d, J=5.0 Hz, 1H), 4.53 (s, 2H), 7.17 (s, 1H), 7.30 (dd, J=1.3, 8.4 Hz, 1H), 7.51 (d, J=8.4 Hz, 1H), 7.77 (s, 1H), 8.19 (d, J=8.4 Hz, 1H), 8.19 (d, J=8.9 Hz, 1H), 8.39 (br s, 1H), 9.39 (s, 1H), 10.3 (br s, 1H), 13.8 (br s, 1H).

EXAMPLE 227

4-Methanesulfonyloxy-7-[H-5-(piperidinomethyl)indol-2-yl]isoindolinone hydrochloride
(Compound 227)

Step 1

4-Hydroxy-7-[1-(tert-butoxycarbonyl)-5-(piperidinomethyl)indol-2-yl]isoindolinone (0.230 g, 0.498 mmol) was dissolved in dichloromethane (4.6 mL), and the solution was added with triethylamine (0.139 mL, 0.997 mmol) and methanesulfonyl chloride (0.0460 mL, 0.598 mmol), followed by stirring under ice-cooling for 1.5 hours. The reaction mixture was added with water and extracted with chloroform. The organic layer was washed with saturated brine and dried over anhydrous sodium sulfate. The solvent was evaporated under reduced pressure and the residue was purified by flash column chromatography (chloroform/methanol=85/15) to obtain 4-methanesulfonyloxy-7-[1-(tert-butoxycarbonyl)-5-(piperidinomethyl)indol-2-yl]isoindolinone (0.104 g, yield 61%).

ESI-MS m/z: 540 [M+H]$^+$; $^1$H-NMR (CDCl$_3$) δ(ppm): 1.31 (s, 9H), 1.38-1.48 (m, 2H), 1.53-1.62 (m, 4H), 2.35-2.54 (m, 4H), 3.29 (s, 1H), 3.58 (s, 2H), 4.54 (s, 2H), 6.55 (s, 1H), 7.31 (dd, J=1.3, 8.8 Hz, 1H), 7.45-7.53 (m, 3H), 8.18 (d, J=8.4 Hz, 1H).

Step 2

In a similar manner to Step 2 of Example 8, 4-methanesulfonyloxy-7-[1-(tert-butoxycarbonyl)-5-(piperidinomethyl)indol-2-yl]isoindolinone (0.373 g, 0.691 mmol) was treated with 10% hydrogen chloride-methanol solution (7.5 mL), followed by purification by slurry using diisopropylether and methanol to obtain Compound 227 (0.237 g, yield 72%).

mp 222-225° C.; ESI-MS m/z: 375 [M+H]$^+$; $^1$H-NMR (DMSO-d$_6$) δ(ppm): 1.30-1.44 (m, 1H), 1.59-1.87 (m, 5H), 2.78-2.95 (m, 2H), 3.32-3.68 (m, 2H), 3.58 (s, 3H), 4.29-4.36 (m, 2H), 4.59 (s, 2H), 7.31 (d, J=8.4 Hz, 1H), 7.34 (d, J=0.8 Hz, 1H), 7.58 (d, J=8.4 Hz, 1H), 7.68 (d, J=8.8 Hz, 1H), 7.78 (d, J=0.8 Hz, 1H), 8.31 (d, J=8.8 Hz, 1H), 9.55 (s, 1H), 9.76 (br s, 1H), 13.9 (s, 1H).

EXAMPLE 228

4-(a-Toluenesulfonyloxy)-7-[1H-(piperidinomethyl)indol-2-yl]isoindolinone hydrochloride
(Compound 228)

Step 1

In a similar manner to Step 1 of Example 227, 4-hydroxy-7-[1-(tert-butoxycarbonyl)-5-(piperidinomethyl)indol-2-yl]isoindolinone (0.184 g, 0.399 mmol) was dissolved in dichloromethane (3.6 mL), and the solution was treated with triethylamine (0.250 mL, 1.79 mmol) and a-toluenesulfonyl chloride (0.152 g, 0.797 mmol), followed by purification by flash column chromatography (chloroform/methanol=85/15) to obtain 4-(a-toluenesulfonyloxy)-7-[1-(tert-butoxycarbonyl)-5-(piperidinomethyl)indol-2-yl]isoindolinone (0.0908 g, yield 37%).

ESI-MS m/z: 616 [M+H]$^+$; $^1$H-NMR (CDCl$_3$) δ(ppm): 1.29 (s, 9H), 1.38-1.48 (m, 2H), 1.54-1.67 (m, 4H), 2.36-2.46 (m, 4H), 3.58 (s, 2H), 4.16 (s, 2H), 4.64 (s, 2H), 6.51 (s, 1H), 6.60 (s, 1H), 6.72 (br s, 1H), 7.11 (s, 1H), 7.17-7.55 (m, 6H), 8.17 (d, J=8.6 Hz, 1H).

Step 2

In a similar manner to Step 2 of Example 8, 4-(a-toluenesulfonyloxy)-7-[(1-(tert-butoxycarbonyl)-5-(piperidinomethyl)indol-2-yl]isoindolinone (0.0900 g, 0.319 mmol) was treated with 10% hydrogen chloride-methanol solution (5.0 mL), followed by purification by slurry using diisopropylether and methanol to obtain Compound 228 (0.0795 g, yield 99%).

ESI-MS m/z: 516 [M+H]$^+$; $^1$H-NMR (DMSO-d$_6$) δ(ppm): 1.28-1.44 (m, 1H), 1.59-1.87 (m, 5H), 2.78-2.95 (m, 2H), 3.32-3.68 (m, 2H), 4.32 (d, J=3.6 Hz, 2H), 4.38 (s, 2H), 5.18 (s, 2H), 7.29-7.36 (m, 2H), 7.43-7.61 (m, 7H), 7.79 (s, 1H), 8.27 (d, J=8.7 Hz, 1H), 9.50 (s, 1H), 10.0 (br s, 1H), 13.8 (s, 1H).

EXAMPLE 229

4-Benzenesulfonyloxy-7-[1H-5-(piperidinomethyl)indol-2-yl]isoindolinone hydrochloride
(Compound 229)

Step 1

In a similar manner to Step 1 of Example 227, 4-hydroxy-7-[1-(tert-butoxycarbonyl)-5-(piperidinomethyl)indol-2-yl]isoindolinone (0.171 g, 0.371 mmol) was dissolved in dichloromethane (3.5 mL), and the solution was treated with triethylamine (0.103 mL, 0.741 mmol) and benzenesulfonyl chloride (0.0570 mL, 0.446 mmol), followed by purification by flash column chromatography (chloroform/methanol=85/15) to obtain 4-benzenesulfonyloxy-7-[1-(tert-butoxycarbonyl)-5-(piperidinomethyl)indol-2-yl]isoindolinone (0.192 g. yield 86%).

ESI-MS m/z: 602 [M+H]$^+$; $^1$H-NMR (CDCl$_3$) d (ppm): 1.29 (s, 9H), 1.38-1.48 (m, 2H), 1.54-1.64 (m, 4H), 2.36-2.54 (m, 4H), 3.65 (s, 2H), 3.28 (s, 2H), 6.53 (d, J=1.6 Hz, 1H), 6.77-6.88 (m, 1H), 7.10 (d, J=8.3 Hz, 1H), 7.31 (dd, J=1.6, 8.6 Hz, 1H), 7.37 (d, J=8.3 Hz, 1H), 7.56-7.65 (m, 2H), 7.71-7.78 (m, 1H), 7.89-7.97 (m, 2H), 8.19 (d, J=8.6 Hz, 1H).

Step 2

In a similar manner to Step 2 of Example 8, 4-benzenesulfonyloxy-7-[1-(tert-butoxycarbonyl)-5-(piperidinomethyl)indol-2-yl]isoindolinone (0.192 g, 0.319 mmol) was treated with 10% hydrogen chloride-methanol solution (3.8 mL), followed by purification by slurry using diisopropylether and methanol to obtain Compound 229 (0.126 g, yield 75%).

ESI-MS m/z: 502 [M+H]$^+$; $^1$H-NMR (DMSO-d$_6$) δ(ppm): 1.28-1.44 (m, 1H), 1.59-1.87 (m, 5H), 2.78-2.95 (m, 2H), 3.32-3.68 (m, 2H), 4.20 (s, 2H), 4.29-4.36 (m, 2H), 7.29-7.35 (m, 3H), 7.56 (d, J=8.4 Hz, 1H), 7.69-7.80 (m, 3H), 7.86-7.94 (m, 1H), 7.96-8.00 (m, 2H), 8.24 (d, J=8.9 Hz, 1H), 9.45 (s, 1H), 9.91 (br s, 1H), 13.8 (s, 1H).

EXAMPLE 230

4-Ethanesulfonyloxy-7-[1H-5-(piperidinomethyl)indol-2-yl]isoindolinone hydrochloride
(Compound 230)

Step 1

In a similar manner to Step 1 of Example 227, 4-hydroxy-7-[1-(tert-butoxycarbonyl)-5-(piperidinomethyl)indol-2-yl]isoindolinone (0.140 g, 0.310 mmol) was dissolved in dichloromethane (3.5 mL), and the solution was treated with triethylamine (0.0860 mL, 0.620 mmol) and ethanesulfonyl choloride (0.0350 mL, 0.372 mmol), followed by purification by flash column chromatography (chloroform/methanol=85/15) to obtain 4-ethanesulfonyloxy-7-[1-(tert-butoxycarbonyl)-5-(piperidinomethyl)indol-2-yl]isoindolinone (0.143 g, yield 84%).

ESI-MS m/z: 554 [M+H]$^+$; $^1$H-NMR (CDCl$_3$) δ(ppm): 1.31 (s, 9H), 1.39-1.48 (m, 2H), 1.55-1.66 (m, 7H), 2.36-2.53 (m, 4H), 3.43 (q, J=7.6 Hz, 2H), 3.63 (s, 2H), 4.55 (s, 2H), 6.55 (s, 1H), 6.85-6.94 (m, 1H), 7.31 (dd, J=1.8, 8.7 Hz, 1H), 7.44-7.53 (m, 3H), 8.19 (d, J=8.7 Hz, 1H).

Step 2

In a similar manner to Step 2 of Example 8, 4-ethanesulfonyloxy-7-[1-(tert-butoxycarbonyl)-5-(piperidinomethyl)indol-2-yl]isoindolinone (0.143 g, 0.258 mmol) was treated with 10% hydrogen chloride-methanol solution (5.0 mL), followed by purification by slurry using diisopropylether and methanol to obtain Compound 230 (0.0860 g, yield 68%).

ESI-MS m/z: 454 [M+H]$^+$; $^1$H-NMR (DMSO-d$_6$) δ(ppm): 1.30-1.39 (m, 1H), 1.44 (t, J=7.7 Hz, 3H), 1.62-1.86 (m, 5H), 2.78-2.95 (m, 2H), 3.32-3.68 (m, 2H), 3.74 (q, J=7.7 Hz, 2H), 4.29-4.36 (m, 2H), 4.58 (s, 2H), 7.32 (d. J=8.2 Hz, 1H), 7.34 (s, 1H), 7.58 (d, J=8.2 Hz, 1H), 7.66 (d, J=8.6 Hz, 1H), 7.78 (s, 1H), 8.30 (d. J=8.6 Hz, 1H), 9.54 (s, 1H), 9.83 (br s, 1H), 13.9 (s, 1H).

EXAMPLE 231

4-Sulfamoyloxy-7-[1H-5-(piperidinomethyl)indol-2-yl]isoindolinone hydrochloride (Compound 231)

Step 1

4-Hydroxy-7-[1-(tert-butoxycarbonyl)-5-(piperidinomethyl)indol-2-yl]isoindolinone (0.145 g, 0.314 mmol) was dissolved in N,N-dimethylacetoamide (1.5 mL), and the solution was added with chlorosulfonamide (0.0440 mL, 0.377 mmol), followed by stirring at room temperature for 1 hour. The reaction mixture was added with water and extracted with chloroform. The organic layer was washed with saturated brine and dried over anhydrous sodium sulfate. The solvent was evaporated under reduced pressure and the residue was purified by flash column chromatography (chloroform/methanol=85/15) to obtain 4-sulfamoyloxy-7-[1-(tert-butoxycarbonyl)-5-(piperidinomethyl)indol-2-yl]isoindolinone (0.0914 g, yield 54%).

APCI-MS m/z: 541 [M+H]$^+$; $^1$H-NMR (CD$_3$OD) δ(ppm): 1.15 (s, 9H), 1.31-1.90 (m, 6H), 2.78-2.98 (m, 4H), 3.18-3.23 (m, 2H), 3.33 (br s, 2H), 4.27 (s, 2H), 4.49 (s, 2H), 6.56 (s, 1H), 7.33 (d, J=8.7 Hz, 1H), 7.46 (d, J=8.2 Hz, 1H), 7.55 (d, J=8.7 Hz, 1H), 7.62 (s, 1H), 8.24 (d, J=8.2 Hz, 1H).

Step 2

In a similar manner to Step 2 of Example 8, 4-sulfamoyloxy-7-[1-(tert-butoxycarbonyl)-5-(piperidinomethyl)indol-2-yl]isoindolinone (0.0914 g, 0.169 mmol) was treated with 10% hydrogen chloride-methanol solution (5.0 mL), followed by purification by slurry using diisopropylether and methanol to obtain Compound 231 (0.0390 g, yield 49%).

mp >300° C.; ESI-MS m/z: 441 [M+H]$^+$; $^1$H-NMR (DMSO-d$_6$) δ(ppm): 1.26-1.44 (m, 1H), 1.61-1.86 (m, 5H), 2.80-2.94 (m, 2H), 3.15 (br s, 2H), 3.32-3.68 (m, 2H), 4.31 (s, 2H), 4.58 (s, 2H), 7.02-7.36 (m, 3H), 8.26-8.35 (m, 2H), 9.48 (s, 1H), 9.95 (br s, 1H), 13.9 (s, 1H).

EXAMPLE 232

4-[2-(Ethylamino)ethanesulfonyloxy]-7-[1H-5-(piperidinomethyl)indol-2-yl]isoindolinone (Compound 232)

Step 1

4-Hydroxy-7-[1-(tert-butoxycarbonyl)-5-(piperidinomethyl)indol-2-yl]isoindolinone (0.298 g, 0.645 mmol) was dissolved in acetonitrile (9.0 mL), and the solution was added with N,N,N',N'-tetramethyl-1,3-propanediamine (0.431 mL, 2.58 mmol) and 2-chloroethanesulfonyl choloride (0.202 mL, 1.94 mmol), followed by stirring at room temperature for 1 hour. The reaction mixture was added with water and extracted with ethyl acetate. The organic layer was washed with saturated brine and dried over anhydrous sodium sulfate. The solvent was evaporated under reduced pressure and the residue was purified by flash column chromatography (chloroform/methanol=85/15) to obtain 4-ethenesulfonyloxy-7-[1-(tert-butoxycarbonyl)-5-(piperidinomethyl)indol-2-yl]isoindolinone (0.225 g, yield 63%).

ESI-MS m/z: 552 [M+H]$^+$; $^1$H-NMR (CDCl$_3$) δ(ppm): 1.29 (s, 9H), 1.39-1.48 (m, 2H), 1.55-1.66 (m, H), 2.36-2.53 (m, 4H), 3.63 (s, 2H), 3.63 (s, 2H), 4.53 (s, 2H), 6.28° (d, J=9.8 Hz, 1H), 6.48 (d, J=16.5 Hz, 1H), 6.55 (s, 1H), 6.78 (dd, J=9.8, 16.5 Hz, 1H), 7.28-7.54 (m, 4H), 8.20 (d, J=8.7 Hz, 1H).

Step 2

4-Ethenesulfonyloxy-7-[1-(tert-butoxycarbonyl)-5-(piperidinomethyl)indol-2-yl]isoindolinone (0.0734 g, 0.133 mmol) was dissolved in methanol (1.5 mL), and the solution was added with 70% aqueous ethylamine solution (1.5 mL), followed by stirring at room temperature for 5 hours. The solvent was evaporated under reduced pressure and the residue was purified by thin-layer chromatography (chloroform/methanol=6/1) to obtain 4-[2-(ethylamino)ethanesulfonyloxy]-7-[1-(tert-butoxycarbonyl)-5-(piperidinomethyl)indol-2-yl]isoindolinone (0.0338 g, 43%).

ESI-MS m/z: 597 [M+H]$^+$; $^1$H-NMR (CDCl$_3$) δ(ppm): 1.15 (t, J=7.1 Hz, 3H), 1.30 (s, 9H), 1.39-1.48 (m, 2H), 1.55-1.68 (m, 4H), 2.36-2.53 (m, 4H), 2.73 (q, J=7.1 Hz, 2H), 3.29 (t, J=7.1 Hz, 2H), 3.43 (t, J=7.1 Hz, 2H), 3.56 (s, 2H), 4.54 (s, 2H), 6.55 (s, 1H), 7.28-7.35 (m, 2H), 7.48-7.51 (s, 3H), 8.18 (d, J=8.6 Hz, 1H).

Step 3

In a similar manner to Step 2 of Example 8, 4-[2-(ethylamino)ethanesulfonyloxy]-7-[1-(tert-butoxycarbonyl)-5-(piperidinomethyl)indol-2-yl]isoindolinone (0.154 g, 0.258 mmol) was treated with 10% hydrogen chloride-methanol solution (8.0 mL), followed by purification by thin-layer chromatography (chloroform/methanol/ammonia=6/1/0.02) to obtain Compound 232 (0.0538 g, yield 42%).

ESI-MS m/z: 497 [M+H]$^+$; $^1$H-NMR (DMSO-d$_6$) δ(ppm): 1.01 (t, J=7.3 Hz, 3H), 1.3-1.54 (m, 6H), 2.29-2.39 (m, 2H), 2.58 (q, J=7.3 Hz, 3H), 3.06 (t, J=6.9 Hz, 3H), 3.47 (s, 2H), 3.81 (t, J=6.9 Hz, 2H), 4.56 (s, 2H) 7.09 (d, J=8.4 Hz, 1H), 7.21 (s, 1H), 7.40 (d, J=8.4 Hz, 1H), 7.45 (s, 1H), 7.66 (d, J=8.8 Hz, 1H), 8.25 (d, J=8.8 Hz, 1H), 9.48 (s, 1H), 13.6 (s, 1H).

EXAMPLE 233

4-(2-Fluoro-4-chlorobenzenesulfonyloxy)-7-[1H-5-(piperidinomethyl)indol-2-yl]isoindolinone (Compound 233)

Step 1

4-Hydroxy-7-[1-(tert-butoxycarbonyl)-5-(piperidinomethyl)indol-2-yl]isoindolinone (0.0300 g, 0.0650 mmol) was dissolved in acetonitrile (0.650 mL), and the solution was added with triethylamine (0.0540 mL, 0.390 mmol) and 4-chloro-2-fluorobenzenesulfonyl chloride (0.0450 g, 0.195 mmol), followed by stirring at room temperature for 12 hours. The reaction mixture was added with water and the solvent was evaporated. The residue was added with water and extracted with chloroform. The organic layer was washed with saturated brine and dried over anhydrous magnesium sulfate, and then filtered through a column filled with SCX (positive-ion exchange resin). The SCX was washed with 2 mol/L ammonia-methanol solution and the filtrate was evaporated to obtain 4-(2-fluoro-4-chlorobenzenesulfonyloxy)-7-[1-(tert-butoxycarbonyl)-5-(piperidinomethyl)indol-2-yl]isoindolinone (0.0116 g, yield 27%).

ESI-MS m/z: 655 [M+H]$^+$

Step 2

4-(2-Fluoro-4-chlorobenzenesulfonyloxy)-7-[1-(tert-butoxycarbonyl)-5-(piperidinomethyl)indol-2-yl]isoindolinone (0.0116 g, 0.0177 mmol) was dissolved in 10% hydrogen chloride-methanol solution (0.650 mL) and the solution was stirred at 55° C. for 12 hours. The reaction mixture was concentrated and added with 1,1,1,3,3,3-hexafluoro-2-propanol (0.500 mL) and AG 1-X8 resin, followed by stirring at room temperature for 2 hours. The mixture was filtered, and the filtrate was concentrated and filtered through a column filled with SCX (positive-ion exchange resin). The SCX was washed with 2 mol/L ammonia-methanol solution and the filtrate was evaporated to obtain Compound 233 (0.00740 g, yield 75%).

ESI-MS m/z: 555 [M+H]$^+$

EXAMPLE 234

4-(3,4-Dimethylbenzenesulfonyloxy)-7-[1H-5-(piperidinomethyl)indol-2-yl]isoindolinone (Compound 234)

Step 1

In a similar manner to Step 1 of Example 233, 4-hydroxy-7-[1-(tert-butoxycarbonyl)-5-(piperidinomethyl)indol-2-yl] isoindolinone (0.0300 g, 0.0650 mmol) was dissolved in acetonitrile (0.650 mL), and the solution was treated with triethylamine (0.0540 mL, 0.390 mmol) and 3,4-dimethylbenzenesulfonyl chloride (0.0400 g, 0.195 mmol) to obtain 4-(3,4-dimethylbenzenesulfonyloxy)-7-[1-(tert-butoxycarbonyl)-5-(piperidinomethyl)indol-2-yl]isoindolinone (0.0149 g. yield 36%).

ESI-MS m/z: 630 [M+H]$^+$

Step 2

In a similar manner to Step 2 of Example 233, 4-(3,4-dimethylbenzenesulfonyloxy)-7-[1-(tert-butoxycarbonyl)-5-(piperidinomethyl)indol-2-yl]isoindolinone (0.0149 g, 0.0237 mmol) was treated with 10% hydrogen chloride-methanol solution (0.650 mL) to obtain Compound 234 (0.00790 g, yield 63%).

ESI-MS m/z: 530 [M+H]$^+$

EXAMPLE 235

4-(3-Fluoro-4-methylbenzenesulfonyloxy)-7-[1H-5-(piperidinomethyl)indol-2-yl]isoindolinone (Compound 235)

Step 1

In a similar manner to Step 1 of Example 233, 4-hydroxy-7-[1-(tert-butoxycarbonyl)-5-(piperidinomethyl)indol-2-yl] isoindolinone (0.0300 g, 0.0650 mmol) was dissolved in acetonitrile (0.650 mL), and the solution was treated with triethylamine (0.0540 mL, 0.390 mmol) and 3-fluoro-4-methylbenzenesulfonyl chloride (0.0410 g, 0.195 mmol) to obtain 4-(3-fluoro-4-methylbenzenesulfonyloxy)-7-[1-(tert-butoxycarbonyl)-5-(piperidinomethyl)indol-2-yl]isoindolinone (0.0191 g, yield 46%).

ESI-MS m/z: 634 [M+H]$^+$

Step 2

In a similar manner to Step 2 of Example 233, 4-(3-fluoro-4-methylbenzenesulfonyloxy)-7-[1-(tert-butoxycarbonyl)-5-(piperidinomethyl)indol-2-yl]isoindolinone (0.0191 g, 0.0301 mmol) was treated with 10% hydrogen chloride-methanol solution (0.650 mL) to obtain Compound 235 (0.00310 g, yield 19%).

ESI-MS m/z: 534 [M+H]$^+$

EXAMPLE 236

4-(3-Fluorobenzenesulfonyloxy)-7-[1H-5-(piperidinomethyl)indol-2-yl]isoindolinone (Compound 236)

Step 1

In a similar manner to Step 1 of Example 233, 4-hydroxy-7-[1-(tert-butoxycarbonyl)-5-(piperidinomethyl)indol-2-yl] isoindolinone (0.0300 g, 0.0650 mmol) was dissolved in acetonitrile (0.650 mL), and the solution was treated with triethylamine (0.0540 mL, 0.390 mmol) and 3-fluorobenzenesulfonyl chloride (0.0260 mL, 0.195 mmol) to obtain 4-(3-fluorobenzenesulfonyloxy)-7-[1-(tert-butoxycarbonyl)-5-(piperidinomethyl)indol-2-yl]isoindolinone (0.0241 g, yield 60%).

ESI-MS m/z: 620 [M+H]$^+$

Step 2

In a similar manner to Step 2 of Example 233, 4-(3-fluorobenzenesulfonyloxy)-7-[1-(tert-butoxycarbonyl)-5-(piperidinomethyl)indol-2-yl]isoindolinone (0.0241 g, 0.0389 mmol) was treated with 10% hydrogen chloride-methanol solution (0.650 mL) to obtain Compound 236 (0.00570 g, yield 28%).

ESI-MS m/z: 520 [M+H]$^+$

EXAMPLE 237

4-(2-Methyl-3-chlorobenzenesulfonyloxy)-7-[1H-5-(piperidinomethyl)indol-2-yl]isoindolinone (Compound 237)

Step 1

In a similar manner to Step 1 of Example 233, 4-hydroxy-7-[1-(tert-butoxycarbonyl)-5-(piperidinomethyl)indol-2-yl] isoindolinone (0.0300 g, 0.0650 mmol) was dissolved in acetonitrile (0.650 mL), and the solution was treated with triethylamine (0.0540 mL, 0.390 mmol) and 3-chloro-2-methylbenzenesulfonyl chloride (0.0440 g, 0.195 mmol) to obtain 4-(2-methyl-3-chlorobenzenesulfonyloxy)-7-[1-(tert-butoxycarbonyl)-5-(piperidinomethyl)indol-2-yl]isoindolinone (0.0211 g, yield 50%).

ESI-MS m/z: 651 [M+H]$^+$

Step 2

In a similar manner to Step 2 of Example 233, 4-(2-methyl-3-chlorobenzenesulfonyloxy)-7-[(1-(tert-butoxycarbonyl)-5-(piperidinomethyl)indol-2-yl]isoindolinone (0.0241 g, 0.0324 mmol) was treated with 10% hydrogen chloride-methanol solution (0.650 mL) to obtain Compound 237 (0.00460 g, yield 26%).

ESI-MS m/z: 551 [M+H]$^+$

EXAMPLE 238

4-(4-Methyl-3-chlorobenzenesulfonyloxy)-7-[1H-5-(piperidinomethyl)indol-2-yl]isoindolinone (Compound 238)

Step 1

In a similar manner to Step 1 of Example 233, 4-hydroxy-7-[1-(tert-butoxycarbonyl)-5-(piperidinomethyl)indol-2-yl]isoindolinone (0.0300 g, 0.0650 mmol) was dissolved in acetonitrile (0.650 mL), and the solution was treated with triethylamine (0.0540 mL, 0.390 mmol) and 3-chloro-4-methylbenzenesulfonyl chloride (0.0440 g, 0.195 mmol) to obtain 4-(4-methyl-3-chlorobenzenesulfonyloxy)-7-[1-(tert-butoxycarbonyl)-5-(piperidinomethyl)indol-2-yl]isoindolinone (0.0200 g, yield 47%).

ESI-MS m/z: 651 [M+H]$^+$

Step 2

In a similar manner to Step 2 of Example 233, 4-(4-methyl-3-chlorobenzenesulfonyloxy)-7-[1-(tert-butoxycarbonyl)-5-(piperidinomethyl)indol-2-yl]isoindolinone (0.0200 g, 0.0308 mmol) was treated with 10% hydrogen chloride-methanol solution (0.650 mL) to obtain Compound 238 (0.00015 g, yield 8.8%).

ESI-MS m/z: 551 [M+H]$^+$

EXAMPLE 239

4-(3-Chloro-4-fluorobenzenesulfonyloxy)-7-[1H-5-(piperidinomethyl)indol-2-yl]isoindolinone (Compound 239)

Step 1

In a similar manner to Step 1 of Example 233, 4-hydroxy-7-[1-(tert-butoxycarbonyl)-5-(piperidinomethyl)indol-2-yl]isoindolinone (0.0300 g, 0.0650 mmol) was dissolved in acetonitrile (0.650 mL), and the solution was treated with triethylamine (0.0540 mL, 0.390 mmol) and 3-chloro-4-fluorobenzenesulfonyl chloride (0.0280 mL, 0.195 mmol) to obtain 4-(3-chloro-4-fluorobenzenesulfonyloxy)-7-[1-(tert-butoxycarbonyl)-5-(piperidinomethyl)indol-2-yl]isoindolinone (0.00740 g, yield 17%).

ESI-MS m/z: 655 [M+H]$^+$

Step 2

In a similar manner to Step. 2 of Example 233, 4-(3-chloro-4-fluorobenzenesulfonyloxy)-7-[1-(tert-butoxycarbonyl)-5-(piperidinomethyl)indol-2-yl]isoindolinone (0.00740 g, 0.0113 mmol) was treated with 10% hydrogen chloride-methanol solution (0.650 mL) to obtain 4-(3-chloro-4-fluorobenzenesulfonyloxy)-7-[1H-5-(piperidinomethyl)indol-2-yl]isoindolinone (0.00520 g, yield 83%).

ESI-MS m/z: 555 [M+H]$^+$

EXAMPLE 240

4-(2-Methylbenzenesulfonyloxy)-7-[1H-(piperidinomethyl)indol-2-yl]isoindolinone (Compound 240)

Step 1

In a similar manner to Step 1 of Example 233, 4-hydroxy-7-[1-(tert-butoxycarbonyl)-5-(piperidinomethyl)indol-2-yl]isoindolinone (0.0304 g, 0.0659 mmol) was dissolved in acetonitrile (0.650 mL), and the solution was treated with triethylamine (0.0550 mL, 0.395 mmol) and 2-methylbenzenesulfonyl chloride (0.0280 mL, 0.198 mmol) to obtain 4-(2-methylbenzenesulfonyloxy)-7-[1-(tert-butoxycarbonyl)-5-(piperidinomethyl)indol-2-yl]isoindolinone (0.0280 g, yield 69%).

ESI-MS m/z: 616 [M+H]$^+$

Step 2

In a similar manner to Step 2 of Example 233, 4-(2-methylbenzenesulfonyloxy)-7-[1-(tert-butoxycarbonyl)-5-(piperidinomethyl)indol-2-yl]isoindolinone (0.0280 g, 0.0455 mmol) was treated with 10% hydrogen chloride-methanol solution (0.650 mL) to obtain Compound 240 (0.0183 mg, yield 85%).

ESI-MS m/z: 516 [M+H]$^+$

EXAMPLE 241

4-(3,4-Dichlorobenzenesulfonyloxy)-7-[1H-5-(piperidinomethyl)indol-2-yl]isoindolinone (Compound 241)

Step 1

In a similar manner to Step 1 of Example 233, 4-hydroxy-7-[1-(tert-butoxycarbonyl)-5-(piperidinomethyl)indol-2-yl]isoindolinone (0.0322 g, 0.0698 mmol) was dissolved in acetonitrile (0.650 mL), and the solution was treated with triethylamine (0.0540 mL, 0.390 mmol) and 3,4-dichlorobenzenesulfonyl chloride (0.0305 mL, 0.195 mmol) to obtain 4-(3,4-dichlorobenzenesulfonyloxy)-7-[1-(tert-butoxycarbonyl)-5-(piperidinomethyl)indol-2-yl]isoindolinone (0.0132 g, yield 28%).

ESI-MS m/z: 671 [M+H]$^+$

Step 2

In a similar manner to Step 2 of Example 233, 4-(3,4-dichlorobenzenesulfonyloxy)-7-[1-(tert-butoxycarbonyl)-5-(piperidinomethyl)indol-2-yl]isoindolinone (0.0132 g, 0.0197 mmol) was treated with 10% hydrogen chloride-methanol solution (0.650 mL) to obtain Compound 241 (0.00330 g, yield 29%).

ESI-MS m/z: 571 [M+H]$^+$

EXAMPLE 242

4-(4-Trifluoromethylbenzenesulfonyloxy)-7-[1H-5-(piperidinomethyl)indol-2-yl]isoindolinone (Compound 242)

Step 1

In a similar manner to Step 1 of Example 233, 4-hydroxy-7-[1-(tert-butoxycarbonyl)-5-(piperidinomethyl)indol-2-yl]isoindolinone (0.0310 g, 0.0672 mmol) was dissolved in acetonitrile (0.650 mL), and the solution was treated with triethylamine (0.0540 mL, 0.390 mmol) and 4-trifluoromethylbenzenesulfonyl chloride (0.0477 mL, 0.195 mmol) to obtain 4-(4-trifluoromethylbenzenesulfonyloxy)-7-[1-(tert-butoxycarbonyl)-5-(piperidinomethyl)indol-2-yl]isoindolinone (0.0122 g, yield 27%).

ESI-MS m/z: 670 [M+H]$^+$

Step 2

In a similar manner to Step 2 of Example 233, 4-(4-trifluoromethylbenzenesulfonyloxy)-7-[1-(tert-butoxycarbonyl)-5-(piperidinomethyl)indol-2-yl]isoindolinone (0.0122 g, 0.0182 mmol) was treated with 10% hydrogen chloride-methanol solution (0.6.50 mL) to obtain Compound 242 (0.00340 g, yield 33%).

ESI-MS m/z: 570 [M+H]$^+$

EXAMPLE 243

4-(2-Chlorobenzenesulfonyloxy)-7-[1H-5-(piperidinomethyl)indol-2-yl]isoindolinone hydrochloride (Compound 243)

Step 1

In a similar manner to Step 1 of Example 227, 4-hydroxy-7-[1-(tert-butoxycarbonyl)-5-(piperidinomethyl)indol-2-yl]isoindolinone (0.126 g, 0.274 mmol) was dissolved in acetonitrile (6.0 mL), and the solution was treated with triethylamine (0.0760 mL, 0.548 mmol) and 2-chlorobenzenesulfonyl chloride (0.0867 g, 0.411 mmol) to obtain 4-(2-chlorobenzenesulfonyloxy)-7-[1-(tert-butoxycarbonyl)-5-(piperidinomethyl)indol-2-yl]isoindolinone (0.130 g, yield 75%).

ESI-MS m/z: 636 [M+H]$^+$; $^1$H-NMR (CDCl$_3$) δ(ppm): 1.24 (s, 9H), 1.39-1.50 (m, 2H), 1.58-1.71 (m, 4H), 2.50-2.61 (m, 4H), 3.75 (s, 2H), 4.48 (s, 2H), 6.50 (s, 1H), 7.23 (d, J=8.2 Hz, 1H), 7.29 (dd, J=1.6, 8.7 Hz, 1H), 7.37 (d, J=8.2 Hz, 1H), 7.42-7.49 (m, 1H), 7.52 (s, 1H), 7.60 (s, 1H), 7.62-7.73 (m, 2H), 8.02 (d, J=1.5, 8.2 Hz, 1H), 8.21 (d, J=8.7 Hz, 1H).

Step 2

In a similar manner to Step 2 of Example 8, 4-(2-chlorobenzenesulfonyloxy)-7-[1-(tert-butoxycarbonyl)-5-(piperidinomethyl)indol-2-yl]isoindolinone (0.129 g, 0.203 mmol) was treated with 10% hydrogen chloride-methanol solution (5.0 mL) to obtain Compound 243 (0.0834 g, yield 72%).

ESI-MS m/z: 536 [M+H]$^+$; $^1$H-NMR (DMSO-d$_6$) δ(ppm): 1.28-1.44 (m, 1H), 1.59-1.87 (m, 5H), 2.78-2.95 (m, 2H), 3.32-3.68 (m, 2H), 4.32 (s, 2H), 4.46 (s, 2H), 7.24-7.33 (m, 3H), 7.57 (d, J=8.1 Hz, 1H), 7.61-7.69 (m, 1H), 7.75 (s, 1H), 7.86-7.98 (m, 2H), 8.08 (dd, J=1.5, 8.1 Hz, 1H), 8.21 (d, J=9.0 Hz, 1H), 9.50 (s, 1H), 9.54 (br s, 1H), 13.8 (s, 1H).

EXAMPLE 244

4-(2-Trifluoromethylbenzenesulfonyloxy)-7-[1H-(piperidinomethyl)indol-2-yl]isoindolinone (Compound 244)

Step 1

In a similar manner to Step 1 of Example 233, 4-hydroxy-7-[1-(tert-butoxycarbonyl)-5-(piperidinomethyl)indol-2-yl]isoindolinone (0.0319 g, 0.0691 mmol) was dissolved in acetonitrile (0.650 mL), and the solution was treated with triethylamine (0.0540 mL, 0.390 mmol) and 2-trifluoromethylbenzenesulfonyl chloride (0.0301 mL, 0.195 mmol) to obtain 4-(2-trifluoromethylbenzenesulfonyloxy)-7-[1-(tert-butoxycarbonyl)-5-(piperidinomethyl)indol-2-yl]isoindolinone (0.0191 g, yield 41%).

ESI-MS m/z: 670 [M+H]$^+$

Step 2

In a similar manner to Step 2 of Example 233, 4-(2-trifluoromethylbenzenesulfonyloxy)-7-[(1-(tert-butoxycarbonyl)-5-(piperidinomethyl)indol-2-yl]isoindolinone (0.0191 g, 0.0285 mmol) was treated with 10% hydrogen chloride-methanol solution (0.650 mL) to obtain Compound 244 (0.0118 g. yield 73%).

ESI-MS m/z: 570 [M+H]$^+$

EXAMPLE 245

4-(3-Chlorobenzenesulfonyloxy)-7-[1H-5-(piperidinomethyl)indol-2-yl]isoindolinone (Compound 245)

Step 1

In a similar manner to Step 1 of Example 233, 4-hydroxy-7-[1-(tert-butoxycarbonyl)-5-(piperidinomethyl)indol-2-yl]isoindolinone (0.0306 g, 0.0663 mmol) was dissolved in acetonitrile (0.650 mL), and the solution was treated with triethylamine (0.0540 mL, 0.390 mmol) and 3-chlorobenzenesulfonyl chloride (0.0275 mL, 0.195 mmol) to obtain 4-(3-chlorobenzenesulfonyloxy)-7-[1-(tert-butoxycarbonyl)-5-(piperidinomethyl)indol-2-yl]isoindolinone (0.0168 g, yield 40%).

ESI-MS m/z: 637 [M+H]$^+$

Step 2

In a similar manner to Step 2 of Example 233, 4-(3-chlorobenzenesulfonyloxy)-7-[1-(tert-butoxycarbonyl)-5-(piperidinomethyl)indol-2-yl]isoindolinone (0.0168 g, 0.0264 mmol) was treated with 10% hydrogen chloride-methanol solution (0.650 mL) to obtain Compound 245 (0.00640 g, yield 45%).

ESI-MS m/z: 537 [M+H]$^+$

EXAMPLE 246

4-(2,6-Dichlorobenzenesulfonyloxy)-7-[1H-5-(piperidinomethyl)indol-2-yl]isoindolinone (Compound 246)

Step 1

In a similar manner to Step 1 of Example 233, 4-hydroxy-7-[1-(tert-butoxycarbonyl)-5-(piperidinomethyl)indol-2-yl]isoindolinone (0.0313 g, 0.0678 mmol) was dissolved in acetonitrile (0.650 mL), and the solution was treated with triethylamine (0.0540 mL, 0.390 mmol) and 2,6-dichlorobenzenesulfonylchloride (0.0479 g, 0.195 mmol) to obtain 4-(2,6-dichlorobenzenesulfonyloxy)-7-[1-(tert-butoxycarbonyl)-5-(piperidinomethyl)indol-2-yl]isoindolinone (0.0168 g, yield 37%).

ESI-MS m/z: 671 [M+H]$^+$

Step 2

In a similar manner to Step 2 of Example 233, 4-(2,6-dichlorobenzenesulfonyloxy)-7-[1-(tert-butoxycarbonyl)-5-(piperidinomethyl)indol-2-yl]isoindolinone (0.0168 g, 0.0250 mmol) was treated with 10% hydrogen chloride-methanol solution (0.650 mL) to obtain Compound 246 (0.00720 g, yield 43%).

ESI-MS m/z: 571 [M+H]$^+$

EXAMPLE 247

4-(2,3-Dichlorobenzenesulfonyloxy)-7-[1H-(piperidinomethyl)indol-2-yl]isoindolinone (Compound 247)

Step 1

In a similar manner to Step 1 of Example 233, 4-hydroxy-7-[1-(tert-butoxycarbonyl)-5-(piperidinomethyl)indol-2-yl]isoindolinone (0.0280 g, 0.0607 mmol) was dissolved in acetonitrile (0.650 mL), and the solution was treated with triethylamine (0.0540 mL, 0.390 mmol) and 2,3-dichlorobenzenesulfonyl chloride (0.0479 g, 0.195 mmol) to obtain 4-(2, 3-dichlorobenzenesulfonyloxy)-7-[1-(tert-butoxycarbonyl)-5-(piperidinomethyl)indol-2-yl]isoindolinone (0.0186 g, yield 37%).

ESI-MS m/z: 671 [M+H]$^+$

Step 2

In a similar manner to Step 2 of Example 233, 4-(2,3-dichlorobenzenesulfonyloxy)-7-[1-(tert-butoxycarbonyl)-5-(piperidinomethyl)indol-2-yl]isoindolinone (0.0186 g, 0.0277 mmol) was treated with 10% hydrogen chloride-methanol solution (0.650 mL) to obtain Compound 247 (0.0109 g, yield 69%).

ESI-MS m/z: 571 [M+H]$^+$

EXAMPLE 248

4-(2-Methyl-5-fluorobenzenesulfonyloxy)-7-[1H-5-(piperidinomethyl)indol-2-yl]isoindolinone (Compound 248)

Step 1

In a similar manner to Step 1 of Example 233, 4-hydroxy-7-[1-(tert-butoxycarbonyl)-5-(piperidinomethyl)indol-2-yl]isoindolinone (0.0287 g, 0.0622 mmol) was dissolved in acetonitrile (0.650 mL), and the solution was treated with triethylamine (0.0540 mL, 0.390 mmol) and 5-fluoro-2-methylbenzenesulfonyl chloride (0.0286 mL, 0.195 mmol) to obtain 4-(2-methyl-5-fluorobenzenesulfonyloxy)-7-[1-(tert-butoxycarbonyl)-5-(piperidinomethyl)indol-2-yl]isoindolinone (0.0157 g, yield 40%).

ESI-MS m/z: 634 [M+H]$^+$

Step 2

In a similar manner to Step 2 of Example 233, 4-(2-methyl-5-fluorobenzenesulfonyloxy)-7-[1-(tert-butoxycarbonyl)-5-(piperidinomethyl)indol-2-yl]isoindolinone (0.0157 g, 0.0248 mmol) was treated with 10% hydrogen chloride-methanol solution (0.650 mL) to obtain Compound 248 (0.00590 g. yield 45%).

ESI-MS m/z: 534 [M+H]$^+$

EXAMPLE 249

4-(3-Methoxybenzenesulfonyloxy)-7-[1H-5-(piperidinomethyl)indol-2-yl]isoindolinone (Compound 249)

Step 1

In a similar manner to Step 1 of Example 233, 4-hydroxy-7-[1-(tert-butoxycarbonyl)-5-(piperidinomethyl)indol-2-yl]isoindolinone (0.0314 g, 0.0680 mmol) was dissolved in acetonitrile (0.650 mL), and the solution was treated with triethylamine (0.0540 mL, 0.390 mmol) and 3-methoxybenzenesulfonyl chloride (0.0403 g, 0.195 mmol) to obtain 4-(3-methoxybenzenesulfonyloxy)-7-[1-(tert-butoxycarbonyl)-5-(piperidinomethyl)indol-2-yl]isoindolinone (0.0191 g, yield 44%).

ESI-MS m/z: 632 [M+H]$^+$

Step 2

In a similar manner to Step 2 of Example 233, 4-(3-methoxybenzenesulfonyloxy)-7-[1-(tert-butoxycarbonyl)-5-(piperidinomethyl)indol-2-yl]isoindolinone (0.0191 g, 0.0302 mmol) was treated with 10% hydrogen chloride-methanol solution (0.650 mL) to obtain Compound 249 (0.00590 g, yield 37%).

ESI-MS m/z: 532 [M+H]$^+$

EXAMPLE 250

4-(2,5-Fluoro-4-chlorobenzenesulfonyloxy)-7-[1H-5-(piperidinomethyl)indol-2-yl]isoindolinone (Compound 250)

Step 1

In a similar manner to Step 1 of Example 233, 4-hydroxy-7-[1-(tert-butoxycarbonyl)-5-(piperidinomethyl)indol-2-yl]isoindolinone (0.0305 g, 0.0661 mmol) was dissolved in acetonitrile (0.650 mL), and the solution was treated with triethylamine (0.0540 mL, 0.390 mmol) and 4-chloro-2,5-difluorobenzenesulfonyl chloride (0.0482 g, 0.195 mmol) to obtain 4-(2,5-fluoro-4-chlorobenzenesulfonyloxy)-7-[1-(tert-butoxycarbonyl)-5-(piperidinomethyl)indol-2-yl]isoindolinone (0.0152 g, yield 34%).

ESI-MS m/z: 672 [M+H]$^+$

Step 2

In a similar manner to Step 2 of Example 233, 4-(2,5-fluoro-4-chlorobenzenesulfonyloxy)-7-[1-(tert-butoxycarbonyl)-5-(piperidinomethyl)indol-2-yl]isoindolinone (0.0152 g, 0.0226 mmol) was treated with 10% hydrogen chloride-methanol solution (0.650 mL) to obtain Compound 250 (0.00610 g, yield 47%).

ESI-MS-m/z: 572 [M+H]$^+$

EXAMPLE 251

4-(2-Chloro-4-fluorobenzenesulfonyloxy)-7-[1H-5-(piperidinomethyl)indol-2-yl]isoindolinone (Compound 251)

Step 1

In a similar manner to Step 1 of Example 233, 4-hydroxy-7-[1-(tert-butoxycarbonyl)-5-(piperidinomethyl)indol-2-yl]isoindolinone (0.0290 g, 0.0628 mmol) was dissolved in acetonitrile (0.650 mL), and the solution was treated with triethylamine (0.0540 mL, 0.390 mmol) and 2-chloro-4-fluorobenzenesulfonyl chloride (0.0447 g, 0.195 mmol) to obtain 4-(2-chloro-4-fluorobenzenesulfonyloxy)-7-[1-(tert-butoxycarbonyl)-5-(piperidinomethyl)indol-2-yl]isoindolinone (0.0133 g, yield 34%).

ESI-MS m/z: 632 [M+H]$^+$

Step 2

In a similar manner to Step 2 of Example 233, 4-(2-chloro-4-fluorobenzenesulfonyloxy)-7-[1-(tert-butoxycarbonyl)-5-(piperidinomethyl)indol-2-yl]isoindolinone (0.0133 g, 0.0211 mmol) was treated with 10% hydrogen chloride-methanol solution (0.650 mL) to obtain Compound 251 (0.0050 g, yield 45%).

ESI-MS m/z: 0.532 [M+H]$^+$

EXAMPLE 252

4-(2,4-Difluoro-5-chlorobenzenesulfonyloxy)-7-[1H-5-(piperidinomethyl)indol-2-yl]isoindolinone (Compound 252)

Step 1

In a similar manner to Step 1 of Example 233, 4-hydroxy-7-[1-(tert-butoxycarbonyl)-5-(piperidinomethyl)indol-2-yl]isoindolinone (0.0283 g, 0.0613 mmol) was dissolved in acetonitrile (0.650 mL), and the solution was treated with triethylamine (0.0540 mL, 0.390 mmol) and 5-chloro-2,4- difluorobenzenesulfonyl chloride (0.0482 g, 0.195 mmol) to obtain 4-(2,4-difluoro-5-chlorobenzenesulfonyloxy)-7-[1-(tert-butoxycarbonyl)-5-(piperidinomethyl)indol-2-yl]isoindolinone (0.0117 g, yield 28%).

ESI-MS m/z: 673 [M+H]$^+$

Step 2

In a similar manner to Step 2 of Example 233, 4-(2,4-difluoro-5-chlorobenzenesulfonyloxy)-7-[1-(tert-butoxycarbonyl)-5-(piperidinomethyl)indol-2-yl]isoindolinone (0.0117 g, 0.0174 mmol) was treated with 10% hydrogen chloride-methanol solution (0.650 mL) to obtain Compound 252 (0.00470 g, yield 47%).

ESI-MS m/z: 573 [M+H]$^+$

EXAMPLE 253

4-(2,4-Dimethoxybenzenesulfonyloxy)-7-[1H-5-(piperidinomethyl)indol-2-yl]isoindolinone (Compound 253)

Step 1

In a similar manner to Step 1 of Example 233, 4-hydroxy-7-[1-(tert-butoxycarbonyl)-5-(piperidinomethyl)indol-2-yl]isoindolinone (0.0289 g, 0.0626 mmol) was dissolved in acetonitrile (0.650 mL), and the solution was treated with triethylamine (0.0540 mL, 0.390 mmol) and 2,4-dimethoxybenzenesulfonyl chloride (0.0462 g, 0.195 mmol) to obtain 4-(2,4-dimethoxybenzenesulfonyloxy)-7-[1-(tert-butoxycarbonyl)-5-(piperidinomethyl)indol-2-yl]isoindolinone (0.0117 g, yield 20%).

ESI-MS m/z: 662 [M+H]$^+$

Step 2

In a similar manner to Step 2 of Example 233, 4-(2,4-dimethoxybenzenesulfonyloxy)-7-[1-(tert-butoxycarbonyl)-5-(piperidinomethyl)indol-2-yl]isoindolinone (0.0117 mg, 0.0127 mmol) was treated with 10% hydrogen chloride-methanol solution (0.650 mL) to obtain Compound 253 (0.00450 g, yield 63%).

ESI-MS m/z: 562 [M+H]$^+$

EXAMPLE 254

4-(2-Methoxy-5-chlorobenzenesulfonyloxy)-7-[1H-5-(piperidinomethyl)indol-2-yl]isoindolinone (Compound 254)

In a similar manner to Step 1 of Example 233, 4-hydroxy-7-[1-(tert-butoxycarbonyl)-5-(piperidinomethyl)indol-2-yl]isoindolinone (0.0279 g, 0.0604 mmol) was dissolved in acetonitrile (0.650 mL), and the solution was treated with triethylamine (0.0540 mL, 0.390 mmol) and 5-chloro-2-methoxybenzenesulfonyl chloride (0.0470 g, 0.195 mmol) to obtain 4-(2-methoxy-5-chlorobenzenesulfonyloxy)-7-[1-(tert-butoxycarbonyl)-5-(piperidinomethyl)indol-2-yl]isoindolinone (0.0172 g, yield 434).

ESI-MS m/z: 667 [M+H]$^+$

Step 2

In a similar manner to Step 2 of Example 233, 4-(2-methoxy-5-chlorobenzenesulfonyloxy)-7-[1-(tert-butoxycarbonyl)-5-(piperidinomethyl)indol-2-yl]isoindolinone (0.0172 g, 0.0258 mmol) was treated with 10% hydrogen chloride-methanol solution (0.650 mL) to obtain Compound 254 (0.00330 g, yield 23%).

ESI-MS m/z: 567 [M+H]$^+$

EXAMPLE 255

4-(3,5-Dimethylisoxazol-4-ylsulfonyloxy)-7-[1H-5-(piperidinomethyl)indol-2-yl]isoindolinone (Compound 255)

Step 1

In a similar manner to Step 1 of Example 233, 4-hydroxy-7-[1-(tert-butoxycarbonyl)-5-(piperidinomethyl)indol-2-yl]isoindolinone (0.0291 g, 0.0630 mmol) was dissolved in acetonitrile (0.650 mL), and the solution was treated with triethylamine (0.0540 mL, 0.390 mmol) and 3,5-dimethylisoxazol-4-sulfonyl chloride (0.0382 g, 0.195 mmol) to obtain 4-(3,5-dimethylisoxazol-4-ylsulfonyloxy)-7-[1-(tert-butoxycarbonyl)-5-(piperidinomethyl)indol-2-yl]isoindolinone (0.0092 g, yield 23%).

ESI-MS m/z: 621 [M+H]$^+$

Step 2

In a similar manner to Step 2 of Example 233, 4-(3,5-dimethylisoxazol-4-ylsulfonyloxy)-7-[1-(tert-butoxycarbonyl)-5-(piperidinomethyl)indol-2-yl]isoindolinone (0.0092 g, 0.0148 mmol) was treated with 10% hydrogen chloride-methanol solution (0.650 mL) to obtain Compound 255 (0.00250 g, yield 32%).

ESI-MS m/z: 521 [M+H]$^+$

EXAMPLE 256

4-(2-Trifluoromethyl-5-methyl-3-furansulfonyloxy)-7-[1H-5-(piperidinomethyl)indol-2-yl]isoindolinone (Compound 256)

Step 1

In a similar manner to Step 1 of Example 233, 4-hydroxy-7-[1-(tert-butoxycarbonyl)-5-(piperidinomethyl)indol-2-yl]isoindolinone (0.0277 g, 0.0600 mmol) was dissolved in acetonitrile (0.650 mL), and the solution was treated with triethylamine (0.0540 mL, 0.390 mmol) and 5-methyl-2-trifluoromethyl-3-furansulfonyl chloride (0.0486 g, 0.195 mmol) to obtain 4-(2-trifluoromethyl-5-methyl-3-furansulfonyloxy)-7-[1-(tert-butoxycarbonyl)-5-(piperidinomethyl)indol-2-yl]isoindolinone (0.0092 g, yield 23%).

ESI-MS m/z: 674 [M+H]$^+$

Step 2

In a similar manner to Step 2 of Example 233, 4-(2-trifluoromethyl-5-methyl-3-furansulfonyloxy)-7-[1-(tert-butoxycarbonyl)-5-(piperidinomethyl)indol-2-yl]isoindolinone (0.000920 g, 0.0137 mmol) was treated with 10% hydrogen chloride-methanol solution (0.650 mL) to obtain Compound 256 (0.00650 g, yield 82%).

ESI-MS m/z: 574 [M+H]$^+$

EXAMPLE 257

4-(3-Thiophenesulfonyloxy)-7-[1H-5-(piperidinomethyl)indol-2-yl]isoindolinone hydrochloride (Compound 257)

Step 1

In a similar manner to Step 1 of Example 227, 4-hydroxy-7-[1-(tert-butoxycarbonyl)-5-(piperidinomethyl)indol-2-yl]isoindolinone (0.0951 g, 0.206 mmol) was dissolved in acetonitrile (4.0 mL), and the solution was treated with triethylamine (0.0860 mL, 0.618 mmol) and 3-thiophenesulfonyl chloride (0.0754 g, 0.412 mmol) to obtain 4-(3-thiophenesulfonyloxy)-7-[1-(tert-butoxycarbonyl)-5-(piperidinomethyl)indol-2-yl]isoindolinone (0.0796 g, yield 64%).

ESI-MS m/z: 608 [M+H]$^+$; $^1$H-NMR (CDCl$_3$) d (ppm): 1.29 (s, 9H), 1.39-1.48 (m, 2H), 1.75-1.94 (m, 4H), 2.68-2.93 (m, 4H), 4.03 (s, 2H), 4.36 (s, 2H), 6.55 (s, 1H), 7.01-7.19 (m, 3H), 7.31-7.50 (m, 2H), 7.52-7.61 (m, 1H), 7.67 (s, 1H), 8.05-8.11 (m, 1H), 8.23 (d, J=8.8 Hz, 1H).

Step 2

In a similar manner to Step 2 of Example 8, 4-(3-thiophenesulfonyloxy)-7-[(1-(tert-butoxycarbonyl)-5-(piperidinomethyl)indol-2-yl]isoindolinone (0.0790 g, 0.130 mmol) was treated with 10% hydrogen chloride-methanol solution (5.0 mL) to obtain Compound 257 (0.0442 g, yield 63%).

ESI-MS m/z: 508 [M+H]$^+$; $^1$H-NMR (DMSO-d$_6$) δ(ppm): 1.28-1.44 (m, 1H), 1.59-1.87 (m, 5H), 2.78-2.95 (m, 2H), 3.32-3.68 (m, 2H), 4.21 (s, 2H), 4.56 (s, 2H), 6.65 (s, 1H), 7.15-7.28 (m, 2H), 7.36-7.68 (m, 3H), 7.54-7.68 (m, 1H), 7.67 (s, 1H), 8.05-8.11 (m, 1H), 9.52 (br s, 1H), 9.69 (s, 1H), 13.8 (s, 1H).

EXAMPLE 258

4-(Benzothiophene-2-sulfonyloxy)-7-[1H-5-(piperidinomethyl)indol-2-yl]isoindolinone (Compound 258)

Step 1

In a similar manner to Step 1 of Example 233, 4-hydroxy-7-[1-(tert-butoxycarbonyl)-5-(piperidinomethyl)indol-2-yl]isoindolinone (0.0300 g, 0.0650 mmol) was dissolved in acetonitrile (0.650 mL), and the solution was treated with triethylamine (0.0540 mL, 0.390 mmol) and 1-benzothiophene-2-sulfonylchloride (0.0357 g, 0.195 mmol) to obtain 4-(benzothiophene-2-sulfonyloxy)-7-[1-(tert-butoxycarbonyl)-5-(piperidinomethyl)indol-2-yl]isoindolinone (0.0120 g, yield 33%).

ESI-MS m/z: 658 [M+H]$^+$

Step 2

In a similar manner to Step 2 of Example 233, 4-(benzothiophene-2-sulfonyloxy)-7-[1-(tert-butoxycarbonyl)-5-(piperidinomethyl)indol-2-yl]isoindolinone (0.0120 g, 0.0195 mmol) was treated with 10% hydrogen chloride-methanol solution (0.650 mL) to obtain Compound 258 (0.00690 g, yield 63%).

ESI-MS m/z: 558 [M+H]$^+$

EXAMPLE 259

4-(1,3-Dimethyl-5-chloro-1H-pyrazol-4-ylsulfonyloxy)-7-[1H-5-(piperidinomethyl)indol-2-yl]isoindolinone (Compound 259)

Step 1

In a similar manner to Step 1 of Example 233, 4-hydroxy-7-[1-(tert-butoxycarbonyl)-5-(piperidinomethyl)indol-2-yl]isoindolinone (0.0292 g, 0.0633 mmol) was dissolved in acetonitrile (0.650 mL), and the solution was treated with triethylamine (0.0540 mL, 0.390 mmol) and 5-chloro-1,3-dimethyl-1H-pyrazole-4-sulfonyl chloride (0.0447 g, 0.195 mmol) to obtain 4-(1,3-dimethyl-5-chloro-1H-pyrazol-4-ylsulfonyloxy)-7-[1-(tert-butoxycarbonyl)-5-(piperidinomethyl)indol-2-yl]isoindolinone (0.0120 g, yield 29%).

ESI-MS m/z: 655 [M+H]$^+$

Step 2

In a similar manner to Step 1 of Example 233, 4-(1,3-dimethyl-5-chloro-1H-pyrazol-4-ylsulfonyloxy)-7-[1-(tert-butoxycarbonyl)-5-(piperidinomethyl)indol-2-yl]isoindolinone (0.0120 g, 0.0183 mmol) was treated with 10% hydrogen chloride-methanol solution (0.650 mL) to obtain Compound 259 (0.0097 g, yield 96%).

ESI-MS m/z: 555 [M+H]$^+$

EXAMPLE 260

4-(1,3,5-Trimethyl-1H-pyrazol-4-ylsulfonyloxy)-7-[1H-5-(piperidinomethyl)indol-2-yl]isoindolinone (Compound 260)

Step 1

In a similar manner to Step 1 of Example 233, 4-hydroxy-7-[1-(tert-butoxycarbonyl)-5-(piperidinomethyl)indol-2-yl]isoindolinone (0.0316 g, 0.0685 mmol) was dissolved in acetonitrile (0.650 mL), and the solution was treated with triethylamine (0.0540 mL, 0.390 mmol) and 1,3,5-trimethyl-1H-pyrazol-4-sulfonyl chloride (0.0407 g, 0.195 mmol) to obtain 4-(1,3,5-trimethyl-1H-pyrazol-4-ylsulfonyloxy)-7-[1-(tert-butoxycarbonyl)-5-(piperidinomethyl)indol-2-yl]isoindolinone (0.0118 g, yield 27%).

ESI-MS m/z: 634 [M+H]$^+$

Step 2

In a similar manner to Step 2 of Example 233, 4-(1,3,5-trimethyl-1H-pyrazol-4-ylsulfonyloxy)-7-[1-(tert-butoxycarbonyl)-5-(piperidinomethyl)indol-2-yl]isoindolinone (0.0118 g, 0.0186 mmol) was treated with 10% hydrogen chloride-methanol solution (0.650 mL) to obtain Compound 260 (0.00990 g, yield 47%).

ESI-MS m/z: 534 [M+H]$^+$

EXAMPLE 261

4-(2-Pyridinesulfonyloxy)-7-[1H-5-(piperidinomethyl)indol-2-yl]isoindolinone hydrochloride (Compound 261)

Step 1

In a similar manner to Step 1 of Example 227, 4-hydroxy-7-[1-(tert-butoxycarbonyl)-5-(piperidinomethyl)indol-2-yl]isoindolinone (0.0728 g, 0.158 mmol) was dissolved in acetonitrile (2.0 mL), and the solution was treated with triethylamine (0.0660 mL, 0.473 mmol) and 2-pyridinesulfonyl chloride (0.0680 g, 0.315 mmol) to obtain 4-(2-pyridinesulfonyloxy)-7-[1-(tert-butoxycarbonyl)-5-(piperidinomethyl)indol-2-yl]isoindolinone (0.698 g, yield 73%).

ESI-MS m/z: 603 [M+H]$^+$; $^1$H-NMR (CDCl$_3$) δ(ppm): 1.28 (s, 9H), 1.38-1.48 (m, 2H), 1.53-1.62 (m, 4H), 2.35-2.54 (m, 4H), 3.57 (s, 2H), 4.43 (s, 2H), 6.52 (s, 1H), 7.26-7.43 (m, 3H), 7.48 (s, 1H), 7.63-7.70 (m, 1H), 7.69-8.04 (m, 1H), 8.09 (d, J=7.7 Hz, 1H), 8.18 (d, J=8.6 Hz, 1H), 8.83-8.88 (m, 1H).

Step 2

In a similar manner to Step 2 of Example 8, 4-(2-pyridinesulfonyloxy)-7-[1-(tert-butoxycarbonyl)-5-(piperidinomethyl)indol-2-yl]isoindolinone (0.0690 g, 0.114 mmol) was treated with 10% hydrogen chloride-methanol solution (5.0 mL) to obtain Compound 261 (0.416 g, yield 63%).

ESI-MS m/z: 503 [M+H]$^+$

EXAMPLE 262

4-(Dimethylsulfamoyloxy)-7-[(1H-(piperidinomethyl)indol-2-yl]isoindolinone hydrochloride (Compound 262)

Step 1

4-Hydroxy-7-[(1-(tert-butoxycarbonyl)-5-(piperidinomethyl)indol-2-yl]isoindolinone (0.236 g, 0.511 mmol) was dissolved in acetonitrile (10.0 mL), and the solution was added with N,N,N',N'-tetramethyl-1,3-propanediamine (0.256 mL, 1.53 mmol) and dimethylsulfamoyl chloride (0.110 mL, 1.02 mmol), followed by stirring at room temperature for 1 hour. The reaction mixture was added with water and extracted with a mixture of chloroform and 2-propanol. The organic layer was washed with saturated brine and dried over anhydrous sodium sulfate. The solvent was evaporated under reduced pressure and the residue was purified by flash column chromatography (chloroform/methanol=85/15) to obtain 4-dimethylsulfamoyloxy-7-[1-(tert-butoxycarbonyl)-5-(piperidinomethyl)indol-2-yl]isoindolinone (0.197 g, yield 63%).

ESI-MS m/z: 569 [M+H]$^+$; $^1$H-NMR (CDCl$_3$) δ(ppm): 1.27 (s, 9H), 1.39-1.48 (m, 2H), 1.55-1.66 (m, 4H), 2.36-2.53 (m, 4H), 3.08 (s, 6H), 3.63 (s, 2H), 4.54 (s, 2H), 6.55 (s, 1H), 7.31 (dd, J=1.3, 8.6 Hz, 1H), 7.49-7.54 (m, 3H), 7.68-7.91 (m, 1H), 8.19 (d, J=8.6 Hz, 1H).

Step 2

In a similar manner to Step 2 of Example 8, 4-dimethylsulfamoyloxy-7-[1-(tert-butoxycarbonyl)-5-(piperidinomethyl)indol-2-yl]isoindolinone (0.197 g, 0.346 mmol) was treated with 10% hydrogen chloride-methanol solution (10.0 mL) to obtain Compound 262 (0.0966 g, yield 55%).

ESI-MS m/z: 454 [M+H]$^+$; $^1$H-NMR (DMSO-d$_6$) δ(ppm): 1.28-1.44 (m, 1H), 1.59-1.87 (m, 5H), 2.78-2.95 (m, 2H), 3.01 (s, 6H), 3.32-3.68 (m, 2H), 4.29 (s, 2H), 4.57 (s, 2H), 7.30 (s, 1H), 7.33 (d, J=8.4 Hz, 1H), 7.56 (d, J=8.4 Hz, 1H), 7.62 (d, J=8.7 Hz, 1H), 7.74-7.86 (m, 1H), 8.28 (d, J=8.7 Hz, 1H), 9.53 (s, 1H), 10.2 (br s, 1H), 13.8 (s, 1H).

EXAMPLE 263

4-(4-Methoxybenzenesulfonyloxy)-7-[1H-5-(piperidinomethyl)indol-2-yl]isoindolinone (Compound 263)

Step 1

In a similar manner to Step 1 of Example 233, 4-hydroxy-7-[1-(tert-butoxycarbonyl)-5-(piperidinomethyl)indol-2-yl]isoindolinone (0.0315 g, 0.0682 mmol) was dissolved in acetonitrile (0.650 mL), and the solution was treated with triethylamine (0.0570 mL, 0.409 mmol) and 4-methoxybenzenesulfonyl chloride (0.0420 g, 0.205 mmol) to obtain 4-(4-methoxybenzenesulfonyloxy)-7-[1-(tert-butoxycarbonyl)-5-(piperidinomethyl)indol-2-yl]isoindolinone (0.0194 g, yield 45%).

ESI-MS m/z: 632 [M+H]$^+$

Step 2

In a similar manner to Step 2 of Example 233, 4-(4-methoxybenzenesulfonyloxy)-7-[1-(tert-butoxycarbonyl)-5-(piperidinomethyl)indol-2-yl]isoindolinone (0.0194 g, 0.0307 mmol) was treated with 10% hydrogen chloride-methanol solution (0.650 mL) to obtain Compound 263 (0.00620 g, yield 38%).

ESI-MS m/z: 532 [M+H]$^+$

EXAMPLE 264

4-(4-Chlorobenzenesulfonyloxy)-7-[1H-5-(piperidinomethyl)indol-2-yl]isoindolinone (Compound 264)

Step 1

In a similar manner to Step 1 of Example 233, 4-hydroxy-7-[1-(tert-butoxycarbonyl)-5-(piperidinomethyl)indol-2-yl]isoindolinone (0.0295 g, 0.0639 mmol) was dissolved in acetonitrile (0.650 mL), and the solution was treated with triethylamine (0.0530 mL, 0.383 mmol) and 4-chlorobenzenesulfonyl chloride (0.0400 g, 0.192 mmol) to obtain 4-(4-chlorobenzenesulfonyloxy)-7-[1-(tert-butoxycarbonyl)-5-(piperidinomethyl)indol-2-yl]isoindolinone (0.0167 g, yield 41%).

ESI-MS m/z: 637 [M+H]$^+$

Step 2

In a similar manner to Step 2 of Example 233, 4-(4-chlorobenzenesulfonyloxy)-7-[(1-(tert-butoxycarbonyl)-5-(piperidinomethyl)indol-2-yl]isoindolinone (0.0167 g, 0.0262 mmol) was treated with 10% hydrogen chloride-methanol solution (0.650 mL) to obtain Compound 264 (0.00871 g, yield 62%).

ESI-MS m/z: 537 [M+H]$^+$

EXAMPLE 265

4-(4-Methylbenzenesulfonyloxy)-7-[1H-5-(piperidinomethyl)indol-2-yl]isoindolinone (Compound 265)

Step 1

In a similar manner to Step 1 of Example 233, 4-hydroxy-7-[1-(tert-butoxycarbonyl)-5-(piperidinomethyl)indol-2-yl]isoindolinone (0.0327 g, 0.0708 mmol) was dissolved in acetonitrile (0.650 mL), and the solution was treated with triethylamine (0.0590 mL, 0.425 mmol) and p-tosylchloride (0.0410 g, 0.213 mmol) to obtain 4-(4-methylbenzenesulfonyloxy)-7-[1-(tert-butoxycarbonyl)-5-(piperidinomethyl)indol-2-yl]isoindolinone (0.0253 g, yield 58%).

ESI-MS m/z: 616 [M+H]$^+$

Step 2

In a similar manner to Step 2 of Example 233, 4-(4-methylbenzenesulfonyloxy)-7-[1-(tert-butoxycarbonyl)-5-(piperidinomethyl)indol-2-yl]isoindolinone (0.0253 g, 0.0411 mmol) was treated with 10% hydrogen chloride-methanol solution (0.650 mL) to obtain Compound 265 (0.00762 g. yield 36%).

ESI-MS m/z: 516 [M+H]$^+$

EXAMPLE 266

4-(3,5-Dichlorobenzenesulfonyloxy)-7-[1H-5-(piperidinomethyl)indol-2-yl]isoindolinone (Compound 266)

Step 1

In a similar manner to Step 1 of Example 233, 4-hydroxy-7-[1-(tert-butoxycarbonyl)-5-(piperidinomethyl)indol-2-yl]isoindolinone (0.0332 g, 0.0719 mmol) was dissolved in acetonitrile (0.650 mL), and the solution was treated with triethylamine (0.0600 mL, 0.432 mmol) and 3,5-dichlorobenzenesulfonylchloride (0.0530 g, 0.216 mmol) to obtain 4-(3,5-dichlorobenzenesulfonyloxy)-7-[1-(tert-butoxycarbonyl)-5-(piperidinomethyl)indol-2-yl]isoindolinone (0.0212 g, yield 44%).

ESI-MS m/z: 671 [M+H]$^+$

Step 2

In a similar manner to Step 2 of Example 233, 4-(3,5-dichlorobenzenesulfonyloxy)-7-[1-(tert-butoxycarbonyl)-5-(piperidinomethyl)indol-2-yl]isoindolinone (0.0212 g, 0.0316 mmol) was treated with 10% hydrogen chloride-methanol solution (0.650 mL) to obtain Compound 266 (0.0123 g, yield 68%).

ESI-MS m/z: 571 [M+H]$^+$

EXAMPLE 267

4-(4-Trifluoromethoxybenzenesulfonyloxy)-7-[1H-5-(piperidinomethyl)indol-2-yl]isoindolinone (Compound 267)

Step 1

In a similar manner to Step 1 of Example 233, 4-hydroxy-7-[1-(tert-butoxycarbonyl)-5-(piperidinomethyl)indol-2-yl]isoindolinone (0.0297 g, 0.0643 mmol) was dissolved in acetonitrile (0.650 mL), and the solution was treated with triethylamine (0.0540 mL, 0.386 mmol) and (4-trifluoromethoxy)benzenesulfonyl chloride (0.0330 mL, 0.193 mmol) to obtain 4-(4-trifluoromethoxybenzenesulfonyloxy)-7-[(1-(tert-butoxycarbonyl)-5-(piperidinomethyl)indol-2-yl]isoindolinone (0.0225 g, yield 51%).

ESI-MS m/z: 686 [M+H]$^+$

Step 2

In a similar manner to Step 2 of Example 233, 4-(4-trifluoromethoxybenzenesulfonyloxy)-7-[1-(tert-butoxycarbonyl)-5-(piperidinomethyl)indol-2-yl]isoindolinone (0.0225 g, 0.0328 mmol) was treated with 10% hydrogen chloride-methanol solution (0.650 mL) to obtain Compound 267 (0.00691 g, yield 36%).

ESI-MS m/z: 586 [M+H]$^+$

EXAMPLE 268

4-(4-tert-Butylbenzenesulfonyloxy)-7-[1H-5-(piperidinomethyl)indol-2-yl]isoindolinone (Compound 268)

Step 1

In a similar manner to Step 1 of Example 233, 4-hydroxy-7-[1-(tert-butoxycarbonyl)-5-(piperidinomethyl)indol-2-yl]isoindolinone (0.0294 g, 0.0637 mmol) was dissolved in acetonitrile (0.650 mL), and the solution was treated with triethylamine (0.0530 mL, 0.382 mmol) and 4-tert-butylbenzenesulfonyl chloride (0.0440 g, 0.191 mmol) to obtain 4-(4-tert-butylbenzenesulfonyloxy)-7-[1-(tert-butoxycarbonyl)-5-(piperidinomethyl)indol-2-yl]isoindolinone (0.0180 g, yield 43%).

ESI-MS m/z: 658 [M+H]$^+$

Step 2

In a similar manner to Step 2 of Example 233, 4-(4-tert-butylbenzenesulfonyloxy)-7-[1-(tert-butoxycarbonyl)-5-(piperidinomethyl)indol-2-yl]isoindolinone (0.0180 g, 0.0274 mmol) was treated with 10% hydrogen chloride-methanol solution (0.650 mL) to obtain Compound 268 (0.00657 g, yield 43%).

ESI-MS m/z: 558 [M+H]$^+$

EXAMPLE 269

4-hydroxy-7-[1-(tert-butoxycarbonyl)-5-(piperidinomethyl)indol-2-yl]isoindolinone (Compound 269)

Step 1

In a similar manner to Step 1 of Example 233, 4-hydroxy-7-[1-(tert-butoxycarbonyl)-5-(piperidinomethyl)indol-2-yl]isoindolinone (0.0297 g, 0.0643 mmol) was dissolved in acetonitrile (0.650 mL), and the solution was treated with triethylamine (0.0540 mL, 0.386 mmol) and 8-quinolinesulfonyl chloride (0.0440 g, 0.193 mmol) to obtain 4-(8-quinolinesulfonyloxy)-7-[1-(tert-butoxycarbonyl)-5-(piperidinomethyl)indol-2-yl]isoindolinone (0.0164 g, yield 39%).

ESI-MS m/z: 653 [M+H]$^+$

Step 2

In a similar manner to Step 2 of Example 233, 4-(8-quinolinesulfonyloxy)-7-[1-(tert-butoxycarbonyl)-5-(piperidinomethyl)indol-2-yl]isoindolinone (0.0164 g, 0.0251 mmol) was treated with 10% hydrogen chloride-methanol solution (0.650 mL) to obtain Compound 269 (0.00555 g. yield 40%).

ESI-MS m/z: 553 [M+H]$^+$

EXAMPLE 270

4-(3-Trifluoromethylbenzenesulfonyloxy)-7-[1H-5-(piperidinomethyl)indol-2-yl]isoindolinone (Compound 270)

Step 1

In a similar manner to Step 1 of Example 233, 4-hydroxy-7-[1-(tert-butoxycarbonyl)-5-(piperidinomethyl)indol-2-yl]isoindolinone (0.0298 g, 0.0646 mmol) was dissolved in acetonitrile (0.650 mL), and the solution was treated with triethylamine (0.0540 mL, 0.388 mmol) and 3-trifluoromethylbenzenesulfonyl chloride (0.0310 mL, 0.194 mmol) to obtain 4-(3-trifluoromethylbenzenesulfonyloxy)-7-[1-(tert-butoxycarbonyl)-5-(piperidinomethyl)indol-2-yl]isoindolinone (0.0251 g, yield 58%).

ESI-MS m/z: 670 [M+H]$^+$

Step 2

In a similar manner to Step 2 of Example 233, 4-(3-trifluoromethylbenzenesulfonyloxy)-7-[(1-(tert-butoxycarbonyl)-5-(piperidinomethyl)indol-2-yl]isoindolinone (0.0251 g, 0.0375 mmol) was treated with 10% hydrogen chloride-methanol solution (0.650 mL) to obtain Compound 270 (0.00812 g, yield 38%).

ESI-MS m/z: 570 [M+H]$^+$

EXAMPLE 271

4-(1-Naphthalenesulfonyloxy)-7-[1H-5-(piperidinomethyl)indol-2-yl]isoindolinone (Compound 271)

Step 1

In a similar manner to Step 1 of Example 233, 4-hydroxy-7-[1-(tert-butoxycarbonyl)-5-(piperidinomethyl)indol-2-yl]isoindolinone (0.0358 g, 0.0776 mmol) was dissolved in acetonitrile (0.650 mL), and the solution was treated with triethylamine (0.0650 mL, 0.465 mmol) and 1-naphthalenesulfonyl chloride (0.0530 g, 0.233 mmol) to obtain 4-(1-naphthalenesulfonyloxy)-7-[1-(tert-butoxycarbonyl)-5-(piperidinomethyl)indol-2-yl]isoindolinone (0.0309 g, yield 61%).

ESI-MS m/z: 652 [M+H]$^+$

Step 2

In a similar manner to Step 2 of Example 233, 4-(1-naphthalenesulfonyloxy)-7-[1-(tert-butoxycarbonyl)-5-(piperidinomethyl)indol-2-yl]isoindolinone (0.0309 g, 0.0473 mmol) was treated with 10% hydrogen chloride-methanol solution (0.650 mL) to obtain Compound 271 (0.00731 g, yield 28%).

ESI-MS m/z: 552 [M+H]$^+$

EXAMPLE 272

4-Isopropanesulfonyloxy-7-[1H-5-(piperidinomethyl)indol-2-yl]isoindolinone (Compound 272)

Step 1

In a similar manner to Step 1 of Example 233, 4-hydroxy-7-[1-(tert-butoxycarbonyl)-5-(piperidinomethyl)indol-2-yl]isoindolinone (0.0303 g, 0.0656 mmol) was dissolved in acetonitrile (0.650 mL), and the solution was treated with triethylamine (0.0550 mL, 0.394 mmol) and isopropanesulfonyl chloride (0.0220 mL, 0.197 mmol) to obtain 4-isopropanesulfonyloxy-7-[1-(tert-butoxycarbonyl)-5-(piperidinomethyl)indol-2-yl]isoindolinone (0.0145 g, yield 39%).

ESI-MS m/z: 568 [M+H]$^+$

Step 2

In a similar manner to Step 2 of Example 233, 4-isopropanesulfonyloxy-7-[1-(tert-butoxycarbonyl)-5-(piperidinomethyl)indol-2-yl]isoindolinone (0.0145 g, 0.0256 mmol) was treated with 10% hydrogen chloride-methanol solution (0.650 mL) to obtain Compound 272 (0.00730 g, yield 61%).

ESI-MS m/z: 468 [M+H]$^+$

EXAMPLE 273

4-(4-Bromobenzenesulfonyloxy)-7-[1H-5-(piperidinomethyl)indol-2-yl]isoindolinone (Compound 273)

Step 1

In a similar manner to Step 1 of Example 233, 4-hydroxy-7-[1-(tert-butoxycarbonyl)-5-(piperidinomethyl)indol-2-yl]isoindolinone (0.0332 g, 0.0719 mmol) was dissolved in acetonitrile (0.650 mL), and the solution was treated with triethylamine (0.0600 mL, 0.432 mmol) and 4-bromobenzenesulfonyl, chloride (0.0550 g, 0.216 mmol) to obtain 4-(4-bromobenzenesulfonyloxy)-7-[1-(tert-butoxycarbonyl)-5-(piperidinomethyl)indol-2-yl]isoindolinone (0.0240 g, yield 49%).

ESI-MS m/z: 681 [M+H]$^+$

Step 2

In a similar manner to Step 2 of Example 233, 4-(4-bromobenzenesulfonyloxy)-7-[1-(tert-butoxycarbonyl)-5-(piperidinomethyl)indol-2-yl]isoindolinone (0.0240 g, 0.0352 mmol) was treated with 10% hydrogen chloride-methanol solution (0.650 mL) to obtain Compound 273 (0.0840 g, yield 41%).

ESI-MS m/z: 581 [M+H]$^+$

EXAMPLE 274

4-[(2-Chlorophenyl)methanesulfonyloxy]-7-[1H-5-(piperidinomethyl)indol-2-yl]isoindolinone (Compound 274)

Step 1

In a similar manner to Step 1 of Example 233, 4-hydroxy-7-[1-(tert-butoxycarbonyl)-5-(piperidinomethyl)indol-2-yl]isoindolinone (0.0313 g, 0.0678 mmol) was dissolved in acetonitrile (0.650 mL), and the solution was treated with triethylamine (0.0570 mL, 0.407 mmol) and (2-chlorophenyl)methanesulfonyl chloride (0.0460 g, 0.203 mmol) to obtain 4-[(2-chlorophenyl)methanesulfonyloxy]-7-[1-(tert-butoxycarbonyl)-5-(piperidinomethyl)indol-2-yl]isoindolinone (0.0166 g, yield 29%).

ESI-MS m/z: 651 [M+H]$^+$

Step 2

In a similar manner to Step 2 of Example 233, 4-[(2-chlorophenyl)methanesulfonyloxy]-7-[1-(tert-butoxycarbonyl)-5-(piperidinomethyl)indol-2-yl]isoindolinone (0.0166 g, 0.0256 mmol) was treated with 10% hydrogen chloride-methanol solution (0.650 mL) to obtain Compound 274 (0.00828 g, yield 61%).

ESI-MS m/z: 551 [M+H]$^+$

EXAMPLE 275

4-(2-Methoxy-4-methylbenzenesulfonyloxy)-7-[1H-5-(piperidinomethyl)indol-2-yl]isoindolinone (Compound 275)

Step 1

In a similar manner to Step 1 of Example 233, 4-hydroxy-7-[1-(tert-butoxycarbonyl)-5-(piperidinomethyl)indol-2-yl]isoindolinone (0.0324 g, 0.0702 mmol) was dissolved in acetonitrile (0.650 mL), and the solution was treated with triethylamine (0.0590 mL, 0.421 mmol) and 2-methoxy-4-methylbenzenesulfonyl chloride (0.0460 g, 0.211 mmol) to obtain 4-(2-methoxy-4-methylbenzenesulfonyloxy)-7-[1-(tert-butoxycarbonyl)-5-(piperidinomethyl)indol-2-yl]isoindolinone (0.0227 g, yield 50%).

ESI-MS m/z: 646 [M+H]$^+$

Step 2

In a similar manner to Step 2 of Example 233, 4-(2-methoxy-4-methylbenzenesulfonyloxy)-7-[1-(tert-butoxycarbonyl)-5-(piperidinomethyl)indol-2-yl]isoindolinone (0.0227 g, 0.0351 mmol) was treated with 10% hydrogen chloride-methanol solution (0.650 mL) to obtain Compound 275 (0.00919 g, yield 48%).

ESI-MS m/z: 546 [M+H]$^+$

EXAMPLE 276

4-hydroxy-7-[1-(tert-butoxycarbonyl)-5-(piperidinomethyl)indol-2-yl]isoindolinone (Compound 276)

Step 1

In a similar manner to Step 1 of Example 233, 4-hydroxy-7-[1-(tert-butoxycarbonyl)-5-(piperidinomethyl)indol-2-yl]isoindolinone (0.0269 g, 0.0583 mmol) was dissolved in acetonitrile (0.650 mL), and the solution was treated with triethylamine (0.0490 mL, 0.350 mmol) and trans-β-styrenesulfonyl chloride (0.0350 g, 0.175 mmol) to obtain 4-(trans-β-styrenesulfonyloxy)-7-[1-(tert-butoxycarbonyl)-5-(piperidinomethyl)indol-2-yl]isoindolinone (0.0770 g, yield 21%).

ESI-MS m/z: 628 [M+H]$^+$

Step 2

In a similar manner to Step 2 of Example 233, 4-(trans-β-styrenesulfonyloxy)-7-[1-(tert-butoxycarbonyl)-5-(piperidinomethyl)indol-2-yl]isoindolinone (0.0770 g, 0.0122 mmol) was treated with 10% hydrogen chloride-methanol solution (0.650 mL) to obtain Compound 276 (0.00320 g, yield 49%).

ESI-MS m/z: 528 [M+H]$^+$

EXAMPLE 277

4-(3,4-Dihydro-4-methyl-1,4-benzoxazin-7-ylsulfonyloxy)-7-[1H-5-(piperidinomethyl)indol-2-yl]isoindolinone (Compound 277)

Step 1

In a similar manner to Step 1 of Example 233, 4-hydroxy-7-[1-(tert-butoxycarbonyl)-5-(piperidinomethyl)indol-2-yl]isoindolinone (0.0324 g, 0.0702 mmol) was dissolved in acetonitrile (0.650 mL), and the solution was treated with triethylamine (0.0590 mL, 0.421 mmol) and 3,4-dihydro-4-methyl-1,4-benzoxazine-7-sulfonyl chloride (0.0520 g, 0.211 mmol) to obtain 4-(3,4-dihydro-4-methyl-1,4-benzoxazin-7-ylsulfonyloxy)-7-[1-(tert-butoxycarbonyl)-5-(piperidinomethyl)indol-2-yl]isoindolinone (0.0274 g, yield 58%).

ESI-MS m/z: 673 [M+H]$^+$

Step 2

In a similar manner to Step 2 of Example 233, 4-(3,4-dihydro-4-methyl-1,4-benzoxazin-7-ylsulfonyloxy)-7-[1-(tert-butoxycarbonyl)-5-(piperidinomethyl)indol-2-yl]isoindolinone (0.0274 g, 0.0407 mmol) was treated with 10% hydrogen chloride-methanol solution (0.650 mL) to obtain Compound 277 (0.0140 g, yield 60%).

ESI-MS m/z: 573 [M+H]$^+$

EXAMPLE 278

4-(1,2-Dimethylimidazol-4-ylsulfonyloxy)-7-[1H-5-(piperidinomethyl)indol-2-yl]isoindolinone (Compound 278)

Step 1

In a similar manner to Step 1 of Example 233, 4-hydroxy-7-[1-(tert-butoxycarbonyl)-5-(piperidinomethyl)indol-2-yl]isoindolinone (0.0316 g, 0.0685 mmol) was dissolved in acetonitrile (0.650 mL), and the solution was treated with triethylamine (0.0570 mL, 0.411 mmol) and 1,2-dimethylimidazole-4-sulfonyl chloride (0.0400 mL, 0.205 mmol) to obtain 4-(1,2-dimethylimidazol-4-ylsulfonyloxy)-7-[1-(tert-butoxycarbonyl)-5-(piperidinomethyl)indol-2-yl]isoindolinone (0.0217 g, yield 51%).

ESI-MS m/z: 620 [M+H]$^+$

Step 2

In a similar manner to Step 1 of Example 233, 4-(1,2-dimethylimidazol-4-ylsulfonyloxy)-7-[1-(tert-butoxycarbonyl)-5-(piperidinomethyl)indol-2-yl]isoindolinone (0.02147 g, 0.0349 mmol) was treated with 10% hydrogen chloride-methanol solution (0.650 mL) to obtain Compound 278 (0.00710 g, yield 39%).

ESI-MS m/z: 520 [M+H]$^+$

EXAMPLE 279

4-(4-Ethylbenzenesulfonyloxy)-7-[1H-5-(piperidinomethyl)indol-2-yl]isoindolinone (Compound 279)

Step 1

In a similar manner to Step 1 of Example 233, 4-hydroxy-7-[1-(tert-butoxycarbonyl)-5-(piperidinomethyl)indol-2-yl]isoindolinone (0.0322 g, 0.0698 mmol) was dissolved in acetonitrile (0.650 mL), and the solution was treated with triethylamine (0.0580 mL, 0.419 mmol) and 4-ethylbenzene-1-sulfonyl chloride (0.0430 g, 0.209 mmol) to obtain 4-(4-ethylbenzenesulfonyloxy)-7-[1-(tert-butoxycarbonyl)-5-(piperidinomethyl)indol-2-yl]isoindolinone (0.0224 g, yield 51%).

ESI-MS m/z: 630 [M+H]$^+$

Step 2

In a similar manner to Step 2 of Example 233, 4-(4-ethylbenzenesulfonyloxy)-7-[1-(tert-butoxycarbonyl)-5-(piperidinomethyl)indol-2-yl]isoindolinone (0.0224 g, 0.0356 mmol) was treated with 10% hydrogen chloride-methanol solution (0.650 mL) to obtain Compound 279 (0.00720 g, yield 38%).

ESI-MS m/z: 530 [M+H]$^+$

EXAMPLE 280

4-(2,4-Dichlorobenzenesulfonyloxy)-7-[1H-5-(piperidinomethyl)indol-2-yl]isoindolinone (Compound 280)

Step 1

In a similar manner to Step 1 of Example 233, 4-hydroxy-7-[1-(tert-butoxycarbonyl)-5-(piperidinomethyl)indol-2-yl]isoindolinone (0.0291 g, 0.0630 mmol) was dissolved in acetonitrile (0.650 mL), and the solution was treated with triethylamine (0.0530 mL, 0.378 mmol) and 2,4-dichlorobenzenesulfonyl chloride (0.0436 g, 0.189 mmol) to obtain 4-(2,4-dichlorobenzenesulfonyloxy)-7-[1-(tert-butoxycarbonyl)-5-(piperidinomethyl)indol-2-yl]isoindolinone (0.0232 g. yield 55%).

ESI-MS m/z: 671 [M+H]$^+$

Step 2

In a similar manner to Step 2 of Example 233, 4-(2,4-dichlorobenzenesulfonyloxy)-7-[1-(tert-butoxycarbonyl)-5-(piperidinomethyl)indol-2-yl]isoindolinone (0.0232 g, 0.0347 mmol) was treated with 10% hydrogen chloride-methanol solution (0.650 mL) to obtain Compound 280 (0.00851 g, yield 43%).

ESI-MS m/z: 571 [M+H]$^+$

EXAMPLE 281

4-(3-Chloro-n-propanesulfonyloxy)-7-[1H-(piperidinomethyl)indol-2-yl]isoindolinone (Compound 281)

Step 1

In a similar manner to Step 1 of Example 233, 4-hydroxy-7-[1-(tert-butoxycarbonyl)-5-(piperidinomethyl)indol-2-yl]isoindolinone (0.0316 g, 0.0685 mmol) was dissolved in acetonitrile (0.650 mL), and the solution was treated with triethylamine (0.0570 mL, 0.411 mmol) and 3-chloropropanesulfonyl chloride (0.0250 mL, 0.205 mmol) to obtain 4-(3-chloro-n-propanesulfonyloxy)-7-[1-(tert-butoxycarbonyl)-5-(piperidinomethyl)indol-2-yl]isoindolinone (0.0101 g, yield 24%).

ESI-MS m/z: 617 [M+H]$^+$

Step 2

In a similar manner to Step 2 of Example 233, 4-(3-chloro-n-propanesulfonyloxy)-7-[1-(tert-butoxycarbonyl)-5-(piperidinomethyl)indol-2-yl]isoindolinone (0.0101 g, 0.0164 mmol) was treated with 10% hydrogen chloride-methanol solution (0.650 mL) to obtain Compound 281 (0.00400 g, yield 47%).

ESI-MS m/z: 517 [M+H]$^+$

EXAMPLE 282

4-(2-Cyanobenzenesulfonyloxy)-7-[1H-5-(piperidinomethyl)indol-2-yl]isoindolinone hydrochloride (Compound 282)

Step 1

In a similar manner to Step 1 of Example 227, 4-hydroxy-7-[1-(tert-butoxycarbonyl)-5-(piperidinomethyl)indol-2-yl]isoindolinone (0.115 g, 0.249 mmol) was dissolved in acetonitrile (5.0 mL), and the solution was treated with triethylamine (0.104 mL, 0.747 mmol) and 2-cyanobenzenesulfonyl chloride (0.0750 g, 0.374 mmol) to obtain 4-(2-cyanobenzenesulfonyloxy)-7-[1-(tert-butoxycarbonyl)-5-(piperidinomethyl)indol-2-yl]isoindolinone (0.137 g, yield 88%).

ESI-MS m/z: 627 [M+H]$^+$; $^1$H-NMR (CDCl$_3$) δ(ppm): 1.28 (s, 9H), 1.38-1.53 (m, 2H), 1.63-1.76 (m, 4H), 2.56-2.70 (m, 4H), 3.85 (s, 2H), 4.55 (s, 2H), 6.53 (s, 1H), 7.29 (dd, J=1.8, 8.6 Hz, 1H), 7.37-7.48 (m, 2H), 7.54 (s, 1H), 7.85-7.90 (m, 2H), 8.01-8.05 (m, 1H), 8.17-8.23 (m, 2H).

Step 2

In a similar manner to Step 2 of Example 8, 4-(2-cyanobenzenesulfonyloxy)-7-[1-(tert-butoxycarbonyl)-5-(piperidinomethyl)indol-2-yl]isoindolinone (0.136 g, 0.217 mmol) was treated with 10% hydrogen chloride-methanol solution (5.0 mL) to obtain Compound 282 (0.0885 g, yield 73%).

ESI-MS m/z: 527 [M+H]$^+$; $^1$H-NMR (DMSO-d$_6$) δ(ppm): 1.28-1.44 (m, 1H), 1.59-1.87 (m, 5H), 2.78-2.95 (m, 2H), 3.32-3.68 (m, 2H), 4.31 (d, J=4.8 Hz, 2H), 4.43 (s, 2H), 7.28-7.39 (m, 3H), 7.57 (d, J=8.4 Hz, 1H), 7.77 (s, 1H), 8.01-8.14 (m, 2H), 8.24 (dd, J=1.6, 8.1 Hz, 2H), 8.36 (dd, J=1.2, 7.2 Hz, 1H), 9.51 (s, 1H), 9.77 (br s, 1H), 13.8 (s, 1H).

EXAMPLE 283

4-(2-Methoxy-5-methylbenzenesulfonyloxy)-7-[1H-5-(piperidinomethyl)indol-2-yl]isoindolinone hydrochloride (Compound 283)

Step 1

In a similar manner to Step 1 of Example 227, 4-hydroxy-7-[1-(tert-butoxycarbonyl)-5-(piperidinomethyl)indol-2-yl]isoindolinone (0.136 g, 0.295 mmol) was dissolved in acetonitrile (6.0 mL), and the solution was treated with triethylamine (0.0820 mL, 0.590 mmol) and 6-methoxy-m-toluenesulfonyl chloride (0.0980 g, 0.443 mmol) to obtain 4-(2-methoxy-5-methylbenzenesulfonyloxy)-7-[1-(tert-butoxycarbonyl)-5-(piperidinomethyl)indol-2-yl]isoindolinone (0.131 g, yield 69%).

ESI-MS m/z: 646 [M+H]$^+$; $^1$H-NMR (CDCl$_3$) δ(ppm): 1.22 (s, 9H), 1.38-1.49 (m, 2H), 1.56-1.67 (m, 4H), 2.32 (s, 3H), 2.43-2.53 (m, 4H), 3.66 (s, 2H), 4.00 (s, 3H), 4.42 (s, 2H), 6.51 (s, 1H), 7.03 (d, J=8.6 Hz, 1H), 7.24-7.33 (m, 2H), 7.37 (d, J=8.1 Hz, 1H), 7.46 (dd, J=2.0, 8.6 Hz, 1H), 7.51 (s, 1H), 7.65 (d, J=2.0 Hz, 1H), 7.84 (br s, 1H), 8.21 (d, J=8.6 Hz, 1H).

Step 2

In a similar manner to Step 2 of Example 8, 4-(2-methoxy-5-methylbenzenesulfonyloxy)-7-[1-(tert-butoxycarbonyl)-5-(piperidinomethyl)indol-2-yl]isoindolinone (0.131 g, 0.203 mmol) was treated with 10% hydrogen chloride-methanol solution (5.0 mL) to obtain Compound 283 (0.0687 g, yield 58%).

ESI-MS m/z: 546 [M+H]$^+$; $^1$H-NMR (DMSO-d$_6$) δ(ppm): 1.27-1.45 (m, 1H), 1.63-1.85 (m, 5H), 2.30 (s, 3H), 2.75-2.93 (m, 2H), 3.26-3.37 (m, 2H), 3.96 (s, 3H), 4.32 (d, J=4.8 Hz, 2H), 4.43 (s, 2H), 7.29-7.38 (m, 4H), 7.56 (d, J=8.4 Hz, 1H), 7.62-7.68 (m, 2H), 7.78 (s, 1H), 8.22 (d, J=8.7 Hz, 1H), 9.46 (s, 1H), 9.99 (br s, 1H), 13.8 (s, 1H).

EXAMPLE 284

4-Dimethylcarbamoyloxy-7-[1H-5-(piperidinomethyl)indol-2-yl]isoindolinone hydrochloride (Compound 284)

Step 1

In a similar manner to Step 1 of Example 227, 4-hydroxy-7-[1-(tert-butoxycarbonyl)-5-(piperidinomethyl)indol-2-yl]isoindolinone (0.0806 g, 0.175 mmol) was dissolved in dichloromethane (2.0 mL), and the solution was treated with 4-dimethylaminopyridine (0.0850 g, 0.699 mmol) and dimethylcarbamoyl chloride (0.0640 mL, 0.699 mmol) to obtain 4-dimethylcarbamoyloxy-7-[1-(tert-butoxycarbonyl)-5-(piperidinomethyl)indol-2-yl]isoindolinone (0.0930 g, yield 99%).

ESI-MS m/z: 533 [M+H]$^+$; $^1$H-NMR (CDCl$_3$) δ(ppm): 1.27 (s, 9H), 1.39-1.48 (m, 2H), 1.53-1.63 (m, 4H), 2.34-2.48 (m, 4H), 3.04 (s, 3H), 3.14 (s, 3H), 3.58 (s, 2H), 4.38 (s, 2H), 6.53 (s, 1H), 7.29 (dd, J=1.5, 8.6 Hz, 1H), 7.35 (d. J=8.1 Hz, 1H), 7.43 (d, J=8.1 Hz, 1H), 7.48 (d, J=1.5 Hz, 1H), 7.98 (s, 1H), 8.20 (d, J=8.6 Hz, 1H).

Step 2

In a similar manner to Step 2 of Example 8, 4-dimethylcarbamoyloxy-7-[1-(tert-butoxycarbonyl)-5-(piperidinomethyl)indol-2-yl]isoindolinone (0.103 g, 0.240 mmol) was treated with 10% hydrogen chloride-methanol solution (5.0 mL) to obtain Compound 284 (0.0607 g, yield 67%).

ESI-MS m/z: 433 [M+H]$^+$; $^1$H-NMR (DMSO-d$_6$) δ(ppm): 1.28-1.41 (m, 1H), 1.63-1.85 (m, 5H), 2.77-2.91 (m, 2H), 2.94 (s, 3H), 3.09 (s, 3H), 3.33-3.46 (m, 2H), 4.30 (s, 2H), 4.44 (s, 2H), 7.26 (s, 1H), 7.29 (dd, J=1.5, 8.6 Hz, 1H), 7.51 (d, J=8.6 Hz, 1H), 7.55 (d, J=8.6 Hz, 1H), 7.75 (s, 1H), 8.22 (d, J=8.6 Hz, 1H), 9.42 (s, 1H), 9.70 (br s, 1H), 13.9 (br s, 1H).

EXAMPLE 285

4-(3,4-Dimethoxybenzenesulfonyloxy)-7-[1H-5-(piperidinomethyl)indol-2-yl]isoindolinone (Compound 285)

Step 1

In a similar manner to Step 1 of Example 227, 4-hydroxy-7-[1-(tert-butoxycarbonyl)-5-(piperidinomethyl)indol-2-yl]isoindolinone (0.0315 g, 0.0682 mmol) was dissolved in acetonitrile (0.650 mL), and the solution was treated with triethylamine (0.0570 mL, 0.409 mmol) and 3,4-dimethoxybenzenesulfonyl chloride (0.0480 g, 0.205 mmol) to obtain 4-(3,4-dimethoxybenzenesulfonyloxy)-7-[1-(tert-butoxycarbonyl)-5-(piperidinomethyl)indol-2-yl]isoindolinone (0.0208 g, yield 46%).

ESI-MS m/z: 662 [M+H]$^+$

Step 2

In a similar manner to Step 2 of Example 8, 4-(3,4-dimethoxybenzenesulfonyloxy)-7-[1-(tert-butoxycarbonyl)-5-(piperidinomethyl)indol-2-yl]isoindolinone (0.0208 g, 0.0314 mmol) was treated with 10% hydrogen chloride-methanol solution (0.650 mL) to obtain Compound 285 (0.00780 g, yield 44%).

ESI-MS m/z: 562 [M+H]$^+$

EXAMPLE 286

4-(2,5-Dimethyl-3-thiophenesulfonyloxy)-7-[H1-5-(piperidinomethyl)indol-2-yl]isoindolinone (Compound 286)

Step 1

In a similar manner to Step 1 of Example 233, 4-hydroxy-7-[1-(tert-butoxycarbonyl)-5-(piperidinomethyl)indol-2-yl]isoindolinone (0.0327 g, 0.0708 mmol) was dissolved in acetonitrile (0.650 mL), and the solution was treated with triethylamine (0.0590 mL, 0.425 mmol) and 2,5-dimethyl-3-thiophenesulfonyl chloride (0.0450 g, 0.213 mmol) to obtain 4-(2,5-dimethyl-3-thiophenesulfonyloxy)-7-[(1-(tert-butoxycarbonyl)-5-(piperidinomethyl)indol-2-yl]isoindolinone (0.0261 g, yield 58%).

ESI-MS m/z: 636 [M+H]$^+$

Step 2

In a similar manner to Step 2 of Example 233, 4-(2,5-dimethyl-3-thiophenesulfonyloxy)-7-[1-(tert-butoxycarbonyl)-5-(piperidinomethyl)indol-2-yl]isoindolinone (0.0261 g, 0.0411 mmol) was treated with 10% hydrogen chloride-methanol solution (0.650 mL) to obtain Compound 286 (0.00790 g, yield 36%).

ESI-MS m/z: 536 [M+H]$^+$

EXAMPLE 287

4-Chloromethanesulfonyloxy-7-[1H-5-(piperidinomethyl)indol-2-yl]isoindolinone hydrochloride (Compound 287)

Step 1

In a similar manner to Step 1 of Example 227, 4-hydroxy-7-[1-(tert-butoxycarbonyl)-5-(piperidinomethyl)indol-2-yl]isoindolinone (0.0853 g, 0.185 mmol) was dissolved in dichloromethane (3.0 mL), and the solution was treated with triethylamine (0.129 mL, 0.924 mmol) and chloromethanesulfonyl chloride (0.0490 mL, 0.554 mmol) to obtain 4-chloromethanesulfonyloxy-7-[1-(tert-butoxycarbonyl)-5-(piperidinomethyl)indol-2-yl]isoindolinone (0.0376 g, yield 35%).

ESI-MS m/z: 574 [M+H]$^+$; $^1$H-NMR (CDCl$_3$) δ(ppm): 1.30 (s, 9H), 1.39-1.48 (m, 2H), 1.54-1.66 (m, 4H), 2.36-2.53 (m, 4H), 3.60 (s, 2H), 4.56 (s, 2H), 4.83 (s, 2H), 6.56 (s, 1H), 7.32 (dd, J=1.5, 8.8 Hz, 1H), 7.48-7.59 (m, 3H), 7.71-7.91 (br s, 1H), 8.19 (d, J=8.8 Hz, 1H).

Step 2

In a similar manner to Step 2 of Example 8, 4-chloromethanesulfonyloxy-7-[1-(tert-butoxycarbonyl)-5-(piperidinomethyl)indol-2-yl]isoindolinone (0.0990 g, 0.172 mmol) was treated with 10% hydrogen chloride-methanol solution (5.0 mL) to obtain Compound 287 (0.0530 g, yield 65%).

ESI-MS m/z: 474 [M+H]$^+$; $^1$H-NMR (DMSO-d$_6$) δ(ppm): 1.28-1.44 (m, 1H), 1.59-1.87 (m, 5H), 2.78-2.95 (m, 2H), 3.32-3.68 (m, 2H), 3.59 (s, 2H), 4.64 (s, 2H), 4.83 (s, 2H), 6.66 (s, 1H), 7.30 (s, 1H), 7.33 (d, J=8.4 Hz, 1H), 7.56 (d, J=8.4 Hz, 1H), 7.62 (d, J=8.7 Hz, 1H), 7.74-7.86 (m, 1H), 8.28 (d, J=8.7 Hz, 1H), 9.53 (s, 1H), 13.8 (s, 1H).

EXAMPLE 288

4-Cyclohexylmethanesulfonyloxy-7-[1H-5-(piperidinomethyl)indol-2-yl]isoindolinone hydrochloride (Compound 288)

Step 1

In a similar manner to Step 1 of Example 227, 4-hydroxy-7-[1-(tert-butoxycarbonyl)-5-(piperidinomethyl)indol-2-yl]isoindolinone (0.0843 g, 0.183 mmol) was dissolved in dichloromethane (3.0 mL), and the solution was treated with triethylamine (0.127 mL, 0.913 mmol) and cyclohexylmethanesulfonyl chloride (0.108 g, 0.548 mmol) to obtain 4-cyclohexylmethanesulfonyloxy-7-[1-(tert-butoxycarbonyl)-5-(piperidinomethyl)indol-2-yl]isoindolinone (0.0914 g, yield 80%).

ESI-MS m/z: 622 [M+H]$^+$; $^1$H-NMR (CDCl$_3$) δ(ppm): 1.28 (s, 9H), 1.13-1.56 (m, 5H), 1.68-1.84 (m, 6H), 1.98-2.09 (m, 2H), 2.11-2.24 (m, 1H), 2.64-2.83 (m, 4H), 3.30 (d, J=6.6 Hz, 2H), 3.99 (s, 2H), 4.58 (s, 2H), 6.55 (s, 1H), 7.29 (d, J=1.8 Hz, 1H), 7.47-7.50 (m, 2H), 7.56 (d, J=1.8 Hz, 1H), 8.23 (d, J=8.4 Hz, 1H).

Step 2

In a similar manner to Step 2 of Example 8, 4-cyclohexylmethanesulfonyloxy-7-[1-(tert-butoxycarbonyl)-5-(piperidinomethyl)indol-2-yl]isoindolinone (0.0914 g, 0.147 mmol) was treated with 10% hydrogen chloride-methanol solution (5.0 mL) to obtain Compound 288 (0.0446 g, yield 52%).

ESI-MS m/z: 522 [M+H]$^+$; $^1$H-NMR (DMSO-d$_6$) δ(ppm): 1.07-1.42 (m, 6H), 1.53-2.07 (m, 1H), 2.73-2.95 (m, 2H), 3.32-3.68 (m, 2H), 3.65 (d, J=6.3 Hz, 2H), 4.32 (s, 2H), 4.56 (s, 2H), 7.27 (d, J=8.1 Hz, 1H), 7.32 (s, 1H), 7.57 (d, J=8.1 Hz, 1H), 7.65 (d, J=8.9 Hz, 1H), 7.75 (s, 1H), 8.29 (d, J=8.9 Hz, 1H), 9.48 (br s, 1H), 9.52 (s, 1H), 13.8 (s, 1H).

EXAMPLE 289

4-Methanesulfonyloxy-7-{1H-5-[4-(2-hydroxyethyl)pyperazin-1-ylmethyl]indol-2-yl}isoindolinone dihydrochloride (Compound 289)

Step 1

4-Hydroxy-7-iodoisoindolinone (400 mg, 1.45 mmol) was dissolved in dichloromethane (10 mL), and the solution was added with triethylamine (0.808 mL, 5.80 mmol) and added with methanesulfonyl chloride (0.224 mL, 2.89 mmol) at 0° C., followed by stirring at room temperature for 2 hours. The mixture was added with methanesulfonyl chloride (0.112 mL, 1.45 mmol) at 0° C., followed by stirring at room temperature for 2 hours. The reaction mixture was added with water and hexane. The precipitated solid was collected by filtration, washed with hexane and water and then dried under reduced pressure to obtain 4-methanesulfonyloxy-7-iodoisoindolinone (353 mg, yield 69%).

ESI-MS m/z: 353 [M+H]$^+$; $^1$H-NMR (DMSO-d$_6$) δ(ppm): 3.52 (s, 3H), 4.36 (s, 2H), 7.36 (d, J=8.4 Hz, 1H), 8.01 (d, J=8.4 Hz, 1H), 8.95 (s, 1H).

Step 2

In a similar manner to Step 2 of Example 1, 4-methanesulfonyloxy-7-iodoisoindolinone (54.6 mg, 0.155 mmol) was dissolved in acetonitrile (2 mL), and the solution was treated with Compound BU (160 mg, 0.309 mmol), palladium acetate (2.8 mg, 0.013 mmol) and triethylamine (0.216 mL, 1.55 mmol), followed by purification by preparative thin-layer chromatography (ethyl acetate/methanol=10/1) to obtain 4-methanesulfonyloxy-7-{1-(tert-butoxycarbonyl)-5-[4-(2-hydroxyethyl)pyperazin-1-ylmethyl]indol-2-yl}isoindolinone (65.0 mg, yield 60%).

ESI-MS m/z: 699 [M+H]$^+$; $^1$H-NMR (CDCl$_3$) δ(ppm): 0.05 (s, 6H), 0.88 (s, 9H), 1.31 (s, 9H), 2.44-2.63 (m, 8H), 2.53 (t, J=6.5 Hz, 2H), 3.29 (s, 3H), 3.58 (s, 2H), 3.75 (t, J=6.5 Hz, 2H), 4.55 (s, 2H), 6.55 (s, 1H), 7.03 (s, 1H), 7.18 (d, J=8.1 Hz, 1H), 7.31 (dd, J=1.5, 8.6 Hz, 1H), 7.44 (d, J=8.1 Hz, 1H), 7.50 (d, J=1.5 Hz, 1H), 8.18 (d, J=8.6 Hz, 1H).

Step 3

In a similar manner to Step 2 of Example 8, 4-methanesulfonyloxy-7-{1-(tert-butoxycarbonyl)-5-[4-(2-hydroxyethyl)pyperazin-7-ylmethyl]indol-2-yl}isoindolinone (65 mg, 0.093 mmol) was dissolved in methanol (2 mL), and the solution was treated with 10% hydrogen chloride-methanol solution (2 mL). The obtained solid was collected by filtration and washed with diisopropylether, followed by drying under reduced pressure to obtain Compound 289 (48.6 mg, yield 94%).

ESI-MS m/z: 485 [M+H]$^+$; $^1$H-NMR (DMSO-d$_6$) δ(ppm): 3.00-3.90 (m, 12H), 3.58 (s, 3H), 4.45 (br s, 2H), 4.59 (s, 2H), 7.26-7.39 (m, 2H), 7.58 (m, 1H), 7.69 (d, J=8.6 Hz, 1H), 7.81 (br s, 1H), 8.32 (d, J=8.6 Hz, 1H), 9.55 (s, 1H), 13.88 (s, 1H).

EXAMPLE 290

4-Methanesulfonyloxy-7-[1H-5-(4,4-dimethoxypiperidinomethyl)indol-2-yl]isoindolinone hydrochloride (Compound 290)

Step 1

In a similar manner to Step 2 of Example 1, 4-methanesulfonyloxy-7-iodoisoindolinone (60.0 mg, 0.170 mmol) was suspended in acetonitrile (2 mL) and DMF (1 mL), and the suspension was treated with Compound BT (142 mg, 0.339 mmol), palladium acetate (3.1 mg, 0.014 mmol) and triethylamine (0.237 mL, 1.70 mmol), followed by purification by preparative thin-layer chromatography (ethyl acetate/methanol=20/1) to obtain 4-methanesulfonyloxy-7-[1-(tert-butoxycarbonyl)-5-(4,4-dimethoxy piperidinomethyl)indol-2-yl]isoindolinone (67.1 mg, yield 66%).

ESI-MS m/z: 600[M+H]$^+$; $^1$H-NMR (DMSO-d$_6$) δ(ppm): 1.17 (s, 9H), 1.61-1.70 (m, 4H), 2.32-2.42 (m, 4H), 3.06 (s, 6H), 3.55 (s, 3H), 3.56 (s, 2H), 4.48 (s, 2H), 6.66 (s, 1H), 7.28 (dd, J=1.4, 8.6 Hz, 1H), 7.51 (d, J=1.4 Hz, 1H), 7.57 (d, J=8.2 Hz, 1H), 7.66 (d, J=8.2 Hz, 1H), 8.10 (d, J=8.6 Hz, 1H), 8.84 (s, 1H).

Step 2

In a similar manner to Step 2 of Example 8, 4-methanesulfonyloxy-7-[1-(tert-butoxycarbonyl)-5-(4,4-dimethoxy piperidinomethyl)indol-2-yl]isoindolinone (65.0 mg, 0.108 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 290 (51.7 mg, yield 89%).

ESI-MS m/z: 500 [M+H]$^+$; $^1$H-NMR (DMSO-d$_6$) δ(ppm): 1.77-1.83 (m, 2H), 2.10-2.20 (m, 2H), 2.89-3.16 (m, 2H), 3.11 (s, 6H), 3.26-3.40 (m, 2H), 3.57 (s, 3H), 4.41 (d, J=4.8 Hz, 2H), 4.59 (s, 2H), 7.30 (dd, J=1.1, 8.4 Hz, 1H) 7.35 (d, J=1.1 Hz, 1H), 7.59 (d, J=8.4 Hz, 1H), 7.69 (d, J=8.6 Hz, 1H), 7.78 (s, 1H), 8.32 (d, J=8.6 Hz, 1H), 9.55 (s, 1H), 9.61 (br s, 1H), 13.89 (s, 1H).

EXAMPLE 291

4-Methanesulfonyloxy-7-[1H-5-(4-oxopiperidinomethyl)indol-2-yl]isoindolinone (Compound 291)

Compound 290 (30.0 mg, 0.0560 mmol) was suspended in 10% hydrogen chloride-methanol solution (1 mL) and 1 mol/L hydrochloric acid (1 mL), and the suspension was stirred at 60° C. for 8.5 hours. The reaction mixture was added with water and sodium carbonate, and extracted with ethyl acetate. The organic layer was washed with saturated brine and dried over anhydrous sodium sulfate. The solvent was evaporated under reduced pressure. The residue was purified by preparative thin-layer chromatography (ethyl acetate/methanol=10/1). The obtained solid was suspended in hexane and collected by filtration. The solid was washed with hexane and dried under reduced pressure to obtain Compound 291 (7.7 mg, yield 30%).

ESI-MS m/z: 454 [M+H]$^+$; $^1$H-NMR (CDCl$_3$) δ(ppm): 2.44-2.50 (m, 4H), 2.76-2.84 (m, 4H), 3.31 (s, 3H), 3.72 (s, 2H), 4.66 (s, 2H), 6.50 (br s, 1H), 7.06 (d, J=1.8 Hz, 1H), 7.24 (dd, J=1.8, 8.3 Hz, 1H), 7.48 (d, J=8.3 Hz, 1H), 7.49 (d, J=8.8 Hz, 1H), 7.57 (s, 1H), 8.14 (d, J=8.8 Hz, 1H), 13.28 (s, 1H).

EXAMPLE 292

4-Methanesulfonyloxy-7-{1H-5-[(2-hydroxyethyl)aminomethyl]indol-2-yl}isoindolinone hydrochloride (Compound 292)

Step 1

In a similar manner to Step 2 of Example 1, 4-methanesulfonyloxy-7-iodoisoindolinone (30.0 mg, 0.085 mmol) was suspended in acetonitrile (1 mL) and DMF (0.5 mL), and the suspension was treated with Compound BX (76.2 mg, 0.170 mmol), palladium acetate (1.5 mg, 0.0067 mmol) and triethylamine (0.118 mL, 0.847 mmol), followed by purification by preparative thin-layer chromatography (ethyl acetate/7 mol/L ammonia-methanol solution=20/1) to obtain 4-methanesulfonyloxy-7-(1-(tert-butoxycarbonyl)-5-[(2-hydroxyethyl)aminomethyl]indol-2-yl)isoindolinone (31.5 mg).

Step 2

In a similar manner to Step 2 of Example 8, 4-methanesulfonyloxy-7-{1-(tert-butoxycarbonyl)-5-[(2-hydroxyethyl)aminomethyl]indol-2-yl}isoindolinone (31.0 mg, 0.0492 mmol) was dissolved in methanol (1.5 mL), and the solution was treated with 10% hydrogen chloride-methanol solution (1.5 mL). The mixture was added with diisopropylether. The obtained solid was collected by filtration and washed with diisopropylether, followed by drying under reduced pressure to obtain Compound 292 (9.8 mg, yield 26%, 2 steps).

ESI-MS m/z: 416 [M+H]$^+$; $^1$H-NMR (DMSO-d$_6$) δ(ppm): 2.93-3.02 (m, 2H), 3.57 (s, 3H), 3.63-3.76 (m, 2H), 4.19-4.27 (m, 2H), 4.59 (s, 2H), 5.21 (t, J=4.8 Hz, 1H), 7.29 (dd, J=1.5, 8.4 Hz, 1H), 7.34 (d, J=1.5 Hz, 1H), 7.57 (d, J=8.4 Hz, 1H), 7.69 (t, J=8.8 Hz, 1H), 7.75 (s, 1H), 8.32 (d, J=8.8 Hz, 1H), 8.79 (br s, 2H), 9.55 (s, 1H), 13.87 (s, 1H).

EXAMPLE 293

4-Methanesulfonyloxy-7-[1H-5-[4-(hydroxymethyl) piperidinomethyl]indol-2-yl]isoindolinone hydrochloride (Compound 293)

Step 1

In a similar manner to Step 2 of Example 1, 4-methanesulfonyloxy-7-iodoisoindolinone (88.0 mg, 0.249 mmol) was suspended in acetonitrile (5 mL), and the suspension was treated with Compound BV (250 mg, 0.497 mmol), palladium acetate (4.5 mg, 0.020 mmol), tri(o-tolyl)phosphine (12.1 mg, 0.0398 mmol) and triethylamine (0.347 mL, 2.49 mmol). The mixture was suspended in hexane. The precipitated solid was washed with hexane and dried under reduced pressure to obtain 4-methanesulfonyloxy-7-[1-(tert-butoxycarbonyl)-5-[4-(hydroxymethyl)piperidinomethyl]indol-2-yl]isoindolinone (121 mg, yield 71%).

ESI-MS m/z: 684 [M+H]$^+$; $^1$H-NMR (CDCl$_3$) δ(ppm): 0.03 (s, 6H), 0.88 (s, 9H), 1.17-1.37 (m, 3H), 1.33 (s, 9H), 1.55-1.75 (m, 2H), 1.89-2.03 (m, 2H), 2.88-2.98 (m, 2H), 3.30 (s, 3H), 3.44 (d, J=6.6 Hz, 2H), 3.60 (s, 2H), 4.56 (s, 2H), 6.46 (br s, 1H), 6.55 (s, 1H), 7.30 (dd, J=1.6, 8.3 Hz, 1H), 7.48 (d, J=8.3 Hz, 1H), 7.49 (s, 1H), 7.52 (d, J=8.5 Hz, 1H), 8.17 (d, J=8.5 Hz, 1H).

Step 2

In a similar manner to Step 2 of Example 8, 4-methanesulfonyloxy-7-[1-(tert-butoxycarbonyl)-5-[4-(hydroxymethyl)piperidinomethyl]indol-2-yl]isoindolinone (120 mg, 0.175 mmol) was dissolved in methanol (3 mL), and the solution was treated with 10% hydrogen chloride-methanol solution (3 mL). The mixture was added with diisopropylether. The obtained solid was collected by filtration and washed with diisopropylether, followed by drying under reduced pressure to obtain Compound 293 (66.4 mg, yield 76%).

ESI-MS m/z: 470 [M+H]$^+$; $^1$H-NMR (DMSO-d$_6$) δ(ppm): 1.32-1.89 (m, 5H), 2.85-3.00 (m, 2H), 3.21-3.48 (m, 4H), 3.58 (s, 3H), 4.33 (d, J=4.4 Hz, 2H), 4.59 (s, 2H), 4.64 (t, J=5.0 Hz, 1H), 7.28 (dd, J=1.5, 8.0 Hz, 1H), 7.35 (d, J=1.5 Hz, 1H), 7.59 (d, J=8.0 Hz, 1H), 7.69 (d, J=8.8 Hz, 1H), 7.76 (s, 1H), 8.31 (d, J=8.8 Hz, 1H), 9.43 (br s, 1H), 9.55 (s, 1H), 13.88 (s, 1H).

EXAMPLE 294

4-Methanesulfonyloxy-7-[1H-5-(dimethylaminomethyl)indol-2-yl]isoindolinone hydrochloride (Compound 294)

Step 1

In a similar manner to Step 2 of Example 1, 4-methanesulfonyloxy-7-iodoisoindolinone (544 mg, 1.54 mmol) was suspended in acetonitrile (20 mL), and the suspension was treated with Compound BA (891 mg, 3.08 mmol), palladium acetate (28.0 mg, 0.120 mmol), tri(o-tolyl)phosphine (75.0 mg, 0.250 mmol) and triethylamine (2.10 mL, 15.4 mmol). The mixture was dissolved in methanol, and the solution was added with diisopropylether. The precipitated solid was washed with diisopropylether and dried under reduced pressure to obtain 4-methanesulfonyloxy-7-[1-(tert-butoxycarbonyl)-5-formyl]indolyl isoindolinone (412 mg, yield 57%).

ESI-MS m/z: 471 [M+H]$^+$; $^1$H-NMR (CDCl$_3$) δ(ppm): 1.33 (s, 9H), 3.33 (s, 3H), 4.59 (s, 2H), 6.48 (s, 1H), 6.71 (s, 1H), 7.52 (d, J=8.2 Hz, 1H), 7.56 (d, J=8.2 Hz, 1H), 7.89 (d, J=8.7 Hz, 1H), 8.11 (s, 1H), 8.40 (d, J=8.7 Hz, 1H), 10.07 (s, 1H).

Step 2

In a similar manner to Step 2 of Example 6, 4-methanesulfonyloxy-7-[1-(tert-butoxycarbonyl)-5-formyl]indolylisoindolinone (100 mg, 0.213 mmol) was dissolved in acetonitrile (3 mL), and the solution was treated with dimethylamine hydrochloride (347 mg, 4.26 mmol), triethylamine (0.594 mL, 4.26 mmol), acetic acid (0.211 mL, 4.26 mmol) and sodium triacetoxyborohydride (180 mg, 0.852 mmol) to obtain 4-methanesulfonyloxy-7-[1-(tert-butoxycarbonyl)-5-(dimethylaminomethyl)indol-2-yl]isoindolinone (72.9 mg, yield 69%).

ESI-MS m/z: 500 [M+H]$^+$; $^1$H-NMR (CDCl$_3$) δ(ppm): 1.31 (s, 9H), 2.26 (s, 6H), 3.29 (s, 3H), 3.52 (s, 2H), 4.55 (s, 2H), 6.55 (s, 1H), 7.28 (s, 1H), 7.30 (dd, J=1.5, 8.6 Hz, 1H), 7.48 (d, J=8.3 Hz, 1H), 7.49 (d, J=1.5 Hz, 1H), 7.52 (d, J=8.3 Hz, 1H), 8.19 (d, J=8.6 Hz, 1H).

Step 3

In a similar manner to Step 2 of Example 8, 4-methanesulfonyloxy-7-[1-(tert-butoxycarbonyl)-5-(dimethylaminomethyl)indol-2-yl]isoindolinone (72.5 mg, 0.145 mmol) was dissolved in methanol (3 mL), and the solution was treated with 10% hydrogen chloride-methanol solution (3 mL). The mixture was added with diisopropylether. The obtained solid was collected by filtration and washed with diisopropylether, followed by drying under reduced pressure to obtain Compound 294 (37.6 mg, yield 59%).

ESI-MS m/z: 400 [M+H]$^+$; $^1$H-NMR (DMSO-d$_6$) δ(ppm): 2.72 (s, 6H), 3.56 (s, 3H), 4.32 (d, J=5.0 Hz, 2H), 4.58 (s, 2H), 7.28 (d, J=8.3 Hz, 1H), 7.34 (s, 1H), 7.58 (d, J=8.3 Hz, 1H), 7.68 (d, J=8.6 Hz, 1H), 7.75 (s, 1H), 8.31 (d, J=8.6 Hz, 1H), 9.54 (s, 1H), 10.01 (br s, 1H), 13.88 (s, 1H).

EXAMPLE 295

4-Methanesulfonyloxy-7-[1H-5-(ethylaminomethyl) indol-2-yl]isoindolinone hydrochloride (Compound 295)

Step 1

In a similar manner to Step 2 of Example 6, 4-hydroxy-7-[1-(tert-butoxycarbonyl)-5-formyl]indolylisoindolinone (100 mg, 0.213 mmol) was dissolved in acetonitrile (3 mL), and the solution was treated with 70% aqueous ethylamine solution (0.339 mL, 4.26 mmol), acetic acid (0.211 mL, 4.26 mmol) and sodium triacetoxyborohydride (180 mg, 0.852 mmol) to obtain 4-methanesulfonyloxy-7-[1-(tert-butoxycarbonyl)-5-(ethylaminomethyl)indol-2-yl]isoindolinone (48.5 mg, yield 46%).

ESI-MS m/z: 500 [M+H]$^+$; $^1$H-NMR (CDCl$_3$) δ(ppm): 1.13 (t, J=7.1 Hz, 3H), 1.30 (s, 9H), 2.70 (q, J=7.1 Hz, 2H), 3.30 (s, 3H), 3.91 (s, 2H), 4.56 (s, 2H), 6.53 (s, 1H), 7.02-7.66 (m, 5H), 7.50 (s, 1H), 8.21 (d, J=8.4 Hz, 1H).

Step 2

In a similar manner to Step 2 of Example 8, 4-methanesulfonyloxy-7-[1-(tert-butoxycarbonyl)-5-(ethylaminomethyl)indol-2-yl]isoindolinone (48.0 mg, 0.0960 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 295 (21.1 mg, yield 50%).

ESI-MS m/z: 400 [M+H]+; 1H-NMR (DMSO-d6) δ(ppm): 1.22 (t, J=7.2 Hz, 3H), 2.85-3.00 (m, 2H), 3.56 (s, 3H), 4.18 (br s, 2H), 4.57 (s, 2H), 7.28 (d, J=8.4 Hz, 1H), 7.33 (s, 1H), 7.56 (d, J=8.4 Hz, 1H), 7.68 (d, J=8.8 Hz, 1H), 7.74 (s, 1H), 8.31 (d, J=8.8 Hz, 1H), 8.87 (br s, 2H), 9.55 (s, 1H), 13.87 (s, 1H).

EXAMPLE 296

4-Methanesulfonyloxy-7-[1H-5-(cyclohexylaminomethyl)indol-2-yl]isoindolinone hydrochloride (Compound 296)

Step 1

In a similar manner to Step 2 of Example 6, 4-hydroxy-7-[1-(tert-butoxycarbonyl)-5-formyl]indolylisoindolinone (100 mg, 0.213 mmol) was dissolved in acetonitrile (3 mL), and the solution was treated with cyclohexylamine (0.244 mL, 2.13 mmol), acetic acid (0.211 mL, 4.26 mmol) and sodium triacetoxyborohydride (180 mg, 0.852 mmol) to obtain 4-methanesulfonyloxy-7-[1-(tert-butoxycarbonyl)-5-(cyclohexylaminomethyl)indol-2-yl]isoindolinone (68.9 mg, yield 58%).

ESI-MS m/z: 554 [M+H]+; 1H-NMR (CDCl3) δ(ppm): 0.85-1.42 (m, 6H), 1.29 (s, 9H), 1.40-1.90 (m, 4H), 2.67 (m, 1H), 3.32 (s, 3H), 4.10 (br s, 2H), 4.61 (s, 2H), 6.50 (s, 1H), 7.39 (d, J=8.3 Hz, 1H), 7.42 (d, J=8.3 Hz, 1H), 7.50 (s, 1H), 7.52 (d, J=8.3 Hz, 1H), 7.62 (s, 1H), 8.32 (d, J=8.3 Hz, 1H), 8.36 (br s, 1H).

Step 2

In a similar manner to Step. 2 of Example 8, 4-methanesulfonyloxy-7-[1-(tert-butoxycarbonyl)-5-(cyclohexylaminomethyl)indol-2-yl]isoindolinone (67.5 mg, 0.122 mmol) was dissolved in methanol (3 mL), and the solution was treated with 10% hydrogen chloride-methanol solution (3 mL). The mixture was added with diisopropylether. The obtained solid was collected by filtration and washed with diisopropylether, followed by drying under reduced pressure to obtain Compound 296 (30.5 mg, yield 51%).

ESI-MS m/z: 454 [M+H]+; 1H-NMR (DMSO-d6) δ(ppm): 1.01-1.48 (m, 5H), 1.60 (m, 1H), 1.68-1.88 (m, 2H), 1.98-2.23 (m, 2H), 2.99 (m, 1H), 3.52 (s, 3H), 4.12 (s, 2H), 4.58 (s, 2H), 7.30 (dd, J=1.5, 8.4 Hz, 1H), 7.34 (s, 1H), 7.57 (d, J=8.4 Hz, 1H), 7.69 (d, J=8.8 Hz, 1H), 7.78 (s, 1H), 8.32 (d, J=8.8 Hz, 1H), 8.82 (br s, 2H), 9.56 (s, 1H), 13.88 (s, 1H).

EXAMPLE 297

4-Methanesulfonyloxy-7-[1H-5-(pyrrolidin-1-ylmethyl)indol-2-yl]isoindolinone (Compound 297)

Step 1

In a similar manner to Step 2 of Example 6, 4-hydroxy-7-[1-(tert-butoxycarbonyl)-5-formyl]indolylisoindolinone (100 mg, 0.213 mmol) was dissolved in acetonitrile (3 mL), and the solution was treated with pyrrolidine (0.178 mL, 2.13 mmol), acetic acid (0.211 mL, 4.26 mmol) and sodium triacetoxyborohydride (180 mg, 0.852 mmol) to obtain 4-methanesulfonyloxy-7-[1-(tert-butoxycarbonyl)-5-(pyrrolidin-1-ylmethyl)indol-2-yl]isoindolinone (67.4 mg, yield 60%).

ESI-MS m/z: 526 [M+H]+; 1H-NMR (CDCl3) δ(ppm) 1.30 (s, 9H), 1.66-2.00 (m, 4H), 2.45-2.63 (m, 4H), 3.29 (s, 3H), 3.73 (s, 2H), 4.54 (s, 2H), 6.55 (s, 1H), 7.27 (s, 1H), 7.33 (d, J=8.7 Hz, 1H), 7.45-7.58 (m, 3H), 8.19 (d, J=8.7 Hz, 1H).

Step 2

In a similar manner to Step 2 of Example 8, 4-methanesulfonyloxy-7-[1-(tert-butoxycarbonyl)-5-(pyrrolidin-1-ylmethyl)indol-2-yl]isoindolinone (67.0 mg, 0.127 mmol) was dissolved in methanol (3 mL), and the solution was treated with 10% hydrogen chloride-methanol solution (3 mL). The reaction mixture was added with water and aqueous sodium hydrogencarbonate solution, and extracted with ethyl acetate. The organic layer was washed with saturated brine and dried over anhydrous sodium sulfate. The solvent was evaporated under reduced pressure, and the residue was purified by slurry using diisopropylether to obtain Compound 297 (22.4 mg, yield 44%).

ESI-MS m/z: 426 [M+H]+; 1H-NMR (DMSO-d6) δ(ppm): 1.58-1.80 (m, 4H), 2.32-2.57 (m, 4H), 3.55 (s, 3H), 3.63 (s, 2H), 4.56 (s, 2H), 6.54 (s, 1H), 7.10 (d, J=8.3 Hz, 1H), 7.20 (s, 1H), 7.39 (d, J=8.3 Hz, 1H), 7.47 (s, 1H), 7.65 (d, J=8.6 Hz, 1H), 8.25 (d, J=8.6 Hz, 1H), 9.48 (s, 1H), 13.64 (s, 1H).

EXAMPLE 298

4-Methanesulfonyloxy-7-[1H-5-(pyperazin-1-ylcarbonyl)indol-2-yl]isoindolinone (Compound 298)

Step 1

In a similar manner to Step 2 of Example 1, 4-methanesulfonyloxy-7-iodoisoindolinone (51.0 mg, 0.144 mmol) was suspended in acetonitrile (3 mL), and the suspension was treated with Compound BB (137 mg, 0.289 mmol), palladium acetate (3.6 mg, 0.016 mmol) and triethylamine (0.201 mL, 1.44 mmol), followed by purification by preparative thin-layer chromatography (chloroform/methanol=10/1) to obtain 4-methanesulfonyloxy-7-(1-(tert-butoxycarbonyl)-5-[4-(tert-butoxycarbonyl)pyperazin-1-ylcarbonyl]indol-2-yl)isoindolinone (60.0 mg).

Step 2

In a similar manner to Step 2 of Example 5, 4-methanesulfonyloxy-7-(1-(tert-butoxycarbonyl)-5-[4-(tert-butoxycarbonyl)pyperazin-1-ylcarbonyl]indol-2-yl)isoindolinone (59.6 mg) was treated with 4 mol/L hydrogen chloride-ethyl acetate solution (9 mL). The reaction mixture was added with saturated aqueous sodium hydrogencarbonate solution and extracted with ethyl acetate. The organic layer was washed with saturated aqueous sodium chloride solution and dried over anhydrous sodium sulfate. The solvent was evaporated under reduced pressure and the residue was purified by preparative thin-layer chromatography (chloroform/methanol=10/1) to obtain Compound 298 (4.9 mg, yield 7%, 2 steps).

ESI-MS m/z: 455 [M+H]+; 1H-NMR (DMSO-d6) δ(ppm): 2.64-2.80 (m, 4H), 3.34-3.59 (m, 4H), 3.56 (s, 3H), 4.58 (s, 2H), 7.17 (d, J=8.8 Hz, 1H), 7.33 (s, 1H), 7.52 (d, J=8.8 Hz, 1H), 7.63 (s, 1H), 7.69 (d, J=8.7 Hz, 1H), 8.29 (d, J=8.7 Hz, 1H), 9.53 (s, 1H), 13.87 (s, 1H).

EXAMPLE 299

4-Trifluoromethanesulfonyloxy-7-[1H-5-(piperidinomethyl)indol-2-yl]isoindolinone hydrochloride (Compound 229)

Step 1

4-Hydroxy-7-[1-(tert-butoxycarbonyl)-5-(piperidinomethyl)indol-2-yl]isoindolinone (80.0 mg, 0.173 mmol) was suspended in dichloromethane (4.8 mL), and the suspension was added with triethylamine (0.072 mL, 0.52 mmol) and trifluoromethanesulfonyl chloride (0.022 mL, 0.21 mmol) under ice-cooling, followed by stirring for 0.8 hour. The reaction mixture was filtered and the filtrate was added with water and extracted with ethyl acetate. The organic layer was washed with saturated brine and dried over anhydrous sodium sulfate. The solvent was evaporated under reduced pressure to obtain 4-trifluoromethanesulfonyloxy-7-[1-(tert-butoxycarbonyl)-5-(piperidinomethyl)indol-2-yl]isoindolinone (95.4 mg, yield 93%).

APCI-MS m/z: 594 [M+H]$^+$; $^1$H-NMR (CDCl$_3$) δ(ppm): 1.32 (s, 9H), 1.43 (m, 2H), 1.58 (m, 4H), 2.42 (br s, 4H), 3.58 (s, 2H), 4.54 (s, 2H), 6.57 (s, 1H), 7.05 (s, 1H), 7.32 (dd, J=1.7, 8.6 Hz, 1H), 7.49 (d, J=8.3 Hz, 1H), 7.50 (s, 1H), 7.55 (d, J=8.3 Hz, 1H), 8.18 (d, J=8.6 Hz, 1H).

Step 2

In a similar manner to Step 2 of Example 8, 4-trifluoromethanesulfonyloxy-7-[1-(tert-butoxycarbonyl)-5-(piperidinomethyl)indol-2-yl]isoindolinone (110 mg, 0.185 mmol) was dissolved in methanol (3.3 mL), and the solution was treated with 10% hydrogen chloride-methanol solution (5.5 mL). The reaction mixture was added with diisopropylether and purified by slurry to obtain Compound 299 (95.0 mg, yield 97%).

ESI-MS m/z: 494 [M+H]$^+$; $^1$H-NMR (DMSO-d$_6$) δ(ppm): 1.85-1.96 (s, 6H), 3.06 (m, 2H), 3.50 (m, 2H), 4.51 (s, 2H), 4.80 (s, 2H), 7.52 (d, J=8.2 Hz, 1H), 7.57 (s, 1H), 7.77 (d, J=8.4 Hz, 1H), 7.98 (d, J=8.7 Hz, 1H), 7.99 (s, 1H), 8.56 (d, J=8.7 Hz, 1H), 9.84 (s, 1H), 10.05 (br s, 1H), 13.96 (s, 1H).

EXAMPLE 300

4-Ethyl-7-[1H-5-(piperidinomethyl)indol-2-yl]isoindolinone hydrochloride (Compound 300)

Step 1

In a similar manner to Step 1 of Example 10, 7-amino-4-bromoisoindolinone (300 mg, 1.32 mmol) was dissolved in THF (12 mL), and the solution was treated with vinyltributyltin (1.16 mL, 3.96 mmol) and bis(o-toluoylphosphine) dichloropalladium (166 mg, 0.211 mmol), followed by purification by slurry using hexane and chloroform to obtain 7-amino-4-vinylisoindolinone (155 mg, yield 68%).

ESI-MS m/z: 175 [M+H]$^+$; $^1$H-NMR (CDCl$_3$+CD$_3$OD) δ(ppm): 4.42 (s, 2H), 5.19 (d, J=11.2 Hz, 1H), 5.45 (d, J=17.7 Hz, 1H), 6.60 (dd, J=11.3, 17.6 Hz, 1H), 6.61 (d, J=8.4 Hz, 1H), 7.40 (d, J=8.4 Hz, 1H).

Step 2

7-Amino-4-vinylisoindolinone (50.0 mg, 0.287 mmol) was dissolved in DMF (2.5 mL), and the solution was added with 10% Pd—C (10 mg) followed by stirring at room temperature for 1.8 hours under normal pressure and hydrogen atmosphere. The reaction mixture was filtered using Celite and the solvent of the filtrate was evaporated under reduced pressure to obtain 7-amino-4-ethylisoindolinone (52.0 mg, quantitative).

APCI-MS m/z: 177 [M+H]$^+$; $^1$H-NMR (CDCl$_3$+CD$_3$OD) δ(ppm): 1.21 (t, J=7.6 Hz, 3H), 2.53 (q, J=7.6 Hz, 2H), 4.32 (s, 2H), 6.62 (d, J=8.2 Hz, 1H), 7.14 (d, J=8.1 Hz, 1H).

Step 3

In a similar manner to Step 4 of Example 140, 7-amino-4-ethylisoindolinone (46.0 mg, 0.260 mmol) was dissolved in acetonitrile (6.2 mL), and the solution was treated with potassium iodide (69.1 mg, 0.416 mmol), copper iodide (79.2 mg, 0.416 mmol), iodine (106 mg, 0.416 mmol) and tert-butyl nitrate (0.139 mL, 1.17 mmol), followed by purification by preparative thin-layer chromatography (chloroform/acetonitrile=5/1) to obtain 7-iodo-4-ethylisoindolinone (37.1 mg, yield 50%).

APCI-MS m/z: 288 [M+H]$^+$; $^1$H-NMR (CDCl$_3$) δ(ppm): 1.28 (t, J=7.5 Hz, 3H), 2.63 (q, J=7.6 Hz, 2H), 4.30 (s, 2H), 6.51 (s, 1H), 7.09 (d, J=7.9 Hz, 1H), 7.86 (d, J=7.9 Hz, 1H).

Step 4

In a similar manner to Step 2 of Example 1, 7-iodo-4-ethylisoindolinone (35.9 mg, 0.125 mmol) was dissolved in acetonitrile (2.87 mL), and the solution was treated with Compound BD (90 mg, 0.25 mmol), palladium acetate (2.2 mg, 0.010 mmol), tri(o-tolyl)phosphine (6.1 mg, 0.020 mmol) and triethylamine (0.174 mL, 1.25 mmol), followed by purification by preparative thin-layer chromatography (chloroform/methanol=10/1) to obtain 4-ethyl-7-[1-(tert-butoxycarbonyl)-5-(piperidinomethyl)indol-2-yl]isoindolinone (43.6 mg, yield 74%).

APCI-MS m/z: 474 [M+H]$^+$; $^1$H-NMR (CDCl$_3$) δ(ppm): 1.26 (s, 9H), 1.30 (t, J=7.6 Hz, 3H), 1.43 (br s, 2H), 1.60 (br s, 4H), 2.45 (br s, 4H), 2.70 (q, J=7.6 Hz, 2H), 3.64 (s, 2H), 4.36 (s, 2H), 6.52 (s, 1H), 7.29 (d, J=8.6 Hz, 1H), 7.39 (br s, 2H), 7.50 (s, 1H), 7.91 (br s, 1H), 8.20 (d, J=8.4 Hz, 1H).

Step 5

In a similar manner to Step 2 of Example 8, 4-ethyl-7-[1-(tert-butoxycarbonyl)-5-(piperidinomethyl)indol-2-yl]isoindolinone (43.0 mg, 0.0908 mmol) was dissolved in methanol (1.5 mL), and the solution was treated with 10% hydrogen chloride-methanol solution (2.3 mL). The precipitated solid was collected by filtration and washed with methanol, followed by drying under reduced pressure to obtain Compound 300 (27.5 mg, yield 74%).

APCI-MS m/z: 374 [M+H]$^+$; $^1$H-NMR (DMSO-d$_6$) δ(ppm): 1.24 (t, J=7.5 Hz, 3H), 1.71-1.76 (m, 6H), 2.67 (q, J=7.5 Hz, 2H), 2.85 (m, 2H), 3.30 (br s, 2H), 4.30 (s, 2H), 4.50 (s, 2H), 7.24 (s, 1H), 7.27 (d, J=8.9 Hz, 1H), 7.53 (m, 2H), 7.74 (s, 1H), 8.16 (d, J=8.2 Hz, 1H), 9.33 (s, 1H), 9.91 (br s, 1H), 14.06 (s, 1H).

EXAMPLE 301

4-Methyl-7-[1H-5-(piperidinomethyl)indol-2-yl]isoindolinone hydrochloride (Compound 301)

Step 1

In a similar manner to Step 1 of Example 152, 7-amino-4-bromoisoindolinone (100 mg, 0.440 mmol) was dissolved in dimethoxyethane (5 mL), and the solution was treated with trimethylboroxine (0.184 mL, 1.76 mmol), [bis(diphenylphosphino)ferrocene]dichloropalladium (28.7 mg, 0.0352 mmol), potassium carbonate (304 mg, 2.20 mmol) and water (0.158 mL), followed by purification by preparative thin-layer chromatography (chloroform/acetonitrile=4/1) to obtain a mixture of 7-amino-4-methylisoindolinone and 7-aminoisoindolinone (62.9 mg, ratio 10/1, yield 89%).

7-amino-4-methylisoindolinone

APCI-MS m/z: 163 [M+H]$^+$; $^1$H-NMR (CDCl$_3$+CD$_3$OD) δ(ppm): 2.18 (s, 3H), 4.27 (s, 2H), 6.58 (d, J=8.1 Hz, 1H), 7.09 (d. J=8.1 Hz, 1H).

Step 2

In a similar manner to Step 4 of Example 140, a mixture of 7-amino-4-methylisoindolinone and 7-aminoisoindolinone (10/1, 57.4 mg, 0.357 mmol) was dissolved in acetonitrile (4.6 mL), and the solution was treated with potassium iodide (78 mg, 0.47 mmol), copper iodide (90 mg, 0.47 mmol), iodine (120 mg, 0.471 mmol) and tert-butyl nitrate (0.128 mL, 1.07 mmol), followed by purification by preparative thin-layer chromatography (chloroform/acetonitrile=5/1) to obtain a mixture of 7-iodo-4-methylisoindolinone and 7-iodoisoindolinone (44.8 mg, ratio 10/1, yield 50%).

7-iodo-4-methylisoindolinone

ESI-MS m/z: 274 [M+H]$^+$, $^1$H-NMR (CDCl$_3$+CD$_3$OD) δ(ppm): 2.31 (s, 3H), 4.26 (s, 2H), 7.07 (d, J=7.9 Hz, 1H), 7.81 (d, J=7.9 Hz, 1H).

Step 3

In a similar manner to Step 2 of Example 1, a mixture of 7-iodo-4-methylisoindolinone and 7-iodoisoindolinone (10/1, 40.5 mg, 0.149 mmol) was dissolved in acetonitrile (3.24 mL), and the solution was treated with Compound BD (107 mg, 0.298 mmol), palladium acetate (2.7 mg, 0.012 mmol), tri(o-tolyl)phosphine (7.3 mg, 0.024 mmol) and triethylamine (0.208 mL, 1.49 mmol), followed by purification by preparative thin-layer chromatography (chloroform/methanol=12/1) to obtain a mixture of 4-methyl-7-[1-(tert-butoxycarbonyl)-5-(piperidinomethyl)indol-2-yl]isoindolinone and 7-[1-(tert-butoxycarbonyl)-5-(piperidinomethyl)indol-2-yl]isoindolinone (38.2 mg, ratio 92.9/7.1, yield 56%). 4-methyl-7-[1-(tert-butoxycarbonyl)-5-(piperidinomethyl)indol-2-yl]isoindolinone APCI-MS m/z: 460 [M+H]$^+$; $^1$H-NMR-(CDCl$_3$) δ(ppm): 1.29 (s, 9H) 1.43 (br s, 2H), 1.59 (br s, 4H), 2.37 (s, 3H), 2.44 (br s, 4H), 3.62 (s, 2H), 4.31 (s, 2H), 6.52 (s, 1H), 7.29 (dd, J=1.6, 8.6 Hz, 1H), 7.36 (br s, 2H), 7.49 (s, 1H), 7.98 (br s, 1H), 8.18 (d, J=8.6 Hz, 1H).

Step 4

In a similar manner to Step 2 of Example 8, a mixture of 4-methyl-7-[1-(tert-butoxycarbonyl)-5-(piperidinomethyl)indol-2-yl]isoindolinone and 7-[1-(tert-butoxycarbonyl)-5-(piperidinomethyl)indol-2-yl]isoindolinone (92.9/7.1, 38.2 mg, 0.0833 mmol) was dissolved in methanol (1.5 mL), and the solution was treated with 10% hydrogen chloride-methanol solution (2.3 mL). The precipitated solid was collected by filtration and washed with methanol, followed by drying under reduced pressure to obtain Compound 301 and 7-[1H-5-(piperidinomethyl)indol-2-yl]isoindolinone hydrochloride (20.1 mg, ratio 93.7/6.3, yield 61%).

APCI-MS m/z: 360 [M+H]$^+$; $^1$H-NMR (DMSO-d$_6$) δ(ppm): 1.64-1.76 (m, 6H), 2.33 (s, 3H), 2.83 (m, 2H), 3.29 (m, 2H), 4.30 (s, 2H), 4.45 (s, 2H), 7.23 (s, 1H), 7.28 (d, J=8.9 Hz, 1H), 7.48 (d, J=7.7 Hz, 1H), 7.53 (d, J=8.2 Hz, 1H), 7.75 (s, 1H), 8.11 (d, J=8.2 Hz, 1H), 9.33 (s, 1H), 9.98 (br s, 1H), 14.04 (s, 1H).

EXAMPLE 302

4-Ethyl-7-{1H-5-[4-(2-hydroxyethyl)pyperazin-1-ylmethyl]indol-2-yl}isoindolinone dihydrochloride (Compound 302)

Step 1

In a similar manner to Step 2 of Example 1, 7-iodo-4-ethylisoindolinone (128 mg, 0.446 mmol) was dissolved in acetonitrile (9.0 mL), and the solution was treated with Compound BA (258 mg, 0.892 mmol), palladium acetate (8.0 mg, 0.036 mmol), tri(o-tolyl)phosphine (21.7 mg, 0.0714 mmol) and triethylamine (0.622 mL, 4.46 mmol), followed by purification by preparative thin-layer chromatography (chloroform/acetone=6/1) to obtain 4-ethyl-7-[1-(tert-butoxycarbonyl)-5-formylindol-2-yl]isoindolinone (163 mg, yield 90%).

APCI-MS m/z: 405 [M+H]$^+$; $^1$H-NMR (CDCl$_3$) δ(ppm): 1.29 (s, 9H), 1.32 (t, J=7.6 Hz, 3H), 2.72 (q, J=7.6 Hz, 2H), 4.39 (s, 2H), 6.67 (s, 1H), 6.97 (s, 1H), 7.44 (s, 2H), 7.87 (dd, J=1.6, 8.7 Hz, 1H), 8.08 (d, J=1.6 Hz, 1H), 8.39 (d, J=8.7 Hz, 1H), 10.07 (s, 1H).

Step 2

In a similar manner to Step 2 of Example 6, 4-ethyl-7-[1-(tert-butoxycarbonyl)-5-formylindol-2-yl]isoindolinone (87.6 mg, 0.217 mmol) was dissolved in acetonitrile (7 mL), and the solution was treated with 1-(2-hydroxyethyl)piperazine (113 mg, 0.868 mmol), acetic acid (0.248 mL, 4.34 mmol) and sodium triacetoxyborohydride (184 mg, 0.868 mmol). The reaction mixture was added with 1 mol/L hydrochloric acid and extracted with ethyl acetate. The organic layer was washed with sodium carbonate and saturated brine, and dried over anhydrous sodium sulfate. The solvent was evaporated under reduced pressure to obtain 4-ethyl-7-{1-(tert-butoxycarbonyl)-5-[4-(2-hydroxyethyl)pyperazin-1-yl-methyl]indol-2-yl}isoindolinone (102 mg, yield 91%).

APCI-MS m/z: 519 [M+H]$^+$; $^1$H-NMR (CDCl$_3$) δ(ppm): 1.25 (s, 9H), 1.29 (t, J=7.6 Hz, 3H), 2.55 (br s, 10H), 2.69 (q, J=7.6 Hz, 2H), 3.61 (br s, 4H), 4.35 (s, 2H), 6.52 (s, 1H), 7.28 (dd, J=1.6, 8.7 Hz, 1H), 7.39 (s, 2H), 7.48 (s, 1H), 7.90 (s, 1H), 8.20 (d, J=8.6 Hz, 1H).

Step 3

In a similar manner to Step 2 of Example 8, 4-ethyl-7-{1-(tert-butoxycarbonyl)-5-[4-(2-hydroxyethyl)pyperazin-1-yl-methyl]indol-2-yl}isoindolinone (106 mg, 0.204 mmol) was dissolved in methanol (2.7 mL), and the solution was treated with 10% hydrogen chloride-methanol solution (2.7 mL). The precipitated solid was collected by filtration and washed with methanol, followed by drying under reduced pressure to obtain Compound 302 (72.2 mg, yield 72%).

APCI-MS m/z: 419 [M+H]$^+$; $^1$H-NMR (DMSO-d$_6$) δ(ppm): 1.24 (t, J=7.6 Hz, 3H), 2.67 (q, J=7.6 Hz, 2H), 3.19-3.44 (m, 12H), 3.74 (s, 2H), 4.43 (br s, 1H), 4.50 (s, 2H), 7.24 (s, 1H), 7.33 (d, J=8.6 Hz, 1H), 7.52 (d, J=8.1 Hz, 1H), 7.53 (d, J=8.3 Hz, 1H), 7.80 (s, 1H), 8.16 (d, J=8.3 Hz, 1H), 9.34 (s, 1H), 11.08 (br s, 1H), 11.85 (br s, 1H), 1.4.07 (s, 1H).

EXAMPLE 303

4-Methyl-7-{1H-5-[4-(2-hydroxyethyl)pyperazin-1-ylmethyl]indol-2-yl}isoindolinone dihydrochloride (Compound 303)

Step 1

In a similar manner to Step 1 of Example 299, 4-hydroxy-7-[1-(tert-butoxycarbonyl)-5-formylindol-2-yl]isoindolinone (300 mg, 0.765 mmol) was dissolved in dichloromethane (12 mL), and the solution was treated with triethylamine (0.533 mL, 3.83 mmol) and trifluoromethanesulfonyl chloride (0.138 mL, 1.30 mmol) under ice-cooling, followed by purification by flash column chromatography (chloroform/methanol=100/0 to 98/2) to obtain 4-trifluoromethanesulfonyloxy-7-[1-(tert-butoxycarbonyl)-5-formylindol-2-yl]isoindolinone (249 mg, yield 62%).

APCI-MS m/z: 525 [M+H]$^+$; $^1$H-NMR (CDCl$_3$) δ(ppm): 1.32 (s, 9H), 4.56 (s, 2H), 6.73 (s, 1H), 7.16 (s, 1H), 7.54 (d, J=8.4 Hz, 1H), 7.59 (d, J=8.2 Hz, 1H), 7.91 (dd, J=1.7, 8.6 Hz, 1H), 8.12 (d, J=1.3 Hz, 1H), 8.42 (d, J=8.6 Hz, 1H), 10.08 (s, 1H).

Step 2

In a similar manner to Step 1 of Example 152, 4-trifluoromethanesulfonyloxy-7-[1-(tert-butoxycarbonyl)-5-formylindol-2-yl]isoindolinone (176 mg, 0.336 mmol) was dissolved in dimethoxyethane (8.8 mL), and the solution was treated with trimethylboroxine (0.140 mL, 1.01 mmol), [bis(diphenylphosphino)ferrocene]dichloropalladium (32.9 mg, 0.0403 mmol), potassium carbonate (231 mg, 1.68 mmol) and water (0.121 mL), followed by purification by preparative thin-layer chromatography (chloroform/acetonitrile=4/1) to obtain 4-methyl-7-[1-(tert-butoxycarbonyl)-5-formylindol-2-yl]isoindolinone (112 mg, yield 86%).

ESI-MS m/z: 391 [M+H]$^+$; $^1$H-NMR (CDCl$_3$) δ(ppm): 1.29 (s, 9H), 2.38 (s, 3H), 4.32 (s, 2H), 6.67 (s, 1H), 7.39 (s, 2H), 7.69 (s, 1H), 7.87 (dd, J=1.8, 8.8 Hz, 1H), 8.08 (d, J=1.5 Hz, 1H), 8.39 (d, J=8.8 Hz, 1H), 10.06 (s, 1H).

Step 3

In a similar manner to Step 2 of Example 6, 4-methyl-7-[1-(tert-butoxycarbonyl)-5-formylindol-2-yl]isoindolinone (100 mg, 0.256 mmol) was dissolved in acetonitrile (8 mL), and the solution was treated with 1-(2-hydroxyethyl)piperazine (133 mg, 1.02 mmol), acetic acid (0.307 mL, 5.12 mmol) and sodium triacetoxyborohydride (218 mg, 1.02 mmol). The reaction mixture was added with 1 mol/L hydrochloric acid and extracted with ethyl acetate. The organic layer was washed with sodium carbonate and saturated brine, and dried over anhydrous sodium sulfate. The solvent was evaporated under reduced pressure to obtain 4-methyl-7-(1-(tert-butoxycarbonyl)-5-[4-(2-hydroxyethyl)pyperazin-1-ylmethyl]indol-2-yl)isoindolinone (126 mg, yield 98%).

APCI-MS m/z: 505 [M+H]$^+$; $^1$H-NMR (CDCl$_3$) δ(ppm): 1.29 (s, 9H), 2.36 (s, 3H), 2.54 (m, 10H), 3.58 (m, 2H), 4.31 (s, 2H), 3.61 (s, 2H), 6.52 (s, 2H), 7.28 (dd, J=1.7, 8.4 Hz, 1H), 7.36 (s, 2H), 7.47 (s, 1H), 7.79 (s, 1H), 8.18 (d, J=8.6 Hz, 1H).

Step 4

In a similar manner to Step. 2 of Example 8, 4-methyl-7-{1-(tert-butoxycarbonyl)-5-[4-(2-hydroxyethyl)pyperazin-1-ylmethyl]indol-2-yl}-isoindolinone (126 mg, 0.250 mmol) was dissolved in methanol (3.2 mL), and the solution was treated with 10% hydrogen chloride-methanol solution (6.3 mL). The precipitated solid was collected by filtration and washed with methanol, followed by drying under reduced pressure to obtain Compound 303 (95 mg, yield 80%).

ESI-MS m/z: 405 [M+H]$^+$; $^1$H-NMR (DMSO-d$_6$) δ(ppm): 2.33 (s, 3H), 3.19-3.74 (m, 10H), 4.45 (m, 4H), 7.24 (s, 1H), 7.32 (d, J=8.6 Hz, 1H), 7.48 (d, J=8.3 Hz, 1H), 7.54 (d, J=8.6 Hz, 1H), 7.79 (s, 1H), 8.12 (d, J=7.9 Hz, 1H), 9.33 (s, 1H), 11.06 (br s, 1H), 11.76 (br s, 1H), 14.06 (s, 1H).

EXAMPLE 304

4-(4-Hydroxy-3-methoxyphenyl)-7-[1H-5-(piperidinomethyl)indol-2-yl]isoindolinone hydrochloride (Compound 304)

Step 1

7-Amino-4-(4-hydroxy-3-methoxyphenyl)isoindolinone (50.0 mg, 0.185 mmol) was dissolved in acetonitrile (2.5 mL), and the solution was added with tert-butyldimethylsilyl chloride (33.5 mg, 0.222 mmol), 1,8-diazabicyclo[5.4.0]undec-7-ene (DBU) (0.033 mL, 0.22 mmol), followed by stirring at room temperature for 1.3 hours. The mixture was added with tert-butyldimethylsilyl chloride (33.5 mg, 0.222 mmol) and DBU (0.033 mL, 0.22 mmol), followed by further stirring for 1 hour. The reaction mixture was added with water and extracted with ethyl acetate. The organic layer was washed with saturated brine and dried over anhydrous sodium sulfate. The solvent was evaporated under reduced pressure and the residue was purified by preparative thin-layer chromatography (chloroform/acetonitrile=2/1) to obtain 7-amino-4-(4-tert-butyldimethylsilyloxy-3-methoxyphenyl)isoindolinone (51.1 mg, yield 72%).

APCI-MS m/z: 385 [M+H]$^+$; $^1$H-NMR (CDCl$_3$) δ(ppm): 0.19 (s, 6H), 1.01 (s, 9H), 3.83 (s, 3H), 4.45 (s, 2H), 5.28 (s, 1H), 5.99 (s, 1H), 6.66 (d, J=8.2 Hz, 1H), 6.82-6.89 (m, 3H), 7.32 (d, J=8.2 Hz, 1H).

Step 2

In a similar manner to Step 4 of Example 140, 7-amino-4-(4-tert-butyldimethylsilyloxy-3-methoxyphenyl)isoindolinone (43.0 mg, 0.110 mmol) was dissolved in acetonitrile (6 mL), and the solution was treated with potassium iodide (29.2 mg, 0.176 mmol), copper iodide (33.5 mg, 0.896 mmol), iodine (44.7 mg, 0.896 mmol) and tert-butyl nitrate (0.059 mL, 0.50 mmol), followed by purification by preparative thin-layer chromatography (chloroform/acetonitrile=5/1) to obtain 7-iodo-4-(4-tert-butyldimethylsilyloxy-3-methoxyphenyl)isoindolinone (33.8 mg, yield 62%).

APCI-MS m/z: 496 [M+H]$^+$; $^1$H-NMR (CDCl$_3$) δ(ppm): 0.20 (s, 6H), 1.02 (s, 9H), 3.84 (s, 3H), 4.39 (s, 2H), 6.56 (br s, 1H), 6.86-6.94 (m, 3H), 7.23 (d, J=7.9 Hz, 1H), 7.97 (d, J=7.9 Hz, 1H).

Step 3

In a similar manner to Step 2 of Example 1, 7-iodo-4-(4-tert-butyldimethylsilyloxy-3-methoxyphenyl)isoindolinone (32.8 mg, 0.0662 mmol) was dissolved in acetonitrile (3.3 mL), and the solution was treated with Compound BD (47 mg, 0.13 mmol), palladium acetate (1.5 mg, 0.0066 mmol), tri(o-tolyl)phosphine (4.0 mg, 0.013 mmol) and triethylamine (0.092 mL, 0.66 mmol), followed by purification by preparative thin-layer chromatography (chloroform/methanol=8/1) to obtain 4-(4-tert-butyldimethylsilyloxy-3-methoxyphenyl)-7-(1-(tert-butoxycarbonyl)-5-(piperidinomethyl)indol-2-yl isoindolinone (34.7 mg, yield 77%).

APCI-MS m/z: 682 [M+H]$^+$; $^1$H-NMR (CDCl$_3$) δ(ppm): 0.22 (s, 6H), 1.04 (s, 9H), 1.33 (s, 9H), 1.43 (br s, 2H), 1.63 (br s, 4H), 2.48 (br s, 4H), 3.66 (s, 2H), 3.86 (s, 3H), 4.48 (s, 2H), 6.58 (s, 1H), 6.95 (m, 3H), 7.30 (d, J=8.7 Hz, 1H), 7.51 (d, J=8.1 Hz, 1H), 7.52 (br s, 1H), 7.58 (d, J=7.7 Hz, 1H), 7.62 (br s, 1H), 8.18 (d, J=8.4 Hz, 1H).

Step 4

In a similar manner to Step 2 of Example 8, 4-(4-tert-butyldimethylsilyloxy-3-methoxyphenyl)-7-[1-(tert-butoxycarbonyl)-5-(piperidinomethyl)indol-2-yl]isoindolinone (34.7 mg, 0.0509 mmol) was dissolved in methanol (1.4 mL), and the solution was treated with 10% hydrogen chloride-methanol solution (1.4 mL). The precipitated solid was collected by filtration and washed with methanol, followed by drying under reduced pressure to obtain Compound 304 (15.9 mg, yield 62%).

APCI-MS m/z: 468 [M+H]$^+$; $^1$H-NMR (DMSO-d$_6$) δ(ppm): 1.66-1.77 (m, 6H), 2.86 (m, 2H), 3.31 (m, 2H), 3.83 (s, 3H), 4.31 (s, 2H), 4.62 (s, 2H), 6.90 (d, J=8.4 Hz, 1H), 7.04 (d, J=8.1 Hz, 1H), 7.15 (s, 1H), 7.31 (br s, 2H), 7.55 (d, J=8.2

Hz, 1H), 7.67 (d, J=7.2 Hz, 1H), 7.77 (s, 1H), 8.27 (d, J=7.7 Hz, 1H), 9.28 (s, 1H), 9.41 (s, 1H), 10.05 (br. s, 1H), 14.15 (s, 1H).

EXAMPLE 305

4-(4-Hydroxyphenyl)-7-[1H-5-(piperidinomethyl)indol-2-yl]isoindolinone hydrochloride (Compound 305)

Step 1

In a similar manner to Step 1 of Example 152, 7-amino-4-bromoisoindolinone (200 mg, 0.880 mmol) was dissolved in dimethoxyethane (14 mL); and the solution was treated with 4-(4,4,5,5-tetramethyl-1,3,2-dioxaboran-2-yl)phenol (387 mg, 1.76 mmol), [bis(diphenylphosphino)ferrocene]dichloropalladium (57.4 mg, 0.0704 mmol), potassium carbonate (607 mg, 4.40 mmol) and water (0.32 mL), followed by purification by slurry using chloroform to obtain 7-amino-4-(4-hydroxyphenyl)isoindolinone (192 mg, yield 91%).

APCI-MS m/z: 241 [M+H]$^+$; $^1$H-NMR (DMSO-d$_6$) δ(ppm): 4.34 (s, 2H), 6.10 (s, 2H), 6.62 (d, J=8.4 Hz, 1H), 6.78 (d, J=8.4 Hz, 2H), 7.22 (d, J=8.4 Hz, 1H), 7.26 (d, J=8.6 Hz, 2H), 8.20 (s, 1H), 9.40 (s, 1H).

Step 2

In a similar manner to Step 1 of Example 304, 7-amino-4-(4-hydroxyphenyl)isoindolinone (182 mg, 0.760 mmol) was dissolved in acetonitrile (9.1 mL), and the solution was treated with tert-butyldimethylsilyl chloride (206 mg, 1.37 mmol) and DBU (0.205 mL, 1.37 mmol), followed by purification by flash column chromatography (chloroform) to obtain 7-amino-4-(4-tert-butyldimethylsilyloxyphenyl)isoindolinone (182 mg, yield 68%).

APCI-MS m/z: 355 [M+H]$^+$; $^1$H-NMR (CDCl$_3$) δ(ppm): 0.23 (s, 6H), 1.00 (s, 9H), 4.44 (s, 2H), 5.93 (br s, 1H), 6.66 (d, J=8.4 Hz, 1H), 6.88 (d, J=8.6 Hz, 2H), 7.24 (d, J=8.8 Hz, 2H), 7.30 (d, J=8.2 Hz, 1H).

Step 3

In a similar manner to Step 4 of Example 140, 7-amino-4-(4-tert-butyldimethylsilyloxyphenyl)isoindolinone (179 mg, 0.505 mmol) was dissolved in acetonitrile (12.5 mL), and the solution was treated with potassium iodide (133 mg, 0.808 mmol), copper iodide (152 mg, 0.808 mmol), iodine (203 mg, 0.808 mmol) and tert-butyl nitrate (0.127 mL, 1.06 mmol), followed by purification by flash column chromatography (chloroform) to obtain 7-iodo-4-(4-tert-butyldimethylsilyloxyphenyl)isoindolinone (109 mg, yield 47%).

APCI-MS m/z: 466 [M+H]$^+$; $^1$H-NMR (CDCl$_3$) δ(ppm): 0.24 (s, 6H), 1.01 (s, 9H), 4.39 (s, 2H), 6.39 (br s, 1H), 6.92 (d, J=8.6 Hz, 2H), 7.21 (d, J=8.1 Hz, 1H), 7.28 (d, J=8.6 Hz, 2H), 7.98 (d, J=8.1 Hz, 1H).

Step 4

In a similar manner to Step 2 of Example 1, 7-iodo-4-(4-tert-butyldimethylsilyloxyphenyl)isoindolinone (59.4 mg, 0.128 mmol) was dissolved in acetonitrile (4.8 mL), and the solution was treated with Compound BD (92.0 mg, 0.256 mmol), palladium acetate (2.3 mg, 0.0102 mmol), tri(o-tolyl)phosphine (6.2 mg, 0.020 mmol) and triethylamine (0.178 mL, 1.28 mmol), followed by purification by preparative thin-layer chromatography (chloroform/methanol=7/1) to obtain 4-(4-tert-butyldimethylsilyloxyphenyl)-7-[1-(tert-butoxycarbonyl)-5-(piperidinomethyl)indol-2-yl]isoindolinone (53.6 mg, yield 64%).

APCI-MS m/z: 652 [M+H]$^+$; $^1$H-NMR (CDCl$_3$) δ(ppm): 0.26 (s, 6H), 1.02 (s, 9H), 1.30 (s, 9H), 1.44 (br s, 2H), 1.62 (br s, 4H), 2.48 (br s, 4H), 3.66 (s, 2H), 4.47 (s, 2H), 6.67 (s, 1H), 6.94 (d, J=8.6 Hz, 2H), 7.29 (dd, J=1.6, 8.7 Hz, 1H), 7.34 (d, J=8.6 Hz, 2H), 7.49 (d, J=7.8 Hz, 1H), 7.52 (s, 1H), 7.55 (d, J=7.6 Hz, 1H), 7.77 (br s, 1H), 8.19 (d, J=8.6 Hz, 1H).

Step 5

In a similar manner to Step 2 of Example 8, 4-(4-tert-butyldimethylsilyloxyphenyl)-7-[1-(tert-butoxycarbonyl)-5-(piperidinomethyl)indol-2-yl]isoindolinone (49.2 mg, 0.0755 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 305 (31.5 mg, yield 88%).

APCI-MS m/z: 438 [M+H]$^+$; $^1$H-NMR (DMSO-d$_6$) δ(ppm): 1.77 (m, 6H), 2.86 (m, 2H), 3.30 (m, 2H), 4.31 (d, J=4.6 Hz, 2H), 4.59 (s, 2H), 6.90 (d, J=8.4 Hz, 2H), 7.29 (d, J=7.9 Hz, 1H), 7.30 (s, 1H), 7.45 (d, J=8.4 Hz, 2H), 7.55 (d, J=8.4 Hz, 1H), 7.63 (d, J=8.1 Hz, 1H), 7.76 (s, 1H), 8.26 (d, J=8.3 Hz, 1H), 9.40 (s, 1H), 9.73 (s, 1H), 9.90 (br s, 1H), 14.15 (s, 1H).

EXAMPLE 306

4-(3-Hydroxyphenyl)-7-[1H-5-(piperidinomethyl)indol-2-yl]isoindolinone hydrochloride (Compound 306)

Step 1

In a similar manner to Step 1 of Example 152, 7-amino-4-bromoisoindolinone (150 mg, 0.661 mmol) was dissolved in dimethoxyethane (10.5 mL), and the solution was treated with 3-(4,4,5,5-tetramethyl-1,3,2-dioxaboran-2-yl)phenol (291 mg, 1.32 mmol), [bis(diphenylphosphino)ferrocene]dichloropalladium (43 mg, 0.053 mmol), potassium carbonate (455 mg, 3.31 mmol) and water (0.24 mL), followed by purification by slurry using chloroform to obtain 7-amino-4-(3-hydroxyphenyl)isoindolinone (140 mg, yield 88%).

APCI-MS m/z: 241 [M+H]$^+$; $^1$H-NMR (DMSO-d$_6$) δ(ppm): 4.35 (s, 2H), 6.19 (s, 2H), 6.66 (m, 2H), 6.82 (dd, J=1.7, 2.0 Hz, 1H), 6.88 (d, J=7.7 Hz, 1H), 7.18 (dd, J=7.8, 7.8 Hz, 1H), 7.27 (d, J=8.4 Hz, 1H), 8.23 (s, 1H), 9.39 (s, 1H).

Step 2

In a similar manner to Step 1 of Example 304, 7-amino-4-(3-hydroxyphenyl)isoindolinone (137 mg, 0.569 mmol) was dissolved in acetonitrile (7.0 mL), and the solution was treated with tert-butyldimethylsilyl chloride (155 mg, 1.02 mmol) and DBU (0.154 mL, 1.02 mmol), followed by purification by flash column chromatography (chloroform) to obtain 7-amino-4-(3-tert-butyldimethylsilyloxyphenyl)isoindolinone (120 mg, yield 59%).

APCI-MS m/z: 355 [M+H]$^+$; $^1$H-NMR (CDCl$_3$) δ(ppm): 0.22 (s, 6H), 1.00 (s, 9H), 4.46 (s, 2H), 6.67 (d, J=8.2 Hz, 1H), 6.79 (ddd, J=0.9, 2.4, 8.1 Hz, 1H), 6.86 (dd, J=1.8, 2.0 Hz, 1H), 6.97 (ddd. J=1.0, 1.7, 7.6 Hz, 1H), 7.24-7.29 (m, 2H), 7.33 (d, J=8.2 Hz, 1H).

Step 3

In a similar manner to Step 4 of Example 140, 7-amino-4-(3-tert-butyldimethylsilyloxyphenyl)isoindolinone (115 mg, 0.324 mmol) was dissolved in acetonitrile (8.0 mL), and the solution was treated with potassium iodide (73.8 mg, 0.441 mmol), copper iodide (84.8 mg, 0.441 mmol), iodine (113 mg, 0.441 mmol) and tert-butyl nitrate (0.071 mL, 0.551 mmol), followed by purification by flash column chromatography (chloroform) to obtain 7-iodo-4-(3-tert-butyldimethyl-silyloxyphenyl)isoindolinone (78.6 mg, yield 52%).

APCI-MS m/z: 466 [M+H]$^+$; $^1$H-NMR (CDCl$_3$) δ(ppm): 0.23 (s, 6H), 1.00 (s, 9H), 4.38 (s, 2H), 6.51 (br s, 1H), 6.87 (d, J=1.3 Hz, 1H), 6.89 (ddd, J=0.9, 2.4, 7.9 Hz, 1H), 6.99 (ddd, J=1.3, 1.3, 7.7 Hz, 1H), 7.22 (d, J=7.9 Hz, 1H), 7.32 (ddd, J=1.3, 7.4, 7.4 Hz, 1H), 7.99 (d, J=8.1 Hz, 1H).

Step 4

In a similar manner to Step 2 of Example 1, 7-iodo-4-(3-tert-butyldimethylsilyloxyphenyl)isoindolinone (78.0 mg, 0.168 mmol) was dissolved in acetonitrile (6.2 mL), and the solution was treated with Compound BD (120 mg, 0.336 mmol), palladium acetate (3.0 mg, 0.013 mmol), tri(o-tolyl)phosphine (8.2 mg, 0.027 mmol) and triethylamine (0.234 mL, 1.68 mmol), followed by purification by flash column chromatography (chloroform/methanol=100/1 to 95/5) to obtain 4-(3-tert-butyldimethylsilyloxyphenyl)-7-[1-(tert-butoxycarbonyl)-5-(piperidinomethyl)indol-2-yl]isoindolinone (75.0 mg, yield 68%).

APCI-MS m/z: 652 [M+H]$^+$; $^1$H-NMR (CDCl$_3$) δ(ppm): 0.24 (s, 6H), 1.01 (s, 9H), 1.35 (s, 9H), 1.57 (m, 6H), 2.42 (br s, 4H), 3.59 (s, 2H), 4.47 (s, 2H), 6.58 (s, 1H), 6.70 (s, 1H), 6.89 (ddd, J=0.9, 2.4, 8.1 Hz, 1H), 6.94 (dd, J=1.7, 2.1. Hz, 1H), 7.05 (ddd, J=1.3, 1.7, 8.1 Hz, 1H), 7.27-7.36 (m, 2H), 7.50 (d, J=1.2 Hz, 1H), 7.52 (d, J=7.8 Hz, 1H), 7.57 (d, J=7.8 Hz, 1H), 8.16 (d, J=8.4 Hz, 1H).

Step 5

In a similar manner to Step 2 of Example 8, 4-(3-tert-butyldimethylsilyloxyphenyl)-7-[1-(tert-butoxycarbonyl)-5-(piperidinomethyl)indol-2-yl]isoindolinone (74.0 mg, 0.114 mmol) was dissolved in methanol (2.2 mL), and the solution was treated with 10% hydrogen chloride-methanol solution (2.2 mL). The precipitated solid was collected by filtration and washed with methanol, followed by drying under reduced pressure to obtain Compound 306 (38.0 mg, yield 73%).

APCI-MS m/z: 438 [M+H]$^+$; $^1$H-NMR (DMSO-d$_6$) δ(ppm): 1.66-1.77 (m, 6H), 2.86 (br s, 2H), 3.35 (m, 2H), 4.30 (s, 2H), 4.58 (s, 2H), 6.84 (dd, J=1.7, 8.1 Hz, 1H), 6.98 (br s, 1H), 7.04 (d, J=8.1 Hz, 1H), 7.30 (m, 3H), 7.56 (d, J=8.4 Hz, 1H), 7.66 (d, J=8.1 Hz, 1H), 7.76 (s, 1H), 8.29 (d, J=8.2 Hz, 1H), 9.41 (s, 1H), 9.65 (br s, 1H), 9.68 (s, 1H), 14.15 (s, 1H).

EXAMPLE 307

4-(4-Acetylaminophenyl)-7-[1H-5-(piperidinomethyl)indol-2-yl]isoindolinone hydrochloride (Compound 307)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (47.3 mg, 0.0797 mmol) was dissolved in dimethoxyethane (3.8 mL), and the solution was treated with 4'-(4,4,5,5-tetramethyl-1,3,2-dioxaboran-2-yl)acetoalinide (41.6 mg, 0.159 mmol), [bis(diphenylphosphino)ferrocene]dichloropalladium (52 mg, 0.0064 mmol), potassium carbonate (55 mg, 0.40 mmol) and water (0.029 mL), followed by purification by preparative thin-layer chromatography (chloroform/methanol=6/1) to obtain 4-(4-acetylaminophenyl)-7-[1-(tert-butoxycarbonyl)-5-(piperidino methyl)indol-2-yl]isoindolinone (31.6 mg, yield 69%).

ESI-MS m/z: 579 [M+H]$^+$: $^1$H-NMR (CDCl$_3$) δ(ppm): 1.28 (s, 9H), 1.43 (s, 2H), 1.58 (s, 4H), 2.18 (s, 3H), 2.45 (s, 4H), 3.61 (s, 2H), 4.24 (s, 2H), 6.54 (s, 1H), 7.17-7.36 (m, 2H), 7.30 (d, J=8.1 Hz, 2H), 7.48 (br s, 2H), 7.60 (d, J=8.4 Hz, 2H), 7.70 (br s, 1H), 8.10 (br s, 1H), 8.17 (d, J=8.6 Hz, 1H).

Step 2

In a similar manner to Step 2 of Example 8, 4-(4-acetylaminophenyl)-7-[1-(tert-butoxycarbonyl)-5-(piperidinomethyl)indol-2-yl]isoindolinone (31.6 mg, 0.0546 mmol) was dissolved in methanol (1.3 mL), and the solution was treated with 10% hydrogen chloride-methanol solution (1.3 mL). The precipitated solid was collected by filtration and washed with methanol, followed by drying under reduced pressure to obtain Compound 307 (17.2 mg, yield 61%).

ESI-MS m/z: 479 [M+H]$^+$; $^1$H-NMR (DMSO-d$_6$) δ(ppm): 1.66-1.76 (m, 6H), 2.48 (s, 3H), 2.85 (br s, 2H), 3.31 (m; 2H), 4.30 (d, J=4.5 Hz, 1H), 4.61 (s, 2H), 7.31 (m, 4H), 7.56 (d, J=8.4 Hz, 1H), 7.66 (m, 4H), 7.78 (s, 1H), 8.30 (d, J=8.3 Hz, 1H), 9.46 (s, 1H), 10.08 (br s, 1H), 14.14 (s, 1H).

EXAMPLE 308

4-[4-(Hydroxymethyl)phenyl]-7-[1H-5-(piperidinomethyl)indol-2-yl]isoindolinone hydrochloride (Compound 308)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (80.0 mg, 0.135 mmol) was dissolved in dimethoxyethane (9.6 mL), and the solution was treated with 4-(hydroxymethyl)phenylborate (62.0 mg, 0.405 mmol), [bis(diphenylphosphino)ferrocene]dichloropalladium (22 mg, 0.027 mmol), potassium carbonate (93.0 mg, 0.675 mmol) and water (0.098 mL), followed by purification by preparative thin-layer chromatography (chloroform/methanol=6/1) to obtain 4-[4-(hydroxymethyl)phenyl]-7-[1-(tert-butoxycarbonyl)-5-(piperidinomethyl)indol-2-yl]isoindolinone (47.7 mg, yield 64%).

APCI-MS m/z: 552 [M+H]$^+$; $^1$H-NMR (CDCl$_3$) δ(ppm): 1.27 (s, 9H), 1.44 (br s, 2H), 1.61 (br s, 4H), 2.44 (br s, 4H), 3.58 (s, 2H), 4.34 (br s, 2H), 4.77 (s, 2H), 6.53 (s, 1H), 7.24 (d, J=9.6 Hz, 1H), 7.42 (m, 3H), 7.48-7.55 (m, 4H), 8.03 (br s, 1H), 8.14 (d, J=8.6 Hz, 1H).

Step 2

In a similar manner to Step 2 of Example 8, 4-[4-(hydroxymethyl)phenyl]-7-[1-(tert-butoxycarbonyl)-5-(piperidinomethyl)indol-2-yl]isoindolinone (46.0 mg, 0.0834 mmol) was dissolved in methanol (1.6 mL), and the solution was treated with 10% hydrogen chloride-methanol solution (2.3 mL). The precipitated solid was collected by filtration and washed with methanol, followed by drying under reduced pressure to obtain Compound 308 (30.2 mg, yield 74%).

APCI-MS m/z: 452 [M+H]$^+$; $^1$H-NMR (DMSO-d$_6$) δ(ppm): 1.77 (m, 6H), 2.84 (m, 2H), 3.32 (m, 2H), 4.31 (d, J=4.9 Hz, 2H), 4.57 (s, 2H), 4.61 (s, 2H), 7.31 (dd, J=1.4, 8.4 Hz, 1H), 7.33 (s, 1H), 7.45 (d, J=8.2 Hz, 2H), 7.57 (d, J=8.2 Hz, 1H), 7.60 (d, J=8.7 Hz, 2H), 7.68 (d, J=8.2 Hz, 1H), 7.78 (s, 1H), 8.30 (d, J=8.4 Hz, 1H), 9.44 (s, 1H), 10.01 (br s, 1H), 14.16 (s, 1H).

EXAMPLE 309

4-(4-Hydroxy-3,5-dimethylphenyl)-7-[1H-5-(piperidinomethyl)indol-2-yl]isoindolinone hydrochloride (Compound 309)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (80.0 mg, 0.135 mmol) was dissolved in dimethoxyethane (9.6 mL), and the solution was treated with 2,6-dimethyl-4-(4,4,5,5-tetramethyl-1,3,2-dioxaboran-2-yl)phenol (42.0 mg, 0.168 mmol), [bis(diphenylphosphino)ferrocene]dichloropalladium (5.5 mg, 0.0067 mmol), potassium carbonate (58.0 mg, 0.421 mmol) and water (0.030 mL), followed by purification by preparative thin-layer chromatography (chloroform/methanol=6/1) to obtain 4-(4-hydroxy-3,5-dimethylphenyl)-7-[1-(tert-butoxycarbonyl)-5-(piperidinomethyl)indol-2-yl]isoindolinone (39.1 mg, yield 82%).

APCI-MS m/z: 566 [M+H]$^+$; $^1$H-NMR (CDCl$_3$) δ(ppm): 1.30 (s, 9H), 1.45 (br s, 2H), 1.64 (m, 4H), 2.29 (s, 6H), 2.52 (br s, 4H), 3.67 (s, 2H), 4.48 (s, 2H), 6.49 (s, 1H), 7.07 (s, 2H), 7.23 (dd, J=1.5, 8.4 Hz, 1H), 7.44 (br s, 1H), 7.45 (d, J=7.6 Hz, 1H), 7.48 (br s, 1H), 7.52 (d, J=7.8 Hz, 1H), 8.17 (d, J=8.4 Hz, 1H).

Step 2

In a similar manner to Step 2 of Example 8, 4-(4-hydroxy-3,5-dimethylphenyl)-7-[1-(tert-butoxycarbonyl)-5-(piperidinomethyl)indol-2-yl]isoindolinone (39.0 mg, 0.0689 mmol) was dissolved in methanol (1.6 mL), and the solution was treated with 10% hydrogen chloride-methanol solution (1.6 mL). The precipitated solid was collected by filtration and washed with methanol, followed by drying under reduced pressure to obtain Compound 309 (25.4 mg, yield 73%).

APCI-MS m/z: 466 [M+H]$^+$; $^1$H-NMR (DMSO-d$_6$) δ(ppm): 1.66-1.77 (m, 6H), 2.23 (s, 6H), 2.87 (m, 2H), 3.31 (s, 2H), 4.32 (s, 2H), 4.60 (s, 2H), 7.19 (s, 2H), 7.28 (m, 2H), 7.56 (d, J=8.6 Hz, 1H), 7.61 (d, J=8.1 Hz, 1H), 7.76 (s, 1H), 8.25 (d, J=8.2 Hz, 1H), 8.50 (s, 1H), 9.40 (s, 1H), 9.78 (br s, 1H), 14.16 (s, 1H).

EXAMPLE 310

4-(4-Methanesulfonylaminophenyl)-7-[1H-5-(piperidinomethyl)indol-2-yl]isoindolinone hydrochloride (Compound 310)

Step 1

In a similar manner to Step 1 of Example 152, 4-trifluoromethanesulfonyloxy-7-[(1-(tert-butoxycarbonyl)-5-(piperidinomethyl)indol-2-yl]isoindolinone (50.0 mg, 0.0840 mmol) was dissolved in dimethoxyethane (3.5 mL), and the solution was treated with N-[4-(4,4,5,5-tetramethyl-1,3,2-dioxaboran-2-yl)phenyl]methanesulfonamide (49.9 mg, 0.168 mmol), [bis(diphenylphosphino)ferrocene]dichloropalladium (5.5 mg, 0.0067 mmol), potassium carbonate (58.0 mg, 0.420 mmol) and water (0.030 mL), followed by purification by preparative thin-layer chromatography (chloroform/methanol=5/1) to obtain 4-(4-methanesulfonylaminophenyl)-7-[1-(tert-butoxycarbonyl)-5-(piperidinomethyl)indol-2-yl]isoindolinone (31.3 mg, yield 61%).

APCI-MS m/z: 615 [M+H]$^+$; $^1$H-NMR (CDCl$_3$+CD$_3$OD) δ(ppm): 1.34 (s, 9H), 1.50 (br s, 2H), 1.73 (br s, 4H), 2.66 (br s, 4H), 3.06 (s, 3H), 3.86 (br s, 2H), 4.50 (s, 2H), 6.61 (s, 1H), 7.33 (m, 1H), 7.37 (d, J=8.6 Hz, 2H), 7.47 (d, J=8.6 Hz, 2H), 7.55 (d, J=7.7 Hz, 1H), 7.59 (br s, 1H), 7.60 (d, J=7.9 Hz, 1H), 8.22 (d, J=8.6 Hz, 1H).

Step 2

In a similar manner to Step 2 of Example 8, 4-(4-methanesulfonylaminophenyl)-7-[1-(tert-butoxycarbonyl)-5-(piperidinomethyl)indol-2-yl]isoindolinone (30.0 mg, 0.0488 mmol) was dissolved in methanol (1.0 mL), and the solution was treated with 10% hydrogen chloride-methanol solution (1.0 mL). The precipitated solid was collected by filtration and washed with methanol, followed by drying under reduced pressure to obtain Compound 310 (10.7 mg, yield 40%).

APCI-MS m/z: 515 [M+H]$^+$; $^1$H-NMR (DMSO-d$_6$) δ(ppm): 1.71-1.77 (m, 6H), 2.85 (m, 2H), 3.06 (s, 3H), 3.32 (m, 2H), 4.31 (d, J=4.6 Hz, 2H), 4.63 (s, 2H), 7.29 (dd, J=1.3, 8.4 Hz, 1H), 7.33 (d, J=8.4 Hz, 2H), 7.34 (s, 1H), 7.56 (d, J=8.4 Hz, 1H), 7.62 (d, J=8.6 Hz, 2H), 7.68 (d, J=8.2 Hz, 1H), 7.77 (s, 1H), 8.30 (d, J=8.4 Hz, 1H), 9.46 (s, 1H), 9.84 (br s, 1H), 9.99 (s, 1H), 14.16 (s, 1H).

EXAMPLE 311

4-(3-Acetylphenyl)-7-[1H-5-(piperidinomethyl)indol-2-yl]isoindolinone hydrochloride (Compound 311)

Step 1

In a similar manner to Step 1 of Example 152, 4-trifluoromethanesulfonyloxy-7-[(1-(tert-butoxycarbonyl)-5-(piperidinomethyl)indol-2-yl]isoindolinone (65.7 mg, 0.111 mmol) was dissolved in dimethoxyethane (5.3 mL), and the solution was treated with 3-acetylphenylboronic acid (54.0 mg, 0.333 mmol), [bis(diphenylphosphino)ferrocene]dichloropalladium (14.4 mg, 0.0178 mmol), potassium carbonate (77.0 mg, 0.555 mmol) and water (0.040 mL), followed by purification by preparative thin-layer chromatography (chloroform/methanol/acetonitrile=6/0.5/0.5) to obtain 4-(3-acetylphenyl)-7-[1-(tert-butoxycarbonyl)-5-(piperidinomethyl)indol-2-yl]isoindolinone (31.1 mg, yield 62%).

ESI-MS m/z: 564 [M+H]$^+$; $^1$H-NMR (CDCl$_3$) δ(ppm): 1.35 (s, 9H), 1.45 (m, 2H), 1.63 (br s, 4H), 2.48 (br s, 4H), 2.69 (s, 3H), 3.66 (s, 2H), 4.48 (s, 2H), 6.61 (s, 1H), 7.32 (d, J=8.6 Hz, 1H), 7.54 (s, 1H), 7.59 (m, 2H), 7.63 (d, J=7.7 Hz, 1H), 7.70 (d, J=7.7 Hz, 1H), 8.03 (d, J=7.6 Hz, 1H), 8.12 (m, 1H), 8.20 (d, J=8.6 Hz, 1H).

Step 2

In a similar manner to Step 2 of Example 8, 4-(3-acetylphenyl)-7-[1-(tert-butoxycarbonyl)-5-(piperidinomethyl)indol-2-yl]isoindolinone (39.0 mg, 0.0692 mmol) was dissolved in methanol (1.6 mL), and the solution was treated with 10% hydrogen chloride-methanol solution (1.6 mL). The precipitated solid was collected by filtration and washed with methanol, followed by drying under reduced pressure to obtain Compound 311 (15.7 mg, yield 45%).

APCI-MS m/z: 464 [M+H]$^+$; $^1$H-NMR (DMSO-d$_6$) δ(ppm): 1.70-1.77 (m, 6H), 2.66 (s, 3H), 2.85 (m, 2H), 3.31 (m, 2H), 4.32 (d, J=4.6 Hz, 2H), 4.63 (s, 2H), 7.31 (d, J=8.3 Hz, 1H), 7.37 (s, 1H), 7.57 (d, J=8.3 Hz, 1H), 7.67 (dd, J=7.6, 7.9 Hz, 1H), 7.77 (d, J=8.6 Hz, 1H), 7.78 (s, 1H), 7.92 (d, J=7.6 Hz, 1H), 8.01 (d, J=7.6 Hz, 1H), 8.14 (s, 1H), 8.35 (d, J=8.3 Hz, 1H), 9.47 (s, 1H), 9.94 (br s, 1H), 14.16 (s, 1H).

EXAMPLE 312

4-(Benzo[1,3]dioxol-5-yl)-7-[1H-5-(piperidinomethyl)indol-2-yl]isoindolinone hydrochloride (Compound 312)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (50.0 mg, 0.0842 mmol) was dissolved in dimethoxyethane (4 mL), and the solution was treated with 3,4-methylenedioxybenzeneboronic acid (70.0 mg, 0.421 mmol). [bis(diphenylphosphino)

ferrocene]dichloropalladium (13.7 mg, 0.0168 mmol), potassium carbonate (116 mg, 0.842 mmol) and water (0.060 mL), followed by purification by preparative thin-layer chromatography (chloroform/methanol/acetonitrile=8/0.5/0.5 to 0.4/0.5/0.5) to obtain 4-(benzo[1,3]dioxol-5-yl)-7-[1-(tert-butoxycarbonyl)-5-(piperidinomethyl)indol-2-yl]isoindolinone (22.2 mg, yield 47%).

APCI-MS m/z: 566 [M+H]$^+$; $^1$H-NMR (CDCl$_3$) δ(ppm): 1.31 (s, 9H), 1.43 (m, 2H), 1.60 (m, 4H), 2.44 (br s, 4H), 3.62 (s, 2H), 4.45 (s, 2H), 6.04 (s, 2H), 6.57 (s, 1H), 6.92 (m, 3H), 7.29 (dd, J=1.2, 8.6 Hz, 1H), 7.49 (d, J=7.9 Hz, 1H), 7.50 (m, 1H), 7.53 (d, J=7.9 Hz, 1H), 7.58 (s, 1H), 8.18 (d, J=8.3 Hz, 1H).

Step 2

In a similar manner to Step 2 of Example 8, 4-(benzo[1,3]dioxol-5-yl)-7-[1-(tert-butoxycarbonyl)-5-(piperidinomethyl)indol-2-yl]isoindolinone (22.2 mg, 0.0392 mmol) was dissolved in methanol (1.3 mL), and the solution was treated with 10% hydrogen chloride-methanol solution (1.3 mL). The precipitated solid was collected by filtration and washed with methanol, followed by drying under reduced pressure to obtain Compound 312 (15.1 mg, yield 78%).

APCI-MS m/z: 466 [M+H]$^+$; $^1$H-NMR (DMSO-d$_6$) δ(ppm): 1.69-1.77 (m, 6H), 2.86 (m, 2H), 3.30 (m, 2H), 4.31 (d, J=4.8 Hz, 2H), 4.60 (s, 2H), 6.09 (s, 2H), 7.04 (d, J=8.1 Hz, 1H), 7.10 (dd, J=1.4, 8.2 Hz, 1H), 7.28 (m, 3H), 7.56 (d, J=8.6 Hz, 1H), 7.64 (d, J=8.3 Hz, 1H), 7.77 (s, 1H), 8.27 (d, J=8.3 Hz, 1H), 9.43 (s, 1H), 9.91 (br s, 1H), 14.15 (s, 1H).

EXAMPLE 313

4-(4-Aminophenyl)-7-[1H-5-(piperidinomethyl)indol-2-yl]isoindolinone hydrochloride
(Compound 313)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (150 mg, 0.250 mmol) was dissolved in dimethoxyethane (10.5 mL), and the solution was treated with 4-(4,4,5,5-tetramethyl-1,3,2-dioxaboran-2-yl)aniline (110 mg, 0.500 mmol), [bis(diphenylphosphino)ferrocene]dichloropalladium (25 mg, 0.030 mmol), potassium carbonate (173 mg, 1.25 mmol) and water (0.090 mL), followed by purification by preparative thin-layer chromatography (chloroform/methanol=5/1) to obtain 4-(4-aminophenyl)-7-[1-(tert-butoxycarbonyl)-5-(piperidinomethyl)indol-2-yl]isoindolinone (76.5 mg, yield 57%).

ESI-MS m/z: 53.7 [M+H]$^+$; $^1$H-NMR (CDCl$_3$) δ(ppm): 1.29 (s, 9H), 1.44 (br s, 2H), 1.61 (br s, 4H), 2.46 (br s, 4H), 3.63 (s, 2H), 3.85 (br s, 2H), 4.45 (s, 2H), 6.56 (s, 1H), 6.76 (d, J=8.4 Hz, 2H), 7.25-7.31 (m, 3H), 7.47 (d, J=7.9 Hz, 1H), 7.50 (s, 1H), 7.53 (d, J=7.7 Hz, 1H), 8.03 (s, 1H), 8.20 (d, J=8.6 Hz, 1H).

Step 2

4-(4-Aminophenyl)-7-[1-(tert-butoxycarbonyl)-5-(piperidinomethyl)indol-2-yl]isoindolinone (21.2 mg, 0.0395 mmol) was suspended in water (1.7 mL), and the suspension was added with urea (12.0 mg, 0.198 mmol), acetic acid (0.034 mL) and concentrated hydrochloric acid (0.034 mL), followed by stirring at 100° C. for 1.7 hours. The reaction mixture was cooled to room temperature, and the precipitated solid was collected by filtration and washed with water, followed by drying under reduced pressure to obtain Compound 313 (17.3 mg, yield 93%).

APCI-MS m/z: 437 [M+H]$^+$; $^1$H-NMR (DMSO-d$_6$) δ(ppm): 1.65-1.77 (m, 6H), 2.86 (m, 2H), 3.32 (m, 2H), 4.31 (s, 2H), 4.60 (s, 2H), 6.99 (d, J=8.3 Hz, 2H), 7.29 (m, 2H), 7.48 (d, J=8.3 Hz, 2H), 7.55 (d, J=8.3 Hz, 1H), 7.64 (d, J=8.3 Hz, 1H), 7.77 (s, 1H), 8.26 (d, J=8.3 Hz, 1H), 9.42 (s, 1H), 9.98 (s, 1H), 14.14 (s, 1H).

EXAMPLE 314

4-(4-Ureidophenyl)-7-[1H-5-(piperidinomethyl)indol-2-yl]isoindolinone hydrochloride
(Compound 314)

Step 1

4-(4-Aminophenyl)-7-[1-(tert-butoxycarbonyl)-5-(piperidinomethyl)indol-2-yl]isoindolinone (39.2 mg, 0.0730 mmol) was dissolved in acetic acid (1.57 mL) and water (1.57 mL), and the solution was added with aqueous sodium cyanate solution (0.139 mol/L, 1.57 mL, 0.219 mmol), followed by stirring at 40° C. for 2.3 hours. The reaction mixture was added with saturated aqueous sodium hydrogencarbonate solution and extracted with ethyl acetate. The organic layer was washed with saturated brine and dried over anhydrous sodium sulfate. The solvent was evaporated under reduced pressure and the residue was purified by preparative thin-layer chromatography (chloroform/methanol/7 mol/L ammonia-methanol solution=10/0.5/0.5) to obtain 4-(4-ureidophenyl)-7-[1-(tert-butoxycarbonyl)-5-(piperidinomethyl)indol-2-yl]isoindolinone (23.7 mg, yield 56%).

ESI-MS m/z: 580 [M+H]$^+$; $^1$H-NMR (CDCl$_3$) δ(ppm): 1.30 (s, 9H), 1.43 (br s, 2H), 1.56 (br s, 4H), 2.39 (br s, 4H), 3.53 (s, 2H), 4.25 (s, 2H), 4.95 (s, 2H), 6.53 (s, 1H), 7.26-7.46 (m, 10H), 8.14 (d, J=8.4 Hz, 1H).

Step 2

In a similar manner to Step 2 of Example 8, 4-(4-ureidophenyl)-7-[1-(tert-butoxycarbonyl)-5-(piperidinomethyl)indol-2-yl]isoindolinone (20.7 mg, 0.0357 mmol) was dissolved in methanol (1.0 mL), and the solution was treated with 10% hydrogen chloride-methanol solution (1.0 mL). The precipitated solid was collected by filtration and washed with methanol, followed by drying under reduced pressure to obtain Compound 314 (14.6 mg, yield 79%).

ESI-MS m/z: 480 [M+H]$^+$; $^1$H-NMR (DMSO-d$_6$) δ(ppm): 1.65-1.77 (m, 6H), 2.86 (m, 2H), 3.32 (m, 2H), 4.30 (d, J=4.3 Hz, 2H), 4.61 (s, 2H), 7.30 (m, 2H), 7.48-7.56 (m, 5H), 7.66 (d, J=8.3 Hz, 1H), 7.77 (s, 1H), 8.27 (d, J=8.3 Hz, 1H), 8.95 (s, 1H), 9.42 (s, 1H), 10.00 (br s, 1H), 14.15 (s, 1H).

EXAMPLE 315

4-(4-Methanesulfonyloxyphenyl)-7-[1H-5-(piperidinomethyl)indol-2-yl]isoindolinone hydrochloride
(Compound 315)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (300 mg, 0.505 mmol) was dissolved in dimethoxyethane (21 mL), and the solution was treated with 4-(4,4,5,5-tetramethyl-1,3,2-dioxaboran-2-yl)phenol (222 mg, 1.01 mmol), [bis(diphenylphosphino)ferrocene]dichloropalladium (33.0 mg, 0.0404 mmol), potassium carbonate (349 mg, 2.53 mmol) and water (0.182 mL), followed by purification by flash column chromatography (chloroform/methanol=90/10 to 80/20)

to obtain 4-(4-hydroxyphenyl)-7-[1-(tert-butoxycarbonyl)-5-(piperidinomethyl)indol-2-yl]isoindolinone (179 mg, yield 66%).

ESI-MS m/z: 538 [M+H]$^+$; $^1$H-NMR (DMSO-d$_6$) δ(ppm): 1.17 (s, 9H), 1.35-1.49 (m, 6H), 2.34 (m, 4H), 3.51 (s, 2H), 4.47 (s, 2H), 6.61 (s, 1H), 6.89 (d, J=8.6 Hz, 2H), 7.26 (d, J=8.4 Hz, 1H), 7.46 (m, 4H), 7.60 (d, J=7.7 Hz, 1H), 8.08 (d, J=8.2 Hz, 1H), 8.64 (s, 1H), 9.66 (s, 1H).

Step 2

4-(4-Hydroxyphenyl)-7-[1-(tert-butoxycarbonyl)-5-(piperidinomethyl)indol-2-yl]isoindolinone (178 mg, 0.330 mmol) was suspended in dichloromethane (14 mL), and the suspension was added with triethylamine (0.092 mL, 0.66 mmol) and methanesulfonyl chloride (0.031 mL, 0.40 mmol) under ice-cooling, followed by stirring for 2.5 hours. The reaction mixture was filtered, and the filtrate was added with water and extracted with ethyl acetate and chloroform. The organic layer was washed with saturated brine and dried over anhydrous sodium sulfate. The solvent was evaporated under reduced pressure and the residue was purified by preparative thin-layer chromatography (chloroform/methanol/7 mol/L ammonia-methanol solution=10/0.5/0.5) to obtain 4-(4-methanesulfonyloxyphenyl)-7-[1-(tert-butoxycarbonyl)-5-(piperidinomethyl)indol-2-yl]isoindolinone (53.4 mg, yield 26%).

APCI-MS m/z: 616 [M+H]$^+$; $^1$H-NMR (CDCl$_3$) δ(ppm): 1.37 (s, 9H), 1.42-1.61 (m, 6H), 2.43 (br s, 4H), 3.23 (s, 3H), 3.60 (s, 2H), 4.47 (s, 2H), 6.59 (s, 1H), 6.61 (br s, 1H), 7.26-7.56 (m, 8H), 8.15 (d, J=8.6 Hz, 1H).

Step 3

In a similar manner to Step 2 of Example 8, 4-(4-methanesulfonyloxyphenyl)-7-[1-(tert-butoxycarbonyl)-5-(piperidinomethyl)indol-2-yl]isoindolinone (50.9 mg, 0.0827 mmol) was dissolved in methanol (2.0 mL), and the solution was treated with 10% hydrogen chloride-methanol solution (2.0 mL). The precipitated solid was collected by filtration and washed with methanol, followed by drying under reduced pressure to obtain Compound 315 (27.2 mg, yield 59%).

APCI-MS m/z: 516 [M+H]$^+$; $^1$H-NMR (DMSO-d$_6$) δ(ppm): 1.66-1.78 (m, 6H), 2.87 (m, 2H), 3.32 (m, 2H), 3.45 (s, 3H), 4.32 (d, J=4.4 Hz, 2H), 4.64 (s, 2H), 7.29 (d, J=8.4 Hz, 1H), 7.37 (s, 1H), 7.49 (d, J=8.4 Hz, 2H), 7.58 (d, J=8.4 Hz, 1H), 7.72 (d, J=8.1 Hz, 1H), 7.77 (d, J=8.8 Hz, 2H), 7.77 (s, 1H), 8.33 (d, J=8.4 Hz, 1H), 9.48 (s, 1H), 9.73 (br s, 1H), 14.17 (s, 1H).

EXAMPLE 316

4-(4-Sulfamoyloxyphenyl)-7-[1H-5-(piperidinomethyl)indol-2-yl]isoindolinone hydrochloride (Compound 316)

Step 1

4-(4-Hydroxyphenyl)-7-[1-(tert-butoxycarbonyl)-5-(piperidinomethyl)indol-2-yl]isoindolinone (56.2 mg, 0.105 mmol) was dissolved in N,N-dimethylacetoamide (3.9 mL), and the solution was added with sulfamoyl chloride (61 mg, 0.53 mmol), followed by stirring at room temperature for 17 hours. The reaction mixture was added with water and extracted with ethyl acetate and chloroform. The organic layer was washed with saturated brine and dried over anhydrous sodium sulfate. The solvent was evaporated under reduced pressure and the residue was purified by preparative thin-layer chromatography (chloroform/methanol=5/1) to obtain 4-(4-sulfamoyloxyphenyl)-7-[1-(tert-butoxycarbonyl)-5-(piperidinomethyl)indol-2-yl]isoindolinone (36.2 mg, yield 56%).

ESI-MS m/z: 617 [M+H]$^+$; $^1$H-NMR (CDCl$_3$+CD$_3$OD) δ(ppm): 1.34 (s, 9H), 1.87 (m, 2H), 2.06 (m, 4H), 2.92 (br s, 4H), 4.12 (s, 2H), 4.50 (s, 2H), 6.64 (s, 1H), 7.39 (m, 1H), 7.47-7.64 (m, 6H), 7.69 (s, 1H), 8.28 (d, J=8.8 Hz, 1H).

Step 2

In a similar manner to Step 2 of Example 8, 4-(4-sulfamoyloxyphenyl)-7-[1-(tert-butoxycarbonyl)-5-(piperidinomethyl)indol-2-yl]isoindolinone (49.6 mg, 0.0804 mmol) was dissolved in methanol (1.7 mL), and the solution was added with 10% hydrogen chloride-methanol solution (2.7 mL). The precipitated solid was collected by filtration and washed with methanol, followed by drying under reduced pressure to obtain Compound 316 (35.7 mg, yield 80%).

ESI-MS m/z: 517 [M+H]$^+$; $^1$H-NMR (DMSO-d$_6$) δ(ppm): 1.79 (m, 6H), 2.87 (m, 2H), 3.34 (m, 2H), 4.33 (d, J=4.6 Hz, 2H), 4.65 (s, 2H), 7.33 (dd, J=1.4, 8.3 Hz, 1H), 7.38 (s, 1H), 7.43 (d, J=8.6 Hz, 2H), 7.59 (d, J=8.4 Hz, 1H), 7.72 (d, J=8.1 Hz, 1H), 7.77 (d, J=8.8 Hz, 2H), 7.80 (s, 1H), 8.14 (s, 2H), 8.35 (d, J=8.3 Hz, 1H), 9.49 (s, 1H), 9.93 (br s, 1H), 14.17 (s, 1H).

EXAMPLE 317

4-(3-Carbamoylphenyl)-7-[1H-5-(piperidinomethyl)indol-2-yl]isoindolinone (Compound 317)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (80.0 mg, 0.135 mmol) was dissolved in dimethoxyethane (5.6 mL), and the solution was added with (3-aminocarbonylphenyl)boronic acid (89 mg, 0.54 mmol), [bis(diphenylphosphino)ferrocene]dichloropalladium (17.6 mg, 0.0216 mmol), potassium carbonate (93.0 mg, 0.675 mmol) and water (0.049 mL), followed by purification by preparative thin-layer chromatography (chloroform/methanol=5/1) to obtain 4-(3-carbamoylphenyl)-7-[1-(tert-butoxycarbonyl)-5-(piperidinomethyl)indol-2-yl]isoindolinone (36.1 mg, yield 47%).

ESI-MS m/z: 565 [M+H]$^+$; $^1$H-NMR (CDCl$_3$+CD$_3$OD) δ(ppm): 1.33 (s, 9H), 1.45 (m, 2H), 1.62 (m, 4H), 2.49 (br s, 4H), 3.65 (s, 2H), 4.50 (s, 2H), 6.58 (s, 1H), 7.29 (dd, J=1.6, 8.6 Hz; 1H), 7.50 (s, 1H), 7.55-7.66 (m, 4H), 7.89 (d, J=7.4 Hz, 1H), 8.01 (br s, 1H), 8.18 (d, J=8.6 Hz, 1H).

Step 2

In a similar manner to Step 2 of Example 8, 4-(3-carbamoylphenyl)-7-[1-(tert-butoxycarbonyl)-5-(piperidinomethyl)indol-2-yl]isoindolinone (36.1 mg, 0.0639 mmol) was dissolved in methanol (1.44 mL), and the solution was added with 10% hydrogen chloride-methanol solution (1.44 mL), followed by purification by preparative thin-layer chromatography (chloroform/methanol/7 mol/L ammonia-methanol solution=12/0.5/0.5 to 20/0.5/0.5) to obtain Compound 317 (12.6 mg, yield 41%) and Compound 318 (14.7 mg, yield 50%).

APCI-MS m/z: 465 [M+H]$^+$; $^1$H-NMR (CDCl$_3$+CD$_3$OD) δ(ppm): 1.44 (m, 2H), 1.60 (m, 4H), 2.48 (br s, 4H), 3.62 (s, 2H), 4.50 (s, 2H), 7.09 (s, 1H), 7.16 (dd, J=1.5, 8.4 Hz, 1H), 7.42 (d, J=8.4 Hz, 1H), 7.52-7.61 (m, 4H), 7.87 (ddd, J=1.7, 1.9, 7.0 Hz, 1H), 7.98 (d, J=1.8 Hz, 1H), 8.16 (d, J=8.3 Hz, 1H).

EXAMPLE 318

4-(3-Methoxycarbonylphenyl)-7-[1H-5-(piperidinomethyl)indol-2-yl]isoindolinone (Compound 318)

In Step 2 of Example 317, Compound 318 (14.7 mg, yield 50%) was obtained.

ESI-MS m/z: 480 [M+H]$^+$; $^1$H-NMR (CDCl$_3$+CD$_3$OD) δ(ppm): 1.46 (m, 2H), 1.60 (m, 4H), 2.48 (br s, 4H), 3.62 (s, 2H), 3.97 (s, 3H), 4.52 (s, 2H), 7.12 (s, 1H), 7.17 (d, J=8.4 Hz, 1H), 7.44 (d, J=8.3 Hz, 1H), 7.55-7.60 (m, 3H), 7.66 (d, J=7.8 Hz, 1H), 8.09 (d, J=7.6 Hz, 1H), 8.14 (s, 1H), 8.20 (d, J=8.1 Hz, 1H).

EXAMPLE 319

4-(4-Methoxyphenyl)-7-[1H-5-(piperidinomethyl)indol-2-yl]isoindolinone hydrochloride (Compound 319)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (80.0 mg, 0.135 mmol) was dissolved in dimethoxyethane (5.6 mL), and the solution was added with 4-methoxyphenylboronic acid (62 mg, 0.41 mmol), [bis(diphenylphosphino)ferrocene]dichloropalladium (13.2 mg, 0.0166 mmol), potassium carbonate (93.0 mg, 0.675 mmol) and water (0.049 mL), followed by purification by preparative thin-layer chromatography (chloroform/methanol=8/1) to obtain 4-(4-methoxyphenyl)-7-[1-(tert-butoxycarbonyl)-5-(piperidinomethyl)indol-2-yl]isoindolinone (53.2 mg, yield 71%).

ESI-MS m/z: 552 [M+H]$^+$; $^1$H-NMR (CDCl$_3$) δ(ppm): 1.32 (s, 9H), 1.44 (m, 2H), 1.64 (m, 4H), 2.52 (br s, 4H), 3.72 (s, 2H), 3.89 (s, 3H), 4.49 (s, 2H), 6.57 (s, 1H), 7.02 (d, J=8.7 Hz, 2H), 7.23 (br s, 1H), 7.27 (m, 1H), 7.42 (d, J=8.7 Hz, 2H), 7.49-7.58 (m, 3H), 8.1.9 (d, J=8.6 Hz, 1H).

Step 2

In a similar manner to Step 2 of Example 8, 4-(4-methoxyphenyl)-7-[1-(tert-butoxycarbonyl)-5-(piperidinomethyl)indol-2-yl]isoindolinone (47.2 mg, 0.0856 mmol) was dissolved in methanol (1.7 mL), and the solution was added with 10% hydrogen chloride-methanol solution (2.7 mL). The precipitated solid was collected by filtration and washed with methanol, followed by drying under reduced pressure to obtain Compound 319 (3.0.5 mg, yield 73%).

APCI-MS m/z: 452 [M+H]$^+$; $^1$H-NMR (DMSO-d$_6$) δ(ppm): 1.70 (m, 6H), 2.86 (m, 2H), 3.32 (m, 2H), 3.82 (s, 3H), 4.30 (d, J=4.6 Hz, 2H), 4.60 (s, 2H), 7.06 (d, J=8.8 Hz, 2H), 7.30 (m, 2H), 7.55 (d, J=8.1 Hz, 1H), 7.58 (d, J=8.8 Hz, 2H), 7.65 (d, J=8.3 Hz, 1H), 7.77 (s, 1H), 8.28 (d, J=8.3 Hz, 1H), 9.43 (s, 1H), 10.03 (br s, 1H), 14.15 (s, 1H).

EXAMPLE 320

4-(4-Hydroxy-1-butynyl)-7-[1H-5-(piperidinomethyl)indol-2-yl]isoindolinone hydrochloride (Compound 320)

Step 1

4-Trifluoromethanesulfonyloxy-7-[1-(tert-butoxycarbonyl)-5-(piperidinomethyl)indol-2-yl]isoindolinone (80.0 mg, 0.135 mmol) was dissolved in acetonitrile (4.8 mL), and the solution was added with tetrakis(triphenylphosphine)palladium (23.4 mg, 0.0203 mmol), copper iodide (10 mg, 0.054 mmol), tetrabutylammonium chloride (150 mg, 0.405 mmol), 3-butyn-1-ol (0.051 mL, 0.68 mmol) and triethylamine (0.96 mL, 0.70 mmol), followed by stirring at room temperature for 40.7 hours under argon atmosphere. The reaction mixture was added with water and extracted with ethyl acetate. The organic layer was washed with saturated brine and dried over anhydrous sodium sulfate. The solvent was evaporated under reduced pressure, and the residue was purified by preparative thin-layer chromatography (chloroform/methanol=5/1) to obtain 4-(4-hydroxy-1-butynyl)-7-[1-(tert-butoxycarbonyl)-5-(piperidino methyl)indol-2-yl]isoindolinone (35.5 mg, yield 51%).

ESI-MS m/z: 514 [M+H]$^+$; $^1$H-NMR (CDCl$_3$+CD$_3$OD) δ(ppm): 1.28 (s, 9H), 1.52 (br s, 2H), 1.75 (br s, 4H), 2.59-2.76 (m, 6H), 3.70-3.91 (m, 4H), 4.46 (s, 2H), 6.58 (s, 1H), 7.34 (d, J=8.6 Hz, 1H), 7.42 (d, J=7.7 Hz, 1H), 7.59 (s, 1H), 7.62 (d, J=7.7 Hz, 1H), 8.23 (d, J=8.6 Hz, 1H).

Step 2

In a similar manner to Step 2 of Example 8, 4-(4-hydroxy-1-butynyl)-7-[1-(tert-butoxycarbonyl)-5-(piperidino methyl)indol-2-yl]isoindolinone (34.0 mg, 0.0662 mmol) was dissolved in methanol (1.7 mL), and the solution was added with 10% hydrogen chloride-methanol solution (1.0 mL). The precipitated solid was collected by filtration and washed with methanol, followed by drying under reduced pressure to obtain Compound 320 (11.8 mg, yield 40%).

ESI-MS m/z: 414 [M+H]$^+$; $^1$H-NMR (DMSO-d$_6$) δ(ppm): 1.34 (m, 2H), 1.76 (m, 4H), 2.64 (t, J=6.8 Hz, 2H), 2.85 (m, 2H), 3.33 (m, 2H), 3.62 (t, J=6.8 Hz, 2H), 4.30 (d, J=4.8 Hz, 2H), 4.48 (s, 2H), 7.31 (m, 2H), 7.55 (d, J=8.4 Hz, 1H), 7.64 (d, J=8.3 Hz, 1H), 7.76 (s, 1H), 8.18 (d, J=8.3 Hz, 1H), 9.45 (s, 1H), 9.92 (br s, 1H), 14.03 (s, 1H).

EXAMPLE 321

4-(3-Hydroxy-1-propinyl)-7-[1H-5-(piperidinomethyl)indol-2-yl]isoindolinone hydrochloride (Compound 321)

Step 1

In a similar manner to Step 2 of Example 161, 4-trifluoromethanesulfonyloxy-7-[1-(tert-butoxycarbonyl)-5-(piperidinomethyl)indol-2-yl]isoindolinone (60.0 mg, 0.101 mmol) was dissolved in diethylamine (3.0 mL), and the solution was treated with bis(triphenylphosphine)dichloropalladium (8.6 mg, 0.012 mmol), copper iodide (6.9 mg, 0.036 mmol), propargyl alcohol (0.029 mL, 0.51 mmol), followed by purification by preparative thin-layer chromatography (chloroform/methanol=5/1) to obtain 4-(3-hydroxy-1-propinyl)-7-[1-(tert-butoxycarbonyl)-5-(piperidinomethyl)indol-2-yl]isoindolinone (18.8 mg, yield 37%).

ESI-MS m/z: 500 [M+H]$^+$; $^1$H-NMR (CDCl$_3$) δ(ppm): 1.21 (m, 9H), 1.44 (m, 2H), 1.63 (m, 4H), 2.49 (br s, 4H), 3.66 (br s, 2H), 4.12 (s, 2H), 4.56 (s, 2H), 6.49 (s, 1H), 7.33-7.38 (m, 2H), 7.54 (d, J=7.6 Hz, 1H), 7.5.5 (s, 1H), 7.96 (s, 1H), 8.24 (d, J=8.6 Hz, 1H).

Step 2

In a similar manner to Step 2 of Example 8, 4-(3-hydroxy-1-propinyl)-7-[(1-(tert-butoxycarbonyl)-5-(piperidinomethyl)indol-2-yl]isoindolinone (18.2 mg, 0.0364 mmol) was dissolved in methanol (1.1 mL), and the solution was treated with 10% hydrogen chloride-methanol solution (2.2 mL). The precipitated solid was collected by filtration and washed with methanol, followed by drying under reduced pressure to obtain Compound 321 (9.2 mg, yield 58%).

mp >300° C.; ESI-MS m/z: 400 [M+H]$^+$; $^1$H-NMR (DMSO-d$_6$) δ(ppm): 1.66-1.76 (m, 6H), 2.80 (m, 2H), 3.32 (m, 2H), 4.30 (d, J=4.6 Hz, 2H), 4.38 (s, 2H), 4.49 (s, 2H), 7.30 (d, J=8.3 Hz, 1H), 7.35 (s, 1H), 7.56 (d, J=8.4 Hz, 1H), 7.67 (d, J=8.3 Hz, 1H), 7.77 (s, 1H), 8.21 (d, J=8.4 Hz, 1H), 9.47 (s, 1H), 9.85 (br s, 1H), 14.03 (s, 1H).

EXAMPLE 322

4-(3-Methylamino-1-propinyl)-7-[1H-5-(piperidinomethyl)indol-2-yl]isoindolinone dihydrochloride (Compound 322)

Step 1

In a similar manner to Step 2 of Example 161, 4-trifluoromethanesulfonyloxy-7-[1-(tert-butoxycarbonyl)-5-(piperidinomethyl)indol-2-yl]isoindolinone (80.0 mg, 0.135 mmol) was dissolved in diethylamine (4.0 mL), and the solution was treated with bis(triphenylphosphine)dichloropalladium (14.3 mg, 0.203 mmol), copper iodide (11.6 mg, 0.0608 mmol) and N-methylpropargylamine (0.114 mL, 1.35 mmol), followed by purification by preparative thin-layer chromatography (chloroform/methanol=5/1 to 3/1) to obtain 4-(3-methylamino-1-propinyl)-7-[1-(tert-butoxycarbonyl)-5-(piperidinomethyl)indol-2-yl]isoindolinone (32.6 mg, yield 47%).

ESI-MS m/z: 513 [M+H]$^+$; $^1$H-NMR (CDCl$_3$) δ(ppm): 1.31 (s, 9H), 1.43 (m, 2H), 1.59 (m, 4H), 2.45 (m, 4H), 2.57 (s, 3H), 3.60 (s, 2H), 3.69 (s, 2H), 4.44 (s, 2H), 6.55 (s, 1H), 7.30 (dd, J=1.3, 8.6 Hz, 1H), 7.41 (d, J=7.6 Hz, 1H), 7.50 (br s, 2H), 7.59 (d, J=7.6 Hz, 1H), 8.17 (d, J=8.6 Hz, 1H).

Step 2

In a similar manner to Step 2 of Example 8, 4-(3-methylamino-1-propinyl)-7-[1-(tert-butoxycarbonyl)-5-(piperidinomethyl)indol-2-yl]isoindolinone (44.8 mg, 0.0874 mmol) was dissolved in methanol (1.6 mL), and the solution was treated with 10% hydrogen chloride-methanol solution (3.8 mL). The precipitated solid was collected by filtration and washed with methanol, followed by drying under reduced pressure to obtain Compound 322 (21.8 mg, yield 51%).

ESI-MS m/z: 413 [M+H]$^+$; $^1$H-NMR (DMSO-d$_6$) δ(ppm): 1.65-1.76 (m, 6H), 2.66 (s, 3H), 2.85 (m, 2H), 3.28 (m, 2H), 4.20 (s, 2H), 4.30 (d, J=4.0 Hz, 2H), 4.57 (s, 2H), 7.33 (d, J=8.3 Hz, 1H), 7.38 (s, 1H), 7.56 (d, J=8.3 Hz, 1H), 7.73 (d, J=8.3 Hz, 1H), 7.79 (s, 1H), 8.25 (d, J=8.4 Hz, 1H), 9.55 (br s, 3H), 10.08 (br s, 1H), 14.02 (s, 1H).

EXAMPLE 323

4-Vinyl-7-[1H-5-(piperidinomethyl)indol-2-yl]isoindolinone hydrochloride (Compound 32.3)

Step 1

In a similar manner to Step 1 of Example 152, 4-trifluoromethanesulfonyloxy-7-[1-(tert-butoxycarbonyl)-5-(piperidinomethyl)indol-2-yl]isoindolinone (60.0 mg, 0.114 mmol) was dissolved in dimethoxyethane (3.0 mL), and the solution was treated with 2,4,6-trivinylcyclotriboroxane-pyridine complex (55.0 mg, 0.228 mmol), [bis(diphenylphosphino)ferrocene]dichloropalladium (7.4 mg, 0.0091 mmol), potassium carbonate (79 mg, 0.57 mmol) and water (0.041 mL), followed by purification by preparative thin-layer chromatography (chloroform/methanol=8/1) to obtain 4-vinyl-7-[1-(tert-butoxycarbonyl)-5-(piperidinomethyl)indol-2-yl]isoindolinone (36.0 mg, yield 67%).

ESI-MS m/z: 472 [M+H]$^+$; $^1$H-NMR (CDCl$_3$) δ(ppm): 1.28 (s, 9H), 1.42 (m, 2H), 1.62 (m, 4H), 2.49 (br s, 4H), 3.68 (s, 2H), 4.45 (s, 2H), 5.47 (d, J=11.2 Hz, 1H), 5.79 (d, J=17.5 Hz, 1H), 6.54 (s, 1H), 6.75 (dd, J=11.2, 17.7 Hz, 1H), 7.30 (dd, J=1.4, 8.5 Hz, 1H), 7.43 (d, J=7.9 Hz, 1H), 7.51 (s, 1H), 7.67 (d, J=7.9 Hz, 1H), 8.09 (s, 1H), 8.19 (d, J=8.4 Hz, 1H).

Step 2

In a similar manner to Step 2 of Example 8, 4-vinyl-7-[1-(tert-butoxycarbonyl)-5-(piperidinomethyl)indol-2-yl]isoindolinone (35.0 mg, 0.0742 mmol) was dissolved in methanol (1.4 mL), and the solution was treated with 10% hydrogen chloride-methanol solution (2.8 mL). The precipitated solid was collected by filtration and washed with methanol, followed by drying under reduced pressure to obtain Compound 323 (17.6 mg, yield 58%).

ESI-MS m/z: 372 [M+H]$^+$; $^1$H-NMR (DMSO-d$_6$) δ(ppm): 1.65-1.76 (m, 6H), 3.29 (m, 2H), 3.32 (m, 2H), 4.30 (d, J=4.8 Hz, 2H), 4.59 (s, 2H), 5.50 (d, J=11.1 Hz, 1H), 5.98 (d, J=17.8 Hz, 1H), 6.83 (dd, J=11.2, 17.7 Hz, 1H), 7.30 (d, J=8.9 Hz, 1H), 7.32 (s, 1H), 7.54 (d, J=8.3 Hz, 1H), 7.77 (s, 1H), 7.88 (d, J=8.3 Hz, 1H), 8.21 (d, J=8.3 Hz, 1H), 9.43 (s, 1H), 10.01 (br s, 1H), 14.11 (s, 1H).

EXAMPLE 324

4-Ethyl-7-{1H-5-[(2-hydroxyethylamino)methyl]indol-2-yl}isoindolinone hydrochloride (Compound 324)

Step 1

In a similar manner to Step 2 of Example 6, 4-ethyl-7-[1-(tert-butoxycarbonyl)-5-formylindol-2-yl]isoindolinone (68.0 mg, 0.168 mmol) was dissolved in acetonitrile (5.4 mL), and the solution was treated with ethanolamine (0.041 mL, 0.67 mmol), acetic acid (0.192 mL, 3.36 mmol) and sodium triacetoxyborohydride (71.0 mg, 0.336 mmol). The reaction mixture was added with 1 mol/L hydrochloric acid and extracted with ethyl acetate. The organic layer was washed with sodium carbonate and saturated brine, and dried over anhydrous sodium sulfate. The solvent was evaporated under reduced pressure to obtain 4-ethyl-7-{1-(tert-butoxycarbonyl)-5-[(2-hydroxyethylamino)methyl]indol-2-yl}isoindolinone (72.0 mg, yield 95%).

ESI-MS m/z: 450 [M+H]$^+$; $^1$H-NMR (CDCl$_3$) δ(ppm): 1.25 (s, 9H), 1.28 (t, J=7.6 Hz, 3H), 2.68 (q, J=7.6 Hz, 2H), 2.79 (t, J=5.1 Hz, 2H), 3.64 (t, J=5.1 Hz, 2H), 3.87 (s, 2H), 4.32 (s, 2H), 6.50 (s, 1H), 7.24 (dd, J=1.5, 8.1 Hz, 1H), 7.38 (br s, 2H), 7.45 (s, 1H), 8.00 (s, 1H), 8.21 (d, J=8.6 Hz, 1H).

Step 2

In a similar manner to Step 2 of Example 8, 4-ethyl-7-{1-(tert-butoxycarbonyl)-5-[(2-hydroxyethylamino)methyl]indol-2-yl}isoindolinone (72.0 mg, 0.160 mmol) was dissolved in methanol (2.2 mL), and the solution was treated with 10% hydrogen chloride-methanol solution (4.3 mL). The precipitated solid was collected by filtration and washed with methanol, followed by drying under reduced pressure to obtain Compound 324 (30.5 mg, yield 49%).

ESI-MS m/z: 350 [M+H]$^+$; $^1$H-NMR (DMSO-d$_6$) δ(ppm): 1.24 (t, J=7.5 Hz, 3H), 2.67 (q, J=7.5 Hz, 2H), 2.94 (br s, 2H), 3.66 (m, 2H), 4.20 (s, 2H), 4.50 (s, 2H), 5.22 (m, 1H), 7.23 (s, 1H), 7.27 (d, J=8.4 Hz, 1H), 7.51 (d, J=8.3 Hz, 2H), 7.73 (s, 1H), 8.15 (d, J=8.1 Hz, 1H), 9.00 (br s, 2H), 9.34 (s, 1H), 14.04 (s, 1H).

EXAMPLE 325

4-Methyl-7-{1H-5-[(2-hydroxyethylamino)methyl]
indol-2-yl}isoindolinone hydrochloride
(Compound 325)

Step 1

In a similar manner to Step 2 of Example 6, 4-methyl-7-[1-(tert-butoxycarbonyl)-5-formylindol-2-yl]isoindolinone (54.0 mg, 0.138 mmol) was dissolved in acetonitrile (4.3 mL), and the solution was treated with ethanolamine (0.034 mL, 0.55 mmol), acetic acid (0.158 mL, 2.76 mmol) and sodium triacetoxyborohydride (58.0 mg, 0.276 mmol). The reaction mixture was added with 1 mol/L hydrochloric acid and extracted with ethyl acetate. The organic layer was washed with sodium carbonate and saturated brine, and dried over anhydrous sodium sulfate. The solvent was evaporated under reduced pressure to obtain 4-methyl-7-{1-(tert-butoxycarbonyl)-5-[(2-hydroxyethylamino)methyl]indol-2-yl}isoindolinone (48.5 mg, yield 81%).

ESI-MS m/z: 436 [M+H]$^+$; $^1$H-NMR (CDCl$_3$) δ(ppm): 1.28 (s, 9H), 2.35 (s, 3H), 2.79 (t, J=5.1 Hz, 2H), 3.64 (t, J=5.1 Hz, 2H), 3.87 (s, 2H), 4.27 (s, 2H), 6.50 (s, 1H), 7.24 (dd, J=1.7, 8.4 Hz, 1H), 7.35 (br s, 2H), 7.45 (s, 1H), 7.98 (s, 1H), 8.18 (d, J=8.6 Hz, 1H).

Step 2

In a similar manner to Step 2 of Example 8, 4-methyl-7-{1-(tert-butoxycarbonyl)-5-[(2-hydroxyethylamino)methyl]indol-2-yl}isoindolinone (48.5 mg, 0.111 mmol) was dissolved in methanol (1.5 mL), and the solution was treated with 10% hydrogen chloride-methanol solution (3.5 mL). The precipitated solid was collected by filtration and washed with methanol, followed by drying under reduced pressure to obtain Compound 325 (24.8 mg, yield 60%).

ESI-MS m/z: 336 [M+H]$^+$; $^1$H-NMR (DMSO-d$_6$) δ(ppm): 2.33 (s, 3H), 2.94 (br s, 2H), 3.66 (br s, 2H), 4.20 (s, 2H), 4.45 (s, 2H), 5.22 (br s, 1H), 7.22 (s, 1H), 7.26 (d, J=9.4 Hz, 1H), 7.48 (d, J=7.9 Hz, 1H), 7.51 (d, J=8.6 Hz, 1H), 7.72 (s, 1H), 8.12 (d, J=7.9 Hz, 1H), 8.99 (br s, 2H), 9.34 (s, 1H), 14.02 (s, 1H).

EXAMPLE 326

4-Vinyl-7-{1H-5-[4-(2-hydroxyethyl)pyperazin-1-ylmethyl]indol-2-yl}isoindolinone dihydrochloride
(Compound 326)

Step 1

In a similar manner to Step 2 of Example 1, 7-iodo-4-hydroxyisoindolinone (3.00 mg, 1.09 mmol) was dissolved in acetonitrile (18 mL), and the solution was treated with Compound BU (2.21 g, 3.27 mmol), palladium acetate (19.6 mg, 0.0872 mmol), tri(o-tolyl)phosphine (53.1 mg, 0.174 mmol) and triethylamine (1.5 mL, 11 mmol), followed by purification by flash column chromatography (chloroform/methanol=100/0 to 95/5) to obtain 4-hydroxy-7-(1-(tert-butoxycarbonyl)-5-[4-(2-tert-butyldimethylsilyloxyethyl)pyperazin-1-ylmethyl]indol-2-yl)isoindolinone (537 mg, yield 79%).

ESI-MS m/z: 621 [M+H]$^+$; $^1$H-NMR (CDCl$_3$) δ(ppm): 0.04 (s, 6H), 0.88 (s, 9H), 1.27 (s, 9H), 2.53-2.59 (m, 10H), 3.63 (s, 2H), 3.76 (t, J=6.3 Hz, 2H), 4.05 (m, 2H), 6.28 (m, 1H), 6.62 (br s, 1H), 6.69 (dd, J=1.7, 8.0 Hz, 1H), 7.10 (d, J=8.1 Hz, 1H), 7.20 (d, J=8.9 Hz, 1H), 7.26 (br s, 1H), 7.35 (s, 1H), 8.15 (d, J=8.4 Hz, H).

Step 2

In a similar manner to Step 1 of Example 299, 4-hydroxy-7-(1-(tert-butoxycarbonyl)-5-[4-(2-tert-butyldimethylsilyloxyethyl)pyperazin-1-ylmethyl]indol-2-yl)isoindolinone (150 mg, 0.240-mmol) was suspended in dichloromethane (6.0 mL), and the suspension was treated with triethylamine (0.167 mL, 1.20 mmol) and trifluoromethanesulfonyl chloride (0.046 mL, 0.43 mmol) under ice-cooling, followed by purification by preparative thin-layer chromatography (chloroform/methanol=13/1) to obtain 4-trifluoromethanesulfonyloxy-7-{1-(tert-butoxycarbonyl)-5-[4-(2-tert-butyldimethylsilyloxyethyl)pyperazin-1-ylmethyl]indol-2-yl}isoindolinone (139 mg, yield 77%).

ESI-MS m/z: 753 [M+H]$^+$; $^1$H-NMR (CDCl$_3$) δ(ppm): 0.49 (s, 6H), 0.88 (s, 9H), 1.31 (s, 9H), 2.52-2.57 (m, 8H), 2.55 (t, J=6.4 Hz, 2H), 3.60 (s, 2H), 3.76 (t, J=6.4 Hz, 2H), 4.54 (s, 2H), 6.57 (s, 1H), 7.22 (br s, 1H), 7.33 (dd, J=1.2, 8.7 Hz, 1H), 7.49 (m, 2H), 7.55 (d, J=8.4 Hz, 1H), 8.19 (d, J=8.7 Hz, 1H).

Step 3

In a similar manner to Step 1 of Example 152, 4-trifluoromethanesulfonyloxy-7-{1-(tert-butoxycarbonyl)-5-[4-(2-tert-butyldimethylsilyloxyethyl)pyperazin-1-ylmethyl]indol-2-yl}isoindolinone (46.0 mg, 0.0611 mmol) was dissolved in dimethoxyethane (2.8 mL), and the solution was treated with 2,4,6-trivinylcyclotriboroxane-pyridine complex (32 mg, 0.13 mmol), [bis(diphenylphosphino)ferrocene]dichloropalladium (4.4 mg, 0.0054 mmol), potassium carbonate (46 mg, 0.34 mmol) and water (0.024 mL), followed by purification by preparative thin-layer chromatography (chloroform/methanol=12/1) to obtain 4-vinyl-7-{1-(tert-butoxycarbonyl)-5-[4-(2-tert-butyldimethylsilyloxyethyl)pyperazin-1-ylmethyl]indol-2-yl}isoindolinone (31.6 mg, yield 82%).

ESI-MS m/z: 631 [M+H]$^+$; $^1$H-NMR (CDCl$_3$) δ(ppm): 0.05 (s, 6H), 0.88 (s, 9H), 1.28 (s, 9H), 2.52-2.57 (m, 10H), 2.54 (t, J=6.4 Hz, 2H), 3.60 (s, 2H), 3.76 (t, J=6.4 Hz, 2H), 4.44 (s, 2H), 5.47 (d, J=11.4 Hz, 1H), 5.80 (d, J=17.5 Hz, 1H), 6.54 (s, 1H), 6.75 (dd, J=11.1, 17.8 Hz, 1H), 7.30 (dd, J=1.7, 8.6 Hz, 1H), 7.44 (d, J=7.8 Hz, 1H), 7.49 (s, 1H), 7.67 (d, J=7.9 Hz, 1H), 8.02 (br s, 1H), 8.19 (d, J=8.6 Hz, 1H).

Step 4

In a similar manner to Step 2 of Example 8, 4-vinyl-7-{1-(tert-butoxycarbonyl)-5-[4-(2-tert-butyldimethylsilyloxyethyl)pyperazin-1-ylmethyl]indol-2-yl}isoindolinone (28.2 mg, 0.0447 mmol) was dissolved in methanol (1.4 mL), and the solution was treated with 10% hydrogen chloride-methanol solution (1.4 mL). The precipitated solid was collected by filtration and washed with methanol, followed by drying under reduced pressure to obtain Compound 326 (18.5 mg, yield 85%).

ESI-MS m/z: 417 [M+H]$^+$; $^1$H-NMR (DMSO-d$_6$) δ(ppm): 3.19-3.74 (m, 12H), 4.43 (br s, 2H), 4.59 (s, 2H), 5.50 (d, J=11.5 Hz, 1H), 5.99 (d, J=17.6 Hz, 1H), 6.83 (dd, J=11.1, 17.5 Hz, 1H), 7.34 (m, 2H), 7.56 (d, J=8.4 Hz, 1H), 7.82 (s, 1H), 7.88 (d, J=8.4 Hz, 1H), 8.22 (d, J=8.4 Hz, 1H), 9.44 (s, 1H), 11.08 (br s, 1H), 11.80 (br s, 1H), 14.12 (s, 1H).

EXAMPLE 327

4-Cyclopropyl-7-{1H-5-[4-(2-hydroxyethyl)pyperazin-1-ylmethyl]indol-2-yl}-isoindolinone dihydrochloride (Compound 327)

Step 1

In a similar manner to Step 1 of Example 152, 4-trifluoromethanesulfonyloxy-7-{1-(tert-butoxycarbonyl)-5-[4-(2-tert-butyldimethylsilyloxyethyl)pyperazin-1-ylmethyl]indol-2-yl}isoindolinone (81.7 mg, 0.109 mmol) was dissolved in dimethoxyethane (4.1 mL), and the solution was treated with cyclopropylboronic acid (28.0 mg, 0.327 mmol), [bis(diphenylphosphino)ferrocene]dichloropalladium (7.1 mg, 0.0087 mmol), potassium carbonate (75.0 mg, 0.545 mmol) and water (0.058 mL), followed by purification by preparative thin-layer chromatography (chloroform/methanol=12/1) to obtain 4-cyclopropyl-7-{1-(tert-butoxycarbonyl)-5-[4-(2-tert-butyldimethylsilyloxyethyl)pyperazin-1-ylmethyl]indol-2-yl}isoindolinone (47.7 mg, yield 68%).

ESI-MS m/z: 645 [M+H]$^+$; $^1$H-NMR (CDCl$_3$) δ(ppm): 0.05 (s, 6H), 0.77 (m, 2H), 0.88 (s, 9H), 1.03 (m, 2H), 1.26 (s, 9H), 1.85 (m, 1H), 2.52-2.56 (m, 8H), 2.54 (t, J=6.5 Hz, 2H), 3.59 (s, 2H), 3.76 (t, J=6.5 Hz, 2H), 4.46 (s, 2H), 6.50 (s, 1H), 7.09 (d, J=7.7 Hz, 1H), 7.26 (s, 1H), 7.28 (dd, J=1.5, 8.9 Hz, 1H), 7.35 (d, J=7.7 Hz, 1H), 7.48 (s, 1H), 8.11 (br s, 1H), 8.19 (d, J=8.6 Hz, 1H).

Step 2

In a similar manner to Step 2 of Example 8, 4-cyclopropyl-7-{1-(tert-butoxycarbonyl)-5-[4-(2-tert-butyldimethylsilyloxyethyl)pyperazin-1-ylmethyl]indol-2-yl}isoindolinone (47.0 mg, 0.0729-mmol) was dissolved in methanol (1.9 mL), and the solution was treated with 10% hydrogen chloride-methanol solution (1.9 mL). The precipitated solid was collected by filtration and washed with methanol, followed by drying under reduced pressure to obtain Compound 327(27.6 mg, yield 75%).

APCI-MS m/z: 431 [M+H]$^+$; $^1$H-NMR (DMSO-d$_6$) δ(ppm): 0.81 (m, 2H), 1.02 (m, 2H), 1.94 (m, 1H), 3.19-3.74 (m, 12H), 4.43 (br s, 2H), 4.58 (s, 2H), 7.18 (d, J=8.2 Hz, 1H), 7.22 (s, 1H), 7.33 (d, J=8.8 Hz, 1H), 7.53 (d, J=8.4 Hz, 1H), 7.80 (s, 1H), 8.10 (d, J=8.2 Hz, 1H), 9.37 (s, 1H), 11.14 (br s, 1H), 11.90 (br s, 1H), 14.06 (br s, 1H).

EXAMPLE 328

4-(3-Hydroxypropyl)-7-[1H-5-(piperidinomethyl)indol-2-yl]isoindolinone hydrochloride (Compound 328)

Step 1

4-(3-Hydroxy-1-propynyl)-7-[1-(tert-butoxycarbonyl)-5-(piperidinomethyl)indol-2-yl]isoindolinone (89.7 mg, 0.180 mmol) was dissolved in methanol (5.4 mL), and the solution was added with 10% Pd—C (16.8 mg), followed by stirring at room temperature for 2.7 hours under hydrogen atmosphere at normal pressure. The mixture was added with 10% Pd—C (8.9 mg), and further stirred for 2.5 hours. The reaction mixture was filtered using Celite. The solvent of filtrate was evaporated under reduced pressure to obtain 4-(3-hydroxypropyl)-7-[1-(tert-butoxycarbonyl)-5-(piperidinomethyl)indol-2-yl]isoindolinone (84.6 mg, yield 93%).

ESI-MS m/z: 504 [M+H]$^+$; $^1$H-NMR (CDCl$_3$) δ(ppm): 1.25 (s, 9H), 1.44 (m, 2H), 1.61 (br s, 4H), 1.92 (m, 2H), 2.48 (br s, 4H), 2.79 (t, J=7.8 Hz, 2H), 3.65 (m, 2H), 3.72 (t, J=6.2 Hz, 2H), 4.35 (s, 2H), 6.51 (s, 1H), 7.33 (d, J=8.6 Hz, 1H), 7.42 (m, 2H), 7.49 (s, 1H), 7.78 (s, 1H), 8.25 (d, J=8.6 Hz, 1H).

Step 2

In a similar manner to Step 2 of Example 8, 4-(3-hydroxypropyl)-7-[1-(tert-butoxycarbonyl)-5-(piperidinomethyl)indol-2-yl]isoindolinone (84.6 mg, 0.168 mmol) was dissolved in methanol (2.1 mL), and the solution was treated with 10% hydrogen chloride-methanol solution (3.4 mL). The precipitated solid was collected by filtration and washed with methanol, followed by drying under reduced pressure to obtain Compound 328 (15.6 mg, yield 21%).

APCI-MS m/z: 404 [M+H]$^+$; $^1$H-NMR (DMSO-d$_6$) δ(ppm): 1.66-1.82 (m, 6H), 2.68 (t, J=7.6 Hz, 2H), 3.15 (m, 2H), 3.34 (br s, 4H), 3.44 (t, J=6.2 Hz, 2H), 4.30 (m, 2H), 4.49 (s, 2H), 7.24 (s, 1H), 7.26 (d, J=8.8 Hz, 1H), 7.50 (d, J=7.8 Hz, 1H), 7.53 (d, J=7.9 Hz, 1H), 7.74 (s, 1H), 8.14 (d, J=8.1 Hz, 1H), 9.33 (s, 1H), 9.85 (br s, 1H), 14.06 (s, 1H).

EXAMPLE 329

4-(3-Methoxy-1-propinyl)-7-[1H-5-(piperidinomethyl)indol-2-yl]isoindolinone hydrochloride (Compound 329)

Step 1

In a similar manner to Step 2 of Example 161, 4-trifluoromethanesulfonyloxy-7-[1-(tert-butoxycarbonyl)-5-(piperidinomethyl)indol-2-yl]isoindolinone (400 mg, 0.674 mmol) was dissolved in diethylamine (16 mL), and the solution was treated with bis(triphenylphosphine)dichloropalladium (56.7 mg, 0.012 mmol), copper iodide (46.2 mg, 0.243 mmol) and methyl propargyl ether (0.398 mL, 4.72 mmol), followed by purification by preparative thin-layer chromatography (chloroform/methanol=6/1 to 8/1) to obtain 4-(3-methoxy-1-propinyl)-7-[1-(tert-butoxycarbonyl)-5-(piperidinomethyl)indol-2-yl]isoindolinone (250 mg, yield 72%).

APCI-MS m/z: 514 [M+H]$^+$; $^1$H-NMR (CDCl$_3$) δ(ppm): 1.30 (s, 9H), 1.43-1.58 (m, 6H), 2.43 (br s, 4H), 3.48 (s, 3H), 3.60 (s, 2H), 4.38 (s, 2H), 4.45 (s, 2H), 6.56 (s, 1H), 7.30 (d, J=8.6 Hz, 1H), 7.43 (d, J=7.9 Hz, 1H), 7.50 (s, 1H)—, 7.63 (d, J=7.7 Hz, 1H), 7.70 (br s, 1H), 8.18 (d, J=8.6 Hz, 1H).

Step 2

In a similar manner to Step 2 of Example 8, 4-(3-methoxy-1-propinyl)-7-[1'-(tert-butoxycarbonyl)-5-(piperidinomethyl)indol-2-yl]isoindolinone (92.3 mg, 0.180 mmol) was dissolved in methanol (2.3 mL), and the solution was treated with 10% hydrogen chloride-methanol solution (4.6 mL). The precipitated solid was collected by filtration and washed with methanol, followed by drying under reduced pressure to obtain Compound 329 (41.4 mg, yield 51%).

APCI-MS m/z: 4.14 [M+H]$^+$; $^1$H-NMR (DMSO-d$_6$) δ(ppm): 1.77 (m, 6H), 2.86 (m, 2H), 3.32 (m, 2H), 3.37 (s, 3H), 4.31 (s, 2H), 4.41 (s, 2H), 4.52 (s, 2H), 7.32 (d, J=8.3 Hz, 1H), 7.37 (s, 1H), 7.56 (d, J=8.3 Hz, 1H), 7.72 (d, J=8.1 Hz, 1H), 7.78 (s, 1H), 8.22 (d, J=8.3 Hz, 1H), 9.49 (s, 1H), 9.96 (br s, 1H), 14.03 (s, 1H).

EXAMPLE 330

4-(3-Methoxypropyl)-7-[1H5-(piperidinomethyl)indol-2-yl]isoindolinone (Compound 330)

Step 1

In a similar manner to Step 1 of Example 328, 4-(3-methoxy-1-propinyl)-7-[1-(tert-butoxycarbonyl)-5-(piperidinomethyl)indol-2-yl]isoindolinone (157 mg, 0.306 mmol) was dissolved in methanol (6.3 mL), and the solution was added with 10% Pd—C (46 mg) to react hydrogen. The reaction mixture was filtered using Celite. The solvent of the filtrate was evaporated under reduced pressure to obtain 4-(3-methoxypropyl)-7-[1-(tert-butoxycarbonyl)-5-(piperidinomethyl)indol-2-yl]isoindolinone (152 mg, yield 96%).

APCI-MS m/z: 518 [M+H]$^+$; $^1$H-NMR (CDCl$_3$) δ(ppm): 1.27 (s, 9H), 1.43 (m, 2H), 1.60 (m, 4H), 1.94 (m, 2H), 2.49

(br s, 4H), 2.76 (t, J=7.8 Hz, 2H), 3.37 (s, 3H), 3.42 (t, J=6.2 Hz, 2H), 3.68 (s, 2H), 4.40 (s, 2H), 6.51 (s, 1H), 7.22-7.26 (m, 2H), 7.39 (s, 1H), 7.45 (m, 2H), 8.18 (d, J=8.4 Hz, 1H).

Step 2

In a similar manner to Step 2 of Example 8, 4-(3-methoxypropyl)-7-[1-(tert-butoxycarbonyl)-5-(piperidinomethyl)indol-2-yl]isoindolinone (151 mg, 0.291 mmol) was dissolved in methanol (3 mL), and the solution was treated with 10% hydrogen chloride-methanol solution (4.5 mL). The precipitated solid was collected by filtration and washed with methanol, followed by drying under reduced pressure to obtain Compound 330 (38.1 mg, yield 31%).

APCI-MS m/z: 418 [M+H]$^+$; $^1$H-NMR (CDCl$_3$) δ(ppm): 1.43 (m, 2H), 1.62 (m, 4H), 1.91 (m, 2H), 2.48 (br s, 4H), 2.67 (t, J=7.2 Hz, 2H), 3.34 (s, 3H), 3.38 (t, J=6.0 Hz, 2H), 3.64 (s, 2H), 4.42 (s, 2H), 7.01 (s, 1H), 7.15 (br s, 1H), 7.31 (d, J=9.7 Hz, 1H), 7.37 (d, J=8.3 Hz, 1H), 7.44 (d, J=8.3 Hz, 1H), 7.55 (s, 1H), 8.02 (d, J=8.3 Hz, 1H), 13.37 (s, 1H).

EXAMPLE 331

4-Hydroxymethyl-7-[1H-5-(piperidinomethyl)indol-2-yl]isoindolinone hydrochloride (Compound 331)

Step 1

4-Trifluoromethanesulfonyloxy-7-[1-(tert-butoxycarbonyl)-5-(piperidinomethyl)indol-2-yl]isoindolinone (80.0 mg, 0.135 mmol) was dissolved in 1,4-dioxane (2.4 mL), and the solution was added with hydroxymethyltributyltin (87 mg, 0.27 mmol) synthesized in a similar manner to the method described in Synthetic Communications, 1994, vol. 24, p. 1117, and tetrakis(triphenylphosphine)palladium (12.5 mg, 0.0108 mmol), followed by stirring at 90° C. for 2.7 hours under argon atmosphere. The mixture was further added with tetrakis(triphenylphosphine)palladium (6.3 mg, 0.054 mmol) and stirred for 2.3 hours. Further, the mixture was added with hydroxymethyltributyltin (44 mg, 0.14 mmol), tetrakis(triphenylphosphine)palladium (6.3 mg, 0.0054 mmol) and 1,4-dioxane (1.2 mL), followed by stirring for 4 hours. The reaction mixture was added with 10% aqueous ammonium fluoride solution and extracted with ethyl acetate. The organic layer was washed with saturated brine and dried over sodium sulfate. The solvent was evaporated under reduced pressure. The residue was purified by preparative thin-layer chromatography (chloroform/methanol=10/1) to obtain 4-hydroxymethyl-7-[1-(tert-butoxycarbonyl)-5-(piperidinomethyl)indol-2-yl]isoindolinone (15.0 mg, yield 23%).

APCI-MS m/z: 476 [M+H]$^+$; $^1$H-NMR (CDCl$_3$) δ(ppm): 1.23 (s, 9H), 1.48 (br s, 2H), 1.72 (br s, 4H), 2.67 (br s, 4H), 3.83 (s, 2H), 4.29 (s, 2H), 4.71 (s, 2H), 6.38 (s, 1H), 7.35 (m, 1H), 7.37 (d, J=7.7 Hz, 1H), 7.55-7.58 (m, 3H), 8.20 (d, J=8.6 Hz, 1H).

Step 2

In a similar manner to Step 2 of Example 8, 4-hydroxymethyl-7-[1-(tert-butoxycarbonyl)-5-(piperidinomethyl)indol-2-yl]isoindolinone (32.0 mg, 0.0673 mmol) was dissolved in methanol (1.28 mL), and the solution was treated with 10% hydrogen chloride-methanol solution (1.92 mL). The precipitated solid was collected by filtration and washed with methanol, followed by drying under reduced pressure to obtain Compound 331 (14.9 mg, yield 54%).

APCI-MS m/z: 376 [M+H]$^+$; $^1$H-NMR (DMSO-d$_6$) δ(ppm): 1.67-1.76 (m, 6H), 2.74-2.86 (m, 2H), 3.32 (m, 2H), 4.30 (m, 2H), 4.51 (s, 2H), 4.61 (s, 2H), 7.26 (s, 1H), 7.28 (d, J=7.1 Hz, 1H), 7.54 (d, J=8.1 Hz, 1H), 7.65 (d, J=8.1 Hz, 1H), 7.75 (s, 1H), 8.20 (d, J=8.3 Hz, 1H), 9.32 (s, 1H), 9.85 (br s, 1H), 14.08 (s, 1H).

EXAMPLE 332

4-Cyano-7-[1H-5-(piperidinomethyl)indol-2-yl]isoindolinone hydrochloride (Compound 332)

Step 1

4-Trifluoromethanesulfonyloxy-7-[1-(tert-butoxycarbonyl)-5-(piperidinomethyl)indol-2-yl]isoindolinone (300 mg, 0.505 mmol) was dissolved in acetonitrile (15 mL), and the solution was added with zinc cyanide (178 mg, 1.52 mmol) and [bis(diphenylphosphino)ferrocene]dichloropalladium (33 mg, 0.0404 mmol), followed by stirring at 90° C. for 17 hours under argon atmosphere. The reaction mixture was added with water and extracted with ethyl acetate. The organic layer was washed with saturated brine and dried over sodium sulfate. The solvent was evaporated under reduced pressure. The residue was purified by preparative thin-layer chromatography (chloroform/methanol=8/1) to obtain 4-cyano-7-[1-(tert-butoxycarbonyl)-5-(piperidinomethyl)indol-2-yl]isoindolinone (198 mg, yield 83%).

APCI-MS m/z: 471 [M+H]$^+$; $^1$H-NMR (CDCl$_3$) δ(ppm): 1.42 (s, 9H), 1.58 (br s, 6H), 2.42 (br s, 4H), 3.59 (s, 2H), 4.60 (s, 2H), 6.46 (s, 1H), 6.63 (s, 1H), 7.33 (d, J=8.6 Hz, 1H), 7.52 (s, 1H), 7.60 (d, J=7.9 Hz, 1H), 7.87 (d, J=7.9 Hz, 1H), 8.11 (d, J=8.7 Hz, 1H).

Step 2

In a similar manner to Step 2 of Example 8, 4-cyano-7-[1-(tert-butoxycarbonyl)-5-(piperidinomethyl)indol-2-yl]isoindolinone (52.8 mg, 0.112 mmol) was dissolved in methanol (1.58 mL), and the solution was treated with 10% hydrogen chloride-methanol solution (3.16 mL). The precipitated solid was collected by filtration and washed with methanol, followed by drying under reduced pressure to obtain Compound 332 (27.4 mg, yield 60%).

APCI-MS m/z: 371 [M+H]$^+$; $^1$H-NMR (DMSO-d$_6$) δ(ppm): 1.67-1.77 (m, 6H), 2.83-2.87 (m, 2H), 3.34 (m, 2H), 4.33 (m, 2H), 4.71 (s, 2H), 7.38 (d, J=8.4 Hz, 1H), 7.54 (s, 1H), 7.60 (d, J=8.4 Hz, 1H), 7.83 (s, 1H), 8.11 (d, J=8.2 Hz, 1H), 8.39 (d, J=8.2 Hz, 1H), 9.68 (s, 1H), 10.06 (s, 1H), 14.04 (s, 1H).

EXAMPLE 333

4-Amino-7-[1H-5-(piperidinomethyl)indol-2-yl]isoindolinone (Compound 333)

Step 1

4-Amino-7-bromophtalimide (1.18 g, 4.90 mmol) was dissolved in THF (60 mL), and the solution was added with borane dimethylsulfide complex (1.40 mL, 14.7 mmol) at room temperature, followed by stirring at 60° C. for 30 minutes. The reaction mixture was added with methanol (10 mL) under ice-cooling and stirred at room temperature for 30 minutes. The solvent of the reaction mixture was evaporated under reduced pressure and the residue was purified by flash column chromatography (chloroform/methanol=100/0 to 90/10) to obtain 4-amino-7-bromoisoindolinone (0.41 g, yield 37%).

ESI-MS m/z: 228 [M+H]$^+$; $^1$H-NMR (DMSO-d$_6$) δ(ppm): 4.06 (s, 2H), 5.52 (s, 1H), 6.67 (d, J=8.4 Hz, 1H), 7.24 (d, J=8.4 Hz, 1H), 8.50 (s, 1H).

Step 2

In a similar manner to Step 2 of Example 1, 4-amino-7-bromoisoindolinone (0.41 g, 1.81 mmol) was dissolved in acetonitrile (16 mL), and the solution was treated with Compound BD (1.29 g, 3.61 mmol), palladium acetate (4.1 mg, 0.0018 mmol), tri(o-tolyl)phosphine (11 mg, 0.037 mmol) and triethylamine (0.255 mL, 1.83 mmol) to obtain Compound 333 (0.382 g, yield 46%).

ESI-MS m/z: 461 [M+H]$^+$; $^1$H-NMR (DMSO-d$_6$) δ(ppm): 1.29 (s, 9H), 1.36-1.48 (m, 1H), 1.50-1.63 (m, 3H), 1.78-1.95 (m, 2H), 2.33-2.47 (m, 2H), 3.56 (s, 2H), 3.79 (s, 2H), 4.13 (s, 2H), 6.46 (d, J=0.7 Hz, 1H), 6.80 (d, J=8.1 Hz, 1H), 7.20-7.28 (m, 2H), 7.46 (d, J=0.7 Hz, 1H), 7.73 (br s, 1H), 8.15 (d, J=8.1 Hz, 1H).

Step 3

4-Amino-7-[1-(tert-butoxycarbonyl)-5-(piperidinomethyl)indol-2-yl]isoindolinone (0.0654 g, 0.142 mmol) was dissolved in 10% hydrogen chloride-methanol solution (5 mL), and the solution was stirred under reflux for 1.5 hours. The solvent was evaporated under reduced pressure and the residue was purified by slurry using diisopropylether to obtain Compound 333 (0.0203 g, yield 36%).

ESI-MS m/z: 361 [M+H]$^+$; $^1$H-NMR (DMSO-d$_6$) δ(ppm): 1.31-1.55 (m, 6H), 2.27-2.39 (m, 4H), 3.45 (s, 2H), 4.25 (s, 2H), 5.63 (s, 2H), 6.84 (s, 1H), 6.88 (d, J=8.4 Hz, 1H), 6.97 (dd, J=1.2, 8.4 Hz, 1H), 7.29 (d, J=8.4 Hz, 1H), 7.35 (d, J=1.2 Hz, 1H), 7.87 (d, J=8.4 Hz, 1H), 9.11 (br s, 1H), 13.6 (br s, 1H).

EXAMPLE 334

4-Methanesulfonylamino-7-[1H-5-(piperidinomethyl)indol-2-yl]isoindolinone hydrochloride (Compound 334)

Step 1

4-Amino-7-[1-(tert-butoxycarbonyl)-5-(piperidinomethyl)indol-2-yl]isoindolinone (0.0820 g, 0.178 mmol) was dissolved in dichloromethane (4.0 mL), and the solution was added with pyridine (0.0430 mL, 0.534 mmol) and methanesulfonyl chloride (0.0210 mL, 0.267 mmol), followed by stirring for 1.5 hours under ice-cooling. The reaction mixture was added with water and extracted with ethyl acetate. The organic layer was washed with saturated brine and dried over anhydrous sodium sulfate. The solvent was evaporated under reduced pressure and the residue was purified by flash column chromatography (chloroform/methanol=4/1) to obtain 4-methanesulfonylamino-7-[1-(tert-butoxycarbonyl)-5-(piperidinomethyl)indol-2-yl]isoindolinone (0.0423 g, yield 44%).

ESI-MS m/z: 539 [M+H]$^+$; $^1$H-NMR (DMSO-d$_6$) δ(ppm): 1.19 (s, 9H), 1.40-1.64 (m, 6H), 2.66-2.81 (m, 4H), 2.85 (s, 3H), 3.29 (br s, 1H), 3.80 (s, 2H), 3.94 (s, 2H), 6.35 (s, 1H), 7.32 (d, J=8.1 Hz, 1H), 7.39 (d, J=8.6 Hz, 1H), 7.64 (d, J=8.1 Hz, 1H), 7.73 (s, 1H), 8.31 (d, J=8.6 Hz, 1H).

Step 2

In a similar manner to Step 2 of Example 8, 4-methanesulfonylamino-7-[1-(tert-butoxycarbonyl)-5-(piperidinomethyl)indol-2-yl]isoindolinone (0.0420 g, 0.0780 mmol) was treated with 10% hydrogen chloride-methanol solution (5.0 mL) to obtain Compound 334 (0.0310 g, yield 84%).

mp >295° C.; ESI-MS m/z: 439 [M+H]$^+$; $^1$H-NMR (DMSO-d$_6$) δ(ppm): 1.33-1.59 (m, 1H), 1.61-1.87 (m, 5H), 2.86 (m, 2H), 3.12 (s, 3H), 3.31-3.41 (m, 2H), 4.32 (d, J=4.5. Hz, 2H), 4.54 (s, 2H), 7.24-7.32 (m, 2H), 7.55 (d, J=8.1 Hz, 1H), 7.64 (d, J=8.7 Hz, 1H), 7.76 (s, 1H), 8.23 (d, J=8.7 Hz, 1H), 9.76 (m, 2H), 13.9 (br s, 1H).

EXAMPLE 335

4-Cyclopropylcarbonylamino-7-[1H-5-(piperidinomethyl)indol-2-yl]isoindolinone (Compound 335)

Step 1

4-Amino-7-[1-(tert-butoxycarbonyl)-5-(piperidinomethyl)indol-2-yl]isoindolinone (0.0940 g, 0.204 mmol) was dissolved in ethyl acetate (4.0 mL), and the solution was added with triethylamine (0.0570 mL, 0.408 mmol) and cyclopropanecarbonyl chloride (0.0280 mL, 0.306 mmol), followed by stirring at room temperature for 1.5 hours. The reaction mixture was added with water and extracted with ethyl acetate. The organic layer was washed with saturated brine and dried over anhydrous sodium sulfate. The solvent was evaporated under reduced pressure and the residue was purified by flash column chromatography (chloroform/methanol=85/15) to obtain 4-cyclopropylcarbonylamino-7-[1-(tert-butoxycarbonyl)-5-(piperidinomethyl)indol-2-yl]isoindolinone (0.0280 g, yield 26%).

ESI-MS m/z: 529 [M+H]$^+$; $^1$H-NMR (CD$_3$OD) δ(ppm): 1.14 (s, 9H), 1.05-1.18 (m, 4H), 1.32-1.42 (m, 2H), 1.46-1.57 (m, 5H), 2.36-2.48 (m, 4H), 3.57 (s, 2H), 4.39 (s, 2H), 6.43 (s, 1H), 7.17 (dd, J=1.6, 8.6 Hz, 1H), 7.35 (d, J=8.1 Hz, 1H), 7.41 (dd, J=1.6, 8.1 Hz, 1H), 7.79 (s, 1H), 8.08 (d, J=8.6 Hz, 1H).

Step 2

In a similar manner to Step 2 of Example 8, 4-cyclopropylcarbonylamino-7-[1-(tert-butoxycarbonyl)-5-(piperidinomethyl)indol-2-yl]isoindolinone (0.0280 g, 0.0530 mmol) was treated with 10% hydrogen chloride-methanol solution (5.0 mL), followed by purification by thin-layer chromatography (chloroform/methanol/0.2% ammonia-methanol solution=85/15/0.02) to obtain Compound 335 (0.00760 g, yield 33%).

ESI-MS m/z: 429 [M+H]$^+$; $^1$H-NMR (DMSO-d$_6$) δ(ppm): 0.84 (d, J=5.9 Hz, 4H), 1.33-1.59 (m, 1H), 1.61-1.87 (m, 5H), 1.96-2.09 (m, 1H), 2.75-2.95 (m, 2H), 3.31-3.41 (m, 2H), 4.29 (s, 2H), 4.52 (s, 2H), 7.21 (s, 1H), 7.26 (d, J=8.1 Hz, 1H), 752 (d, J=8.1 Hz, 1H), 7.73 (s, 1H), 8.05 (d, J=8.7 Hz, 1H), 8.16 (d, J=8.7 Hz, 1H), 9.34 (s, 1H), 10.05 (s, 1H), 13.9 (br s, 1H).

EXAMPLE 336

7-[1H-5-(piperidinomethyl)indol-2-yl]isoindolinone hydrochloride (Compound 336)

Step 1

In a similar manner to Step 1 of Example 16, benzoyl chloride (10.0 g, 71.1 mmol) was dissolved in dichloromethane (200 mL), and the solution was treated with cumylamine (11.3 mL, 78.3 mmol), triethylamine (14.9 mL, 107 mmol) and DMAP (870 mg, 7.11 mmol), followed by purification by slurry using diisopropylether to obtain N-(1-methyl-1-phenylethyl)benzamide (16.6 g, yield 98%).

APCI-MS m/z: 240 [M+H]$^+$; $^1$H-NMR (CDCl$_3$) δ(ppm): 1.82 (s, 6H), 6.43 (br s, 1H), 7.22-7.47 (m, 8H), 7.76 (d, J=6.6 Hz, 2H).

Step 2

In a similar manner to Step 2 of Example 16. N-(1-methyl-1-phenylethyl)benzamide (5.00 g, 20.9 mmol) was dissolved in THF (200 mL), and the solution was treated with TMEDA (10.0 mL, 66.9 mmol), sec-butyl lithium-hexane solution (1.01 mol/L, 66.0 mL, 66.9 mmol) and DMF (3.60 mL, 46.0 mmol), followed by purification by slurry using diisopropylether to obtain 3-hydroxy-2-(1-methyl-1-phenylethyl)isoindolinone (5.40 g, yield 97%).

APCI-MS m/z: 268 [M+H]$^+$; $^1$H-NMR (CDCl$_3$) d (ppm): 1.84 (s, 3H), 1.89 (s, 3H), 6.13 (s, 1H), 7.10-7.42 (m, 6H), 7.50-7.57 (m, 3H).

Step 3

In a similar manner to Step 3 of Example 16, 3-hydroxy-2-(1-methyl-1-phenylethyl)isoindolinone (2.00 g, 7.48 mmol) was dissolved in THF (80 mL), and the solution was treated with TMEDA (2.50 mL, 16.5 mmol), sec-butyl lithium-hexane solution (0.99 mol/L, 16.6 mL, 16.5 mmol) and 1,2-dibromotetrachloroethane (2.92 g, 8.98 mmol), followed by purification by flash column chromatography (chloroform/methanol=95/5 to 90/10) to obtain 3-hydroxy-7-bromo-2-(1-methyl-1-phenylethyl)isoindolinone (2.20 g, yield 85%).

APCI-MS m/z: 344 [M−H]$^−$; $^1$H-NMR (CDCl$_3$) δ(ppm): 1.94 (s, 3H), 1.98 (s, 3H), 2.35 (m, 1H), 6.05 (m, 1H), 7.20-7.49 (m, 8H).

Step 4

In a similar manner to Step 4 of Example 16, 3-hydroxy-7-bromo-2-(1-methyl-1-phenylethyl)isoindolinone (3.00 mg, 0.867 mmol) was dissolved in nitromethane (12 mL), and the solution was treated with trifluoroacetic acid (0.668 mL, 8.67 mmol) and triethylsilane (0.277 mL, 1.73 mmol), followed by purification by preparative thin-layer chromatography (chloroform/methanol=12/1) to obtain 7-bromoisoindolinone (140 mg, yield 76%).

$^1$H-NMR (DMSO-d$_6$) δ(ppm): 4.33 (m, 2H), 7.42-7.60 (m, 3H), 8.67 (br s, 1H).

Step 5

In a similar manner to Step 2 of Example 1, 7-bromoisoindolinone (70.0 mg, 0.330 mmol) was dissolved in acetonitrile (5.6 mL), and the solution was treated with Compound BD (236 mg, 0.660 mmol), palladium acetate (5.9 mg, 0.026 mmol), tri(o-tolyl)phosphine (16.1 mg, 0.0528 mmol) and triethylamine (0.460 mL, 3.30 mmol), followed by purification by preparative thin-layer chromatography (chloroform/methanol=10/1) to obtain, 7-[1-(tert-butoxycarbonyl)-5-(piperidinomethyl)indol-2-yl]isoindolinone (78.2 mg, yield 53%).

APCI-MS m/z: 446 [M+H]$^+$; $^1$H-NMR (CDCl$_3$) δ(ppm): 1.25 (s, 9H), 1.43 (m, 2H), 1.60 (m, 4H), 2.44 (br s, 4H), 3.62 (s, 2H), 4.39 (s, 2H), 6.54 (s, 1H), 7.30 (d, J=7.4 Hz, 1H), 7.43 (d, J=7.3 Hz, 2H), 7.50-7.59 (m, 3H), 8.01 (br s, 1H), 8.21 (d, J=8.6 Hz, 1H).

Step 6

In a similar manner to Step 2 of Example 8, 7-[1-(tert-butoxycarbonyl)-5-(piperidinomethyl)indol-2-yl]isoindolinone (73.8 mg, 0.166 mmol) was dissolved in methanol (2.2 mL), and the solution was treated with 10% hydrogen chloride-methanol solution (2.2 mL). The precipitated solid was collected by filtration and washed with methanol, followed by drying under reduced pressure to obtain Compound 336 (37.0 mg, yield 58%).

APCI-MS m/z: 346 [M+H]$^+$; $^1$H-NMR (DMSO-d$_6$) δ(ppm): 1.65-1.76 (m, 6H), 2.85 (m, 2H), 3.31 (m, 2H), 4.29 (d, J=4.6 Hz, 2H), 4.51 (s, 2H), 7.29 (s, 1H), 7.30 (d, J=8.4 Hz, 1H), 7.51 (d, J=7.1 Hz, 1H), 7.54 (d, J=7.7 Hz, 1H), 7.67 (dd, J=7.2, 7.9 Hz, 1H), 7.77 (s, 1H), 8.19 (d, J=8.1 Hz, 1H), 9.32 (s, 1H), 1.05 (br s, 1H), 14.08 (s, 1H).

EXAMPLE 337

4-Fluoro-7-[1H-5-(piperidinomethyl)indol-2-yl]isoindolinone hydrochloride (Compound 337)

Step 1

In a similar manner to Step 2 of Example 1, 4-fluoro-7-iodoisoindolinone (150 mg, 0.541 mmol) was dissolved in acetonitrile (10.5 mL), and the solution was treated with Compound BD (388 mg, 1.08 mmol), palladium acetate (9.7 mg, 0.043 mmol), tri(o-tolyl)phosphine (26.3 mg, 0.0866 mmol) and triethylamine (0.754 mL, 5.41 mmol), followed by purification by preparative thin-layer chromatography (chloroform/methanol=15/1 to 10/1) to obtain 4-fluoro-7-[1-(tert-butoxycarbonyl)-5-(piperidinomethyl)indol-2-yl]isoindolinone (165 mg, yield 66%).

ESI-MS m/z: 464 [M+H]$^+$; $^1$H-NMR (CDCl$_3$) δ(ppm): 1.35 (s, 9H), 1.43 (m, 2H), 1.62 (m, 4H), 2.46 (br s, 4H), 3.64 (s, 2H), 4.47 (s, 2H), 6.53 (s, 1H), 7.04 (s, 1H), 7.23-7.32 (m, 2H), 7.44 (dd, J=4.5, 8.1 Hz, 1H), 7.52 (s, 1H), 8.16 (d, J=8.6 Hz, 1H).

Step 2

In a similar manner to Step 2 of Example 8, 4-fluoro-7-[(1-(tert-butoxycarbonyl)-5-(piperidinomethyl)indol-2-yl]isoindolinone (113 mg, 0.244 mmol) was dissolved in methanol (3.4 mL), and the solution was treated with 10% hydrogen chloride-methanol solution (5.7 mL). The precipitated solid was collected by filtration and washed with methanol, followed by drying under reduced pressure to obtain Compound 337 (58.5 mg, yield 60%).

ESI-MS m/z: 364 [M+H]$^+$; $^1$H-NMR (DMSO-d$_6$) δ(ppm): 1.65-1.75 (m, 6H), 2.83 (m, 2H), 3.28 (m, 2H), 4.29 (d, J=5.0 Hz, 2H), 4.58 (s, 2H), 7.25 (s, 1H), 7.31 (d, J=8.6 Hz, 1H), 7.52-7.59 (m, 2H), 7.77 (s, 1H), 8.24 (dd, J=4.7, 8.8 Hz, 1H), 9.51 (s, 1H), 10.14 (br s, 1H), 13.77 (s, 1H).

EXAMPLE 338

4,5-Dichloro-7-[1H-5-(piperidinomethyl)indol-2-yl]isoindolinone hydrochloride (Compound 338)

Step 1

In a similar manner to Step 1 of Example 16, 3,4-dichlorobenzoyl chloride (3.00 g, 14.3 mmol) was dissolved in dichloromethane (60 mL), and the solution was treated with cumylamine (2.30 mL, 15.7 mmol), triethylamine (3.00 mL, 21.5 mmol) and DMAP (175 mg, 1.43 mmol), followed by purification by slurry using chloroform to obtain 3,4-dichloro-N-(1-methyl-1-phenylethyl)benzamide (3.85 g, yield 88%).

APCI-MS m/z: 308 [M+H]$^+$; $^1$H-NMR (CDCl$_3$) δ(ppm): 1.82 (s, 6H) 6.31 (br s, 1H), 7.23-7.51 (m, 6H), 7.57 (dd, J=2.1, 8.3 Hz, 1H), 7.84 (d, J=2.0 Hz, 1H).

Step 2

In a similar manner to Step 2 of Example 16, 3,4-dichloro-N-(1-methyl-1-phenylethyl)benzamide (2.85 g, 9.25 mmol) was dissolved in THF (114 mL), and the solution was treated with TMEDA (4.50 mL, 29.6 mmol), sec-butyl lithium-hexane solution (1.01 mol/L, 29.3 mL, 29.6 mmol) and DMF (1.60 mL, 20.4 mmol), followed by purification by slurry using diisopropylether to obtain 4,5-dichloro-3-hydroxy-2-(1-methyl-1-phenylethyl)isoindolinone (2.58 g, yield 83%).

APCI-MS m/z: 336 [M+H]$^+$; $^1$H-NMR (CDCl$_3$) δ(ppm): 1.94 (s, 3H), 1.98 (s, 3H), 2.64 (d, J=8.4 Hz, 1H), 6.23 (d, J=8.2 Hz, 1H), 7.24 (m, 1H), 7.34 (m, 2H), 7.43 (m, 2H), 7.52 (d, J=7.9 Hz, 1H), 7.58 (d, J=7.9 Hz, 1H).

Step 3

In a similar manner to Step 3 of Example 16, 4,5-dichloro-3-hydroxy-2-(1-methyl-1-phenylethyl)isoindolinone (400 mg, 1.19 mmol) was dissolved in THF (16 mL), and the solution was treated with TMEDA (0.718 mL, 4.76 mmol), sec-butyl lithium-hexane solution (0.99 mol/L, 4.8 mL, 4.76 mmol) and iodine (453 mg, 1.79 mmol), followed by purification by flash column chromatography (chloroform/methanol=95/5 to 90/10) to obtain 3-hydroxy-4,5-dichloro-7-iodo-2-(1-methyl-1-phenylethyl)isoindolinone (350 mg, yield 64%).

APCI-MS m/z: 462 [M+H]$^+$; $^1$H-NMR (DMSO-d$_6$) δ(ppm): 1.77 (s, 3H), 1.80 (s, 3H), 6.26 (d, J=10.2 Hz, 1H), 6.75 (d, J=10.2 Hz, 1H), 7.51 (m, 1H), 7.25 (m, 2H), 7.38 (m, 2H), 8.19 (s, 1H).

Step 4

In a similar manner to Step 4 of Example 16, 3-hydroxy-4,5-dichloro-7-iodo-2-(1-methyl-1-phenylethyl)isoindolinone (347 mg, 0.750 mmol) was dissolved in nitromethane (14 mL), and the solution was treated with trifluoroacetic acid (0.867 mL, 11.3 mmol) and triethylsilane (0.240 mL, 1.50 mmol), followed by purification by slurry using chloroform to obtain 4,5-dichloro-7-iodoisoindolinone (182 mg, yield 74%).

APCI-MS m/z: 328 [M+H]$^+$; $^1$H-NMR (DMSO-d$_6$) δ(ppm): 4.29 (s, 2H), 8.17 (s, 1H), 9.01 (s, 1H).

Step 5

In a similar manner to Step 2 of Example 1, 4,5-dichloro-7-iodoisoindolinone (60.0 mg, 0.180 mmol) was dissolved in acetonitrile (4.8 mL), and the solution was treated with Compound BD (194 mg, 0.540 mmol), palladium acetate (4.8 mg, 0.022 mmol), tri(o-tolyl)phosphine (13.2 mg, 0.043 mmol) and triethylamine (0.376 mL, 2.70 mmol), followed by purification by flash column chromatography (chloroform/methanol=100/1 to 0.99/1) to obtain 4,5-dichloro-7-[1-(tert-butoxycarbonyl)-5-(piperidinomethyl)indol-2-yl]isoindolinone (78.2 mg, yield 53%).

APCI-MS m/z: 514 [M+H]$^+$; $^1$H-NMR (CDCl$_3$) δ(ppm): 1.43 (s, 9H), 1.56 (br s, 6H), 2.43 (br s, 4H), 3.60 (br s, 2H), 4.42 (s, 2H), 6.31 (s, 1H), 6.59 (s, 1H), 7.32 (d, J=8.6 Hz, 1H), 7.51 (s, 1H), 7.60 (s, 1H), 8.10 (d, J=8.2 Hz, 1H).

Step 6

In a similar manner to Step 2 of Example 8, 4,5-dichloro-7-[1-(tert-butoxycarbonyl)-5-(piperidinomethyl)indol-2-yl]isoindolinone (53.0 mg, 0.103 mmol) was dissolved in methanol (1.6 mL), and the solution was treated with 10% hydrogen chloride-methanol solution (1.6 mL). The precipitated solid was collected by filtration and washed with methanol, followed by drying under reduced pressure to obtain Compound 338 (33.6 mg, yield 72%).

APCI-MS m/z: 414 [M+H]$^+$; $^1$H-NMR (DMSO-d$_6$) δ(ppm): 1.66-1.76 (m, 6H), 2.86 (m, 2H), 3.28 (m, 2H), 4.31 (d, J=5.3 Hz, 2H), 4.52 (s, 2H), 7.34 (dd, J=1.5, 8.4 Hz, 1H), 7.50 (s, 1H), 7.56 (d, J=8.4 Hz, 1H), 7.79 (s, 1H), 8.46 (s, 1H), 9.61 (s, 1H), 10.01 (br s, 1H), 13.82 (s, 1H).

EXAMPLE 339

4,5-Dichloro-7-{1H-5-[4-(2-hydroxyethyl)pyperazin-1-ylmethyl]indol-2-yl}isoindolinone dihydrochloride (Compound 339)

Step 1

In a similar manner to Step 2 of Example 1, 4,5-dichloro-7-iodoisoindolinone (100 mg, 0.305 mmol) was dissolved in acetonitrile (7.0 mL), and the solution was treated with Compound BA (176 mg, 0.610 mmol), palladium acetate (5.5 mg, 0.024 mmol), tri(o-tolyl)phosphine (14.9 mg, 0.0488 mmol) and triethylamine (0.425 mL, 3.05 mmol), followed by purification by preparative thin-layer chromatography (chloroform/methanol=15/1) to obtain 4,5-dichloro-7-[1-(tert-butoxycarbonyl)-5-formylindol-2-yl]isoindolinone (116 mg, yield 85%).

APCI-MS m/z: 445 [M+H]$^+$; $^1$H-NMR (CDCl$_3$) δ(ppm): 1.36 (s, 9H), 4.34 (s, 2H), 6.73 (s, 1H), 7.61 (s, 1H), 7.89 (dd, J=1.5, 8.8 Hz, 1H), 8.01 (s, 1H), 8.08 (d, J=1.5 Hz, 1H), 8.35 (d, J=8.8 Hz, 1H), 10.06 (s, 1H).

Step 2

In a similar manner to Step 2 of Example 6, 4,5-dichloro-7-[1-(tert-butoxycarbonyl)-5-formylindol-2-yl]isoindolinone (115 mg, 0.258 mmol) was dissolved in acetonitrile (8.1 mL), and the solution was treated with 1-(2-hydroxyethyl)piperazine (134 mg, 1.03 mmol), acetic acid (0.295 mL, 5.16 mmol) and sodium triacetoxyborohydride (191 mg, 0.903 mmol). The reaction mixture was added with 1 mol/L hydrochloric acid and extracted with ethyl acetate. The organic layer was washed with sodium carbonate and saturated brine and dried over anhydrous sodium sulfate. The solvent was evaporated under reduced pressure to obtain 4,5-dichloro-7-{1-(tert-butoxycarbonyl)-5-[4-(2-hydroxyethyl)pyperazin-1-ylmethyl]indol-2-yl}isoindolinone (136 mg, yield 94%).

APCI-MS m/z: 559 [M+H]$^+$; $^1$H-NMR (CDCl$_3$) δ(ppm): 1.36 (s, 9H), 2.54 (m, 10H), 3.60 (br s, 4H), 4.33 (s, 2H), 6.58 (s, 1H), 7.32 (dd, J=1.7, 8.6 Hz, 1H), 7.49 (d, J=1.7 Hz, 1H), 7.58 (s, 1H), 8.15 (d. J=8.6 Hz, 1H), 8.20 (br s, 1H).

Step 3

In a similar manner to Step 2 of Example 8, 4,5-dichloro-7-{1-(tert-butoxycarbonyl)-5-[4-(2-hydroxyethyl)pyperazin-1-ylmethyl]indol-2-yl}isoindolinone (136 mg, 0.243 mmol) was dissolved in methanol (3.4 mL), and the solution was treated with 10% hydrogen chloride-methanol solution (13.6 mL). The precipitated solid was collected by filtration and washed with methanol, followed by drying under reduced pressure to obtain Compound 339 (109 mg, yield 84%).

APCI-MS m/z: 459 [M+H]$^+$; $^1$H-NMR (DMSO-d$_6$) δ(ppm): 3.15-3.75 (m, 12H), 4.43 (br s, 2H), 4.52 (s, 2H), 7.39 (d, J=8.1 Hz, 1H), 7.51 (s, 1H), 7.57 (d, J=8.4 Hz, 1H), 7.84 (s, 1H), 8.47 (s, 1H), 9.61 (s, 1H), 11.18 (br s, 1H), 11.86 (br s, 1H), 13.83 (s, 1H).

EXAMPLE 340

4-Chloro-5-fluoro-7-[1H-5-(piperidinomethyl)indol-2-yl]isoindolinone hydrochloride (Compound 340)

Step 11

In a similar manner to Step 1 of Example 16, 3-chloro-4-fluorobenzoyl chloride (3.00 g, 15.5 mmol) was dissolved in dichloromethane (60 mL), and the solution was treated with cumylamine (2.45 mL, 17.1 mmol), triethylamine (3.24 mL, 23.3 mmol) and DMAP (189 mg, 1.05 mmol), followed by purification by slurry using diisopropylether to obtain 3-chloro-4-fluoro-N-(1-methyl-1-phenylethyl)benzamide (4.39 g, yield 97%).

APCI-MS m/z: 292 [M+H]$^+$; $^1$H-NMR (CDCl$_3$) δ(ppm): 1.82 (s, 6H), 6.29 (s, 1H), 7.18 (dd, J=8.4, 8.6 Hz, 1H), 7.23-7.29 (m, 1H), 7.33-7.39 (m, 2H), 7.42-7.46 (m, 2H), 7.64 (ddd, J=2.2, 4.6, 8.6 Hz, 1H), 7.82 (dd, J=2.2, 7.0 Hz, 1H).

Step 2

In a similar manner to Step 2 of Example 16, 3-chloro-4-fluoro-N-(1-methyl-1-phenylethyl)benzamide (3.00 g, 10.3 mmol) was dissolved in THF (120 mL), and the solution was treated with TMEDA (5.00 mL, 32.9 mmol), sec-butyl lithium-hexane solution (1.01 mol/L, 32.6 mL, 32.9 mmol) and DMF (1.80 mL, 22.6 mmol), followed by purification by flash column chromatography (chloroform) and by slurry (chloroform) to obtain 4-chloro-3-hydroxy-5-fluoro-2-(1-methyl-1-phenylethyl)isoindolinone (1.50 g, yield 46%).

APCI-MS m/z: 320 [M+H]$^+$; $^1$H-NMR (CDCl$_3$) δ(ppm): 1.93 (s, 3H), 1.97 (s, 3H), 2.74 (d, J=8.8 Hz, 1H), 6.23 (d, J=8.6 Hz, 1H), 7.21-7.28 (m, 2H), 7.33 (m, 2H), 7.42 (m, 2H), 7.56 (dd, J=4.3, 8.1 Hz, 1H).

Step 3

In a similar manner to Step 3 of Example 16, 4-chloro-3-hydroxy-5-fluoro-2-(1-methyl-1-phenylethyl)isoindolinone (1.20 g, 3.75 mmol) was dissolved in THF (48 mL), and the solution was treated with TMEDA (2.30 mL, 15.0 mmol), sec-butyl lithium-hexane solution (1.01 mol/L, 15.0 mL, 15.0 mmol) and iodine (1.430 g, 5.63 mmol), followed by purification by flash column chromatography (hexane/ethyl acetate=80/20 to 70/30) to obtain 3-hydroxy-4-chloro-5-fluoro-7-iodo-2-(1-methyl-1-phenylethyl)isoindolinone (830 mg, yield 50%).

APCI-MS m/z: 446 [M+H]$^+$; $^1$H-NMR (CDCl$_3$) δ(ppm): 1.95 (s, 3H), 1.98 (s, 3H), 2.49 (dd, J=1.3, 8.2 Hz, 1H), 6.06 (d, J=7.6 Hz, 1H), 7.25 (m, 1H), 7.34 (m, 2H), 7.44 (m, 2H), 7.72 (dd, J=1.2, 8.6 Hz, 1H).

Step 4

In a similar manner to Step 4 of Example 16, 3-hydroxy-4-chloro-5-fluoro-7-iodo-2(1-methyl-1-phenylethyl)isoindolinone (806 mg, 1.81 mmol) was dissolved in nitromethane (32 mL), and the solution was treated with trifluoroacetic acid (1.40 mL, 18.1 mmol) and triethylsilane (0.578 mL, 3.62 mmol), followed by purification by slurry using diisopropylether to obtain 4-chloro-5-fluoro-7-iodoisoindolinone (477 mg, yield 85%).

APCI-MS m/z: 312 [M+H]$^+$; $^1$H-NMR DMSO-d$_6$) δ(ppm): 4.30 (s, 2H), 8.01 (d, J=8.8 Hz, 1H), 8.96 (s, 1H).

Step 5

In a similar manner to Step 2 of Example 1, 4-chloro-5-fluoro-7-iodoisoindolinone (100 mg, 0.321 mmol) was dissolved in acetonitrile (7.0 mL), and the solution was treated with Compound BD (230 mg, 0.642 mmol), palladium acetate (5.8 mg, 0.0257 mmol), tri(o-tolyl)phosphine (15.6 mg, 0.0514 mmol) and triethylamine (0.447 mL, 3.21 mmol), followed by purification by preparative thin-layer chromatography (chloroform/methanol=12/1) to obtain 4-chloro-5-fluoro-7-[1-(tert-butoxycarbonyl)-5-(piperidinomethyl)indol-2-yl]isoindolinone (95.0 mg, yield 60%).

APCI-MS m/z: 498 [M+H]$^+$; $^1$H-NMR (CDCl$_3$) δ(ppm): 1.36 (s, 9H), 1.43 (m, 2H), 1.62 (m, 4H), 2.47 (br s, 4H), 3.65 (s, 2H), 4.36 (s, 2H), 6.57 (s, 1H), 7.28 (d, J=9.9 Hz, 1H), 7.34 (dd. J=1.6, 8.6 Hz, 1H), 7.53 (s, 1H), 8.16 (d, J=8.7 Hz, 1H), 8.17 (br s, 1H).

Step 6

In a similar manner to Step 2 of Example 8, 4-chloro-5-fluoro-7-[1-(tert-butoxycarbonyl)-5-(piperidinomethyl)indol-2-yl]isoindolinone (95.0 mg, 0.191 mmol) was dissolved in methanol (2.9 mL), and the solution was treated with 10% hydrogen chloride-methanol solution (2.9 mL). The precipitated solid was collected by filtration and washed with methanol, followed by drying under reduced pressure to obtain Compound 340 (55.7 mg, yield 67%).

ESI-MS m/z: 398 [M+H]$^+$; $^1$H-NMR (DMSO-d$_6$) δ(ppm): 1.69-1.76 (m, 6H), 2.85 (m, 2H), 3.31 (m, 2H), 4.30 (d, J=4.8 Hz, 2H), 4.53 (s, 2H), 7.33 (d, J=8.4 Hz, 1H), 7.47 (s, 1H), 7.56 (d, J=8.4 Hz, 1H), 7.79 (s, 1H), 8.29 (d, J=11.7 Hz, 1H), 9.57 (s, 1H), 9.99 (br s, 1H), 13.91 (s, 1H).

EXAMPLE 341

4-Chloro-5-methoxy-7-[1H-5-(piperidinomethyl) indol-2-yl]isoindolinone hydrochloride (Compound 341)

Step 1

In a similar manner to Step 1 of Example 137, 3-chloro-4-methoxybenzoic acid (1.00 g, 5.36 mmol) was dissolved in DMF (20 mL), and the solution was treated with EDCI (2.06 g, 10.7 mmol), HOBT monohydrate (724 mg, 5.36 mmol) and cumylamine (1.54 mL, 10.7 mmol). The reaction mixture was added with water. The precipitated solid was collected by filtration and washed with water, followed by drying under reduced pressure to obtain 3-chloro-4-methoxy-N-(1-methyl-1-phenylethyl)benzamide (1.59 g, yield 97%).

APCI-MS m/z: 304 [M+H]$^+$; $^1$H-NMR (CDCl$_3$) δ(ppm): 1.82 (s, 6H), 3.94 (s, 3H), 6.27 (br s, 1H), 6.94 (d, J=8.6 Hz, 1H), 7.26 (m, 1H), 7.31-7.39 (m, 2H), 7.42-7.48 (m, 2H), 7.68 (dd, J=2.3, 8.6 Hz, 1H), 7.77 (d, J=2.3 Hz, 1H).

Step 2

In a similar manner to Step 2 of Example 16, 3-chloro-4-methoxy-N-(1-methyl-1-phenylethyl)benzamide (500 mg, 1.65 mmol) was dissolved in THF (20 mL), and the solution was treated with TMEDA (0.80 mL, 5.3 mmol), sec-butyl lithium-hexane solution (0.99 mol/L, 5.3 mL, 5.3 mmol) and DMF (0.281 mL, 3.63 mmol), followed by purification by slurry using diisopropylether to obtain 4-chloro-5-methoxy-3-hydroxy-2-(1-methyl-1-phenylethyl)isoindolinone (385 mg, yield 71%).

APCI-MS m/z: 332 [M+H]$^+$; $^1$H-NMR-(CDCl$_3$) δ(ppm): 1.95 (s, 3H), 1.98 (s, 3H), 2.58 (d, J=8.2 Hz, 1H), 3.97 (s, 3H), 6.23 (d, J=8.2 Hz, 1H), 7.01 (d, J=8.2 Hz, 1H), 7.22 (m, 1H), 7.28-7.37 (m, 2H), 7.39-7.47 (m, 2H), 7.56 (d, J=8.2 Hz, 1H).

Step 3

In a similar manner to Step 3 of Example 16, 4-chloro-5-methoxy-3-hydroxy-2-(1-methyl-1-phenylethyl)isoindolinone (300 mg, 0.904 mmol) was dissolved in THF (12 mL), and the solution was treated with TMEDA (0.30 mL, 2.0 mmol), sec-butyl lithium-hexane solution (1.01 mol/L, 2.0 mL, 2.0 mmol) and iodine (275 mg, 1.08 mmol), followed by purification by slurry using diisopropylether and hexane to obtain 4-chloro-5-methoxy-3-hydroxy-7-iodo-2-(1-methyl-1-phenylethyl)isoindolinone (350 mg, yield 85%).

APCI-MS m/z: 457 [M+H]$^+$; $^1$H-NMR (CDCl$_3$) δ(ppm): 1.94 (s, 3H), 1.99 (s, 3H), 2.39 (s, 1H), 3.97 (s, 3H), 6.06 (s, 1H), 7.23-7.38 (m, 3H), 7.40 (s, 1H), 7.41-7.48 (m, 2H).

Step 4

In a similar manner to Step 4 of Example 16, 4-chloro-5-methoxy-3-hydroxy-7-iodo-2-(1-methyl-1-phenylethyl) isoindolinone (300 mg, 0.655 mmol) was dissolved in nitromethane (5 mL), and the solution was treated with trifluoroacetic acid (0.505 mL, 6.55 mmol) and triethylsilane (0.212 mL, 1.31 mmol), followed by stirring at room temperature for 24 hours. The reaction mixture was added with water, ethyl acetate and hexane. The precipitated solid was collected by filtration and washed with hexane and water, followed by drying under reduced pressure to obtain 4-chloro-5-methoxy-7-iodoisoindolinone (136 mg, yield 64%).

APCI-MS m/z: 323 [M+H]$^+$; $^1$H-NMR (CDCl$_3$) δ(ppm): 3.99 (s, 3H), 4.30 (s, 2H), 6.28 (br s, 1H), 7.44 (s, 1H).

Step 5

In a similar manner to Step 2 of Example 1, 4-chloro-5-methoxy-7-iodoisoindolinone (25.0 mg, 0.0773 mmol) was suspended in acetonitrile (1 mL), and the suspension was treated with Compound. BD (55.4 mg, 0.155 mmol), palladium acetate (1.4 mg, 0.006 mmol) and triethylamine (0.108 mL, 0.775 mmol), followed by purification by slurry using hexane to obtain 4-chloro-5-methoxy-7-[1-(tert-butoxycarbonyl)-5-(piperidinomethyl)indol-2-yl]isoindolinone (37.3 mg, yield 95%).

ESI-MS m/z: 510 [M+H]$^+$; $^1$H-NMR (CDCl$_3$) δ(ppm): 1.35-1.68 (m, 6H), 1.40 (s, 9H), 2.35-2.46 (m, 4H), 3.58 (s, 2H), 4.01 (s, 3H), 4.39 (s, 2H), 6.23 (br s, 1H), 6.58 (s, 1H), 7.05 (s, 1H), 7.29 (dd, J=1.7, 8.6 Hz, 1H), 7.49 (s, 1H), 8.11 (d, J=8.6 Hz, 1H).

Step 6

In a similar manner to Step 2 of Example 8, 4-chloro-5-methoxy-7-[1-(tert-butoxycarbonyl)-5-(piperidinomethyl)indol-2-yl]isoindolinone (35.0 mg, 0.0686 mmol) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 341 (24.1 mg, yield 79%).

ESI-MS m/z: 410[M+H]$^+$; $^1$H-NMR (DMSO-d$_6$) δ(ppm): 1.36 (m, 1H), 1.54-1.90 (m, 5H), 2.80-2.99 (m, 2H), 3.25-3.45 (m, 2H), 4.10 (s, 3H), 4.36 (br s, 2H), 4.47 (s, 2H), 7.28 (dd, J=1.7, 8.5 Hz, 1H), 7.51 (d, J=1.7 Hz, 1H), 7.59 (d, J=8.5 Hz, 1H), 7.75 (s, 1H), 7.81 (s, 1H), 9.32 (s, 2H), 14.05 (s, 1H).

EXAMPLE 342

4-Chloro-5-methyl-7-[1H-5-(piperidinomethyl)indol-2-yl]isoindolinone hydrochloride (Compound 342)

Step 1

In a similar manner to Step 1 of Example 137, 3-chloro-4-methylbenzoic acid (1.00 g, 5.86 mmol) was dissolved in DMF (20 mL), and the solution was treated with EDCI (2.25 g, 11.7 mmol), HOBT monohydrate (792 mg, 5.86 mmol) and cumylamine (1.69 mL, 11.7 mmol). The reaction mixture was added with water. The precipitated solid was collected by filtration and washed with water, followed by drying under reduced pressure. The obtained solid was purified by slurry using diisopropylether to obtain 3-chloro-4-methyl-N-(1-methyl-1-phenylethyl)benzamide (1.64 g, yield 97%).

APCI-MS m/z: 288 [M+H]$^+$; $^1$H-NMR (CDCl$_3$) δ(ppm): 1.83 (s, 6H), 2.41 (s, 3H), 6.32 (br s, 1H), 7.22-7.30 (m, 2H), 7.31-7.39 (m, 2H), 7.42-7.49 (m, 2H), 7.54 (dd, J=1.8, 7.9 Hz, 1H), 7.73 (d, J=1.8 Hz, 1H).

Step 2

In a similar manner to Step 2 of Example 16, 3-chloro-4-methyl-N-(1-methyl-7-phenylethyl)benzamide (500 mg, 1.74 mmol) was dissolved in THF (20 mL), and the solution was treated with TMEDA (0.84 mL, 5.6 mmol), sec-butyl lithium-hexane solution (1.01 mol/L, 5.51 mL, 5.57 mmol), and DMF (0.296 mL, 3.82 mmol), followed by purification by slurry using diisopropylether and hexane to obtain 4-chloro-5-methyl-3-hydroxy-2-(1-methyl-1-phenylethyl)isoindolinone (465 mg, yield 85%).

APCI-MS m/z: 316 [M+H]$^+$; $^1$H-NMR (CDCl$_3$) δ(ppm): 1.94 (s, 3H), 1.99 (s, 3H), 2.46 (s, 3H), 2.48 (d, J=8.0 Hz, 1H), 6.25 (d, J=8.0 Hz, 1H), 7.23 (m, 1H), 7.29-7.39 (m, 2H), 7.39-7.45 (m, 2H), 7.49 (d, J=7.5 Hz, 1H).

Step 3

In a similar manner to Step. 3 of Example 16, 4-chloro-5-methyl-3-hydroxy-2-(1-methyl-1-phenylethyl)isoindolinone (400 mg, 1.27 mmol) was dissolved in THF (16 mL), and the solution was treated with TMEDA (0.33 mL, 2.2 mmol), sec-butyl lithium-hexane solution (1.01 mol/L, 2.8 mL, 2.8 mmol) and iodine (387 mg, 1.52 mmol), followed by purification by flash column chromatography (hexane/ethyl acetate=95/5 to 80/20 to 70/30) to obtain 4-chloro-5-methyl-3-hydroxy-7-iodo-2-(1-methyl-1-phenylethyl)isoindolinone (352 mg, yield 63%).

APCI-MS m/z: 442 [M+H]$^+$; $^1$H-NMR (CDCl$_3$) δ(ppm): 1.95 (s, 3H), 1.99 (s, 3H), 2.40 (d, J=7.7 Hz, 1H), 2.41 (s, 3H), 6.06 (d, J=7.7 Hz, 1H), 7.24 (m, 1H), 7.30-7.37 (m, 2H), 7.41-7.47 (m, 2H), 7.81 (s, 1H).

Step 4

In a similar manner to Step 4 of Example 16, 4-chloro-5-methyl-3-hydroxy-7-iodo-2-(1-methyl-1-phenylethyl)isoindolinone (300 mg, 0.679 mmol) was dissolved in nitromethane (5 mL), and the solution was added with trifluoroacetic acid (0.523 mL, 6.79 mmol) and triethylsilane (0.219 mL, 1.36 mmol), followed by stirring at room temperature for 24 hours. The reaction mixture was added with water, ethyl acetate and hexane. The precipitated solid was collected by filtration and washed with hexane and water, followed by drying under reduced pressure to obtain 4-chloro-5-methyl-7-iodoisoindolinone (140 mg, yield 67%).

APCI-MS m/z: 307 [M+H]$^+$; $^1$H-NMR (CDCl$_3$) δ(ppm): 2.44 (s, 3H), 4.31 (s, 2H), 6.47 (br s, 1H), 7.82 (s, 1H).

Step 5

In a similar manner to Step 2 of Example 1, 4-chloro-5-methyl-7-iodoisoindolinone (25.0 mg, 0.0813 mmol) was suspended in acetonitrile (1 mL), and the suspension was treated with Compound BD (58.2 mg, 0.162 mmol), palladium acetate (1.5 mg, 0.007 mmol) and triethylamine (0.113 mL, 0.811 mmol), followed by purification by slurry using hexane to obtain 4-chloro-5-methyl-7-[1-(tert-butoxycarbonyl)-5-(piperidinomethyl)indol-2-yl]isoindolinone (43.2 mg).

Step 6

In a similar manner to Step 2 of Example 8, 4-chloro-5-methyl-7-[1-(tert-butoxycarbonyl)-5-(piperidinomethyl)indol-2-yl]isoindolinone (43.0 mg) was dissolved in methanol (1 mL), and the solution was treated with 10% hydrogen chloride-methanol solution (1 mL). The mixture was added with diisopropylether. The obtained solid was collected by filtration and washed with diisopropylether, followed by drying under reduced pressure to obtain Compound 342 (23.6 mg, yield 68%, 2 steps).

ESI-MS m/z: 394 [M+H]$^+$; $^1$H-NMR (DMSO-d$_6$) δ(ppm): 1.37 (m, 1H), 1.60-1.90 (m, 5H), 2.51 (s, 3H), 2.77-2.97 (m, 2H), 3.25-3.45 (m, 2H), 4.32 (d, J=4.5 Hz, 2H), 4.49 (s, 2H), 7.29 (dd, J=1.3, 8.5 Hz, 1H), 7.36 (d, J=1.3 Hz, 1H), 7.56 (d, J=8.5 Hz, 1H), 7.77 (s, 1H), 8.26 (s, 1H), 9.46 (s, 1H), 9.72 (br s, 1H), 13.92 (s, 1H).

EXAMPLE 343

4-Chloro-5-methoxy-7-{1H-5-[4-(2-hydroxyethyl)pyperazin-1-ylmethyl]indol-2-yl}isoindolinone dihydrochloride (Compound 343)

Step 1

In a similar manner to Step 2 of Example 1, 4-chloro-5-methoxy-7-iodoisoindolinone (80.0 mg, 0.247 mmol) was suspended in acetonitrile (3 mL), and the suspension was treated with Compound BU (256 mg, 0.495 mmol), palladium acetate (4.4 mg, 0.020 mmol) and triethylamine (0.337 mL, 2.47 mmol), followed by purification by preparative thin-layer chromatography (ethyl acetate/7 mol/L ammonia-methanol solution=10/1) to obtain 4-chloro-5-methoxy-7-(1-(tert-butoxycarbonyl)-5-[(4-(2-hydroxyethyl)pyperazin-1-ylmethyl]indol-2-yl)isoindolinone (121 mg, yield 73%).

ESI-MS m/z: 669 [M+H]$^+$; $^1$H-NMR (CDCl$_3$) δ(ppm): 0.05 (s, 6H), 0.89 (s, 9H), 1.40 (s, 9H), 2.44-2.60 (m, 8H), 2.53 (t, J=6.6 Hz, 2H), 3.58 (s, 2H), 3.75 (t, J=6.6 Hz, 2H), 4.01 (s, 3H), 4.39 (s, 2H), 6.25 (br s, 1H), 6.58 (s, 1H), 7.05 (s, 1H), 7.30 (dd, J=1.5, 8.6 Hz, 1H), 7.49 (d, J=1.5 Hz, 1H), 8.12 (d, J=8.6 Hz, 1H).

Step 2

In a similar manner to Step 2 of Example 8, 4-chloro-5-methoxy-7-(1-(tert-butoxycarbonyl)-5-[4-(2-hydroxyethyl)pyperazin-1-ylmethyl]indol-2-yl)isoindolinone (119 mg, 0.178 mmol) was dissolved in methanol (1.5 mL), and the solution was treated with 10% hydrogen chloride-methanol solution (1.5 mL). The mixture was added with diisopropylether. The obtained solid was collected by filtration and washed with diisopropylether, followed by drying under reduced pressure to obtain Compound 343 (91.5 mg, yield 97%).

ESI-MS m/z: 455 [M+H]$^+$: $^1$H-NMR (CDCl$_3$) δ(ppm): 3.10-3.80 (m, 12H), 4.10 (s, 3H), 4.47 (s, 4H), 7.35 (br s, 1H), 7.51 (s, 1H), 7.57 (d, J=7.1 Hz, 1H), 7.82 (s, 1H), 7.83 (m, 1H), 9.32 (s, 1H), 14.03 (s, 1H).

EXAMPLE 344

4-Chloro-5-methoxy-7-{1H-5-[(2,2-dimethyl-3-(dimethylamino)propyl)aminomethyl]indol-2-yl}isoindolinone dihydrochloride (Compound 344)

Step 1

In a similar manner to Step 2 of Example 1, 4-chloro-5-methoxy-7-iodoisoindolinone (30.0 mg, 0.0927 mmol) was suspended in acetonitrile (2 mL), and the suspension was treated with Compound BW (75.0 mg, 0.186 mmol), palladium acetate (1.7 mg, 0.0076 mmol) and triethylamine (0.126 mL, 0.924 mmol), followed by purification by preparative thin-layer chromatography (ethyl acetate/7 mol/L ammonia-methanol solution=30/1) to obtain 4-chloro-5-methoxy-7-{1-(tert-butoxycarbonyl)-5-[(2,2-dimethyl-3-(dimethylamino)propyl)aminomethyl]indol-2-yl}isoindolinone (22.7 mg).

Step 2

In a similar manner to Step 2 of Example 8, 4-chloro-5-methoxy-7-{1-(tert-butoxycarbonyl)-5-[(2,2-dimethyl-3-(dimethylamino)propyl)aminomethyl]indol-2-yl}isoindolinone (22.7 mg) was dissolved in methanol (1 mL), and the solution was treated with 10% hydrogen chloride-methanol solution-(1 mL). The mixture was added with diethylether. The obtained solid was collected by filtration and washed with diethylether, followed by drying under reduced pressure to obtain Compound 344 (8.8 mg, yield 18%, 2 steps).

ESI-MS m/z: 455 [M+H]$^+$; $^1$H-NMR (DMSO-d$_6$) δ(ppm): 1.14 (s, 6H), 2.70-3.00 (m, 4H), 2.78 (s, 3H), 2.80 (s, 3H), 4.10 (s, 3H), 4.27 (br s, 2H), 4.47 (s, 2H), 7.39 (dd, J=1.2, 8.2 Hz, 1H), 7.51 (d, J=1.2 Hz, 1H), 7.57 (d, J=8.2 Hz, 1H), 7.82 (s, 1H), 7.86 (s, 1H), 9.11 (br s, 2H), 9.33 (s, 1H), 9.81 (brs, 1H), 14.02 (s, 1H).

EXAMPLE 345

4-Chloro-5-methyl-7-{1H-5-[4-(2-hydroxyethyl)pyperazin-1-ylmethyl]indol-2-yl}isoindolinone dihydrochloride (Compound 345)

Step 1

In a similar, manner to Step 2 of Example 1, 4-chloro-5-methyl-7-iodoisoindolinone (88.6 mg, 0.288 mmol) was suspended in acetonitrile (5 mL), and the suspension was treated with Compound BU (298 mg, 0.576 mmol), palladium acetate (5.2 mg, 0.023 mmol) and triethylamine (0.393 mL, 2.88 mmol), followed by purification by slurry using hexane to obtain 4-chloro-5-methyl-7-{1-(tert-butoxycarbonyl)-5-[4-(2-hydroxyethyl)pyperazin-1-ylmethyl]indol-2-yl}isoindolinone (184 mg, yield 98%).

ESI-MS m/z: 653 [M+H]$^+$; $^1$H-NMR (CDCl$_3$) δ(ppm): 0.05 (s, 6H), 0.85 (s, 9H), 1.40 (s, 9H), 2.45-2.65 (m, 8H), 2.52 (t, J=6.5 Hz, 2H), 2.54 (s, 3H), 3.58 (s, 2H), 3.76 (t, J=6.5 Hz, 2H), 4.39 (s, 2H), 6.31 (br s, 1H), 6.54 (s, 1H), 7.28 (dd, J=1.4, 8.6 Hz, 1H), 7.37 (s, 1H), 7.49 (d, J=1.4 Hz, 1H), 8.11 (d, J=8.6 Hz, 1H).

Step 2

In a similar manner to Step 2 of Example 8, 4-chloro-5-methyl-7-{1-(tert-butoxycarbonyl)-5-[4-(2-hydroxyethyl)pyperazin-1-ylmethyl]indol-2-yl}isoindolinone (180 mg, 0.276 mmol) was dissolved in methanol (2 mL), and the solution was treated with 10% hydrogen chloride-methanol solution (2 mL). The mixture was added with diisopropylether. The obtained solid was collected by filtration and washed with diisopropylether, followed by drying under reduced pressure to obtain Compound 345 (133 mg, yield 94%).

ESI-MS m/z: 439 [M+H]$^+$; $^1$H-NMR (DMSO-d$_6$) δ(ppm): 2.52 (s, 3H), 3.08-3.87 (m, 12H), 4.46 (br s, 2H), 4.49 (s, 2H), 7.23-7.40 (m, 2H), 7.57 (d, J=8.3 Hz, 1H), 7.81 (s, 1H), 8.26 (s, 1H), 9.46 (s, 1H), 13.93 (s, 1H).

EXAMPLE 346

4-Hydroxy-5-methoxymethyl-7-[1H-5-(piperidinomethyl)indol-2-yl]isoindolinone hydrochloride (Compound 346)

Step 1

4-Formyl-3-hydroxybenzoic acid (2.20 g, 13.2 mmol) was suspended in dichloromethane (40 mL), and the suspension was added with diisopropylethylamine (9.20 mL, 52.8 mmol) and chloromethyl methyl ether (2.01 mL, 26.5 mmol) under ice-cooling. Then, the reaction mixture was warmed to room temperature and stirred for 1 hour. The solvent was evaporated under reduced pressure and the residue was dissolved in methanol (40 mL), and the solution was added with 2 mol/L aqueous potassium hydroxide solution (40 mL), and stirred at room temperature for 1 hour. Methanol was evaporated under reduced pressure and the residue was added with 4 mol/L hydrochloric acid and water. The precipitated solid was collected by filtration and washed with water, followed by drying under reduced pressure to obtain 4-formyl-3-methoxymethoxybenzoic acid (2.21 g, yield 80%).

ESI-MS m/z: 211 [M+H]$^+$; $^1$H-NMR (DMSO-d$_6$) δ(ppm): 3.46 (s, 3H), 5.47 (s, 2H), 7.67 (dd, J=1.3, 7.9 Hz, 1H), 7.807 (d, J=1.3 Hz, 1H), 7.812 (d, J=7.9 Hz, 1H), 10.44 (s, 1H), 13.47 (s, 1H).

Step 2

4-Formyl-3-methoxymethoxybenzoic acid (2.57 g, 12.2 mmol) was dissolved in DMF (50 mL), and the solution was added with EDCI (4.68 g, 24.4 mmol), HOBT monohydrate (1.65 g, 12.2 mmol) and cumylamine (4.03 mL, 24.4 mmol), followed by stirring at room temperature for 4 hours. The reaction mixture was added with water (10 mL) and 1 mol/L hydrochloric acid (10 mL) and stirred at room temperature for 1 hour. The reaction mixture was added with water and extracted with ethyl acetate. The organic layer was washed with water and saturated aqueous sodium hydrogencarbonate solution and saturated brine, followed by drying over anhydrous sodium sulfate. The solvent was evaporated under reduced pressure and the residue was purified by flash column chromatography (hexane/ethyl acetate=95/5 to 80/20 to 70/30) to obtain 4-formyl-3-methoxymethoxy-N-(1-methyl-1-phenylethyl)benzamide (3.12 g, yield 78%).

ESI-MS m/z: 328 [M+H]$^+$; $^1$H-NMR (CDCl$_3$) δ(ppm): 1.84 (s, 6H), 3.52 (s, 3H), 5.34 (s, 2H), 6.44 (br s, 1H), 7.27 (m, 1H), 7.32-7.41 (m, 4H), 7.42-7.50 (m, 2H), 7.68 (d, J=1.5 Hz, 1H), 7.88 (d, J=7.9 Hz, 1H).

Step 3

4-Formyl-3-methoxymethoxy-N-(1-methyl-1-phenylethyl)benzamide (3.12 g, 9.53 mmol) was dissolved in methanol (30 mL), and the solution was added with trimethyl orthoformate (2.09 mL, 19.1 mmol) and p-toluenesulfonic acid monohydrate (16.4 mg, 0.0952 mmol), followed by stirring at room temperature for 1 hour. The reaction mixture was added with saturated aqueous sodium hydrogencarbonate solution and water, and extracted with ethyl acetate. The organic layer was washed with saturated brine and dried over anhydrous sodium sulfate. The solvent was evaporated under reduced pressure to obtain 3-methoxymethoxy-4-dimethoxymethyl-N-(1-methyl-1-phenylethyl)benzamide (3.61 g, yield 100%).

ESI-MS m/z: 374 [M+H]$^+$; $^1$H-NMR (CDCl$_3$) δ(ppm): 1.82 (s, 6H), 3.35 (s, 6H), 3.48 (s, 3H), 5.25 (s, 2H), 5.69 (s, 1H), 6.40 (brs, 1H), 7.23-7.41 (m, 4H), 7.43-7.50 (m, 2H), 7.55-7.62 (m, 2H).

Step 4

In a similar manner to Step 2 of Example 16, 3-methoxymethoxy-4-dimethoxymethyl-N-(1-methyl-1-phenylethyl)benzamide (3.61 g, 9.67 mmol) was dissolved in THF (100 mL), and the solution was treated with TMEDA (4.70 mL, 31.0 mmol), sec-butyl lithium-hexane solution (1.03 mol/L, 30.0 mL, 30.9 mmol) and DMF (1.65 mL, 21.3 mmol), followed by purification by slurry using chloroform and hexane to obtain 4-methoxymethoxy-5-dimethoxymethyl-3-hydroxy-2-(1-methyl-1-phenylethyl)isoindolinone (2.95 g, yield 85%).

ESI-MS m/z: 402 [M+H]$^+$; $^1$H-NMR (DMSO-d$_6$) δ(ppm): 1.80 (s, 3H), 1.82 (s, 3H), 3.30 (s, 3H), 3.32 (s, 3H), 3.53 (s, 3H), 5.25 (d, J=5.9 Hz, 1H), 5.52 (d, J=5.9 Hz, 1H), 5.66 (s, 1H), 6.37 (d, J=10.7 Hz, 1H), 6.66 (d, J=10.7 Hz, 1H), 7.15 (m, 1H), 7.22-7.29 (m, 3H), 7.34-7.40 (m, 2H), 7.57 (d, J=7.7 Hz, 1H).

Step 5

In a similar manner to Step 3 of Example 16, 4-methoxymethoxy-5-dimethoxymethyl-3-hydroxy-2-(1-methyl-1-phenylethyl)isoindolinone (3.34 g, 8.31 mmol) was dissolved in THF (100 mL), and the solution was treated with TMEDA (4.00 mL, 27.0 mmol), sec-butyl lithium-hexane solution (1.03 mol/L, 25.8 mL, 26.6 mmol) and iodine (3.16 g, 12.5 mmol), followed by purification by slurry using methanol and diisopropylether to obtain 4-methoxymethoxy-5-dimethoxymethyl-3-hydroxy-7-iodo-2-(1-methyl-1-phenylethyl)isoindolinone (2.24 g, yield 51%).

ESI-MS m/z: 528 [M+H]$^+$; $^1$H-NMR (CDCl$_3$) δ(ppm): 1.94 (s, 3H), 1.98 (s, 3H), 3.31 (s, 3H), 3.38 (s, 3H), 3.58 (s, 3H), 3.87 (d, J=5.3 Hz, 1H), 5.15 (d, J=15.6 Hz, 1H), 5.18 (d, J=15.6 Hz, 1H), 5.58 (s, 1H), 6.14 (d, J=5.3 Hz, 1H), 7.23 (m, 1H) 7.28-7.36 (m, 2H), 7.43-7.48 (m, 2H), 8.09 (s, 1H).

Step 6

In a similar manner to Step 4 of Example 16, 4-methoxymethoxy-5-dimethoxymethyl-3-hydroxy-7-iodo-2-(1-methyl-1-phenylethyl)isoindolinone (200 mg, 0.379 mmol) was dissolved in nitromethane (10 mL), and the solution was treated with trifluoroacetic acid (0.584 mL, 7.58 mmol) and triethylsilane (0.612 mL, 3.79 mmol), followed y purification by slurry using chloroform to obtain 4-hydroxy-5-methoxymethyl-7-iodoisoindolinone (103 mg, yield-86%).

ESI-MS m/z: 319 [M+H]$^+$; $^1$H-NMR (DMSO-d$_6$) δ(ppm): 3.34 (s, 3H), 4.17 (s, 2H), 4.46 (s, 2H), 7.69 (s, 1H), 8.65 (br s, 1H), 9.82 (s, 1H).

Step 7

In a similar manner to Step 2 of Example 1, 4-hydroxy-5-methoxymethyl-7-iodoisoindolinone (100 mg, 0.313 mmol) was suspended in acetonitrile (4 mL), and the suspension was treated with Compound BD (224 mg, 0.625 mmol), palladium acetate (5.6 mg, 0.025 mmol) and triethylamine (0.427 mL, 3.13 mmol), followed by purification by preparative thin-layer chromatography (ethyl acetate/7 mol/L ammonia-methanol solution=10/1) to obtain 4-hydroxy-5-methoxymethyl-7-[1-(tert-butoxycarbonyl)-5-(piperidinomethyl)indol-2-yl]isoindolinone (70.9 mg, yield 43%).

ESI-MS m/z: 506 [M+H]$^+$; $^1$H-NMR (CDCl$_3$) δ(ppm): 1.34 (s, 9H), 1.38-1.47 (m, 2H), 1.51-1.63 (m, 4H), 2.35-2.46 (m, 4H), 3.52 (s, 3H), 3.58 (s, 2H), 4.35 (s, 2H), 4.80 (s, 2H), 6.46 (s, 1H), 6.70 (br s, 1H), 6.77 (br s, 1H), 7.10 (s, 1H), 7.25 (dd, J=1.5, 8.6 Hz, 1H), 7.45 (d, J=1.5 Hz, 1H), 8.13 (d, J=8.6 Hz, 1H).

Step 8

In a similar manner to Step 2 of Example 8, 4-hydroxy-5-methoxymethyl-7-[1-(tert-butoxycarbonyl)-5-(piperidinomethyl)indol-2-yl]isoindolinone (19.8 mg, 0.0392 mmol) was dissolved in methanol (1 mL), and the solution was treated with 10% hydrogen chloride-methanol solution (1 mL). The solvent was evaporated under reduced pressure and the residue was added with methanol and diisopropylether. The obtained solid was collected by filtration and washed with diisopropylether, followed by drying under reduced pressure to obtain Compound 346 (15.9 mg, yield 92%).

ESI-MS m/z: 406 [M+H]$^+$; $^1$H-NMR (DMSO-d$_6$) δ(ppm): 1.35 (m, 1H), 1.57-1.86 (m, 5H), 2.79-2.95 (m, 2H), 3.27-3.39 (m, 2H), 3.40 (s, 3H), 4.31 (d, J=4.8 Hz, 2H), 4.42 (s, 2H), 4.57 (s, 2H), 7.07 (s, 1H), 7.22 (d, J=8.4 Hz, 1H), 7.52 (d, J=8.4 Hz, 1H), 7.70 (s, 1H), 8.05 (s, 1H), 9.26 (s, 1H), 9.51 (br s, 1H), 9.88 (s, 1H), 13.89 (s, 1H).

EXAMPLE 347

4-Chloro-5-hydroxy-7-[1H-5-(piperidinomethyl) indol-2-yl]isoindolinone hydrochloride (Compound 347)

Step 1

3-Chloro-4-hydroxybenzoic acid 0.5 hydrate (2.00 g, 11.6 mmol) was suspended in dichloromethane (50 mL), and the suspension was added with diisopropylethylamine (8.10 mL, 46.5 mmol) and chloromethyl methyl ether (1.80 mL, 23.7 mmol), under ice-cooling. The reaction mixture was warmed to room temperature and stirred for 1.5 hours. The reaction mixture was added with chloromethyl methyl ether (0.45 mL, 5.92 mmol) under ice-cooling, and stirred at room temperature for 1.5 hours. The reaction mixture was added with methanol (100 mL) and 4 mol/L aqueous potassium hydroxide solution (50 mL) and stirred at room temperature for 18 hours. The solvent was evaporated under reduced pressure, and the residue was added with 4 mol/L hydrochloric acid and water, followed by extracting with ethyl acetate. The organic layer was washed with saturated brine and dried over anhydrous sodium sulfate. The solvent was evaporated under reduced pressure to obtain 3-chloro-4-methoxymethoxybenzoic acid (2.39 g, yield 95%).

ESI-MS m/z: 215 [M−H]$^-$; $^1$H-NMR (CDCl$_3$) δ(ppm): 3.41 (s, 3H), 5.37 (s, 2H), 7.32 (d, J=8.7 Hz, 1H), 7.86 (dd, J=2.1, 8.7 Hz, 1H), 7.92 (d, J=2.1 Hz, 1H), 13.01 (br s, 1H).

Step 2

In a similar manner to Step 1 of Example 137, 3-chloro-4-methoxymethoxybenzoic acid (2.39 g, 11.0 mmol) was dissolved in DMF (47 mL), and the solution was treated with EDCI (4.23 g, 22.1 mmol), HOBT monohydrate (1.69 g, 11.0 mmol) and cumylamine (3.20 mL, 22.0 mmol). The reaction mixture was added with water. The precipitated solid was collected by filtration and washed with water, followed by drying under reduced pressure to obtain 3-chloro-4-methoxymethoxy-N-(1-methyl-1-phenylethyl)benzamide (2.83 g, yield 77%).

ESI-MS m/z: 332 [M−H]$^-$; $^1$H-NMR (CDCl$_3$) δ(ppm): 1.81 (s, 6H), 3.51 (s, 3H), 5.29 (s, 2H), 6.28 (s, 1H), 7.13-7.53 (m, 6H), 7.62 (dd, J=2.3, 8.6 Hz, 1H), 7.92 (d, J=2.3 Hz, 1H).

Step 3

In a similar manner to Step 2 of Example 16, 3-chloro-4-methoxymethoxy-N-(1-methyl-1-phenylethyl)benzamide (2.83 g, 8.48 mmol) was dissolved in THF (110 mL), and the solution was treated with TMEDA (4.10 mL, 27.2 mmol), sec-butyl lithium-hexane solution (1.01 mol/L, 27.0 mL, 27.2 mmol) and DMF (1.40 mL, 18.1 mmol), followed by purification by flash column chromatography (chloroform/methanol=100/0 to 97/3) to obtain 4-chloro-5-methoxymethoxy-3-hydroxy-2-(1-methyl-1-phenylethyl)isoindolinone (3.01 g, yield 98%).

APCI-MS m/z: 362 [M+H]$^+$; $^1$H-NMR (CDCl$_3$) δ(ppm): 1.93 (s, 3H), 1.98 (s, 3H), 2.54 (d, J=8.3 Hz, 1H), 3.35 (s, 3H), 5.30 (s, 2H), 6.23 (d, J=8.4 Hz, 1H), 7.19-7.48 (m, 6H), 7.54 (d, J=8.4 Hz, 1H).

Step 4

In a similar manner to Step 3 of Example 16, 4-chloro-5-methoxymethoxy-3-hydroxy-2-(1-methyl-1-phenylethyl) isoindolinone (3.01 g, 8.32 mmol) was dissolved in THF (110 mL), and the solution was treated with TMEDA (4.00 mL, 26.5 mmol), sec-butyl lithium-hexane solution (0.95 mol/L, 28.0 mL, 26.6 mmol) and iodine (2.53 g, 9.98 mmol), followed by purification by slurry using diisopropylether to obtain 4-chloro-5-methoxymethoxy-3-hydroxy-7-iodo-2-(1-methyl-1-phenylethyl)isoindolinone (3.90 g, yield 96%).

APCI-MS m/z: 488 [M+H]$^+$; $^1$H-NMR (CDCl$_3$) δ(ppm): 1.94 (s, 3H), 1.99 (s, 3H), 3.52 (s, 3H), 5.29 (s, 2H), 6.06 (s, 1H), 7.20-7.51 (m, 5H), 7.68 (s, 1H).

Step 5

In a similar manner to Step 4 of Example 16, 4-chloro-5-methoxymethoxy-3-hydroxy-7-iodo-2-(1-methyl-1-phenylethyl)isoindolinone (100 mg, 0.21 mmol) was dissolved in nitromethane (4 mL), and the solution was treated with trifluoroacetic acid (0.097 mL, 1.26 mmol) and triethylsilane (0.200 mL, 1.25 mmol). The mixture was added with water and saturated aqueous sodium hydrogencarbonate solution and extracted with ethyl acetate. The organic layer was washed with saturated brine and dried over anhydrous sodium sulfate. The solvent was evaporated under reduced pressure to obtain 4-chloro-5-hydroxy-7-iodo-2-(1-methyl-1-phenylethyl)isoindolinone (97.0 mg, yield 98%).

ESI-MS m/z: 472 [M+H]$^+$; $^1$H-NMR (CDCl$_3$) δ(ppm): 1.94 (s, 6H), 3.52 (s, 3H), 4.21 (s, 2H), 5.29 (s, 2H), 7.20-7.50 (m, 5H), 7.69 (s, 1H).

Step 6

In a similar manner to Step 6 of Example 139, 4-chloro-5-hydroxy-7-iodo-2-(1-methyl-1-phenylethyl)isoindolinone (97.1 mg, 0.206 mmol) was treated with 10% hydrogen chloride-methanol solution (3 mL), followed by purification by slurry using diisopropylether to obtain 4-chloro-5-hydroxy-7-iodoisoindolinone (36.9 mg, yield 58%).

ESI-MS m/z: 310 [M+H]$^+$; $^1$H-NMR (CDCl$_3$) δ(ppm): 4.18 (s, 2H), 7.44 (s, 1H), 8.59 (s, 1H), 11.22 (br s, 1H).

Step 7

In a similar manner to Step 2 of Example 1, 4-chloro-5-hydroxy-7-iodoisoindolinone (34.5 mg, 0.111 mmol) was dissolved in acetonitrile (1.5 mL), and the solution was treated with Compound BD (80.0 mg, 0.223 mmol), palladium acetate (2.0 mg, 0.0089 mmol), tri(o-tolyl)phosphine (6.1 mg, 0.020 mmol) and triethylamine (0.155 mL, 1.11 mmol), followed by purification by slurry using hexane to obtain 4-chloro-5-hydroxy-7-[1-(tert-butoxycarbonyl)-5-(piperidinomethyl)indol-2-yl]isoindolinone (45.3 mg, yield 82%).

ESI-MS m/z: 496 [M+H]$^+$; $^1$H-NMR-(DMSO-d$_6$) δ(ppm): 1.21 (s, 9H), 1.44-1.58 (m, 6H), 3.17-3.33 (m, 6H), 4.31 (s, 2H), 6.65 (s, 1H), 7.06 (s, 1H), 7.35 (d, J=8.7 Hz, 1H), 7.60 (br s, 1H), 8.12 (d, J=8.7 Hz, 1H), 8.32 (s, 1H), 8.48 (s, 1H).

Step 8

In a similar manner to Step 2 of Example 8, 4-chloro-5-hydroxy-7-[1-(tert-butoxycarbonyl)-5-(piperidinomethyl) indol-2-yl]isoindolinone (43.5 mg, 0.0880 mmol) was dissolved in methanol (1 mL), and the solution was treated with 10% hydrogen chloride-methanol solution (1 mL). The obtained solid was collected by filtration and washed with diisopropylether, followed by drying under reduced pressure to obtain Compound 347 (13.9 mg, yield 46%).

ESI-MS m/z: 396 [M+H]$^+$; $^1$H-NMR (DMSO-d$_6$) δ(ppm): 1.34 (m, 1H), 1.54-1.86 (m, 5H), 2.73-2.96 (m, 2H), 3.19-3.45 (m, 2H), 4.31 (d, J=4.6 Hz, 2H), 4.43 (s, 2H), 7.04 (s, 1H), 7.28 (d, J=8.0 Hz, 1H), 7.55 (d, J=8.0 Hz, 1H), 7.73 (s, 1H), 7.76 (s, 1H), 9.21 (s, 1H), 9.60 (br s, 1H), 11.26 (s, 1H), 14.05 (s, 1H).

EXAMPLE 348

4-Methanesulfonyloxy-5-methoxymethyl-7-[1H-5-(piperidinomethyl)indol-2-yl]isoindolinone hydrochloride (Compound 348)

Step 1

4-Methoxymethoxy-5-dimethoxymethyl-3-hydroxy-7-iodo-2-(1-methyl-1-phenylethyl)isoindolinone (490 mg, 0.929 mmol) was dissolved in methanol (10 mL), and the solution was treated with 10% hydrogen chloride-methanol solution (5 mL), followed by stirring at room temperature for 3 hours. The solvent was evaporated under reduced pressure and the residue was dissolved in acetonitrile (5 mL). The solution was added with 1 mol/L hydrochloric acid (5 mL) and stirred at room temperature for 1 hour. The precipitated solid was collected by filtration and washed with water, followed by drying under reduced pressure to obtain 4-hydroxy-5-formyl-3-methoxy-7-iodo-2-(1-methyl-1-phenylethyl)isoindolinone (329 mg, yield 79%).

ESI-MS m/z: 452 [M+H]$^+$; $^1$H-NMR (CDCl$_3$) δ(ppm): 1.90 (s, 3H), 2.00 (s, 3H), 3.06 (s, 3H), 6.12 (s, 1H), 7.23 (m, 1H), 7.28-7.36 (m, 2H), 7.37-7.48 (m, 2H), 8.10 (s, 1H), 9.95 (s, 1H), 11.13 (s, 1H).

Step 2

In a similar manner to Step 1 of Example 289, 4-hydroxy-5-formyl-3-methoxy-7-iodo-2-(1-methyl-1-phenylethyl)isoindolinone (325 mg, 0.720 mmol) was dissolved in dichloromethane (10 mL), and the solution was treated with triethylamine (0.401 mL, 2.88 mmol) and methanesulfonyl chloride (0.111 mL, 1.43 mmol), followed by purification by flash column chromatography (hexane/ethyl acetate=95/5 to 80/20) to obtain 4-methanesulfonyloxy-5-formyl-3-methoxy-7-iodo-2-(1-methyl-1-phenylethyl)isoindolinone (381 mg, yield 58%).

ESI-MS m/z: 530 [M+H]$^+$; $^1$H-NMR (CDCl$_3$) δ(ppm): 1.90 (s, 3H), 2.01 (s, 3H), 2.95 (s, 3H), 3.49 (s, 3H), 6.46 (s, 1H), 7.24 (m, 1H), 7.28-7.43 (m, 4H), 8.48 (s, 1H), 10.27 (s, 1H).

Step 3

4-Methanesulfonyloxy-5-formyl-3-methoxy-7-iodo-2-(1-methyl-1-phenylethyl)isoindolinone (220 mg, 0.416 mmol) was dissolved in methanol (4 mL), and the solution was added with trimethyl orthoformate (0.091 mL, 0.83 mmol) and p-toluenesulfonic acid monohydrate (1.0 mg, 0.0058 mmol), followed by stirring at 50° C. for 5 hours. The reaction mixture was added with saturated aqueous sodium hydrogencarbonate solution and water. The precipitated solid was collected by filtration and washed with water, followed by drying under reduced pressure to obtain 4-methanesulfonyloxy-5-dimethoxymethyl-3-methoxy-7-iodo-2-(1-methyl-1-phenylethyl)isoindolinone (231 mg, yield 96%).

ESI-MS m/z: 576 [M+H]$^+$; $^1$H-NMR (CDCl$_3$) (ppm): 1.88 (s, 3H), 2.00 (s, 4H), 2.89 (s, 3H), 3.34 (s, 3H), 3.40 (s, 3H), 3.46 (s, 3H), 5.69 (s, 1H), 6.44 (s, 1H), 7.23 (m, 1H), 7.28-7.35 (m, 2H), 7.36-7.42 (m, 2H), 8.25 (s, 1H).

Step 4

In a similar manner to Step 4 of Example 16, 4-methanesulfonyloxy-5-dimethoxymethyl-3-methoxy-7-iodo-2-(1-methyl-1-phenylethyl)isoindolinone (226 mg, 0.393 mmol) was dissolved in nitromethane (5 mL), and the solution was added with trifluoroacetic acid (0.775 mL, 10.1 mmol) and triethylsilane (0.406 mL, 2.51 mmol), followed by stirring at 50° C. for 1 hour. The reaction mixture was added with water, ethyl acetate and hexane. The precipitated solid was collected by filtration and washed with water, followed by drying under reduced pressure to obtain 4-methanesulfonyloxy-5-methoxymethyl-7-iodoisoindolinone (113 mg, yield 72%).

ESI-MS m/z: 397 [M+H]$^+$; $^1$H-NMR (CDCl$_3$) δ(ppm): 3.37 (s, 3H), 3.43 (s, 3H), 4.52 (s, 2H), 4.59 (s, 2H), 6.43 (br s, 1H), 8.07 (s, 1H).

Step 5

In a similar manner to Step 2 of Example 1, 4-methanesulfonyloxy-5-methoxymethyl-7-iodoisoindolinone (50.0 mg, 0.126 mmol) was dissolved in acetonitrile (4 mL), and the solution was treated with Compound BD (90.3 mg, 0.252 mmol), palladium acetate (2.3 mg, 0.010 mmol), tri(o-tolyl)phosphine (6.1 mg, 0.020 mmol) and triethylamine (0.172 mL, 1.26 mmol), followed by purification by preparative thin-layer chromatography (chloroform/methanol=5/1) to obtain 4-methanesulfonyloxy-5-methoxymethyl-7-[1-(tert-butoxycarbonyl)-5-(piperidinomethyl)indol-2-yl]isoindolinone (65.9 mg, yield 90%).

ESI-MS m/z: 584 [M+H]$^+$; $^1$H-NMR (CDCl$_3$) δ(ppm): 1.24-1.36 (m, 2H), 1.33 (s, 9H), 1.38-1.48 (m, 2H), 1.53-1.61 (m, 2H), 2.36-2.47 (m, 4H), 3.40 (s, 3H), 3.44 (s, 3H), 3.59 (s, 2H), 4.61 (s, 2H), 4.67 (s, 2H), 6.28 (br s, 1H), 6.58 (s, 1H), 7.30 (dd, J=1.2, 8.6 Hz, 1H), 7.49 (d, J=1.2 Hz, 1H), 7.60 (s, 1H), 8.18 (d, J=8.6 Hz, 1H).

Step 6

In a similar manner to Step 2 of Example 8, 4-methanesulfonyloxy-5-methoxymethyl-7-[1-(tert-butoxycarbonyl)-5-(piperidinomethyl)indol-2-yl]isoindolinone (55.0 mg, 0.0942 mmol) was dissolved in methanol (2 mL), and the solution was treated with 10% hydrogen chloride-methanol solution (2 mL). The reaction mixture was added with diisopropylether. The precipitated solid was collected by filtration and washed with diisopropylether, followed by drying under reduced pressure to obtain Compound 348 (45.9 mg, yield 94%).

ESI-MS m/z: 484 [M+H]$^+$; $^1$H-NMR (DMSO-d$_6$) δ(ppm): 1.38 (m, 1H), 1.57-1.87 (m, 5H), 2.80-2.96 (m, 2H), 3.28-3.38 (m, 2H), 3.40 (s, 3H), 3.68 (s, 3H), 4.33 (d, J=4.6 Hz, 2H), 4.60 (s, 2H), 4.66 (s, 2H), 7.30 (dd, J=1.0, 8.4 Hz, 1H), 7.33 (d, J=1.0 Hz, 1H), 7.59 (d, J=8.4 Hz, 1H), 7.77 (s, 1H), 8.28 (s, 1H), 9.52 (s, 1H), 9.54 (br s, 1H), 13.86 (s, 1H).

EXAMPLE 349

4-Methanesulfonyloxy-5-methoxymethyl-7-[1H-5-(dimethylaminomethyl)indol-2-yl]isoindolinone hydrochloride (Compound 349)

Step 1

In a similar manner to Step 2 of Example 1, 4-methanesulfonyloxy-5-methoxymethyl-7-iodoisoindolinone (50.0 mg, 0.126 mmol) was dissolved in acetonitrile (4 mL), and the solution was treated with Compound BZ (80.2 mg, 0.252 mmol), palladium acetate (2.3 mg, 0.010 mmol), tri(o-tolyl)phosphine (6.1 mg, 0.020 mmol) and triethylamine (0.172 mL, 1.26 mmol), followed by purification by preparative thin-layer chromatography (chloroform/methanol=5/1) to obtain 4-methanesulfonyloxy-5-methoxymethyl-7-[1-(tert-butoxycarbonyl)-5-(dimethylaminomethyl)indol-2-yl]isoindolinone (34.5 mg, yield 50%).

ESI-MS m/z: 544 [M+H]$^+$; $^1$H-NMR (CDCl$_3$) δ(ppm): 1.32 (s, 9H), 2.27 (s, 6H), 3.40 (s, 3H), 3.44 (s, 3H), 3.53 (s, 2H), 4.61 (s, 2H), 4.67 (s, 2H), 6.31 (br s, 1H), 6.58 (s, 1H), 7.29 (dd, J=1.5, 8.5 Hz, 1H), 7.48 (d, J=1.5 Hz, 1H), 7.60 (s, 1H), 8.20 (d, J=8.6 Hz, 1H).

Step 2

In a similar manner to Step 2 of Example 8, 4-methanesulfonyloxy-5-methoxymethyl-7-[1-(tert-butoxycarbonyl)-5-(dimethylaminomethyl)indol-2-yl]isoindolinone (23.0 mg, 0.0423 mmol) was dissolved in methanol (1 mL) and the solution was treated with 10% hydrogen chloride-methanol solution (1 mL). The solvent was evaporated under reduced pressure. The residue was purified by slurry using methanol and ethyl acetate to obtain Compound 349 (18.9 mg, yield 93%).

ESI-MS m/z: 444 [M+H]$^+$; $^1$H-NMR (DMSO-d$_6$) δ(ppm): 2.73 (d, J=4.2 Hz, 6H), 3.40 (s, 3H), 3.68 (s, 3H), 4.34 (d, J=4.6 Hz, 2H), 4.60 (s, 2H), 4.66 (s, 2H), 7.28 (dd, J=1.1, 8.3 Hz, 1H), 7.58 (d, J=1.1 Hz, 1H), 7.59 (d, J=8.3 Hz, 1H), 7.76 (s, 1H), 8.28 (s, 1H), 9.53 (s, 1H), 9.88 (br s, 1H), 13.86 (s, 1H).

EXAMPLE 350

4-Chloro-5-methanesulfonyloxy-7-{1H-5-[4-(2-hydroxyethyl)pyperazin-1-ylmethyl]indol-2-yl}isoindolinone dihydrochloride (Compound 350)

Step 1

In a similar manner to Step 2 of Example 1, 4-chloro-5-hydroxy-7-iodoisoindolinone (50.4 mg, 0.163 mmol) was dissolved in acetonitrile (2.5 mL), and the solution was treated with Compound BU (171 mg, 0.330 mmol), palladium acetate (3.0 mg, 0.013 mmol), tri(o-tolyl)phosphine (7.9 mg, 0.026 mmol) and triethylamine (0.227 mL, 1.63 mmol), followed by purification by slurry using hexane to obtain 4-chloro-5-hydroxy-7-{1-(tert-butoxycarbonyl)-5-[4-(2-hydroxyethyl)pyperazin-1-ylmethyl]indol-2-yl}isoindolinone (65.3 mg, yield 61%).

ESI-MS m/z: 462 [M+H]$^+$; $^1$H-NMR (CDCl$_3$) δ(ppm): 0.04 (s, 6H), 0.86 (s, 9H), 1.36 (s, 9H), 2.06-2.75 (m, 10H), 3.58 (s, 2H), 3.75 (t, J=5.9 Hz, 2H), 4.34 (s, 2H), 6.08-6.27 (m, 2H), 6.88 (s, 1H), 7.26 (m, 1H), 7.36 (s, 1H), 8.13 (d, J=8.6 Hz, 1H).

Step 2

In a similar manner to Step 1 of Example 289, 4-chloro-5-hydroxy-7-{1-(tert-butoxycarbonyl)-5-[4-(2-hydroxyethyl)pyperazin-1-ylmethyl]indol-2-yl}isoindolinone (62.5 mg, 0.0950 mmol) was dissolved in dichloromethane (2.4 mL), and the solution was treated with triethylamine (0.053 mL, 0.38 mmol) and methanesulfonyl chloride (0.015 mL, 0.019 mmol), followed by purification by slurry using hexane to obtain 4-chloro-5-methanesulfonyloxy-7-{1-(tert-butoxycarbonyl)-5-[4-(2-hydroxyethyl)pyperazin-1-ylmethyl]indol-2-yl}isoindolinone (50.1 mg, yield 72%).

ESI-MS m/z: 733 [M+H]$^+$: $^1$H-NMR (CDCl$_3$) δ(ppm): 0.05 (s, 6H), 0.88 (s, 9H), 1.41 (s, 9H), 2.37-2.68 (m, 10H), 3.34 (s, 3H), 3.58 (s, 2H), 3.75 (t, J=6.1 Hz, 2H), 4.45 (s, 2H), 6.41 (s, 1H), 6.61 (s, 1H), 7.23 (m, 1H), 7.31 (d, J=8.4 Hz, 1H), 7.49 (s, 1H), 7.56 (s, 1H), 8.10 (d, J=8.4 Hz, 1H).

Step 3

In a similar manner to Step 2 of Example 8, 4-chloro-5-methanesulfonyloxy-7-{1-(tert-butoxycarbonyl)-5-[4-(2-hydroxyethyl)pyperazin-1-ylmethyl]indol-2-yl}isoindolinone (48.0 mg, 0.0650 mmol) was dissolved in methanol (3 mL), and the solution was treated with 10% hydrogen chloride-methanol solution (3 mL). The obtained solid was collected by filtration and washed with diisopropylether, followed by drying under reduced pressure to obtain Compound 350 (24.4 mg, yield 63%).

ESI-MS m/z: 519 [M+H]$^+$; $^1$H-NMR (DMSO-d$_6$) δ(ppm): 3.10-3.85 (m, 12H), 3.67 (s, 3H), 4.46 (br s, 2H), 4.55 (s, 2H), 7.36 (d, J=8.6 Hz, 1H), 7.46 (s, 1H), 7.59 (d, J=8.6 Hz, 1H), 7.84 (br s, 1H), 8.24 (s, 1H), 9.64 (s, 1H), 11.55 (br s, 2H), 13.81 (s, 1H).

EXAMPLE 351

4-Hydroxy-5-methoxy-7-[1H-5-(piperidinomethyl)indol-2-yl]isoindolinone hydrochloride (Compound 351)

Step 1

In a similar manner to Step 1 of Example 347, isovanillic acid (5.00 g, 29.7 mmol) was suspended in dichloromethane (100 mL), and the suspension was treated with diisopropylethylamine (22.8 mL, 131 mmol) and chloromethyl methyl ether (4.96 mL, 65.4 mmol). The solvent was evaporated under reduced pressure. The residue was dissolved in methanol (50 mL) and treated with 4 mol/L aqueous potassium hydroxide solution (50 mL). The solvent was evaporated under reduced pressure. The residue was added with 4 mol/L hydrochloric acid. The precipitated solid was collected by filtration and washed with water, followed by drying under reduced pressure to obtain 3-methoxymethoxy-4-methoxybenzoic acid (4.82 g, yield 76%).

ESI-MS m/z: 213 [M+H]$^+$, $^1$H-NMR (CDCl$_3$) δ(ppm): 3.54 (s, 3H), 3.96 (s, 3H), 5.28 (s, 2H), 6.95 (d, J=8.4 Hz, 1H), 7.82 (dd, J=1.9, 8.4 Hz, 1H), 7.86 (d, J=1.9 Hz, 1H).

Step 2

In a similar manner to Step 11 of Example 137, 3-methoxymethoxy-4-methoxybenzoic acid (6.41 g, 30.2 mmol) was dissolved in DMF (100 mL), and the solution was treated with EDCI (5.75 g, 30.0 mmol), HOBT monohydrate (4.05 g, 30.0 mmol) and cumylamine (8.63 mL, 60.0 mmol). The reaction mixture was added with water. The precipitated solid was collected by filtration and washed with water, followed by drying under reduced pressure to obtain 3-methoxymethoxy-4-methoxy-N-(1-methyl-1-phenylethyl)benzamide (7.89 g, yield 80%).

ESI-MS m/z: 330 [M+H]$^+$; $^1$H-NMR (CDCl$_3$) δ(ppm): 1.82 (s, 6H), 3.51 (s, 3H), 3.92 (s, 3H), 5.25 (s, 2H), 6.32 (br s, 1H), 6.89 (d, J=8.4 Hz, 1H), 7.24 (m, 1H), 7.31-7.42 (m, 3H), 7.43-7.49 (m, 2H), 7.60 (d, J=2.2 Hz, 1H).

Step 3

In a similar manner to Step 2 of Example 16, 3-methoxymethoxy-4-methoxy-N-(1-methyl-1-phenylethyl)benzamide (7.50 g, 22.8 mmol) was dissolved in THF (200-mL), and the solution was treated with TMEDA (11.0 mL, 72.9 mmol), sec-butyl lithium-hexane solution (0.95 mol/L, 77.0 mL, 73.2 mmol) and DMF (3.88 mL, 50.1 mmol), followed by purification by slurry using isopropylether and hexane to obtain 4-methoxymethoxy-5-methoxy-3-hydroxy-2-(1-methyl-1-phenylethyl)isoindolinone (6.41 g, yield 79%).

ESI-MS m/z: 358 [M+H]$^+$; $^1$H-NMR (CDCl$_3$) δ(ppm): 1.91 (s, 3H), 1.96 (s, 3H), 3.57 (s, 3H), 3.91 (s, 3H), 5.18 (d, J=15.6 Hz, 1H), 5.20 (d, J=15.6 Hz, 1H), 6.31 (s, 1H), 7.00 (d, J=8.2 Hz, 1H), 7.20 (m, 1H), 7.27-7.35 (m, 3H), 7.41-7.48 (m, 3H).

Step 4

In a similar manner to Step 3 of Example 16, 4-methoxymethoxy-5-methoxy-3-hydroxy-2-(1-methyl-1-phenylethyl)isoindolinone (2.00 g, 5.60 mmol) was dissolved in THF (60 mL), and the solution was treated with TMEDA (2.70 mL, 17.9 mmol), sec-butyl lithium-hexane solution (0.95 mol/L, 18.9 mL, 18.0 mmol) and iodine (2.13 g, 8.39 mmol), followed by purification by flash column chromatography (hexane/ethyl acetate=95/5 to 80/20 to 70/30) to obtain 4-methoxymethoxy-5-methoxy-3-hydroxy-7-iodo-2-(1-methyl-1-phenyl ethyl)isoindolinone (2.08 g, yield 77%).

ESI-MS m/z: 484 [M+H]$^+$; $^1$H-NMR (CDCl$_3$) δ(ppm): 1.92 (s, 3H), 1.97 (s, 3H), 3.57 (s, 3H), 3.68 (d, J=4.5 Hz, 1H), 3.91 (s, 3H), 5.15 (d, J=21.2 Hz, 1H), 5.17 (d, J=21.2 Hz, 1H), 6.13 (d, J=4.5 Hz, 1H), 7.21 (m, 1H), 7.27-7.35 (m, 2H), 7.37 (s, 1H), 7.42-7.47 (m, 2H).

Step 5

In a similar manner to Step 4 of Example 16, 4-methoxymethoxy-5-methoxy-3-hydroxy-7-iodo-2-(1-methyl-1-phenylethyl)isoindolinone (763 mg, 1.58 mmol) was dissolved in nitromethane (12 mL), and the solution was treated with trifluoroacetic acid (1.22 mL, 15.8 mmol) and triethylsilane (2.55 mL, 15.8 mmol), followed by purification by slurry using chloroform to obtain 4-hydroxy-5-methoxy-7-iodoisoindolinone (341 mg, yield 71%).

ESI-MS m/z: 305 [M+H]$^+$; $^1$H-NMR (DMSO-d$_6$) δ(ppm): 3.87 (s, 3H), 4.11 (s, 2H), 7.36 (s, 1H), 8.47 (s, 1H), 9.57 (s, 1H).

Step 6

In a similar manner to Step 2 of Example 1, 4-hydroxy-5-methoxy-7-iodoisoindolinone (30.0 mg, 0.0983 mmol) was dissolved in acetonitrile (2 mL), and the solution was treated with Compound BD (70.4 mg, 0.197 mmol), palladium acetate (1.8 mg, 0.0080 mmol), tri(o-tolyl)phosphine (4.8 mg, 0.016 mmol) and triethylamine (0.137 mL, 0.983 mmol), followed by purification by slurry using chloroform and hexane to obtain 4-hydroxy-5-methoxy-7-[1-(tert-butoxycarbonyl)-5-(piperidinomethyl)indol-2-yl]isoindolinone (49.8 mg).

Step 7

In a similar manner to Step 2 of Example 8, 4-hydroxy-5-methoxy-7-[1-(tert-butoxycarbonyl)-5-(piperidinomethyl)indol-2-yl]isoindolinone (49.0 mg) was dissolved in methanol (1 mL), and the solution was treated with 10% hydrogen chloride-methanol solution (1 mL). The solvent was evaporated under reduced pressure. The residue was purified by slurry using methanol and diisopropylether to obtain Compound 351 (22.4 mg, yield 53%, 2 steps).

ESI-MS m/z: 392 [M+H]$^+$; $^1$H-NMR (DMSO-d$_6$) δ(ppm): 1.34-1.58 (m, 6H), 2.30-2.56 (m, 4H), 4.01 (s, 3H), 4.34 (s, 2H), 6.55 (s, 1H), 7.05 (d, J=8.4 Hz, 1H), 7.12 (s, 1H), 7.36 (d, J=8.4 Hz, 1H), 7.43 (br s, 1H), 7.65 (s, 1H), 9.03 (s, 1H), 9.64 (br s, 1H), 13.80 (s, 1H).

EXAMPLE 352

4-Methanesulfonyloxy-5-methoxy-7-[1H-5-(piperidinomethyl)indol-2-yl]isoindolinone hydrochloride (Compound 352)

Step 1

In a similar manner to Step 1 of Example 289, 4-hydroxy-5-methoxy-7-iodoisoindolinone (250 mg, 0.819 mmol) was dissolved in dichloromethane (5 mL), and the solution was treated with triethylamine (0.685 mL, 4.91 mmol) and methanesulfonyl chloride (0.190 mL, 2.45 mmol). The mixture was added with water and hexane. The precipitated solid was collected by filtration and washed with water, followed by drying under reduced pressure to obtain 4-methanesulfonyloxy-5-methoxy-7-iodoisoindolinone (284 mg, yield 91%).

ESI-MS m/z: 383 [M+H]$^+$; $^1$H-NMR (CDCl$_3$) δ(ppm): 3.49 (s, 3H), 3.95 (s, 3H), 4.30 (s, 2H), 7.67 (s, 1H), 8.68 (br s, 1H).

Step 2

In a similar manner to Step 2 of Example 1, 4-methanesulfonyloxy-5-methoxy-7-iodoisoindolinone (30.0 mg, 0.0783 mmol) was dissolved in acetonitrile (2 mL), and the solution was treated with Compound BD (56.0 mg, 0.156 mmol), palladium acetate (1.4 mg, 0.0062 mmol), tri(o-tolyl)phosphine (3.8 mg, 0.012 mmol) and triethylamine (0.109 mL, 0.782 mmol), followed by purification by slurry using chloroform and hexane to obtain 4-methanesulfonyloxy-5-methoxy-7-[(1-(tert-butoxycarbonyl)-5-(piperidinomethyl)indol-2-yl]isoindolinone (46.5 mg).

Step 3

In a similar manner to Step 2 of Example 8, 4-methanesulfonyloxy-5-methoxy-7-[1-(tert-butoxycarbonyl)-5-(piperidinomethyl)indol-2-yl]isoindolinone (46.0 mg) was dissolved in methanol (1 mL), and the solution was treated with 10% hydrogen chloride-methanol solution (1 mL). The reaction mixture was added with diisopropylether. The precipitated solid was collected by filtration and washed with diisopropylether, followed by drying under reduced pressure to obtain Compound 352 (38.2 mg, yield 96%, 2 steps).

ESI-MS m/z: 469 [M+H]$^+$; $^1$H-NMR (DMSO-d$_6$) δ(ppm): 1.37 (m, 1H), 1.60-1.88 (m, 5H), 2.77-2.96 (m, 2H), 3.28-3.50 (m, 2H), 3.55 (s, 3H), 4.09 (s, 3H), 4.33 (d, J=−4.9 Hz, 2H), 4.53 (s, 2H), 7.31 (dd, J=1.4, 8.4 Hz, 1H), 7.50 (d, J=1.4 Hz, 1H), 7.58 (d, J=8.4 Hz, 1H), 7.80 (s, 1H), 7.87 (s, 1H), 9.29 (s, 1H), 9.81 (br s, 1H), 14.61 (s, 1H).

EXAMPLE 353

4-Hydroxy-5-methyl-7-[1H-5-(piperidinomethyl)indol-2-yl]isoindolinone hydrochloride (Compound 353)

Step 1

In a similar manner to Step 1 of Example 347, 3-hydroxy-4-methylbenzoic acid (2.00 g, 13.1 mmol) was suspended in dichloromethane (50 mL), and the suspension was treated with diisopropylethylamine (13.7 mL, 78.6 mmol) and chloromethyl methyl ether (5.00 mL, 65.8 mmol). The solvent was evaporated under reduced pressure. The residue was dissolved in methanol (50 mL), and the solution was treated with 2 mol/L aqueous potassium hydroxide solution (50 mL). The solvent was evaporated under reduced pressure. The residue was added with 4 mol/L hydrochloric acid and extracted with ethyl acetate. The organic layer was washed with saturated brine and dried over anhydrous sodium sulfate. The solvent was evaporated under reduced pressure to obtain 3-methoxymethoxy-4-methylbenzoic acid (2.69 g).

Step 2

In a similar manner to Step 1 of Example 137, 3-methoxymethoxy-4-methylbenzoic acid (2.69 g) was dissolved in DMF (53 mL), and the solution was treated with EDCI (5.04 g, 26.3 mmol), HOBT monohydrate (2.01 g, 13.1 mmol) and cumylamine (3.80 mL, 26.4 mmol), followed by purification by slurry using hexane to obtain 3-methoxymethoxy-4-methyl-N-(1-methyl-1-phenylethyl)benzamide (3.42 g, yield 83%, 2 steps).

ESI-MS m/z: 314 [M+H]$^+$; $^1$H-NMR (CDCl$_3$) δ(ppm): 1.82 (s, 6H), 2.28 (s, 3H), 3.48 (s, 3H), 5.23 (s, 2H), 6.36 (br s, 1H), 7.13-7.63 (m, 8H).

Step 3

In a similar manner to Step 2 of Example 16, 3-methoxymethoxy-4-methyl-N-(1-methyl-1-phenylethyl)benzamide (3.40 g, 10.9 mmol) was dissolved in THF (130 mL), and the solution was treated with TMEDA (5.20 mL, 34.5 mmol), sec-butyl lithium-hexane solution (0.95 mol/L, 36.5 mL, 34.7 mmol) and DMF (1.85 mL, 23.9 mmol), followed by purification by flash column chromatography (hexane/ethyl acetate=4/1 to 7/3 to 6/4). The obtained solid was purified by slurry using isopropylether and hexane to obtain 4-methoxymethoxy-5-methyl-3-hydroxy-2-(1-methyl-1-phenylethyl)isoindolinone (2.96 g, yield 80%).

ESI-MS m/z: 342 [M+H]$^+$; $^1$H-NMR (CDCl$_3$) δ(ppm): 1.92 (s, 3H), 1.97 (s, 3H), 2.34 (s, 3H), 3.59 (s, 3H), 3.68 (d, J=6.1 Hz, 1H), 5.19 (d, J=15.9 Hz, 1H), 5.22 (d, J=15.9 Hz, 1H), 6.31 (d, J=6.1 Hz, 1H), 7.10-7.53 (m, 7H).

Step 4

In a similar manner to Step 3 of Example 16, 4-methoxymethoxy-5-methyl-3-hydroxy-2-(1-methyl-1-phenylethyl)isoindolinone (2.94 g, 8.61 mmol) was dissolved in THF (110 mL), and the solution was treated with TMEDA (4.20 mL, 27.8 mmol), sec-butyl lithium-hexane solution (0.95 mol/L, 29.0 mL, 27.6 mmol) and iodine (2.62 g, 10.3 mmol), followed by purification by flash column chromatography (hexane/ethyl acetate=4/1 to 7/3 to 6/4). The obtained solid was purified by slurry using hexane to obtain 4-methoxymethoxy-5-methyl-3-hydroxy-7-iodo-2-(1-methyl-1-phenylethyl)isoindolinone (2.40 g, yield 60%).

ESI-MS m/z: 468 [M+H]$^+$; $^1$H-NMR (CDCl$_3$) δ(ppm): 1.94 (s, 3H), 1.98 (s, 3H), 2.29 (s, 3H), 3.53 (d, J=5.8 Hz, 1H), 3.56 (s, 3H), 5.14 (d, J=10.1 Hz, 1H), 5.16 (d, J=10.1 Hz, 1H), 6.12 (d, J=5.8 Hz, 1H), 7.18-7.49 (m, 5H), 7.75 (s, 1H).

Step 5

In a similar manner to Step. 4 of Example 16, 4-methoxymethoxy-5-methyl-3-hydroxy-7-iodo-2-(1-methyl-1-phenylethyl)isoindolinone (500 mg, 1.07 mmol) was dissolved in nitromethane (20 mL), and the solution was treated with trifluoroacetic acid (0.742 mL, 9.63 mmol) and triethylsilane (1.54 mL, 9.64 mmol). The reaction mixture was added with saturated aqueous sodium hydrogencarbonate solution and ethyl acetate. The precipitated solid was collected by filtration and washed with water, followed by drying under reduced pressure to obtain 4-hydroxy-5-methyl-7-iodoisoindolinone (161 mg, yield 52%).

ESI-MS m/z: 289 [M+H]$^+$; $^1$H-NMR (CDCl$_3$) δ(ppm): 2.24 (s, 3H), 3.35 (br s, 1H), 4.19 (s, 2H), 7.58 (s, 1H).

Step 6

In a similar manner to Step 2 of Example 1, 4-hydroxy-5-methyl-7-iodoisoindolinone (100 mg, 0.347 mmol) was dissolved in acetonitrile (5 mL), and the solution was treated with Compound BD (249 mg, 0.695 mmol), palladium acetate (6.3 mg, 0.028 mmol), tri(o-tolyl)phosphine (18.3 mg, 0.060 mmol) and triethylamine (0.484 mL, 3.47 mmol), followed by purification by slurry using hexane to obtain 4-hydroxy-5-methyl-7-[1-(tert-butoxycarbonyl)-5-(piperidinomethyl)indol-2-yl]isoindolinone (165 mg, yield 100%).

ESI-MS m/z: 476 [M+H]$^+$; $^1$H-NMR (CDCl$_3$) δ(ppm): 1.30 (s, 9H), 1.32-1.78 (m, 6H), 2.25 (s, 3H), 2.28-2.61 (m, 4H), 3.56 (s, 2H), 3.90-4.15 (m, 2H), 6.12 (br s, 1H), 6.26 (s, 1H), 7.06-7.39 (m, 4H), 8.10 (d, J=8.8 Hz, 1H).

Step 7

In a similar manner to Step 2 of Example 8, 4-hydroxy-5-methyl-7-[1-(tert-butoxycarbonyl)-5-(piperidinomethyl)indol-2-yl]isoindolinone (80.7 mg, 0.170 mmol) was dissolved in methanol (3 mL), and the solution was treated with 10% hydrogen chloride-methanol solution (3 mL). The solvent was evaporated under reduced pressure and the residue was purified by slurry using methanol and diisopropylether to obtain Compound 353 (50.0 mg, yield 71%).

ESI-MS m/z: 376 [M+H]$^+$; $^1$H-NMR (DMSO-d$_6$) δ(ppm): 1.70-2.10 (m, 6H), 2.35 (s, 3H), 3.00-3.15 (m, 2H), 3.45-3.60 (m, 2H), 4.49 (d, J=4.6 Hz, 2H), 4.58 (s, 2H), 7.29 (s, 1H), 7.41 (d, J=8.4 Hz, 1H), 7.68 (d, J=8.4 Hz, 1H), 7.89 (s, 1H), 8.17 (s, 1H), 9.36 (s, 1H), 9.83 (s, 1H), 14.12 (s, 1H).

EXAMPLE 354

4-Methanesulfonyloxy-5-methyl-7-[1H-5-(piperidinomethyl)indol-2-yl]isoindolinone hydrochloride (Compound 354)

Step 1

In a similar manner to Step 1 of Example 289, 4-hydroxy-5-methyl-7-[1-(tert-butoxycarbonyl)-5-(piperidinomethyl)indol-2-yl]isoindolinone (80.5 mg, 0.170 mmol) was dissolved in dichloromethane (3 mL), and the solution was treated with triethylamine (0.095 mL, 0.68 mmol) and methanesulfonyl chloride (0.026 mL, 0.34 mmol), followed by purification by slurry using hexane to obtain 4-methanesulfonyloxy-5-methyl-7-[1-(tert-butoxycarbonyl)-5-(piperidinomethyl)indol-2-yl]isoindolinone (80.3 mg, yield 85%).

APCI-MS m/z: 554 [M+H]$^+$; $^1$H-NMR (CDCl$_3$) δ(ppm): 1.19-1.54 (m, 6H), 1.34 (s, 9H), 2.30-2.53 (m, 4H), 2.50 (s, 3H), 3.36 (s, 3H), 3.61 (s, 2H), 4.58 (s, 2H), 6.36 (s, 1H), 6.55 (s, 1H), 7.28 (d, J=8.4 Hz, 1H), 7.37 (s, 1H), 7.49 (s, 1H), 8.16 (d, J=8.4 Hz, 1H).

Step 2

In a similar manner to Step 2 of Example 8, 4-methanesulfonyloxy-5-methyl-7-[1-(tert-butoxycarbonyl)-5-(piperidinomethyl)indol-2-yl]isoindolinone (78.0 mg, 0.141 mmol) was dissolved in methanol (3 mL), and the solution was treated with 10% hydrogen chloride-methanol solution (3 mL). The solvent was evaporated under reduced pressure. The residue was purified by slurry using diisopropylether to obtain Compound 354 (30.1 mg, yield 47%).

ESI-MS m/z: 454 [M+H]$^+$; $^1$H-NMR (DMSO-d$_6$) δ(ppm): 1.30-1.60 (m, 6H), 2.23-2.47 (m, 4H), 2.48 (s, 3H), 3.30 (s, 3H), 3.65 (s, 2H), 4.57 (s, 2H), 7.10 (d, J=8.3 Hz, 1H), 7.23 (s, 1H), 7.40 (d, J=8.3 Hz, 1H), 7.45 (s, 1H), 8.18 (s, 1H), 9.38 (s, 1H), 13.68 (s, 1H).

EXAMPLE 355

4,5-Dimethoxy-7-[1H-5-(piperidinomethyl)indol-2-yl]isoindolinone hydrochloride (Compound 355)

Step 1

4-Hydroxy-5-methoxy-7-iodoisoindolinone (30.0 mg, 0.0983 mmol) was dissolved in DMF (2 mL), and the solution was treated with potassium carbonate (26.0 mg, 0.188 mmol) and methyl iodide (0.020 mL, 0.32 mmol), followed by stirring at room temperature for 1.5 hours. The reaction mixture was added with water and the precipitated solid was collected by filtration and washed with water, followed by drying under reduced pressure to obtain 4,5-dimethoxy-7-iodoisoindolinone (22.0 mg, yield 70%).

ESI-MS m/z: 319 [M+H]$^+$; $^1$H-NMR (DMSO-d$_6$) δ(ppm): 3.82 (s, 3H), 3.89 (s, 3H), 4.26 (s, 2H), 7.47 (s, 1H), 8.57 (br s, 1H).

Step 2

In a similar manner to Step 2 of Example 1, 4,5-dimethoxy-7-iodoisoindolinone (20.0 mg, 0.0627 mmol) was dissolved in acetonitrile (1 mL), and the solution was treated with Compound BD (45.0 mg, 0.126 mmol), palladium acetate (1.1 mg, 0.0049 mmol), tri(o-tolyl)phosphine (3.1 mg, 0.010 mmol) and triethylamine (0.087 mL, 0.624 mmol), followed by purification by slurry using hexane to obtain 4,5-dimethoxy-7-[1-(tert-butoxycarbonyl)-5-(piperidinomethyl)indol-2-yl]isoindolinone (27.0 mg, yield 85%).

ESI-MS m/z: 506 [M+H]$^+$; $^1$H-NMR (CDCl$_3$) δ(ppm): 1.23-1.65 (m, 6H), 1.37 (s, 9H), 2.32-2.48 (m, 4H), 3.58 (br s, 2H), 3.96 (s, 3H), 3.97 (s, 3H), 4.42 (s, 2H), 6.00 (br s, 1H), 6.54 (s, 1H), 7.02 (s, 1H), 7.27 (dd, J=1.7, 8.6 Hz, 1H), 7.48 (s, 1H), 8.13 (d, J=8.6 Hz, 1H).

Step 3

In a similar manner to Step 2 of Example 8, 4,5-dimethoxy-7-[1-(tert-butoxycarbonyl)-5-(piperidinomethyl)indol-2-yl]isoindolinone (26.5 mg, 0.0524 mmol) was dissolved in methanol (1.5 mL), and the solution was treated with 10% hydrogen chloride-methanol solution (1.5 mL). The solvent was evaporated under reduced pressure and the residue was purified by slurry using methanol and diisopropylether to obtain Compound 355 (17.2 mg, yield 72%).

ESI-MS m/z: 406 [M+H]$^+$; $^1$H-NMR (DMSO-d$_6$) δ(ppm): 1.37 (m, 1H), 1.55-1.89 (m, 5H), 2.79-2.98 (m, 2H), 3.26-3.43 (m, 2H), 3.88 (s, 3H), 4.03 (s, 3H), 4.34 (s, 2H), 4.48 (s, 2H), 7.25 (dd, J=1.4, 8.5 Hz, 1H), 7.35 (s, 1H), 7.55 (d, J=8.5 Hz, 1H), 7.73 (s, 1H), 7.75 (s, 1H), 9.16 (s, 1H), 9.45 (br s, 1H), 14.08 (s, 1H).

EXAMPLE 356

4-Methanesulfonyloxy-5-methyl-7-{1H-5-[4-(2-hydroxyethyl)pyperazin-1-ylmethyl]indol-2-yl}isoindolinone dihydrochloride (Compound 356)

Step 1

In a similar manner to Step 2 of Example 1, 4-hydroxy-5-methyl-7-iodoisoindolinone (81.5 mg, 0.282 mmol) was dissolved in acetonitrile (4 mL), and the solution was treated with Compound, BU (292 mg, 0.560 mmol), palladium acetate (5.1 mg, 0.023 mmol), tri(o-tolyl)phosphine (13.7 mg, 0.045 mmol) and triethylamine (0.393 mL, 2.82 mmol), followed by purification by slurry using diisopropylether to obtain 4-hydroxy-5-methyl-7-{1-(tert-butoxycarbonyl)-5-[4-(2-hydroxyethyl)pyperazin-1-ylmethyl]indol-2-yl}isoindolinone (148 mg, yield 83%).

ESI-MS m/z: 635 [M+H]$^+$; $^1$H-NMR (CDCl$_3$) δ(ppm): 0.05 (s, 6H), 0.87 (s, 9H), 1.37 (s, 9H), 2.25-2.50 (m, 10H), 3.32 (s, 3H), 3.53 (s, 2H), 3.67 (t, J=5.9 Hz, 2H), 4.28 (s, 2H), 6.50 (s, 1H), 7.19 (s, 1H), 7.23 (d, J=8.0 Hz, 1H), 7.47 (s, 1H), 8.07 (d, J=8.0 Hz, 1H), 8.43 (s, 1H), 9.50 (br s, 1H).

Step 2

In a similar manner to Step 1 of Example 289, 4-hydroxy-5-methyl-7-(1-(tert-butoxycarbonyl)-5-[4-(2-hydroxyethyl)pyperazin-1-ylmethyl]indol-2-yl)isoindolinone (178 mg, 0.280 mmol) was dissolved in dichloromethane (6 mL), and the solution was treated with triethylamine (0.156 mL, 1.12 mmol) and methanesulfonyl chloride (0.043 mL, 0.56 mmol), followed by purification by slurry using hexane to obtain 4-methanesulfonyloxy-5-methyl-7-{1-(tert-butoxycarbonyl)-5-[4-(2-hydroxyethyl)pyperazin-1-ylmethyl]indol-2-yl}isoindolinone (152 mg, yield 76%).

ESI-MS m/z: 713 [M+H]$^+$; $^1$H-NMR (CDCl$_3$) δ(ppm): 0.05 (s, 6H), 0.88 (s, 9H), 1.34 (s, 9H), 2.41-2.74 (m, 10H), 2.50 (s, 3H), 3.36 (s, 3H), 3.60 (s, 2H), 3.70-3.84 (m, 2H), 4.59 (s, 2H), 6.32 (s, 1H), 6.54 (s, 1H), 7.29 (d, J=8.6 Hz, 1H), 7.37 (s, 1H), 7.50 (s, 1H), 8.17 (d, J=8.6 Hz, 1H)

Step 3

In a similar manner to Step 2 of Example 8, 4-methanesulfonyloxy-5-methyl-7-{1-(tert-butoxycarbonyl)-5-[4-(2-hydroxyethyl)pyperazin-1-ylmethyl]indol-2-yl}isoindolinone (150 mg, 0.210 mmol) was dissolved in methanol (6 mL), and the solution was treated with 10% hydrogen chloride-methanol solution (6 mL). The precipitated solid was collected by filtration and washed with diisopropylether, followed by drying under reduced pressure to obtain Compound 356 (100 mg, yield 84%).

ESI-MS m/z: 499 [M+H]$^+$; $^1$H-NMR (DMSO-d$_6$) δ(ppm): 2.48 (s, 3H), 3.00-3.90 (m, 12H), 3.66 (s, 3H), 4.44 (br s, 2H), 4.58 (s, 2H), 7.34 (m, 1H), 7.35 (s, 1H), 7.57 (d, J=8.1 Hz, 1H), 7.83 (s, 1H), 8.24 (s, 1H), 9.43 (s, 1H), 11.60 (s, 2H), 13.91 (s, 1H).

EXAMPLE 357

4-Hydroxy-5-methoxy-7-[1H-5-(dimethylaminomethyl)indol-2-yl]isoindolinone hydrochloride (Compound 357)

Step 1

In a similar manner to Step 2 of Example 1, 4-hydroxy-5-methoxy-7-iodoisoindolinone (0.390 g, 1.28 mmol) was dissolved in acetonitrile (16 mL), and the solution was treated with Compound BA (0.740 g, 2.56 mmol), palladium acetate (0.0290 g, 0.128 mmol), tri(o-tolyl)phosphine (0.0780 g, 0.256 mmol) and triethylamine (1.80 mL, 12.8 mmol), followed by purification of the residue by slurry using diisopropylether to obtain a crude product of 4-hydroxy-5-methoxy-7-[1-(tert-butoxycarbonyl)-5-formylindol-2-yl]isoindolinone (0.713 g).

ESI-MS m/z: 423 [M+H]$^+$; $^1$H-NMR (DMSO-d$_6$) δ(ppm): 1.20 (s, 9H), 3.91 (s, 3H), 4.25 (s, 2H), 6.80 (s, 1H), 7.10 (s, 1H), 7.86 (d, J=8.7 Hz, 1H), 8.20 (s, 1H), 8.31 (d, J=8.4 Hz, 1H), 8.37 (s, 1H), 10.1 (s, 1H).

Step 2

In a similar manner to Step 2 of Example 6, a crude product of 4-hydroxy-5-methoxy-7-[1-(tert-butoxycarbonyl)-5-formylindol-2-yl]isoindolinone (0.713 g) was dissolved in acetonitrile (20 mL), and the solution was treated with dimethylamine hydrochloride (2.75 g, 33.8 mmol), triethylamine (4.70 mL, 33.8 mmol), acetic acid (1.90 mL, 33.8 mmol) and sodium triacetoxyborohydride (1.10 g, 5.07 mmol), followed by purification of the residue by flash column chromatography (chloroform/methanol=4/1) to obtain 4-hydroxy-5-methoxy-7-[1-(tert-butoxycarbonyl)-5-(dimethylaminomethyl)indol-2-yl]isoindolinone (0.138 g, yield 19%).

ESI-MS-m/z: 452 [M+H]$^+$; $^1$H-NMR (CD$_3$OD) δ(ppm): 1.23 (s, 9H), 2.28 (s, 6H), 3.59 (s, 2H), 3.59 (s, 3H), 4.34 (s, 2H), 6.52 (s, 1H), 7.04 (s, 1H), 7.24 (d. J=8.4 Hz, 1H), 7.47 (s, 1H), 7.88 (s, 1H), 8.18 (d, J=−8.4 Hz, 1H).

Step 3

In a similar manner to Step 2 of Example 8, 4-hydroxy-5-methoxy-7-[1-(tert-butoxycarbonyl)-5-(dimethylaminomethyl)indol-2-yl]isoindolinone (0.137 g, 0.303 mmol) was treated with 10% hydrogen chloride-methanol solution (5.0 mL) to obtain Compound 357 (0.0791 g, yield 67%).

EXAMPLE 358

4-Hydroxy-5-methoxy-7-[1H-5-(pyrrolidin-1-ylmethyl)indol-2-yl]isoindolinone hydrochloride (Compound 358)

Step 1

In a similar manner to Step 2 of Example 6, 4-hydroxy-5-methoxy-7-[1-(tert-butoxycarbonyl)-5-formylindol-2-yl]isoindolinone (0.582 g, 1.38 mmol) was dissolved in acetonitrile (15.0 mL), and the solution was treated with pyrrolidine (2.30 mL, 27.8 mmol), acetic acid (1.60 mL, 27.8 mmol) and sodium triacetoxyborohydride (0.876 g, 4.13 mmol), followed by purification by flash column chromatography (chloroform/methanol=85/15) to obtain 4-hydroxy-5-methoxy-7-[1-(tert-butoxycarbonyl)-5-(pyrrolidin-1-ylmethyl)indol-2-yl]isoindolinone (0.200 g, 30%).

ESI-MS m/z: 478 [M+H]$^+$; $^1$H-NMR (CD$_3$OD) δ(ppm): 1.87-1.98 (m, 4H), 3.06-3.16 (m, 4H), 3.86 (s, 3H), 4.23 (s, 2H), 4.27 (s, 2H), 6.48 (s, 2H), 6.96 (s, 1H), 7.18-7.28 (m, 1H), 7.51 (s, 1H), 8.18 (m, 1H).

Step 2

In a similar manner to Step 2 of Example 8, 4-hydroxy-5-methoxy-7-[1-(tert-butoxycarbonyl)-5-(pyrrolidin-1-ylmethyl)indol-2-yl]isoindolinone (0.200 g, 0.419 mmol) was treated with 10% hydrogen chloride-methanol solution (10.0 mL) to obtain Compound 358 (0.111 g, yield 64%).

ESI-MS m/z: 378 [M+H]$^+$; $^1$H-NMR (DMSO-d$_6$) δ(ppm): 1.80-2.08 (m, 4H), 3.00-3.14 (m, 2H), 3.26-3.40 (m, 2H), 4.02 (s, 3H), 4.36 (s, 2H), 4.38 (s, 2H), 7.23 (m, 1H), 7.29 (d, J=8.4 Hz, 1H), 7.49 (d, J=8.4 Hz, 1H), 7.69 (s, 1H), 7.77 (s, 1H), 9.08 (s, 1H), 9.71 (br s, 1H), 14.0 (s, 1H).

EXAMPLE 359

4-Hydroxy-5-methoxy-7-[1H-5-(diethylaminomethyl)indol-2-yl]isoindolinone hydrochloride (Compound 359)

Step 1

In a similar manner to Step 2 of Example 6, 4-hydroxy-5-methoxy-7-[1-(tert-butoxycarbonyl)-5-formylindol-2-yl]isoindolinone (0.415 g, 0.985 mmol) was dissolved in acetonitrile (16.0 mL), and the solution was treated with diethylamine (2.04 mL, 19.7 mmol), acetic acid (1.10 mL, 19.7 mmol) and sodium triacetoxyborohydride (0.626 g, 2.96 mmol) to obtain 4-hydroxy-5-methoxy-7-[1-(tert-butoxycarbonyl)-5-(diethylaminomethyl)indol-2-yl]isoindolinone (0.202 g, 43%).

ESI-MS m/z: 480 [M+H]$^+$; $^1$H-NMR (DMSO-d$_6$) δ(ppm): 1.18 (s, 9H), 1.18 (t. J=7.4 Hz, 6H), 3.03 (q, J=7.4 Hz, 4H), 3.17 (s, 1H), 3.90 (s, 3H), 4.23 (s, 2H), 6.61 (s, 1H), 7.06 (s, 1H), 7.38 (d, J=8.6 Hz, 1H), 7.65 (s, 1H), 8.12 (d, J=8.6 Hz, 1H), 8.33 (s, 1H), 9.50 (br s, 1H).

Step 2

In a similar manner to Step 2 of Example 8, 4-hydroxy-5-methoxy-7-[1-(tert-butoxycarbonyl)-5-(diethylaminomethyl)indol-2-yl]isoindolinone (0.202 g, 0.421 mmol) was treated with 10% hydrogen chloride-methanol solution (10.0 mL) to obtain Compound 359 (0.0674 g, yield 42%).

ESI-MS m/z: 380 [M+H]$^+$; $^1$H-NMR (DMSO-d$_6$) δ(ppm): 1.26 (t, J=7.4 Hz, 6H), 2.97-3.15 (m, 4H), 4.02 (s, 3H), 4.33 (s, 2H), 4.36 (s, 2H), 7.24 (m, 1H), 7.27 (d, J=8.4 Hz, 1H), 7.51 (d, J=8.4 Hz, 1H), 7.69 (s, 1H), 7.76 (s, 1H), 9.08 (s, 1H), 9.72 (s, 1H), 9.93 (br s, 1H), 14.0 (s, 1H).

EXAMPLE 360

4-Hydroxy-5-methoxy-7-[1H-5-(methylaminomethyl)indol-2-yl]isoindolinone hydrochloride (Compound 360)

Step 1

In a similar manner to Step 2 of Example 6, 4-hydroxy-5-methoxy-7-[1-(tert-butoxycarbonyl)-5-formylindol-2-yl]isoindolinone (0.494 g, 1.17 mmol) was dissolved in acetonitrile (16.0 mL), and the solution was treated with methylamine hydrochloride (1.60 mL, 23.4 mmol), triethylamine (3.30 mL, 23.4 mmol), acetic acid (1.30 mL, 23.4 mmol) and sodium triacetoxyborohydride (0.744 g, 3.51 mmol), followed by purification by flash column chromatography (chloroform/methanol=85/15) to obtain 4-hydroxy-5-methoxy-7-[1-(tert-butoxycarbonyl)-5-(methylaminomethyl)indol-2-yl]isoindolinone (0.159 g, 31%).

ESI-MS m/z: 438 [M+H]$^+$; $^1$H-NMR (CD$_3$OD) δ(ppm): 1.89 (s, 9H), 2.32 (s, 3H), 3.82 (s, 2H), 3.90 (s, 3H), 4.22 (s, 2H), 6.56 (s, 1H), 7.04 (s, 1H), 7.28 (d, J=8.4 Hz, 1H), 7.53 (s, 1H), 8.08 (d, J=8.4 Hz, 1H), 8.31 (s, 1H).

Step 2

In a similar manner to Step 2 of Example 8, 4-hydroxy-5-methoxy-7-[1-(tert-butoxycarbonyl)-5-(methylaminomethyl)indol-2-yl]isoindolinone (0.158 g, 0.361 mmol) was treated with 10% hydrogen chloride-methanol solution (10.0 mL) to obtain Compound 360 (0.0491 g, yield 36%).

ESI-MS m/z: 338 [M+H]$^+$; $^1$H-NMR (DMSO-d$_6$) δ(ppm): 2.52-2.59 (m, 3H), 4.02 (s, 3H), 4.13-4.20 (m, 2H), 4.35 (s, 2H), 7.21 (d, J=8.4 Hz, 1H), 7.23 (s, 1H), 7.49 (d, J=8.4 Hz, 1H), 7.67 (s, 2H), 8.87-9.01 (m, 2H), 9.08 (s, 1H), 14.0 (s, 1H).

EXAMPLE 361

4-Methanesulfonyloxy-5-methoxy-7-{1H-5-[4-(2-hydroxyethyl)pyperazin-1-ylmethyl]indol-2-yl}isoindolinone dihydrochloride (Compound 361)

Step 1

In a similar manner to Step 2 of Example 1, 4-methanesulfonyloxy-5-methoxy-7-iodoisoindolinone (60.0 mg, 0.157 mmol) was dissolved in acetonitrile (5 mL), and the solution was treated with Compound BU (138 mg, 0.267 mmol), palladium acetate (2.8 mg, 0.013 mmol), tri(o-tolyl)phosphine (7.6 mg, 0.025 mmol) and triethylamine (0.214 mL, 1.57 mmol), followed by purification by slurry using diisopropylether and hexane to obtain 4-methanesulfonyloxy-5-methoxy-7-{1-(tert-butoxycarbonyl)-5-[4-(2-hydroxyethyl)pyperazin-1-ylmethyl]indol-2-yl}isoindolinone (96.3 mg, yield 84%).

ESI-MS m/z: 729 [M+H]$^+$; $^1$H-NMR (CDCl$_3$) δ(ppm): 0.05 (s, 6H), 0.88 (s, 9H), 1.36 (s, 9H), 2.46-2.63 (m, 10H), 3.35 (s, 3H), 3.59 (s, 2H), 3.71-3.81 (m, 2H), 4.00 (s, 3H), 4.56 (s, 2H), 5.96 (br s, 1H), 6.57 (s, 1H), 7.10 (s, 1H), 7.30 (d, J=8.8 Hz, 1H), 7.50 (s, 1H), 8.16 (d, J=8.8 Hz, 1H).

Step 2

In a similar manner to Step 2 of Example 8, 4-methanesulfonyloxy-5-methoxy-7-(1-(tert-butoxycarbonyl)-5-[4-(2-hydroxyethyl)pyperazin-1-ylmethyl]indol-2-yl)isoindolinone (94.0 mg, 0.129 mmol) was dissolved in methanol (3 mL), and the solution was treated with 1.0% hydrogen chloride-methanol solution (3 mL). The reaction mixture was added with diisopropylether. The precipitated solid was collected by filtration and washed with diisopropylether, followed by drying under reduced pressure to obtain Compound 361 (62.5 mg, yield 83%).

ESI-MS m/z: 514 [M+H]$^+$; $^1$H-NMR (DMSO-d$_6$) δ(ppm): 3.07-3.67 (m, 10H), 3.54 (s, 3H), 3.72 (br s, 2H), 4.09 (s, 3H), 4.47 (brs, 2H), 4.53 (s, 2H), 7.32 (m, 1H), 7.45-7.63 (m, 2H), 7.83 (m, 1H), 7.87 (s, 1H), 9.28 (s, 1H), 14.01 (s, 1H).

EXAMPLE 362

4-Methanesulfonyloxy-5-methoxy-7-[1H-5-(dimethylaminomethyl)indol-2-yl]isoindolinone (Compound 362)

Step 1

In a similar manner to Step 2 of Example 1, 4-methanesulfonyloxy-5-methoxy-7-iodoisoindolinone (128 mg, 0.334 mmol) was dissolved in acetonitrile (5 mL), and the solution was treated with Compound BA (193 mg, 0.668 mmol), palladium acetate (6.0 mg, 0.027 mmol), tri(o-tolyl)phosphine (16.3 mg, 0.0536 mmol) and triethylamine (0.455 mL, 3.34 mmol), followed by purification by slurry using chloroform and diisopropylether to obtain 4-methanesulfonyloxy-5-methoxy-7-[1-(tert-butoxycarbonyl)-5-form yl]indolylisoindolinone (127 mg, yield 76%).

ESI-MS m/z: 501 [M+H]$^+$; $^1$H-NMR (CDCl$_3$) δ(ppm): 1.36 (s, 9H), 3.36 (s, 3H), 4.03 (s, 3H), 4.58 (s, 2H), 6.15 (s, 1H), 6.72 (s, 1H), 7.14 (s, 1H), 7.89 (dd, J=1.3, 8.6 Hz, 1H), 8.10 (d, J=1.3 Hz, 1H), 8.39 (d, J=8.6 Hz, 1H), 10.07 (s, 1H).

Step 2

In a similar manner to Step 2 of Example 6, 4-methanesulfonyloxy-5-methoxy-7-[1-(tert-butoxycarbonyl)-5-formyl]indolylisoindolinone (80 mg, 0.1.60 mmol) was dissolved in acetonitrile (5 mL), and the solution was treated with dimethylamine hydrochloride (260 mg, 3.19 mmol), triethylamine (0.446 ml, 3.20 mmol), acetic acid (0.183 mL, 3.20 mmol) and sodium triacetoxyborohydride (158 mg, 0.744 mmol) to obtain 4-methanesulfonyloxy-5-methoxy-7-[1-(tert-butoxycarbonyl)-5-(dimethylaminomethyl)indol-2-yl]isoindolinone (78.5 mg, yield 93%).

ESI-MS m/z: 530 [M+H]$^+$; $^1$H-NMR (CDCl$_3$) δ(ppm): 1.18 (s, 9H), 2.15 (s, 6H), 3.47 (s, 2H), 3.49 (s, 3H), 3.98 (s, 3H), 4.40 (s, 2H), 6.70 (s, 1H), 7.27 (dd, J=1.5, 8.5 Hz, 1H), 7.31 (s, 1H), 7.50 (d, J=1.5 Hz, 1H), 8.09 (d, J=8.5 Hz, 1H), 8.56 (s, 1H).

Step 3

In a similar manner to Step 2 of Example 8, 4-methanesulfonyloxy-5-methoxy-7-[1-(tert-butoxycarbonyl)-5-(dimethylaminomethyl)indol-2-yl]isoindolinone (78.0 mg, 0.147 mmol) was dissolved in methanol (1.5 mL), and the solution was treated with 10% hydrogen chloride-methanol solution (1.5 mL). The reaction mixture was added with saturated aqueous sodium hydrogencarbonate solution and extracted with ethyl acetate. The organic layer was washed with saturated brine and dried over anhydrous sodium sulfate. The solvent was evaporated under reduced pressure and the residue was purified by slurry using diisopropylether to obtain Compound 362 (33.3 mg, yield 53%).

mp 232-234° C.; ESI-MS m/z: 430 [M+H]$^+$; $^1$H-NMR (DMSO-d$_6$) δ(ppm): 2.16 (s, 6H), 3.45 (s, 2H), 3.53 (s, 3H), 4.08 (s, 3H), 4.52 (s, 2H), 7.11 (dd, J=0.9, 8.6 Hz, 1H), 7.37 (d, J=0.9 Hz, 1H), 7.41 (d, J=8.6 Hz, 1H), 7.46 (s, 1H), 7.83 (s, 1H), 9.24 (s, 1H), 13.80 (s, 1H).

EXAMPLE 363

4-Methanesulfonyloxy-5-methoxy-7-[1H-5-(Cyclopropylaminomethyl)indol-2-yl]isoindolinone hydrochloride (Compound 363)

Step 1

In a similar manner to Step 2 of Example 6, 4-methanesulfonyloxy-5-methoxy-7-[1-(tert-butoxycarbonyl)-5-formylindol-2-yl]isoindolinone (50 mg, 0.100 mmol) was dissolved in acetonitrile (2.9 mL), and the solution was treated with cyclopropylamine (0.069 mL, 1.0 mmol), acetic acid (0.115 mL, 2.00 mmol) and sodium triacetoxyborohydride (64 mg, 0.30 mmol) to obtain 4-methanesulfonyloxy-5-methoxy-7-[1-(tert-butoxycarbonyl)-5-(cyclopropylaminomethyl)indol-2-yl]isoindolinone (39.1 mg, yield 72%).

ESI-MS m/z: 542 [M+H]$^+$; $^1$H-NMR (CDCl$_3$) δ(ppm): 0.36-0.53 (m, 4H), 1.36 (s, 9H), 2.16 (m, 1H), 3.35 (s, 3H), 3.95 (s, 2H), 4.01 (s, 3H), 4.56 (s, 2H), 6.37 (br s, 1H), 6.57 (s, 1H), 7.11 (s, 1H), 7.30 (dd, J=1.4, 8.9 Hz, 1H), 7.50 (s, 1H), 8.21 (d, J=8.8 Hz, 1H).

Step 2

In a similar manner to Step 2 of Compound 8, 4-methanesulfonyloxy-5-methoxy-7-[1-(tert-butoxycarbonyl)-5-(cyclopropylaminomethyl)indol-2-yl]isoindolinone (36.6 mg, 0.068 mmol) was dissolved in methanol (1.5 mL), and the solution was treated with 10% hydrogen chloride-methanol solution (1.5 mL). The precipitated solid was collected by filtration and washed with methanol, followed by drying under reduced-pressure to obtain Compound 363 (24.0 mg, yield 74%).

ESI-MS m/z: 442 [M+H]$^+$; $^1$H-NMR (DMSO-d$_6$) δ(ppm): 0.68-0.78 (m, 2H), 0.81-0.92 (m, 2H), 2.65 (m, 1H), 3.53 (s, 3H), 4.08 (s, 3H), 4.26 (s, 2H), 4.52 (s, 2H), 7.30 (dd, J=1.5, 8.4 Hz, 1H), 7.48 (s, 1H), 7.54 (d, J=8.4 Hz, 1H), 7.76 (s, 1H), 7.86 (s, 1H), 8.95-9.25 (m, 2H), 9.27 (s, 1H), 13.99 (s, 1H).

EXAMPLE 364

4-Methanesulfonyloxy-5-methoxy-7-[1H-5-(ethylaminomethyl)indol-2-yl]isoindolinone hydrochloride (Compound 364)

Step 1

In a similar manner to Step 2 of Example 6, 4-methanesulfonyloxy-5-methoxy-7-[1-(tert-butoxycarbonyl)-5-formyl]indolylisoindolinone (80 mg, 0.160 mmol) was dissolved in acetonitrile (5 mL), and the solution was treated with 70% aqueous ethylamine solution (0.254 mL, 3.19 mmol), acetic acid (0.183 mL, 3.20 mmol) and sodium triacetoxyborohydride (158 mg, 0.744 mmol) to obtain 4-methanesulfonyloxy-5-methoxy-7-[1-(tert-butoxycarbonyl)-5-(ethylaminomethyl)indol-2-yl]isoindolinone (59.0 mg, yield 70%).

ESI-MS m/z: 530 [M+H]$^+$; $^1$H-NMR (CDCl$_3$) δ(ppm): 1.14 (t, J=7.1 Hz, 3H), 1.34 (s, 9H), 2.70 (q, J=7.1 Hz, 2H), 3.34 (s, 3H), 3.89 (s, 2H), 4.00 (s, 3H), 4.55 (s, 2H), 6.57 (s, 1H), 6.72 (br s, 1H), 7.10 (s, 1H), 7.30 (dd, J=1.7, 8.6 Hz, 1H), 7.50 (d, J=1.7 Hz, 1H), 8.19 (d, J=8.6 Hz, 1H).

Step 2

In a similar manner to Step 2 of Example 8, 4-methanesulfonyloxy-5-methoxy-7-[1-(tert-butoxycarbonyl)-5-(ethylaminomethyl)indol-2-yl]isoindolinone (59.0 mg, 0.111 mmol) was dissolved in methanol (1.5 mL), and the solution was treated with 10% hydrogen chloride-methanol solution (1.5 mL). The reaction mixture was added with diisopropylether. The precipitated solid was collected by filtration and washed with diisopropylether, followed by drying under reduced pressure to obtain Compound 364 (30.1 mg, yield 58%).

ESI-MS m/z: 430 [M+H]$^+$; $^1$H-NMR (DMSO-d$_6$) δ(ppm): 1.23 (t, J=7.2 Hz, 3H), 2.98 (q, J=7.2 Hz, 2H), 3.54 (s, 3H), 4.10 (s, 3H), 4.20 (s, 2H), 4.54 (s, 2H), 7.28 (dt, J=1.3, 8.3 Hz, 1H), 7.50 (d, J=1.3 Hz, 1H), 7.57 (d, J=8.3 Hz, 1H), 7.75 (s, 1H), 7.88 (s, 1H), 8.76 (br s, 2H), 9.30 (s, 1H), 14.03 (s, 1H).

EXAMPLE 365

4-Methanesulfonyloxy-5-methoxy-7-[1H-5-(cyclohexylaminomethyl)indol-2-yl]isoindolinone (Compound 365)

Step 1

In a similar manner to Step 2 of Example 6, 4-methanesulfonyloxy-5-methoxy-7-[1-(tert-butoxycarbonyl)-5-formyl]indolylisoindolinone (80 mg, 0.160 mmol) was dissolved in acetonitrile (5 mL), and the solution was treated with cyclohexylamine (0.254 mL, 3.19 mmol), acetic acid (0.183 mL, 3.20 mmol) and sodium triacetoxyborohydride (158 mg, 7.44 mmol) to obtain 4-methanesulfonyloxy-5-methoxy-7-[1-(tert-butoxycarbonyl)-5-(cyclohexylaminomethyl)indol-2-yl]isoindolinone (53.9 mg, yield 58%).

ESI-MS m/z: 584 [M+H]$^+$; $^1$H-NMR (CDCl$_3$) δ(ppm): 1.00-2.00 (m, 10H), 1.33 (s, 9H), 2.51 (m, 1H), 3.34 (s, 3H), 3.91 (s, 2H), 4.00 (s, 3H), 4.55 (s, 2H), 6.57 (s, 1H), 6.85 (br s, 1H), 7.10 (s, 1H), 7.29 (dd, J=1.5, 8.16 Hz, 1H), 7.50 (d, J=1.5 Hz, 1H), 8.18 (d, J=8.6 Hz, 1H).

Step 2

In a similar manner to Step 2 of Example 8, 4-methanesulfonyloxy-5-methoxy-7-[1-(tert-butoxycarbonyl)-5-(cyclohexylaminomethyl)indol-2-yl]isoindolinone (53.0 mg, 0.091 mmol) was dissolved in methanol (1.5 mL), and the solution was treated with 10% hydrogen chloride-methanol solution (1.5 mL). The reaction mixture was added with saturated aqueous sodium hydrogencarbonate solution and extracted with ethyl acetate. The organic layer was washed with saturated brine and dried over anhydrous sodium sulfate. The solvent was evaporated under reduced pressure and the residue was purified by slurry using diisopropylether to obtain Compound 365 (28.6 mg, yield 65%).

mp 196-199° C.; ESI-MS m/z: 484 [M+H]$^+$; $^1$H-NMR (DMSO-d$_6$) δ(ppm): 1.02-1.28 (m, 6H), 1.56 (m, 1H), 1.62-1.75 (m, 2H), 1.85-1.95 (m, 2H), 3.53 (s, 3H), 3.83 (s, 2H), 4.09 (s, 3H), 4.52 (s, 2H), 7.16 (d, J=8.4 Hz, 1H), 7.39 (s, 1H), 7.42 (d, J=8.4 Hz, 1H), 7.54 (s, 1H), 7.84 (s, 1H), 9.25 (s, 1H), 13.80 (s, 1H).

EXAMPLE 366

4-Methanesulfonyloxy-5-methoxy-7-[1H-5-(pyrrolidin-1-ylmethyl)indol-2-yl]isoindolinone (Compound 366)

Step 1

In a similar manner to Step 2 of Example 6, 4-methanesulfonyloxy-5-methoxy-7-[1-(tert-butoxycarbonyl)-5-formyl]indolylisoindolinone (80 mg, 0.160 mmol) was dissolved in acetonitrile (5 mL), and the solution was treated with pyrrolidine (0.134 mL, 1.61 mmol), acetic acid (0.183 mL, 3.20 mmol) and sodium triacetoxyborohydride (158 mg, 7.44 mmol) to obtain 4-methanesulfonyloxy-5-methoxy-7-[1-(tert-butoxycarbonyl)-5-(pyrrolidin-1-ylmethyl)indol-2-yl]isoindolinone (92.6 mg).

Step 2

In a similar manner to Step 2 of Example 8, 4-methanesulfonyloxy-5-methoxy-7-[1-(tert-butoxycarbonyl)-5-(pyrrolidin-1-ylmethyl)indol-2-yl]isoindolinone (92.0 mg) was dissolved in methanol (1.5 mL), and the solution was treated with 10% hydrogen chloride-methanol solution (1.5 mL). The reaction mixture was added with saturated aqueous sodium hydrogencarbonate solution and extracted with ethyl acetate. The organic layer was washed with saturated brine and dried over anhydrous sodium sulfate. The solvent was evaporated under reduced pressure and the residue was purified by slurry using diisopropylether to obtain Compound 366 (33.8 mg, yield 46%, 2 steps).

mp 187-189° C.; ESI-MS m/z: 456 [M+H]$^+$; $^1$H-NMR (DMSO-d$_6$) δ(ppm): 1.64-1.76 (m, 4H), 2.40-2.49 (m, 4H), 3.53 (s, 3H), 3.64 (s, 2H), 4.08 (s, 3H), 4.52 (s, 2H), 7.12 (d, J=8.4 Hz, 1H), 7.37 (s, 1H), 7.41 (d, J=8.4 Hz, 1H), 7.48 (s, 1H), 7.82 (s, 1H), 9.24 (s, 1H), 13.79 (s, 1H).

EXAMPLE 367

4-Methanesulfonyloxy-5-methoxy-7-[1H-5-(pyperazin-1-ylcarbonyl)indol-2-yl]isoindolinone (Compound 367)

Step 1

In a similar manner to Step 2 of Example 1, 4-methanesulfonyloxy-5-methoxy-7-iodoisoindolinone (50.3 mg, 0.132 mmol) was dissolved in acetonitrile (3 mL), and the solution was treated with Compound BB (125 mg, 0.264 mmol), palladium acetate (2.4 mg, 0.010 mmol), tri(o-tolyl)phosphine (6.4 mg, 0.020 mmol) and triethylamine (0.184 mL, 1.32 mmol), followed by purification by preparative thin-layer chromatography (chloroform/methanol=10/1) to obtain 4-methanesulfonyloxy-5-methoxy-7-[1-(tert-butoxycarbonyl)-5-(pyperazin-1-ylcarbonyl)indol-2-yl]isoindolinone (59.6 mg, yield 66%).

ESI-MS m/z: 685 [M+H]$^+$; $^1$H-NMR (CDCl$_3$) δ(ppm): 1.35 (s, 9H), 1.48 (s, 9H), 3.81-3.86 (m, 8H), 3.35 (s, 3H), 4.02 (s, 3H), 4.57 (s, 2H), 6.44 (s, 1H), 6.63 (s, 1H), 7.12 (s, 1H), 7.38 (dd, J=1.6, 8.7 Hz, 1H), 7.65 (s, 1H), 8.29 (d, J=8.7 Hz, 1H).

Step 2

In a similar manner to Step 2 of Example 5, 4-methanesulfonyloxy-5-methoxy-7-[1-(tert-butoxycarbonyl)-5-(pyperazin-1-ylcarbonyl)indol-2-yl]isoindolinone (59.6 mg, 0.0870 mmol) was treated with 4 mol/L hydrogen chloride-ethyl acetate solution (9 mL). The reaction mixture was added with saturated aqueous sodium hydrogencarbonate solution and extracted with ethyl acetate. The organic layer was washed with saturated brine and dried over anhydrous sodium sulfate. The solvent was evaporated under reduced pressure and the residue was purified by preparative thin-layer chromatography (chloroform/methanol=9/0.1) to obtain Compound 367 (4.8 mg, yield 11%, 2 steps).

ESI-MS m/z: 485 [M+H]$^+$; $^1$H-NMR (DMSO-d$_6$) δ(ppm): 2.61-2.82 (m, 4H), 3.35-3.57 (m, 4H), 3.53 (s, 3H), 4.08 (s, 3H), 4.52 (s, 2H), 7.17 (d, J=8.3 Hz, 1H), 7.45-7.60 (m, 2H), 7.62 (s, 1H), 7.85 (s, 1H), 9.27 (s, 1H), 14.01 (s, 1H).

EXAMPLE 368

4-Methanesulfonyloxy-5-methoxy-7-[1H-5-(4-methylpyperazin-1-ylmethyl)indol-2-yl]isoindolinone dihydrochloride (Compound 368)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with 1-methylpiperazine (0.089 mL, 0.80 mmol), acetic acid (0.229 mL, 4.00 mmol) and sodium triacetoxyborohydride (169 mg, 0.797 mmol), followed by purification by preparative thin-layer chromatography (chloroform/methanol=9/1) to obtain 4-methanesulfonyloxy-5-methoxy-7-[1-(tert-butoxycarbonyl)-5-(4-methylpyperazin-1-ylmethyl)indol-2-yl]isoindolinone (77.5 mg, yield 66%).

ESI-MS m/z: 585 [M+H]$^+$; $^1$H-NMR (CDCl$_3$) δ(ppm): 1.36 (s, 9H), 2.30 (s, 3H), 2.36-2.70 (m, 8H), 3.35 (s, 3H), 3.60 (s, 2H), 4.00 (s, 3H), 4.56 (s, 2H), 6.22 (s, 1H), 6.57 (s, 1H), 7.10 (s, 1H), 7.32 (d, J=8.5 Hz, 1H), 7.50 (s, 1H), 8.17 (d, J=8.5 Hz, 1H).

Step 2

In a similar manner to Step 2 of Example 8, 4-methanesulfonyloxy-5-methoxy-7-[1-(tert-butoxycarbonyl)-5-(4-methylpyperazin-1-ylmethyl)indol-2-yl]isoindolinone (75.0 mg, 0.128 mmol) was dissolved in methanol (3 mL), and the solution was treated with 10% hydrogen chloride-methanol solution (5 mL). The precipitated solid was collected by filtration and washed with methanol, followed by drying under reduced pressure to obtain Compound 368 (62.2 mg, yield 87%).

ESI-MS m/z: 485 [M+H]$^+$; $^1$H-NMR (DMSO-d$_6$) δ(ppm): 2.78 (br s, 3H), 3.09-3.78 (m, 8H), 3.53 (s, 3H), 4.08 (s, 3H), 4.44 (br s, 2H), 4.52 (s, 2H), 7.33 (m, 1H), 7.48 (s, 1H), 7.56 (d, J=8.6 Hz, 1H), 7.84 (m, 1H), 7.86 (s, 1H), 9.26 (s, 1H), 14.00 (br s, 1H).

EXAMPLE 369

4-Methanesulfonyloxy-5-methoxy-7-{1H-5-[(1,1-dimethylethyl)aminomethyl]indol-2-yl}isoindolinone hydrochloride (Compound 369)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with tert-butylamine (0.198 mL, 2.00 mmol), acetic-acid (0.229 mL, 4.00 mmol) and sodium triacetoxyborohydride (211 mg, 0.996 mmol), followed by purification by preparative thin-layer chromatography (chloroform/methanol=9/1) to obtain 4-methanesulfonyloxy-5-methoxy-7-{1-(tert-butoxycarbonyl)-5-[(1,1-dimethylethyl)aminomethyl]indol-2-yl}isoindolinone (31.9 mg, yield 29%).

ESI-MS m/z: 558 [M+H]$^+$; $^1$H-NMR (CDCl$_3$) δ(ppm): 1.18 (s, 9H), 1.33 (s, 9H), 3.34 (s, 3H), 3.89 (s, 2H), 4.00 (s, 3H), 4.44 (br s, 2H), 4.55 (s, 2H), 6.54 (s, 1H), 7.10 (s, 1H), 7.29 (dd, J=1.7, 8.8 Hz, 1H), 7.54 (s, 1H), 8.19 (d, J=8.8 Hz, 1H).

Step 2

In a similar manner to Step 2 of Example 8, 4-methanesulfonyloxy-5-methoxy-7-{1-(tert-butoxycarbonyl)-5-[(1,1-dimethylethyl)aminomethyl]indol-2-yl}isoindolinone (29.0 mg, 0.0520 mmol) was dissolved in methanol (1 mL), and the solution was treated with 10% hydrogen chloride-methanol solution (1 mL). The solvent was evaporated under reduced pressure. The residue was purified by slurry using diisopropylether to obtain Compound 369 (19.8 mg, yield 77%).

ESI-MS m/z: 458 [M+H]$^+$; $^1$H-NMR (DMSO-d$_6$) δ(ppm): 1.39 (s, 9H), 3.53 (s, 3H), 4.09 (s, 3H), 4.16 (br s, 2H), 4.52 (s, 2H), 7.32 (dd, J=1.4, 8.5 Hz, 1H), 7.48 (s, 1H), 7.57 (d, J=8.5 Hz, 1H), 7.79 (s, 1H), 7.88 (s, 1H), 8.78 (br s, 2H), 9.28 (s, 1H), 14.04 (br s, 1H).

EXAMPLE 370

4-Methanesulfonyloxy-5-methoxy-7-(1H-5-aminoindol-2-yl)isoindolinone hydrochloride (Compound 370)

Step 1

In a similar manner to Step 2 of Example 1, 4-methanesulfonyloxy-5-methoxy-7-iodoisoindolinone (50.0 mg, 0.130 mmol) was dissolved in acetonitrile (3 mL), and the solution was treated with Compound BP (98.2 mg, 0.261 mmol), palladium acetate (2.3 mg, 0.010 mmol), tri(o-tolyl) phosphine (6.3 mg, 0.020 mmol) and triethylamine (0.181 mL, 1.30 mmol), followed by purification by flash column chromatography (hexane/ethyl acetate=4/1 to 7/3 to 6/4 to 1/1) to obtain 4-methanesulfonyloxy-5-methoxy-7-[1-(tert-butoxycarbonyl)-5-(ter t-butoxycarbonylamino)indol-2-yl]isoindolinone (57.1 mg, yield 75%).

ESI-MS m/z: 588 [M+H]$^+$; $^1$H-NMR (CDCl$_3$) δ(ppm): 1.54 (s, 9H), 1.57 (s, 9H), 3.34 (s, 3H), 4.01 (s, 3H), 4.55 (s, 2H), 6.15 (s, 1H), 6.50-6.58 (m, 2H), 7.10 (s, 1H), 7.13 (dd, J=2.1, 8.9 Hz, 1H), 7.75 (br s, 1H), 8.13 (d, J=8.9 Hz, 1H).

Step 2

In a similar manner to Step 2 of Example 8, 4-methanesulfonyloxy-5-methoxy-7-[1-(tert-butoxycarbonyl)-5-(ter t-butoxycarbonylamino)indol-2-yl]isoindolinone (55.0 mg, 0.0940 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 370 (31.5 mg, yield 79%).

ESI-MS m/z: 388 [M+H]$^+$; $^1$H-NMR (DMSO-d$_6$) δ(ppm): 3.53 (s, 3H), 4.08 (s, 3H), 4.53 (s, 2H), 7.12 (dd, J=2.0, 8.7 Hz, 1H), 7.51 (s, 1H), 7.59-7.68 (m, 2H), 7.85 (s, 1H), 9.31 (s, 1H), 10.02 (br s, 3H), 14.09 (s, 1H).

EXAMPLE 371

4-Methanesulfonyloxy-5-methoxy-7-[1H-5-(4-piperidinopiperidinomethyl)indol-2-yl]isoindolinone dihydrochloride (Compound 371)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with 4-piperidinopiperidine (135 mg, 0.802 mmol), acetic acid (0.229 mL, 4.00 mmol) and sodium triacetoxyborohydride (169 mg, 0.797 mmol), followed by purification by preparative thin-layer chromatography (chloroform/methanol=6/1) to obtain 4-methanesulfonyloxy-5-methoxy-7-[1-(tert-butoxycarbonyl)-5-(4-piperidinopiperidinomethyl)indol-2-yl]isoindolinone (115 mg, yield 87%).

ESI-MS m/z: 653 [M+H]$^+$; $^1$H-NMR (CDCl$_3$) δ(ppm): 1.36 (s, 9H), 1.38-1.91 (m, 10H), 1.94-2.02 (m, 2H), 2.35 (m, 1H), 2.45-2.70 (m, 4H), 2.95-3.04 (m, 2H), 3.35 (s, 3H), 3.59 (s, 2H), 4.00 (s, 3H), 4.56 (s, 2H), 6.15 (s, 1H), 6.57 (s, 1H), 7.10 (s, 1H), 7.29 (m, 1H), 7.49 (s, 1H), 8.17 (d, J=8.9 Hz, 1H).

Step 2

In a similar manner to Step 2 of Example 8, 4-methanesulfonyloxy-5-methoxy-7-[1-(tert-butoxycarbonyl)-5-(4-piperidinopiperidinomethyl)indol-2-yl]isoindolinone (29.0 mg, 0.0520 mmol) was dissolved in methanol (2 mL), and the solution was treated with 10% hydrogen chloride-methanol solution (2 mL). The precipitated solid was collected by filtration and washed with methanol, followed by drying under reduced pressure to obtain Compound 371 (93.1 mg, yield 86%).

ESI-MS m/z: 553 [M+H]$^+$; $^1$H-NMR (DMSO-d$_6$) δ(ppm): 1.40 (m, 1H), 1.60-1.95 (m, 5H), 2.02-2.35 (m, 4H), 2.80-3.03 (m, 4H), 3.24-3.50 (m, 4H), 3.51 (m, 1H), 3.53 (s, 3H), 4.08 (s, 3H), 4.35 (br s, 2H), 4.53 (s, 2H), 7.33 (d, J=28.4 Hz, 1H), 7.51 (s, 1H), 7.57 (d, J=8.4 Hz, 1H), 7.82 (s, 1H), 7.87 (s, 1H), 9.29 (s, 1H), 10.51 (br s, 1H), 10.77 (br s, 1H), 14.01 (s, 1H).

EXAMPLE 372

4-Methanesulfonyloxy-5-methoxy-7-[1H-5-(3,5-dimethylpiperidinomethyl)indol-2-yl]isoindolinone hydrochloride (Compound 372)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with 3,5-dimethylpiperidine (0.106 mL, 0.799 mmol), acetic acid (0.229 mL, 4.00 mmol) and sodium triacetoxyborohydride (211 mg, 0.996 mmol), followed by purification by preparative thin-layer chromatography (chloroform/methanol=15/1) to obtain 4-methanesulfonyloxy-5-methoxy-7-[1-(tert-butoxycarbonyl)-5-(3,5-dimethylpiperidinomethyl)indol-2-yl]isoindolinone (68.6 mg, yield 57%).

ESI-MS m/z: 598 [M+H]$^+$; $^1$H-NMR (CDCl$_3$) δ(ppm) 0.83 (d, J=6.6 Hz, 6H), 1.24-2.15 (m, 6H), 1.36 (s, 9H), 2.83-2.93 (m, 2H), 3.35 (s, 3H), 3.62 (s, 2H), 4.00 (s, 3H), 4.56 (s, 2H), 6.16 (s, 1H), 6.58 (s, 1H), 7.11 (s, 1H), 7.31 (dd, J=1.5, 8.6 Hz, 1H), 7.51 (d, J=1.5 Hz, 1H), 8.18 (d, J=8.6 Hz, 1H).

Step 2

In a similar manner to Step 2 of Example 8, 4-methanesulfonyloxy-5-methoxy-7-[1-(tert-butoxycarbonyl)-5-(3,5-dimethylpiperidinomethyl)indol-2-yl]isoindolinone (66.0 mg, 0.110 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 372 (41.7 mg, yield 71%).

ESI-MS m/z: 498 [M+H]$^+$; $^1$H-NMR (DMSO-d$_6$) δ(ppm): 0.76 (m, 1H), 0.85 (d, J=6.6 Hz, 6H), 1.08 (m, 1H), 1.72 (m, 1H), 1.96 (m, 1H), 2.40-2.50 (m, 2H), 3.35-3.45 (m, 2H), 3.53 (s, 3H), 4.08 (s, 3H), 4.33 (br s, 2H), 4.52 (s, 2H), 7.32 (m, 1H), 7.50 (s, 1H), 7.57 (d, J=8.4 Hz, 1H), 7.81 (s, 1H), 7.86 (s, 1H), 9.28 (s, 1H), 10.10 (br s, 1H), 13.99 (s, 1H).

EXAMPLE 373

4-Methanesulfonyloxy-5-methoxy-7-[1H-5-(1-propylaminomethyl)indol-2-yl]isoindolinone hydrochloride (Compound 373)

Step 1

In a similar manner to Step. 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with n-propylamine (0.329 mL, 4.00 mmol), acetic acid (0.229 mL, 4.00 mmol) and sodium triacetoxyborohydride (169 mg, 0.797 mmol), followed by purification by preparative thin-layer chromatography (chloroform/methanol=6/1) to obtain 4-methanesulfonyloxy-5-methoxy-7-[1-(tert-butoxycarbonyl)-5-(1-propylaminomethyl)indol-2-yl]isoindolinone (72.6 mg, yield 67%).

ESI-MS m/z: 544 [M+H]$^+$; $^1$H-NMR (CDCl$_3$) (ppm): 0.82 (t, J=7.5 Hz, 3H), 1.34 (s, 9H), 1.49-1.59 (m, 2H), 2.53-2.63 (m, 2H), 3.34 (s, 3H), 3.95-4.03 (m, 2H), 4.00 (s, 3H), 4.58 (s, 2H), 6.55 (s, 1H), 6.90 (br s, 1H), 7.10 (s, 1H), 7.31 (dd. J=1.3, 8.6 Hz, 1H), 7.51 (d, J=1.3 Hz, 1H), 8.19 (d, J=8.6 Hz, 1H).

Step 2

In a similar manner to Step 2 of Example 8, 4-methanesulfonyloxy-5-methoxy-7-[(1-(tert-butoxycarbonyl)-5-(1-propylaminomethyl)indol-2-yl]isoindolinone (70.0 mg, 0.129 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 373 (43.2 mg, yield 70%).

ESI-MS m/z: 444 [M+H]$^+$; $^1$H-NMR (DMSO-d$_6$) δ(ppm): 0.90 (t, J=7.5 Hz, 3H), 1.61-1.71 (m, 2H), 2.80-2.90 (m, 2H), 3.53 (s, 3H), 4.08 (s, 3H), 4.19 (br s, 2H), 4.52 (s, 2H), 7.29 (dd, J=1.6, 8.4 Hz, 1H), 7.49 (d, J=1.6 Hz, 1H), 7.55 (d, J=8.4 Hz, 1H), 7.76 (s, 1H), 7.86 (s, 1H), 8.93 (br s, 2H), 9.27 (s, 1H), 14.00 (s, 1H).

EXAMPLE 374

4-Methanesulfonyloxy-5-methoxy-7-[1H-5-(2-methoxyethylaminomethyl)indol-2-yl]isoindolinone (Compound 374)

Step 1

In a similar manner to Step 2 of Example 6, 4-methanesulfonyloxy-5-methoxy-7-[1-(tert-butoxycarbonyl)-5-formylindol-2-yl]isoindolinone (1.02 g, 2.66 mmol) was dissolved in acetonitrile (13.0 mL), and the solution was treated with 2-methoxyethylamine (3.47 mL, 39.9 mmol), acetic acid (2.28 mL, 13.3 mmol) and sodium triacetoxyborohydride (2.82 g, 39.9 mmol), followed by purification by flash column chromatography (chloroform/methanol=4/1) to obtain 4-methanesulfonyloxy-5-methoxy-7-[1-(tert-butoxycarbonyl)-5-(2-methoxyethylaminomethyl)indol-2-yl]isoindolinone (0.83 g, 56%).

ESI-MS m/z: 560 [M+H]$^+$; $^1$H-NMR (CDCl$_3$) δ(ppm): 1.34 (s, 9H), 2.83 (t, J=5.4 Hz, 2H), 3.32 (s, 3H), 3.34 (s, 3H), 3.54 (t, J=5.4 Hz, 2H), 3.97 (s, 2H), 4.00 (s, 3H), 4.56 (s, 2H), 6.56 (s, 1H), 6.77 (br s, 1H), 7.10 (s, 1H), 7.23 (dd, J=1.8, 6.9 Hz, 1H), 7.52 (d. J=1.8 Hz, 1H), 8.20 (d, J=6.9 Hz, 1H).

Step 2

4-Methanesulfonyloxy-5-methoxy-7-[1-(tert-butoxycarbonyl)-5-(2-methoxyethylaminomethyl)indol-2-yl]isoindolinone (1.58 g, 2.82 mmol) was dissolved in 10% hydrogen chloride-methanol solution (30.0 mL), and the solution was stirred under reflux for 1.5 hours. The solvent was evaporated under reduced pressure and the residue was added with water, followed by extracting with ethyl acetate/methanol (9/1). The organic layer was washed with saturated brine and dried over anhydrous sodium sulfate. The solvent was evaporated under reduced pressure and the residue was purified by slurry using diisopropylether and methanol to obtain Compound 374 (837 mg, yield 64%).

mp 188-190° C.; ESI-MS m/z: 460 [M+H]$^+$; $^1$H-NMR (DMSO-d$_6$) δ(ppm): 2.67 (t, J=5.9 Hz, 2H), 3.23 (s, 3H), 3.41 (t, J=5.9 Hz, 2H), 3.53 (s, 3H), 3.77 (s, 2H), 4.08 (s, 3H), 4.52 (s, 2H), 7.13 (d, J=8.4 Hz, 1H), 7.37 (s, 1H), 7.40 (d, J=8.4 Hz, 1H), 7.50 (s, 1H), 7.83 (s, 1H), 9.23 (s, 1H), 14.1 (s, 1H).

EXAMPLE 375

4-Methanesulfonyloxy-5-methoxy-7-[1H-5-(methylaminomethyl)indol-2-yl]isoindolinone hydrochloride (Compound 375)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with methylamine hydrochloride (270 mg, 4.00 mmol), triethylamine (0.558 mL, 4.00 mL), acetic acid (0.229 mL, 4.00 mmol) and sodium triacetoxyborohydride (254 mg, 1.20 mmol), followed by purification by preparative thin-layer chromatography (chloroform/methanol=6/1) to obtain 4-methanesulfonyloxy-5-methoxy-7-[1-(tert-butoxycarbonyl)-5-(methylaminomethyl)indol-2-yl]isoindolinone (67.7 mg, yield 66%).

ESI-MS m/z: 516 [M+H]$^+$, $^1$H-NMR (CDCl$_3$) δ(ppm): 1.34 (s, 9H), 2.46 (s, 3H), 3.34 (s, 3H), 3.85 (s, 2H), 4.00 (s, 3H), 4.55 (s, 2H), 6.55 (br s, 1H), 6.57 (s, 1H), 7.10 (s, 1H), 7.28 (dd, J=1.5, 8.6 Hz, 1H), 7.50 (d, J=1.5 Hz, 1H), 8.19 (d, J=8.6 Hz, 1H).

Step 2

In a similar manner to Step 2 of Example 8, 4-methanesulfonyloxy-5-methoxy-7-[1-(tert-butoxycarbonyl)-5-(methylaminomethyl)indol-2-yl]isoindolinone (81.0 mg, 0.157 mmol) was dissolved in methanol (2 mL), and the solution was treated with 10% hydrogen chloride-methanol solution (2 mL). The precipitated solid was collected by filtration and washed with methanol, followed by drying under reduced pressure to obtain Compound 375 (54.3 mg, yield 77%).

mp 251-253° C.: ESI-MS m/z: 416 [M+H]$^+$; $^1$H-NMR (DMSO-d$_6$) δ(ppm): 2.48 (s, 3H), 3.53 (s, 3H), 4.08 (s, 3H), 4.17 (br s, 2H), 4.52 (s, 2H), 7.27 (dd, J=1.5, 8.4 Hz, 1H), 7.49 (s, 1H), 7.55 (d, J=8.4 Hz, 1H), 7.74 (s, 1H), 7.86 (s, 1H), 8.96 (br s, 2H), 9.28 (s, 1H), 14.00 (s, 1H).

EXAMPLE 376

4-Methanesulfonyloxy-5-methoxy-7-[1H-5-(diethylaminomethyl)indol-2-yl]isoindolinone hydrochloride (Compound 376)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with diethylamine (0.207 mL, 2.00 mmol), acetic acid (0.229 mL, 4.00 mmol) and sodium triacetoxyborohydride (254 mg, 1.20 mmol), followed by purification by preparative thin-layer chromatography (chloroform/methanol=6/11) to obtain 4-methanesulfonyloxy-5-methoxy-7-[1-(tert-butoxycarbonyl)-5-(diethylaminomethyl)indol-2-yl]isoindolinone (50.4 mg, yield 45%).

ESI-MS m/z: 558 [M+H]$^+$; $^1$H-NMR (CDCl$_3$) δ(ppm): 1.10 (t, J=7.0 Hz, 6H), 1.36 (s, 9H), 2.59 (q, J=7.0 Hz, 4H), 3.34 (s, 3H), 3.71 (br s, 2H), 4.00 (s, 3H), 4.56 (s, 2H), 6.23 (br s, 1H), 6.58 (s, 1H), 7.10 (s, 1H), 7.33 (dd, J=1.7, 8.6 Hz, 1H), 7.54 (s, 1H), 8.17 (d, J=8.6 Hz, 1H).

Step 2

In a similar manner to Step 2 of Example 8, 4-methanesulfonyloxy-5-methoxy-7-[1-(tert-butoxycarbonyl)-5-(diethylaminomethyl)indol-2-yl]isoindolinone (48.0 mg, 0.0860 mmol) was dissolved in methanol (1.5 mL), and the solution was treated with 10% hydrogen chloride-methanol solution (1.5 mL). The reaction mixture was added with diisopropylether. The precipitated solid was collected by filtration and washed with diisopropylether, followed by drying under reduced pressure to obtain Compound 376 (28.3 mg, yield 67%).

mp 181-183° C.; ESI-MS m/z: 458 [M+H]$^+$; $^1$H-NMR (DMSO-d$_6$) δ(ppm): 1.24 (t, J=7.1 Hz, 6H), 2.92-3.18 (m, 4H), 3.52 (s, 3H), 4.07 (s, 3H), 4.34 (br s, 2H), 4.51 (s, 2H), 7.31 (d, J=8.5 Hz, 1H), 7.48 (s, 1H), 7.57 (d, J=8.5 Hz, 1H), 7.79 (s, 1H), 7.85 (s, 1H), 9.26 (s, 1H), 9.76 (br s, 1H), 14.20 (s, 1H).

EXAMPLE 377

4-Methanesulfonyloxy-5-methoxy-7-[1H-5-(morpholinomethyl)indol-2-yl]isoindolinone hydrochloride (Compound 377)

Step 1

In a similar manner to, Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with morpholine (0.070 mL, 0.80 mmol), acetic acid (0.229 mL, 4.00 mmol) and sodium triacetoxyborohydride (127 mg, 0.599 mmol), followed by purification by preparative thin-layer chromatography (chloroform/methanol=9/1) to obtain 4-methanesulfonyloxy-5-methoxy-7-[1-(tert-butoxycarbonyl)-5-(morpholinomethyl)indol-2-yl]isoindolinone (80.3 mg, yield 70%).

ESI-MS m/z: 572 [M+H]⁺; ¹H-NMR (CDCl₃) δ(ppm): 1.36 (s, 9H), 2.38-2.57 (m, 4H), 3.35 (s, 3H), 3.59 (s, 2H), 3.56-3.78 (m, 4H), 4.00 (s, 3H), 4.56 (s, 2H), 6.20 (br s, 1H), 6.58 (s, 1H), 7.10 (s, 1H), 7.32 (dd, J=1.7, 8.6 Hz, 1H), 7.51 (s, 1H), 8.18 (d, J=8.6 Hz, 1H).

Step 2

In a similar manner to Step 2 of Example 8, 4-methanesulfonyloxy-5-methoxy-7-[1-(tert-butoxycarbonyl)-5-(morpholinomethyl)indol-2-yl]isoindolinone (78.0 mg, 0.136 mmol) was dissolved in methanol (2 mL), and the solution was treated with 10% hydrogen chloride-methanol solution (2 mL). The precipitated solid was collected by filtration and washed with methanol, followed by drying under reduced pressure to obtain Compound 377 (54.4 mg, yield 79%).

ESI-MS m/z: 472 [M+H]⁺; ¹H-NMR (DMSO-d₆) δ(ppm): 3.05-3.16 (m, 2H), 3.20-3.30 (m, 2H), 3.53 (s, 3H), 3.70-3.77 (m, 2H), 3.88-3.98 (m, 2H), 4.08 (s, 3H), 4.39 (d, J=4.6 Hz, 2H), 4.52 (s, 2H), 7.33 (d, J=8.3 Hz, 1H), 7.50 (s, 1H), 7.57 (d, J=8.3 Hz, 1H), 7.82 (s, 1H), 7.86 (s, 1H), 9.27 (s, 1H), 10.62 (br s, 1H), 14.00 (s, 1H).

EXAMPLE 378

4-Methanesulfonyloxy-5-methoxy-7-(1H-5-aminomethylindol-2-yl)isoindolinone hydrochloride (Compound 378)

Step 1

4-Methanesulfonyloxy-5-methoxy-7-[1-(tert-butoxycarbonyl)-5-formyl]indolylisoindolinone (100 mg, 0.200 mmol) was dissolved in acetonitrile (4 mL), and the solution was added with tert-butylcarbamate (280 mg, 2.39 mmol), trifluoroacetic acid (0.062 mL, 0.80 mmol) and triethylsilane (0.388 mL, 2.40 mmol), followed by stirring at room temperature for 8 days. The reaction mixture was added with water and sodium carbonate and extracted with ethyl acetate. The organic layer was washed with saturated brine and dried over anhydrous sodium sulfate. The solvent was evaporated under reduced pressure and the residue was purified by flash column chromatography (hexane/ethyl acetate=7/3 to 1/1 to 3/7) and preparative thin-layer chromatography (hexane/ethyl acetate=1/2) to obtain 4-methanesulfonyloxy-5-methoxy-7-[1-(tert-butoxycarbonyl)-5-(N-tert-butoxycarbonylaminomethyl)indol-2-yl]isoindolinone (43.4 mg, yield 36%).

ESI-MS m/z: 602 [M+H]⁺; ¹H-NMR (CDCl₃) δ(ppm): 1.35 (s, 9H), 1.47 (s, 9H), 3.34 (s, 3H), 4.01 (s, 3H), 4.39 (d, J=5.8 Hz, 2H), 4.55 (s, 2H), 4.85 (br s, 1H), 6.18 (s, 1H), 6.57 (s, 1H), 7.10 (s, 1H), 7.27 (m, 1H), 7.48 (s, 1H), 8.19 (d, J=8.7 Hz, 1H).

Step 2

In a similar manner to Step 2 of Example 8, 4-methanesulfonyloxy-5-methoxy-7-[1-(tert-butoxycarbonyl)-5-(N-tert-butoxycarbonylaminomethyl)indol-2-yl]isoindolinone (41.0 mg, 0.0680 mmol) was dissolved in methanol (1 mL), and the solution was treated with 10% hydrogen chloride-methanol solution (1 mL). The precipitated solid was collected by filtration and washed with methanol, followed by drying under reduced pressure to obtain Compound 378 (22.3 mg, yield 75%).

ESI-MS m/z: 402 [M+H]⁺; ¹H-NMR (DMSO-d₆) δ(ppm): 3.51 (s, 3H), 3.98-4.17 (m, 5H), 3.88-3.98 (m, 2H), 4.50 (s, 2H), 7.24 (d, J=8.4 Hz, 1H), 7.47 (s, 1H), 7.52 (d, J=8.4 Hz, 1H), 7.69 (s, 1H), 7.85 (s, 1H), 8.22 (s, 1H), 9.27 (s, 1H), 14.21 (s, 1H).

EXAMPLE 379

4-Methanesulfonyloxy-5-methoxy-7-(1H-5-bromoindol-2-yl)isoindolinone (Compound 379)

Step 1

In a similar manner to Step 2 of Example 1, 4-methanesulfonyloxy-5-methoxy-7-iodoisoindolinone (50.0 mg, 0.130 mmol) was dissolved in acetonitrile (4 mL), and the solution was treated with Compound BF (88.0 mg, 0.259 mmol), palladium acetate (2.3 mg, 0.010 mmol) and triethylamine (0.177 mL, 1.30 mmol), followed by purification by preparative thin-layer chromatography (hexane/ethyl acetate=1/1) to obtain 4-methanesulfonyloxy-5-methoxy-7-[1-(tert-butoxycarbonyl)-5-bromoindol-2-yl]isoindolinone (52.1 mg, yield 73%).

ESI-MS m/z: 552 [M+H]⁺; ¹H-NMR (CDCl₃) δ(ppm): 1.34 (s, 9H), 3.35 (s, 3H), 4.01 (s, 3H), 4.56 (s, 2H), 6.21 (br s, 1H), 6.54 (s, 1H), 7.10 (s, 1H), 7.43 (dd, J=1.8, 9.0 Hz, 1H), 7.68 (d, J=1.8 Hz, 1H), 8.13 (d, J=9.0 Hz, 1H).

Step 2

In a similar manner to Step 2 of Example 8, 4-methanesulfonyloxy-5-methoxy-7-[1-(tert-butoxycarbonyl)-5-bromoindol-2-yl]isoindolinone (31.8 mg, 0.0577 mmol) was dissolved in methanol (1 mL), and the solution was treated with 10% hydrogen chloride-methanol solution (1 mL). The precipitated solid was collected by filtration and washed with methanol, followed by drying under reduced pressure to obtain Compound 379 (21.0 mg, yield 81%).

ESI-MS m/z: 452 [M+H]⁺; ¹H-NMR (DMSO-d₆) δ(ppm): 3.54 (s, 3H), 4.09 (s, 3H), 4.53 (s, 2H), 7.25 (dd, J=1.8, 8.6 Hz, 1H), 7.41 (s, 1H), 7.49 (d, J=8.6 Hz, 1H), 7.78 (d, J=1.8 Hz, 1H), 7.85 (s, 1H), 9.31 (s, 1H), 14.06 (s, 1H).

EXAMPLE 380

4-Methanesulfonyloxy-5-methoxy-7-(1H-5-hydroxyindol-2-yl)isoindolinone (Compound 380)

Step 1

In a similar manner to Step 2 of Example 1, 4-methanesulfonyloxy-5-methoxy-7-iodoisoindolinone (46.0 mg, 0.120 mmol) was dissolved in acetonitrile (4 mL), and the solution was treated with Compound BR (94.1 mg, 0.240 mmol), palladium acetate (2.2 mg, 0.0098 mmol), tri(o-tolyl)phosphine (5.8 mg, 0.019 mmol) and triethylamine (0.163 mL, 1.20 mmol), followed by purification by preparative thin-layer chromatography (hexane/ethyl acetate=1/1) to obtain 4-methanesulfonyloxy-5-methoxy-7-[1-(tert-butoxycarbonyl)-5-(ter t-butyldimethylsilyloxy)indol-2-yl]isoindolinone (68.2 mg, yield 94%).

ESI-MS m/z: 603 [M+H]⁺; ¹H-NMR (CDCl₃) δ(ppm): 0.20 (s, 6H), 1.01 (s, 9H), 1.35 (s, 9H), 3.35 (s, 3H), 4.00 (s, 3H), 4.56 (s, 2H), 6.13 (br s, 1H), 6.50 (s, 1H), 6.87 (dd, J=2.2, 9.0 Hz, 1H), 6.98 (d, J=2.2 Hz, 1H), 7.10 (s, 1H), 8.07 (d, J=9.0 Hz, 1H).

Step 2

In a similar manner to Step 2 of Example 8, 4-methanesulfonyloxy-5-methoxy-7-[1-(tert-butoxycarbonyl)-5-(ter t-butyldimethylsilyloxy)indol-2-yl]isoindolinone (56.8 mg, 0.0942 mmol) was dissolved in methanol (2 mL), and the solution was treated with 10% hydrogen chloride-methanol solution (2 mL). The precipitated solid was collected by filtration and washed with methanol, followed by drying under reduced pressure to obtain Compound 380 (28.7 mg, yield 78%).

ESI-MS m/z: 389 [M+H]+; 1H-NMR (DMSO-d6) δ(ppm): 3.52 (s, 3H), 4.07 (s, 3H), 4.51 (s, 2H), 6.69 (dd, J=2.4, 8.8 Hz, 1H), 6.89 (d, J=2.4 Hz, 1H), 7.22 (s, 1H), 7.28 (d, J=8.8. Hz, 1H), 7.79 (s, 1H), 8.78 (s, 1H), 9.21 (s, 1H), 13.60 (s, 1H).

EXAMPLE 381

4-Methanesulfonyloxy-5-methoxy-7-(1H-indol-2-yl) isoindolinone hydrochloride (Compound 381)

Step 1

In a similar manner to Step 2 of Example 1, 4-methanesulfonyloxy-5-methoxy-7-iodoisoindolinone (50.0 mg, 0.130 mmol) was dissolved in acetonitrile (3 mL), and the solution was treated with 1-(tert-butoxycarbonyl)indole-2-boronic acid (68.1 mg, 0.261 mmol), palladium acetate (2.3 mg, 0.010 mmol), tri(o-tolyl)phosphine (6.3 mg, 0.021 mmol) and triethylamine (0.181 mL, 1.30 mmol), followed by purification by flash column chromatography (hexane/ethyl acetate=7/3 to 1/1 to 3/7) to obtain 4-methanesulfonyloxy-5-methoxy-7-(1-(tert-butoxycarbonyl)indol-2-yl)isoindolinone (56.9 mg, yield 93%).

ESI-MS m/z: 473 [M+H]+; 1H-NMR (CDCl3) δ(ppm): 1.36 (s, 9H), 3.35 (s, 3H), 4.01 (s, 3H), 4.56 (s, 2H), 6.22 (br s, 1H), 6.61 (s, 1H), 7.11 (s, 1H), 7.23 (m, 1H), 7.34 (m, 1H), 7.56 (d, J=7.9 Hz, 1H), 8.25 (d, J=7.9 Hz, 1H).

Step 2

In a similar manner to Step 2 of Example 8, 4-methanesulfonyloxy-5-methoxy-7-(1-(tert-butoxycarbonyl)indol-2-yl)isoindolinone (54.5 mg, 0.115 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 381 (31.0 mg, yield 72%).

ESI-MS m/z: 373 [M+H]+; 1H-NMR (DMSO-d6) δ(ppm): 3.52 (s, 3H), 4.08 (s, 3H), 4.51 (s, 2H), 7.03 (m, 1H), 7.15 (m, 1H), 7.43 (s, 1H), 7.47 (d, J=8.1 Hz, 1H), 7.60 (d, J=7.9 Hz, 1H), 7.84 (s, 1H), 9.24 (s, 1H), 13.84 (s, 1H).

EXAMPLE 382

4-Methanesulfonyloxy-5-methoxy-7-{1H-5-[(2,2-dimethyl-3-(dimethylamino)propyl)aminomethyl]indol-2-yl}isoindolinone dihydrochloride (Compound 382)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with N,N,2,2-tetramethyl-1,3-propanediamine (0.318 mL, 2.00 mmol), acetic acid (0.229 mL, 4.00 mmol) and sodium triacetoxyborohydride (169 mg, 0.797 mmol), followed by purification by preparative thin-layer chromatography (chloroform/methanol/7 mol/L ammonia-methanol solution=128/21/1) to obtain 4-methanesulfonyloxy-5-methoxy-7-(1-(tert-butoxycarbonyl)-5-[(2, 2-dimethyl-3-(dimethylamino)propyl)aminomethyl]indol-2-yl)isoindolinone (88.5 mg, yield 74%).

ESI-MS m/z: 615 [M+H]+; 1H-NMR (CDCl3) δ(ppm): 0.95 (s, 6H), 1.35 (s, 9H), 2.04 (s, 2H), 2.21 (s, 6H), 2.56 (br s, 2H), 3.35 (s, 3H), 3.96 (br s, 2H), 4.01 (s, 3H), 4.56 (s, 2H), 6.19 (br s, 1H), 6.59 (s, 1H), 7.11 (s, 1H), 7.31 (dd, J=1.6, 8.6 Hz, 1H), 7.55 (s, 1H), 8.21 (d, J=8.6 Hz, 1H).

Step 2

In a similar manner to Step 2 of Example 8, 4-methanesulfonyloxy-5-methoxy-7-(1-(tert-butoxycarbonyl)-5-[(2,2-dimethyl-3-(dimethylamino)propyl)aminomethyl]indol-2-yl)isoindolinone (86.0 mg, 0.140 mmol) was dissolved in methanol (2 mL), and the solution was treated with 10% hydrogen chloride-methanol solution (2 mL). The precipitated solid was collected by filtration and washed with methanol, followed by drying under reduced pressure to obtain Compound 382 (75.5 mg, yield 91%).

ESI-MS m/z: 515 [M+H]+; 1H-NMR (DMSO-d6) δ(ppm): 1.15 (s, 6H), 2.78 (s, 6H), 2.95 (br s, 2H), 3.25 (br s, 2H), 3.53 (s, 3H), 4.08 (s, 3H), 4.26 (br s, 2H), 4.52 (s, 2H), 7.40 (d, J=8.6 Hz, 1H), 7.49 (s, 1H), 7.55 (d, J=8.6 Hz, 1H), 7.86 (s, 1H) 7.87 (s, 1H), 9.21 (br s, 2H), 9.28 (s, 1H), 10.00 (br s, 1H), 13.97 (s, 1H).

EXAMPLE 383

4-Methanesulfonyloxy-5-methoxy-7-{1H-5-[3-(N,N-dimethylamino)propylaminomethyl]indol-2-yl}isoindolinone dihydrochloride (Compound 383)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with N,N-dimethyl-1,3-propanediamine (0.252 mL, 2.00 mmol), acetic acid (0.229 mL, 4.00 mmol) and sodium triacetoxyborohydride (254 mg, 1.20 mmol), followed by purification by preparative thin-layer chromatography (chloroform/methanol/7 mol/L ammonia-methanol solution=12/1/1) to obtain 4-methanesulfonyloxy-5-methoxy-7-(1-(tert-butoxycarbonyl)-5-[3-(N,N-dimethylamino)propylaminomethyl]indol-2-yl)isoindolinone (85.4 mg, yield 73%).

ESI-MS m/z: 587 [M+H]+; 1H-NMR (CDCl3) δ(ppm): 1.35 (s, 9H), 1.61-1.77 (m, 2H), 2.22 (s, 6H), 2.33 (t, J=7.0 Hz, 2H), 2.70 (t, J=7.0 Hz, 2H), 3.35 (s, 3H), 3.90 (s, 2H), 4.01 (s, 3H), 4.56 (s, 2H), 6.21 (br s, 1H), 6.58 (s, 1H), 7.11 (s, 1H), 7.29 (d, J=8.6 Hz, 1H), 7.50 (s, 1H), 8.19 (d, J=8.6 Hz, 1H).

Step 2

In a similar manner to Step 2 of Example 8, 4-methanesulfonyloxy-5-methoxy-7-{1-(tert-butoxycarbonyl)-5-[(3-(N,N-dimethylamino)propylaminomethyl]indol-2-yl}isoindolinone (83.0 mg, 0.141 mmol) was dissolved in methanol (2 mL), and the solution was treated with 10% hydrogen chloride-methanol solution (2 mL). The precipitated solid was collected by filtration and washed with methanol, followed by drying under reduced pressure to obtain Compound 383 (64.0 mg, yield 81%).

ESI-MS m/z: 487 [M+H]+; 1H-NMR (DMSO-d6) δ(ppm): 2.05-2.15 (m, 2H), 2.73 (s, 6H), 2.96-3.05 (m, 2H), 3.10-3.20 (m, 2H), 3.53 (s, 3H), 4.08 (s, 3H), 4.21 (br s, 2H), 4.52 (s, 2H), 7.33 (d, J=8.2 Hz, 1H), 7.49 (s, 1H), 7.55 (d, J=8.2 Hz, 1H), 7.80 (s, 1H), 7.86 (s, 1H), 9.28 (br s, 3H), 10.50 (br s, 1H), 14.00 (s, 1H).

EXAMPLE 384

4-Methanesulfonyloxy-5-methoxy-7-[1H-5-(2,2,6,6-tetramethylpiperidin-4-ylaminomethyl)indol-2-yl]isoindolinone dihydrochloride (Compound 384)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with 4-amino-2,2,6,6-tetramethylpiperidine (0.685 mL, 4.00 mmol), acetic acid (0.229 mL, 4.00 mmol) and sodium triacetoxyborohydride (254 mg, 1.20 mmol), followed by purification by preparative thin-layer chromatography (chloroform/methanol/7 mol/L ammonia-methanol solution=43/7/1) to obtain 4-methanesulfonyloxy-5-methoxy-7-[1-(tert-butoxycarbonyl)-5-(2,2,6,6-tetramethylpiperidin-4-ylaminomethyl)indol-2-yl]isoindolinone (63.8 mg, yield 51%).

ESI-MS m/z: 641 [M+H]$^+$; $^1$H-NMR (CDCl$_3$) δ(ppm): 1.18 (s, 6H), 1.22 (s, 6H), 1.34 (s, 9H), 1.55-1.65 (m, 2H), 1.86-1.96 (m, 2H), 3.00 (m, 1H), 3.35 (s, 3H), 3.90 (s, 2H), 4.01 (s, 3H), 4.57 (s, 2H), 6.57 (s, 1H), 7.11 (s, 1H), 7.30 (dd, J=1.5, 8.7 Hz, 1H), 7.52 (s, 1H), 8.21 (d, J=8.7 Hz, 1H).

Step 2

In a similar manner to Step 2 of Example 8, 4-methanesulfonyloxy-5-methoxy-7-[1-(tert-butoxycarbonyl)-5-(2,2,6,6-tetramethylpiperidin-4-ylaminomethyl)indol-2-yl]isoindolinone (61.2 mg, 0.0960 mmol) was dissolved in methanol (1.5 mL), and the solution was treated with 10% hydrogen chloride-methanol solution (1.5 mL). The solvent was evaporated under reduced pressure. The residue was purified by slurry using methanol and ethyl acetate to obtain Compound 384 (40.8 mg, yield 69%).

ESI-MS m/z: 541 [M+H]$^+$; $^1$H-NMR (DMSO-d$_6$) (ppm): 1.39 (s, 6H), 1.47 (s, 6H), 1.76-1.86 (m, 2H), 2.23-2.31 (m, 2H), 3.53 (s, 3H), 3.78 (m, 1H), 4.09 (s, 3H), 4.27 (br s, 2H), 4.52 (s, 2H), 7.34 (d, J=8.4 Hz, 1H), 7.49 (s, 1H), 7.56 (d, J=8.4 Hz, 1H), 7.82 (s, 1H), 7.87 (s, 1H), 8.44 (s, 1H), 9.28 (s, 1H), 9.42 (br s, 3H), 14.03 (s, 1H).

EXAMPLE 385

4-Methanesulfonyloxy-5-methoxy-7-{1H-5-[di(2-methoxyethyl)aminomethyl]indol-2-yl}isoindolinone hydrochloride (Compound 385)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with di(2-methoxyethyl)amine (0.591 mL, 4.00 mmol), acetic acid (0.229 mL, 4.00 mmol) and sodium triacetoxyborohydride (127 mg, 0.599 mmol), followed by purification by preparative thin-layer chromatography (chloroform/methanol=20/1) to obtain 4-methanesulfonyloxy-5-methoxy-7-{1-(tert-butoxycarbonyl)-5-[di(2-methoxyethyl)aminomethyl]indol-2-yl}isoindolinone (91.6 mg, yield 74%).

ESI-MS m/z: 618 [M+H]$^+$; $^1$H-NMR (CDCl$_3$) δ(ppm): 1.36 (s, 9H), 2.78 (t, J=6.1 Hz, 4H), 3.33 (s, 6H), 3.34 (s, 3H), 3.51 (t, J=6.1 Hz, 4H), 3.80 (s, 2H), 4.00 (s, 3H), 4.56 (s, 2H), 6.15 (br s, 1H), 6.57 (s, 1H), 7.10 (s, 1H), 7.32 (dd, J=1.5, 8.5 Hz, 1H), 7.51 (s, 1H), 8.16 (d, J=8.5 Hz, 1H).

Step 2

In a similar manner to Step 2 of Example 8, 4-methanesulfonyloxy-5-methoxy-7-(1-(tert-butoxycarbonyl)-5-[(di(2-methoxyethyl)aminomethyl]indol-2-yl)isoindolinone (89.0 mg, 0.144 mmol) was dissolved in methanol (2 mL), and the solution was treated with 10% hydrogen chloride-methanol solution (2 mL). The solvent was evaporated under reduced pressure. The residue was purified by slurry using methanol and ethyl acetate to obtain Compound 385 (65.5 mg, yield 82%).

ESI-MS m/z: 518 [M+H]$^+$; $^1$H-NMR (DMSO-d$_6$) δ(ppm): 3.23-3.43 (m, 4H), 3.29 (s, 6H), 3.53 (s, 3H), 3.64-3.83 (m, 4H), 4.08 (s, 3H), 4.46 (d, J=3.9 Hz, 2H), 4.52 (s, 2H), 7.34 (d, J=9.0 Hz, 1H), 7.50 (s, 1H), 7.58 (d, J=9.0 Hz, 1H), 7.82 (s, 1H), 7.86 (s, 1H), 9.28 (s, 1H), 9.81 (br s, 1H), 14.01 (s, 1H).

EXAMPLE 386

4-Methanesulfonyloxy-5-methoxy-7-{1H-5-[(pyridin-3-ylmethyl)aminomethyl]indol-2-yl}isoindolinone dihydrochloride (Compound 386)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with 3-aminomethylpyridine (0.204 mL, 2.00 mmol), acetic acid (0.229 mL, 4.00 mmol) and sodium triacetoxyborohydride (213 mg, 1.01 mmol), followed by purification by preparative thin-layer chromatography (chloroform/methanol=9/1) to obtain 4-methanesulfonyloxy-5-methoxy-7-{1-(tert-butoxycarbonyl)-5-[(pyridin-3-ylmethyl)aminomethyl]indol-2-yl}isoindolinone (65.3 mg, yield 55%).

ESI-MS m/z: 593 [M+H]$^+$; $^1$H-NMR (CDCl$_3$) δ(ppm): 1.36 (s, 9H), 3.35 (s, 3H), 3.82 (s, 2H), 3.91 (s, 2H), 4.01 (s, 3H), 4.56 (s, 2H), 6.17 (br s, 1H), 6.58 (s, 1H), 7.11 (s, 1H), 7.24-7.36 (m, 3H), 7.51 (s, 1H), 7.72 (d, J=7.7 Hz, 1H), 8.21 (d, J=8.7 Hz, 1H), 8.51 (dd, J=1.9, 4.8 Hz, 1H), 8.59 (d, J=1.9 Hz, 1H).

Step 2

In a similar manner to Step 2 of Example 8, 4-methanesulfonyloxy-5-methoxy-7-(1-(tert-butoxycarbonyl)-5-[(pyridin-3-ylmethyl)aminomethyl]indol-2-yl)isoindolinone (62.5 mg, 0.105 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 386 (50.3 mg, yield 85%).

ESI-MS m/z: 493 [M+H]$^+$; $^1$H-NMR (DMSO-d$_6$) δ(ppm): 3.53 (s, 3H), 4.08 (s, 3H), 4.17-4.45 (m, 4H), 4.52 (s, 2H), 7.33 (dd, J=1.5, 8.4 Hz, 1H), 7.49 (s, 1H) 7.55 (d, J=8.3 Hz, 1H), 7.78 (m, 1H), 7.81 (s, 1H), 7.86 (s, 1H), 8.40 (d, J=8.0 Hz, 1H), 8.76 (s, 1H), 8.77 (s, 1H), 9.28 (s, 1H), 9.83 (br s, 2H), 14.00 (s, 1H).

EXAMPLE 387

4-Methanesulfonyloxy-5-methoxy-7-[1H-5-(1-ethylpyrrolidin-2-ylmethylaminomethyl)indol-2-yl]isoindolinone dihydrochloride (Compound 387)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with 2-aminomethyl-1-ethylpyrrolidine (0.289 mL, 2.00 mmol) acetic acid (0.229 mL, 4.00 mmol) and sodium triacetoxyborohydride (170 mg, 0.802 mmol), followed by purification by preparative thin-layer chromatography (chloroform/methanol/7 mol/L ammonia-methanol solution=128/21/1) to obtain 4-methanesulfonyloxy-5-methoxy-7-[1-(tert-butoxycarbonyl)-5-(1-ethylpyrrolidin-2-ylmethylaminomethyl)indol-2-yl]isoindolinone (93.5 mg, yield 77%).

ESI-MS m/z: 613 [M+H]$^+$; $^1$H-NMR (CDCl$_3$) δ(ppm): 1.10 (t, J=7.2 Hz, 3H), 1.36 (s, 9H), 1.50-2.04 (m, 4H), 2.10-2.30 (m, 2H), 2.52-2.62 (m, 2H), 2.75-2.87 (m, 2H), 3.19 (m, 1H), 3.34 (s, 3H), 3.91 (d, J=5.6 Hz, 2H), 4.01 (s, 3H), 4.56 (s, 2H), 6.19 (br s, 1H), 6.57 (s, 1H), 7.11 (s, 1H), 7.30 (dd, J=1.5, 8.7 Hz, 1H), 7.50 (s, 1H), 8.18 (d, J=8.7 Hz, 1H).

Step 2

In a similar manner to Step 2 of Compound 8, 4-methanesulfonyloxy-5-methoxy-7-[1-(tert-butoxycarbonyl)-5-(1-ethylpyrrolidin-2-ylmethylaminomethyl)indol-2-yl]isoindolinone (90.5 mg, 0.148 mmol) was dissolved in methanol (2 mL), and the solution was treated with 10% hydrogen chloride-methanol solution (2 mL). The solvent was evaporated under reduced pressure. The residue was purified by slurry using methanol and ethyl acetate to obtain Compound 387 (61.0 mg, yield 70%).

ESI-MS m/z: 513 [M+H]$^+$; $^1$H-NMR (DMSO-d$_6$) δ(ppm): 1.27 (t, J=6.8 Hz, 3H), 1.80-2.08 (m, 3H), 2.31 (m, 1H), 3.00-3.20 (m, 2H), 3.20-3.50 (m, 4H), 3.53 (s, 3H), 3.82 (m, 1H), 4.08 (s, 3H), 4.27 (br s, 2H), 4.52 (s, 2H), 7.36 (d, J=8.4 Hz, 1H), 7.50 (s, 1H), 7.55 (d, J=8.4 Hz, 1H), 7.85 (s, 1H), 7.87 (s, 1H), 9.28 (s, 1H), 9.63 (br s, 2H), 11.03 (br s, 1H), 14.01 (s, 1H).

EXAMPLE 388

4-Methanesulfonyloxy-5-methoxy-7-{1H-5-[2-(dimethylamino)ethylaminomethyl]indol-2-yl}isoindolinone dihydrochloride (Compound 388)

Step 1

In a similar manner to Step 2 of Example 6, 4-methanesulfonyloxy-5-methoxy-7-[1-(tert-butoxycarbonyl)-5-formyl]indolylisoindolinone (78 mg, 0.156 mmol) was dissolved in acetonitrile (4.5 mL), and the solution was treated with N,N-dimethylethylenediamine (0.171 mL, 1.56 mmol), acetic acid (0.179 mL, 3.13 mmol) and sodium triacetoxyborohydride (132 mg, 0.623 mmol), followed by purification by preparative thin-layer chromatography (chloroform/methanol/7 mol/L ammonia-methanol solution=43/7/1) to obtain 4-methanesulfonyloxy-5-methoxy-7-{1-(tert-butoxycarbonyl)-5-[(2-(dimethylamino)ethylaminomethyl]indol-2-yl}isoindolinone (62.4 mg, yield 70%).

ESI-MS m/z: 573 [M+H]$^+$; $^1$H-NMR (CDCl$_3$) δ(ppm): 1.35 (s, 9H), 2.21 (s, 6H), 2.47 (t, J=5.8 Hz, 2H), 2.73 (t, J=5.8 Hz, 3H), 3.34 (s, 3H), 3.93 (s, 2H), 4.01 (s, 3H), 4.56 (s, 2H), 6.19 (br s, 1H), 6.57 (s, 1H), 7.11 (s, 1H), 7.30 (dd, J=1.7, 8.6 Hz, 1H), 7.52 (s, 1H), 8.19 (d, J=8.6 Hz, 1H).

Step 2

In a similar manner to Step 2 of Example 8, 4-methanesulfonyloxy-5-methoxy-7-{1-(tert-butoxycarbonyl)-5-[2-(dimethylamino)ethylaminomethyl]indol-2-yl}isoindolinone (60.0 mg, 0.105 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 388 (44.9 mg, yield 78%).

ESI-MS m/z: 473 [M+H]$^+$; $^1$H-NMR (DMSO-d$_6$) (ppm): 2.82 (s, 6H), 3.31-3.53 (m, 4H), 3.53 (s, 3H), 4.08 (s, 3H), 4.26 (s, 2H), 4.52 (s, 2H), 7.34 (d, J=8.5 Hz, 1H), 7.50 (s, 1H), 7.56 (d, J=8.5 Hz, 1H), 7.83 (s, 1H), 7.87 (s, 1H), 9.29 (s, 1H), 9.51 (br s, 2H), 10.79 (br s, 1H), 14.02 (s, 1H).

EXAMPLE 389

4-Methanesulfonyloxy-5-methoxy-7-{1H-5-[di(2-hydroxyethyl)aminomethyl]indol-2-yl}isoindolinone hydrochloride (Compound 389)

Step 1

In a similar manner to Step 2 of Example 6, 4-methanesulfonyloxy-5-methoxy-7-[1-(tert-butoxycarbonyl)-5-formyl]indolylisoindolinone (78.0 mg, 0.156 mmol) was dissolved in acetonitrile (4.5 mL), and the solution was treated with diethanolamine (0.299 mL, 3.12 mmol), acetic acid (0.179 mL, 3.13 mmol) and sodium triacetoxyborohydride (429 mg, 2.02 mmol), followed by purification by preparative thin-layer chromatography (chloroform/methanol=4/1) to obtain 4-methanesulfonyloxy-5-methoxy-7-(1-(tert-butoxycarbonyl)-5-[di(2-hydroxyethyl)aminomethyl]indol-2-yl)isoindolinone (70.7 mg, yield 77%).

ESI-MS m/z: 590 [M+H]$^+$; $^1$H-NMR (CDCl$_3$) δ(ppm): 1.36 (s, 9H), 2.77 (t, J=5.3 Hz, 4H), 3.35 (s, 3H), 3.65 (t, J=5.3 Hz, 4H), 3.82 (s, 2H), 4.00 (s, 3H), 4.56 (s, 2H), 6.28 (br s, 1H), 6.57 (s, 1H), 7.10 (s, 1H), 7.27 (dd, J=1.7, 8.7 Hz, 1H), 7.48 (s, 1H), 8.19 (d, J=8.7 Hz, 1H).

Step 2

In a similar manner to Step 2 of Example 8, 4-methanesulfonyloxy-5-methoxy-7-{1-(tert-butoxycarbonyl)-5-[di(2-hydroxyethyl)aminomethyl]indol-2-yl}isoindolinone (68.5 mg, 0.116 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 389 (50.4 mg, yield 83%).

ESI-MS m/z: 490 [M+H]$^+$; $^1$H-NMR (DMSO-d$_6$) (ppm): 3.08-3.31 (m, 4H), 3.54 (s, 3H), 3.68-3.90 (m, 4H), 4.08 (s, 3H), 4.40-4.60 (m, 2H), 4.52 (s, 2H), 5.32 (s, 2H), 7.35 (d, J=8.6 Hz, 1H), 7.50 (s, 1H), 7.57 (d, J=8.6 Hz, 1H), 7.83 (s, 1H), 7.86 (s, 1H), 9.28 (s, 1H), 9.52 (br s, 1H), 13.99 (s, 1H).

EXAMPLE 390

4-Methanesulfonyloxy-5-methoxy-7-{1H-5-[N-(2-(dimethylamino)ethyl)-N-methylaminomethyl]indol-2-yl}isoindolinone dihydrochloride (Compound 390)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with N,N,N'-trimethylethylenediamine (0.260 mL, 2.00 mmol), acetic acid (0.229 mL, 4.00 mmol) and sodium triacetoxyborohydride (127 mg, 0.599 mmol), followed by purification by preparative thin-layer chromatography (chloroform/methanol/7 mol/L ammonia-methanol solution=86/14/1) to obtain 4-methanesulfonyloxy-5-methoxy-7-{1-(tert-butoxycarbonyl)-5-[N-(2-(dimethylamino)ethyl)-N-methylaminomethyl]indol-2-yl}isoindolinone (82.7 mg, yield 72%).

ESI-MS m/z: 587 [M+H]$^+$; $^1$H-NMR (CDCl$_3$) δ(ppm): 1.36 (s, 9H), 2.25 (s, 6H), 2.26 (s, 3H), 2.24-2.62 (m, 4H), 3.34 (s, 3H), 3.63 (s, 2H), 4.00 (s, 3H), 4.56 (s, 2H), 6.21 (br s, 1H), 6.57 (s, 1H), 7.11 (s, 1H), 7.31 (dd, J=1.5, 8.6 Hz, 1H), 7.50 (s, 1H), 8.17 (d, J=8.6 Hz, 1H).

Step 2

In a similar manner to Step 2 of Example 8, 4-methanesulfonyloxy-5-methoxy-7-(1-(tert-butoxycarbonyl)-5-[N-(2-(dimethylamino)ethyl)-N-methylaminomethyl]indol-2-yl)isoindolinone (80.2 mg, 0.140 mmol) was dissolved in methanol (1.5 mL), and the solution was treated with 10% hydrogen chloride-methanol solution (1.5 mL). The solvent was evaporated under reduced pressure and the residue was purified by slurry using methanol and ethyl acetate to obtain Compound 390 (48.5 mg, yield 62%).

ESI-MS m/z: 487 [M+H]$^+$; $^1$H-NMR (DMSO-d$_6$) δ(ppm): 2.48 (s, 3H), 2.49 (s, 3H), 2.50 (s, 3H), 3.20-3.40 (m, 2H), 3.53 (s, 3H), 3.42-3.75 (m, 2H), 4.08 (s, 3H), 4.32 (m, 1H), 4.52 (s, 2H), 4.60 (m, 1H), 7.38 (d, J=8.4 Hz, 1H), 7.51 (s, 1H), 7.58 (d, J=8.4 Hz, 1H), 7.87 (s, 2H), 9.29 (s, 1H), 10.76 (br s, 1H), 10.86 (br s, 1H), 14.02 (s, 1H).

EXAMPLE 391

4-Methanesulfonyloxy-5-methoxy-7-(1H-5-[N-(2-(diethylamino)ethyl)-N-ethylaminomethyl]indol-2-yl)isoindolinone dihydrochloride (Compound 391)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with N,N,N'-triethylethylenediamine (0.359 mL, 2.00 mmol), acetic acid (0.229 mL, 4.00 mmol) and sodium triacetoxyborohydride (169 mg, 0.797 mmol), followed by purification by preparative thin-layer chromatography (chloroform/methanol/7 mol/L ammonia-methanol solution=128/21/1) to obtain 4-methanesulfonyloxy-5-methoxy-7-{1-(tert-butoxycarbonyl)-5-[N-(2-(diethylamino)ethyl)-N-ethylaminomethyl]indol-2-yl}isoindolinone (76.9 mg, yield 61%).

ESI-MS m/z: 629 [M+H]$^+$; $^1$H-NMR (CDCl$_3$) δ(ppm): 1.04 (t, J=7.3 Hz, 6H), 1.06 (d, J=7.3 Hz, 3H), 1.36 (s, 9H), 2.45-2.71 (m, 10H), 3.34 (s, 3H), 3.70 (s, 2H), 4.00 (s, 3H), 4.56 (s, 2H), 6.17 (br s, 1H), 6.57 (s, 1H), 7.11 (s, 1H), 7.32 (dd, J=1.6, 8.6 Hz, 1H), 7.51 (s, 1H), 8.16 (d, J=8.6 Hz, 1H).

Step 2

In a similar manner to Step 2 of Example 8, 4-methanesulfonyloxy-5-methoxy-7-{1-(tert-butoxycarbonyl)-5-[N-(2-(diethylamino)ethyl)-N-ethylaminomethyl]indol-2-yl}isoindolinone (74.4 mg, 0.118 mmol) was dissolved in methanol (1.5 mL), and the solution was treated with 10% hydrogen chloride-methanol solution (1.5 mL). The solvent was evaporated under reduced pressure and the residue was purified by slurry using methanol and ethyl acetate to obtain Compound 391 (59.7 mg, yield 84%).

ESI-MS m/z: 529 [M+H]$^+$; $^1$H-NMR (DMSO-d$_6$) δ(ppm): 1.02-1.40 (m, 9H), 2.94-3.25 (m, 4H), 3.20-3.40 (m, 2H), 3.40-3.60 (m, 4H), 3.53 (s, 3H), 4.08 (s, 3H), 4.40 (m, 1H), 4.52 (s, 2H), 4.53 (m, 1H), 7.41 (d. J=8.0 Hz, 1H), 7.51 (s, 1H), 7.59 (d, J=8.0 Hz, 1H), 7.87 (s, 1H), 7.92 (s, 1H), 9.29 (s, 1H), 10.77 (br s, 1H), 11.08 (br s, 1H), 14.02 (s, 1H).

EXAMPLE 392

4-Methanesulfonyloxy-5-methoxy-7-{1H-5-[3-(diethylamino)propylaminomethyl]indol-2-yl}isoindolinone dihydrochloride (Compound 392)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with 3-diethylaminopropylamine (0.126 mL, 0.799 mmol), acetic acid (0.229 mL, 4.00 mmol) and sodium triacetoxyborohydride (127 mg, 0.599 mmol), followed by purification by preparative thin-layer chromatography (chloroform/methanol/7 mol/L ammonia-methanol solution=12/1/1) to obtain 4-methanesulfonyloxy-5-methoxy-7-{1-(tert-butoxycarbonyl)-5-[3-(diethylamino)propylaminomethyl]indol-2-yl}isoindolinone (79.4 mg, yield 65%).

ESI-MS m/z: 615 [M+H]$^+$; $^1$H-NMR (CDCl$_3$) δ(ppm): 1.02 (t, J=7.1 Hz, 6H), 1.35 (s, 9H), 1.57-1.79 (m, 2H), 2.49 (t, J=6.8 Hz, 2H), 2.53 (q, J=7.1 Hz, 4H), 2.68 (t, J=6.8 Hz, 2H), 3.34 (s, 3H), 3.89 (s, 2H), 4.01 (s, 3H), 4.56 (s, 2H), 6.21 (br s, 1H), 6.57 (s, 1H), 7.11 (s, 1H), 7.29 (dd, J=1.5, 8.7 Hz, 1H), 7.50 (s, 1H), 8.19 (d, J=8.7 Hz, 1H).

Step 2

In a similar manner to Step 2 of Example 8, 4-methanesulfonyloxy-5-methoxy-7-{1-(tert-butoxycarbonyl)-5-[3-(diethylamino)propylaminomethyl]indol-2-yl}isoindolinone (77.0 mg, 0.125 mmol) was dissolved in methanol (1.5 mL), and the solution was treated with 10% hydrogen chloride-methanol solution (1.5 mL). The solvent was evaporated under reduced pressure and the residue was purified by slurry using methanol and ethyl acetate to obtain Compound 392 (49.8 mg, yield 68%).

ESI-MS m/z: 515 [M+H]$^+$; $^1$H-NMR (DMSO-d$_6$) δ(ppm): 1.08-1.27 (m, 6H), 2.00-2.15 (m, 2H), 2.87-3.20 (m, 6H), 3.22-3.50 (m, 2H), 3.53 (s, 3H), 4.09 (s, 3H), 4.21 (s, 2H), 4.52 (s, 2H), 7.33 (d, J=8.5 Hz, 1H), 7.49 (s, 1H), 7.55 (d, J=8.5 Hz, 1H), 7.80 (s, 1H), 7.87 (s, 1H), 9.28 (s, 1H), 9.29 (br s, 2H), 10.35 (br s, 1H), 14.00 (s, 1H).

EXAMPLE 393

4-Methanesulfonyloxy-5-methoxy-7-{1H-5-[N-(2-hydroxyethyl)-N-ethylaminomethyl]indol-2-yl}isoindolinone hydrochloride (Compound 393)

Step 1

In a similar manner to Step 2 of Example 6, 4-methanesulfonyloxy-5-methoxy-7-[1-(tert-butoxycarbonyl)-5-formylindol-2-yl]isoindolinone (100 mg, 0.200 mmol) was dissolved in acetonitrile (5.8 mL), and the solution was treated with 2-(ethylamino)ethanol (0.195 mL, 2.00 mmol), acetic acid (0.229 mL, 4.00 mmol) and sodium triacetoxyborohydride (212 mg, 1.00 mmol), followed by purification by preparative thin-layer chromatography (chloroform/methanol=4/1) to obtain 4-methanesulfonyloxy-5-methoxy-7-{1-(tert-butoxycarbonyl)-5-[N-(2-hydroxyethyl)-N-ethylaminomethyl]indol-2-yl}isoindolinone (68.3 mg, yield 60%).

ESI-MS m/z: 574 [M+H]$^+$; $^1$H-NMR (CDCl$_3$) δ(ppm): 1.11 (t, J=7.0 Hz, 3H), 1.36 (s, 9H), 2.65 (q, J=7.0 Hz, 2H), 2.72 (t, J=5.3 Hz, 2H), 3.35 (s, 3H), 3.61 (t, J=5.3 Hz, 2H), 3.77 (br s, 2H), 4.00 (s, 3H), 4.56 (s, 2H), 6.28 (br s, 1H), 6.58 (s, 1H), 7.11 (s, 1H), 7.27 (dd, J=1.5, 8.6 Hz, 1H), 7.50 (s, 1H), 8.19 (d, J=8.6 Hz, 1H).

Step 2

In a similar manner to Step 2 of Example 8, 4-methanesulfonyloxy-5-methoxy-7-{1-(tert-butoxycarbonyl)-5-[N-(2-hydroxyethyl)-N-ethylaminomethyl]indol-2-yl}isoindolinone (66.0 mg, 0.115 mmol) was dissolved in methanol (1.5 mL), and the solution was treated with 10% hydrogen chloride-methanol solution (1.5 mL). The solvent was evaporated under reduced pressure. The residue was purified by slurry using methanol and ethyl acetate to obtain Compound 393 (36.3 mg, yield 62%).

ESI-MS m/z: 474 [M+H]$^+$; $^1$H-NMR (DMSO-d$_6$) δ(ppm): 1.29 (t, J=7.0 Hz, 3H), 3.00-3.27 (m, 4H), 3.53 (s, 3H), 3.65-3.80 (m, 2H), 4.08 (s, 3H), 4.42 (br s, 2H), 4.52 (s, 2H), 5.32 (br s, 1H), 7.34 (d, J=8.7 Hz, 1H), 7.49 (s, 1H), 7.57 (d, J=8.7 Hz, 1H), 7.82 (s, 1H), 7.86 (s, 1H), 9.28 (s, 1H), 9.71 (br s, 1H), 14.00 (s, 1H).

EXAMPLE 394

4-Methanesulfonyloxy-5-methoxy-7-[1H-5-(benzylaminomethyl)indol-2-yl]isoindolinone hydrochloride (Compound 394)

Step 1

In a similar manner to Step 2 of Example 6, 4-methanesulfonyloxy-5-methoxy-7-[1-(tert-butoxycarbonyl)-5-formylindol-2-yl]isoindolinone (100 mg, 0.200 mmol) was dissolved in acetonitrile (5.8 mL), and the solution was treated with N-methylbenzylamine (0.258 mL, 2.00 mmol), acetic acid (0.229 mL, 4.00 mmol) and sodium triacetoxyborohydride (127 mg, 0.599 mmol), followed by purification by preparative thin-layer chromatography (chloroform/methanol=20/1) to obtain 4-methanesulfonyloxy-5-methoxy-7-[1-(tert-butoxycarbonyl)-5-(benzylaminomethyl)indol-2-yl]isoindolinone (22.6 mg, yield 19%) and 4-methanesulfonyloxy-5-methoxy-7-[1-(tert-butoxycarbonyl)-5-(N-methylbenzylaminomethyl)indol-2-yl]isoindolinone (72.1 mg, yield 60%).

4-methanesulfonyloxy-5-methoxy-7-[1-(tert-butoxycarbonyl)-5-(benzylaminomethyl)indol-2-yl]isoindolinone ESI-MS m/z: 592 [M+H]$^+$; $^1$H-NMR (CDCl$_3$) δ(ppm): 1.35 (s, 9H), 3.34 (s, 3H), 3.86 (s, 2H), 3.92 (s, 2H), 4.00 (s, 3H), 4.55 (s, 2H), 6.35 (br s, 1H), 6.58 (s, 1H), 7.11 (s, 1H), 7.18-7.42 (m, 6H), 7.53 (s, 1H), 8.20 (d, J=−8.6 Hz, 1H).

4-methanesulfonyloxy-5-methoxy-7-[1-(tert-butoxycarbonyl)-5-(N-methylbenzylaminomethyl)indol-2-yl]isoindolinone ESI-MS m/z: 606 [M+H]$^+$; $^1$H-NMR (CDCl$_3$) δ(ppm): 1.36 (s, 9H), 2.20 (s, 3H), 3.34 (s, 3H), 3.55 (s, 2H)—, 3.61 (s, 2H), 4.00 (s, 3H), 4.56 (s, 2H), 6.14 (br s, 1H), 6.59 (s, 1H), 7.11 (s, 1H), 7.20-7.45 (m, 6H), 7.54 (s, 1H), 8.18 (d, J=8.4 Hz, 1H).

Step 2

In a similar manner to Step 2 of Example 8, 4-methanesulfonyloxy-5-methoxy-7-[1-(tert-butoxycarbonyl)-5-(benzylaminomethyl)indol-2-yl]isoindolinone (22.3 mg, 0.0380 mmol) was dissolved in methanol (1 mL), and the solution was treated with 10% hydrogen chloride-methanol solution (1 mL). The precipitated solid was collected by filtration and washed with methanol, followed by drying under reduced pressure to obtain Compound 394 (13.6 mg, yield 68%).

ESI-MS m/z: 492 [M+H]$^+$; $^1$H-NMR (DMSO-d$_6$) δ(ppm): 3.53 (s, 3H), 4.08 (s, 3H), 4.15 (s, 2H), 4.22 (s, 2H), 4.52 (s, 2H), 7.29 (dd, J=1.5, 8.4 Hz, 1H), 7.38-7.60 (m, 7H), 7.75 (s, 1H), 7.86 (s, 1H), 9.28 (s, 1H), 9.37 (br s, 1H), 14.01 (s, 1H).

EXAMPLE 395

4-Methanesulfonyloxy-5-methoxy-7-{1H-5-[(2-(pyridin-4-yl)ethyl)aminomethyl]indol-2-yl}isoindolinone dihydrochloride (Compound 395)

Step 1

In a similar manner to Step 2 of Example 6, 4-methanesulfonyloxy-5-methoxy-7-[(1-(tert-butoxycarbonyl)-5-formylindol-2-yl]isoindolinone (100 mg, 0.200 mmol) was dissolved in acetonitrile (5.8 mL), and the solution was treated with 4-(2-aminoethyl)pyridine (0.239 mL, 2.00 mmol), acetic acid (0.229 mL, 4.00 mmol) and sodium triacetoxyborohydride (127 mg, 0.599 mmol) followed by purification by preparative thin-layer chromatography (chloroform/methanol=4/1) to obtain 4-methanesulfonyloxy-5-methoxy-7-(1-(tert-butoxycarbonyl)-5-[(2-(pyridin-4-yl)ethyl)aminomethyl]indol-2-yl)isoindolinone (85.9 mg, yield 71%).

ESI-MS m/z: 607 [M+H]$^+$; $^1$H-NMR (CDCl$_3$) δ(ppm): 1.35 (s, 9H), 2.71-2.85 (m, 2H), 2.85-2.99 (m, 2H), 3.34 (s, 3H), 3.90 (s, 2H), 4.00 (s, 3H), 4.56 (s, 2H), 6.19 (br s, 1H), 6.56 (s, 1H), 7.10-7.16 (m, 3H), 7.17-7.30 (m, 2H), 7.44 (m, 1H), 8.18 (d, J=8.6 Hz, 1H), 8.41-8.53 (m, 2H).

Step 2

In a similar manner to Step 2 of Example 8, 4-methanesulfonyloxy-5-methoxy-7-{1-(tert-butoxycarbonyl)-5-[(2-(pyridin-4-yl)ethyl)aminomethyl]indol-2-yl}isoindolinone (83.2 mg, 0.137 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 395 (57.7 mg, yield 73%).

ESI-MS m/z: 507 [M+H]$^+$; $^1$H-NMR (DMSO-d$_6$) δ(ppm): 3.09-3.85 (m, 4H), 3.54 (s, 3H), 4.09 (s, 3H), 4.26 (br s, 2H), 4.53 (s, 2H), 7.31 (d. J=8.4 Hz, 1H), 7.50 (s, 1H), 7.56 (d. J=8.4 Hz, 1H), 7.79-7.89 (m, 2H), 7.87 (s, 1H), 7.88 (s, 1H), 8.75-8.85 (m, 2H), 9.29 (s, 1H), 9.47 (br s, 2H), 14.01 (s, 1H).

EXAMPLE 396

4-Methanesulfonyloxy-5-methoxy-7-[1H-5-(N-methylbenzylaminomethyl)indol-2-yl]isoindolinone hydrochloride (Compound 396)

In a similar manner to Step 2 of Example 8, 4-methanesulfonyloxy-5-methoxy-7-[1-(tert-butoxycarbonyl)-5-(N-methylbenzylaminomethyl)indol-2-yl]isoindolinone (69.5 mg, 0.115 mmol) was dissolved in methanol (1.5 mL), and the solution was treated with 10% hydrogen chloride-methanol solution (1.5 mL). The solvent was evaporated under reduced pressure and the residue was purified by slurry using ethyl acetate to obtain Compound 396 (45.4 mg, yield 73%).

ESI-MS m/z: 506 [M+H]$^+$; $^1$H-NMR (DMSO-d$_6$) δ(ppm): 2.54 (d, J=3.9 Hz, 3H), 3.53 (s, 3H), 4.08 (s, 3H), 4.10-4.45 (m, 2H), 4.41-4.55 (m, 2H), 4.52 (s, 2H), 7.33 (d, J=8.7 Hz, 1H), 7.40-7.70 (m, 7H), 7.81 (s, 1H), 7.86 (s, 1H), 9.27 (s, 1H), 10.34 (s, 1H), 14.01 (s, 1H).

EXAMPLE 397

4-Methanesulfonyloxy-5-methoxy-7-{1H-5-[(2-(pyridin-3-yl)ethyl)aminomethyl]indol-2-yl}isoindolinone dihydrochloride (Compound 397)

Step 1

In a similar manner to Step 2 of Example 6, 4-methanesulfonyloxy-5-methoxy-7-[1-(tert-butoxycarbonyl)-5-formylindol-2-yl]isoindolinone (100 mg, 0.200 mmol) was dissolved in acetonitrile (5.8 mL), and the solution was treated with 3-(2-aminoethyl)pyridine (0.235 mL, 2.00 mmol), acetic acid (0.229 mL, 4.00 mmol) and sodium triacetoxyborohydride (127 mg, 0.599 mmol), followed by purification by preparative thin-layer chromatography (chloroform/methanol=4/1) to obtain 4-methanesulfonyloxy-5-methoxy-7-{1-(tert-butoxycarbonyl)-5-[(2-(pyridin-3-yl)ethyl)aminomethyl]indol-2-yl}isoindolinone (80.5 mg, yield 66%).

ESI-MS m/z: 607 [M+H]$^+$; $^1$H-NMR (CDCl$_3$) δ(ppm): 1.35 (s, 9H), 2.77-2.97 (m, 4H), 3.34 (s, 3H), 3.92 (s, 2H), 4.01 (s, 3H), 4.56 (s, 2H), 6.30 (br s, 1H), 6.56 (s, 1H), 7.11 (s, 1H), 7.14-7.30 (m, 3H), 7.46 (s, 1H), 7.51 (d, J=7.6 Hz, 1H), 8.19 (d, J=8.6 Hz, 1H), 8.39-8.51 (m, 2H).

Step 2

In a similar manner to Step 2 of Example 8, 4-methanesulfonyloxy-5-methoxy-7-{1-(tert-butoxycarbonyl)-5-[(2-(pyridin-3-yl)ethyl)aminomethyl]indol-2-yl}isoindolinone (78.0 mg, 0.129 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 397 (53.8 mg, yield 72%).

ESI-MS m/z: 507 [M+H]$^+$; $^1$H-NMR (DMSO-d$_6$) δ(ppm): 3.12-3.25 (m, 4H), 3.54 (s, 3H), 4.09 (s, 3H), 4.24 (br s, 2H), 4.53 (s, 2H), 7.33 (dd, J=1.3, 8.5 Hz, 1H), 7.49 (s, 1H), 7.56 (d, J=8.5 Hz, 1H), 7.81 (s, 1H), 7.85 (m, 1H), 7.87 (s, 1H), 8.30 (d, J=7.9 Hz, 1H), 8.73 (d, J=4.9 Hz, 1H), 8.80 (s, 1H), 9.29 (s, 1H), 9.36 (br s, 2H), 14.01 (s, 1H).

EXAMPLE 398

4-Methanesulfonyloxy-5-methoxy-7-{1H-5-[(2-(pyridin-2-yl)ethyl)aminomethyl]indol-2-yl}isoindolinone dihydrochloride (Compound 398)

Step 1

In a similar manner to Step 2 of Example 6, 4-methanesulfonyloxy-5-methoxy-7-[1-(tert-butoxycarbonyl)-5-formylindol-2-yl]isoindolinone (100 mg, 0.200 mmol) was dissolved in acetonitrile (5.8 mL), and the solution was treated with 2-(2-aminoethyl)pyridine (0.239 mL, 2.00 mmol), acetic acid (0.229 mL, 4.00 mmol) and sodium triacetoxyborohydride (127 mg, 0.599 mmol), followed by purification by preparative thin-layer chromatography (chloroform/methanol=4/1) to obtain 4-methanesulfonyloxy-5-methoxy-7-(1-(tert-butoxycarbonyl)-5-[(2-(pyridin-2-yl)ethyl)aminomethyl]indol-2-yl)isoindolinone (85.7 mg, yield 71%).

ESI-MS m/z: 607 [M+H]$^+$; $^1$H-NMR (CDCl$_3$) δ(ppm): 1.35 (s, 9H), 2.99-3.15 (m, 4H), 3.34 (s, 3H), 3.96 (s, 2H), 4.00 (s, 3H), 4.55 (s, 2H), 6.22 (br s, 1H), 6.56 (s, 1H), 7.10 (s, 1H), 7.11 (m, 1H), 7.16 (d, J=7.5 Hz, 1H), 7.27 (m, 1H), 7.51 (s, 1H), 7.59 (m, 1H), 8.18 (d, J=8.6 Hz, 1H), 8.51 (d, J=4.0 Hz, 1H).

Step 2

In a similar manner to Step 2 of Example 8, 4-methanesulfonyloxy-5-methoxy-7-{1-(tert-butoxycarbonyl)-5-[(2-(pyridin-2-yl)ethyl)aminomethyl]indol-2-yl}isoindolinone (83.2 mg, 0.137 mmol) was dissolved in methanol (1.5 mL), and the solution was treated with 10% hydrogen chloride-methanol-solution (1.5 mL). The precipitated solid was collected by filtration and washed with methanol, followed by drying under reduced pressure to obtain Compound 398 (63.6 mg, yield 80%).

ESI-MS m/z: 507 [M+H]$^+$; $^1$H-NMR (DMSO-d$_6$) δ(ppm): 3.25-3.48 (m, 4H), 3.53 (s, 3H), 4.08 (s, 3H), 4.28 (br s, 2H), 4.52 (s, 2H), 7.34 (d, J=8.8 Hz, 1H), 7.49 (s, 1H), 7.55 (d, J=8.8 Hz, 1H), 7.61 (m, 1H), 7.65 (d, J=7.4 Hz, 1H), 7.81 (s, 1H), 7.87 (s, 1H), 8.11 (m, 1H), 8.65 (d, J=4.8 Hz, 1H), 9.28 (s, 1H), 9.38 (br s, 2H), 14.00 (s, 1H).

EXAMPLE 399

4-Methanesulfonyloxy-5-methoxy-7-[1H-5-(N-ethyl-1-propylaminomethyl)indol-2-yl]isoindolinone hydrochloride (Compound 399)

Step 1

In a similar manner to Step 2 of Example 6, 4-methanesulfonyloxy-5-methoxy-7-[1-(tert-butoxycarbonyl)-5-formylindol-2-yl]isoindolinone (100 mg, 0.200 mmol) was dissolved in acetonitrile (5.8 mL), and the solution was treated with N-ethyl-1-propylamine (0.242 mL, 2.00 mmol), acetic acid (0.229 mL, 4.00 mmol) and sodium triacetoxyborohydride (253 mg, 1.19 mmol), followed by purification by preparative thin-layer chromatography (chloroform/methanol=6/1) to obtain 4-methanesulfonyloxy-5-methoxy-7-[1-(tert-butoxycarbonyl)-5-(N-ethyl-1-propylaminomethyl)indol-2-yl]isoindolinone (68.4 mg, yield 60%).

ESI-MS m/z: 572 [M+H]$^+$; $^1$H-NMR (CDCl$_3$) δ(ppm): 0.89 (t, J=7.3 Hz, 3H), 1.00-1.30 (m, 3H), 1.37 (s, 9H), 1.40-1.70 (m, 2H), 2.35-2.65 (m, 4H), 3.35 (s, 3H), 3.71 (br s, 2H), 4.00 (s, 3H), 4.56 (s, 2H), 6.20 (br s, 1H), 6.58 (s, 1H), 7.11 (s, 1H), 7.33 (dd, J=1.6, 8.7 Hz, 1H), 7.53 (br s, 1H), 8.17 (d, J=8.7 Hz, 1H).

Step 2

In a similar manner to Step 2 of Example 8, 4-methanesulfonyloxy-5-methoxy-7-[1-(tert-butoxycarbonyl)-5-(N-ethyl-1-propylaminomethyl)indol-2-yl]isoindolinone (66.0 mg, 0.115 mmol) was dissolved in methanol (1.5 mL), the solution was treated with 10% hydrogen chloride-methanol solution (1.5 mL). The solvent was evaporated under reduced pressure and the residue was purified by slurry using methanol and ethyl acetate to obtain Compound 399 (50.1 mg, yield 86%).

ESI-MS m/z: 472 [M+H]$^+$; $^1$H-NMR (DMSO-$d_6$) δ(ppm): 0.87 (t, J=7.3 Hz, 3H), 1.27 (t, J=7.0 Hz, 3H), 1.60-1.90 (m, 2H), 2.80-3.20 (m, 4H), 3.53 (s, 3H), 4.08 (s, 3H), 4.37 (br s, 2H), 4.52 (s, 2H), 7.33 (d, J=8.7 Hz, 1H), 7.49 (s, 1H), 7.58 (d, J=8.7 Hz, 1H), 7.82 (s, 1H), 7.86 (s, 1H), 9.27 (s, 1H), 9.91 (br s, 1H), 14.00 (s, 1H).

EXAMPLE 400

4-Methanesulfonyloxy-5-methoxy-7-[1H-5-(N-methylethylaminomethyl)indol-2-yl]isoindolinone hydrochloride (Compound 400)

Step 1

In a similar manner to Step 2 of Example 6, 4-methanesulfonyloxy-5-methoxy-7-[1-(tert-butoxycarbonyl)-5-formylindol-2-yl]isoindolinone (100 mg, 0.200 mmol) was dissolved in acetonitrile (5.8 mL), and the solution was treated with N-methylethylamine (0.160 mL, 2.00 mmol), acetic acid (0.229 mL, 4.00 mmol) and sodium triacetoxyborohydride (211 mg, 0.996 mmol), followed by purification by preparative thin-layer chromatography (chloroform/methanol=4/1) to obtain 4-methanesulfonyloxy-5-methoxy-7-[1-(tert-butoxycarbonyl)-5-(N-methylethylaminomethyl)indol-2-yl]isoindolinone (67.0 mg, yield 62%).

ESI-MS m/z: 544 [M+H]$^+$; $^1$H-NMR (CDCl$_3$) δ(ppm): 1.14 (t, J=6.8 Hz, 3H), 1.35 (s, 9H), 2.25 (s, 3H), 2.51 (q, J=6.8 Hz, 2H), 3.34 (s, 3H), 3.63 (br s, 2H), 4.00 (s, 3H), 4.55 (s, 2H), 6.38 (br s, 1H), 6.57 (s, 1H), 7.10 (s, 1H), 7.31 (d, J=8.4 Hz, 1H), 7.51 (s, 1H), 8.18 (d, J=8.4 Hz, 1H).

Step 2

In a similar manner to Step 2 of Example 8, 4-methanesulfonyloxy-5-methoxy-7-[1-(tert-butoxycarbonyl)-5-(N-methylethylaminomethyl)indol-2-yl]isoindolinone (64.5 mg, 0.119 mmol) was dissolved in methanol (1.5 mL), and the solution was treated with 10% hydrogen chloride-methanol solution (1.5 mL). The solvent was evaporated under reduced pressure and the residue was purified by slurry using diisopropylether to obtain Compound 400 (42.6 mg, yield 75%).

ESI-MS m/z: 444 [M+H]$^+$; $^1$H-NMR (DMSO-$d_6$) δ(ppm): 1.27 (t, J=7.2 Hz, 3H), 2.63 (s, 3H), 2.81-3.24 (m, 2H), 3.53 (s, 3H), 4.08 (s, 3H), 4.19-4.51 (m, 2H), 4.52 (s, 2H), 7.30 (d, J=8.5 Hz, 1H), 7.49 (s, 1H), 7.57 (d, J=8.5 Hz, 1H), 7.78 (s, 1H), 7.86 (s, 1H), 9.27 (s, 1H), 9.94 (br s, 1H), 14.00 (s, 1H).

EXAMPLE 401

4-Methanesulfonyloxy-5-methoxy-7-[1H-5-(4,4-dimethoxypiperidinomethyl)indol-2-yl]isoindolinone hydrochloride (Compound 401)

Step 1

In a similar manner to Step 2 of Example 1, 4-methanesulfonyloxy-5-methoxy-7-iodoisoindolinone (60.0 mg, 0.157 mmol) was dissolved in acetonitrile (3.6 mL), and the solution was treated with Compound BT (94.1 mg, 0.240 mmol), palladium acetate (2.8 mg, 0.013 mmol), tri(o-tolyl)phosphine (7.6 mg, 0.025 mmol) and triethylamine (0.219 mL, 1.57 mmol), followed by purification by flash column chromatography (hexane/ethyl acetate=3/7 to 2/8 to 1/9 to 0/10) to obtain 4-methanesulfonyloxy-5-methoxy-7-[1-(tert-butoxycarbonyl)-5-(4,4-dimethoxypiperidinomethyl)indol-2-yl]isoindolinone (67.6 mg, yield 68%).

ESI-MS m/z: 630 [M+H]$^+$; $^1$H-NMR (CDCl$_3$) δ(ppm): 1.36 (s, 9H), 1.71-1.88 (m, 4H), 2.38-2.58 (m, 4H), 3.18 (s, 6H), 3.34 (s, 3H), 3.61 (s, 2H), 4.00 (s, 3H), 4.56 (s, 2H), 6.15 (s, 1H), 6.57 (s, 1H), 7.10 (s, 1H), 7.31 (d, J=8.6 Hz, 1H), 7.50 (s, 1H), 8.17 (d, J=8.6 Hz, 1H).

Step 2

In a similar manner to Step 2 of Example 8, 4-methanesulfonyloxy-5-methoxy-7-[1-(tert-butoxycarbonyl)-5-(4,4-dimethoxypiperidinomethyl)indol-2-yl]isoindolinone (65.0 mg, 0.103 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 401 (37.1 mg, yield 64%).

ESI-MS m/z: 530 [M+H]$^+$; $^1$H-NMR (DMSO-$d_6$) δ(ppm): 1.75-1.85 (m, 2H), 2.06-2.16 (m, 2H), 2.86-2.96 (m, 2H), 3.18 (s, 6H), 3.24-3.34 (m, 2H), 3.53 (s, 3H), 4.08 (s, 3H), 4.39 (br s, 2H), 4.52 (s, 2H), 7.34 (d, J=8.3 Hz, 1H), 7.49 (s, 1H), 7.56 (d, J=8.3 Hz, 1H), 7.82 (s, 1H), 7.86 (s, 1H), 9.27 (s, 1H), 10.19 (br s, 1H), 13.99 (s, 1H).

EXAMPLE 402

4-Methanesulfonyloxy-5-methoxy-7-[1H-5-diethylaminoindol-2-yl]isoindolinone hydrochloride (Compound 402)

In a similar manner to Step 2 of Example 6, 4-methanesulfonyloxy-5-methoxy-7-[1H-5-aminoindol-2-yl]isoindolinone (0.133 g, 0.314 mmol) was dissolved in acetonitrile (4.0 mL), and the solution was treated with acetic acid (0.0540 mL, 0.941 mmol), acetaldehyde (0.00530 mL, 0.941 mmol) and sodium triacetoxyborohydride (0.333 g, 1.57 mmol) to obtain Compound 402 (0.0478 g, yield 36%).

ESI-MS m/z: 444 [M+H]$^+$; $^1$H-NMR (DMSO-$d_6$) δ(ppm): 1.06 (t, J=7.1 Hz, 6H), 3.52-3.64 (m, 7H), 4.09 (s, 3H), 4.53 (s, 2H), 7.56 (d, J=9.1 Hz, 1H), 7.58 (s, 1H), 7.72 (d, J=9.1 Hz, 1H), 7.88 (s, 1H), 8.15 (s, 1H), 9.33 (s, 1H), 12.8 (br s, 1H), 14.1 (s, 1H).

EXAMPLE 403

4-Methanesulfonyloxy-5-methoxy-7-[1H-5-(2-dimethylaminoacetylamino)indol-2-yl]isoindolinone (Compound 403)

4-Methanesulfonyloxy-5-methoxy-7-[1H-5-aminoindol-2-yl]isoindolinone (0.0664 g, 0.157 mmol) was dissolved in DMF (3.0 mL), and the solution was added with dimethylglycine (0.0323 g, 0.313 mmol), EDCI (0.0645 g, 0.313 mmol) and DMAP (0.0383 g, 0.313 mmol), followed by stirring at room temperature for 4.5 hours. The reaction mixture was added with water and the precipitated crystal was collected by filtration. The crude product was purified by slurry using DMSO and methanol to obtain Compound 403 (0.0226 g, yield 30%).

ESI-MS m/z: 473 [M+H]⁺; ¹H-NMR (DMSO-d₆) δ(ppm): 2.50 (s, 6H), 3.32 (m, 2H), 3.53 (s, 3H), 4.08 (s, 3H), 4.52 (s, 2H), 6.84 (dd, J=2.0, 8.4 Hz, 1H), 7.15 (d, J=2.0 Hz, 1H), 7.31 (s, 1H), 7.40 (d, J=8.4 Hz, 1H), 7.81 (s, 1H), 9.23 (s, 1H), 13.8 (s, 1H).

EXAMPLE 404

4-Methanesulfonyloxy-5-methoxy-7-[1H-5-(pyrrol-1-yl)indol-2-yl]isoindolinone (Compound 404)

4-Methanesulfonyloxy-5-methoxy-7-[1H-5-aminoindol-2-yl]isoindolinone (0.0830 g, 0.196 mmol) was dissolved in methanol (2.0 mL), and the solution was added with a solution of sodium borohydride (0.148 g, 3.92 mmol), 2,5-dimethoxytetrahydrofuran (0.127 mL, 0.979 mmol) and 2 mol/L sulfuric acid (0.979 mL, 2.45 mmol) in THF (2.0 mL), followed by stirring at room temperature for 4 hours. The reaction mixture was added with water and the precipitated crystal was collected by filtration. The crude product was purified by slurry using DMSO and water to obtain Compound 404 (0.0151 g, yield 18%).

ESI-MS m/z: 438 [M+H]⁺; ¹H-NMR (DMSO-d₆) δ(ppm): 3.53 (s, 3H), 4.09 (s, 3H), 4.53 (s, 2H), 6.24 (t, J=2.4 Hz, 2H), 7.29 (t, J=2.4 Hz, 2H), 7.34 (dd, J=2.1, 8.7 Hz, 1H), 7.45 (s, 1H), 7.57 (d, J=8.7 Hz, 1H), 7.67 (d, J=2.1 Hz, 1H), 7.86 (s, 1H), 9.26 (s, 1H), 14.0 (s, 1H).

EXAMPLE 405

4-Methanesulfonyloxy-5-methoxy-7-[1H-5-(piperidinoethoxy)indol-2-yl]isoindolinone hydrochloride (Compound 405)

Step 1

In a similar manner to Step 2 of Example 1, 4-hydroxy-5-methoxy-7-iodoisoindolinone (0.0800 g, 0.209 mmol) was dissolved in acetonitrile (10.0 mL), and the solution was treated with Compound BS (0.162 g, 0.418 mmol), palladium acetate (0.00470 g, 0.0209 mmol), tri(o-tolyl)phosphine (0.0130 g, 0.418 mmol) and triethylamine (0.291 mL, 2.09 mmol) to obtain 4-hydroxy-5-methoxy-7-[1-(tert-butoxycarbonyl)-5-(piperidinoethoxy)indol-2-yl]isoindolinone (0.0290 g, yield 23%).

ESI-MS m/z: 600 [M+H]⁺; ¹H-NMR (DMSO-d₆) δ(ppm): 1.18 (s, 9H), 1.35-1.43 (m, 2H), 1.46-1.56 (m, 2H), 2.41-2.49 (m, 2H), 2.68 (t, J=5.8 Hz, 2H), 3.50 (s, 3H), 3.99 (s, 3H), 4.11 (t, J=5.8 Hz, 2H), 4.41 (s, 2H), 6.64 (s, 1H), 6.96 (dd, J=2.8, 8.9 Hz, 1H), 7.15 (d, J=2.8 Hz, 1H), 7.31 (s, 1H), 8.04 (d, J=8.9 Hz, 1H), 8.55 (s, 1H).

Step 2

In a similar manner to Step 2 of Example 8, 4-hydroxy-5-methoxy-7-[1-(tert-butoxycarbonyl)-5-(piperidinoethoxy)indol-2-yl]isoindolinone (0.0290 g, 0.0484 mmol) was treated with 10% hydrogen chloride-methanol solution (10.0 mL) to obtain Compound 405 (0.0127 g, yield 52%).

ESI-MS m/z: 500 [M+H]⁺; ¹H-NMR (DMSO-d₆) δ(ppm): 1.28-1.44 (m, 1H), 1.59-1.87 (m, 5H), 2.78-2.95 (m, 2H), 2.41-2.49 (m, 2H), 3.24-3.36 (m, 2H), 2.70 (t, J=5.4 Hz, 2H), 3.52 (s, 3H), 4.03 (s, 3H), 4.19 (t, J=5.4 Hz, 2H), 4.43 (s, 2H), 6.84 (s, 1H), 7.14 (m, 1H), 7.35 (m, 1H), 7.74 (s, 1H), 8.04 (d, J=8.9 Hz, 1H), 8.55 (s, 1H).

EXAMPLE 406

4-(2-Cyanobenzenesulfonyloxy)-7-[1H-5-(piperidinomethyl)indol-2-yl-]isoindolinone hydrochloride (Compound 406)

Step 1

In a similar manner to Step 1 of Example 227, 4-hydroxy-7-[1-(tert-butoxycarbonyl)-5-(piperidinomethyl)indol-2-yl]-isoindolinone (0.115 g, 0.249 mmol) was dissolved in acetonitrile (5.0 mL), and the solution was treated with triethylamine (0.104 mL, 0.747 mmol) and 2-cyanobenzenesulfonyl chloride (0.0750 g, 0.374 mmol), followed by purification of the residue by flash column chromatography (chloroform/methanol=85/15) to obtain 4-(2-cyanobenzenesulfonyloxy)-7-[1-(tert-butoxycarbonyl)-5-(piperidinomethyl)indol-2-yl]isoindolinone (0.137 g, yield 88%).

ESI-MS m/z: 627 [M+H]⁺; ¹H-NMR (CDCl₃) δ(ppm): 1.28 (s, 9H), 1.38-1.53 (m, 2H), 1.63-1.76 (m, 4H), 2.56-2.70 (m, 4H), 3.85 (s, 2H), 4.55 (s, 2H), 6.53 (s, 1H), 7.29 (dd, J=1.8, 8.6 Hz, 1H), 7.37-7.48 (m, 2H), 7.54 (s, 1H), 7.85-7.90 (m, 2H), 8.01-8.05 (m, 1H), 8.17-8.23 (m, 2H).

Step 2

In a similar manner to Step 2 of Example 8, 4-(2-cyanobenzenesulfonyloxy)-7-[1-(tert-butoxycarbonyl)-5-(piperidinomethyl)indol-2-yl]isoindolinone (0.136 g, 0.217 mmol) was treated with 10% hydrogen chloride-methanol solution (5.0 mL) to obtain Compound 406 (0.0885 g, yield 73%).

ESI-MS m/z: 527 [M+H]⁺; ¹H-NMR (DMSO-d₆) δ(ppm): 1.28-1.44 (m, 1H), 1.59-1.87 (m, 5H), 2.78-2.95 (m, 2H), 3.32-3.68 (m, 2H), 4.31 (d, J=4.8 Hz, 2H), 4.43 (s, 2H), 7.28-7.39 (m, 3H), 7.57 (d. J=8.4 Hz, 1H), 7.77 (s, 1H), 8.01-8.14 (m, 2H), 8.24 (dd, J=1.6, 8.1 Hz, 2H), 8.36 (dd, J=1.2, 7.2 Hz, 1H), 9.51 (s, 1H), 9.77 (br s, 1H), 13.8 (s, 1H).

EXAMPLE 407

4-(3-Thiophenesulfonyloxy)-5-methoxy-7-[1H-5-(piperidinomethyl)indol-2-yl]isoindolinone hydrochloride (Compound 407)

Step 1

In a similar manner to Step 1 of Example 227, 4-hydroxy-5-methoxy-7-iodoisoindolinone (0.265 g, 0.869 mmol) was dissolved in acetonitrile (8.0 mL), and the solution was treated with triethylamine (0.242 mL, 1.74 mmol) and 3-thiophenesulfonyl chloride (0.191 g, 1.04 mmol) to obtain 4-(3-thiophenesulfonyloxy)-5-methoxy-7-iodoisoindolinone (0.316 g, yield 81%).

ESI-MS m/z: 451 [M+H]⁺; ¹H-NMR (DMSO-d₆) δ(ppm): 3.63 (s, 3H), 4.15 (s, 2H), 7.47-7.50 (m, 1H), 7.56 (s, 1H), 7.87-7.90 (m, 1H), 8.51-8.53 (m, 1H), 8.64 (s, 1H).

Step 2

In a similar manner to Step 2 of Example 1, 4-(3-thiophenesulfonyloxy)-5-methoxy-7-iodoisoindolinone (0.140 g, 0.310 mmol) was dissolved in acetonitrile (5.6 mL), and the solution was treated with Compound BD (0.222 g, 0.620 mmol), palladium acetate (0.0070 mg, 0.031 mmol), tri(o-tolyl)phosphine (0.0190 mg, 0.0620 mmol) and triethylamine (0.432 mL, 3.10 mmol), followed by purification of the residue by flash column chromatography (chloroform/methanol=9/1) to obtain 4-(3-thiophenesulfonyloxy)-5-methoxy-7-[1-(tert-butoxycarbonyl)-5-(piperidinomethyl)indol-2-yl]isoindolinone (0.243 g, yield 100%).

ESI-MS m/z: 638 [M+H]⁺; ¹H-NMR (CDCl₃) δ(ppm): 1.33 (s, 9H), 1.56-1.86 (m, 6H), 2.83 (br s, 4H), 3.49 (s, 3H), 4.03 (br s, 2H), 4.56 (s, 2H), 6.57 (d, J=0.8 Hz, 1H), 6.73 (br s, 1H), 6.98 (s, 1H), 7.26-7.30 (m, 1H), 7.51-7.66 (m, 3H), 8.12 (dd, J=1.6, 2.4 Hz, 1H), 8.12 (d, J=8.6 Hz, 1H).

Step 3

In a similar manner to Step 2 of Example 8, 4-(3-thiophenesulfonyloxy)-5-methoxy-7-[1-(tert-butoxycarbonyl)-5-(piperidinomethyl)indol-2-yl]isoindolinone (0.190 g, 0.298 mmol) was treated with 10% hydrogen chloride-methanol solution (10.0 mL) to obtain Compound 407 (0.0976 g, yield 62%).

ESI-MS m/z: 538 [M+H]⁺; ¹H-NMR (DMSO-d₆) δ(ppm): 1.29-1.43 (m, 1H), 1.67-1.77 (m, 5H), 2.78-2.92 (m, 2H), 3.29-3.34 (m, 2H), 3.78 (s, 3H), 4.32 (d, J=4.6 Hz, 2H), 4.40 (s, 2H), 7.34 (dd, J=1.1, 8.4 Hz, 1H), 7.47 (d, J=1.1 Hz, 1H), 7.53-7.58 (m, 2H), 7.76 (s, 1H), 7.82 (s, 1H), 7.92 (ddd, J=0.5, 3.0, 5.1 Hz, 1H), 8.58 (ddd, J=0.5, 1.4, 3.0 Hz, 1H), 9.25 (s, 1H), 10.16 (br s, 1H), 13.98 (s, 1H).

EXAMPLE 408

4-(3-Thiophenesulfonyloxy)-5-methoxy-7-[1H-5-(dimethylaminomethyl)indol-2-yl]isoindolinone hydrochloride (Compound 408)

Step 1

In a similar manner to Step 2 of Example 1, 4-(3-thiophenesulfonyloxy)-5-methoxy-7-iodoisoindolinone (0.171 g, 0.381 mmol) was dissolved in acetonitrile (7.0 mL), and the solution was treated with Compound BA (0.230 g, 0.758 mmol), palladium acetate (0.00850 g, 0.0381 mmol), tri(o-tolyl)phosphine (0.0230 g, 0.0758 mmol) and triethylamine (0.528 mL, 3.79 mmol) to obtain 4-(3-thiophenesulfonyloxy)-5-methoxy-7-[1-(tert-butoxycarbonyl)-5-formylindol-2-yl]isoindolinone (0.138 g, 62%).

ESI-MS m/z: 569 [M+H]⁺

Step 2

In a similar manner to Step 2 of Example 6, 4-(3-thiophenesulfonyloxy)-5-methoxy-7-[1-(tert-butoxycarbonyl)-5-formylindol-2-yl]isoindolinone (0.219 g, 0.385 mmol) was dissolved in acetonitrile (6.0 mL), and the solution was treated with dimethylamine hydrochloride (0.630 g, 7.70 mmol), triethylamine (1.10 mL, 7.70 mmol), acetic acid (0.441 mL, 7.70 mmol) and sodium triacetoxyborohydride (0.245 g, 1.16 mmol), followed by purification of the residue by flash column chromatography (chloroform/methanol=85/15) to obtain 4-(3-thiophenesulfonyloxy)-5-methoxy-7-[1-(tert-butoxycarbonyl)-5-(dimethylaminomethyl)indol-2-yl]isoindolinone (0.104 g, 45%).

ESI-MS m/z: 598 [M+H]⁺; ¹H-NMR (CDCl₃) δ(ppm): 1.32 (s, 9H), 2.50 (s, 6H), 3.68 (s, 3H), 3.90 (s, 2H), 4.52 (s, 2H), 6.55 (s, 1H), 6.98 (s, 1H), 7.22-7.28 (m, 2H), 7.50-7.56 (m, 3H), 8.11 (dd, J=1.8, 2.5 Hz, 1H), 8.19 (d, J=8.6 Hz, 1H).

Step 3

In a similar manner to Step 2 of Example 8, 4-(3-thiophenesulfonyloxy)-5-methoxy-7-[1-(tert-butoxycarbonyl)-5-(dimethylaminomethyl)indol-2-yl]isoindolinone (0.104 g, 0.174 mmol) was treated with 10% hydrogen chloride-methanol solution (5.0 mL) to obtain Compound 408 (0.0364 g, yield 39%).

ESI-MS m/z: 498 [M+H]⁺; ¹H-NMR (DMSO-d₆) δ(ppm): 2.70 (s, 3H), 2.72 (s, 3H), 3.78 (s, 3H), 4.33 (d, J=4.8 Hz, 2H), 4.40 (s, 2H), 7.30 (d, J=8.4 Hz, 1H), 7.48 (s, 1H), 7.54 (dd, J=1.6, 5.1 Hz, 0.1H), 7.57 (d, J=8.4 Hz, 1H), 7.76 (s, 1H), 7.78 (s, 1H), 7.92 (dd, J=3.0, 5.1 Hz, 1H), 8.58 (dd, J=1.6, 3.0 Hz, 1H), 9.29 (s, 1H), 10.2 (br s, 1H), 14.0 (s, 1H).

EXAMPLE 409

4-(3-Thiophenesulfonyloxy)-5-methoxy-7-[1H-5-(pyrrolidin-1-ylmethyl)indol-2-yl]isoindolinone hydrochloride (Compound 409)

Step 1

In a similar manner to Step 2 of Example 6, 4-(3-thiophenesulfonyloxy)-5-methoxy-7-[1-(tert-butoxycarbonyl)-5-formylindol-2-yl]isoindolinone (0.0650 g, 0.114 mmol) was dissolved in acetonitrile (5.0 mL), and the solution was treated with pyrrolidine (0.191 mL, 2.29 mmol), acetic acid (0.131 mL, 2.29 mmol) and sodium triacetoxyborohydride (0.0730 g, 0.343 mmol), followed by purification of the residue by flash column chromatography (chloroform/methanol=85/15, 80/20) to obtain 4-(3-thiophenesulfonyloxy)-5-methoxy-7-[1-(tert-butoxycarbonyl)-5-(pyrrolidin-1-ylmethyl)indol-2-yl]isoindolinone (0.0501 g, 70%).

ESI-MS m/z: 624 [M+H]⁺; ¹H-NMR (CDCl₃) δ(ppm): 1.35 (s, 9H), 1.83-1.92 (m, 4H), 2.75-2.85 (m, 4H), 3.66 (s, 3H), 3.95 (s, 2H), 4.52 (s, 2H), 6.57 (s, 1H), 6.97 (s, 1H), 7.26 (s, 1H), 7.32 (dd, J=1.5, 8.5 Hz, 1H), 7.51 (d, J=2.5 Hz, 1H), 7.57 (d, J=1.5 Hz, 1H), 8.11 (dd, J=2.5 Hz, 1H), 8.21 (d, J=8.5 Hz, 1H).

Step 2

In a similar manner to Step 2 of Example 8, 4-(3-thiophenesulfonyloxy)-5-methoxy-7-[1-(tert-butoxycarbonyl)-5-(pyrrolidin-1-ylmethyl)indol-2-yl]isoindolinone (0.0501 g, 0.0803 mmol) was treated with 10% hydrogen chloride-methanol solution (5.0 mL) to obtain Compound 409 (0.0239 g, yield 53%).

ESI-MS m/z: 524 [M+H]⁺; ¹H-NMR (DMSO-d₆) δ(ppm): 1.81-2.01 (m, 4H), 3.05-3.16 (m, 2H), 3.31-3.39 (m, 2H), 3.78 (s, 3H), 4.39 (s, 2H), 4.40 (d, J=4.8 Hz, 2H), 7.33 (dd, J=1.3, 8.4 Hz, 1H), 7.48 (s, 1H), 7.53 (dd, J=0.7, 5.1 Hz, 1H), 7.57 (d, J=8.4 Hz, 1H), 7.77 (s, 1H), 7.78 (s, 1H), 7.92 (dd, J=3.0, 5.1 Hz, 1H), 8.59 (dd, J=1.6, 3.0 Hz, 1H), 9.29 (s, 1H), 10.2 (br s, 1H), 14.0 (s, 1H).

EXAMPLE 410

4-(2-Cyanobenzenesulfonyloxy)-5-methoxy-7-[1H-5-(dimethylaminomethyl)indol-2-yl]isoindolinone hydrochloride (Compound 410)

Step 1

In a similar manner to Step 2 of Example 1, 4-(2-cyanobenzenesulfonyloxy)-5-methoxy-7-iodoisoindolinone (0.241 g, 0.513 mmol) was dissolved in acetonitrile (10.0 mL), and the solution was treated with Compound BA (0.296 g, 1.03 mmol), palladium acetate (0.0120 g, 0.0513 mmol), tri(o-tolyl)phosphine (0.0320 g, 0.103 mmol) and triethylamine (0.714 mL, 5.13 mmol) to obtain 4-(2-cyanobenzenesulfonyloxy)-5-methoxy-7-[1-(tert-butoxycarbonyl)-5-formylindol-2-yl]isoindolinone (0.256 g, 90%).

ESI-MS m/z: 588 [M+H]⁺

Step 2

In a similar manner to Step 2 of Example 6, 4-(2-cyanobenzenesulfonyloxy)-5-methoxy-7-[1-(tert-butoxycarbonyl)-5-formylindol-2-yl]isoindolinone (0.179 g, 0.305 mmol) was dissolved in acetonitrile (6.0 mL), and the solution was treated with dimethylamine hydrochloride (0.497 g, 6.09 mmol), triethylamine (0.845 mL, 6.09 mmol), acetic acid (0.349 mL, 6.09 mmol) and sodium triacetoxyborohydride (0.194 g, 0.914 mmol), followed by purification of the residue by flash column chromatography (chloroform/methanol=85/15) to obtain 4-(2-cyanobenzenesulfonyloxy)-5-methoxy-7-[(1-(tert-butoxycarbonyl)-5-(dimethylaminomethyl)indol-2-yl]isoindolinone (0.121 g, 64%).

ESI-MS m/z: 617 [M+H]$^+$; $^1$H-NMR (CD$_3$OD) δ(ppm): 1.17 (s, 9H), 2.24 (s, 6H), 3.36 (s, 3H), 3.59 (s, 2H), 4.45 (s, 2H), 6.52 (s, 1H), 6.98 (s, 1H), 7.19 (d, J=8.6 Hz, 1H), 7.40 (s, 1H), 7.74-7.95 (m, 3H), 8.06 (d, J=7.2 Hz, 1H), 8.11 (d, J=8.6 Hz, 1H).

Step 3

In a similar manner to Step 2 of Example 8, 4-(2-cyanobenzenesulfonyloxy)-5-methoxy-7-[1-(tert-butoxycarbonyl)-5-(dimethylaminomethyl)indol-2-yl]isoindolinone (0.121 g, 0.196 mmol) was treated with 10% hydrogen chloride-methanol solution (5.0 mL) to obtain Compound 410 (0.0949 g, yield 87%).

ESI-MS m/z: 517 [M+H]$^+$; $^1$H-NMR (DMSO-d$_6$) δ(ppm): 2.71 (s, 6H), 3.52 (s, 3H), 4.33 (s, 2H), 4.56 (s, 2H), 7.29 (d, J=8.6 Hz, 1H), 7.46 (s, 1H), 7.54 (dd, J=8.6 Hz, 1H), 7.69 (s, 1H), 7.75 (s, 1H), 7.96-8.17 (m, 3H), 8.33 (d, J=7.6 Hz, 1H), 9.32 (s, 1H), 10.0 (br s, 1H), 14.0 (s, 1H).

EXAMPLE 411

4-(2-Cyanobenzenesulfonyloxy)-5-methoxy-7-[1H-5-(pyrrolidin-1-ylmethyl)indol-2-yl]isoindolinone hydrochloride (Compound 411)

Step 1

In a similar manner to Step 2 of Example 6, 4-(2-cyanobenzenesulfonyloxy)-5-methoxy-7-[1-(tert-butoxycarbonyl)-5-formylindol-2-yl]isoindolinone (0.140 g, 0.238 mmol) was dissolved in acetonitrile (6.0 mL), and the solution was treated with pyrrolidine (0.398 mL, 4.77 mmol), acetic acid (0.273 mL, 4.77 mmol) and sodium triacetoxyborohydride (0.151 g, 0.715 mmol), followed by purification of the residue by flash column chromatography (chloroform/methanol=85/15, 80/20) to obtain 4-(2-cyanobenzenesulfonyloxy)-5-methoxy-7-[1-(tert-butoxycarbonyl)-5-(pyrrolidin-1-ylmethyl)indol-2-yl]isoindolinone (0.0773 g, ESI-MS m/z: 643 [M+H]$^+$; $^1$H-NMR (CD$_3$OD)δ(ppm): 1.18 (s, 9H), 1.83-1.92 (m, 4H), 2.88-2.96 (m, 4H), 3.25 (s, 3H), 4.04 (s, 2H), 4.49 (s, 2H), 6.55 (s, 1H), 7.00 (s, 1H), 7.28 (dd, J=1.6, 8.7 Hz, 1H), 7.52 (d, J=1.6 Hz, 1H), 7.77-7.93 (m, 3H), 8.08 (dd, J=1.6, 7.3 Hz, 1H), 8.17 (d, J=8.7 Hz, 1H).

Step 2

In a similar manner to Step 2 of Example 8, 4-(2-cyanobenzenesulfonyloxy)-5-methoxy-7-[(1-(tert-butoxycarbonyl)-5-(pyrrolidin-1-ylmethyl)indol-2-yl]isoindolinone (0.0770 g, 0.120 mmol) was treated with 10% hydrogen chloride-methanol solution (5.0 mL) to obtain Compound 411 (0.0541 g, yield 78%).

mp 182-184° C.; ESI-MS m/z: 543 [M+H]$^+$; $^1$H-NMR (DMSO-d$_6$) δ(ppm): 1.80-2.09 (m, 4H), 3.05-3.16 (m, 2H), 3.31-3.39 (m, 2H), 3.52 (s, 3H), 4.38 (s, 2H), 4.56 (s, 2H), 7.32 (d, J=8.6 Hz, 1H), 7.45 (s, 1H), 7.56 (d, J=8.6 Hz, 1H), 7.68 (s, 1H), 7.78 (s, 1H), 7.95-8.17 (m, 3H), 8.33 (d, J=7.4 Hz, 1H), 9.31 (s, 1H), 10.2 (br s, 1H), 14.0 (s, 1H).

EXAMPLE 412

4-(2-Pyridinesulfonyloxy)-5-methoxy-7-[1H-5-(dimethylaminomethyl)indol-2-yl]isoindolinone hydrochloride (Compound 412)

Step 1

4-Hydroxy-5-methoxy-7-iodoisoindolinone (0.465 g, 1.52 mmol) was dissolved in acetonitrile (10.0 mL), and the solution was added with triethylamine (0.850 mL, 6.09 mmol) and 2-pyridinesulfonyl chloride hydrochloride (0.488 g, 2.28 mmol), followed by stirring at room temperature for 5 hours. The reaction mixture was added with water (8.0 mL) and stirred at room temperature for 30 minutes. The precipitated crystal was collected by filtration to obtain 4-(2-pyridinesulfonyloxy)-5-methoxy-7-iodoisoindolinone (0.468 g, yield 69%).

ESI-MS m/z: 447 [M+H]$^+$; $^1$H-NMR (DMSO-d$_6$) δ(ppm): 3.49 (s, 3H), 4.22 (s, 2H), 7.54 (s, 1H), 7.85-7.92 (m, 1H), 8.11 (dd, J=0.7, 7.9 Hz, 1H), 8.17-8.258 (m, 1H), 8.67 (s, 1H), 8.82-8.88 (m, 1H).

Step 2

In a similar manner to Step 2 of Example 1, 4-(2-pyridinesulfonyloxy)-5-methoxy-7-iodoisoindolinone (0.467 g, 1.05 mmol) was dissolved in acetonitrile (18.0 mL), and the solution was treated with Compound BA (0.605 g, 2.09 mmol), palladium acetate (0.0230 g, 0.105 mmol), tri(o-tolyl)phosphine (0.0640 g, 0.209 mmol) and triethylamine (1.50 mL, 10.5 mmol), followed by purification of the residue by flash column chromatography (chloroform/methanol=80/20) to obtain 4-(2-pyridinesulfonyloxy)-5-methoxy-7-[1-(tert-butoxycarbonyl)-5-formylindol-2-yl]isoindolinone (0.558 g, 99%).

ESI-MS m/z: 564 [M+H]$^+$

Step 3

In a similar manner to Step 2 of Example 6, 4-(2-pyridinesulfonyloxy)-5-methoxy-7-[1-(tert-butoxycarbonyl)-5-formylindol-2-yl]isoindolinone (0.455 g, 0.807 mmol) was dissolved in acetonitrile (16.0 mL), and the solution was treated with dimethylamine hydrochloride (1.31 g, 16.1 mmol), triethylamine (2.20 mL, 16.1 mmol), acetic acid (0.924 mL, 16.1 mmol) and sodium triacetoxyborohydride (0.513 g, 2.42 mmol), followed by purification of the residue by flash column chromatography (chloroform/methanol=80/20) to obtain 4-(2-pyridinesulfonyloxy)-5-methoxy-7-[1-(tert-butoxycarbonyl)-5-(dimethylaminomethyl)indol-2-yl]isoindolinone (0.192 g, 40%).

ESI-MS m/z: 593 [M+H]$^+$; $^1$H-NMR (CD$_3$OD) δ(ppm): 1.28 (s, 9H), 2.40 (s, 6H), 3.53 (s, 3H), 3.77 (s, 2H), 4.51 (s, 2H), 6.62 (s, 1H), 7.10 (s, 1H), 7.30 (d. J=8.6 Hz, 1H), 7.53 (s, 1H), 7.74-7.83 (m, 1H), 8.04-8.26 (m, 3H), 8.77-8.82 (m, 1H).

Step 4

In a similar manner to Step 2 of Example 8, 4-(2-pyridinesulfonyloxy)-5-methoxy-7-[(1-(tert-butoxycarbonyl)-5-(dimethylaminomethyl)indol-2-yl]isoindolinone (0.192 g, 0.324 mmol) was treated with 10% hydrogen chloride-methanol solution (5.0 mL) to obtain Compound 412 (0.123 g, yield 67%).

mp 184-186° C.; ESI-MS m/z: 493 [M+H]$^+$; $^1$H-NMR (DMSO-d$_6$) δ(ppm): 2.68 (s, 3H), 2.70 (s, 3H), 3.63 (s, 3H), 4.33 (d, J=4.8 Hz, 1H), 4.46 (s, 2H), 7.35 (d, J=8.7 Hz, 1H), 7.47 (s, 1H), 7.56 (d, J=8.7 Hz, 1H), 7.74 (s, 1H), 7.82 (s, 1H), 7.91 (dd, J=4.8, 7.1 Hz, 1H), 8.15 (d, J=7.7 Hz, 1H), 8.25 (dd, J=7.1, 7.7 Hz, 1H), 8.88 (d, J=4.8 Hz, 1H), 9.29 (s, 1H), 10.8 (br s, 1H), 14.0 (s, 1H).

EXAMPLE 413

4-(2-Pyridinesulfonyloxy)-5-methoxy-7-[1H-5-(pyrrolidin-1-ylmethyl)indol-2-yl]isoindolinone hydrochloride (Compound 413)

Step 1

In a similar manner to Step 2 of Example 6, 4-(2-pyridinesulfonyloxy)-5-methoxy-7-[1-(tert-butoxycarbonyl)-5-formylindol-2-yl]isoindolinone (0.332 g, 0.589 mmol) was dissolved in acetonitrile (10.0 mL), and the solution was treated with pyrrolidine (0.983 mL, 11.8 mmol), acetic acid (0.674 mL, 11.8 mmol) and sodium triacetoxyborohydride (0.375 g, 1.77 mmol), followed by purification of the residue by flash column chromatography (chloroform/methanol=85/15) to obtain 4-(2-pyridinesulfonyloxy)-5-methoxy-7-[1-(tert-butoxycarbonyl)-5-(pyrrolidin-1-ylmethyl)indol-2-yl]isoindolinone (0.116 g, 32%).

ESI-MS m/z: 619 [M+H]$^+$; $^1$H-NMR (CD$_3$OD) δ(ppm): 1.19 (s, 9H), 1.74-1.82 (m, 4H), 2.64-2.73 (m, 4H), 3.43 (s, 3H), 3.82 (s, 2H), 4.42 (s, 2H), 6.51 (s, 1H), 7.01 (s, 1H), 7.23 (dd, J=1.6, 8.7 Hz, 1H), 7.52 (d, J=1.6 Hz, 1H), 7.67-7.73 (m, 1H), 7.96-8.04 (m, 3H), 8.68-8.73 (m, 1H).

Step 2

In a similar manner to Step 2 of Example 8, 4-(2-pyridinesulfonyloxy)-5-methoxy-7-[1-(tert-butoxycarbonyl)-5-(pyrrolidin-1-ylmethyl)indol-2-yl]isoindolinone (0.116 g, 0.187 mmol) was treated with 10% hydrogen chloride-methanol solution (5.0 mL) to obtain Compound 413 (0.0716 g, yield 65%).

ESI-MS m/z: 519 [M+H]$^+$; $^1$H-NMR (DMSO-d$_6$) δ(ppm): 1.80-2.09 (m, 4H), 3.05-3.16 (m, 2H), 3.31-3.39 (m, 2H), 3.64 (s, 3H), 4.39 (s, 2H), 4.46 (s, 2H), 7.31 (d, J=8.6 Hz, 1H), 7.46 (s, 1H), 7.57 (d, J=8.6 Hz, 1H), 7.73 (s, 1H), 7.77 (s, 1H), 7.90 (ddd, J=1.1, 4.6, 7.7 Hz, 1H), 8.15 (d, J=7.7 Hz, 1H), 8.24 (ddd, J=1.1, 7.7, 7.7 Hz, 1H), 8.85-8.90 (m, 1H), 9.26 (s, 1H), 10.0 (br s, 1H), 14.0 (s, 1H).

EXAMPLE 414

4-(2-Pyridinesulfonyloxy)-5-methoxy-7-[1H-5-(piperidinomethyl)indol-2-yl]isoindolinone hydrochloride (Compound 414)

Step 1

In a similar manner to Step 2 of Example 6, 4-(2-pyridinesulfonyloxy)-5-methoxy-7-[1-(tert-butoxycarbonyl)-5-formylindol-2-yl]isoindolinone (0.318 g, 0.564 mmol) was dissolved in acetonitrile (10.0 mL), and the solution was treated with piperidine (1.10 mL, 11.3 mmol), acetic acid (0.646 mL, 11.3 mmol) and sodium triacetoxyborohydride (0.359 g, 1.69 mmol), followed by purification by flash column chromatography (chloroform/methanol=85/15) to obtain 4-(2-pyridinesulfonyloxy)-5-methoxy-7-[1-(tert-butoxycarbonyl)-5-(piperidinomethyl)indol-2-yl]isoindolinone (0.126 g, 35%).

ESI-MS m/z: 643 [M+H]$^+$; $^1$H-NMR (CD$_3$OD) δ(ppm): 1.18 (s, 9H), 1.45-1.55 (m, 2H), 1.61-1.72 (m, 4H), 2.84-2.94 (m, 4H), 3.42 (s, 3H), 4.04 (s, 2H), 4.42 (d, J=2.5 Hz, 2H), 6.53 (d, J=3.5 Hz, 1H), 7.01 (d, J=2.5 Hz, 1H), 7.26 (dd, J=1.6, 8.7 Hz, 1H), 7.51 (d, J=1.6 Hz, 1H), 7.67-7.75 (m, 1H), 7.94-8.13 (m, 2H), 8.17 (dd, J=3.5, 8.6 Hz, 1H), 8.67-8.73 (m, 1H).

Step 2

In a similar manner to Step 2 of Example 8, 4-(2-pyridinesulfonyloxy)-5-methoxy-7-[1-(tert-butoxycarbonyl)-5-(piperidinomethyl)indol-2-yl]isoindolinone (0.125 g, 0.198 mmol) was treated with 10% hydrogen chloride-methanol solution (5.0 mL) to obtain Compound 414 (0.0525 g, yield 44%).

ESI-MS m/z: 543 [M+H]$^+$; $^1$H-NMR (DMSO-d$_6$) δ(ppm): 1.27-1.45 (m, 1H), 1.63-1.86 (m, 5H), 2.75-2.94 (m, 2H), 3.26-3.45 (m, 2H), 3.64 (s, 3H), 4.32 (s, 2H), 4.46 (s, 2H), 7.34 (dd, J=1.5, 8.4 Hz, 1H), 7.47 (s, 1H), 7.56 (d, J=8.4 Hz, 1H), 7.73 (s, 1H), 7.81 (s, 1H), 7.91 (ddd, J=1.1, 4.8, 7.4 Hz, 1H), 8.15 (dd, J=1.5, 7.4 Hz, 1H), 8.24 (ddd, J=1.5, 7.4, 7.4 Hz, 1H), 8.85-8.90 (m, 1H), 9.26 (s, 1H), 10.0 (br s, 1H), 14.0 (s, 1H).

EXAMPLE 415

4-(3-Fluoro-4-methylbenzenesulfonyloxy)-5-methoxy-7-[1H-5-(piperidinomethyl)indol-2-yl]isoindolinone hydrochloride (Compound 415)

Step 1

In a similar manner to Step 1 of Example 227, 4-hydroxy-5-methoxy-7-[1-(tert-butoxycarbonyl)-5-(piperidinomethyl)indol-2-yl]isoindolinone (0.188 g, 0.382 mmol) was dissolved in acetonitrile (8.0 mL), and the solution was treated with triethylamine (0.160 mL, 1.15 mmol) and 3-fluoro-4-methylbenzenesulfonyl chloride (0.120 mg, 0.574 mmol) to obtain 4-(3-fluoro-4-methylbenzenesulfonyloxy)-5-methoxy-7-[1-(tert-butoxycarbonyl)-5-(piperidinomethyl)indol-2-yl]isoindolinone (0.0690 g, yield 27%).

ESI-MS m/z: 664 [M+H]$^+$; $^1$H-NMR (CD$_3$OD) δ(ppm): 1.19 (s, 9H), 1.38-1.48 (m, 2H), 1.53-1.62 (m, 4H), 2.33 (d, J=1.8 Hz, 3H), 2.35-2.54 (m, 4H), 3.50 (s, 3H), 4.11 (s, 2H), 4.42 (s, 2H), 6.57 (s, 1H), 7.04 (s, 1H), 7.14-7.65 (m, 6H), 8.22 (d, J=8.9 Hz, 1H).

Step 2

In a similar manner to Step 2 of Example 8, 4-(3-fluoro-4-methylbenzenesulfonyloxy)-5-methoxy-7-[1-(tert-butoxycarbonyl)-5-(piperidinomethyl)indol-2-yl]isoindolinone (0.0690 g, 0.104 mmol) was treated with 10% hydrogen chloride-methanol solution (5.0 mL) to obtain Compound 415 (0.0444 g, yield 71%).

ESI-MS m/z: 543 [M+H]$^+$; $^1$H-NMR (DMSO-d$_6$) δ(ppm): 1.29-1.46 (m, 1H), 1.62-1.87 (m, 5H), 2.40 (d, J=1.7 Hz, 3H), 2.78-2.93 (m, 2H), 3.31-3.45 (m, 2H), 3.71 (s, 3H), 4.31 (d, J=4.8 Hz, 2H), 4.45 (s, 2H), 7.32 (dd, J=1.3, 8.4 Hz, 1H), 7.48 (s, 1H), 7.57 (d, J=8.4 Hz, 1H), 7.62-7.83 (m, 5H), 9.26 (s, 1H), 9.95 (br s, 1H), 14.0 (s, 1H).

EXAMPLE 416

4-(Sulfamoyloxy)-5-methoxy-7-[1H-5-(pyrrolidin-1-ylmethyl)indol-2-yl]isoindolinone hydrochloride (Compound 416)

4-Hydroxy-5-methoxy-7-[1H-5-(pyrrolidin-1-ylmethyl)indol-2-yl]isoindolinone hydrochloride (0.0850 g, 0.205 mmol) was dissolved in DMF (4.0 mL), and the solution was added with chlorosulfonamide (0.0470 g, 0.411 mmol), followed by stirring at room temperature for 1.5 hours. The reaction mixture was added with water and the solvent was evaporated under reduced pressure. The residue was purified by thin-layer column chromatography (chloroform/0.1% ammonia-methanol solution=80/20) and by slurry using 1% hydrogen chloride-methanol solution to obtain Compound 416 (0.0171 g, 17%).

ESI-MS m/z: 457 [M+H]$^+$; $^1$H-NMR (DMSO-d$_6$) δ(ppm): 1.83-2.91 (m, 4H), 3.06-3.45 (m, 4H), 4.03 (s, 3H), 4.34 (s, 2H), 4.56 (s, 2H), 7.30 (d, J=8.3 Hz, 1H), 7.46 (s, 1H), 7.55 (d, J=8.3 Hz, 1H), 7.77 (s, 1H), 7.83 (s, 1H), 8.14 (br s, 1H), 9.22 (s, 1H), 14.0 (s, 1H).

EXAMPLE 417

4-(Dimethylsulfamoyloxy)-5-methoxy-7-[1H-5-(pyrrolidin-1-ylmethyl)indol-2-yl]isoindolinone hydrochloride (Compound 417)

4-Hydroxy-5-methoxy-7-[1H-5-(pyrrolidin-1-ylmethyl) indol-2-yl]isoindolinone hydrochloride (0.109 g, 0.262 mmol) was dissolved in DMF (2.0 mL), and the solution was added with N,N,N',N'-tetramethyl-1,3-propanediamine (0.132 mL, 0.787 mmol) and dimethylsulfamoyl chloride (0.0570 mL, 0.525 mmol), followed by stirring at room temperature for 1 hour. The reaction mixture was added with water and extracted with ethyl acetate. The organic layer was washed with saturated brine and dried over anhydrous sodium sulfate. The solvent was evaporated under reduced pressure and the residue was purified by thin-layer column chromatography (chloroform/0.1% ammonia-methanol solution=80/20) and by slurry using by 1% hydrogen chloride-methanol solution to obtain Compound 417 (0.0431 g. yield 32%).

mp 212-214° C.; ESI-MS m/z: 569 [M+H]$^+$; $^1$H-NMR (CDCl$_3$) δ(ppm): 1.82-2.10 (m, 4H), 2.99 (s, 6H), 3.04-3.15 (m, 2H), 3.24-3.39 (m, 2H), 4.11 (s, 3H), 4.40 (s, 2H), 4.55 (s, 2H), 7.30-7.38 (m, 1H), 7.48 (s, 1H), 7.56 (d, J=8.5 Hz, 1H), 7.82 (d, J=5.6 Hz, 1H), 7.85 (s, 1H), 9.26 (s, 1H), 10.3 (br s, 1H), 14.0 (s, 1H).

EXAMPLE 418

4-(Sulfamoyloxy)-5-methoxy-7-[1H-5-(diethylaminomethyl)indol-2-yl]isoindolinone (Compound 418)

In a similar manner to Step 1 of Example 416, 4-hydroxy-5-methoxy-7-[1H-5-(diethylaminomethyl)indol-2-yl]isoindolinone hydrochloride (0.113 g, 0.298 mmol) was dissolved in DMF (3.0 mL), and the solution was treated with chlorosulfonamide (0.103 g, 0.893 mmol) to obtain Compound 418 (0.0100 g, yield 7.3%).

ESI-MS m/z: 459 [M+H]$^+$; $^1$H-NMR (DMSO-d$_6$) δ(ppm): 1.09-1.25 (m, 6H), 2.97-3.15 (m, 4H), 3.54 (s, 3H), 3.70 (s, 2H), 4.09 (s, 3H), 4.45 (s, 2H), 7.24 (m, 1H), 7.27 (m, 1H), 7.51 (m, 1H), 7.69 (s, 1H), 7.76 (s, 1H), 9.76 (s, 1H), 14.0 (s, 1H).

EXAMPLE 419

4-Methanesulfonyloxy-5-methoxy-7-[1H-4-(dimethylaminomethyl)indol-2-yl]isoindolinone hydrochloride (Compound 419)

Step 1

In a similar manner to Step 2 of Example 1, 4-methanesulfonyloxy-5-methoxy-7-iodoisoindolinone (0.537 g, 1.40 mmol) was dissolved in acetonitrile (21.0 mL), and the solution was treated with Compound BF (0.810 g, 2.80 mmol), palladium acetate (0.0310 g, 0.140 mmol), tri(o-tolyl)phosphine (0.0850 g, 0.280 mmol) and triethylamine (1.95 mL, 14.0 mmol), followed by purification by slurry using n-hexane to obtain 4-methanesulfonyloxy-5-methoxy-7-[1-(tert-butoxycarbonyl)-4-formylindol-2-yl]isoindolinone (0.700 g, 99%).

ESI-MS m/z: 501 [M+H]$^+$

Step 2

In a similar manner to Step 2 of Example 6, 4-methanesulfonyloxy-5-methoxy-7-[1-(tert-butoxycarbonyl)-4-formylindol-2-yl]isoindolinone (0.262 g, 1.17 mmol) was dissolved in acetonitrile (15.0 mL), and the solution was treated with 2.0 mol/L methylamine-THF solution (5.20 mL, 10.5 mmol), acetic acid (0.600 mL, 10.5 mmol) and sodium triacetoxyborohydride (0.555 g, 2.62 mmol), followed by purification of the residue by flash column chromatography (chloroform/methanol=3/1) to obtain 4-methanesulfonyloxy-5-methoxy-7-[1-(tert-butoxycarbonyl)-4-(dimethylaminomethyl)indol-2-yl]isoindolinone (0.0839 g, 30%).

ESI-MS m/z: 530 [M+H]$^+$, $^1$H-NMR (DMSO-d$_6$) δ(ppm): 1.21 (s, 9H), 2.64 (s, 6H), 3.52 (s, 3H), 4.01 (s, 3H), 4.39 (s, 2H), 4.43 (s, 2H), 7.12 (s, 1H), 7.39-7.46 (m, 3H), 8.21-8.28 (m, 1H), 8.59 (s, 1H).

Step 3

In a similar manner to Step 2 of Example 8, 4-methanesulfonyloxy-5-methoxy-7-[1-(tert-butoxycarbonyl)-4-(dimethylaminomethyl)indol-2-yl]isoindolinone (0.0839 g, 0.158 mmol) was treated with 10% hydrogen chloride-methanol solution (5.0 mL) to obtain Compound 419 (0.0730 g, yield 99%).

ESI-MS m/z: 430 [M+H]$^+$; $^1$H-NMR (DMSO-d$_6$) δ(ppm): 2.79 (s, 6H), 3.55 (s, 3H), 4.12 (s, 3H), 4.53-4.59 (m, 4H), 7.22-7.27 (m, 2H), 7.58-7.64 (m, 1H), 7.75 (s, 1H), 7.87 (s, 1H), 9.31 (s, 1H), 14.1 (s, 1H).

EXAMPLE 420

4-Methanesulfonyloxy-5-methoxy-7-[1H-4-(diethylaminomethyl)indol-2-yl]isoindolinone hydrochloride Step 1

In a similar manner to Step 2 of Example 6, 4-methanesulfonyloxy-5-methoxy-7-[1-(tert-butoxycarbonyl)-4-formylindol-2-yl]isoindolinone (0.226 g, 0.452 mmol) was dissolved in acetonitrile (15.0 mL) and the solution was treated with diethylamine (0.935 mL, 9.03 mmol), acetic acid (0.517 mL, 9.03 mmol) and sodium triacetoxyborohydride (0.479 g, 2.26 mmol), followed by purification of the residue by flash column chromatography (chloroform/methanol=3/1) to obtain 4-methanesulfonyloxy-5-methoxy-7-[1-(tert-butoxycarbonyl)-4-(diethylaminomethyl)indol-2-yl]isoindolinone (0.144 g, 57%).

ESI-MS m/z: 558 [M+H]$^+$; $^1$H-NMR (DMSO-d$_6$) δ(ppm): 1.00 (t, J=7.1 Hz, 3H), 1.03 (t, J=7.1 Hz, 3H), 1.19 (s, 9H), 2.49-2.54 (m, 4H), 3.51 (s, 3H), 3.79 (s, 2H), 4.00 (s, 3H), 4.42 (s, 2H), 6.88 (s, 1H), 7.21-7.33 (m, 3H), 8.07 (d, J=7.9 Hz, 1H), 8.55 (s, 1H).

Step 2

In a similar manner to Step 2 of Example 8, 4-methanesulfonyloxy-5-methoxy-7-[1-(tert-butoxycarbonyl)-4-(diethylaminomethyl)indol-2-yl]isoindolinone (0.144 g, 0.258 mmol) was treated with 10% hydrogen chloride-methanol solution (5.0 mL) to obtain Compound 420 (0.0776 g, yield 61%).

ESI-MS m/z: 458 [M+H]$^+$; $^1$H-NMR (DMSO-d$_6$) δ(ppm): 1.30 (t, J=7.2 Hz, 6H), 3.17 (q, J=7.2 Hz, 2H), 3.18 (q, J=7.2 Hz, 2H), 3.55 (s, 3H), 4.12 (s, 3H), 4.55 (s, 2H), 4.57-4.63 (m, 2H), 7.21-7.33 (m, 2H), 7.61 (d, J=7.2 Hz, 1H), 7.78 (s, 1H), 7.90 (s, 1H), 9.30 (s, 1H), 9.86 (br s, 1H), 14.1 (s, 1H).

EXAMPLE 421

4-Methanesulfonyloxy-5-methoxy-7-[1H-4-(2-methoxyethylaminomethyl)indol-2-yl]isoindolinone hydrochloride (Compound 421)

Step 1

In a similar manner to Step 2 of Example 6, 4-methanesulfonyloxy-5-methoxy-7-[1-(tert-butoxycarbonyl)-4-formylindol-2-yl]isoindolinone (0.252 g, 0.503 mmol) was dissolved in acetonitrile (15.0 mL), and the solution was treated with 2-methoxyethylamine (0.875 mL, 10.1 mmol), acetic acid (0.576 mL, 10.1 mmol) and sodium triacetoxyborohydride (0.533 g, 2.52 mmol), followed by purification of the residue by flash column chromatography (chloroform/methanol=3/1) to obtain 4-methanesulfonyloxy-5-methoxy-7-[1-(tert-butoxycarbonyl)-4-(2-methoxyethylaminomethyl)indol-2-yl]isoindolinone (0.0968 g, yield 34%).

ESI-MS m/z: 560 [M+H]$^+$; $^1$H-NMR (DMSO-d$_6$) δ(ppm): 1.19 (s, 9H), 2.70 (t, J=5.8 Hz, 2H), 3.22 (s, 3H), 3.41 (t, J=5.8 Hz, 2H), 3.50 (s, 3H), 3.99 (s, 2H), 4.00 (s, 3H), 4.41 (s, 2H), 6.89 (s, 1H), 7.21-7.35 (m, 4H), 8.06 (d, J=8.4 Hz, 1H), 8.55 (s, 1H).

Step 2

In a similar manner to Step 2 of Example 8, 4-methanesulfonyloxy-5-methoxy-7-[1-(tert-butoxycarbonyl)-4-(2-methoxyethylaminomethyl)indol-2-yl]isoindolinone (0.144 g, 0.258 mmol) was treated with 10% hydrogen chloride-methanol solution (5.0 mL) to obtain Compound 421 (0.0776 g, yield 61%).

ESI-MS m/z: 460 [M+H]$^+$; $^1$H-NMR (DMSO-d$_6$) δ(ppm): 3.14 (t, J=5.6 Hz, 2H), 3.31 (s, 3H), 3.55 (s, 3H), 3.65 (t, J=5.6 Hz, 2H), 4.11 (s, 3H), 4.47 (s, 2H), 4.55 (s, 2H), 7.19-7.29 (m, 2H), 7.56 (d, J=6.6 Hz, 1H), 7.78 (s, 1H), 7.90 (s, 1H), 9.27 (br s, 1H), 9.31 (s, 1H), 14.1 (s, 1H).

EXAMPLE 422

4-Methanesulfonyloxy-5-methoxy-7-[1H-4-(pyrrolidin-1-ylaminomethyl)indol-2-yl]isoindolinone hydrochloride (Compound 422)

Step 1

In a similar manner to Step 2 of Example 6, 4-methanesulfonyloxy-5-methoxy-7-[1-(tert-butoxycarbonyl)-4-formylindol-2-yl]isoindolinone (0.299 g, 0.597 mmol) was dissolved in acetonitrile (15.0 mL), and the solution was treated with pyrrolidine (0.997 mL, 11.9 mmol), acetic acid (0.684 mL, 11.9 mmol) and sodium triacetoxyborohydride (0.633 g, 2.99 mmol), followed by purification of the residue by flash column chromatography (chloroform/methanol=3/1) to obtain 4-methanesulfonyloxy-5-methoxy-7-[1-(tert-butoxycarbonyl)-4-(pyrrolidin-1-ylmethyl)indol-2-yl]isoindolinone (0.117 g, yield 35%).

ESI-MS m/z: 556 [M+H]$^+$; $^1$H-NMR (DMSO-d$_6$) δ(ppm): 1.19 (s, 9H), 1.65-1.75 (m, 4H), 2.48-2.58 (m, 4H), 3.50 (s, 3H), 3.99-4.03 (m, 5H), 4.42 (s, 2H), 6.86-6.91 (m, 1H), 7.18-7.35 (m, 3H), 8.05-8.12 (m, 1H), 8.55 (s, 1H).

Step 2

In a similar manner to Step 2 of Example 8, 4-methanesulfonyloxy-5-methoxy-7-[1-(tert-butoxycarbonyl)-4-(pyrrolidin-1-ylaminomethyl)indol-2-yl]isoindolinone (0.117 g, 0.211 mmol) was treated with 10% hydrogen chloride-methanol solution (5.0 mL) to obtain Compound 422 (0.0865 g, yield 84%).

ESI-MS m/z: 456 [M+H]$^+$; $^1$H-NMR (DMSO-d$_6$) δ(ppm): 1.84-2.09 (m, 4H), 3.08-3.23 (m, 2H), 3.38-3.49 (m, 2H), 3.55 (s, 3H), 4.12 (s, 3H), 4.55 (s, 2H), 4.64 (s, 1H), 4.66 (s, 1H), 7.19-7.32 (m, 2H), 7.59 (d, J=8.1 Hz, 1H), 7.90 (s, 1H), 7.94 (s, 1H), 9.30 (s, 1H), 10.6 (br s, 1H), 14.1 (s, 1H).

EXAMPLE 423

4-Chloro-5-vinyl-7-[1H-5-(piperidin-1-ylmethyl)indol-2-yl]isoindolinone hydrochloride (Compound 423)

Step 1

In a similar manner to Step 1 of Example 299, 4-chloro-5-hydroxy-7-[1-(tert-butoxycarbonyl)-5-(piperidin-1-ylmethyl)indol-2-yl]Isoindolinone (550 mg, 1.12 mmol) was dissolved in dichloromethane (22 mL), and the solution was treated with triethylamine (0.78 ml, 5.56 mmol) and trifluoromethanesulfonyl chloride (0.356 mL, 3.34 mmol), followed by purification by flash chromatography (chloroform, chloroform/methanol=99/1, 95/1) to obtain 4-chloro-5-trifluoromethanesulfonyloxy-7-[1-(tert-butoxycarbonyl)-5-(piperidin-1-ylmethyl)indol-2-yl]isoindolinone (491 mg, yield 71%).

ESI-MS m/z: 628 [M+H]$^+$; $^1$H-NMR (CDCl$_3$) δ(ppm): 1.12-1.60 (m, 15H), 2.42 (br s, 4H), 3.60 (s, 2H), 4.43 (s, 2H), 6.60 (s, 1H), 7.34 (dd, J=1.5, 8.4 Hz, 1H), 7.47 (s, 1H), 7.52 (d, J=1.5 Hz, 1H), 8.15 (d, J=8.4 Hz, 1H).

Step 2

In a similar manner to Step 1 of Example 152, 4-chloro-5-trifluoromethanesulfonyloxy-7-[1-(tert-butoxycarbonyl)-5-(piperidin-1-ylmethyl)indol-2-yl]isoindolinone (70.0 mg, 0.111 mmol) was dissolved in dimethoxyethane (3.5 mL), and the solution was treated with 2,4,6-trivinylcyclotriboroxane-pyridine complex (53.6 mg, 0.222 mmol), [bis(diphenylphosphino)ferrocene]dichloropalladium (7.3 mg, 0.0090 mmol), potassium carbonate (76.7 mg, 0.355 mmol) and water (0.060 mL), followed by purification by preparative thin-layer chromatography (chloroform/methanol=9/1) to obtain 4-chloro-5-vinyl-7-[1-(tert-butoxycarbonyl)-5-(piperidin-1-ylmethyl)indol-2-yl]isoindolinone (33.6 mg, yield 60%).

ESI-MS m/z: 506 [M+H]$^+$; $^1$H-NMR (CDCl$_3$) δ(ppm): 1.24-1.45 (m, 11H), 1.58-1.67 (m, 4H), 2.46 (br s, 4H), 3.64 (s, 2H), 4.39 (s, 2H), 5.55 (d, J=11.4 Hz, 1H), 5.91 (d, J=17.7 Hz, 1H), 6.59 (s, 1H), 7.18 (dd, J=11.4, 17.7 Hz, 1H), 7.31 (dd, J=1.5, 9.0 Hz, 1H), 7.51 (br s, 2H), 7.69 (s, 1H), 8.15 (d, J=9.0 Hz, 1H).

Step 3

In a similar manner to Step 2 of Example 8, 4-chloro-5-vinyl-7-[1-(tert-butoxycarbonyl)-5-(piperidin-1-ylmethyl)indol-72-yl]isoindolinone (33.3 mg, 0.066 mmol) was dissolved in methanol (1 mL), and the solution was treated with 10% hydrogen chloride-methanol solution (1 mL). The reaction mixture was added with diisopropylether. The obtained solid was collected by filtration and washed with diisopropylether, followed by drying under reduced pressure to obtain Compound 423 (14.4 mg, yield 54%).

ESI-MS m/z: 406 [M+H]$^+$; $^1$H-NMR (DMSO-d$_6$) δ(ppm): 1.30-1.39 (m, 1H), 1.65-1.81 (m, 5H), 2.80-2.90 (m, 2H), 3.28 (br s, 2H), 4.31 (d, J=4.5 Hz, 2H), 4.49 (s, 2H), 5.70 (d, J=11.4 Hz, 1H), 6.34 (d, J=17.4 Hz, 1H), 7.11 (dd, J=11.4, 17.4 Hz, 1H), 7.29 (d, J=8.4 Hz, 1H), 7.53 (s, 1H), 7.55 (d, J=8.4 Hz, 1H), 7.77 (s, 1H), 8.43 (s, 1H), 9.50 (s, 1H), 9.77 (bras, 1H), 13.84 (s, 1H).

EXAMPLE 424

4-Chloro-5-phenyl-7-[1H-5-(piperidin-1-ylmethyl)indol-2-yl]isoindolinone hydrochloride
(Compound 424)

Step 1

4-Chloro-5-trifluoromethanesulfonyloxy-7-[1-(tert-butoxycarbonyl)-5-(piperidin-1-ylmethyl)indol-2-yl]isoindolinone (100 mg, 0.159 mmol) was dissolved in dimethoxyethane (5.0 mL), and the solution was added with phenylboronic acid (58.2 mg, 0.478 mmol), [bis(diphenylphosphino)ferrocene]dichloropalladium (10.4 mg, 0.0130 mmol) and cesium fluoride (145 mg, 0.954 mmol), followed by stirring at 90° C. for 6.0 hours under argon atmosphere. The reaction mixture was added with water and extracted with ethyl acetate. The organic layer was washed with saturated brine and dried over anhydrous sodium sulfate. The solvent was evaporated under reduced pressure and the residue was purified by preparative thin-layer chromatography (chloroform/methanol=9/1) to obtain 4-chloro-5-phenyl-7-[1-(tert-butoxycarbonyl)-5-(piperidin-1-ylmethyl)indol-2-yl]isoindolinone (44.5 mg, yield 50%).

ESI-MS m/z: 556 [M+H]$^+$; $^1$H-NMR (CDCl$_3$) δ(ppm): 1.25-1.34 (m, 11H), 1.63-1.67 (m, 4H), 3.80 (s, 1H), 4.47 (s, 2H), 6.56 (s, 1H), 7.25 (dd, J=1.8, 8.7 Hz, 1H), 7.42-7.68 (m, 8H), 8.15 (d, J=8.7 Hz, 1H).

Step 2

In a similar manner to Step 2 of Example 8, 4-chloro-5-phenyl-7-[1-(tert-butoxycarbonyl)-5-(piperidin-1-ylmethyl)indol-2-yl]isoindolinone (44.5 mg, 0.080 mmol) was dissolved in methanol (0.5 mL), and the solution was treated with 10% hydrogen chloride-methanol solution (0.5 mL). The reaction mixture was added with diisopropylether. The obtained solid was collected by filtration and washed with diisopropylether, followed by drying under reduced pressure to obtain Compound 424 (17.8 mg, yield 45%).

ESI-MS m/z: 456 [M+H]$^+$; $^1$H-NMR (DMSO-d$_6$) δ(ppm): 1.27-1.39 (m, 1H), 1.65-1.76 (m, 5H), 2.28-2.88 (m, 2H), 3.28-3.33 (m, 2H), 4.30 (d. J=4.8 Hz, 2H), 4.54 (s, 2H), 7.32 (dd, J=0.9, 8.7 Hz, 1H), 7.45 (d, J=0.9 Hz, 1H), 4.48-7.57 (m, 6H), 7.74 (s, 1H), 8.19 (s, 1H), 9.57 (s, 1H), 9.97 (br s, 1H), 13.85 (s, 1H).

EXAMPLE 425

4-Chloro-5-(2-furyl)-7-[1H-5-(piperidin-1-ylmethyl)indol-2-yl]isoindolinone hydrochloride
(Compound 424)

Step 1

4-Chloro-5-trifluoromethanesulfonyloxy-7-[1-(tert-butoxycarbonyl)-5-(piperidin-1-ylmethyl)indol-2-yl]isoindolinone (100 mg, 0.159 mmol) was dissolved in 1,4-dioxane (3.0 mL), and the solution was added with 2-(tributylstannyl) furan (0.150 mL, 0.477 mmol), tetrakis(triphenylphosphine)palladium (15.0 mg, 0.0130 mmol) and lithium chloride (60.6 mg, 1.43 mmol), followed by stirring at 90° C. for 6.0 hours under argon atmosphere. The reaction mixture was added with 10% aqueous ammonium fluoride solution and filtered using Celite. The filtrate was extracted with ethyl acetate. The organic layer was washed with saturated brine and dried over anhydrous sodium sulfate. The solvent was evaporated under reduced pressure and the residue was purified by preparative thin-layer chromatography (chloroform/methanol=6/1) to obtain 4-chloro-5-(2-furyl)-7-[1-(tert-butoxycarbonyl)-5-(piperidin-1-ylmethyl)indol-2-yl]isoindolinone (52.2 mg, yield 60%).

ESI-MS m/z: 546 [M+H]$^+$: $^1$H-NMR (CDCl$_3$) δ(ppm): 1.20-1.42 (m, 11H), 1.60-1.64 (m, 4H), 2.47 (br s, 4H), 3.65 (s, 2H), 4.42 (s, 2H), 6.58 (dd, J=1.9, 3.9 Hz, 1H), 6.63 (s, 1H), 7.30-7.33 (m, 2H), 7.52-7.55 (m, 2H), 7.82 (s, 1H), 8.02 (s, 1H), 8.18 (d, J=8.6 Hz, 1H).

Step 2

In a similar manner to Step 2 of Example 8, 4-chloro-5-(2-furyl)-7-[1-(tert-butoxycarbonyl)-5-(piperidin-1-ylmethyl) indol-2-yl]isoindolinone (48.5 mg, 0.089 mmol) was dissolved in methanol (0.5 mL), and the solution was treated with 10% hydrogen chloride-methanol solution (0.5 mL). The reaction mixture was added with diisopropylether. The obtained solid was collected by filtration and washed with diisopropylether, followed by drying under reduced pressure to obtain Compound 425 (21.5 mg, yield 50%).

ESI-MS m/z: 446 [M+H]$^+$; $^1$H-NMR (DMSO-d$_6$) δ(ppm): 1.27-1.40 (m, 1H), 1.66-1.77 (m, 5H), 2.83-2.88 (m, 2H), 3.29 (br s, 2H), 4.31 (d, J=4.5 Hz, 2H), 4.54 (s, 2H), 6.77 (dd, J=1.5, 3.3 Hz, 1H), 7.34 (dd, J=1.2, 8.4 Hz, 1H), 7.39-7.40 (m, 2H), 7.56 (d. J=8.4 Hz, 1H), 7.80 (s, 1H), 8.00 (d, J=1.2 Hz, 1H), 8.51 (s, 1H), 9.55 (s, 1H), 10.04 (br s, 1H), 13.83 (s, 1H).

EXAMPLE 426

4-Chloro-5-ethyl-7-[1H-5-(piperidin-1-ylmethyl)indol-2-yl]isoindolinone hydrochloride
(Compound 426)

Step 1

4-Chloro-5-trifluoromethanesulfonyloxy-7-[1-(tert-butoxycarbonyl)-5-(piperidin-1-ylmethyl)indol-2-yl]isoindolinone (93.5 mg, 0.149 mmol) was dissolved in dimethoxyethane (4.7 mL), and the solution was added with 1.1 mmol/L diethyl zinc-toluene solution (0.68 mL, 0.744 mmol) and [bis(diphenylphosphino)ferrocene]dichloropalladium (34.4 mg, 0.030 mmol), followed by stirring at 90° C. for 12 hours under argon atmosphere. The reaction mixture was added with water and filtered using Celite. The filtrate was extracted with ethyl acetate. The organic layer was washed with saturated brine, followed by drying over sodium sulfate. The solvent was evaporated under reduced pressure and the residue was purified by preparative thin-layer chromatography (chloroform/methanol=6/1) to obtain 4-chloro-5-ethyl-7-[1-(tert-butoxycarbonyl)-5-(piperidin-1-ylmethyl)indol-2-yl]isoindolinone (39.0 mg, yield 52%).

ESI-MS m/z: 508 [M+H]$^+$; $^1$H-NMR (CDCl$_3$) δ(ppm): 1.24-1.33 (m, 13H), 1.44 (br s, 1H), 1.61-1.65 (m, 4H), 2.53 (br s, 4H), 2.88 (g, J=7.5 Hz, 2H), 3.72 (s, 2H), 4.38 (s, 2H), 6.55 (s, 1H), 7.26-7.68 (m, 4H), 8.15 (d, J=8.4 Hz, 1H).

Step 2

In a similar manner to Step 2 of Example 8, 4-chloro-5-ethyl-7-[1-(tert-butoxycarbonyl)-5-(piperidin-1-ylmethyl)indol-2-yl]isoindolinone (36.8 mg, 0.072 mmol) was dissolved in methanol (0.5 mL), and the solution was treated with 10% hydrogen chloride-methanol solution (0.5 mL). The reaction mixture was added with diisopropylether. The obtained solid was collected by filtration and washed with diisopropylether, followed by drying under reduced pressure to obtain Compound 426 (7.4 mg, yield 23%).

ESI-MS m/z: 408 [M+H]$^+$; $^1$H-NMR (DMSO-d$_6$) δ(ppm): 1.24-1.34 (m, 4H), 1.66-1.76 (m, 5H), 2.83-2.90 (m, 4H), 3.28 (br s, 2H), 4.38 (d, J=4.5 Hz, 2H), 4.47 (s, 2H), 7.32 (dd, J=1.2, 8.4 Hz, 1H), 7.37 (d, J=1.2 Hz, 1H), 7.54 (d, J=8.4 Hz, 1H), 7.78 (s, 1H), 8.12 (s, 1H), 9.46 (s, 1H), 10.11 (br s, 1H), 13.88 (s, 1H).

EXAMPLE 427

4-Chloro-5-[(4-(hydroxymethyl)phenyl]-7-[1H-5-(piperidin-1-ylmethyl)indol-2-yl]isoindolinone hydrochloride (Compound 424)

Step 1

Cesium fluoride (154 mg, 0.954 mmol) was suspended in dimethoxyethane (5.0 mL) and the suspension was added with Molecular Sieves 4A (100 mg), followed by stirring at room temperature for 0.5 hour. The reaction mixture was added with 4-(hydroxymethyl)phenylboronic acid (72.6 mg, 0.478 mmol), 4-chloro-5-trifluoromethanesulfonyloxy-7-[1-(tert-butoxycarbonyl)-5-(piperidin-1-ylmethyl)indol-2-yl]isoindolinone (100 mg, 0.159 mmol) and [bis(diphenylphosphino)ferrocene]dichloropalladium (10.4 mg, 0.013 mmol), followed by stirring at 90° C. for 12 hours under argon atmosphere. The reaction mixture was added with water and filtered using Celite. The filtrate was extracted with ethyl acetate. The organic layer was washed with saturated brine and dried over sodium sulfate. The solvent was evaporated under reduced pressure and the residue was purified by preparative thin-layer chromatography (chloroform/methanol=6/1) to obtain 4-chloro-5-[4-(hydroxymethyl)phenyl]-7-[(1-(tert-butoxycarbonyl)-5-(piperidin-1-ylmethyl)indol-2-yl]isoindolinone (81.9 mg, yield 88%).

ESI-MS m/z: 586 [M+H]$^+$; $^1$H-NMR (CD$_3$OD) δ(ppm): 1.29 (s, 9H), 1.50 (br s, 2H), 1.64 (br s, 4H), 3.87 (s, 2H), 4.47 (s, 2H), 4.67 (s, 2H), 6.62 (s, 1H), 6.75-7.59 (m, 6H), 7.87 (s, 1H), 8.21 (d, J=8.7 Hz, 1H).

Step 2

In a similar manner to Step 2 of Example 8, 4-chloro-5-[4-(hydroxymethyl)phenyl]-7-[1-(tert-butoxycarbonyl)-5-(piperidin-1-ylmethyl)indol-2-yl]isoindolinone (65.2 mg, 0.107 mmol) was dissolved in methanol (0.5 mL), and the solution was treated with 10% hydrogen chloride-methanol solution (0.5 mL). The obtained solid was collected by filtration and washed with methanol, followed by drying under reduced pressure to obtain Compound 427 (22.2 mg, yield 38%).

ESI-MS m/z: 486 [M+H]$^+$; $^1$H-NMR (DMSO-d$_6$) δ(ppm): 1.29-1.40 (m, 1H), 1.66-1.77 (m, 5H), 2.80-2.90 (m, 2H), 3.29 (br s, 2H), 4.31 (d, J=4.2 Hz, 2H), 4.55 (s, 2H), 4.61 (s, 2H), 5.35 (br s, 1H), 7.33 (dd, J=1.5, 8.4 Hz, 1H), 7.42 (d, J=1.5 Hz, 1H), 7.48-7.59 (m, 5H), 7.76 (s, 1H), 8.19 (s, 1H), 9.58 (s, 1H), 9.98 (br s, 1H), 13.87 (s, 1H).

EXAMPLE 428

4-Chloro-5-(3-hydroxypropoxy)-7-[1H-5-(piperidin-1-ylmethyl)indol-2-yl]isoindolinone hydrochloride (Compound 428)

Step 1

In a similar manner to Step 1 of Example 149, 4-chloro-5-hydroxy-7-[1-(tert-butoxycarbonyl)-5-(piperidinomethyl)indol-2-yl]isoindolinone (65.7 mg, 0.136 mmol) was dissolved in THF (3.5 mL), and the solution was treated with triphenylphosphine (178 mg, 0.680 mmol), 3-(tert-butyldimethylsiloxy)-1-propanol (0.145 mL, 0.680 mmol) and 40% DEAD-toluene solution (0.310 mL, 0.680 mmol), followed by purification by preparative thin-layer chromatography (chloroform/methanol=6/1) to obtain 4-chloro-5-[3-(tert-butyldimethylsiloxy)propoxy]-7-[1-(tert-butoxycarbonyl)-5-(piperidin-1-ylmethyl)indol-2-yl]isoindolinone (58.2 mg, yield 64%).

APCI-MS m/z: 668 [M+H]$^+$; $^1$H-NMR (CDCl$_3$) δ(ppm): 0.04 (s, 6H), 0.87 (s, 9H), 1.26-1.43 (m, 11H), 1.58-1.61 (m, 4H), 2.03-2.11 (m, 2H), 2.44 (br s, 4H), 3.62 (s, 2H), 3.86 (t, J=5.7 Hz, 2H), 4.24 (t, J=6.0 Hz, 2H), 4.36 (s, 2H), 6.55 (s, 1H), 7.05 (s, 1H), 7.26-7.36 (m, 2H), 7.50 (d, J=0.9 Hz, 1H), 8.16 (d, J=8.7 Hz, 1H).

Step 2

In a similar manner to Step 2 of Example 8, 4-chloro-5-[3-(tert-butyldimethylsiloxy)propoxy]-7-[1-(tert-butoxycarbonyl)-5-(piperidin-1-ylmethyl)indol-2-yl]isoindolinone (58.0 mg, 0.087 mmol) was dissolved in methanol (0.5 mL), and the solution was treated with 10% hydrogen chloride-methanol solution (0.5 mL). The reaction mixture was added with diisopropylether. The obtained solid was collected by filtration and washed with diisopropylether, followed by drying under reduced pressure to obtain Compound 4-28 (22.6 mg, yield 53%).

ESI-MS m/z: 454 [M+H]$^+$; $^1$H-NMR (DMSO-d$_6$) δ(ppm): 1.27-1.40 (m, 1H), 1.66-1.76 (m, 5H), 1.91-1.99 (m, 2H), 2.77-2.89 (m, 2H), 3.28 (br s, 2H), 3.60-3.65 (m, 2H), 4.30 (d, J=4.5 Hz, 2H), 4.39 (t, J=6.0 Hz, 2H), 4.44 (s, 2H), 4.68 (br s, 1H), 7.32 (dd, J=1.2, 8.4 Hz, 1H), 7.48 (d, J=1.2 Hz, 1H), 7.54 (d, J=8.4 Hz, 1H), 7.80 (s, 1H), 7.82 (s, 1H), 9.31 (s, 1H), 10.14 (br s, 1H), 14.01 (s, 1H).

EXAMPLE 429

4-Chloro-5-(2-hydroxyethoxy)-7-[1H-5-(piperidin-1-ylmethyl)indol-2-yl]isoindolinone hydrochloride (Compound 429)

Step 1

4-Chloro-5-hydroxy-7-iodoisoindolinone (100 mg, 0.323 mmol) was dissolved in DMF (2.0 mL), and the solution was added with potassium carbonate (134 mg, 0.969 mmol), tetrabutylammonium iodide (11.9 mg, 0.032 mmol) and tert-butyl(2-bromoethoxy)dimethylsilane (0.083 mL, 0.388 mmol), followed by stirring at 50° C. for 7 hours under nitrogen atmosphere. The reaction mixture was added with water and extracted with ethyl acetate. The organic layer was washed with saturated brine and dried over sodium sulfate. The solvent was evaporated under reduced pressure and the residue was purified by flash column chromatography (chloroform/methanol=19/1) to obtain 4-chloro-5-[3-(tert-butyldimethylsiloxy)ethoxy]-7-iodoisoindolinone (57.7 mg, yield 38%).

ESI-MS m/z: 467 [M+H]+; 1H-NMR (CDCl3) δ(ppm): 0.11 (s, 6H), 0.91 (s, 9H), 4.04 (t, J=4.5 Hz, 2H), 4.21 (t, J=4.5 Hz, 2H), 4.29 (s, 2H), 6.28 (br s, 1H), 7.50 (s, 1H).

Step 2

In a similar manner to Step 2 of Example 1, 4-chloro-5-[3-(tert-butyldimethylsiloxy)ethoxy]-7-iodoisoindolinone (57.7 mg, 0.123 mmol) was dissolved in acetonitrile (1.8 mL), and the solution was treated with Compound BD (88.4 mg, 0.246 mmol), palladium acetate (2.2 mg, 0.0098 mmol), tri(o-tolyl)phosphine (6.0 mg, 0.017 mmol) and triethylamine (0.171 mL, 1.23 mmol), followed by purification by flash column chromatography (chloroform/methanol=9/1) to obtain 4-chloro-5-[3-(tert-butyldimethylsiloxy)ethoxy]-7-[1-(tert-butoxycarbonyl)-5-(piperidin-1-ylmethyl)indol-2-yl]isoindolinone (79.9 mg, yield 99%).

APCI-MS m/z: 654 [M+H]+; 1H-NMR (CDCl3) δ(ppm): 0.12 (s, 6H), 0.90 (s, 9H), 1.24-1.47 (m, 11H), 1.58-1.61 (m, 4H), 2.43 (br s, 4H), 3.61 (s, 2H), 4.06 (t, J=5.1 Hz, 2H), 4.21 (t, J=5.1 Hz, 2H), 4.37 (s, 2H), 6.56 (s, 1H), 7.07 (s, 1H), 7.10 (br s, 1H), 7.30 (dd, J=1.5, 8.7 Hz, 1H), 7.50 (d, J=1.5 Hz, 1H), 8.14 (d, J=8.7 Hz, 1H).

Step 3

In a similar manner to Step 2 of Example 8, 4-chloro-5-[3-(tert-butyldimethylsiloxy)ethoxy]-7-[1-(tert-butoxycarbonyl)-5-(piperidin-1-ylmethyl)indol-2-yl]isoindolinone (58.0 mg, 0.087 mmol) was dissolved in methanol (0.5 mL), and the solution was treated with 10% hydrogen chloride-methanol solution (0.5 mL). The obtained solid was collected by filtration and washed with methanol, followed by drying under reduced pressure to obtain Compound 429 (34.8 mg, yield 61%).

ESI-MS m/z: 440 [M+H]+; 1H-NMR (DMSO-d6) δ(ppm): 1.27-1.37 (m, 1H), 1.66-1.76 (m, 5H), 2.77-2.89 (m, 2H), 3.28 (br s, 2H), 3.82 (t, J=4.8 Hz, 2H), 4.31 (d, J=4.5 Hz, 2H), 4.36 (t, J=4.8 Hz, 2H), 4.45 (s, 2H), 5.02 (br s, 1H), 7.31 (d, J=8.4 Hz, 1H), 7.49 (br s, 1H), 7.55 (d, J=8.4 Hz, 1H), 7.79 (s, 1H), 7.83 (s, 1H), 9.31 (s, 1H), 10.04 (br s, 1H), 14.00 (s, 1H).

EXAMPLE 430

4-Chloro-5-[3-(methanesulfonylamino)propoxy]-7-[1H-5-(piperidin-1-ylmethyl)indol-2-yl]isoindolinone monohydrochloride (Compound 430)

Step 1

4-Chloro-5-(3-aminopropoxy)-7-iodoisoindolinone hydrochloride (100 mg, 0.248 mmol) was suspended in dichloromethane (3.0 mL), and the suspension was added with triethylamine (0.104 mL, 0.744 mmol) and methanesulfonyl chloride (0.029 mL, 0.372 mmol), followed by stirring at room temperature for 13 hours. The solvent was evaporated under reduced pressure, and the residue was purified by slurry using water and acetonitrile to obtain 4-chloro-5-[3-(methanesulfonylamino)propoxy]-7-iodoisoindolinone (51.8 mg, yield 47%).

ESI-MS m/z: 445 [M+H]+; 1H-NMR (DMSO-d6) δ(ppm): 1.90-1.98 (m, 2H), 2.89 (s, 3H), 3.10-3.31 (m, 2H), 4.21-4.25 (m, 4H), 7.07 (t, J=5.7 Hz, 1H), 7.59 (s, 1H), 8.70 (s, 1H).

Step 2

In a similar manner to Step 2 of Example 1, 4-chloro-5-[3-(methanesulfonylamino)propoxy]-7-iodoisoindolinone (80.0 mg, 0.180 mmol) was dissolved in acetonitrile (2.4 mL), and the solution was treated with Compound BD (129 mg, 0.360 mmol), palladium acetate (3.2 mg, 0.014 mmol), tri(o-tolyl)phosphine (8.8 mg, 0.029 mmol) and triethylamine (0.251 mL, 1.80 mmol), followed by purification by slurry using diisopropylether and hexane to obtain 4-chloro-5-[3-(methanesulfonylamino)propoxy]-7-[1-(tert-butoxycarbonyl)-5-(piperidin-1-ylmethyl)indol-2-yl]isoindolinone (128 mg, yield 100%).

ESI-MS m/z: 631 [M+H]+; 1H-NMR (DMSO-d6) δ(ppm): 1.20 (s, 9H), 1.39-1.48 (m, 8H), 1.95-1.99 (m, 2H), 2.33 (br s, 4H), 2.89 (s, 3H), 3.12-3.18 (m, 2H), 3.51 (s, 2H), 4.27 (t, J=6.0 Hz, 2H), 4.33 (s, 1H), 6.67 (s, 1H), 7.07 (t, J=5.7 Hz, 1H), 7.25-7.28 (m, 2H), 7.49 (s, 1H), 8.07 (d, J=8.7 Hz, 1H), 8.58 (s, 1H).

Step 3

In a similar manner to Step 2 of Example 8, 4-chloro-5-[3-(methanesulfonylamino)propoxy]-7-[1-(tert-butoxycarbonyl)-5-(piperidin-1-ylmethyl)indol-2-yl]isoindolinone (128 mg, 0.203 mmol) was dissolved in methanol (1.0 mL), and the solution was treated with 10% hydrogen chloride-methanol solution (1.0 mL). The obtained solid was collected by filtration and washed with methanol, followed by drying under reduced pressure to obtain Compound 430 (61.1 mg, yield 53%).

ESI-MS m/z: 531 [M+H]+; 1H-NMR (DMSO-d6) δ(ppm): 1.28-1.41 (m, 1H), 1.66-1.76 (m, 5H), 1.97-2.05 (m, 2H), 2.77-2.92 (m, 5H), 3.16-3.22 (m, 2H), 3.28-3.31 (m, 2H), 4.31 (d, J=5.1 Hz, 2H), 4.39 (t, J=5.7 Hz, 2H), 4.45 (s, 2H), 7.15 (t, J=5.7 Hz, 1H), 7.32 (dd, J=1.5, 8.4 Hz, 1H), 7.48 (d, J=1.5 Hz, 1H), 7.54 (d, J=8.4 Hz, 1H), 7.80 (s, 1H), 7.81 (s, 1H), 9.31 (s, 1H), 10.16 (br s, 1H), 14.01 (s, 1H).

EXAMPLE 431

4-Chloro-5-(3-hydroxypropoxy)-7-[1H-5-(dimethylaminomethyl)indol-2-yl]isoindolinone hydrochloride (Compound 431)

Step 1

In a similar manner to Step 1 of Example 429, 4-chloro-5-hydroxy-7-iodoisoindolinone (100 mg, 0.323 mmol) was dissolved in DMF (3.0 mL), and the solution was treated with potassium carbonate (134 mg, 0.969 mmol), tetrabutylammonium iodide (11.8 mg, 0.032 mmol) and tert-butyl(3-bromopropoxy)dimethylsilane (0.112 mL, 0.485 mmol), followed by purification by flash column chromatography (chloroform/methanol=99/1, 19/1) to obtain 4-chloro-5-[3-(tert-butyldimethylsiloxy)propoxy]-7-iodoisoindolinone (124 mg, yield 79%).

ESI-MS m/z: 482 [M+H]+; 1H-NMR (CDCl3) δ(ppm): 0.05 (s, 6H), 0.89 (s, 9H), 2.02-2.10 (m, 2H), 3.85 (t, J=6.0 Hz, 2H), 4.22 (t, J=6.0 Hz, 2H), 4.29 (s, 2H), 6.20 (br s, 1H), 7.45 (s, 1H).

Step 2

In a similar manner to Step 2 of Example 1, 4-chloro-5-[3-(tert-butyldimethylsiloxy)propoxy]-7-iodoisoindolinone (124 mg, 0.257 mmol) was dissolved in acetonitrile (3.7 mL), and the solution was treated with Compound BA (149 mg, 0.514 mmol), palladium acetate (4.6 mg, 0.021 mmol), tri(o-tolyl)phosphine (12.5 mg, 0.041 mmol) and triethylamine (0.358 mL, 2.57 mmol), followed by purification by flash column chromatography (chloroform/methanol=99/1, 9/1) to obtain 4-chloro-5-[3-(tert-butyldimethylsiloxy)propoxy]-7-[1-(tert-butoxycarbonyl)-5-formylindol-2-yl]isoindolinone (151 mg, yield 98%).

APCI-MS m/z: 599 [M+H]+; 1H-NMR (CDCl3) δ(ppm): 0.04 (s, 6H), 0.87 (s, 9H), 1.38 (s, 9H), 2.05-2.16 (m, 2H), 3.87 (t, J=6.0 Hz, 2H), 4.27 (t, J=5.7 Hz, 2H), 4.40 (s, 2H), 6.31 (br s, 1H), 6.70 (s, 1H), 7.09 (s, 1H), 7.87 (dd, J=1.5, 8.7 Hz, 1H), 8.09 (d, J=1.5 Hz, 1H), 8.36 (d, J=8.7 Hz, 1H), 10.07 (s, 1H).

Step 3

In a similar manner to Step 2 of Example 6, 4-chloro-5-[3-(tert-butyldimethylsiloxy)propoxy]-7-[1-(tert-butoxycarbonyl)-5-formylindol-2-yl]isoindolinone (74.9 mg, 0.125 mmol) was dissolved in acetonitrile (2.5 mL), and the solution was treated with 2.0 mol/L dimethylamine-THF solution (0.63 mL, 1.25 mmol), acetic acid (0.072 mL, 1.25 mmol) and sodium triacetoxyborohydride (76.5 mg, 0.375 mmol), followed by purification by flash column chromatography (chloroform/methanol=19/1, 4/1) to obtain 4-chloro-5-[3-(tert-butyldimethylsiloxy)propyloxy]-7-[1-(tert-butoxycarbonyl)-5-(dimethylaminomethyl)indol-2-yl]isoindolinone (65.0 mg, yield 83%).

APCI-MS m/z: 628 [M+H]$^+$; $^1$H-NMR (CDCl$_3$) δ(ppm): 0.04 (s, 6H), 0.87 (s, 9H), 1.36 (s, 9H), 2.03-2.11 (m, 2H), 2.27 (s, 6H), 3.54 (s, 2H), 3.86 (t, J=5.7 Hz, 2H), 4.25 (t, J=5.7 Hz, 2H), 4.37 (s, 2H), 6.55 (s, 1H), 6.93 (br s, 1H), 7.06 (s, 1H), 7.30 (dd, J=1.5, 8.4 Hz, 1H), 7.48 (d, J=1.5 Hz, 1H), 8.16 (d, J=8.4 Hz, 1H).

Step 4

In a similar manner to Step 2 of Example 8, 4-chloro-5-[3-(tert-butyldimethylsiloxy)propoxy]-7-[1-(tert-butoxycarbonyl)-5-(dimethylaminomethyl)indol-2-yl]isoindolinone (80.0 mg, 0.127 mmol) was dissolved in methanol (1 mL), and the solution was treated with 10% hydrogen chloride-methanol solution (1 mL). The obtained solid was collected by filtration and washed with methanol, followed by drying under reduced pressure to obtain Compound 431 (26.7 mg, yield 47%).

mp 204-206° C.; ESI-MS m/z: 414 [M+H]$^+$; $^1$H-NMR (DMSO-d$_6$) δ(ppm): 1.91-2.00 (m, 2H), 2.70 (s, 6H), 3.60-3.66 (m, 2H), 4.32 (s, 2H), 4.39 (t, J=6.9 Hz, 2H), 4.45 (s, 2H), 4.66 (br s, 1H), 7.28 (dd, J=1.5, 9.3 Hz, 1H), 7.49 (d, J=1.5 Hz, 1H), 7.53 (d, J=9.3 Hz, 1H), 7.76 (s, 1H), 7.83 (s, 1H), 9.30 (s, 1H), 10.18 (br s, 1H), 14.02 (s, 1H).

EXAMPLE 432

4-Chloro-5-(3-hydroxypropoxy)-7-[1H-5-(pyrrolidin-1-ylmethyl)indol-2-yl]isoindolinone hydrochloride (Compound 432)

Step 1

In a similar manner to Step 2 of Example 6, 4-chloro-5-[3-(tert-butyldimethylsiloxy)propoxy]-7-[1-(tert-butoxycarbonyl)-5-formylindol-2-yl]isoindolinone (71.8 mg, 0.120 mmol) was dissolved in acetonitrile (2.5 mL), and the solution was treated with pyrrolidine (0.100 mL, 1.198 mmol), acetic acid (0.069 mL, 1.198 mmol) and sodium triacetoxyborohydride (76.3 mg, 0.360 mmol), followed by purification by flash column chromatography (chloroform/methanol=19/1, 4/1) to obtain 4-chloro-5-[3-(tert-butyldimethylsiloxy)propoxy]-7-[1-(tert-butoxycarbonyl)-5-(pyrrolidin-1-ylmethyl)indol-2-yl]isoindolinone (51.4 mg, yield 66%).

APCI-MS m/z: 654 [M+H]$^+$; $^1$H-NMR (CDCl$_3$) δ(ppm): 0.04 (s; 6H), 0.87 (s, 9H), 1.35 (s, 9H), 1.84-1.89 (m, 4H), 2.03-2.11 (m, 2H), 2.67 (br s, 4H), 3.83 (s, 2H), 3.86 (t, J=6.3 Hz, 2H), 4.25 (t, J=6.0 Hz, 2H), 4.37 (s, 2H), 6.56 (s, 1H), 7.03 (br s, 1H), 7.05 (s, 1H), 7.33 (dd, J=1.5, 8.4 Hz, 1H), 7.55 (d, J=1.5 Hz, 1H), 8.17 (d, J=8.4 Hz, 1H).

Step 2

In a similar manner to Step 2 of Example 8, 4-chloro-5-[3-(tert-butyldimethylsiloxy)propoxy]-7-[1-(tert-butoxycarbonyl)-5-(pyrrolidin-1-ylmethyl)indol-2-yl]isoindolinone (51.4 mg, 0.079 mmol) was dissolved in methanol (1 mL), and the solution was treated with 10% hydrogen chloride-methanol solution (1 mL). The obtained solid was collected by filtration and washed with methanol, followed by drying under reduced pressure to obtain Compound 432 (22.7 mg, yield 61%).

ESI-MS m/z: 440 [M+H]$^+$; $^1$H-NMR (DMSO-d$_6$) δ(ppm): 1.85-2.02 (m, 6H), 3.02-3.15 (m, 2H), 3.34 (br s, 2H), 3.63 (t, J=6.3 Hz, 2H), 4.37-4.44 (m, 6H), 4.63 (br s, 1H), 7.34 (dd, J=1.5, 8.4 Hz, 1H), 7.48 (d, J=1.5 Hz, 1H), 7.54 (d, J=8.4 Hz, 1H), 7.80 (s, 1H), 7.82 (s, 1H), 9.31 (s, 1H), 10.60 (br s, 1H), 14.01 (s, 1H).

EXAMPLE 433

4-Chloro-5-(3-pyridylmethoxy)-7-[1H-5-(piperidin-1-ylmethyl)indol-2-yl]isoindolinone dihydrochloride (Compound 433)

Step 1

4-Chloro-5-hydroxy-7-[1-(tert-butoxycarbonyl)-5-(piperidin-1-ylmethyl)indol-2-yl]isoindolinone (70.0 mg, 0.141 mmol) was suspended in acetonitrile (3.5 mL), and the suspension was added with cesium carbonate (91.9 mg, 0.282 mmol) and 3-pyridylmethyl chloride hydrochloride (23.1 mg, 0.141 mmol), followed by stirring at 50° C. for 12 hours under nitrogen atmosphere. The reaction mixture was added with water. The obtained solid was collected by filtration and washed with water, followed by drying under reduced pressure to obtain 4-chloro-5-(3-pyridylmethoxy)-7-[1-(tert-butoxycarbonyl)-5-(piperidin-1-ylmethyl)indol-2-yl]isoindolinone (49.7 mg, yield 60%).

ESI-MS m/z: 587 [M+H]$^+$; $^1$H-NMR (DMSO-d$_6$) δ(ppm): 1.15 (s, 9H), 1.37-1.51 (m, 6H), 2.33 (br s, 4H), 3.51 (s, 2H), 4.34 (s, 2H), 5.44 (s, 2H), 6.64 (s, 1H), 7.27 (dd, J=1.2, 8.4 Hz, 1H), 7.42 (s, 1H), 7.45 (dd, J=4.9, 7.8 Hz, 1H), 7.51 (d, J=1.2 Hz, 1H), 7.90 (ddd, J=1.5, 1.5, 7.8 Hz, 1H), 8.07 (d, J=8.4 Hz, 1H), 8.56 (dd, J=1.5, 4.9 Hz, 1H), 8.63, (s, 1H), 8.70 (d, J=1.5 Hz, 1H).

Step 2

In a similar manner to Step 2 of Example 8, 4-chloro-5-(3-pyridylmethoxy)-7-[1-(tert-butoxycarbonyl)-5-(piperidin-1-ylmethyl)indol-2-yl]isoindolinone (49.5 mg, 0.084 mmol) was dissolved in methanol (1 mL), and the solution was treated with 10% hydrogen chloride-methanol solution (1 mL). The obtained solid was collected by filtration and washed with methanol, followed by drying under reduced pressure to obtain Compound 433 (29.2 mg, yield 62%).

ESI-MS m/z: 487 [M+H]$^+$; $^1$H-NMR (DMSO-d$_6$) δ(ppm): 1.27-1.41 (m, 1H), 1.66-1.86 (m, 5H), 2.77-2.89 (m, 2H), 3.27-3.30 (m, 2H), 4.30 (d, J=5.1 Hz, 2H), 4.46 (s, 2H), 5.67 (s, 2H), 7.34 (dd, J=1.2, 8.4 Hz, 1H), 7.52 (d, J=1.2 Hz, 1H), 7.54 (d, J=8.4 Hz, 1H), 7.87 (s, 1H), 7.94 (dd, J=5.6, 8.1 Hz, 1H), 7.98 (s, 1H), 8.47 (d, J=8.1 Hz, 1H), 8.84 (dd, J=0.9, 5.6 Hz, 1H), 8.99 (d, J=0.9 Hz, 1H), 9.39 (s, 1H), 10.48 (br s, 1H), 14.00 (s, 1H).

EXAMPLE 434

4-Chloro-5-(4-pyridylmethoxy)-7-[1H-5-(piperidin-1-ylmethyl)indol-2-yl]isoindolinone dihydrochloride (Compound 434)

Step 1

In a similar manner to Step 1 of Example 433, 4-chloro-5-hydroxy-7-[1-(tert-butoxycarbonyl)-5-(piperidin-1-ylmethyl)indol-2-yl]isoindolinone (71.4 mg, 0.144 mmol) was suspended in acetonitrile (3.5 mL), and the suspension was treated with cesium carbonate (141 mg, 0.432 mmol) and 4-pyridylmethyl chloride hydrochloride (35.4 mg, 0.216 mmol) to obtain 4-chloro-5-(4-pyridylmethoxy)-7-[(1-(tert-butoxycarbonyl)-5-(piperidin-1-ylmethyl)indol-2-yl]isoindolinone (49.7 mg, yield 60%).

ESI-MS m/z: 587 [M+H]$^+$; $^1$H-NMR (DMSO-d$_6$) δ(ppm): 1.15 (s, 9H), 1.36-1.52 (m, 6H), 2.32 (br s, 4H), 3.50 (s, 2H), 4.36 (s, 2H), 5.47 (s, 2H), 6.62 (s, 1H), 7.26 (dd, J=1.2, 8.4 Hz, 1H), 7.35 (s, 1H), 7.45 (d, J=6.0 HZ, 2H), 7.50 (d, J=1.2 Hz, 1H), 8.06 (d, J=8.4 HZ, 1H), 8.60 (d, J=6.0 Hz, 2H), 8.64 (s, 1H).

Step 2

In a similar manner to Step 2 of Example 8, 4-chloro-5-(4-pyridylmethoxy)-7-[1-(tert-butoxycarbonyl)-5-(piperidin-1-ylmethyl)indol-2-yl]isoindolinone (70.4 mg, 0.120 mmol) was dissolved in methanol (0.5 mL), and the solution was treated with 10% hydrogen chloride-methanol solution (0.5 mL). The obtained solid was collected by filtration and washed with methanol, followed by drying under reduced pressure to obtain Compound 434 (38.2 mg, yield 57%).

ESI-MS m/z: 487 [M+H]$^+$; $^1$H-NMR (DMSO-d$_6$) δ(ppm): 1.27-1.41 (m, 1H), 1.65-1.86 (m, 5H), 2.76-2.89 (m, 2H), 3.26-3.30 (m, 2H), 4.29 (d, J=4.8 hz, 2H), 4.49 (s, 2H), 5.81 (s, 2H), 7.33 (dd, J=1.5, 8.4 Hz, 1H), 7.47 (d, J=1.5 Hz, 1H), 7.53 (d, J=8.4 Hz, 1H), 7.86 (s, 1H), 7.93 (s, 1H), 8.00 (d, J=6.3 Hz, 2H), 8.91 (d, J=6.3 Hz, 2H), 9.40 (s, 1H), 10.49 (br s, 1H), 13.98 (s, 1H).

EXAMPLE 435

4-Chloro-5-(4-hydroxybutoxy)-7-[1H-5-(piperidin-1-ylmethyl)indol-2-yl]isoindolinone hydrochloride (Compound 435)

Step 1

In a similar manner to Step 1 of Example 429, 4-chloro-5-hydroxy-7-iodoisoindolinone (70.0 mg, 0.226 mmol) was dissolved in DMF (2.1 mL), and the solution was treated with potassium carbonate (93.8 mg, 0.679 mmol) and tert-butyl(4-iodobutoxy)dimethylsilane (0.176 mL, 0.679 mmol), followed by purification by flash column chromatography (chloroform/methanol=99/1, 19/1) to obtain 4-chloro-5-[4-(tert-butyldimethylsiloxy)butoxy]-7-iodoisoindolinone (94.2 mg, yield 84%).

ESI-MS m/z: 495 [M+H]$^+$; $^1$H-NMR (CDCl$_3$) δ(ppm): 0.06 (s, 6H), 0.90 (s, 9H), 1.69-1.78 (m, 2H), 1.90-2.00 (m, 2H), 3.71 (t, J=6.3 HZ, 2H), 4.15 (t, J=6.6 Hz, 2H), 4.29 (s, 2H), 6.45 (br s, 1H), 7.42 (s, 1H).

Step 2

In a similar manner to Step 2 of Example 1, 4-chloro-5-[4-(tert-butyldimethylsiloxy)butoxy]-7-iodoisoindolinone (72.2 mg, 0.146 mmol) was dissolved in acetonitrile (2.2 mL), and the solution was treated with Compound BD (88.4 mg, 0.246 mmol), palladium acetate (2.7 mg, 0.012 mmol), tri(o-tolyl)phosphine (7.1 mg, 0.023 mmol) and triethylamine (0.203 mL, 1.46 mmol), followed by purification by flash column chromatography (chloroform/methanol=99/1, 9/1) to obtain 4-chloro-5-[4-(tert-butyldimethylsiloxy)butoxy]-7-[1-(tert-butoxycarbonyl)-5-(piperidin-1-ylmethyl) indol-2-yl]isoindolinone (87.0 mg, yield 88%).

APCI-MS m/z: 582 [M+H]$^+$; $^1$H-NMR (CDCl$_3$) δ(ppm): 0.06 (s, 6H), 0.90 (s, 9H), 1.36-1.47 (m, 11H), 1.58-1.67 (m, 4H), 1.70-1.79 (m, 2H), 1.91-1.98 (m, 2H), 2.44 (br s, 4H), 3.62 (s, 2H), 3.71 (t, J=6.3 Hz, 2H), 4.17 (t, J=6.0 Hz, 2H), 4.36 (t, J=2H), 6.56 (s, 1H), 7.03 (s, 1H), 7.24-7.32 (s, 1H), 7.50 (s, 1H), 8.14 (d, J=8.7 Hz, 1H).

Step 3

In a similar manner to Step 2 of Example 8, 4-chloro-5-[4-(tert-butyldimethylsiloxy)butoxy]-7-[1-(tert-butoxycarbonyl)-5-(piperidin-1-ylmethyl)indol-2-yl]isoindolinone (87.0 mg, 0.127 mmol) was dissolved in methanol (0.5 mL), and the solution was treated with 10% hydrogen chloride-methanol solution (0.5 mL). The obtained solid was collected by filtration and washed with methanol, followed by drying under reduced pressure to obtain Compound 435 (25.3 mg, yield 39%).

ESI-MS m/z: 468 [M+H]$^+$; $^1$H-NMR (DMSO-d$_6$) δ(ppm): 1.27-1.40 (m, 1H), 1.59-1.87 (m, 9H), 2.77-2.89 (m, 2H), 3.28-3.33 (m, 2H), 3.49 (t, J=5.4 Hz, 2H), 4.30-4.35 (m, 4H), 4.44 (s, 2H), 4.52 (br s, 1H), 7.32 (dd, J=1.2, 8.4 Hz, 1H), 7.48 (d, J=1.2 Hz, 1H), 7.54 (J=8.4 Hz, 1H), 7.79 (s, 1H), 7.80 (s, 1H), 9.30 (s, 1H), 10.11 (br s, 1H), 14.01 (s, 1H).

EXAMPLE 436

4-Chloro-5-(2-amino-2-oxoethoxy)-7-[1H-5-(piperidin-1-ylmethyl)indol-2-yl]isoindolinone (Compound 436)

Step 1

In a similar manner to Step 1 of Example 433, 4-chloro-5-hydroxy-7-[1-(tert-butoxycarbonyl)-5-(piperidin-1-ylmethyl)methylindol-2-yl]isoindolinone (72.0 mg, 0.145 mmol) was suspended in acetonitrile (3.5 mL), and the suspension was treated with cesium carbonate (70.9 mg, 0.218 mmol), chloroacetonitrile (0.276 mL, 0.435 mmol), followed by purification by flash column chromatography (chloroform/methanol=19/1, 4/1) to obtain 4-chloro-5-(cyanomethoxy)-7-[(1-(tert-butoxycarbonyl)-5-(piperidin-1-ylmethyl)indol-2-yl]isoindolinone (40.3 mg, yield 52%).

ESI-MS m/z: 535 [M+H]$^+$; $^1$H-NMR (CDCl$_3$) δ(ppm): 1.39-1.48 (m, 11H), 1.60-1.66 (m, 4H), 2.49 (br s, 4H), 3.66 (s, 2H), 4.40 (s, 2H), 4.96 (s, 2H), 6.60 (s, 1H), 6.94 (br s, 1H), 7.17 (s, 1H), 7.31 (dd, J=1.2, 8.7 Hz, 1H), 7.51 (d, J=1.2 Hz, 1H), 8.13 (d, J=8.7 Hz, 1H).

Step 2

4-Chloro-5-(cyanomethoxy)-7-[1-(tert-butoxycarbonyl)-5-(piperidin-1-ylmethyl)indol-2-yl]isoindolinone (40.3 mg, 0.075 mmol) was added with 4 mol/L hydrogen chloride-1,4-dioxane solution (1 mL) and stirred at 60° C. for 12 hours. The solvent was evaporated under reduced pressure and the residue was purified by preparative thin-layer chromatography (chloroform/methanol=4/1) to obtain Compound 436 (5.4 mg, yield 16%).

ESI-MS m/z: 4.54 [M+H]$^+$; $^1$H-NMR (DMSO-d$_6$) δ(ppm): 1.48-1.69 (m, 6H), 2.08-4.13 (m, 6H), 4.46 (s, 2H), 4.87 (s, 2H), 7.26 (d, J=7.5 Hz, 1H), 7.34 (s, 1H), 7.51 (d, J=7.5 Hz, 1H), 7.54 (br s, 2H), 7.71 (s, 1H), 7.72 (s, 1H), 9.33 (s, 1H), 13.93 (br s, 1H).

EXAMPLE 437

4-Chloro-5-(3-aminopropoxy)-7-[1H-5-(piperidin-1-ylmethyl)indol-2-yl]isoindolinone dihydrochloride (Compound 437)

Step 1

In a similar manner to Step 1 of Example 429, 4-chloro-5-hydroxy-7-iodoisoindolinone (283 mg, 0.916 mmol) was dissolved in DMF (8.4 mL), and the solution was treated with potassium carbonate (190 mg, 1.37 mmol), tetrabutylammonium iodide (33.8 mg, 0.092 mmol) and 3-bromopropylcarbamic acid tert-butyl ester (654 mg, 2.75 mmol). The reaction mixture was added with water. The obtained solid was collected by filtration and purified by slurry using hexane and diisopropylether to obtain 4-chloro-5-[3-(tert-butoxycarbonylamino)propoxy]-7-iodoisoindolinone (350 mg, yield 84%).

ESI-MS m/z: 467 [M+H]$^+$; $^1$H-NMR (CDCl$_3$) δ(ppm): 1.45 (s, 1H), 2.04-2.12 (m, 2H), 3.36-3.42 (m, 2H), 4.19 (t, J=5.7 Hz, 2H), 4.30 (s, 2H), 4.99 (br s, 1H), 6.32 (br s, 1H), 7.42 (s, 1H).

Step 2

In a similar manner to Step 2 of Example 1, 4-chloro-5-[3-(tert-butoxycarbonylamino)propoxy]-7-iodoisoindolinone (82.7 mg, 0.177 mmol) was dissolved in acetonitrile (2.5 mL), and the solution was treated with Compound BD (127 mg, 0.354 mmol), palladium acetate (3.2 mg, 0.014 mmol), tri(o-tolyl)phosphine (8.5 mg, 0.028 mmol) and triethylamine (0.247 mL, 1.77 mmol), followed by purification by flash column chromatography (chloroform/methanol=20/1, 4/1) to obtain 4-chloro-5-[3-(tert-butoxycarbonylamino)propoxy]-7-[1-(tert-butoxycarbonyl)-5-(piperidin-1-ylmethyl)indol-2-yl]isoindolinone (127 mg, yield 100%).

ESI-MS m/z: 653 [M+H]$^+$; $^1$H-NMR (CDCl$_3$) δ(ppm): 1.38-1.44 (m, 20H), 1.55-1.62 (m, 4H), 2.08 (t, J=5.7 Hz, 2H), 2.42 (br s, 4H), 3.37-3.43 (m, 2H), 3.60 (s, 2H), 4.21 (t, J=5.4 Hz, 2H), 4.36 (s, 2H), 5.13 (br s, 1H), 6.56 (s, 1H), 7.03 (s, 1H), 7.28-7.49 (m, 3H), 8.13 (d, J=8.4 Hz, 1H).

Step 3

In a similar manner to Step 2 of Example 8, 4-chloro-5-[3-(tert-butoxycarbonylamino)propoxy]-7-[1-(tert-butoxycarbonyl)-5-(piperidin-1-ylmethyl)indol-2-yl]isoindolinone (127 mg, 0.194 mmol) was dissolved in methanol (1 mL), and the solution was treated with 10% hydrogen chloride-methanol solution (1 mL). The obtained solid was collected by filtration and washed with methanol, followed by drying under reduced pressure to obtain Compound 437 (34.5 mg, yield 34%).

ESI-MS m/z: 453 [M+H]$^+$; $^1$H-NMR (DMSO-d$_6$) δ(ppm): 1.27-1.40 (m, 1H), 1.66-1.77 (m, 5H), 2.10-2.19 (m, 2H), 2.77-2.89 (m, 2H), 2.99-3.05 (m, 2H), 3.26-3.37 (m, 2H), 4.30 (s, 2H), 4.43-4.46 (m, 4H), 7.33 (dd, J=1.5, 8.4 Hz, 1H), 7.51 (d, J=1.5 Hz, 1H), 7.54 (d, J=8.4 Hz, 1H), 7.83 (s, 1H), 7.84 (s, 1H), 8.16 (br s, 3H), 9.34 (s, 1H), 10.39 (br s, 1H), 14.00 (s, 1H).

EXAMPLE 438

4-Chloro-5-(3-hydroxy-3-methylbutoxy)-7-[1H-5-(piperidin-1-ylmethyl)indol-2-yl]isoindolinone hydrochloride (Compound 438)

Step 1

In a similar manner to Step 1 of Example 429, 4-chloro-5-hydroxy-7-iodoisoindolinone (70.8 mg, 0.229 mmol) was dissolved in DMF (2.1 mL), and the solution was treated with potassium carbonate (94.8 mg, 0.686 mmol), tetrabutylammonium iodide (8.5 mg, 0.023 mmol) and (4-bromo-2-methyl-2-butoxy)triethylsilane (193 mg, 0.686 mmol), followed by purification by flash column chromatography (chloroform/methanol=99/1) to obtain 4-chloro-5-[3-methyl-3-(triethylsiloxy)butoxy]-7-iodoisoindolinone (40.7 mg, yield 35%).

ESI-MS m/z: 510 [M+H]$^+$; $^1$H-NMR (CDCl$_3$) δ(ppm): 0.59 (q, J=7.6 Hz, 6H), 0.96 (t, J=7.6 Hz, 9H), 1.34 (s, 6H), 2.01 (t, J=6.8 Hz, 2H), 4.28 (t, J=6.8 Hz, 2H), 4.30 (s, 2H), 7.17 (br s, 1H), 7.43 (s, 1H).

Step 2

In a similar manner to Step 2 of Example 1, 4-chloro-5-[3-methyl-3-(triethylsiloxy)butoxy]-7-iodoisoindolinone (71.5 mg, 0.140 mmol) was dissolved in acetonitrile (2.1 mL), and the solution was treated with Compound BD (100 mg, 0.280 mmol), palladium acetate (2.5 mg, 0.011 mmol), tri(o-tolyl)phosphine (6.7 mg, 0.022 mmol) and triethylamine (0.195 mL, 1.40 mmol), followed by purification by flash column chromatography (chloroform/methanol=99/1, 9/1) to obtain 4-chloro-5-[3-methyl-3-(triethylsiloxy)butoxy]-7-[1-(tert-butoxycarbonyl)-5-(piperidin-1-ylmethyl)indol-2-yl]isoindolinone (81.2 mg, yield 83%).

APCI-MS m/z: 696 [M]$^+$; $^1$H-NMR (CDCl$_3$) δ(ppm): 0.56 (q, J=7.8 Hz, 6H), 0.92 (t, J=7.8 Hz, 9H), 1.33-1.67 (m, 21H), 2.04 (t, J=6.6 Hz, 2H), 2.52 (br s, 4H), 3.71 (s, 2H), 4.31 (t, J=6.6 Hz, 2H), 4.36 (s, 2H), 6.56 (s, 1H), 7.06 (s, 1H), 7.31 (dd, J=1.2, 8.7 Hz, 1H), 7.40 (br s, 1H), 7.54 (d, J=1.2 Hz, 1H), 8.18 (d, J=8.7 Hz, 1H).

Step 3

In a similar manner to Step 2 of Example 8, 4-chloro-5-[3-methyl-3-(triethylsiloxy)butoxy]-7-[1-(tert-butoxycarbonyl)-5-(piperidin-1-ylmethyl)indol-2-yl]isoindolinone (78.4 mg, 0.113 mmol) was dissolved in methanol (0.5 mL), and the solution was treated with 10% hydrogen chloride-methanol solution (0.5 mL). The obtained solid was collected by filtration and washed with methanol, followed by drying under reduced pressure to obtain Compound 438 (32.0 mg, yield 55%).

ESI-MS m/z: 482 [M]$^+$; $^1$H-NMR (DMSO-d$_6$) δ(ppm): 1.22 (s, 6H), 1.27-1.43 (m, 1H), 1.64-1.82 (m, 5H), 1.94 (t, J=7.2 Hz, 2H), 2.72-2.93 (m, 2H), 3.31 (br s, 2H), 4.28 (br s, 1H), 4.40-4.50 (m, 6H), 7.26 (d, J=8.1 Hz, 1H), 7.48 (s, 1H), 7.54 (d, J=8.1 Hz, 1H), 7.77 (s, 1H), 7.82 (s, 1H), 9.30 (s, 1H), 10.08 (br s, 1H), 14.01 (s, 1H).

EXAMPLE 439

4-Chloro-5-[3-(acetylamino)propoxy]-7-[1H-5-(piperidin-1-ylmethyl)indol-2-yl]isoindolinone hydrochloride Step 1

4-Chloro-5-[3-(tert-butoxycarbonylamino)propoxy]-7-iodoisoindolinone (101 mg, 0.216 mmol) was suspended in methanol (1.5 mL), and the suspension was added with 10% hydrogen chloride-methanol solution (1.5 mL), followed by stirring at 60° C. for 1.0 hour. The reaction mixture was added with diisopropylether. The obtained solid was collected by filtration and washed with diisopropylether, followed by drying under reduced pressure to obtain 4-chloro-5-(3-aminopropoxy)-7-iodoisoindolinone hydrochloride (84.0 mg, yield 96%).

ESI-MS m/z: 367 [M+H]$^+$; $^1$H-NMR (DMSO-d$_6$) δ(ppm): 2.02-2.11 (m, 2H), 2.96 (t, J=7.5 Hz, 2H), 4.22 (s, 2H), 4.27 (t, J=6.0 Hz, 2H), 7.59 (s, 1H), 8.00 (br s, 3H), 8.73 (s, 1H).

Step 2

4-Chloro-5-(3-aminopropoxy)-7-iodoisoindolinone hydrochloride (84.0 mg, 0.208 mmol) was suspended in dichloromethane, and the suspension was added with triethylamine (0.090 mL, 0.648 mmol) and anhydrous acetic acid (0.031 mL, 0.324 mmol), followed by stirring at room temperature for 12 hours. The solvent was evaported under reduced pressure and the residue was purified by slurry using water and acetonitrile to obtain 4-chloro-5-[3-(acetylamino)propoxy]-7-iodoisoindolinone (78.6 mg, yield 92%).

ESI-MS m/z: 409 [M+H]$^+$; $^1$H-NMR (DMSO-d$_6$) δ(ppm): 1.79 (s, 3H), 1.82-1.91 (m, 2H), 3.17-3.23 (m, 2H), 4.18 (t, J=6.0 Hz, 2H), 4.21 (s, 2H), 7.56 (s, 1H), 7.90 (t, J=5.4 Hz, 1H), 8.71 (s, 1H).

Step 3

In a similar manner to Step 2 of Example 1, 4-chloro-5-[3-(acetylamino)propoxy]-7-iodoisoindolinone (78.2 mg, 0.191 mmol) was dissolved in acetonitrile (2.4 mL), and the solution was treated with Compound BD (137 mg, 0.383 mmol), palladium acetate (3.4 mg, 0.015 mmol), tri(o-tolyl)phosphine (8.5 mg, 0.031 mmol) and triethylamine (0.226 mL, 1.91 mmol), followed by purification by slurry using diisopropylether to obtain 4-chloro-5-[3-(acetylamino)propoxy]-7-[1-(tert-butoxycarbonyl)-5-(piperidin-1-ylmethyl)indol-2-yl]isoindolinone (94.8 mg, yield 83%).

ESI-MS m/z: 595 [M+H]$^+$; $^1$H-NMR (DMSO-d$_6$) δ(ppm): 1.20 (s, 9H), 1.35-1.52 (m, 6H), 1.78 (s, 3H), 1.86-1.94 (m, 2H), 2.33 (br s, 4H), 3.18-3.25 (m, 2H), 3.51 (s, 2H), 4.23 (t, J=6.3 Hz, 2H), 4.33 (s, 2H), 6.67 (s, 1H), 7.23 (s, 1H), 7.26 (dd, J=1.5, 8.7 Hz, 1H), 7.50 (d, J=1.5 Hz, 1H), 7.91 (t, J=5.1 Hz, 1H), 8.07 (d, J=8.7 Hz, 1H), 8.59 (s, 1H).

Step 4

4-Chloro-5-[3-(acetylamino)propoxy]-7-[1-(tert-butoxycarbonyl)-5-(piperidin-1-ylmethyl)indol-2-yl]isoindolinone (92.8 mg, 0.156 mmol) was added with 4 mol/L hydrogen chloride-ethyl acetate solution (3 mL), followed by stirring at 60° C. for 12 hours. The solvent was evaporated under reduced pressure and the residue was purified by slurry using methanol to obtain Compound 439 (18.6 mg, yield 22%).

ESI-MS m/z: 495 [M+H]$^+$; $^1$H-NMR (DMSO-d$_6$) δ(ppm): 1.26-1.41 (m, 1H), 1.66-1.81 (m, 8H), 1.87-1.98 (m, 2H), 2.78-2.89 (m, 2H), 3.22-3.34 (m, 4H), 4.30-4.36 (m, 4H), 4.44 (s, 1H), 7.32 (dd, J=0.9, 8.4 Hz, 1H), 7.48 (d, J=0.9 Hz, 1H), 7.55 (d, J=8.4 Hz, 1H), 7.80 (br s, 2H), 8.00 (t, J=5.4 Hz, 1H), 9.31 (s, 1H), 10.08 (br s, 1H), 14.01 (s, 1H).

EXAMPLE 440

4-Chloro-5-[3-[N-ethyl(2-hydroxyethyl)amino]propoxy]-7-[1H-5-(piperidin-1-ylmethyl)indol-2-yl]isoindolinone dihydrochloride Step 1

In a similar manner to Step 1 of Example 433, 4-chloro-5-hydroxy-7-[1-(tert-butoxycarbonyl)-5-(piperidin-1-ylmethyl)methylindol-2-yl]isoindolinone (100 mg, 0.202 mmol) was suspended in acetonitrile (5.0 mL), and the suspension was treated with cesium carbonate (98.7 mg, 0.303 mmol) and 1-chloro-3-iodopropane (0.026 mL, 0.242 mmol), followed by purification by flash column chromatography (chloroform/methanol=19/1, 4/1) to obtain 4-chloro-5-(3-chloropropoxy)-7-[1-(tert-butoxycarbonyl)-5-(piperidin-1-ylmethyl)indol-2-yl]isoindolinone (97.7 mg, yield 84%).

ESI-MS m/z: 572 [M+H]$^+$; $^1$H-NMR (CDCl$_3$) δ(ppm): 1.33-1.47 (m, 11H), 1.56-1.63 (m, 4H), 2.29-2.37 (m, 2H), 2.43 (br s, 4H), 3.61 (s, 2H), 3.82 (t, J=6.0 Hz, 2H), 4.29 (t, J=5.7 Hz, 2H), 4.36 (s, 2H), 6.58 (s, 1H), 7.07 (s, 1H), 7.26-7.50 (m, 2H), 7.50 (d, J=1.8 Hz, 1H), 8.13 (d, J=8.7 Hz, 1H).

Step 2

4-Chloro-5-(3-chloropropoxy)-7-[1-(tert-butoxycarbonyl)-5-(piperidin-1-ylmethyl)indol-2-yl]isoindolinone (90.4 mg, 0.158 mmol) was dissolved in N,N-dimethylacetoamide (1.0 mL), and the solution was added with 2-(ethylamino)ethanol (0.321 mL, 2.37 mmol), followed by stirring at 90° C. for 72 hours. The reaction mixture was added with water. The obtained solid was collected by filtration and washed with water, followed by drying under reduced pressure to obtain 4-chloro-5-[3-[N-ethyl(2-hydroxyethyl)amino]propoxy]-7-[1-(tert-butoxycarbonyl)-5-(piperidin-1-ylmethyl)indol-2-yl]isoindolinone (79.8 mg, yield 81%).

ESI-MS m/z: 625 [M+H]$^+$; $^1$H-NMR (CD$_3$OD) δ(ppm): 1.06 (t, J=7.2 Hz, 3H), 1.26 (s, 9H), 1.45-1.47 (m, 1H), 1.56-1.63 (m, 4H), 1.98-2.07 (m, 2H), 2.45 (br s, 4H), 2.59-2.67 (m, 4H), 2.75-2.80 (m, 2H), 3.60 (s, 2H), 3.65 (t, J=6.6 Hz, 2H), 4.25 (t, J=5.7 Hz, 2H), 4.41 (s, 2H), 6.63 (s, 1H), 7.20 (s, 1H), 7.29 (dd, J=1.8, 8.7 Hz, 1H), 7.55 (d, J=1.8 HZ, 1H), 8.16 (d, J=8.7 Hz, 1H).

Step 3

In a similar manner to Step 2 of Example 8, 4-chloro-5-[3-[N-ethyl(2-hydroxyethyl)amino]propoxy]-7-[1-(tert-butoxycarbonyl)-5-(piperidin-1-ylmethyl)indol-2-yl]isoindolinone (79.8 mg, 0.128 mmol) was dissolved in methanol (0.5 mL), and the solution was treated with 10% hydrogen chloride-methanol solution (0.5 mL). The solvent was evaporated under reduced pressure. The residue was purified by slurry using methanol and diisopropylether to obtain Compound 440 (37.0 mg, yield 48%).

ESI-MS m/z: 525 [M+H]$^+$; $^1$H-NMR (DMSO-d$_6$) δ(ppm): 1.25-1.40 (m, 4H), 1.65-1.77 (m, 5H), 2.22-2.31 (m, 2H), 2.77-2.88 (m, 2H), 3.22-3.26 (m, 8H), 3.77-3.82 (m, 2H), 4.30 (d, J=4.2 Hz, 2H), 4.42-4.46 (m, 4H), 5.38 (t, J=5.1 Hz, 1H), 7.34 (dd, J=0.9, 8.4 Hz, 1H), 7.50 (d, J=0.9 Hz, 1H), 7.54 (d, J=8.4 Hz, 1H), 7.83 (s, 1H), 7.85 (s, 1H), 9.34 (s, 1H), 10.25 (br s, 1H), 10.45 (br s, 1H), 13.99 (s, 1H).

EXAMPLE 441

4-Chloro-5-[2-hydroxy-3-(piperidin-1-yl)propoxy]-7-[1H-5-(piperidin-1-ylmethyl)indol-2-yl]isoindolinone dihydrochloride Step 1

In a similar manner to Step 1 of Example 429, 4-chloro-5-hydroxy-7-iodoisoindolinone (100 mg, 0.323 mmol) was dissolved in DMF (3.0 mL), and the solution was treated with potassium carbonate (93.8 mg, 0.679 mmol), tetrabutylammonium iodide (11.9 mg, 0.032 mmol) and epibromohydrin (0.083 mL, 0.969 mmol). The reaction mixture was added with water. The obtained solid was collected by filtration and washed with water, followed by drying under reduced pressure to obtain 4-chloro-5-(2,3-epoxypropoxy)-7-[1-(tert-butoxycarbonyl)-5-(piperidin-1-ylmethyl)methylindol-2-yl]isoindolinone (49.7 mg, yield 60%).

ESI-MS m/z: 365 [M+H]$^+$; $^1$H-NMR (CDCl$_3$) δ(ppm): 2.86 (dd, J=2.4, 4.8 Hz, 1H), 2.96 (dd, J=4.2, 4.8 Hz, 1H), 3.40-3.45 (m, 1H), 4.09 (dd, J=5.7, 11.1 Hz, 1H), 4.30 (s, 2H), 4.44 (dd, J=2.4, 11.1 Hz, 1H), 6.38 (br s, 1H), 7.46 (s, 1H).

Step 2

In a similar manner to Step 2 of Example 1, 4-chloro-5-(2,3-epoxypropoxy)-7-[1-(tert-butoxycarbonyl)-5-(piperidin- 1-ylmethyl)methylindol-2-yl]isoindolinone (77.1 mg, 0.211 mmol) was dissolved in acetonitrile (2.3 mL), and the solution was treated with Compound BD (151 mg, 0.383 mmol), palladium acetate (3.8 mg, 0.017 mmol), tri(o-tolyl)phosphine (10.3 mg, 0.034 mmol) and triethylamine (0.294 mL, 2.11 mmol), followed by purification by slurry using diisopropylether to obtain 4-chloro-5-(2,3-epoxypropoxy)-7-[1-(tert-butoxycarbonyl)-5-(piperidin-1-ylmethyl)indol-2-yl]isoindolinone (92.3 mg, yield 79%).

ESI-MS m/z: 552 [M+H]$^+$; $^1$H-NMR (CDCl$_3$) δ(ppm): 1.37 (s, 9H), 1.43-1.77 (m, 6H), 2.60 (br s, 4H), 2.85 (dd, J=2.4, 4.8 Hz, 1H), 2.95 (dd, J=4.2, 4.8 Hz, 1H), 3.41-3.46 (m, 1H), 3.80 (s, 2H), 4.12 (dd, J=5.7, 11.4 Hz, 1H), 4.38 (s, 2H), 4.46 (dd, J=3.0, 11.4 Hz, 1H), 6.58 (s, 1H), 6.91 (br s, 1H), 7.08 (s, 1H), 7.33 (dd, J=1.5, 8.7 Hz, 1H), 7.58 (d, J=1.5 Hz, 1H), 8.16 (d, J=8.7 Hz, 1H).

Step 3

4-Chloro-5-(2,3-epoxypropoxy)-7-[1-(tert-butoxycarbonyl)-5-(piperidin-1-ylmethyl)indol-2-yl]isoindolinone (44.9 mg, 0.081 mmol) was dissolved in N,N-dimethylacetoamide (1.0 mL), and the solution was added with piperidine (0.160 mL, 1.61 mmol), followed by stirring at 60° C. for 72 hours. The reaction mixture was added with water. The obtained solid was collected by filtration and washed with water, followed by drying under reduced pressure to obtain 4-chloro-5-[2-hydroxy-3-(piperidin-1-yl)propoxy]-7-[1-(tert-butoxycarbonyl)-5-(piperidin-1-ylmethyl)indol-2-yl]isoindolinone (36.3 mg, yield 70%).

ESI-MS m/z: 637 [M+H]$^+$; $^1$H-NMR (CD$_3$OD) δ(ppm): 1.26 (s, 9H), 1.35-1.66 (m, 12H), 2.40-2.60 (m, 10H), 3.60 (s, 2H), 4.13-4.42 (m, 3H), 6.63 (s, 1H), 7.27-7.30 (m, 2H), 7.52 (s, 1H), 8.16 (d, J=8.4 Hz, 1H).

Step 4

In a similar manner to Step 2 of Example 8, 4-chloro-5-[2-hydroxy-3-(piperidin-1-yl)propoxy]-7-[1-(tert-butoxycarbonyl)-5-(piperidin-1-ylmethyl)indol-2-yl]isoindolinone (36.3 mg, 0.060 mmol) was dissolved in methanol (0.5 mL), and the solution was treated with 10% hydrogen chloride-methanol solution (0.5 mL). The solvent was evaporated under reduced pressure. The residue was purified by slurry using methanol and diisopropylether to obtain Compound 441 (26.4 mg, yield 72%).

ESI-MS m/z: 537 [M+H]$^+$; $^1$H-NMR (DMSO-d$_6$) δ(ppm): 1.28-1.47 (m, 2H), 1.67-1.90 (m, 10H), 2.76-2.89 (m, 2H), 2.92-3.08 (m, 2H), 3.17-3.33 (m, 4H), 3.46-3.59 (m, 2H), 4.30-4.50 (m, 7H), 6.12 (br s, 1H), 7.34 (d, J=8.4 Hz, 1H), 7.52-7.55 (m, 2H), 7.85-7.88 (s, 1H), 9.34 (s, 1H), 10.06 (br s, 1H), 10.45 (br s, 1H), 13.98 (s, 1H).

EXAMPLE 442

4-Chloro-5-[3-(ethylcarbamoylamino)propoxy]-7-[1H-5-(piperidin-1-ylmethyl)indol-2-yl]isoindolinone (Compound 442)

Step 1

4-Chloro-5-(3-aminopropoxy)-7-iodoisoindolinone hydrochloride (100 mg, 0.248 mmol) was suspended in dichloromethane (3.0 mL), and the suspension was added with triethylamine (0.104 mL, 0.744 mmol) and ethyl isocyanate (0.029 mL, 0.372 mmol), followed by stirring at room temperature for 13 hours. The solvent was evaporated under reduced pressure and the residue was purified by slurry using water and acetonitrile to obtain 4-chloro-5-[3-(ethylcarbamoylamino)propoxy]-7-iodoisoindolinone (100 mg, yield 93%).

ESI-MS m/z: 438 [M+H]$^+$; $^1$H-NMR (DMSO-d$_6$) δ(ppm): 0.96 (t, J=6.3 Hz, 3H), 1.82-1.86 (m, 2H), 2.94-3.03 (m, 2H), 3.12-3.18 (m, 2H), 4.16 (t, J=6.0 Hz, 2H), 4.21 (s, 2H), 5.73 (t, J=5.4 Hz, 1H), 5.91 (t, J=5.4 Hz, 1H), 7.57 (s, 1H), 8.70 (s, 1H).

Step 2

In a similar manner to Step 2 of Example 1, 4-chloro-5-[3-(ethylcarbamoylamino)propoxy]-7-iodoisoindolinone (98.5 mg, 0.225 mmol) was dissolved in acetonitrile (3.0 mL), and the solution was treated with Compound BD (161 mg, 0.450 mmol), palladium acetate (4.0 mg, 0.018 mmol), tri(o-tolyl)phosphine (11.0 mg, 0.036 mmol) and triethylamine (0.314 mL, 2.25 mmol), followed by purification by slurry using diisopropylether and hexane to obtain 4-chloro-5-[3-(ethylcarbamoylamino)propoxy]-7-[1-(tert-butoxycarbonyl)-5-(piperidin-1-ylmethyl)indol-2-yl]isoindolinone (69.2 mg, yield 49%).

ESI-MS m/z: 624 [M+H]$^+$; $^1$H-NMR (DMSO-d$_6$) δ(ppm): 0.94 (t, J=7.2 Hz, 3H), 1.20 (s, 9H), 1.39-1.47 (m, 6H), 1.85-1.89 (m, 2H), 2.26-2.36 (m, 4H), 2.92-3.01 (m, 2H), 3.13-3.19 (m, 2H), 3.51 (s, 2H), 4.21 (t, J=6.6 Hz, 2H), 4.33 (s, 2H), 5.73 (t, J=5.7 Hz, 1H), 5.91 (t, J=5.7 Hz, 1H), 6.67 (s, 1H), 7.23-7.28 (m, 2H), 7.49 (s, 1H), 8.06 (d, J=8.7 Hz, 1H), 8.85 (s, 1H).

Step 3

In a similar manner to Step 2 of Example 8, 4-chloro-5-[3-(ethylcarbamoylamino)propoxy]-7-[1-(tert-butoxycarbonyl)-5-(piperidin-1-ylmethyl)indol-2-yl]isoindolinone (69.2 mg, 0.111 mmol) was dissolved in methanol (0.5 mL), and the solution was treated with 10% hydrogen chloride-methanol solution (0.5 mL). The obtained solid was collected by filtration and purified by preparative thin-layer chromatography (chloroform/methanol=4/1) to obtain Compound 442 (25.4 mg, yield 44%).

ESI-MS m/z: 524 [M+H]$^+$; $^1$H-NMR (DMSO-d$_6$) δ(ppm): 0.97 (t, J=7.2 Hz, 3H), 1.44-1.63 (m, 6H), 1.87-1.95 (m, 2H), 2.95-3.04 (m, 2H), 3.17-3.23 (m, 2H), 4.33 (t, J=6.0 Hz, 2H), 4.44 (s, 2H), 5.83 (t, J=5.4 Hz, 1H), 6.04 (t, J=5.7 Hz, 1H), 7.23-7.64 (m, 4H), 7.79 (s, 1H), 9.28 (s, 1H), 13.91 (br s, 1H).

EXAMPLE 443

(S)-4-chloro-5-[3-(2-hydroxymethylpyrrolidin-1-yl)propoxy]-7-[1H-5-(piperidin-1-ylmethyl)indol-2-yl]isoindolinone dihydrochloride (Compound 443)

Step 1

In a similar manner to Step 2 of Example 440, 4-chloro-5-(3-chloropropoxy)-7-[1-(tert-butoxycarbonyl)-5-(piperidin-1-ylmethyl)indol-2-yl]isoindolinone (119 mg, 0.208 mmol) was dissolved in N,N-dimethylacetoamide (1.2 mL), and the solution was treated with (S)-(+)-2-pyrrolidinemethanol (0.205 mL, 2.08 mmol). The reaction mixture was added with water. The obtained solid was collected by filtration and washed with water, followed by drying under reduced pressure to obtain (S)-4-chloro-5-[3-(2-hydroxymethylpyrrolidin-1-yl)propoxy]-7-[1-(tert-butoxycarbonyl)-5-(piperidin-1-ylmethyl)indol-2-yl]isoindolinone (91.0 mg, yield 69%).

ESI-MS m/z: 637 [M+H]$^+$; $^1$H-NMR (CD$_3$OD) δ(ppm): 1.26 (s, 9H), 1.44-1.46 (m, 2H), 1.58-1.79 (m, 7H), 1.90-2.32 (m, 4H), 2.44-2.62 (m, 6H), 3.09-3.18 (m, 2H), 3.44 (dd, J=6.6, 10.8 Hz, 1H), 3.59-3.64 (m, 3H), 4.25 (t, J=5.7 Hz, 2H), 4.40 (s, 2H), 6.63 (s, 1H), 7.19 (s, 1H), 7.29 (dd, J=1.5, 8.4 Hz, 1H), 7.51 (d, J=1.5 Hz, 1H), 8.15 (d, J=8.4 Hz, 1H).

Step 2

In a similar manner to Step 2 of Example 8, (S)-4-chloro-5-[3-(2-hydroxymethylpyrrolidin-1-yl)propoxy]-7-[1-(tert-butoxycarbonyl)-5-(piperidin-1-ylmethyl)indol-2-yl]isoindolinone (91.0 mg, 0.144 mmol) was dissolved in methanol (1.0 mL), and the solution was treated with 10% hydrogen chloride-methanol solution (1.0 mL). The reaction mixture was concentrated and the residue was purified by slurry using diisopropylether to obtain Compound 443 (75.4 mg, yield 86%).

ESI-MS m/z: 537 [M+H]$^+$; $^1$H-NMR (DMSO-d$_6$) δ(ppm): 1.22-1.41 (m, 1H), 1.65-2.39 (m, 9H), 2.77-2.89 (m, 2H), 3.09-3.81 (m, 9H), 4.30 (d, J=4.5 Hz, 2H), 4.43-4.47 (m, 4H), 5.46 (br s, 1H), 7.33 (dd, J=1.5, 8.4 Hz, 1H), 7.53-7.55 (m, 2H), 7.84 (s, 1H), 7.85 (s, 1H), 10.19 (br s, 1H), 10.36 (br s, 1H), 14.00 (s, 1H).

EXAMPLE 444

4-Chloro-5-[3-(4-hydroxymethylpiperidin-1-yl)propoxy]-7-[1H-5-(piperidin-1-ylmethyl)indol-2-yl] isoindolinone dihydrochloride (Compound 444)

Step 1

In a similar manner to Step 2 of Example 440, 4-chloro-5-(3-chloropropoxy)-7-[1-(tert-butoxycarbonyl)-5-(piperidin-1-ylmethyl)indol-2-yl]isoindolinone (97.6 mg, 0.170 mmol) was dissolved in N,N-dimethylacetoamide (1.0 mL), and the solution was treated with 4-piperidine methanol (0.196 mL, 1.70 mmol). The reaction mixture was added with water. The obtained solid was collected by filtration and washed with water, followed by drying under reduced pressure to obtain 4-chloro-5-[3-(4-hydroxymethylpiperidin-1-yl)propoxy]-7-[1-(tert-butoxycarbonyl)-5-(piperidin-1-ylmethyl)indol-2-yl]isoindolinone (87.2 mg, yield 79%).

ESI-MS m/z: 651 [M+H]$^+$; $^1$H-NMR (CD$_3$OD) δ(ppm): 1.26 (s, 9H), 1.44-1.60 (m, 8H), 1.72-1.76 (m, 2H), 1.99-2.12 (m, 5H), 2.44 (br s, 4H), 2.60 (t, J=8.1 Hz, 2H), 2.98-3.02 (m, 2H), 3.36 (d, J=6.3 Hz, 2H), 3.59 (s, 2H), 4.24 (t, J=6.0 Hz, 2H), 4.40 (s, 2H), 6.63 (s, 1H), 7.20 (s, 1H), 7.29 (dd, J=1.8, 8.7 Hz, 1H), 7.51 (d, J=1.8 Hz, 1H), 8.15 (d, J=8.7 Hz, 1H).

Step 2

In a similar manner to Step 2 of Example 8, 4-chloro-5-[3-(4-hydroxymethylpiperidin-1-yl)propoxy]-7-[1-(tert-butoxycarbonyl)-5-(piperidin-1-ylmethyl)indol-2-yl]isoindolinone (86.6 mg, 0.133 mmol) was dissolved in methanol (1.0 mL), and the solution was treated with 10% hydrogen chloride-methanol solution (1.0 mL). The reaction mixture was concentrated and the residue was purified by slurry using diisopropylether to obtain Compound 444 (82.3 mg, yield 99%).

ESI-MS m/z: 551 [M+H]$^+$; $^1$H-NMR (DMSO-d$_6$) δ(ppm): 1.33-2.02 (m, 11H), 2.26-2.36 (m, 2H), 2.77-3.55 (m, 12H), 4.30 (d, J=4.8 Hz, 2H), 4.42-4.45 (m, 4H), 7.34 (dd, J=1.5, 8.4 Hz, 2H), 7.53-7.55 (m, 2H), 7.84 (s, 1H), 7.85 (s, 1H), 9.34 (s, 1H), 10.42 (br s, 1H), 10.51 (br s, 1H), 14.00 (s, 1H).

EXAMPLE 445

4-Chloro-5-[3-(4-hydroxypiperidin-1-yl)propoxy]-7-[1H-5-(piperidin-1-ylmethyl)indol-2-yl]isoindolinone dihydrochloride (Compound 445)

Step 1

In a similar manner to Step 2 of Example 440, 4-chloro-5-(3-chloropropoxy)-7-[1-(tert-butoxycarbonyl)-5-(piperidin-1-ylmethyl)indol-2-yl]isoindolinone (90.2 mg, 0.158 mmol) was dissolved in N,N-dimethylacetoamide (0.9 mL), and the solution was treated with 4-hydroxypiperidine (159 mg, 1.58 mmol). The reaction mixture was added with water. The obtained solid was collected by filtration and washed with water, followed by drying under reduced pressure to obtain 4-chloro-5-[3-(4-hydroxypiperidin-1-yl)propoxy]-7-[1-(tert-butoxycarbonyl)-5-(piperidin-1-ylmethyl)indol-2-yl]isoindolinone (80.6 mg, yield 80%).

ESI-MS m/z: 637 [M+H]$^+$; $^1$H-NMR (CD$_3$OD) δ(ppm): 1.27 (s, 9H), 1.46-1.64 (m, 8H), 1.84-1.89 (m, 2H), 2.02-2.12 (m, 2H), 2.22 (t, J=9.6 Hz, 2H), 2.46 (br s, 4H), 2.59-2.64 (m, 2H), 2.84-2.91 (m, 2H), 3.58-3.65 (m, 3H), 4.26 (t, J=6.0 Hz, 1H), 4.40 (s, 2H), 6.63 (d, J=0.6 Hz, 1H), 7.21 (s, 1H), 7.29 (dd, J=1.2, 8.7 Hz, 1H), 7.51 (d, J=1.2 Hz, 1H), 8.17 (d. J=8.7 Hz, 1H).

Step 2

In a similar manner to Step 2 of Example 8, 4-chloro-5-[3-(4-hydroxypiperidin-1-yl)propoxy]-7-[1-(tert-butoxycarbonyl)-5-(piperidin-1-ylmethyl)indol-2-yl]isoindolinone (77.4 mg, 0.121 mmol) was dissolved in methanol (1.0 mL), and the solution was treated with 10% hydrogen chloride-methanol solution (1.0 mL). The reaction mixture was concentrated and the residue was purified by reslurry using diisopropylether to obtain Compound 445 (71.4 mg, yield 97%).

ESI-MS m/z: 537 [M+H]$^+$; $^1$H-NMR (DMSO-d$_6$) δ(ppm): 1.29-1.40 (m, 1H), 1.65-2.10 (m, 9H), 2.28-2.34 (m, 2H), 2.77-3.65 (m, 10H), 3.95 (br s, 1H), 4.29-4.46 (m, 7H), 7.33 (dd, J=1.2, 8.4 Hz, 1H), 7.53-7.55 (m, 2H), 7.83 (s, 1H), 7.84 (s, 1H), 9.34 (s, 1H), 10.40 (br s, 1H), 10.68 (br s, 1H), 14.00 (s, 1H).

EXAMPLE 446

4-Chloro-5-[3-(1-hydroxy-2-methyl-2-propylamino)propoxy]-7-[1H-5-(piperidin-1-ylmethyl)indol-2-yl]isoindolinone dihydrochloride (Compound 446)

Step 1

In a similar manner to Step 2 of Example 440, 4-chloro-5-(3-chloropropoxy)-7-[1-(tert-butoxycarbonyl)-5-(piperidin-1-ylmethyl)indol-2-yl]isoindolinone (90.6 mg, 0.158 mmol) was dissolved in N,N-dimethylacetoamide (0.9 mL), and the solution was treated with 2-amino-2-methyl-1-propanol (0.159 mL, 1.58 mmol). The reaction mixture was added with water. The obtained solid was collected by filtration and washed with water, followed by drying under reduced pressure to obtain 4-chloro-5-[3-(1-hydroxy-2-methyl-2-propylamino)propoxy]-7-[1-(tert-butoxycarbonyl)-5-(piperidin-1-ylmethyl)indol-2-yl]isoindolinone (37.7 mg, yield 38%).

ESI-MS m/z: 625 [M+H]$^+$; $^1$H-NMR (CD$_3$OD) δ(ppm): 1.08 (s, 6H), 1.28 (s, 9H), 1.46-1.48 (m, 2H), 1.59-1.62 (m, 4H), 2.02-2.10 (m, 2H), 2.46 (br s, 4H), 2.82 (t, J=6.9 Hz, 2H), 3.39 (s, 2H), 3.60 (s, 2H), 4.29 (t, J=5.7 Hz, 2H), 4.40 (s, 1H), 6.63 (d, J=0.3 Hz, 1H), 7.22 (s, 1H), 7.29 (dd, J=1.8, 8.7 Hz, 1H), 7.51 (d, J=1.8 Hz, 1H), 8.17 (d, J=8.7 Hz, 1H).

Step 2

In a similar manner to Step 2 of Example 8, 4-chloro-5-[3-(1-hydroxy-2-methyl-2-propylamino)propoxy]-7-[1-(tert-butoxycarbonyl)-5-(piperidin-1-ylmethyl)indol-2-yl]isoindolinone (33.3 mg, 0.053 mmol) was dissolved in methanol (1.0 mL), and the solution was treated with 10% hydrogen chloride-methanol solution (1.0 mL). The reaction mixture was concentrated and the residue was purified by slurry using diisopropylether to obtain Compound 446 (17.6 mg, yield 56%).

ESI-MS m/z: 525 [M+H]+; 1H-NMR (DMSO-d6) δ(ppm): 1.26-1.38 (m, 7H), 1.65-1.77 (m, 5H), 2.21-2.30 (m, 2H), 2.77-2.89 (m, 2H), 3.06-3.15 (m, 2H), 3.27 (br s, 2H), 3.47 (d, J=3.9 Hz, 2H), 4.30 (d, J=4.8 Hz, 2H), 4.45-4.49 (m, 4H), 5.61 (br s, 1H), 7.34 (dd, J=1.2, 8.4 Hz, 1H), 7.52-7.55 (m, 2H), 7.85 (s, 2H), 8.79 (br s, 2H), 9.34 (s, 1H), 10.42 (br s, 1H), 14.00 (s, 1H).

EXAMPLE 447

4-Chloro-5-[3-(morpholin-1-yl)propoxy]-7-[1H-5-(piperidin-1-ylmethyl)indol-2-yl]isoindolinone dihydrochloride (Compound 447)

Step 1

In a similar manner to Step 2 of Example 440, 4-chloro-5-(3-chloropropoxy)-7-[(1-(tert-butoxycarbonyl)-5-(piperidin-1-ylmethyl)indol-2-yl]isoindolinone (90.2 mg, 0.158 mmol) was dissolved in N,N-dimethylacetoamide (0.9 mL), and the solution was treated with morpholine (0.138 mL, 1.58 mmol). The reaction mixture was added with water. The obtained solid was collected by filtration and washed with water, followed by drying under reduced pressure to obtain 4-chloro-5-[3-(morpholin-1-yl)propoxy]-7-[1-(tert-butoxycarbonyl)-5-(piperidin-1-ylmethyl)indol-2-yl]isoindolinone (79.5 mg, yield 81%).

ESI-MS m/z: 623 [M+H]+; 1H-NMR (CDCl3) δ(ppm): 1.39-1.47 (m, 11H), 1.55-1.62 (m, 4H), 2.01-2.10 (m, 8H), 2.57 (t, J=6.9 Hz, 2H), 3.56 (s, 2H), 3.69-3.72 (m, 4H), 4.21 (t, J=6.3 Hz, 2H), 4.36 (s, 2H), 6.56 (d, J=0.6 Hz, 1H), 7.29 (dd, J=1.8, 8.7 Hz, 1H), 7.49 (d, J=1.8 Hz, 1H), 8.12 (d, J=8.7 Hz, 1H).

Step 2

In a similar manner to Step 2 of Example 8, 4-chloro-5-[3-(morpholin-1-yl)propoxy]-7-[1-(tert-butoxycarbonyl)-5-(piperidin-1-ylmethyl)indol-2-yl]isoindolinone (79.5 mg, 0.128 mmol) was dissolved in methanol (1.0 mL), and the solution was treated with 10% hydrogen chloride-methanol solution (1.0 mL). The reaction mixture was concentrated and the residue was purified by slurry using diisopropylether to obtain Compound 447 (60.3 mg, yield 79%).

ESI-MS m/z: 523 [M+H]+; 1H-NMR (DMSO-d6) δ(ppm): 1.22-1.41 (m, 1H), 1.65-1.77 (m, 5H), 2.28-2.38 (m, 2H), 2.82-2.89 (m, 2H), 3.06-3.16 (m, 2H), 3.26-3.31 (m, 4H), 3.47 (br s, 2H), 3.79-3.98 (m, 4H), 4.29 (d, J=5.1 Hz, 2H), 4.45-4.48 (m, 4H), 7.34 (dd, J=1.5, 8.7 Hz, 1H), 7.53-7.55 (m, 2H), 7.84 (s, 1H), 7.86 (s, 1H), 9.34 (s, 1H), 10.41 (br s, 1H), 11.47 (br s, 1H), 14.00 (s, 1H).

EXAMPLE 448

4-Chloro-5-[3-(4-methylpyperazin-1-yl)propoxy]-7-[1H-5-(piperidin-1-ylmethyl)indol-2-yl]isoindolinone trihydrochloride (Compound 448)

Step 1

In a similar manner to Step 2 of Example 440, 4-chloro-5-(3-chloropropoxy)-7-[1-(tert-butoxycarbonyl)-5-(piperidin-1-ylmethyl)indol-2-yl]isoindolinone (87.1 mg, 0.152 mmol) was dissolved in N,N-dimethylacetoamide (0.9 mL), and the solution was treated with N-methylpiperazine (0.138 mL, 1.58 mmol). The reaction mixture was added with water. The obtained solid was collected by filtration and washed with water, followed by drying under reduced pressure to obtain 4-chloro-5-[3-(4-methylpyperazin-1-yl)propoxy]-7-[1-(tert-butoxycarbonyl)-5-(piperidin-1-ylmethyl)indol-2-yl]isoindolinone (59.5 mg, yield 68%).

ESI-MS m/z: 636 [M+H]+; 1H-NMR (CDCl3) δ(ppm): 1.37-1.43 (m, 11H), 1.56-1.57 (m, 4H), 2.03-2.59 (m, 19H), 3.57 (s, 2H), 4.20 (t, J=6.0 Hz, 2H), 4.35 (s, 2H), 6.56 (s, 1H), 7.06 (s, 1H), 7.11 (br s, 1H), 7.29 (dd, J=1.5, 8.7 Hz, 1H), 7.46 (d, J=1.5 Hz, 1H), 8.12 (d, J=8.7 Hz, 1H).

Step 2

In a similar manner to Step 2 of Example 8, 4-chloro-5-[3-(4-methylpyperazin-1-yl)propoxy]-7-[1-(tert-butoxycarbonyl)-5-(piperidin-1-ylmethyl)indol-2-yl]isoindolinone (60.3 mg, 0.095 mmol) was dissolved in methanol (1.0 mL), and the solution was treated with 10% hydrogen chloride-methanol solution (1.0 mL). The reaction mixture was concentrated and the residue was purified by slurry using diisopropylether to obtain Compound 448 (58.3 mg, yield 95%).

ESI-MS m/z: 536 [M+H]+; 1H-NMR (DMSO-d6) δ(ppm): 1.28-1.38 (m, 1H), 1.65-1.77 (m, 5H), 2.26-2.31 (m, 2H), 2.79-2.82 (m, 5H), 3.26-3.81 (m, 12H), 4.30 (d, J=4.2 Hz, 2H), 4.45-4.48 (m, 4H), 7.34 (d, J=8.4 Hz, 1H), 7.52-7.55 (m, 2H), 7.83 (s, 1H), 7.85 (s, 1H), 9.34 (s, 1H), 10.42 (br s, 1H), 12.08 (br s, 2H), 14.00 (s, 1H).

EXAMPLE 449

4-Chloro-5-(3-chloropropoxy)-7-[1H-5-(piperidin-1-ylmethyl)indol-2-yl]isoindolinone hydrochloride (Compound 449)

In a similar manner to Step 2 of Example 8, 4-chloro-5-(3-chloropropoxy)-7-[1-(tert-butoxycarbonyl)-5-(piperidin-1-ylmethyl)indol-2-yl]isoindolinone (51.6 mg, 0.090 mmol) was dissolved in methanol (1.0 mL), and the solution was treated with 10% hydrogen chloride-methanol solution (1.0 mL). The obtained solid was collected by filtration and washed with methanol, followed by drying under reduced pressure to obtain Compound 449 (27.8 mg, yield 61%).

ESI-MS m/z: 472 [M+H]+; 1H-NMR (DMSO-d6) δ(ppm): 1.28-1.41 (m, 1H), 1.65-1.76 (m, 5H), 2.23-2.31 (m, 2H), 2.77-2.89 (m, 2H), 3.27-3.31 (m, 2H), 3.86 (t, J=6.3 Hz, 2H), 4.30 (d, J=5.1 Hz, 2H), 4.43-4.71 (m, 2H), 7.33 (dd, J=1.5, 8.4 Hz, 1H), 7.50 (d, J=1.5 Hz, 1H), 7.54 (d, J=8.4 Hz, 1H), 7.82 (s, 1H), 7.84 (s, 1H), 9.32 (s, 1H), 10.27 (br s, 1H), 14.00 (s, 1H).

EXAMPLE 450

4-Methanesulfonyloxy-5-methoxy-7-[1H-5-(azetidin-1-ylmethyl)indol-2-yl]isoindolinone hydrochloride (Compound 450)

Step 1

In a similar manner to Step 2 of Example 6, 4-methanesulfonyloxy-5-methoxy-7-[1-(tert-butoxycarbonyl)-5-formyl]indolylisoindolinone (50 mg, 0.100 mmol) was dissolved in acetonitrile (2.9 mL), and the solution was treated with azetidine hydrochloride (47.0 mg, 0.502 mmol), acetic acid (0.115 mL, 2.00 mmol) and sodium triacetoxyborohydride (64 mg, 0.30 mmol) to obtain 4-methanesulfonyloxy-5-methoxy-7-[1-(tert-butoxycarbonyl)-5-(azetidin-1-ylmethyl)indol-2-yl]isoindolinone (36.2 mg, yield 67%).

ESI-MS m/z: 542 [M+H]+; 1H-NMR (CDCl3) δ(ppm): 1.35 (s, 9H), 2.05-2.16 (m, 2H), 3.26 (t, J=7.0 Hz, 4H), 3.34 (s, 3H), 3.95 (s, 2H), 4.00 (s, 3H), 4.55 (s, 2H), 6.24 (br s, 1H), 6.57 (s, 1H), 7.10 (s, 1H), 7.26 (m, 1H), 7.48 (s, 1H), 8.17 (d, J=8.8 Hz, 1H).

Step 2

In a similar manner to Step 2 of Example 8, 4-methanesulfonyloxy-5-methoxy-7-[1-(tert-butoxycarbonyl)-5-(azetidin-1-ylmethyl)indol-2-yl]isoindolinone (33.8 mg, 0.0624 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 450 (21.4 mg, yield 72%).

ESI-MS m/z: 442 [M+H]$^+$; $^1$H-NMR (DMSO-d$_6$) δ(ppm): 2.27-2.37 (m, 2H), 3.53 (s, 3H), 3.80-4.08 (m, 4H), 4.08 (s, 3H), 4.36 (s, 2H), 4.52 (s, 2H), 7.23 (dd, J=1.3, 8.4 Hz, 1H), 7.48 (s, 1H), 7.55 (d, J=8.4 Hz, 1H), 7.74 (s, 1H), 7.86 (s, 1H), 9.26 (s, 1H), 10.50 (br s, 1H), 13.98 (s, 1H).

EXAMPLE 451

4-Methanesulfonyloxy-5-methoxy-7-[1H-5-(3-hydroxypyrrolidin-1-ylmethyl)indol-2-yl]isoindolinone hydrochloride (Compound 451)

Step 1

In a similar manner to Step 2 of Example 6, 4-methanesulfonyloxy-5-methoxy-7-[1-(tert-butoxycarbonyl)-5-formyl]indolylisoindolinone (50 mg, 0.100 mmol) was dissolved in acetonitrile (2.9 mL), and the solution was treated with D,L-3-pyrrolidinol (0.083 mL, 1.0 mmol), acetic acid (0.115 mL, 2.00 mmol) and sodium triacetoxyborohydride (64 mg, 0.30 mmol) to obtain 4-methanesulfonyloxy-5-methoxy-7-[1-(tert-butoxycarbonyl)-5-(3-hydroxypyrrolidin-1-ylmethyl)indol-2-yl]isoindolinone (39.0 mg, yield 68%).

ESI-MS m/z: 572 [M+H]$^+$; $^1$H-NMR (CDCl$_3$) δ(ppm): 1.25 (m, 1H), 1.36 (s, 9H), 1.80 (m, 1H), 2.18 (m, 1H), 2.36 (m, 1H), 2.58 (m, 1H), 2.71 (m, 1H), 2.91 (m, 1H), 3.34 (s, 3H), 3.76 (s, 2H), 4.00 (s, 3H), 4.34 (m, 1H), 4.56 (s, 2H), 6.24 (br s, 1H), 6.57 (s, 1H), 7.10 (s, 1H), 7.31 (d, J=9.0 Hz, 1H), 7.51 (s, 1H), 8.18 (d, J=9.0 Hz, 1H).

Step 2

In a similar manner to Step 2 of Example 8, 4-methanesulfonyloxy-5-methoxy-7-[1-(tert-butoxycarbonyl)-5-(3-hydroxypyrrolidin-1-ylmethyl)indol-2-yl]isoindolinone (36.5 mg, 0.0640 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 451 (27.5 mg, yield 85%).

ESI-MS m/z: 472 [M+H]$^+$; $^1$H-NMR (DMSO-d$_6$) δ(ppm): 1.88 (m, 1H), 2.86-3.60 (m, 6H), 3.53 (s, 3H), 4.08 (s, 3H), 4.35-4.45 (m, 2H), 4.52 (s, 2H), 5.45 (m, 1H), 7.33 (d, J=8.4 Hz, 1H), 7.48 (s, 1H), 7.55 (d, J=8.4 Hz, 1H), 7.80 (s, 1H), 7.86 (s, 1H), 9.27 (s, 1H), 10.50 (br s, 1H), 13.98 (s, 1H).

EXAMPLE 452

4-Methanesulfonyloxy-5-methoxy-7-[1H-5-(isopropylaminomethyl)indol-2-yl]isoindolinone hydrochloride (Compound 452)

Step 1

In a similar manner to Step 2 of Example 6, 4-methanesulfonyloxy-5-methoxy-7-[1-(tert-butoxycarbonyl)-5-formyl]indolylisoindolinone (60 mg, 0.120 mmol) was dissolved in acetonitrile (3.5 mL), and the solution was treated with isopropylamine (0.102 mL, 1.20 mmol), acetic acid (0.137 mL, 2.40 mmol) and sodium triacetoxyborohydride (76 mg, 0.36 mmol) to obtain 4-methanesulfonyloxy-5-methoxy-7-[1-(tert-butoxycarbonyl)-5-(isopropylaminomethyl)indol-2-yl]isoindolinone (32.2 mg, yield 49%).

ESI-MS m/z: 544 [M+H]$^+$; $^1$H-NMR (CDCl$_3$) δ(ppm): 1.11 (d, J=6.1 Hz, 6H), 1.35 (s, 9H), 2.87 (m, 1H), 3.34 (s, 3H), 3.89 (s, 2H), 4.00 (s, 3H), 4.55 (s, 2H), 6.29 (br s, 1H), 6.57 (s, 1H), 7.10 (s, 1H), 7.29 (dd, J=1.4, 8.5 Hz, 1H), 7.50 (d, J=1.4 Hz, 1H), 8.19 (d, J=8.5 Hz, 1H).

Step 2

In a similar manner to Step 2 of Example 8, 4-methanesulfonyloxy-5-methoxy-7-[1-(tert-butoxycarbonyl)-5-(isopropylaminomethyl)indol-2-yl]isoindolinone (29.8 mg, 0.0550 mmol) was dissolved in methanol (1 mL), and the solution was treated with 10% hydrogen chloride-methanol solution (1 mL). The precipitated solid was collected by filtration and washed with methanol, followed by drying under reduced pressure to obtain Compound 452 (17.6 mg, yield 67%).

ESI-MS m/z: 444 [M+H]$^+$; $^1$H-NMR (DMSO-d$_6$) δ(ppm): 1.30 (d, J=6.4 Hz, 6H), 3.25 (m, 1H), 3.53 (s, 3H), 4.08 (s, 3H), 4.19 (s, 2H), 4.52 (s, 2H), 7.32 (dd, J=1.4, 8.4 Hz, 1H), 7.48 (s, 1H), 7.55 (d, J=8.4 Hz, 1H), 7.78 (s, 1H), 7.86 (s, 1H), 8.84 (br s, 2H), 9.28 (s, 1H), 14.00 (s, 1H).

EXAMPLE 453

4-Methanesulfonyloxy-5-methoxy-7-[1H-5-(pyperazin-1-ylmethyl)indol-2-yl]isoindolinone dihydrochloride (Compound 453)

Step 1

In a similar manner to Step 2 of Example 6, 4-methanesulfonyloxy-5-methoxy-7-[1-(tert-butoxycarbonyl)-5-formyl]indolylisoindolinone (60 mg, 0.120 mmol) was dissolved in acetonitrile (3.5 mL), and the solution was treated with 1-tert-butoxycarbonylpiperazine (112 mg, 0.602 mmol), acetic acid (0.137 mL, 2.40 mmol) and sodium triacetoxyborohydride (76 mg, 0.36 mmol) to obtain 4-methanesulfonyloxy-5-methoxy-7-[1-(tert-butoxycarbonyl)-5-(pyperazin-1-ylmethyl)indol-2-yl]isoindolinone (58.6 mg, yield 73%) was obtained.

ESI-MS m/z: 671 [M+H]$^+$; $^1$H-NMR (CDCl$_3$) δ(ppm): 1.36 (s, 9H), 1.46 (s, 9H), 2.33-2.49 (m, 4H), 3.34 (s, 3H), 3.37-3.50 (m, 4H), 3.60 (s, 2H), 4.00 (s, 3H), 4.56 (s, 2H), 6.18 (br s, 1H), 6.57 (s, 1H), 7.10 (s, 1H), 7.31 (dd, J=1.5, 8.7 Hz, 1H), 7.49 (s, 1H), 8.18 (d, J=8.7 Hz, 1H).

Step 2

In a similar manner to Step 2 of Example 8, 4-methanesulfonyloxy-5-methoxy-7-[1-(tert-butoxycarbonyl)-5-(pyperazin-1-ylmethyl)indol-2-yl]isoindolinone (56.0 mg, 0.0830 mmol) was dissolved in methanol (1.5 mL), and the solution was treated with 10% hydrochloric acid-methanol solution (1.5 mL). The precipitated solid was collected by filtration and washed with methanol, followed by drying under reduced pressure to obtain Compound 453 (32.8 mg, yield 78%).

mp 195-198° C.; ESI-MS m/z: 444 [M+H]$^+$; $^1$H-NMR (DMSO-d$_6$) δ(ppm): 1.30 (d, J=6.4 Hz, 6H), 3.25 (m, 1H), 3.53 (s, 3H), 4.08 (s, 3H), 4.19 (s, 2H), 4.52 (s, 2H), 7.32 (dd, J=1.4, 8.4 Hz, 1H), 7.48 (s, 1H), 7.55 (d, J=8.4 Hz, 1H), 7.78 (s, 1H), 7.86 (s, 1H), 8.84 (br s, 2H), 9.28 (s, 1H), 14.00 (s, 1H).

EXAMPLE 454

4-Methanesulfonyloxy-5-methoxy-7-[1H-5-(3-methoxypropylaminomethyl)indol-2-yl]isoindolinone hydrochloride (Compound 454)

Step 1

In a similar manner to Step 2 of Example 6, 4-methanesulfonyloxy-5-methoxy-7-[1-(tert-butoxycarbonyl)-5-formyl]indolylisoindolinone (100 mg, 0.200 mmol) was dissolved in acetonitrile (5.8 mL), and the solution was treated with 3-methoxypropylamine (0.205 mL, 2.00 mmol), acetic acid (0.229 mL, 4.00 mmol) and sodium triacetoxyborohydride (127 mg, 0.600 mmol) to obtain 4-methanesulfonyloxy-5-methoxy-7-[1-(tert-butoxycarbonyl)-5-(3-methoxypropylaminomethyl)indol-2-yl]isoindolinone (80.4 mg, yield 70%).

ESI-MS m/z: 574 [M+H]$^+$; $^1$H-NMR (CDCl$_3$) δ(ppm): 1.35 (s, 9H), 1.77-1.88 (m, 2H), 2.76 (t, J=6.6 Hz, 2H), 3.31 (s, 3H), 3.35 (s, 3H), 3.45 (t, J=6.6 Hz, 2H), 3.93 (s, 2H), 4.01 (s, 3H), 4.56 (s, 2H), 6.41 (br s, 1H), 6.58 (s, 1H), 7.11 (s, 1H), 7.29 (dd, J=1.5, 8.6 Hz, 1H), 7.52 (s, 1H), 8.21 (d, J=8.6 Hz, 1H).

Step 2

In a similar manner to Step 2 of Example 8, 4-methanesulfonyloxy-5-methoxy-7-[1-(tert-butoxycarbonyl)-5-(3-methoxypropylaminomethyl)indol-2-yl]isoindolinone (78.0 mg, 0.136 mmol) was dissolved in methanol (1.5 mL), and the solution was treated with 10% hydrogen chloride-methanol solution (1.5 mL). The precipitated solid was collected by filtration and washed with methanol, followed by drying under reduced pressure to obtain Compound 454 (56.6 mg, yield 829).

mp 208-210° C.; ESI-MS m/z: 474 [M+H]$^+$; $^1$H-NMR (DMSO-d$_6$) δ(ppm): 1.83-1.93 (m, 2H), 2.94 (t, J=7.5 Hz, 2H), 3.22 (s, 3H), 3.37 (t, J=5.8 Hz, 2H), 3.53 (s, 3H), 4.08 (s, 3H), 4.20 (s, 2H), 4.52 (s, 2H), 7.29 (d, J=8.4 Hz, 1H), 7.48 (s, 1H), 7.55 (d, J=8.4 Hz, 1H), 7.75 (s, 1H), 7.86 (s, 1H), 8.88 (br s, 2H), 9.28 (s, 1H), 14.00 (s, 1H).

EXAMPLE 455

4-Methanesulfonyloxy-5-methoxy-7-{1H-5-[N-(2-methoxyethyl)methylaminomethyl]indol-2-yl}isoindolinone (Compound 455)

Step 1

In a similar manner to Step 2 of Example 6, 4-methanesulfonyloxy-5-methoxy-7-[1-(tert-butoxycarbonyl)-5-formylindol-2-yl]isoindolinone (856 mg, 1.71 mmol) was dissolved in acetonitrile (17.0 mL), and the solution was treated with (2-methoxyethyl)methylamine (2.76 mL, 25.7 mmol), acetic acid (1.47 mL, 25.7 mmol) and sodium triacetoxyborohydride (1.81 g, 8.56 mmol), followed by purification by flash column chromatography (chloroform/methanol=4/1) to obtain 4-methanesulfonyloxy-5-methoxy-7-[1-(tert-butoxycarbonyl)-5-[N-(2-methoxyethyl)methylaminomethyl]indol-2-yl]isoindolinone (586 mg, 60%).

ESI-MS m/z: 574 [M+H]$^+$; $^1$H-NMR (CDCl$_3$) δ(ppm): 1.34 (s, 9H), 2.31 (s, 3H), 2.64 (t, J=5.8 Hz, 2H), 3.34 (s, 3H), 3.35 (s, 3H), 3.54 (t, J=5.4 Hz, 2H), 3.67 (s, 2H), 4.00 (s, 3H), 4.54 (s, 2H), 6.57 (s, 1H), 6.74 (br s, 1H), 7.11 (s, 1H), 7.23 (dd, J=1.6, 6.9 Hz, 1H), 7.52 (d, J=1.6 Hz, 1H), 8.18 (d, J=6.9 Hz, 1H).

Step 2

In a similar manner to Step 2 of Example 374, 4-methanesulfonyloxy-5-methoxy-7-[1-(tert-butoxycarbonyl)-5-[N-(2-methoxyethyl)methylaminomethyl]indol-2-yl]isoindolinone (586 mg, 1.02 mmol) was treated with 10% hydrogen chloride-methanol solution (18.0 mL) to obtain Compound 455 (343 mg, yield 71%).

mp 197-199° C.; ESI-MS m/z: 474 [M+H]$^+$; $^1$H-NMR (DMSO-d$_6$) δ(ppm): 2.15 (s, 3H), 2.67 (t, J=5.7 Hz, 2H), 3.20 (s, 3H), 3.43 (t, J=5.7 Hz, 2H), 3.54 (s, 3H), 3.77 (s, 2H), 4.05 (s, 3H), 4.52 (s, 2H), 7.13 (d, J=8.4 Hz, 1H), 7.39 (s, 1H), 7.40 (d, J=8.4 Hz, 1H), 7.55 (s, 1H), 7.85 (s, 1H), 9.16 (s, 1H), 14.1 (s, 1H).

EXAMPLE 456

7-(1H-5-carboxyindol-2-yl)-4-methanesulfonyloxy-5-methoxyisoindolinone (Compound 456)

Step 1

In a similar manner to Step 2 of Example 1, 4-methanesulfonyloxy-5-methoxy-7-iodoisoindolinone (100 mg, 0.261 mmol) was dissolved in DMF (5 mL), and the solution was treated with Compound BG (159 mg, 0.522 mmol), palladium acetate (4.7 mg, 0.020 mmol), tri(o-tolyl)phosphine (13 mg, 0.040 mmol) and triethylamine (0.364 mL, 2.61 mmol), followed by purification by preparative thin-layer chromatography (chloroform/methanol=9/1) to obtain 7-[1-(tert-butoxycarbonyl)-5-carboxyindol-2-yl]-4-methanesulfonyloxy-5-methoxyisoindolinone (29.7 mg).

Step 2

In a similar manner to Step 2 of Example 5, 7-[1-(tert-butoxycarbonyl)-5-carboxyindol-2-yl]-4-methanesulfonyloxy-5-methoxyisoindolinone (29.7 mg) was treated with 4 mol/L hydrogen chloride-ethyl acetate solution (4 mL). The obtained solid was collected by filtration and washed with ethyl acetate, followed by drying under reduced pressure to obtain Compound 456 (11.1 mg, yield 10%, 2 steps).

ESI-MS m/z: 417 [M+H]$^+$; $^1$H-NMR (DMSO-d$_6$) δ(ppm): 3.53 (s, 3H), 4.09 (s, 3H), 4.53 (s, 2H), 7.55 (d, J=8.6 Hz, 1H), 7.56 (s, 1H), 7.75 (dd, J=1.7, 8.6 Hz, 1H), 7.87 (s, 1H), 8.27 (s, 1H), 9.30 (s, 1H), 12.47 (br s, 1H), 14.16 (s, 1H).

EXAMPLE 457

4-Methanesulfonyloxy-5-methoxy-7-[1H-5-(4-methylpyperazin-1-yl)indol-2-yl]isoindolinone dihydrochloride (Compound 457)

Step 1

In a similar manner to Step 2 of Example 1, 4-methanesulfonyloxy-5-methoxy-7-iodoisoindolinone (247 mg, 0.644 mmol) was dissolved in acetonitrile (5.0 mL), and the solution was treated with Compound CA (463 mg, 1.29 mmol), palladium acetate (14.4 mg, 0.0644 mmol), tri(o-tolyl)phosphine (39.3 mg, 0.129 mmol) and triethylamine (0.898 mL, 6.44 mmol), followed by purification by flash column chromatography (chloroform/methanol=9/1) to obtain 4-methanesulfonyloxy-5-methoxy-7-[1-(tert-butoxycarbonyl)-5-(4-methylpyperazin-1-yl)indol-2-yl]isoindolinone (87.5 mg, 24%).

ESI-MS m/z: 571 [M+H]⁺; ¹H-NMR (CDCl₃) δ(ppm): 1.34 (s, 9H), 2.37 (s, 3H), 2.63 (t, J=4.6 Hz, 4H), 3.21 (t, J=4.6 Hz, 4H), 3.33 (s, 1H), 3.99 (s, 3H), 4.54 (s, 2H), 6.35 (s, 1H), 6.52 (s, 1H), 7.03-7.10 (m, 3H), 8.12 (d, J=9.7 Hz, 1H).

Step 2

In a similar manner to Step 2 of Example 8, 4-methanesulfonyloxy-5-methoxy-7-[1-(tert-butoxycarbonyl)-5-(4-methylpyperazin-1-yl)indol-2-yl]isoindolinone (87.5 mg, 0.153 mmol) was treated with 10% hydrogen chloride-methanol solution (5.0 mL), followed by purification by slurry using diisopropylether to obtain Compound 457 (60.3 mg, yield 84%).

mp 257-259° C.; ESI-MS m/z: 471 [M+H]⁺; ¹H-NMR (DMSO-d₆) δ(ppm): 2.85 (s, 3H), 3.10-3.35 (m, 4H), 3.53 (s, 3H), 3.54-3.58 (m, 2H), 3.71 (d, J=12.2 Hz, 2H), 4.08 (s, 3H), 4.18 (br s, 1H), 4.52 (s, 2H), 7.05 (d, J=9.2 Hz, 1H), 7.19 (s, 1H), 7.3.4 (s, 1H), 7.45 (d, J=9.2 Hz, 1H), 7.81 (s, 1H), 9.24 (s, 1H), 10.2 (br s, 1H), 13.8 (br s, 1H).

EXAMPLE 458

4-Chloro-5-fluoro-7-{1H-5-[4-(2-hydroxyethyl)pyperazin-1-ylmethyl]indol-2-yl}isoindolinone dihydrochloride (Compound 458)

Step 1

In a similar manner to Step 2 of Example 1, 4-chloro-5-fluoro-7-iodoisoindolinone (100 mg, 0.320 mmol) was dissolved in acetonitrile (7.0 mL), and the solution was treated with Compound BA (185 mg, 0.640 mmol), palladium acetate (5.7 mg, 0.026 mmol), tri(o-tolyl)phosphine (15.6 mg, 0.0512 mmol) and triethylamine (0.446 mL, 3.20 mmol), followed by purification by flash column chromatography (chloroform/methanol=100/1 to 98/2) to obtain 4-chloro-5-fluoro-7-[1-(tert-butoxycarbonyl)-5-formylindol-2-yl]isoindolinone (98.0 mg, yield 71%).

¹H-NMR (CDCl₃) δ(ppm): 1.43 (s, 9H), 4.45 (s, 2H), 6.45 (s, 1H), 6.73 (d, J=0.7 Hz, 1H), 7.34 (d, J=9.4 Hz, 1H), 7.89 (dd, J=1.7, 8.8 Hz, 1H), 8.10 (d, J=1.2 Hz, 1H), 8.33 (d, J=8.8 Hz, 1H), 10.07 (s, 1H).

Step 2

In a similar manner to Step 2 of Example 6, 4-chloro-5-fluoro-7-[1-(tert-butoxycarbonyl)-5-formylindol-2-yl]isoindolinone (93.7 mg, 0.220 mmol) was dissolved in acetonitrile (6.6 mL), and the solution was treated with 1-(2-hydroxyethyl)piperazine (115 mg, 0.880 mmol), acetic acid (0.252 mL, 4.40 mmol) and sodium triacetoxyborohydride (163 mg, 0.77 mmol). The reaction mixture was added with 1 mol/L hydrochloric acid and extracted with ethyl acetate. The organic layer was washed with saturated aqueous sodium carbonate solution and saturated brine, and dried over anhydrous sodium sulfate. The solvent was evaporated under reduced pressure to obtain 4-chloro-5-fluoro-7-{1-(tert-butoxycarbonyl)-5-[4-(2-hydroxyethyl)pyperazin-1-ylmethyl]indol-2-yl}isoindolinone (102 mg, yield 85%).

APCI-MS m/z: 543 [M+H]⁺; ¹H-NMR (CDCl₃) δ(ppm): 1.41 (s, 9H), 2.54 (m, 10H), 3.59 (m, 4H), 4.41 (s, 2H), 6.58 (s, 1H), 6.79 (br s, 1H), 7.30 (d, J=9.5 Hz, 1H), 7.31 (dd, J=1.7, 8.4 Hz, 1H), 7.50 (d, J=0.7 Hz, 1H), 8.12 (d, J=8.4 Hz, 1H).

Step 3

In a similar manner to Step 2 of Example 8, 4-chloro-5-fluoro-7-{1-(tert-butoxycarbonyl)-5-[4-(2-hydroxyethyl)pyperazin-1-ylmethyl]indol-2-yl}isoindolinone (101 mg, 0.186 mmol) was dissolved in methanol (3.0 mL), and the solution was treated with 10% hydrogen chloride-methanol solution (5.0 mL). The precipitated solid was collected by filtration and washed with methanol, followed by drying under reduced pressure to obtain Compound 458 (77.2 mg, yield 81%).

APCI-MS m/z: 443 [M+H]⁺; ¹H-NMR (DMSO-d₆) δ(ppm): 3.15-3.73 (m, 12H), 4.44 (m, 2H), 4.54 (s, 2H), 7.36 (d, J=8.6 Hz, 1H), 7.48 (s, 1H), 7.58 (d, J=8.4 Hz, 1H), 7.83 (s, 1H), 8.30 (d, J=11.5 Hz, 1H), 9.58 (s, 1H), 11.03 (s, 1H), 11.62 (br s, 1H), 13.93 (s, 1H).

EXAMPLE 459

4-Methanesulfonyloxy-5-methoxy-7-[1H-5-(3-dimethylamino)propylindol-2-yl]isoindolinone hydrochloride (Compound 459)

Step 1

In a similar manner to Step 2 of Example 1, 4-methanesulfonyloxy-5-methoxy-7-iodoisoindolinone (100 mg, 0.261 mmol) was dissolved in acetonitrile (3.0 mL), and the solution was treated with Compound CB (181 mg, 0.523 mmol), palladium acetate (4.7 mg, 0.0209 mmol), tri(o-tolyl)phosphine (12.7 mg, 0.0418 mmol) and triethylamine (0.364 mL, 2.61 mmol), followed by purification by preparative thin-layer chromatography (chloroform/methanol=4/1) to obtain 4-methanesulfonyloxy-5-methoxy-7-[1-(tert-butoxycarbonyl)-5-(3-dimethylamino)propylindol-2-yl]isoindolinone (99.2 mg, 68%).

ESI-MS m/z: 558 [M+H]⁺; ¹H-NMR (CDCl₃) δ(ppm): 1.33 (s, 9H), 1.83-1.93 (m, 2H), 2.29 (s, 6H), 2.38 (t, J=7.8 Hz, 2H), 2.74 (t, J=7.5 Hz, 2H), 3.33 (s, 3H), 3.99 (s, 3H), 4.54 (s, 2H), 6.55 (s, 1H), 6.99 (br s, 1H), 7.09 (s, 1H), 7.18 (dd, J=1.8, 8.7 Hz, 1H), 7.36 (d, J=1.8 Hz, 1H), 8.15 (d, J=8.7 Hz, 1H).

Step 2

In a similar manner to Step 2 of Example 8, 4-methanesulfonyloxy-5-methoxy-7-[1-(tert-butoxycarbonyl)-5-(3-dimethylamino)propylindol-2-yl]isoindolinone (96.5 mg, 0.173 mmol) was dissolved in methanol (1.0 mL), and the solution was treated with 10% hydrogen chloride-methanol solution (1.0 mL). The obtained solid was collected by filtration and washed with methanol, followed by drying under reduced pressure to obtain Compound 459 (60.5 mg, yield 71%).

ESI-MS m/z: 458 [M+H]⁺; ¹H-NMR (DMSO-d₆) δ(ppm): 1.97-2.07 (m, 2H), 2.50-2.68 (m, 8H), 3.00-3.06 (m, 2H), 3.52 (s, 3H), 4.07 (s, 3H), 4.51 (s, 2H), 7.03 (dd, J=1.4, 8.4 Hz, 1H), 7.35 (d, J=1.4 Hz, 1H), 7.40-7.43 (m, 2H), 7.82 (s, 1H), 9.23 (s, 1H), 10.12 (br s, 1H), 13.77 (s, 1H).

EXAMPLE 460

4-Methanesulfonyloxy-5-methoxy-7-{1H-5-[3-(N-(2-hydroxyethyl)ethylamino)-2-hydroxypropoxy]indol-2-yl}isoindolinone hydrochloride (Compound 460)

Step 1

In a similar manner to Step 2 of Example 1, 4-methanesulfonyloxy-5-methoxy-7-iodoisoindolinone (163 mg, 0.424 mmol) was dissolved in acetonitrile (5.0 mL), and the solution was treated with Compound CC (552 mg, 0.849 mmol), palladium acetate (9.5 mg, 0.0424 mmol), tri(o-tolyl)phosphine (0.0258 mg, 0.0849 mmol) and triethylamine (0.591 mL, 4.24 mmol) to obtain 4-methanesulfonyloxy-5-methoxy-7-{1-(tert-butoxycarbonyl)-5-[3-(N-(2-tert-butyldimethylsilyloxyethyl)ethylamino)-2-(tert-butyldimethylsilyloxy)propoxy]indol-2-yl}isoindolinone (254 g, yield 70%).

ESI-MS m/z: 862 [M+H]$^+$; $^1$H-NMR (CDCl$_3$) δ(ppm): 0.05 (s, 6H), 0.11 (s, 3H), 0.13 (s, 3H), 0.89 (s, 9H), 0.91 (s, 9H), 1.02 (t, J=7.6 Hz, 3H), 1.35 (s, 9H), 2.55-2.71 (m, 6H), 3.34 (s, 3H), 3.67 (t, J=6.4 Hz, 2H), 3.84-3.91 (m, 1H), 4.00 (s, 3H), 4.13-4.21 (m, 2H), 4.55 (s, 2H), 6.16 (s, 1H), 6.52 (s, 1H), 6.96 (dd, J=2.6, 8.8 Hz, 1H), 7.01 (d, J=2.6 Hz, 1H), 7.09 (s, 1H), 8.10 (d, J=8.8 Hz, 1H).

Step 2

In a similar manner to Step 2 of Example 8, 4-methanesulfonyloxy-5-methoxy-7-{1-(tert-butoxycarbonyl)-5-[3-(N-(2-tert-butyldimethylsilyloxyethyl)ethylamino)-2-(tert-butyldimethylsilyloxy)propoxy]indol-2-yl}isoindolinone (0.250 g, 0.295 mmol) was treated with 10% hydrogen chloride-methanol solution (5.0 mL). The obtained solid was collected by filtration to obtain Compound 460 (0.112 g, yield 71%).

ESI-MS m/z: 534 [M+H]$^+$; $^1$H-NMR (DMSO-d$_6$) δ(ppm): 1.27 (t, J=6.7 Hz, 3H), 3.21-3.45 (m, 6H), 3.54 (s, 3H), 3.80 (t, J=5.6 Hz, 2H), 3.96-4.05 (m, 2H), 4.08 (s, 3H), 4.35 (br s, 1H), 4.52 (s, 2H), 6.86 (dd, J=2.3, 9.0 Hz, 1H), 7.10 (d, J=2.3 Hz, 1H), 7.33 (s, 1H), 7.42 (d, J=9.0 Hz, 1H), 7.81 (s, 1H), 9.23 (s, 1H), 9.34 (br s, 1H), 13.76 (s, 1H).

EXAMPLE 461

4-Methanesulfonyloxy-5-methoxy-7-[1H-4-hydroxy-indol-2-yl]isoindolinone (Compound 461)

Step 1

In a similar manner to Step 2 of Example 1, 4-methanesulfonyloxy-5-methoxy-7-iodoisoindolinone (165 mg, 0.431 mmol) was dissolved in acetonitrile (10.0 mL), and the solution was treated with Compound CD (337 mg, 0.861 mmol), palladium acetate (9.70 mg, 0.0431 mmol), tri(o-tolyl)phosphine (26.2 mg, 0.0861 mmol) and triethylamine (0.601 mL, 4.31 mmol), followed by purification by flash column chromatography (chloroform/methanol=6/1) to obtain 4-methanesulfonyloxy-5-methoxy-7-[1-(tert-butoxycarbonyl)-4-(tert-butyldimethylsilyloxy)indol-2-yl]isoindolinone (196 mg, yield 76%).

ESI-MS m/z: 603 [M+H]$^+$; $^1$H-NMR (CDCl$_3$) δ(ppm): 0.25 (s, 6H), 1.04 (s, 9H), 1.37 (s, 9H), 3.35 (s, 3H), 4.02 (s, 3H), 4.55 (s, 2H), 6.61-6.67 (m, 2H), 7.11 (s, 1H), 7.18 (dd, J=8.1, 8.1 Hz, 1H), 7.84 (d, J=8.1 Hz, 1H).

Step 2

In a similar manner to Step 2 of Example 8, 4-methanesulfonyloxy-5-methoxy-7-[1-(tert-butoxycarbonyl)-4-(tert-butyldimethylsilyloxy)indol-2-yl]isoindolinone (196 mg, 0.325 mmol) was treated with 10% hydrogen chloride-methanol solution (5.0 mL), followed by purification by flash column chromatography (chloroform/methanol=4/1) to obtain Compound 461 (0.0449 g, yield 36%).

ESI-MS m/z: 603 [M+H]$^+$; $^1$H-NMR (CDCl$_3$) δ(ppm): 3.52 (s, 3H), 4.09 (s, 3H), 4.51 (s, 2H), 6.39 (d, J=7.4 Hz, 1H), 6.87-6.98 (m, 2H), 7.42 (s, 1H), 7.81 (s, 1H), 9.20 (s, 1H), 9.60 (s, 1H), 13.71 (s, 1H).

EXAMPLE 462

4-[1H-5-(piperidinomethyl)indol-2-yl]-1,2-dihydro-1H-pyrrolo[3,4-c]pyridine-3-one (Compound 462)

Step 1

In a similar manner to Step 1 of Example 137, 2-bromonicotinic acid (2.42 g, 12.0 mmol) was dissolved in DMF (48 mL), and the solution was treated with EDCI (3.45 g, 18.0 mmol), HOBT monohydrate (917 mg, 5.99 mmol) and cumylamine (3.40 mL, 24.0 mmol), followed by purification by flash column chromatography (chloroform/methanol=100/1 to 98/2) to obtain 2-bromo-N-(1-methyl-1-phenylethyl)nicotinamide (2.91 g, yield 76%).

APCI-MS m/z: 319 [M+H]$^+$; $^1$H-NMR (CDCl$_3$) δ(ppm): 1.85 (s, 6H), 6.49 (br s, 1H), 7.26-7.40 (m, 4H), 7.51 (m, 2H), 7.91 (dd, J=2.0, 7.6 Hz, 1H), 8.41 (dd, J=2.0, 4.8 Hz, 1H).

Step 2

2-Bromo-N-(1-methyl-1-phenylethyl)nicotinamide (500 mg, 1.57 mmol) was dissolved in THF (20 mL), and the solution was added with LDA-heptane/THF/ethylbenzene solution (2.0 mol/L, 3.5 mL, 7.1 mmol) by drops at −78° C. for 25 minutes under argon atmosphere, followed by stirring at the same temperature for 1.6 hours. Then, the mixture was added with DMF (0.267 mL, 3.45 mmol) and warmed from −78° C. to room temperature over 1 hour. The reaction mixture was added with water and extracted with ethyl acetate. The organic layer was washed with saturated brine and dried over anhydrous sodium sulfate. The solvent was evaporated under reduced pressure and the residue was purified by flash column chromatography (chloroform/methanol=100/1 to 97/3) to obtain 4-bromo-1-hydroxy-2-(1-methyl-1-phenylethyl)-1,2-dihydropyrrolo[3,4-c]pyridine-3-one (138 mg, yield 25%).

APCI-MS m/z: 347 [M+H]$^+$; $^1$H-NMR (CDCl$_3$+CD$_3$OD) δ(ppm): 1.91 (s, 3H), 1.95 (s, 3H), 6.11 (s, 1H), 7.22-7.42 (m, 5H), 7.54 (d, J=5.0 Hz, 1H), 8.51 (s, 1H).

Step 3

In a similar manner to Step 4 of Example 16, 4-bromo-1-hydroxy-2-(1-methyl-1-phenylethyl)-1,2-dihydropyrrolo[3,4-c]pyridine-3-one (239 mg, 0.688 mmol) was dissolved in nitromethane (12 mL), and the solution was treated with trifluoroacetic acid (1.17 mL, 15.1 mmol) and triethylsilane (0.440 mL, 2.75 mmol), followed by purification by preparative thin-layer chromatography (chloroform/methanol=15/1) to obtain 4-bromo-1,2-dihydropyrrolo[3,4-c]pyridine-3-one (49.1 mg, yield 34%).

APCI-MS m/z: 213 [M+H]$^+$; $^1$H-NMR (CDCl$_3$+CD$_3$OD) δ(ppm): 4.47 (d, J=0.7 Hz, 2H), 7.57 (d, J=5.1 Hz, 1H), 8.49 (d, J=5.1 Hz, 1H).

Step 4

In a similar manner to Step 2 of Example 1, 4-bromo-1,2-dihydropyrrolo[3,4-c]pyridine-3-one (23.9 mg, 0.112 mmol) was dissolved in acetonitrile (2.4 mL), and the solution was treated with Compound BD (80.0 mg, 0.224 mmol), palladium acetate (2.5 mg, 0.011 mmol), tri(o-tolyl)phosphine (6.8 mg, 0.022 mmol) and triethylamine (0.156 mL, 1.12 mmol), followed by purification by preparative thin-layer chromatography (chloroform/methanol=5/1) to obtain 4-[1-(tert-butoxycarbonyl)-5-(piperidinomethyl)indol-2-yl]-1,2-dihydro-1H-pyrrolo[3,4-c]pyridine-3-one (19.4 mg, yield 38%).

ESI-MS m/z: 447 [M+H]$^+$; $^1$H-NMR (CDCl$_3$) δ(ppm): 1.32 (s, 9H), 1.43 (m, 2H), 1.60 (m, 4H), 2.45 (br s, 4H), 3.63 (s, 2H), 4.44 (s, 2H), 6.89 (s, 1H), 7.34 (dd, J=1.5, 8.6 Hz, 1H), 7.41 (d, J=4.9 Hz, 1H), 7.54 (s, 1H), 7.66 (br s, 1H), 8.16 (d. J=8.4 Hz, 1H), 8.77 (d, J=5.1 Hz, 1H).

Step 5

In a similar manner to Step 2 of Example 8, 4-[1-(tert-butoxycarbonyl)-5-(piperidinomethyl)indol-2-yl]-1,2-dihydro-1H-pyrrolo[3,4-c]pyridine-3-one (13.8 mg, 0.0309 mmol) was dissolved in methanol (0.97 mL), and the solution was treated with 10% hydrogen chloride-methanol solution (1.45 mL). The obtained solid was collected by filtration and washed with methanol, followed by drying under reduced pressure. The obtained solid was purified by preparative thin-layer chromatography (chloroform/methanol/7 mol/L ammonia-methanol solution=10/0.5/0.5) to obtain Compound 462 (9.5 mg, yield 89%).

ESI-MS m/z: 347 [M+H]$^+$; $^1$H-NMR (DMSO-d$_6$) δ(ppm): 1.40-1.49 (m, 6H), 2.34 (br s, 4H), 3.48 (s, 2H), 4.56 (s, 2H), 7.13 (d, J=8.6 Hz, 1H), 7.44 (d, J=8.4 Hz, 1H), 7.50 (s, 1H), 7.52 (d. J=5.0 Hz, 1H), 7.55 (s, 1H), 8.75 (d, J=5.0 Hz, 1H), 9.34 (s, 1H), 13.44 (s, 1H).

EXAMPLE 463

4-[1H-5-(pyperazin-1-ylmethyl)indol-2-yl]-1,2-dihydro-1H-pyrrolo[3,4-c]pyridine-3-one (Compound 463)

Step 1

In a similar manner to Step 2 of Example 1, 4-bromo-1,2-dihydropyrrolo[3,4-c]pyridine-3-one (49.1 mg, 0.230 mmol) was dissolved in acetonitrile (3.9 mL), and the solution was treated with Compound BB (218 mg, 0.460 mmol), palladium acetate (4.1 mg, 0.018 mmol), tri(o-tolyl)phosphine (11.2 mg, 0.0368 mmol) and triethylamine (0.321 mL, 2.30 mmol), followed by purification by preparative thin-layer chromatography (chloroform/methanol=12/1) to obtain 4-[1-(tert-butoxycarbonyl)-5-(4-tert-butoxycarbonylpyperazin-1-ylmethyl)indol-2-yl]-1,2-dihydro-1H-pyrrolo[3,4-c]pyridine-3-one (43.5 mg, yield 34%).

APCI-MS m/z: 562 [M+H]$^+$; $^1$H-NMR (CDCl$_3$) δ(ppm): 1.31 (s, 9H), 1.49 (s, 9H), 3.48 (m, 8H), 4.46 (s, 2H), 6.94 (s, 1H), 7.42 (dd, J=1.2, 8.6 Hz, 1H), 7.47 (d, J=5.1 Hz, 1H), 7.69 (s, 1H), 7.94 (br s, 1H), 8.29 (d, J=8.6 Hz, 1H), 8.80 (d, J=5.1 Hz, 1H).

Step 2

In a similar manner to Step 2 of Example 8, 4-[1-(tert-butoxycarbonyl)-5-(4-tert-butoxycarbonylpyperazin-1-ylmethyl)indol-2-yl]-1,2-dihydro-1H-pyrrolo[3,4-c]pyridine-3-one (41.6 mg, 0.0740 mmol) was dissolved in methanol (1.7 mL), and the solution was treated with 10% hydrogen chloride-methanol solution (1.7 mL). The obtained solid was collected by filtration and washed with methanol, followed by drying under reduced pressure. The obtained solid was purified by preparative thin-layer chromatography (chloroform/methanol/7 mol/L ammonia-methanol solution=10/0.5/0.5) to obtain Compound 463 (15.7 mg, yield 59%).

APCI-MS m/z: 362 [M+H]$^+$; $^1$H-NMR (DMSO-d$_6$) δ(ppm): 2.69 (m, 4H), 3.44 (m, 4H), 4.56 (s, 2H), 7.19 (d, J=8.2 Hz, 1H), 7.55 (m, 2H), 7.68 (m, 2H), 8.77 (d, J=4.6 Hz, 1H), 9.35 (s, 1H), 13.58 (s, 1H).

EXAMPLE 464

4-[1H-5-(piperidinomethyl)indol-2-yl]-7-chloro-1,2-dihydro-1H-pyrrolo[3,4-c]pyridine-3-one (Compound 464)

Step 1

In a similar manner to Step 1 of Example 16, 2,5-dichloropyridine-3-carbonylchloride (669 mg, 3.19 mmol) was dissolved in dichloromethane (13 mL), and the solution was treated with cumylamine (0.505 mL, 3.51 mmol), triethylamine (0.667 mL, 4.79 mmol) and DMAP (39.0 mg, 0.319 mmol), followed by purification by slurry using diisopropylether/hexane to obtain 2,5-dichloro-N-(1-methyl-1-phenylethyl)nicotinamide (926 mg, yield 94%).

APCI-MS m/z: 309 [M+H]$^+$; $^1$H-NMR (CDCl$_3$) δ(ppm): 1.84 (s, 6H), 6.75 (br s, 1H), 7.27 (m, 1H), 7.37 (m, 2H), 7.47 (m, 2H), 8.05 (d. J=2.6 Hz, 1H), 8.40 (d, J=2.6 Hz, 1H).

Step 2

In a similar manner to Step 2 of Example 16, 2,5-dichloro-N-(1-methyl-1-phenylethyl)nicotinamide (400 mg, 1.29 mmol) was dissolved in THF (16 mL), and the solution was treated with n-butyllithium-hexane solution (2.71 mol/L, 1.20 mL, 3.23 mmol) and DMF (0.250 mL, 3.23 mmol), followed by purification by slurry (diisopropylether) and flash column chromatography (hexane/ethyl acetate=60/40 to 50/50) to obtain 4,7-dichloro-1-hydroxy-2-(1-methyl-1-phenylethyl)-1,2-dihydropyrrolo[3,4-c]pyridine-3-one (312 mg, yield 72%).

ESI-MS m/z: 337 [M+H]$^+$; $^1$H-NMR (CDCl$_3$) δ(ppm): 1.96 (s, 3H), 1.99 (s, 3H), 2.67 (d, J=8.1 Hz, 1H), 6.16 (d, J=8.1 Hz, 1H), 7.25-7.31 (m, 1H), 7.34-7.39 (m, 2H), 7.43-7.47 (m, 2H), 8.48 (s, 1H).

Step 3 in a similar manner to Step 4 of Example 16, 4,7-dichloro-1-hydroxy-2-(1-methyl-1-phenylethyl)-1,2-dihydropyrrolo[3,4-c]pyridine-3-one (38.8 mg, 0.115 mmol) was dissolved in nitromethane (1.6 mL), and the solution was treated with trifluoroacetic acid (0.177 mL, 2.30 mmol) and triethylsilane (55.1 mL, 0.345 mmol), followed by purification by slurry using chloroform/methanol and by preparative thin-layer chromatography (hexane/ethyl acetate=1/1) to obtain 4,7-dichloro-1,2-dihydropyrrolo[3,4-c]pyridine-3-one (16.8 mg, yield 72%).

ESI-MS m/z: 203 [M+H]$^+$; $^1$H-NMR (CDCl$_3$+CD$_3$OD) δ(ppm): 4.46 (s, 2H), 8.49 (s, 1H).

Step 4

In a similar manner to Step 1 of Example 152, 4,7-dichloro-1,2-dihydropyrrolo[3,4-c]pyridine-3-one (21.0 mg, 0.103 mmol) was dissolved in dimethoxyethane (2.1 mL), and the solution was treated with Compound BD (74.0 mg, 0.206 mmol), [bis(diphenylphosphino)ferrocene]dichloropalladium (8.4 mg, 0.010 mmol), potassium carbonate (71.0 mg, 0.515 mmol) and water (0.074 mL), followed by purification by preparative thin-layer chromatography (chloroform/methanol=8/1) to obtain 4-[1-(tert-butoxycarbonyl)-5-(piperidinomethyl)indol-2-yl]-7-chloro-1,2-dihydro-1H-pyrrolo[3,4-c]pyridine-3-one (24.4 mg, yield 49%).

ESI-MS m/z: 481 [M+H]$^+$; $^1$H-NMR (CDCl$_3$) δ(ppm): 1.38 (s, 9H), 1.42 (m, 2H), 1.60 (m, 4H), 2.44 (br s, 4H), 3.63 (s, 2H), 4.41 (s, 2H), 6.90 (s, 1H), 7.36 (dd, J=1.2, 8.6 Hz, 1H), 7.55 (s, 1H), 8.06 (br s, 1H), 8.12 (d, J=8.6 Hz, 1H), 8.70 (s, 1H).

Step 5

In a similar manner to Step 2 of Example 8, 4-[1-(tert-butoxycarbonyl)-5-(piperidinomethyl)indol-2-yl]-7-chloro-1,2-dihydro-1H-pyrrolo[3,4-c]pyridine-3-one (24.0 mg, 0.0499 mmol) was dissolved in methanol (2.4 mL), and the solution was treated with 10% hydrogen chloride-methanol solution (2.4 mL). The obtained solid was collected by filtration and washed with methanol, followed by drying under reduced pressure. The obtained solid was purified by preparative thin-layer chromatography (chloroform/methanol/7 mol/L ammonia-methanol solution=10/0.5/0.5) to obtain Compound 464 (16.6 mg, yield 87%).

APCI-MS m/z: 381 [M+H]$^+$; $^1$H-NMR (DMSO-d$_6$) δ(ppm): 1.34-1.54 (m, 6H), 2.24-2.72 (m, 4H), 3.49 (m, 2H), 4.57 (s, 2H), 7.20 (br s, 1H), 7.48-7.62 (m, 3H), 8.80 (s, 1H), 9.56 (s, 1H), 13.27 (s, 1H).

EXAMPLE 465

4-{1H-5-[4-(2-hydroxyethyl)pyperazin-1-ylmethyl]indol-2-yl}-7-chloro-1,2-dihydro-1H-pyrrolo[3,4-c]pyridine-3-one trihydrochloride (Compound 465)

Step 1

In a similar manner to Step 1 of Example 152, 4,7-dichloro-1,2-dihydropyrrolo[3,4-c]pyridine-3-one (50.0 mg, 0.246 mmol) was dissolved in dimethoxyethane (4.0 mL), and the solution was treated with Compound BU (497 mg, 0.738 mmol), [bis(diphenylphosphino)ferrocene]dichloropalladium (16.0 mg, 0.0197 mmol), potassium carbonate (170 mg, 1.23 mmol) and water (0.133 mL), followed by purification by preparative thin-layer chromatography (chloroform/methanol=10/1) to obtain 4-(1-(tert-butoxycarbonyl)-5-[4-(2-tert-butyldimethylsilyloxyethyl)pyperazin-1-ylmethyl]indol-2-yl)-7-chloro-1,2-dihydro-1H-pyrrolo[3,4-c]pyridine-3-one (89.7 mg, yield 57%).

ESI-MS m/z: 640 [M+H]$^+$; $^1$H-NMR (CDCl$_3$) δ(ppm): 0.50 (s, 6H), 0.88 (s, 9H), 1.42 (s, 9H), 2.54 (m, 10H), 3.59 (s, 2H), 3.76 (t, J=6.3 Hz, 2H), 4.47 (s, 2H), 6.90 (s, 1H), 7.06 (s, 1H), 7.34 (dd, J=1.0, 8.6 Hz, 1H), 7.54 (s, 1H), 8.10 (d, J=8.8 Hz, 1H), 8.71 (s, 1H).

Step 2

In a similar manner to Step 2 of Example 8, 4-(1-(tert-butoxycarbonyl)-5-[4-(2-tert-butyldimethylsilyloxyethyl)pyperazin-1-ylmethyl]indol-2-yl)-7-chloro-1,2-dihydro-1H-pyrrolo[3,4-c]pyridine-3-one (86.3 mg, 0.135 mmol) was dissolved in methanol (2.6 mL), and the solution was treated with 10% hydrogen chloride-methanol solution (2.6 mL). The precipitated solid was collected by filtration and washed with methanol, followed by drying under reduced pressure to obtain Compound 465 (49.7 mg, yield 69%).

APCI-MS m/z: 426 [M+H]$^+$; $^1$H-NMR (DMSO-d$_6$) δ(ppm): 3.15-3.98 (m, 12H), 4.45 (br s, 2H), 4.58 (s, 2H), 7.44 (d, J=8.8 Hz, 1H), 7.62 (d. J=8.4 Hz, 1H), 7.74 (s, 1H), 7.89 (s, 1H), 8.82 (s, 1H), 9.59 (s, 1H), 11.17 (br s, 1H), 11.92 (br s, 1H), 13.34 (s, 1H).

EXAMPLE 466

4-[1H-5-(piperidinomethyl)indol-2-yl]-6-methyl-1,2-dihydro-1H-pyrrolo[3,4-c]pyridine-3-one (Compound 466)

Step 1

In a similar manner to Step 1 of Example 137, 2-chloro-5-methylnicotinic acid (2.00 g, 11.7 mmol) was dissolved in DMF (40 mL), and the solution was treated with EDCI (3.35 g, 17.5 mmol), HOBT monohydrate (890 mg, 5.83 mmol) and cumylamine (3.40 mL, 23.3 mmol). The mixture was added with water. The precipitated solid was collected by filtration and dried under reduced pressure to obtain 2-chloro-6-methyl-N-(1-methyl-1-phenylethyl)nicotinamide (2.09 mg, yield 62%).

APCI-MS m/z: 289 [M+H]$^+$; $^1$H-NMR (CDCl$_3$) δ(ppm): 1.82 (s, 6H), 2.56 (s, 3H), 6.87 (br s, 1H), 7.16 (d, J=7.9 Hz, 1H), 7.23-7.28 (m, 1H), 7.33-7.38 (m, 1H), 7.38-7.50 (m, 2H), 7.98 (d, J=7.7 Hz, 1H).

Step 2

In a similar manner to Step 2 of Example 16, 2-chloro-6-methyl-N-(1-methyl-1-phenylethyl)nicotinamide (500 mg, 1.73 mmol) was dissolved in THF (20 mL), and the solution was treated with n-butyllithium-hexane solution (2.71 mol/L, 4.33 mL, 3.23 mmol) and DMF (0.335 mL, 4.33 mmol), followed by purification by flash column chromatography (hexane/ethyl acetate=80/20 to 75/25) to obtain 4-chloro-1-hydroxy-6-methyl-2-(1-methyl-1-phenylethyl)-1,2-dihydropyrrolo[3,4-c]pyridine-3-one (326 mg, yield 59%).

APCI-MS m/z: 317 [M+H]$^+$; $^1$H-NMR (CDCl$_3$) δ(ppm): 1.93 (s, 3H), 1.96 (s, 3H), 2.61 (s, 3H), 2.83 (br s, 1H), 6.02 (s, 1H), 7.23-7.28 (m, 2H), 7.31-7.36 (m, 2H), 7.42-7.44 (m, 2H).

Step 3

In a similar manner to Step 4 of Example 16, 4-chloro-1-hydroxy-6-methyl-2-(1-methyl-1-phenylethyl)-1,2-dihydropyrrolo[3,4-c]pyridine-3-one (70.0 mg, 0.220 mmol) was dissolved in nitromethane (3.5 mL), and the solution was treated with trifluoroacetic acid (0.509 mL, 6.60 mmol) and triethylsilane (0.141 mL, 0.880 mmol), followed by purification by slurry using isopropylether/hexane to obtain 4-chloro-6-methyl-1,2-dihydropyrrolo[3,4-c]pyridine-3-one (25.5 mg, yield 63%).

ESI-MS m/z: 183 [M+H]$^+$; $^1$H-NMR (CDCl$_3$) d (ppm): 2.66 (s, 3H), 4.44 (s, 2H), 7.23 (br s, 1H), 7.24 (s, 1H).

Step 4

In a similar manner to Step 1 of Example 152, 4-chloro-6-methyl-1,2-dihydropyrrolo[3,4-c]pyridine-3-one (25.0 mg, 0.137 mmol) was dissolved in dimethoxyethane (2.5 mL), and the solution was treated with Compound BD (98.0 mg, 0.274 mmol), [bis(diphenylphosphino)ferrocene]dichloropalladium (11.2 mg, 0.0137 mmol), potassium carbonate (95.0 mg, 0.685 mmol) and water (0.099 mL), followed by purification by preparative thin-layer chromatography (chloroform/methanol=8/1) to obtain 4-[1-(tert-butoxycarbonyl)-5-(piperidinomethyl)indol-2-yl]-6-methyl-1,2-dihydro-1H-pyrrolo[3,4-c]pyridine-3-one (24.1 mg, yield 38%).

APCI-MS m/z: 461 [M+H]$^+$; $^1$H-NMR (CDCl$_3$) δ(ppm): 1.32 (s, 9H), 1.43 (m, 2H), 1.61 (m, 4H), 2.44 (br s, 4H), 2.70 (s, 3H), 3.64 (s, 2H), 4.40 (s, 2H), 6.87 (s, 1H), 7.26 (d, J=2.8 Hz, 1H), 7.32 (d, J=8.6 Hz, 1H), 7.53 (s, 1H), 7.64 (br s, 1H), 8.14 (d, J=8.6 Hz, 1H).

Step 5

In a similar manner to Step 2 of Example 8, 4-[1-(tert-butoxycarbonyl)-5-(piperidinomethyl)indol-2-yl]-6-methyl-1,2-dihydro-1H-pyrrolo[3,4-c]pyridine-3-one (24.1 mg, 0.0523 mmol) was dissolved in methanol (1.45 mL), and the solution was treated with 10% hydrogen chloride-methanol solution (2.9 mL). The obtained solid was collected by filtration and washed with methanol, followed by drying under reduced pressure. The obtained solid was purified by preparative thin-layer chromatography (chloroform/methanol/7 mol/L ammonia-methanol solution=10/0.5/0.5) to obtain Compound 466 (16.9 mg, yield 90%).

ESI-MS m/z: 361 [M+H]$^+$; $^1$H-NMR (DMSO-d$_6$) δ(ppm): 1.35-1.49 (m, 6H), 2.34 (br s, 4H), 2.62 (s, 3H), 3.47 (s, 2H), 4.50 (s, 2H), 7.12 (d, J=8.6 Hz, 1H), 7.35 (s, 1H), 7.43 (d, J=8.4 Hz, 1H), 7.49 (br s, 2H), 9.22 (s, 1H), 13.46 (s, 1H).

EXAMPLE 467

4-{1H-5-[4-(2-hydroxyethyl)pyperazin-1-ylmethyl] indol-2-yl}6-methyl-1,2-dihydro-1H-pyrrolo[3,4-c] pyridine-3-one (Compound 467)

Step 1

In a similar manner to Step 1 of Example 152, 4-chloro-6-methyl-1,2-dihydropyrrolo[3,4-c]pyridine-3-one (65.0 mg, 0.360 mmol) was dissolved in dimethoxyethane (5.6 mL), and the solution was treated with Compound BU (559 mg, 1.08 mmol), [bis(diphenylphosphino)ferrocene]dichloropalladium (23.5 mg, 0.0288 mmol), potassium carbonate (248 mg, 1.80 mmol) and water (0.205 mL), followed by purification by flash column chromatography (chloroform/methanol=100/0 to 92/8) to obtain 4-{1-(tert-butoxycarbonyl)-5-[4-(2-tert-butyldimethylsilyloxyethyl)pyperazin-1-ylmethyl]indol-2-yl}-6-methyl-1,2-dihydro-1H-pyrrolo[3,4-c]pyridine-3-one (55.6 mg, yield 25%).

ESI-MS m/z: 620 [M+H]$^+$; $^1$H-NMR (CDCl$_3$) δ(ppm): 0.05 (s, 6H), 0.88 (s, 9H), 1.35 (s, 9H), 2.51-2.56 (m, 8H), 2.53 (t, J=6.6 Hz, 2H), 2.71 (s, 3H), 3.58 (s, 2H), 3.76 (t, J=6.5 Hz, 2H), 4.43 (s, 2H), 6.65 (br s, 1H), 6.87 (s, 1H), 7.26 (s, 1H), 7.30 (dd, J=1.6, 8.6 Hz, 1H), 7.52 (s, 1H), 8.12 (d, J=8.5 Hz, 1H).

Step 2

In a similar manner to Step 2 of Example 8, 4-(1-(tert-butoxycarbonyl)-5-[4-(2-tert-butyldimethylsilyloxyethyl) pyperazin-1-ylmethyl]indol-2-yl)-6-methyl-1,2-dihydro-1H-pyrrolo[3,4-c]pyridine-3-one (55.6 mg, 0.0897 mmol) was dissolved in methanol (1.7 mL), and the solution was treated with 10% hydrogen chloride-methanol solution (1.7 mL). The precipitated solid was collected by filtration and washed with methanol, followed by drying under reduced pressure to obtain Compound 467 (22.6 mg, yield 49%).

ESI-MS m/z: 406 [M+H]$^+$; $^1$H-NMR (DMSO-d$_6$) δ(ppm): 2.65 (s, 3H), 3.21-3.75 (m, 12H), 4.46-4.52 (m, 4H), 7.42 (s, 1H), 7.44 (d, J=8.4 Hz), 1H), 7.62 (d, J=8.4 Hz, 1H), 7.69 (s, 1H), 7.90 (s, 1H), 9.30 (s, 1H), 11.25-12.40 (br, 3H), 13.60 (s, 1H).

INDUSTRIAL APPLICABILITY

The present invention provides a nitrogen-containing heterocyclic compound or a pharmaceutically acceptable salt thereof having an antitumor activity or the like.

The invention claimed is:

1. A nitrogen-containing heterocyclic compound represented by formula (I):

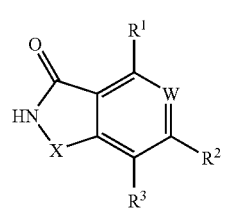

(I)

wherein W represents —CH—;
X represents —CHR$^4$— (wherein R$^4$ represents a hydrogen atom);
R$^1$ represents a group represented by the following formula:

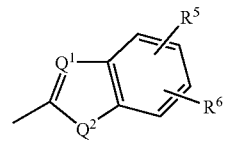

{wherein Q$^1$ represents —CR$^8$— (wherein R$^8$ represents a hydrogen atom),
Q$^2$ represents —NR$^{15}$— (wherein R$^{15}$ represents a hydrogen atom),
R$^5$ represents methyl substituted with NR$^{35b}$R$^{36b}$ (wherein R$^{35b}$ and R$^{36b}$ may be the same or different and each represents a hydrogen atom, C$_{1-10}$ alkyl, C$_{1-10}$ alkyl substituted with hydroxy or C$_{1-10}$ alkoxy), pyrrolidin-1-ylmethyl, piperidin-1-ylmethyl, 4-(2-hydroxyethyl)piperazin-1-ylmethyl, piperazin-1-ylcarbonyl, or 4-methylpiperazin-1-yl, and
R$^6$ represents a hydrogen atom},
R$^2$ represents a hydrogen atom or C$_{1-10}$ alkoxy, and
R$^3$ represents hydroxy, halogen, or —OS(O)$_2$R$^{24a}$ (wherein R$^{24a}$ represents C$_{1-10}$ alkyl, thienyl, pyridyl, amino, or dimethylamino),
or a pharmaceutically acceptable salt thereof.

2. The nitrogen-containing heterocyclic compound or the pharmaceutically acceptable salt thereof according to claim 1, wherein R$^5$ is methyl substituted with NR$^{35a}$R$^{36a}$ (wherein R$^{35a}$ and R$^{36a}$ may be the same or different and each represents a hydrogen atom or C$_{1-10}$ alkyl).

3. A nitrogen-containing heterocyclic compound represented by formula (Ia):

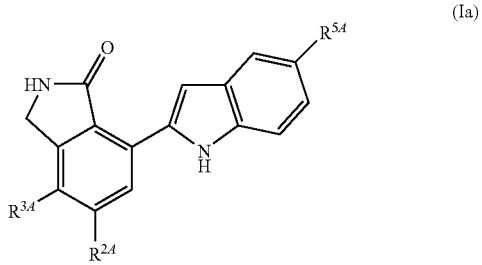

(Ia)

{wherein R$^{2A}$ represents methoxy,
R$^{3A}$ represents methylsulfonyloxy, and
R$^{5A}$ represents (methylamino)methyl, (ethylamino)methyl, (propylamino)methyl, (2,2-dimethylethylamino) methyl, (cyclopropylamino)methyl, (cyclohexylamino) methyl, (dimethylamino)methyl, (diethylamino) methyl, [di(2-hydroxyethyl)amino]methyl, (2-methoxyethylamino)methyl, [di(2-methoxyethyl) amino]methyl, pyrrolidin-1-ylmethyl, piperidinomethyl, (4-piperidinopiperidino)methyl, morpholinomethyl, 4-methylpiperazin-1-ylmethyl or 4-(2-hydroxyethyl)piperazin-1-ylmethyl},
or a pharmaceutically acceptable salt thereof.

4. A pharmaceutical composition comprising, as an active ingredient, the nitrogen-containing heterocyclic compound or the pharmaceutically acceptable salt thereof described in claim 3 together with a pharmaceutically acceptable carrier.

5. The nitrogen-containing heterocyclic compound or the pharmaceutically acceptable salt thereof according to claim 1 or 2, wherein $R^2$ is methoxy.

6. The nitrogen-containing heterocyclic compound or the pharmaceutically acceptable salt thereof according to claim 1 or 2, wherein $R^3$ is methylsulfonyloxy.

7. The nitrogen-containing heterocyclic compound or the pharmaceutically acceptable salt thereof according to claim 5, wherein $R^3$ is methylsulfonyloxy.

8. A nitrogen-containing heterocyclic compound or a pharmaceutically acceptable salt thereof, wherein the compound is selected from the group consisting of:
   4-Methanesulfonyloxy-5-methoxy-7-[1H-5-(methylaminomethyl)indol-2-yl]isoindolinone,
   4-Methanesulfonyloxy-5-methoxy-7-[1H-5-(ethylaminomethyl)indol-2-yl]isoindolinone,
   4-Methanesulfonyloxy-5-methoxy-7-[1H-5-(1-propylaminomethyl)indol-2-yl]isoindolinone,
   4-Methanesulfonyloxy-5-methoxy-7-[1H-5-(cyclopropylaminomethyl)indol-2-yl]isoindolinone,
   4-Methanesulfonyloxy-5-methoxy-7-[1H-5-(cyclohexylaminomethyl)indol-2-yl]isoindolinone, and
   4-Methanesulfonyloxy-5-methoxy-7-[1H-5-(2-methoxyethylaminomethyl)indol-2-yl]isoindolinone.

9. A nitrogen-containing heterocyclic compound or a pharmaceutically acceptable salt thereof, wherein the compound is:
   4-Methanesulfonyloxy-5-methoxy-7-[1H-5-(dimethylaminomethyl)indol-2-yl]isoindolinone, or
   4-Methanesulfonyloxy-5-methoxy-7-[1H-5-(diethylaminomethyl)indol-2-yl]isoindolinone.

10. A nitrogen-containing heterocyclic compound or a pharmaceutically acceptable salt thereof, wherein the compound is:
    4-Methanesulfonyloxy-5-methoxy-7-{1H-5-[di(2-hydroxyethyl)aminomethyl]indol-2-yl}isoindolinone, or
    4-Methanesulfonyloxy-5-methoxy-7-{1H-5-[di(2-methoxyethyl)aminomethyl]indol-2-yl}isoindolinone.

11. A nitrogen-containing heterocyclic compound or a pharmaceutically acceptable salt thereof, wherein the compound is selected from the group consisting of:
    4-Methanesulfonyloxy-5-methoxy-7-[1H-5-(pyrrolidin-1-ylmethyl)indol-2-yl]isoindolinone,
    4-Methanesulfonyloxy-5-methoxy-7-[1H-5-(piperidinomethyl)indol-2-yl]isoindolinone,
    4-Methanesulfonyloxy-5-methoxy-7-[1H-5-(4-piperidinopiperidinomethyl)indol-2-yl] isoindolinone,
    4-Methanesulfonyloxy-5-methoxy-7-[1H-5-(morpholinomethyl)indol-2-yl]isoindolinone,
    4-Methanesulfonyloxy-5-methoxy-7-[1H-5-(4-methylpyperazin-1-ylmethyl)indol-2-yl]isoindolinone, and
    4-Methanesulfonyloxy-5-methoxy-7-[1H-5-[4-(2-hydroxyethyl)pyperazin-1-ylmethyl]indol-2-yl}isoindolinone.

12. A pharmaceutical composition comprising, as an active ingredient, the nitrogen-containing heterocyclic compound or the pharmaceutically acceptable salt thereof described in any one of claim 8 to 11 together with a pharmaceutically acceptable carrier.

13. A method for inhibiting a protein kinase comprising a step of administering the nitrogen-containing heterocyclic compound or the pharmaceutically acceptable salt thereof described in any one of claims 1, 2, 3, 8, 9, 10 or 11.

14. A method for inhibiting a fibroblast growth factor receptor comprising a step of administering the nitrogen-containing heterocyclic compound or the pharmaceutically acceptable salt thereof described in any one of claims 1, 2, 3, 8, 9, 10 or 11.

15. A method for inhibiting an Aurora comprising a step of administering the nitrogen-containing heterocyclic compound or the pharmaceutically acceptable salt thereof described in any one of claims 1, 2, 3, 8, 9, 10 or 11.

16. A method for inhibiting a fms-like tyrosine kinase 3 comprising a step of administering the nitrogen-containing heterocyclic compound or the pharmaceutically acceptable salt thereof described in any one of claims 1, 2, 3, 8, 9, 10 or 11.

17. A method for treating a hematopoietic tumor comprising a step of administering the nitrogen-containing heterocyclic compound or the pharmaceutically acceptable salt thereof described in any one of claims 1, 2, 3, 8, 9, 10 or 11.

18. A method for treating leukemia, myeloma, or lymphoma comprising a step of administering the nitrogen-containing heterocyclic compound or the pharmaceutically acceptable salt thereof described in any one of claims 1, 2, 3, 8, 9, 10 or 11.

19. A method for treating multiple myeloma comprising a step of administering the nitrogen-containing heterocyclic compound or the pharmaceutically acceptable salt thereof described in any one of claims 1, 2, 3, 8, 9, 10 or 11.

20. A method for treating stomach cancer comprising a step of administering the nitrogen-containing heterocyclic compound or the pharmaceutically acceptable salt thereof described in any one of claims 1, 2, 3, 8, 9, 10 or 11.

21. A method for treating colon cancer comprising a step of administering the nitrogen-containing heterocyclic compound or the pharmaceutically acceptable salt thereof described in any one of claims 1, 2, 3, 8, 9, 10 or 11.

* * * * *

UNITED STATES PATENT AND TRADEMARK OFFICE
CERTIFICATE OF CORRECTION

PATENT NO. : 7,745,641 B2
APPLICATION NO. : 11/918778
DATED : June 29, 2010
INVENTOR(S) : Chikara Murakata et al.

It is certified that error appears in the above-identified patent and that said Letters Patent is hereby corrected as shown below:

ON TITLE PAGE AT (56) FOREIGN PATENT DOCUMENTS

"JP 5-163240 6/1993" (second occurrence) should be deleted.

COLUMN 1

Line 27, "FGFR3" should read --FGFR--; and "express," should read --express--.

COLUMN 2

Line 12, "that," should read --that--;
Line 13, "(Fetai" should read --(Fetal--;
Line 22, "mutations" should read --mutation--;
Line 45, "Medicine]," should read --Medicine,--; and
Line 52, "Clinical cancer research," should read --Clinical Cancer Research,--.

COLUMN 5

Line 44, "$R^5$" should read --$R^{15}$--.

COLUMN 7

Line 61, "a" should read --an--.

COLUMN 8

Line 26, "soisoindolinyl" should read --isoindolinyl--.

COLUMN 12

Line 39, "includes" should read --include--.

Signed and Sealed this

Fourteenth Day of December, 2010

David J. Kappos
*Director of the United States Patent and Trademark Office*

CERTIFICATE OF CORRECTION (continued)
U.S. Pat. No. 7,745,641 B2

COLUMN 13

Line 6, "Hodgkin" should read --Hodgkin's--.

COLUMN 18

Line 20, "–NR$_{D1}$R$^{D2}$" should read -- –NR$^{D1}$R$^{D2}$--;
Line 49, "R$_{8b}$" should read --R$^{8b}$--; and
Line 60, "X" should read --X$^1$--.

COLUMN 23

Line 4, "product Compound (AL-2)" should read --product. Compound (AL-2)--.

COLUMN 25

Line 23, "reacting" should read --reacted--; and
Line 30, "Compound (AV) can be produced." should read --Compound (AV).--.

COLUMN 41

Table 2-6 -continued, "100    101" should read --101    101--.

COLUMN 83

Ex. No. 293, " 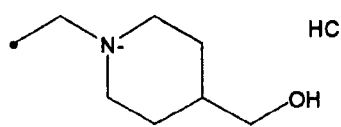 " should read -- 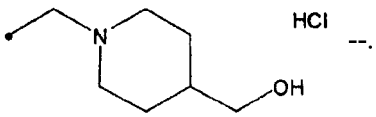 --.

COLUMN 125

Line 59, "reaction A" should read --reaction. A--.

COLUMN 128

Line 39, "wells" should read --well--; and
Line 51, "wells," should read --well,--.

COLUMN 129

Line 40, "wells" should read --well--; and
Line 51, "wells," should read --well,--.

COLUMN 134

Line 37, "744 (s, 1H)," should read --7.44 (s, 1H),--.

CERTIFICATE OF CORRECTION (continued)
U.S. Pat. No. 7,745,641 B2

COLUMN 136

Line 21, "suspenton" should read --suspension--.

COLUMN 142

Line 29 should be deleted.

COLUMN 144

Line 66, "¹H-NMR-(CDCl₃)" should read --$^1$H-NMR (CDCl₃)--.

COLUMN 145
Line 65, "9.09 mmol" should read --9.09 mmol)--.

COLUMN 146

Line 19, "δ(ppm) 0.02" should read --δ(ppm): 0.02--.

COLUMN 152

Line 34, "Compounds BA to BZ" should read --Compounds BA to CD--; and
Line 35, "Reference Examples 1 to 26" should read --Reference Examples 1 to 30--.

COLUMN 157

Table 10-3, Ref. Ex. No. 29,

" 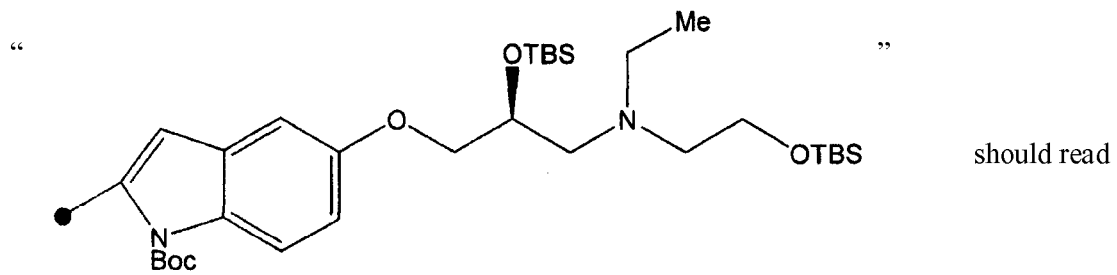 "     should read

-- 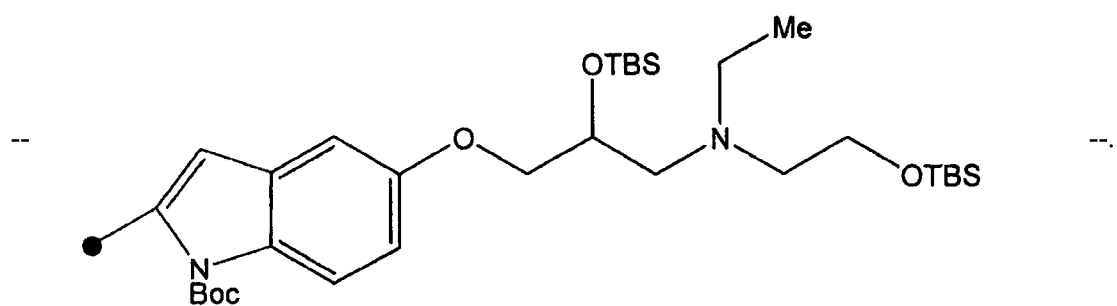 --.

CERTIFICATE OF CORRECTION (continued)
U.S. Pat. No. 7,745,641 B2

COLUMN 163

Line 54, "-6-[(1-(tert-bu–" should read -- –6–{1-(tert–bu– --; and
    Line 56, "–2yl)phthalimide" should read -- –2yl}phthalimide--.

COLUMN 164

Line 48, "–2–yl–]phthalimide" should read -- –2–yl]phthalimide--.

COLUMN 165

Line 3, "–6–(1–(tert–" should read -- –6–{1–(tert– --;
    Line 4, "–2–yl)ph–" should read -- –2–yl}ph– --;
    Line 63, "–6–(1–(tert–" should read -- –6–{1–(tert– --; and
    Line 64, "–2–yl)phthalim–" should read -- –2–yl}phthalim– --.

COLUMN 166

Line 53, "–6 –(1–tert–" should read -- –6–{1–tert– --;
    Line 54, "–2–yl)phthalim–" should read -- –2–yl}phthalim– --.

COLUMN 167

Line 17, "–6–(1–(tert–" should read -- –6–{1–(tert– --; and
    Line 18, "–2–yl)phthalimide" should read -- –2–yl}phthalimide--.

COLUMN 168

Line 3, "–6–(1–(tert–" should read -- –6–{1–(tert– --; and
    Line 18, "–2–yl)phthalimide" should read -- –2–yl}phthalimide--.

COLUMN 169

Line 46, "0-0.8/0.2)" should read --0.8/0.2)--; and
    Line 60, "(110.0 g, 57.1 mmol)" should read --(10.0 g, 57.1 mmol)--.

COLUMN 171

Line 4, "(0.475-mL," should read --(0.475 mL,--.

COLUMN 174

Line 5, "–7–(1–{tert–" should read -- –7–{1–(tert– --;
    Line 6, "indol–2–yl)" should read --indol–2–yl}--;
    Line 14, "4–chloro–7–(1–" should read --4–chloro–7–{1– --; and
    Line 16, "–2–yl)isoindolinone" should read -- –2–yl}isoindolinone--.

COLUMN 175

Line 23, "–7–(1–(tert–" should read -- –7–{1–(tert– --;
    Line 24, "indol–2–yl)" should read --indol-2–yl}--;
    Line 28, "4–chloro–7–(1–" should read --4–chloro–7–{1– --; and
    Line 30, "indol–2–yl)isoindolinone" should read --indol–2–yl}isoindolinone--.

COLUMN 176

Line 13, "4–chloro–7–(1–" should read --4–chloro–7–{1– --; and
    Line 15, "indol–2–yl)isoindolinone" should read --indol–2–yl}isoindolinone--;
    Line 54, "4–chloro–7–(1–(tert–" should read --4–chloro–7–{1–(tert– --; and
    Line 55, "dol–2–yl)isoindolinone" should read --dol–2–yl}isoindolinone--.

COLUMN 177

Line 19, "4–chloro–7–(1–(tert–" should read --4–chloro–7–{1–(tert– --; and
    Line 20, "indol–2–yl)" should read --indol–2–yl}--.

COLUMN 178

Line 19, "4–Chloro–7–(1H–5–" should read --4–Chloro–7–{1H–5– --; and
    Line 20, "indol–2–yl)isoindolinone" should read --indol–2–yl}isoindolinone--.

COLUMN 179

Line 45, "4–chloro–7–(1–(tert–" should read --4–chloro–7–{1–(tert– --;
    Line 46, "indol–2–yl)" should read --indol–2–yl}--; and
    Line 47, "yield 871)." should read --yield 87%).--.

COLUMN 180

Line 6, "4–Chloro–7–(1H–5–" should read --4–Chloro–7–{1H–5– --;
    Line 7, "indol–2–yl)isoindolinone" should read --indol–2–yl}isoindolinone--;
    Line 22, "4–chloro–7–(1–(tert–" should read --4–chloro–7–{1–(tert– --; and
    Line 23, "indol–2–yl)isoindolinone" should read --indol–2–yl}isoindolinone--.

COLUMN 185

Line 64, "3.20-3.80 (m, BH)," should read --3.20-3.80 (m, 8H),--.

COLUMN 187

Line 31, "4–chloro–7–[(1–" should read --4–chloro–7–[1– --.

COLUMN 189

Line 8, "4–chloro–7–[(1–" should read --4–chloro–7–[1– --.

COLUMN 190

Line 27, "of" should be deleted.

COLUMN 193

Line 66, "mp 246° C." should read --mp 246° C.;--.

COLUMN 195

Line 66, "(1–(tert–" should read -- –{1–(tert– --; and
Line 67, "indol–2–yl)isoindolinone" should read --indol–2–yl}isoindolinone--.

COLUMN 196

Line 16, "4–chloro–7–(1–" should read --4–chloro-7–{1– --;
Line 18, "indol–2–yl)isoindolinone." should read --indol–2–yl}isoindolinone.--;
Line 21, "(1–(tert–" should read --{1–(tert– --;
Line 22, "indol–2–yl)isoindolinone" should read --indol–2–yl}isoindolinone--;
Line 43, "(1–(tert–" should read --{1–(tert– --; and
Line 44, "indol–2–yl)isoindolinone" should read --indol–2–yl}isoindolinone--.

COLUMN 197

Line 41, "4–chloro–7–(1–(tert–" should read --4–chloro–7–{1–(tert– --;
Line 43, "indol–2–yl)isoindolinone." should read --indol–2–yl}isoindolinone.--;
Line 47, "(1–(tert–" should read --{1–(tert– --; and
Line 48, "indol–2–yl)isoindolinone" should read --indol–2–yl}isoindolinone--.

COLUMN 198

Line 3, "(1–(tert–" should read --{1–(tert– --;
Line 4, "indol–2–yl)isoindolinone" should read --indol–2–yl}isoindolinone--;
Line 20, "4–chloro–7–(1–(tert–bu–" should read --4–chloro–7–{1–(tert–bu– --;
Line 22, "2–yl)isoindolinone." should read --2–yl}isoindolinone.--;
Line 26, "(1–(tert–" should read --{1–(tert– --; and
Line 27, "indol–2–yl)isoindolinone" should read --indol–2–yl}isoindolinone--.

COLUMN 200

Line 1, "8.26 (d, J=28.6" should read --8.26 (d, J=8.6--.

COLUMN 202

Line 16, "4-chloro-7-[1-(tert-" should read --4-chloro-7-{1-(tert- --; and
   Line 18, "indol-2-yl)isoindolinone." should read --indol-2-yl}isoindolinone.--.

COLUMN 203

Line 65, "4-chloro-7-(1-{tert-" should read --4-chloro-7-{1-(tert- --; and
   Line 67, "indol-2-yl)isoindolinone." should read --indol-2-yl}isoindolinone.--.

COLUMN 205

Line 52, "ESI-MS m/z:472 [M+H]$^-$." should read --ESI-MS m/z:472 [M+H]$^+$.--.

COLUMN 206

Line 22, "4-chloro-7-(1-(tert-bu-" should read --4-chloro-7-{1-(tert-bu- --;
   Line 24, "indol-2-yl)isoindolinone." should read --indol-2-yl}isoindolinone.--;
   Line 45, "4-chloro-7-(1-(tert-bu-" should read --4-chloro-7-{1-(tert-bu- --; and
   Line 47, "indol-2-yl)isoindolinone." should read --indol-2-yl}isoindolinone.--.

COLUMN 207

Line 1, "4-chloro-7-(1-(tert-bu-" should read --4-chloro-7-{1-(tert-bu- --;
   Line 3, "indol-2-yl)isoindolinone." should read --indol-2-yl}isoindolinone.--;
   Line 28, "(1-(tert-butoxycarbonyl)" should read --{1-(tert-butoxycarbonyl)--;
   Line 29, "indol-2-yl)isoindolinone" should read --indol-2-yl}isoindolinone- --;
   Line 46, "4-chloro-7-(1-" should read --4-chloro-7-{1- --; and
   Line 48, "indol-2-yl)isoindolinone." should read --indol-2-yl}isoindolinone.--.

COLUMN 208

Line 35, "1.30-1.80 (m, BH)," should read --1.30-1.80 (m, 8H),--.

COLUMN 210

Line 66, "APCI-MS" should read --¶ APCI-MS--.

COLUMN 211

Line 59, "Compound III" should read --Compound 111--.

COLUMN 212

Line 26, "indol-2'-yl}isoindolinone" should read --indol-2-yl}isoindolinone--.

COLUMN 214

Line 18, "(5, 1H)." should read --(s, 1H).--.

COLUMN 215

Line 25, "Compound 121" should read --Compound 122--.

COLUMN 217

Line 5, "Compound" should be deleted.

COLUMN 219

Line 18, "4–chloro–7–(1–" should read --4–chloro–7–{(1– --; and
   Line 20, "indol–2–yl)isoindolinone" should read --indol–2–yl}isoindolinone--.

COLUMN 220

Line 52, "6–iodophtalimide" should read --6–iodophthalimide--.

COLUMN 221

Line 35, "13.78+(s, 1H)." should read --13.78 (s, 1H).--.

COLUMN 222

Line 7, "(m, 3H), 6–methoxy–" should read --(m, 3H). ¶ 6–methoxy– --;
   Line 23, "(CDCl₃) δ (ppm)" should read --(CDCl₃) δ (ppm):--;
   Line 61, "(1–(tert–butoxycarbonyl)" should read --{1–(tert–butoxycarbonyl)--; and
   Line 62, "indol–2–yl)isoindolinone" should read --indol–2–yl}isoindolinone--.

COLUMN 223

Line 61, "oxy–7–(1–(tert–" should read --oxy–7–{1–(tert– --; and "–5–[(4–(tert–" should
      read -- –5–[4–(tert– --.

COLUMN 226

Line 26, "(60.318 mL," should read --(0.318 mL,--.

COLUMN 227

Line 45, "8.4.0 mL," should read --84.0 mL,--.

COLUMN 228

Line 64, "diisobutylaluminiumhydride" should read --diisobutylaluminumhydride--.

COLUMN 231

Line 24, "Example 11," should read --Example 1,--;
Line 32, "(1–(tert–butoxycarbonyl)–" should read --{1–(tert–butoxycarbonyl)– --;
Line 33, "indol–2–yl)isoindolinone" should read --indol–2–yl}isoindolinone--;
Line 42, "7–(1–(tert–butoxycarbonyl)–" should read --7–{1–(tert–butoxycarbonyl)– --; and
Line 43, "indol–2–yl)isoindolinone" should read --indol–2–yl}isoindolinone--.

COLUMN 232

Line 23, "δ(ppm) 1.66-1.77" should read --δ(ppm): 1.66-1.77--; and
Line 49, "4–hydroxy–7–iodo–2'–" should read --4–hydroxy–7–iodo–2– --.

COLUMN 233

Line 6, "7–(1–(tert–butoxycarbonyl)–" should read --7–{1–(tert–butoxycarbonyl)– --;
Line 7, "indol–2–yl)isoin-" should read --indol–2–yl}isoin- --; and
Line 66, "etonitrile-6/1," should read --etonitrile=6/1,--.

COLUMN 234

Line 65, "7–(1–(tert–butoxycarbonyl)–" should read --7–{1–(tert–butoxycarbonyl)– --; and
Line 66, "indol–2–yl)isoindolinone" should read --indol–2–yl}isoindolinone--.

COLUMN 236

Line 34, "7–(1–(tert–butoxycarbonyl)–" should read --7–{1–(tert–butoxycarbonyl)– --; and
Line 35, "indol–2–yl)isoindolinone" should read --indol–2–yl}isoindolinone--.

COLUMN 239

Line 12, "J=+8.4 Hz, 1H)," should read --J=8.4 Hz, 1H),--.

COLUMN 240

Line 52, "indol–2–yl]phtalimide" should read --indol–2–yl]phthalimide--.

COLUMN 242

Line 51, "(d, J=11.3 Hz, 1H)," should read --(d, J=1.3 Hz, 1H),--.

COLUMN 243

Line 16, "phtalimide" should read --phthalimide--;
Line 20, "indol–2–yl]phtalim–" should read --indol–2–yl]phthalim– --;
Line 30, "iodoindol–2–yl]phtalimide" should read --iodoindol–2–yl]phthalimide--;
Line 37, "phtalimide" should read --phthalimide--;
Line 49, "indol–2–yl]phtalimide" should read --indol–2–yl]phthalimide--; and

CERTIFICATE OF CORRECTION (continued)
U.S. Pat. No. 7,745,641 B2

Line 57, "indol–2–yl]phtalimide" should read --indol–2–yl]phthalimide--.

COLUMN 244

Line 2, "4.31 (t, 34.8 Hz, 1H)," should read --4.31 (t, J=4.8 Hz, 1H),--;
Line 29, "Solution" should read --solution--; and
Line 44, "[(1–(tert–" should read --[1–(tert– --.

COLUMN 245

Line 21, "succineimide" should read --succinimide--;
Line 44, "neimide" should read --nimide--; and
Line 62, "yl]phtalimide" should read --yl]phthalimide--.

COLUMN 246

Line 8, "indol–2–yl}phtalimide" should read --indol–2–yl}phthalimide--;
Line 19, "indol–2–yl}phtalimide" should read --indol–2–yl}phthalimide--;
Line 54, "4–chloro–7–(1–" should read --4–chloro–7–{1– --; and
Line 56, "indol–2–yl)isoindolinone" should read --indol–2–yl}isoindolinone--.

COLUMN 247

Line 3, "phtalimide" should read --phthalimide--;
Line 42, "3–iodophtalim-" should read --3–iodophthalim- --;
Line 49, "3–iodophtalim-" should read --3–iodophthalim- --;
Line 64, "phtalimide" should read --phthalimide--; and
Line 66, "3–iodophtalim-" should read --3–iodophthalim- --.

COLUMN 248

Line 35, "phtalimide" should read --phthalimide--; and
Line 60, "DMF 2mL)," should read --DMF (2 mL),--.

COLUMN 249

Line 8, "4–Chloro–7–(5–" should read --4–Chloro–7–{5– --; and
Line 9, "benzothiophen-2-yl)isoindolinone" should read --benzothiophen-2-yl}isoindolinone--.

COLUMN 252

Line 7, "phtalimide" should read --phthalimide--;
Line 29, "phtalimide" should read --phthalimide--; and
Line 38, "phtalimide" should read --phthalimide--.

COLUMN 253

Line 2, "suspetion" should read --suspension--; and
Line 56, "(chloroform/methanol=9/1," should read --(chloroform/methanol=19/1,--.

COLUMN 256

Line 59, "4–chloro–7–(5–(4–[2–(tert–" should read --4–chloro–7–(5–{4–[2–(tert– --; and
Line 60, "–1–ylmethyl)indol–2–yl)isoindoli–" should read --1–ylmethyl}indol–2–yl)isoindoli- --.

COLUMN 257

Line 31, "4–chloro–7–(5–(4–[2–(tert–bu–" should read --4–chloro–7–(5–{4–[2–(tert–bu– --;
Line 32, "–1–ylmethyl)indol–2–yl)" should read -- –1–ylmethyl}indol–2–yl)--;
Line 37, "(4–[2–(tert–" should read --{4-[2–(tert– --; and
Line 38, "ethyl)indol–2–yl)isoindolinone" should read --ethyl}indol–2–yl)isoindolinone--.

COLUMN 260

Line 14, "4–chloro–7–(1–(tert–" should read --4–chloro–7–{1–(tert– --; and
Line 15, "indol–2–yl)isoindolinone" should read --indol–2–yl}isoindolinone--.

COLUMN 262

Line 63, "4–chloro–7–(1–" should read --4–chloro–7–{1– --; and
Line 65, "indol–2–yl)isoindolinone" should read --indol–2–yl}isoindolinone--.

COLUMN 268

Line 29, "HOBt" should read --HOBT--.

COLUMN 269

Line 25, "(1–(tert–" should read --{1–(tert– --;
Line 26, "indol–2–yl)isoindolinone" should read --indol–2–yl}isoindolinone--;
Line 63, "(1–(tert–" should read --{1–(tert– --; and
Line 64, "indol–2–yl)isoindolinone" should read --indol–2–yl}isoindolinone--.

COLUMN 270

Line 35, "(1–(tert–" should read --{1–(tert– --; and
Line 36, "indol–2–yl)isoindolinone" should read --indol–2–yl}isoindolinone--.

COLUMN 272

Line 2, "4–(2,2–dim–" should read --4–{2,2–dim- --;
Line 3, "–4–ylmethoxy)–7–" should read --4–ylmethoxy}–7– --; and
Line 22, "–7–{1H–5–" should read -- –7–(1H–5– --.

COLUMN 274

Line 26, "7–[(1–(tert–" should read --7–[1–(tert– --; and
　　　Line 41, "–7–[(1–(tert–" should read -- –7–[1–(tert– --.

COLUMN 276

Line 14, "7–[(1–(tert–" should read --7–[1–(tert– --;
　　　Line 35, "7–[(1–(tert–" should read --7–[1–(tert– --; and
　　　Line 42, "–7–[(1–(tert–" should read -- 7–[1–(tert– --.

COLUMN 278

Line 3, "–7–[(1–(tert–" should read --7–[1–(tert– --; and
　　　Line 33, "d (ppm):" should read --δ (ppm):--.

COLUMN 280

Line 23, "6.28° (d," should read --6.28 (d,--; and
　　　Line 54, "4.56 (s, 2H)" should read --4.56 (s, 2H),--.

COLUMN 282

Line 66, "–7–[(1–(tert–" should read -- –7–[1–(tert– --.

COLUMN 285

Line 62, "–7–[(1–(tert–" should read -- –7–[1–(tert– --.

COLUMN 286

Line 39, "zenesulfonylchloride" should read --zenesulfonyl chloride--.

COLUMN 289

Line 57, "yield 434)." should read --yield 43%).--.

COLUMN 291

Line 5, "d (ppm):" should read --δ (ppm):--; and
　　　Line 36, "zothiophene–2–sulfonylchloride" should read --zothiophene–2–sulfonyl
　　　　　　chloride--.

COLUMN 294

Line 19, "–7–[(1–(tert–" should read -- –7–[1–(tert– --.

COLUMN 295

Line 26, "7–[(1–(tert–" should read --7–[1–(tert– --.

COLUMN 296

Line 3, "4–hydroxy–7–[1–(tert–butoxycarbonyl)–5–(piperidi-" should read
        --4–(8–Quinolinesulfonyloxy)–7–[1*H*–5–(piperidi- --; and
    Line 44, "–7–[(1–(tert–" should read -- –7–[1–(tert– --.

COLUMN 297

Line 43, "nesulfonyl," should read --nesulfonyl--.

COLUMN 298

Line 46, "4–hydroxy–7–[1–(tert–butoxycarbonyl)–5–(piperidi-" should read
        --4–(trans-β–Styrenesulfonyloxy)–7–[1*H*–5–(piperidi- --.

COLUMN 303

Line 20, "–7–[(1–(tert–" should read -- –7–[1–(tert– --.

COLUMN 304

Line 43, "pyperazin–1–ylmethyl]" should read --piperazin–1–ylmethyl]--.

COLUMN 305

Line 6, "pyperazin–1–ylmethyl]" should read --piperazin–1–ylmethyl]--;
    Line 17, "pyperazin–7–ylmethyl]" should read --piperazin–1–ylmethyl]--; and
    Line 47, "600[M+H]$^+$;" should read --600 [M+H]$^+$--.

COLUMN 306

Line 47, "–7–(1–(tert–" should read -- –7–{1–(tert– --; and
    Line 48, "indol–2–yl)isoindolinone" should read --indol–2–yl}isoindolinone--.

COLUMN 309

Line 64, "δ(ppm) 1.30" should read --δ(ppm): 1.30--.

COLUMN 310

Line 21, "(pyperazin–1–ylcar-" should read --(piperazin–1–ylcar- --;
    Line 33, "–7–(1–(tert–" should read -- –7–{1–[tert– --;
    Line 34, "pyperazin–1–ylcarbonyl]indol–2-yl)" should read
        --piperazin–1–ylcarbonyl]indol–2–yl}--;

Line 38, "–7–(1–(tert–" should read -- –7–{1–(tert– --; and
Line 39, "pyperazin–1–ylcarbonyl]indol–2-yl)" should read
--piperazin–1–ylcarbonyl]indol–2–yl}--.

COLUMN 313

Line 25, "4–methyl–" should read --¶ 4–methyl– --; and
Line 55, "pyperazin–1–" should read --piperazin–1– --.

COLUMN 314

Line 21, "pyperazin–1–yl-" should read --piperazin–1–yl- --;
Line 31, "pyperazin–1–yl-" should read --piperazin–1–yl- --;
Line 43, "1.4.07 (s, H)." should read --14.07 (s, 1H).--; and
Line 47, "pyperazin–1–" should read --piperazin–1– --.

COLUMN 315

Line 28, "–7–(1–(tert–" should read --7–{1–(tert– --;
Line 29, "pyperazin–1–ylmethyl]in-" should read --piperazin–1–ylmethyl]in- --;
Line 30, "dol–2–yl)isoindolinone" should read --dol–2–yl}isoindolinone--; and
Line 39, "pyperazin–" should read --piperazin– --.

COLUMN 319

Line 56, "(52 mg," should read --(5.2 mg,--.

COLUMN 323

Line 4, "0.4/" should read --4/--; and
Line 50, "53.7 [M+H]$^+$;" should read --537 [M+H]$^+$;--.

COLUMN 327

Line 48, "(3.0.5 mg," should read --(30.5 mg,--.

COLUMN 328

Line 58, "7.5.5. (s, 1H)," should read --7.55 (s, 1H),--.

COLUMN 329

Line 54, "(Compound 32.3)" should read --(Compound 323)--.

COLUMN 331

Line 43, "pyperazin–1–" should read --piperazin–1– --;
Line 55, "–7–(1–(tert–" should read -- –7–{1–(tert– --;

Line 57, "indol–2–yl)isoindolinone" should read --indol–2–yl}isoindolinone--; and
Line 67, "–7–(1–(tert–" should read -- –7–{1–(tert– --.

COLUMN 332

Line 1, "indol–2–yl)isoindolinone" should read --indol–2–yl}isoindolinone--;
Line 2, "0.240-mmol)" should read --0.240 mmol)--;
Line 9, "pyperazin–1–" should read --piperazin–1– --;
Line 20, "pyperazin–1–" should read --piperazin–1– --;
Line 30, "pyperazin–1–" should read --piperazin–1– --;
Line 43, "pyperazin–1–" should read --piperazin–1– --;
Line 59, "pyper-" should read --piper- --; and
Line 67, "pyperazin–1–" should read --piperazin–1– --.

COLUMN 333

Line 9, "pyperazin–1–" should read --piperazin–1– --; and
Line 21, "pyperazin–1–" should read --piperazin–1– --.

COLUMN 334

Line 31, "7.50 (s, 1H)–," should read --7.50 (s, 1H),--;
Line 36, "–7–[1'–(tert–" should read -- – 7–[1–(tert– --; and
Line 43, "4.14 [M+H]$^+$;" should read --414 [M+H]$^+$;--.

COLUMN 336

Line 54, "4–Amino–7–bromophtalimide" should read
--4–Amino–7–bromophthalimide--.

COLUMN 338

Line 42, "752 (d, J=8.1 Hz, 1H)," should read --7.52 (d, J=8.1 Hz, 1H),--.

COLUMN 341

Line 36, "0.99/1)" should read --99/1)--; and
Line 60, "pyper-" should read --piper- --.

COLUMN 342

Line 26, "pyperazin–" should read --piperazin– --;
Line 34, "pyper-" should read --piper- --; and
Line 53, "Step 11" should read --Step 1--.

COLUMN 343

Line 33, "–7–iodo-2(1–methyl–1–" should read -- –7–iodo–2–(1–methyl–1– --.

COLUMN 345

Line 32, "410[M+H]$^+$;" should read --410 [M+H]$^+$;--.

COLUMN 347

Line 4, "pyperazin–1–" should read --piperazin–1– --;
Line 15, "–5–methoxy–7–(1–" should read -- –5–methoxy–7–{1– --;
Line 16, "pyperazin–1–" should read --piperazin–1– --;
Line 17, "indol–2–yl)isoindolinone" should read --indol–2–yl}isoindolinone--;
Line 27, "–7–(1–(tert–" should read -- –7–{1–(tert– --;
Line 28, "pyperazin–1–ylmethyl]indol–2–yl)isoindolinone" should read
--piperazin–1–ylmethyl]indol–2–yl}isoindolinone--; and
Line 66, "solution-(1 mL)." should read --solution (1 mL).--.

COLUMN 348

Line 13, "pyperazin–1–" should read --piperazin–1– --;
Line 25, "pyperazin–1–" should read --piperazin–1– --; and
Line 37, "pyperazin–1–" should read --piperazin–1– --.

COLUMN 350

Line 25, "y" should read --by--; and
Line 27, "yield-86%)." should read --yield 86%).--.

COLUMN 353

Line 54, "(CDCl$_3$) (ppm):" should read --(CDCl$_3$) δ (ppm):--.

COLUMN 355

Line 21, "pyperazin–1–" should read --piperazin–1– --;
Line 33, "pyperazin–1–" should read --piperazin–1– --;
Line 44, "pyperazin–1–" should read --piperazin–1– --;
Line 50, "pyperazin–1–" should read --piperazin–1– --; and
Line 61, "pyperazin–1–" should read --piperazin–1– --.

COLUMN 361

Line 36, "pyperazin–1–" should read --piperazin–1– --;
Line 49, "pyperazin–1–" should read --piperazin–1– --;
Line 59, "–7–(1–(tert–" should read -- –7–{1–(tert– --;
Line 60, "pyperazin–1–ylmethyl]indol–2–yl)isoindolinone" should read
--piperazin–1–ylmethyl]indol–2–yl}isoindolinone--; and
Line 66, "pyperazin–1–" should read --piperazin–1– --.

COLUMN 362

Line 9, "pyperazin–1–" should read --piperazin–1- --.

COLUMN 364

Line 47, "pyperazin–1–" should read --piperazin–1- --; and
Line 61, "pyperazin–1–" should read --piperazin–1- --.

COLUMN 365

Line 3, "–7–(1–(tert–" should read -- –7–{1–(tert– --; and
Line 4, "pyperazin–1–ylmethyl]indol–2–yl)isoindoli-" should read
--piperazin–1–ylmethyl]indol–2–yl}isoindoli- --.

COLUMN 368

Line 39, "–5– (pyper-" should read -- –5–(piper- --;
Line 53, "–5–(pyperazin–1–" should read -- –5–(piperazin–1- --; and
Line 64, "–5–(pyperazin–1–" should read -- –5–(piperazin–1- --.

COLUMN 369

Line 5, "(chloroform/methanol=9/0.1)" should read --(chloroform/methanol=9/1)--;
Line 16, "ylpyperazin–1–" should read --ylpiperazin–1- --;
Line 29, "–5–(4–methylpyperazin–1–" should read -- –5–(4–methylpiperazin–1- --; and
Line 40, "methylpyperazin–1–" should read --methylpiperazin–1- --.

COLUMN 371

Line 39, "7.33 (d, J=28.4 Hz," should read --7.33 (d, J=8.4 Hz,--; and
Line 63, "δ(ppm) 0.83" should read --δ(ppm): 0.83--.

COLUMN 372

Line 35, "$^1$H-NMR (CDCl$_3$) (ppm):" should read --$^1$H-NMR (CDCl$_3$) δ(ppm):--.

COLUMN 374

Line 21, "(chloroform/methano=6/11)" should read --(chloroform/methanol=6/1)--.

COLUMN 377

Line 60, "–7–(1–(tert–" should read -- –7–{1–(tert– --; and
Line 63, "indol–2–yl)isoindolinone" should read --indol–2–yl}isoindolinone--.

COLUMN 378

Line 6, "–7–(1–(tert–" should read -- –7–{1–(tert– --;
Line 8, "2–yl)isoindolinone" should read --2–yl}isoindolinone--;
Line 39, "–7–(1–(tert–" should read --7–{1–(tert– --; and
Line 41, "indol–2–yl)isoindolinone" should read --indol–2–yl}isoindolinone--.

COLUMN 379

Line 39, "¹H-NMR (DMSO-d₆) (ppm):" should read --¹H-NMR (DMSO-d₆) δ(ppm):--.

COLUMN 380

Line 6, "–7–(1–(tert–" should read -- –7–{1–(tert– --;
Line 7, "indol–2–yl)isoindolinone" should read --indol–2–yl}isoindolinone--;
Line 53, "–7–(1–(tert–" should read -- –7–{1–(tert– --; and
Line 54, "indol–2–yl)isoindolinone" should read --indol–2–yl}isoindolinone--.

COLUMN 382

Line 18, "¹H-NMR (DMSO-d₆) (ppm):" should read --¹H-NMR (DMSO-d₆) δ(ppm):--;
Line 42, "–7–(1–(tert–" should read -- –7–{1–(tert– --;
Line 43, "indol–2–yl)" should read --indol–2–yl} --; and
Line 62, "¹H-NMR (DMSO-d₆) (ppm):" should read --¹H-NMR (DMSO-d₆) δ(ppm):--.

COLUMN 383

Line 29, "–7–(1–(tert–" should read -- –7–{1–(tert– --;
Line 31, "yl)isoindolinone" should read --yl}isoindolinone--;
Line 46, "–7–(1H–5–[N–(2–" should read -- –7–{1H–5–[N–(2– --; and
Line 48, "yl)isoindolinone" should read --yl}isoindolinone--.

COLUMN 386

Line 14, "3.55 (s, 2H)—," should read --3.55 (s, 2H),--;
Line 49, "–7–(1–(tert–" should read -- –7–{1–(tert– --; and
Line 50, "indol–2–yl)isoindolinone" should read --indol–2–yl}isoindolinone--.

COLUMN 388

Line 17, "–7–(1–(tert–" should read -- –7–{1–(tert– --; and
Line 18, "indol–2–yl)isoindolinone" should read --indol–2–yl}isoindolinone--.

COLUMN 393

Line 67, "J=1.6, 5.1 Hz, 0.1H)," should read --J=1.6, 5.1 Hz, 1H),--.

CERTIFICATE OF CORRECTION (continued)
U.S. Pat. No. 7,745,641 B2

COLUMN 395

Line 47, "(0.0773 g, ESI-MS" should read --(0.0773 g, 51%). ¶ ESI-MS--.

COLUMN 400

Line 44, "ride" should read --ride (Compound 420)--.

COLUMN 402

Line 26, "Isoindolinone" should read --isoindolinone--;
Line 47, "0.355 mmol)" should read --0.555 mmol)--; and
Line 63, "indol–72–yl]isoindolinone" should read --indol–2–yl]isoindolinone--.

COLUMN 403

Line 9, "(br as, 1H)," should read --(br s, 1H),--;
Line 52, "4.48-7.57" should read --7.48-7.57--;
Line 60, "(Compound 424)" should read --(Compound 425)--; and
Line 66, "2.88 (g, J=7.5 Hz, 2H)," should read --2.88 (q, J=7.5 Hz, 2H),--.

COLUMN 405

Line 21, "–5–[(4–(hydroxymethyl)" should read -- –5–[4–(hydroxymethyl)--;
Line 23, "(Compound 424)" should read --(Compound 427)--; and
Line 45, "[(1–(tert–" should read --[1–(tert– --.

COLUMN 411

Line 20, "7.45 (d, J=6.0 HZ, 2H)," should read --7.45 (d, J=6.0 Hz, 2H),--;
Line 21, "8.06 (d, J=8.4 HZ, 1H)," should read --8.06 (d, J=8.4 Hz, 1H),--; and
Line 59, "3.71 (t, J=6.3 HZ, 2H)," should read --3.71 (t, J=6.3 Hz, 2H),--.

COLUMN 412

Line 46, "–7–[(1–(tert–" should read -- –7–[1–{tert– --; and
Line 63, "ESI-MS m/z: 4.54 [M+H]$^{+}$;" should read --ESI-MS m/z: 454 [M+H]$^{+}$;--.

COLUMN 414

Line 51, "chloride" should read --chloride (Compound 439)--.

COLUMN 415

Line 7, "evaported" should read --evaporated--; and
Line 52, "dihydrochloride" should read --dihydrochloride (Compound 440)--.

COLUMN 416

Line 21, "7.55 (d, J=1.8 HZ," should read --7.55 (d, J=1.8 Hz,--; and
   Line 45, "dihydrochloride" should read --dihydrochloride (Compound 441)--.

COLUMN 417

Line 63, "evaported" should read --evaporated--.

COLUMN 421

Line 17, "–7–[(1–(tert–" should read -- –7–[1–(tert– --;
   Line 53, "(4–methylpyperazin–1–yl)" should read --(4–methylpiperazin–1–yl)--; and
   Line 67, "(4–methylpyperazin–1–yl)" should read --(4–methylpiperazin–1–yl)--.

COLUMN 422

Line 10, "(4–methylpyperazin–1–yl)" should read --(4–methylpiperazin–1–yl)--.

COLUMN 424

Line 31, "–5–(pyper-" should read -- –5–(piper- --;
   Line 44, "–5–(pyper-" should read -- –5–(piper- --;
   Line 46, "73%) was obtained." should read --73%).--; and
   Line 57, "(pyperazin–1–" should read --(piperazin–1– --.

COLUMN 425

Line 38, "yield 829)." should read --yield 82%).--.

COLUMN 426

Line 52, "ylpyperazin–1–" should read --ylpiperazin–1– --; and
   Line 66, "(4–methylpyperazin–1–yl)" should read --(4–methylpiperazin–1–yl)--.

COLUMN 427

Line 8, "methylpyperazin–1–" should read --methylpiperazin–1– --;
   Line 17, "7.3.4 (s, 1H)," should read --7.34 (s, 1H),--;
   Line 23, "pyperazin–1–" should read --piperazin–1– --;
   Line 55, "pyperazin–1–" should read --piperazin–1– --; and
   Line 66, "pyperazin–1–" should read --piperazin–1– --.

COLUMN 431

Line 26, "(pyperazin–1–" should read --(piperazin–1– --;
   Line 41, "(4–tert–butoxycarbonylpyperazin–1–" should read
            --(4–tert–butoxycarbonylpiperazin–1– --; and

CERTIFICATE OF CORRECTION (continued)
U.S. Pat. No. 7,745,641 B2

Line 53, "(4–tert-butoxycarbonylpyperazin–1–" should read
--(4–tert–butoxycarbonylpiperazin–1– --.

COLUMN 433

Line 19, "pyperazin–1–" should read --piperazin–1– --;
Line 32, "4–(1–(tert–" should read --4–{1–(tert– --;
Line 33, "pyperazin–1–" should read --piperazin–1– --;
Line 34, "indol–2–yl)–7–" should read --indol–2–yl}–7– --;
Line 42, "4–(1–(tert–" should read --4–{1–(tert– --; and
Line 44, "pyperazin–1–ylmethyl]indol–2–yl}–7–" should read
--piperazin–1–ylmethyl]indol–2–yl}–7– --.

COLUMN 434

Line 35, "d (ppm):" should read --δ (ppm):--.

COLUMN 435

Line 8, "pyperazin–1–" should read --piperazin–1– --;
Line 9, "indol–2–yl}6–methyl–1," should read --indol–2–yl}–6–methyl–1,--;
Line 22, "pyperazin–1–" should read --piperazin–1– --;
Line 33, "4–(1–(tert–" should read --4–{1–(tert– --; and
Line 35, "pyperazin–1–ylmethyl]indol–2–yl)–6–" should read
--piperazin–1–ylmethyl]indol–2–yl}–6– --.

COLUMN 438

Line 2, "ylpyperazin-1" should read --ylpiperazin-1--;
Line 4, "pyperazin-1" should read --piperazin-1--; and
Line 9, "claim 8 to 11" should read --claims 8 to 11--.